(12) United States Patent
Karlik et al.

(10) Patent No.: US 7,576,101 B2
(45) Date of Patent: Aug. 18, 2009

(54) COMPOSITION FOR AND TREATMENT OF DEMYELINATING DISEASES AND PARALYSIS BY ADMINISTRATION OF REMYELINATING AGENTS

(75) Inventors: Stephen J. Karlik, Ontario (CA); Michael A. Pleiss, Sunnyvale, CA (US); Andrei W. Konradi, Burlingame, CA (US); Francine S. Farouz, Mercer Island, WA (US); Christopher M. Semko, Fremont, CA (US); Darren B. Dressen, San Mateo, CA (US); Elizabeth Messersmith, El Cerrito, CA (US); Stephen Freedman, Walnut Creek, CA (US); Ted Yednock, Forest Knolls, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 602 days.

(21) Appl. No.: 10/763,539

(22) Filed: Jan. 26, 2004

(65) Prior Publication Data
US 2005/0215565 A1  Sep. 29, 2005

Related U.S. Application Data

(60) Provisional application No. 60/500,316, filed on Sep. 5, 2003, provisional application No. 60/442,171, filed on Jan. 24, 2003.

(51) Int. Cl.
*A61K 31/445* (2006.01)
*A61K 31/63* (2006.01)
(52) U.S. Cl. ............ 514/315; 514/155; 514/316
(58) Field of Classification Search .......... 514/155, 514/315, 316
See application file for complete search history.

(56) References Cited

U.S. PATENT DOCUMENTS

| | | | |
|---|---|---|---|
| 6,060,501 A | 5/2000 | Wachtel et al. | |
| 6,291,453 B1* | 9/2001 | Ashwell et al. | 514/227.5 |
| 6,362,341 B1* | 3/2002 | Thorsett et al. | 548/200 |
| 6,436,904 B1* | 8/2002 | Ashwell et al. | 514/19 |
| 6,489,300 B1* | 12/2002 | Thorsett et al. | 514/19 |
| 6,492,421 B1 | 12/2002 | Thorsett et al. | |
| 6,525,026 B2* | 2/2003 | Thorsett et al. | 514/19 |
| 6,559,127 B1* | 5/2003 | Dappen et al. | 514/19 |
| 6,583,139 B1* | 6/2003 | Thorsett et al. | 514/227.5 |
| 6,586,602 B2* | 7/2003 | Thorsett et al. | 548/200 |
| 6,900,179 B2* | 5/2005 | Thorsett et al. | 514/19 |
| 6,939,855 B2* | 9/2005 | Yednock et al. | 514/19 |
| 6,949,570 B2* | 9/2005 | Ashwell et al. | 514/326 |
| 7,030,114 B1* | 4/2006 | Thorsett et al. | 514/235.5 |
| 7,166,580 B2* | 1/2007 | Dappen et al. | 514/19 |
| 7,288,526 B2* | 10/2007 | Thorsett et al. | 514/19 |
| 7,320,960 B2* | 1/2008 | Thorsett et al. | 514/19 |
| 2002/0161006 A1* | 10/2002 | Kawamura et al. | 514/235.8 |
| 2003/0065185 A1* | 4/2003 | Thorsett et al. | 546/232 |
| 2004/0014677 A1* | 1/2004 | Thorsett et al. | 514/19 |
| 2005/0222119 A1* | 10/2005 | Thorsett et al. | 514/210.01 |
| 2005/0272668 A1* | 12/2005 | Yednock et al. | 514/19 |

FOREIGN PATENT DOCUMENTS

| | | |
|---|---|---|
| WO | 98/53814 | 12/1998 |
| WO | 98/53817 | 12/1998 |
| WO | WO 99/06431 A1 | 2/1999 |
| WO | WO 99/06437 A1 | 2/1999 |
| WO | 00/44408 | 8/2000 |
| WO | 01/54690 | 8/2001 |
| WO | 02/02556 | 1/2002 |

OTHER PUBLICATIONS

International Search Report dated Oct. 18, 2005 (2 pp.).
PCT Written Opinion of the International Search Authority dated Oct. 18, 2005 (3 pp.).
N. Tubridy et al., "The Effect of Anti-[Alpha]4 Integrin Antibody on Brain Lesion Activity in MS", Neurology, Vol. 53, No. 3, pp. 466-472, Aug. 1999.
Franz X. Weilbach et al., "Disease Modifying Treatments for Multiple Sclerosis. What is on the Horizon?", CNS Drugs, vol. 11, No. 2, pp. 133-157, Feb. 1999.
W. A. Sheremata et al., "A Safety and Pharmacokinetic Study of Intravenous Natalizumab in Patients with MS", Neurology, vol. 52, No. 5, pp. 1072-1074, Mar. 1999.
Syed A. Rizvi et al, "Other Therapy Options and Future Strategies for Treating Patients with Multiple Sclerosis", Neurology, vol. 63, (Suppl 6), pp. S47-S54, Dec. 2004.
Lin et al., "Specific and Dual Antagonists of $\alpha_4\beta_7$ Integrins", Bioorganic and Medicinal Chemistry Letters, vol. 12, No. 2, Jan. 2002, pp. 133-136.

\* cited by examiner

*Primary Examiner*—Raymond J Henley, III
(74) *Attorney, Agent, or Firm*—Crowell & Moring LLP

(57) ABSTRACT

The application provides for methods and compositions for inhibiting demyelination, promoting remyelination and/or treating paralysis in a subject in need thereof. Preferably, such compositions include immunoglobulins (e.g., antibodies, antibody fragments, and recombinantly produced antibodies or fragments), polypeptides (e.g., soluble forms of the ligand proteins for integrins) and small molecules, which when administered in an effective amount inhibits demyelination and/or promotes remyelination in a patient. The compositions and methods described herein can also utilize other anti-inflammatory agents used to palliate conditions and diseases associated with demyelination.

26 Claims, 25 Drawing Sheets

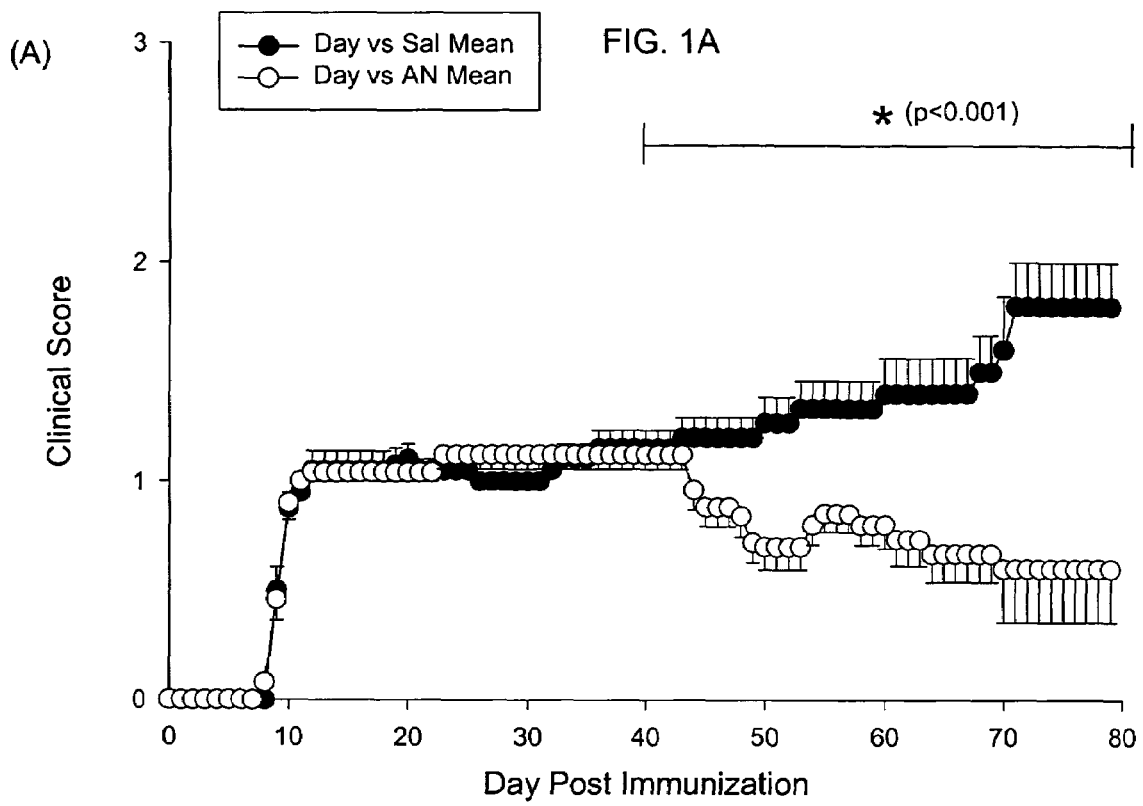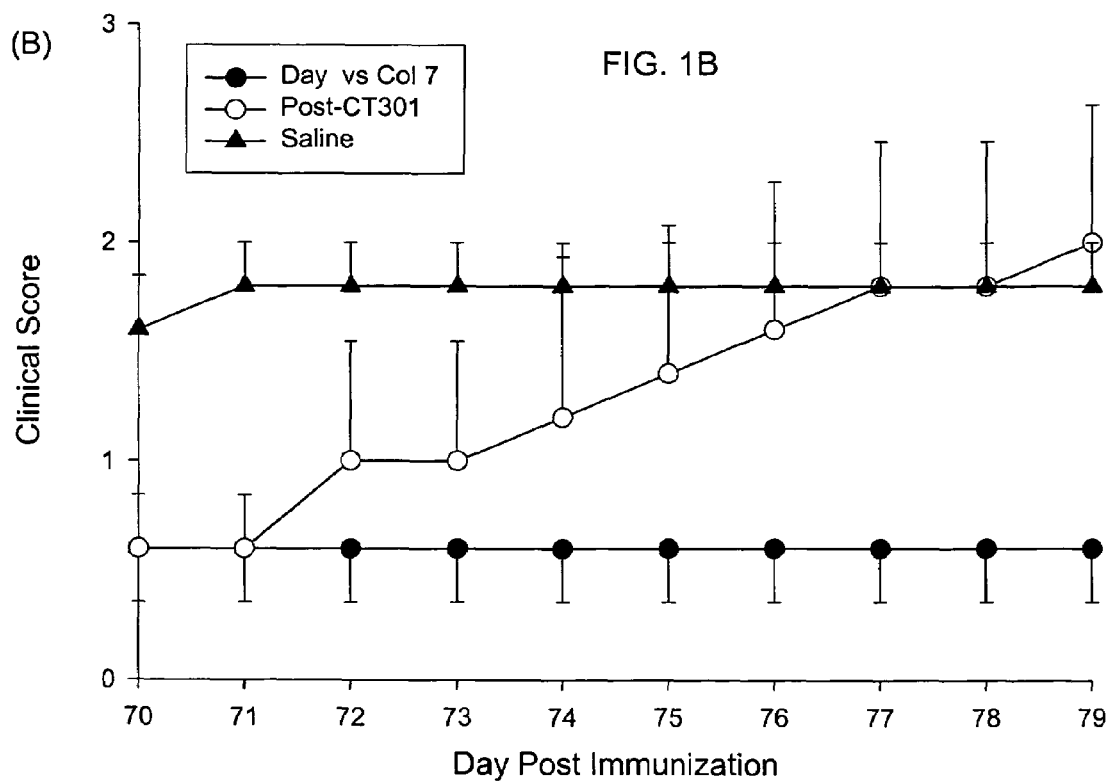

Figure 2A:
Figure 2B:
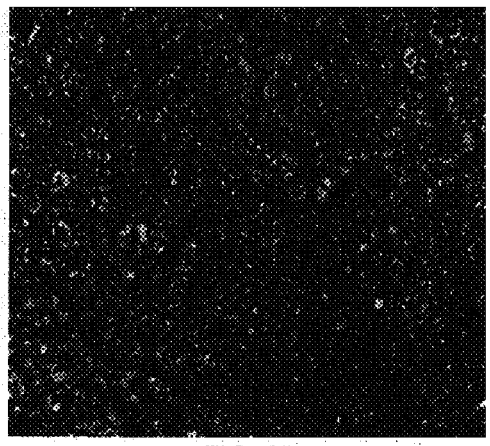

CT301
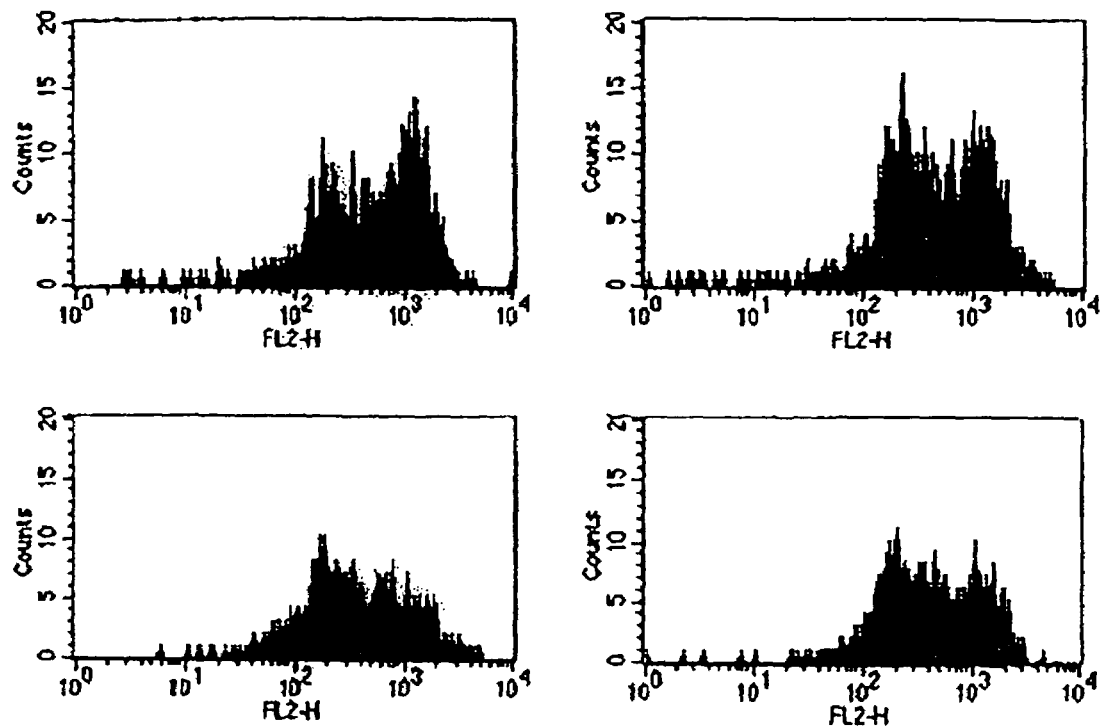
Saline
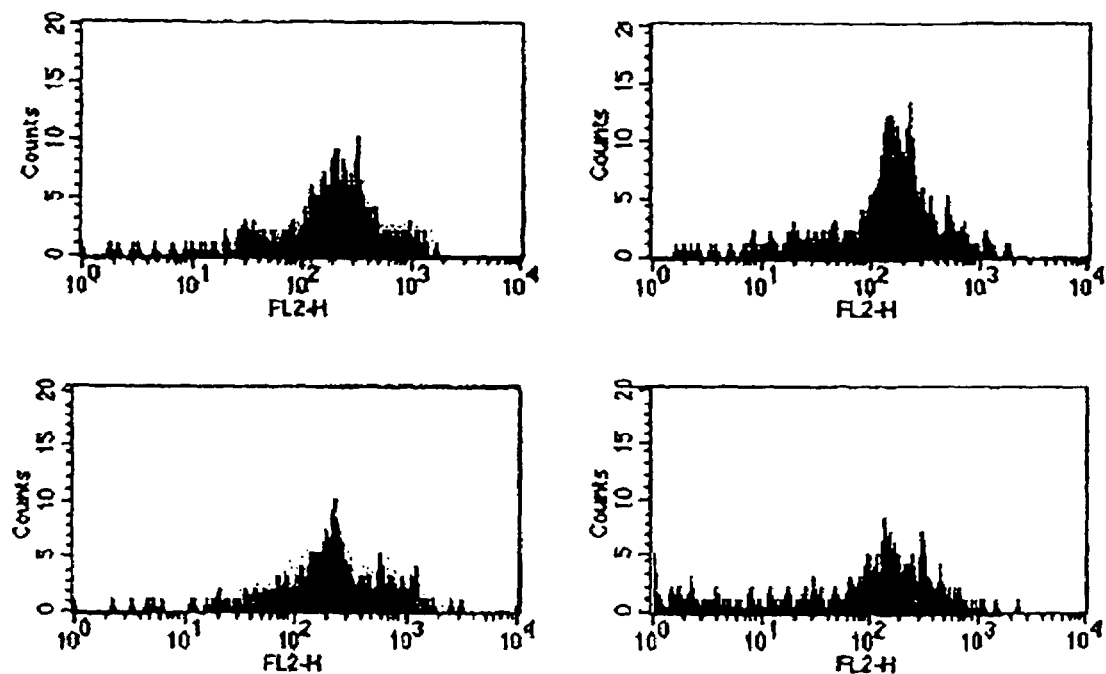
FIG. 6

```
    atgagggcccctgctcagattttcggattcttggtcaggagacgttgt
 1  ------------------------------------------------
    tactcccggggacgagtctaaaaacctaagaaccagtcctctgcaaca agaaatgagaccgtctattcagttcctggggctcttgttgttctggcttcatgg
49  ------------------------------------------------------
    tctttactctggcagataagtcaaggaccccgagaacaacaagaccgaagtacc

[M  R  P  S  I  Q  F  L  G  L  L  L  F  W  L  H  G
                              LEADER tgctcagtgtgacatccagatgacacagtctccatcctcactgtctgcatctct
103 ------------------------------------------------------
    acgagtcacactgtaggtctactgtgtcagaggtaggagtgacagacgtagaga A  Q  C] [D  I  Q  M  T  Q  S  P  S  S  L  S  A  S  L
                                                    FR1 gggaggcaaagtcaccatcacttgcaagacaagccaagacattaacaagtatat
157 ------------------------------------------------------
    ccctccgtttcagtggtagtgaacgttctgttcggttctgtaattgttcatata G  G  K  V  T  I  T  C] [K  T  S  Q  D  I  N  K  Y  M
                                            CDR1 ggcttggtaccaacacaagcctggaaaacgtcctaggctgctcatacattacac
211 ------------------------------------------------------
    ccgaaccatggttgtgttcggacctttcgcaggatccgacgagtatgtaatgtg A] [W  Y  Q  H  K  P  G  K  R  P  R  L  L  I  H] [Y  T
                       FR2 atctgcattacagccaggcatcccatcaaggttcagtggaagtgggtctgggag
265 ------------------------------------------------------
    tagacgtaatgtcggtccgtagggtagttccaagtcaccttcacccagaccctc

S  A  L  Q  P] [G  I  P  S  R  F  S  G  S  G  S  G  R
    CDR2
```

FIG. 11 A

```
     agattattccttcaacatcagcaacctggagcctgaagatattgcaacttatta
319  ------------------------------------------------------
     tctaataaggaagttgtagtcgttggacctcggacttctataacgttgataat

D  Y  S  F  N  I  S  N  L  E  P  E  D  I  A  T  Y  Y
           FR3 ttgtctacagtatgataatctgtggacgttcggtggaggcaccaagctggaaat
373  ------------------------------------------------------
     aacagatgtcatactattagacacctgcaagccacctccgtggttcgacctttα

C] [L  Q  Y  D  N  L  W  T] [F  G  G  G  T  K  L  E  I
            CDR3                                FR4 caaacgggctgatgctgcaccaactgtatccatcttcccaccatccacccggga
427  ------------------------------------------------------
     gtttgcccgactacgacgtggttgacataggtagaagggtggtaggtgggccct

K]

AGG-5'
     tcc
481  ---
     agg
```

FIG. 11B

```
    atgaaatgcagctgggtcatgttcttcctgatggcagtggttacaggg
1   ------------------------------------------------
    tactttacgtcgacccagtacaagaaggactaccgtcaccaatgtccc

[M  K  C  S  W  V  M  F  F  L  M  A  V  V  T  G
                           LEADER gtcaattcagaggttcagctgcagcagtctggggcagagcttgtgaagccaggg
49  -----------------------------------------------------
    cagttaagtctccaagtcgacgtcgtcagacccgtctcgaacacttcggtccc V  N  S] [E  V  Q  L  Q  Q  S  G  A  E  L  V  K  P  G
                                                     FR1 gcctcagtcaagttgtcctgcacagcttctggcttcaacattaaagacacctat
103  -----------------------------------------------------
     cggagtcagttcaacaggacgtgtcgaagaccgaagttgtaatttctgtggata A  S  V  K  L  S  C  T  A  S  G  F  N  I  K] [D  T  Y
                                                       CDR1 atacactgtgtgaagcagaggcctgaacagggcctggagtggattggaaggatt
157  -----------------------------------------------------
     tatgtgacacacttcgtctccggacttgtcccggacctcacctaaccttcctaa I  H] [C  V  K  Q  R  P  E  Q  G  L  E  W  I  G] [R  I
                                       FR2 gatcctgcgaatggttatactaaatatgacccgaagttccagggcaaggccact
211  -----------------------------------------------------
     ctaggacgcttaccaatatgatttatactgggcttcaaggtcccgttccggtga D  P  A  N  G  Y  T  K  Y  D  P  K  F  Q  G] [K  A  T
                        CDR2 ataacagctgacacatcctccaacacagcctacctgcagctcagcagcctgaca
265  -----------------------------------------------------
     tattgtcgactgtgtaggaggttgtgtcggatggacgtcgagtcgtcggactgt I  T  A  D  T  S  S  N  T  A  Y  L  Q  L  S  S  L  T
                                                       FR3
```

FIG. 12A

```
      tctgaggacactgccgtctatttctgtgctagagagggatattatggtaactac
319   ------------------------------------------------------
      agactcctgtgacggcagataaagacacgatctctccctataataccattgatg S  E  D  T  A  V  Y  F  C  A  R] [E  G  Y  Y  G  N  Y
                                                        CDR3 ggggtctatgctatggactactggggtcaaggaacctcagtcaccgtctcctca
373   ------------------------------------------------------
      ccccagatacgatacctgatgaccccagttccttggagtcagtggcagaggagt

G  V  Y  A  M  D  Y] [W  G  Q  C  T  S  V  T  V  S  S]

gccaaaacgacacccccatctgtctatccactggcccgggatcc
427   --------------------------------------------
      cggttttgctgtgggggtagacagataggtgacccgggccctagg

S  S]
```

FIG. 12B

```
            FR1                    CDR1           FR2              CDR2
        1            2              3              4                5
     12345678901234567890123  45678901234  567890123456789  0123456
            *                  ********            *        ***
21.6 DIQMTQSPSSLSASLGGKVTITC  KTSQDINKYMA  WYQHKPGKRPRLLIH  YTSALQP

REI  DIQMTQSPSSLSASVGDRVTITC  QASQDIIKYLN  WYQQTPGKAPKLLIY  EASNLQA

La   DIQMTQSPSSLSASVGDRVTITC  KTSQDINKYMA  WYQQTPGKAPRLLIH  YTSALQP

Lb   ----------------------   -----------  ---------R----   -------

FR3                        CDR3        FR4
         6          7            8            9           10
     789012345678901234567890123456789012345678  901234567  8901234567
            *          *                          *******
21.6 GIPSRFSGSGSGRDYSFNISNLEPEDIATYYC            LQYDNL-WT  FGGGTKLEIK

REI  GVPSRFSGSGSGTDYTFTISSLQPEDIATYYC            QQYQSLPYT  FGQGTKLQIT

La   GIPSRFSGSGSGRDYTFTISSLQPEDIATYYC            LQYDNL-WT  FGQGTKVEIK

Lb   -I----------R-------------------            ---------  ------VE-K
```

FIG. 13

```
              FR1                     CDR1     FR2           CDR2
       1           2           3      4        5             6
       12345678901234567890123456789012345 67890123456789 012A3456789012345
                                   *****  ** *                ****
21.6   EVQLQQSGAELVKPGASVKLSCTASGFNIK     DTYIH  CVKQRPEQGLEWIG RIDPANGYTKYDPKFQG

2*CL   QVQLVQSGAEVKKPGASVKVSCKASGYTFT     SYAMH  WVRQAPGQRLEWMG WINAGNGNTKYSQKFQG

Ha     QVQLVQSGAEVKKPGASVKVSCKASGFNIK     DTYIH  WVRQAPGQRLEWMB RIDPANGYTKYDPKFQG

Hb     ----------------------FNIK         -----  --------G----- -----------------

Hc     ----------------------FNIK         -----  -------------- -----------------

FR3                CDR3           FR4
       7           8           9      10             11
       6789012345678901 2ABC345678901234 567890ABCDEF12 34567890123
                *                              *
21.6   KATITADTSSNTAYLQLSSLTSEDTAVYFCAR   EGYYGNYGVYAMDY WGQGTSVTVSS

2*CL   RVTITRDTSASTAYMELSSLRSEDTAVYYCAR   GGYYGSGS----NY WGQGTLVTVSS

Ha     RVTITADTSASTAYMELSSLRSEDTAVYYCAR   EGYYGNYGVYAMDY WGQGTLVTVSS

Hb     -----A--------------------------   -------------- -----------

Hc     -----A--------------------------   ---F---------- -----------
```

FIG. 14

HindIII KOZAK SEQUENCE
```
      aagcttgccgccaccatgagaccgtctattcagttcctggggctcttgttgttc
    1 ------------------------------------------------------
      ttcgaacggcggtggtactctggcagataagtcaaggaccccgagaacaacaag

[M  R  P  S  I  Q  F  L  G  L  L  F
                                         LEADER tggcttcatggtgctcagtgtgacatccagatgacacagtctccatcctcactg
   55 ------------------------------------------------------
      accgaagtaccacgagtcacactgtaggtctactgtgtcagaggtaggagtgac W  L  H  G  A  Q  C][D  I  Q  M  T  Q  S  P  S  S  L
                                                           FR1 tctgcatctGTAggaGATAGAgtcaccatcacttgcaagacaagccaagacatt
  109 ------------------------------------------------------
      agacgtagaCATcctCTATCTcagtggtagtgaacgttctgttcggttctgtaa S  A  S  V  G  D  R  V  T  I  T  C][K  T  S  Q  D  I
                                                           CDR1 aacaagtatatggcttggtaccaaCAGACAcctggaaaaGCTcctaggctgctc
  163 ------------------------------------------------------
      ttgttcatataccgaaccatggttGTCTGTggaccttttCGAggatccgacgag N  K  Y  M  A][W  Y  Q  Q  T  P  G  K  A  P  R  L  L
                                         FR2 atacattacacatctgcattacagccaggcatcccatcaaggttcagtggaagt
  217 ------------------------------------------------------
      tatgtaatgtgtagacgtaatgtcggtccgtagggtagttccaagtcaccttca I  H][Y  T  S  A  L  Q  P][G  I  P  S  R  F  S  G  S
                        CDR2 gggtctgggagagattatACTttcACCatcagcAGCctgCAGcctgaagatatt
  271 ------------------------------------------------------
      cccagaccctctctaataTGAaagTGGtagtcgTCGgacGTCggacttctataa G  S  F  R  D  Y  T  F  T  I  S  S  L  Q  P  E  D  I
                     FR3
```

FIG. 15A

```
        gcaacttattattgtctacagtatgataatctgtggacgttcggtCAAggcacc
325     ------------------------------------------------------
        cgttgaataataacagatgtcatactattagacacctgcaagccaGTTccgtgg A  T  Y  Y  C] [L  Q  Y  D  N  L  W  T] [F  G  Q  G  T
                                 CDR3                        FR4

SPLICE DONOR SITE  BamHI
        aagGTGgaaatcaaacgtgagtggatcc
379     ----------------------------
        ttcCACctttagtttgcactcacctagg

K  V  E  I  K]
```

FIG. 15B

```
        HindIII KOZAK SEQUENCE
        AAGCTTGCCGCCACCATGGACTGGACCTGGCGCGTGTTTTGCCTGCTCGCCGTG
    1   ----------------------------------------------------
        TTCGAACGGCGGTGGTACCTGACCTGGACCGCGCACAAAACGGACGAGCGGCAC

[M  D  W  T  W  R  V  F  C  L  L  A  V
                                                       LEADER

GCTCCTGGGGCCCACAGCCAGGTGCAACTAGTGCAGTCCGGCGCCGAAGTGAAG
   55   ----------------------------------------------------
        CGAGGACCCCGGGTGTCGGTCCACGTTGATCACGTCAGGCCGCGGCTTCACTTC

A  P  G  A  H  S][Q  V  Q  L  V  Q  S  G  A  E  V  K

AAACCCGGTGCTTCCGTGAAAGTCAGCTGTAAAGCTAGCGGTtttcaacattaaa
  109   -----------------------------------------------------
        TTTGGGCCACGAAGGCACTTTCAGTCGACATTTCGATCGCCAaagttgtaattt

K  P  G  A  S  V  K  V  S  C  K  A  S  G  F  N  I  K][
                  FR1 gacacctatatacacTGGGTTAGACAGGCCCCtGGCCAAaGGCTgGAGTGGATg
  163   -----------------------------------------------------
        ctgtggatatatgtgACCCAATCTGTCCGGgGaCCGGTTtCCGAcCTCACCTAc D  T  Y  I  H][W  V  R  Q  A  P  G  Q  R  L  E  W  M
            CDR1                    FR2
```

FIG. 16A

```
       GGaaggattgatcctgcgaatggttatactaaatatgacccgaagttccagggc
217    ------------------------------------------------------
       CCttcctaactaggacgcttaccaatatgatttatactgggcttcaaggtcccg G] [R  I  D  P  A  N  G  Y  T  K  Y  D  P  K  F  Q  G] [
                                 CDR2 cgggtcACCatcACCgcaGACACCTCTgccagcACCGCCTACATGGAACTGTCC
271    ------------------------------------------------------
       gcccagTGGtagTGGcgtCTGTGGAGAcggtcgTGGCGGATGTACCTTGACAGG R  V  T  I  T  A  D  T  S  A  S  T  A  Y  M  E  L  S
                                                          FR3

AGCCTGCGCTCCGAGGACACTGCAGTCTACTACTGCGCCagagagggatattat
325    ------------------------------------------------------
       TCGGACGCGAGGCTCCTGTGACGTCAGATGATGACGCGGtctctccctataata

S  L  R  S  E  D  T  A  V  Y  Y  C  A  R] [E  G  Y  Y ggtaactacggggtctatgctatgGACTAcTGGGGtCAaGGaACCCTTGTCACC
379    ------------------------------------------------------
       ccattgatgcccagatacgatacCTGATgACCCCaGTtCCtTGGGAACAGTGG G  N  Y  G  V  Y  A  M  D  Y] [W  G  Q  G  T  L  V  T
           CDR3                                           FR4

SPLICE DONOR SITE BamHI
       GTCtccTCAGGTGAGTGGATCC
433    ----------------------
       CAGaggAGTCCACTCACCTAGG

V  S  S]
```

FIG. 16B (i) SEQUENCE CHARACTERISTICS:
    (A) LENGTH: 109 amino acids
    (B) TYPE: amino acid
    (C) STRANDEDNESS: single
    (D) TOPOLOGY: linear
(ii) MOLECULE TYPE: protein

```
N - Asp Ile Gln Met Thr Gln Ser Pro Ser Ser Leu Ser Ala Ser Leu Gly
    Asp Arg Val Thr Ile Thr Cys Arg Ala Ser Gln Asp Asp Ile Ser Asn
    Tyr Leu Asn Trp Tyr Gln Gln Lys Pro Gly Gly Ser Pro Lys Leu Leu
    Ile Tyr Tyr Ala Ser Arg Leu His Ser Gly Val Pro Ser Arg Phe Ser
    Gly Ser Gly Ser Gly Thr Asp Tyr Ser Leu Thr Ile Ser Asn Leu Glu
    Gln Glu Asp Ile Ala Thr Tyr Phe Cys Gln Gln Gly Asn Thr Leu Pro
    Pro Arg Thr Phe Gly Gly Gly Thr Lys Leu Glu Ile Lys - C
```

FIG. 17A (i) SEQUENCE CHARACTERISTICS:
    (A) LENGTH: 114 amino acids
    (B) TYPE: amino acid
    (C) STRANDEDNESS: single
    (D) TOPOLOGY: linear
(ii) MOLECULE TYPE: protein N - Asp Ile Gln Met Thr Gln Ser Pro Ser Ser Leu Ser Ala Ser Val Gly
    Asp Arg Val Thr Ile Thr Cys Arg Ala Ser Gln Asp Ser Leu Val Xaa
    Xaa Ser Ile Ser Asn Tyr Leu Asn Trp Tyr Gln Gln Lys Pro Gly Lys
    Ala Pro Lys Leu Leu Ile Tyr Ala Ala Ser Ser Leu Glu Ser Gly Val
    Pro Ser Arg Phe Ser Gly Ser Gly Ser Gly Thr Asp Phe Thr Leu Thr
    Ile Ser Ser Leu Gln Pro Glu Asp Phe Ala Thr Tyr Tyr Cys Gln Gln
    Tyr Asn Ser Leu Pro Glu Trp Thr Phe Gly Gln Gly Thr Lys Val Glu
    Ile Lys - C

FIG. 17B (i) SEQUENCE CHARACTERISTICS:
            (A) LENGTH: 125 amino acids
            (B) TYPE: amino acid
            (C) STRANDEDNESS: single
            (D) TOPOLOGY: linear
      (ii) MOLECULE TYPE: protein N - Glu Val Gln Leu Gln Gln Ser Gly Ala Glu Leu Val Lys Pro Gly Ala
    Ser Val Lys Leu Ser Cys Thr Ala Ser Gly Phe Asn Ile Lys Asp Thr
    Tyr Met His Trp Val Lys Gln Arg Pro Glu Gln Gly Leu Glu Trp Ile
    Gly Arg Ile Asp Pro Ala Asn Gly Asn Thr Lys Tyr Asp Pro Lys Phe
    Gln Gly Lys Ala Thr Ile Thr Ala Asp Thr Ser Ser Asn Thr Ala Tyr
    Leu Gln Leu Ser Ser Leu Thr Ser Glu Asp Thr Ala Val Tyr Tyr Cys
    Ala Arg Gly Tyr Tyr Tyr Asp Ser Xaa Val Gly Tyr Tyr Ala Met
    Asp Tyr Trp Gly Gln Gly Thr Xaa Val Thr Val Ser Ser - C

FIG. 18A (i) SEQUENCE CHARACTERISTICS:
        (A) LENGTH: 129 amino acids
        (B) TYPE: amino acid
        (C) STRANDEDNESS: single
        (D) TOPOLOGY: linear
    (ii) MOLECULE TYPE: protein N - Gln Val Gln Leu Val Gln Ser Gly Ala Glu Val Lys Lys Pro Gly Ala
    Ser Val Lys Val Ser Cys Lys Ala Ser Gly Tyr Thr Phe Thr Ser Tyr
    Ala Ile Ser Trp Val Arg Gln Ala Pro Gly Gln Gly Leu Glu Trp Met
    Gly Trp Ile Asn Pro Tyr Gly Asn Gly Asp Thr Asn Tyr Ala Gln Lys
    Phe Gln Gly Arg Val Thr Ile Thr Ala Asp Thr Ser Thr Ser Thr Ala
    Tyr Met Glu Leu Ser Ser Leu Arg Ser Glu Asp Thr Ala Val Tyr Tyr
    Cys Ala Arg Ala Pro Gly Tyr Gly Ser Gly Gly Cys Tyr Arg Gly Asp
    Tyr Xaa Phe Asp Tyr Trp Gly Gln Gly Thr Leu Val Thr Val Ser Ser - C

FIG. 18B

COMPOSITION FOR AND TREATMENT OF DEMYELINATING DISEASES AND PARALYSIS BY ADMINISTRATION OF REMYELINATING AGENTS

This application claims the benefit of U.S. Patent Application No. 60/442,171 filed on Jan. 24, 2003, and U.S. Patent Application No. 60/500,316, filed on Sep. 5, 2003, the entire contents of which are incorporated by reference herein.

FIELD OF THE INVENTION

This invention relates generally to compositions, compounds that can be used to treat demyelinating diseases and conditions and/or reduce paralysis in a patient.

BACKGROUND OF THE INVENTION

Inflammation is a response of vascularized tissues to infection or injury and is affected by adhesion of leukocytes to the endothelial cells of blood vessels and their infiltration into the surrounding tissues. In normal inflammation, the infiltrating leukocytes release toxic mediators to kill invading organisms, phagocytize debris and dead cells, and play a role in tissue repair and the immune response. However, in pathologic inflammation, infiltrating leukocytes are over-responsive and can cause serious or fatal damage. See, e.g., Hickey, *Psychoneuroimmunology II* (Academic Press 1990).

The integrins are a family of cell-surface glycoproteins involved in cell-adhesion, immune cell migration and activation. Alpha-4 integrin is expressed by all circulating leukocytes except neutrophils, and forms heterodimeric receptors in conjunction with either the beta-1 ($\beta_1$) or beta-7 ($\beta_7$) integrin subunits; both alpha-4 beta-1 ($\alpha_4\beta_1$) and alpha-4 beta-7 ($\alpha_4\beta_7$) play a role in migration of leukocytes across the vascular endothelium (Springer et al., *Cell* 1994, 76: 301-14; Butcher et al., *Science* 1996, 272: 60-6) and contribute to cell activation and survival within the parenchyma (Damle et al., *J. Immunol.* 1993; 151: 2368-79; Koopman et al., *J. Immunol.* 1994, 152: 3760-7; Leussink et al., *Acta Neuropathol.* 2002, 103: 131-136). $\alpha_4\beta_1$ is constitutively expressed on lymphocytes, monocytes, macrophages, mast cells, basophils and eosinophils.

Alpha-4 beta-1 (also known as very late antigen-4, VLA-4), binds to vascular cell adhesion molecule-1 (Lobb et al., *J. Clin. Invest.* 1994, 94: 1722-8), which is expressed by the vascular endothelium at many sites of chronic inflammation (Bevilacqua et al., 1993 *Annu. Rev. Immunol.* 11: 767-804; Postigo et al., 1993 *Res. Immunol.* 144: 723-35). $\alpha_4\beta_1$ has other ligands, including fibronectin and other extracellular matrix (ECM) components.

The alpha-4 beta-7 dimer interacts with mucosal addressin cell adhesion molecule (MAdCAM-1), and mediates homing of lymphocytes to the gut (Farstad et al., 1997 *Am. J. Pathol.* 150: 187-99; Issekutz, 1991 *J. Immunol.* 147: 4178-84). Expression of MAdCAM-1 on the vascular endothelium is also increased at sites of inflammation in the intestinal tract of patients with inflammatory bowel disease (IBD) (Briskin et al., 1997 *Am. J. Pathol.* 151: 97-110).

Adhesion molecules such as alpha-4 integrins are potential targets for therapeutic agents. For instance, the VLA-4 receptor of which alpha-4 integrin is a subunit is an important target because of its interaction with a ligand residing on brain endothelial cells. Diseases and conditions resulting from brain inflammation have particularly severe consequences. In another example, the alpha-4 beta-7 integrin dimer is an important target due to its involvement in lymphocyte homing and pathological inflammation in the gastrointestinal tract.

Alpha-4 beta-1 integrin is expressed on the extracellular surface of activated lymphocytes and monocytes, which have been implicated in the pathogenesis of acute inflammatory brain lesions and blood brain barrier (BBB) breakdown associated with multiple sclerosis (MS) (Coles et al., 1999 *Ann. Neurol.* 46(3): 296-304). Agents against alpha-4 integrin have been tested for their anti-inflammatory potential both in vitro and in vivo. See Yednock et al., *Nature* 1992, 356: 63-66; U.S. Pat. No. 5,840,299 to Bendig et al., issued Nov. 24, 1998, and U.S. Pat. No. 6,001,809 to Thorsett et al., issued Dec. 14, 1999. The in vitro experiments demonstrate that alpha-4 integrin antibodies block attachment of lymphocytes to brain endothelial cells. Experiments testing the effect of alpha-4 integrin antibodies on animals having the artificially induced condition simulating multiple sclerosis, experimental autoimmune encephalomyelitis (EAE), have demonstrated that administration of anti-alpha-4 integrin antibodies prevents inflammation of the brain and subsequent paralysis in the animals. Collectively, these experiments identify anti-alpha-4 integrin antibodies as potentially useful therapeutic agents for treating multiple sclerosis and other inflammatory diseases and disorders.

To date, no therapies have been discovered which inhibit or prevent demyelination let alone agents that promote remyelination. For example, multiple sclerosis impacts human health and costs for maintaining health more than any other demyelinating disease. No effective treatment exists for MS. It is a disease that afflicts primarily young adults (i.e., mean age of 30) with an incidence of 1 case per 1,000 individuals. Experimental autoimmune encephalomyelitis is the major animal model used for studying MS. However, unlike with EAE, MS is an autoimmune disease with an unknown cause. Disease progression is characterized by an influx of immune cells into the central nerve system that eventually results in edema, demyelination, axonal damage and loss.

New compounds, compositions and methods for using these compounds and compositions to inhibit demyelination, to promote remyelination and/or treat paralysis associated with demyelination are needed and continue to be sought out for the treatment of diseases such as MS, as well as other demyelinating diseases linked with inflammation.

SUMMARY OF THE INVENTION

Based on the above, new compositions and methods of treating these diseases are needed which will effectively treat or inhibit these diseases such that patients can achieve long life spans and better quality of life.

The invention relates to methods of promoting remyelination of nerve cells in a mammal comprising administering to the mammal a remyelination agent in a remyelinating effective amount. Preferably, the mammal in the methods of the present invention is a human, and the human suffers from a condition that demyelinates cells.

Conditions which demyelinate cells according to the invention include multiple sclerosis, congenital metabolic disorder, a neuropathy with abnormal myelination, drug induced demyelination, radiation induced demyelination, a hereditary demyelinating condition, a prion induced demyelinating condition, encephalitis induced demyelination, or a spinal cord injury. Preferably the condition is multiple sclerosis.

The invention further relates to a composition comprising a therapeutically effective amount of a remyelinating agent, which prevents demyelination and/or promotes remyelination when administered to a subject in need thereof.

In the methods and compositions of the invention, the remyelinating agent may be an antibody, an immunologically active fragment of an antibody, a compound, or combinations thereof. The antibody or immunologically active fragment thereof is preferably natalizumab (ANTEGREN®) or an immunologically active fragment thereof.

In the methods and compositions of the invention, the remyelinating agent may be a small compound of formula I, IA, IB, IC, II, IIA, or IIB. The compounds are preferably compounds of the following formula IB

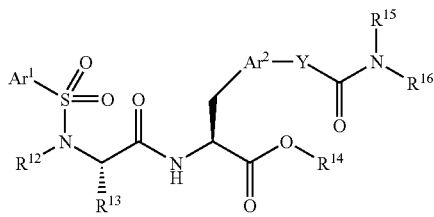

wherein:

Ar$^1$ is selected from the group consisting of aryl, substituted aryl, heteroaryl, and substituted heteroaryl;

Ar$^2$ is selected from the group consisting of aryl, substituted aryl, heteroaryl and substituted heteroaryl;

R$^{12}$ is selected from the group consisting of alkyl, substituted alkyl, cycloalkyl, and substituted cycloalkyl or R$^{12}$ and R$^{13}$ together with the nitrogen atom bound to R$^{12}$ and the carbon atom bound to R$^{13}$ form a heterocyclic or substituted heterocyclic group;

R$^{13}$ is selected from the group consisting of hydrogen, alkyl, and substituted alkyl, or R$^{12}$ and R$^{13}$ together with the nitrogen atom bound to R$^{12}$ and the carbon atom bound to R$^{13}$ form a heterocyclic or substituted heterocyclic group;

R$^{14}$ is selected from the group consisting of hydrogen, alkyl, substituted alkyl, cycloalkyl, substituted cycloalkyl, aryl, and substituted aryl;

R$^{15}$ is selected from the group consisting of alkyl, and substituted alkyl, or R$^{15}$ and R$^{16}$ together with the nitrogen atom to which they are bound form a heterocyclic or substituted heterocyclic group;

R$^{16}$ is selected from the group consisting of alkyl and substituted alkyl or R$^{15}$ and R$^{16}$ together with the nitrogen atom to which they are bound form a heterocyclic or substituted heterocyclic group; and Y is selected from the group consisting of —O—, —NR$^{100}$—, and —CH$_2$— wherein R$^{100}$ is hydrogen or alkyl;

and pharmaceutically acceptable salts thereof.

In a further embodiment, the compounds are preferably compounds of the following formula IC

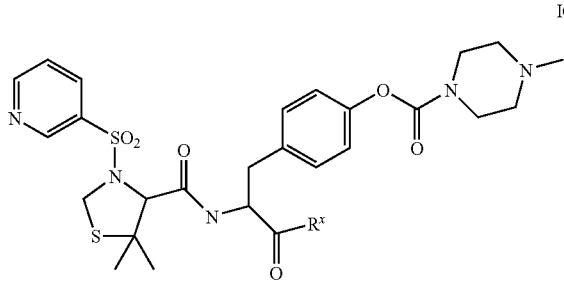

wherein R$_x$ is hydroxy or C$_{1-5}$ alkoxy and pharmaceutically acceptable salts thereof. Preferably, the compound is N-[N-(3-pyridinesulfonyl)-L-3,3-dimethyl-4-thiaprolyl]-O-[1-methylpiperazin-4-ylcarbonyl]-L-tyrosine isopropyl ester.

In another embodiment, the compounds are preferably compounds of the following formula IIB

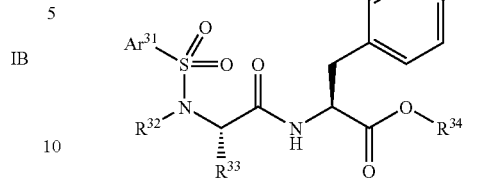

wherein:

Ar$^{31}$ is selected from the group consisting of aryl, substituted aryl, heteroaryl, and substituted heteroaryl;

R$^{32}$ is selected from the group consisting of alkyl, substituted alkyl, cycloalkyl, and substituted cycloalkyl or R$^{32}$ and R$^{33}$ together with the nitrogen atom bound to R$^{32}$ and the carbon atom bound to R$^{33}$ form a heterocyclic or substituted heterocyclic group;

R$^{33}$ is selected from the group consisting of hydrogen, alkyl, and substituted alkyl, or R$^{32}$ and R$^{33}$ together with the nitrogen atom bound to R$^{32}$ and the carbon atom bound to R$^{33}$ form a heterocyclic or substituted heterocyclic group;

R$^{34}$ is selected from the group consisting of hydrogen, alkyl, substituted alkyl, cycloalkyl, substituted cycloalkyl, aryl, and substituted aryl; and R$^{37}$ is aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy;

and pharmaceutically acceptable salts thereof.

In yet another embodiment, the compound is N-[N-(3-pyridinesulfonyl)-L-3,3-dimethyl-4-thiaprolyl]-O-[1-methylpiperazin-4-ylcarbonyl]-L-tyrosine isopropyl ester.

The invention also relates to a pharmaceutical composition comprising a therapeutically effective amount of a compound of formula I, IA, IB, IC, II, IIA, or IIB and pharmaceutically acceptable salts thereof. Preferably, the compound is a compound of the formula IB, IC, or IIB. In a preferred embodiment, the compound is N-[N-(3-pyridinesulfonyl)-L-3,3-dimethyl-4-thiaprolyl]-O-[1-methylpiperazin-4-ylcarbonyl]-L-tyrosine isopropyl ester.

The remyelinating agent of the invention can be administered alone or in combination with other remyelinating agents, anti-alpha-4-agents, or anti-inflammatory agents. The invention further relates to pharmaceutical compositions comprising a pharmaceutically acceptable carrier and a therapeutically effective amount of a remyelinating agent as disclosed herein. The pharmaceutical compositions of the present invention may further comprise one or more additional agents, including other remyelinating agents, anti-alpha-4-agents, or anti-inflammatory agents.

The compositions of the invention may be administered by a variety of modes of administration including oral, parenteral (e.g., subcutaneous, subdural, intravenous, intramuscular, intrathecal, intraperitoneal, intracerebral, intraarterial, or intralesional routes of administration), topical, localized (e.g., surgical application or surgical suppository), rectal, and pulmonary (e.g., aerosols, inhalation, or powder).

Another aspect of the invention provides for a combination therapy comprising a therapeutically effective amount of a reyelinating agent and a therapeutically effective amount of an anti-inflammatory agent. Anti-inflammatory agents include but are not limited to an adrenocorticotropic hormone (ACTH), a corticosteroid (e.g., prednisone, methylprednisolone, dexamethasone cortisol, cortisone, fludrocortisone, prednisolone, 6α-methylprednisolone, triamcinolone, and betamethasone), an interferon (e.g., interferon beta-1b and interferon beta-1a), COPAXONE®, or a nonsteroidal anti-inflammatory drug (e.g., aspirin, a sodium salicylate, choline magnesium trisalicylate, salsalate, diflunisal, sulfasalazine, olsalazine, a para-aminophenol derivatives, an indole, an indene acetic acid, a heteroaryl acetic acid, an anthranilic acid, an enolic acid, an alkanones, a diaryl-substituted furanone, a diaryl-substituted pyrazoles, an indole acetic acids, and a sulfonanilide). The remyelinating agent can be selected from any of the compounds of formula I, IA, IB, IC, II, IIA, or IIB. Alternatively, the remyelinating agent can be an antibody against VLA-4 or an immunologically active fragment thereof or a polypeptide which binds to VLA-4 thereby preventing it from binding to a cognate ligand.

The combination therapy can be used to treat a subject who suffers from multiple sclerosis, a congenital metabolic disorder, a neuropathy with abnormal myelination, drug induced demyelination, radiation induced demyelination, a hereditary demyelinating condition, a prion induced demyelinating condition, encephalitis induced demyelination, or a spinal cord injury.

Yet another aspect of the invention provides for a use of a compound of formula I, IA, IB, IC, II, IIA, or IIB for the preparation of a medicament for the treatment of a demyelinating disease in a subject in need thereof. Preferably, the compound is a compound of the formula IB, IC, or IIB. In a preferred embodiment, the compound is N-[N-(3-pyridinesulfonyl)-L-3,3-dimethyl-4-thiaprolyl]-O-[1-methylpiperazin-4-ylcarbonyl]-L-tyrosine isopropyl ester.

In another aspect of the invention, a method is provided for reversing paralysis in a subject with a demyelinating disease comprising administering to the subject a remyelinating agent in an amount sufficient to inhibit lymphocyte infiltration of immune cells in the spinal cord to promote remyelination of nerve cells in the spinal cord and thereby treating paralysis in said subject in need thereof. Another aspect of the invention provides for a use of a remyelinating agent for the preparation of a medicament for the treatment of a demyelinating disease in a subject in need thereof or for the treatment of paralysis in a subject with a demyelinating disease.

These and other objects, advantages, and features of the invention will become apparent to those persons skilled in the art upon reading the details of the methods and formulations as more fully described below.

BRIEF DESCRIPTIONS OF THE DRAWINGS

FIG. 1A. Prolonged reversal of chronic experimental autoimmune encephalomyelitis during N-[N-(3-pyridinesulfonyl)-L-3,3-dimethyl-4-thiaprolyl]-O-[1-methylpiperzain-4-ylcarbonyl]-L-tyrosine isopropyl ester treatment. EAE was induced in female Hartley guinea pigs via nuchal intradermal injection of 0.6 mL of a 1:1 mixture of homogenized isologous CNS tissue and complete Freund's adjuvant (CFA), with 10 mg/mL of inactivated *M. tuberculosis*. Beginning on day 40 post immunization, animals received either saline (n=20, 0.5 mL/day) or N-[N-(3-pyridinesulfonyl)-L-3,3-dimethyl-4-thiaprolyl]-O-[1-methylpiperzain-4-ylcarbonyl]-L-tyrosine isopropyl ester (n=25, 30 mg/kg, 2×/day) for 10, 20, 30 or 40 days. Over the course of the treatment period, the mean clinical score of animals treated with N-[N-(3-pyridinesulfonyl)-L-3,3-dimethyl-4-thiaprolyl]-O-[1-methylpiperzain-4-ylcarbonyl]-L-tyrosine isopropyl ester was significantly lower than that of the saline control group ($p<0.001$, Mann Whitney rank sum test). Furthermore, there were no adverse side effects observed during prolonged N-[N-(3-pyridinesulfonyl)-L-3,3-dimethyl-4-thiaprolyl]-O-[1-methylpiperzain-4-ylcarbonyl]-L-tyrosine isopropyl ester administration, and no escape from treatment as has been previously observed with antibodies.

FIG. 1B. Return to clinically active disease following removal of N-[N-(3-pyridinesulfonyl)-L-3,3-dimethyl-4-thiaprolyl]-O-[1-methylpiperzain-4-ylcarbonyl]-L-tyrosine isopropyl ester. After 30 days of treatment with N-[N-(3-pyridinesulfonyl)-L-3,3-dimethyl-4-thiaprolyl]-O-[1-methylpiperzain-4-ylcarbonyl]-L-tyrosine isopropyl ester, five animals were maintained for an additional 10 days withoutsmall molecule administration. Once N-[N-(3-pyridinesulfonyl)-L-3,3-dimethyl-4-thiaprolyl]-O-[1-methylpiperzain-4-ylcarbonyl]-L-tyrosine isopropyl ester was withdrawn, animals returned to clinical progression of disease. Between day 70 and day 80, the mean clinical score of post-N-[N-(3-pyridinesulfonyl)-L-3,3-dimethyl-4-thiaprolyl]-O-[1-methylpiperzain-4-ylcarbonyl]-L-tyrosine isopropyl ester animals was significantly higher than that of animals receiving N-[N-(3-pyridinesulfonyl)-L-3,3-dimethyl-4-thiaprolyl]-O-[1-methylpiperzain-4-ylcarbonyl]-L-tyrosine isopropyl ester throughout the treatment period ($p<0.05$, Mann Whitney rank sum test).

FIG. 2. Pathological recovery during prolonged N-[N-(3-pyridinesulfonyl)-L-3,3-dimethyl-4-thiaprolyl]-O-[1-methylpiperzain-4-ylcarbonyl]-L-tyrosine isopropyl ester treatment. Panels A, C, E, G, I and K were solochrome-R-cyanin (SCR) stained spinal cord sections (magnification 40×). Panels B, D, F, H, J and L show high magnification (250×) of hematoxylin-eosin (H-E) stained sections taken from the dorsal medial region of the corresponding SCR-stained photo. This section (2A) taken from a normal guinea pig shows neither inflammation nor demyelination, as does panel (2B), the corresponding H-E section. By day 40 post-immunization, an animal that had received no treatment showed extensive meningeal inflammation and a large dorso-medial plaque of demyelination (2C). The density of infiltrating cells in this area (2D) was much higher than in FIG. 2. Even later in disease, at day 60 post-immunization, a saline-treated animal showed a large subpial area of demyelination (2E), with a very high density of cellular infiltrates (2F). In contrast, an animal that received 20 days of N-[N-(3-pyridinesulfonyl)-L-3,3-dimethyl-4-thiaprolyl]-O-[1-methylpiperzain-4-ylcarbonyl]-L-tyrosine isopropyl ester treatment had a much smaller area of demyelination (2G), and a much lower density of cellular infiltration within the lesion area (2H). The animal represented in 2I received 40 days of saline treatment. Virtually the entire section was infiltrated and demyelinated, including invasion of some areas of gray matter. While the cellular infiltration in 2J was reduced from day 60 post-immunization (see 2F), it was still much higher than normal levels seen in 2B. After 40 days of N-[N-(3-pyridinesulfonyl)-L-3,3-dimethyl-4-thiaprolyl]-O-[1-methylpiperzain-4-ylcarbonyl]-L-tyrosine isopropyl ester treatment, however, there was almost no meningeal and perivascular inflammation, and the myelin was apparently intact (2K). The cellular infiltration (2L) was practically the same as in a normal animal (2B).

FIG. 3. Reduced pathological abnormality in chronic EAE during N-[N-(3-pyridinesulfonyl)-L-3,3-dimethyl-4-thiaprolyl]-O-[1-methylpiperzain-4-ylcarbonyl]-L-tyrosine isopropyl ester treatment. Animals received either saline (n=20) or N-[N-(3-pyridinesulfonyl)-L-3,3-dimethyl-4-thiaprolyl]-O-[1-methylpiperzain-4-ylcarbonyl]-L-tyrosine isopropyl ester (n=25) for 10, 20, 30 or 40 days. Additionally, a subgroup of animals received N-[N-(3-pyridinesulfonyl)-

L-3,3-dimethyl-4-thiaprolyl]-O-[1-methylpiperzain-4-ylcarbonyl]-L-tyrosine isopropyl ester for 30 days, and then treatment was withdrawn for the remaining 10 days of the experiment (Post-N-[N-(3-pyridinesulfonyl)-L-3,3-dimethyl-4-thiaprolyl]-O-[1-methylpiperzain-4-ylcarbonyl]-L-tyrosine isopropyl ester group). Following sacrifice, the brain and spinal cord were fixed in formalin and embedded in paraffin. Five μm sections were stained with hematoxylin-eosin (H-E) or solochrome-R-cyanin, and blindly assigned a 4-digit pathological score based on evaluation in each of four categories: (3A) meningeal inflammation, (3B) perivascular infiltration, (3C) encephalitis, and (3D) demyelination. Note that non-EAE animals would have a score of zero in all categories. Over the course of the treatment period, animals that received N-[N-(3-pyridinesulfonyl)-L-3,3-dimethyl-4-thiaprolyl]-O-[1-methylpiperzain-4-ylcarbonyl]-L-tyrosine isopropyl ester showed a significant decrease in the mean pathological score in each of the four categories with respect to saline-treated animals ($p<0.001$, 2-way ANOVA). When N-[N-(3-pyridinesulfonyl)-L-3,3-dimethyl-4-thiaprolyl]-O-[1-methylpiperzain-4-ylcarbonyl]-L-tyrosine isopropyl ester was removed and animals were maintained for an additional 10 days without treatment, the mean combined pathological score in all four categories returned to significantly higher than animals that continued to receive the small molecule ($p<0.05$, Kruskal Wallis ANOVA on ranks with SNK test).

Figure 4:
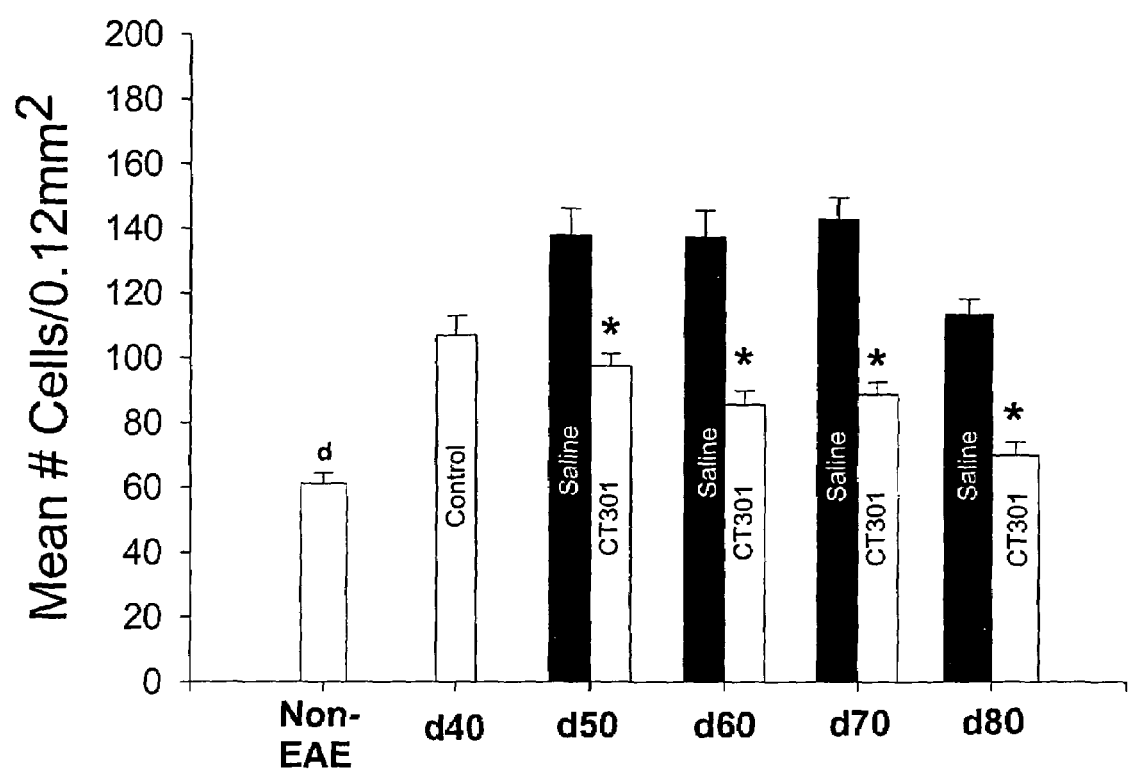

FIG. 4. Reduced spinal cord infiltration with N-[N-(3-pyridinesulfonyl)-L-3,3-dimethyl-4-thiaprolyl]-O-[1-methylpiperzain-4-ylcarbonyl]-L-tyrosine isopropyl ester treatment. The mean number of infiltrating cells was counted in representative areas from twelve pie-shaped areas covering the whole spinal cord (see methods). A significant increase in cellular infiltration occurred with the induction of EAE compared to non-EAE animals (δ, $p<0.05$; Kruskal Wallis ANOVA on ranks with SNKtest). N-[N-(3-pyridinesulfonyl)-L-3,3-dimethyl-4-thiaprolyl]-O-[1-methylpiperzain-4-ylcarbonyl]-L-tyrosine isopropyl ester-treated animals had fewer cells in the spinal cord than saline-treated animals following 10, 20, 30 or 40 days of therapy (*, $p<0.001$, two-way ANOVA). Furthermore, animals treated for 20, 30 or 40 days with N-[N-(3-pyridinesulfonyl)-L-3,3-dimethyl-4-thiaprolyl]-O-[1-methylpiperzain-4-ylcarbonyl]-L-tyrosine isopropyl ester had significantly lower cell counts than control (d40) EAE animals (#, $p<0.05$, Kruskal Wallis ANOVA, on ranks with SNK test). After removal of N-[N-(3-pyridinesulfonyl)-L-3,3-dimethyl-4-thiaprolyl]-O-[1-methylpiperzain-4-ylcarbonyl]-L-tyrosine isopropyl ester, the mean cell count in animals maintained for an additional 10 days without the small molecule was significantly increased compared to animals that received continuous N-[N-(3-pyridinesulfonyl)-L-3,3-dimethyl-4-thiaprolyl]-O-[1-methylpiperzain-4-ylcarbonyl]-L-tyrosine isopropyl ester treatment ($p<0.05$, Kruskal Wallis ANOVA on ranks with SNK test).

Figure 5:
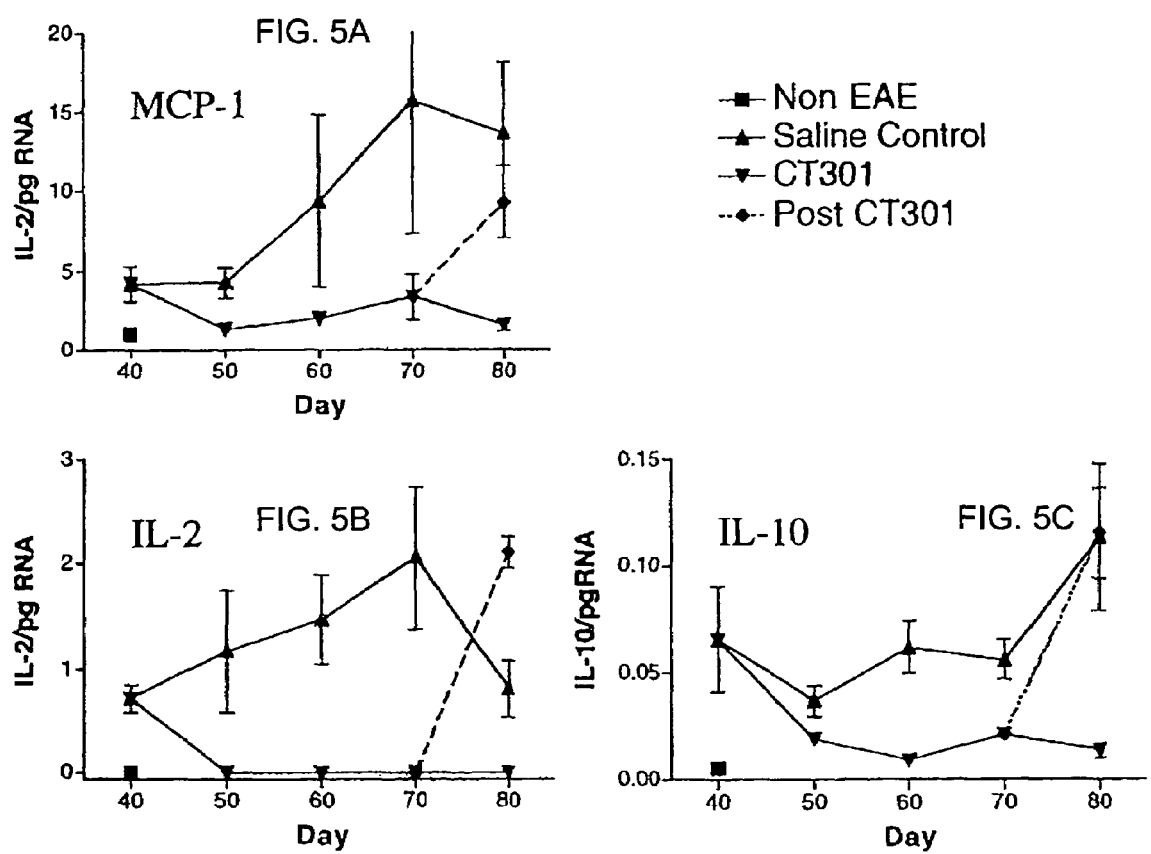

FIG. 5. Reduced expression of inflammatory cytokines with N-[N-(3-pyridinesulfonyl)-L-3,3-dimethyl-4-thiaprolyl]-O-[1-methylpiperzain-4-ylcarbonyl]-L-tyrosine isopropyl ester treatment. A piece of lumbar spinal cord was snap frozen in liquid nitrogen and routinely processed to extract RNA for quantitative PCR analysis. While negligible cytokine RNA levels were detected in non-EAE animals, expression of IL-2(B), IL-10(C) and MCP-1(A) were elevated in d40 control animals with CNS inflammation. While saline-treated animals had increased inflammatory cytokine levels throughout the duration of the experiment, animals receiving N-[N-(3-pyridinesulfonyl)-L-3,3-dimethyl-4-thiaprolyl]-O-[1-methylpiperazin-4-ylcarbonyl]-L-tyrosine isopropyl ester showed a marked decrease in their expression, coincident with clinical and pathological recovery. Upon removal of N-[N-(3-pyridinesulfonyl)-L-3,3-dimethyl-4-thiaprolyl]-O-[1-methylpiperzain-4-ylcarbonyl]-L-tyrosine isopropyl ester and reinfiltration of the CNS, expression of IL-2, IL-10 and MCP-1 again rose to levels comparable to those in saline-treated animals.

FIG. 6. Expression of $\alpha_4$ integrin on lymphocytes. On day 80 post immunization, heparinized blood samples were collected from non-EAE animals, saline-treated animals, N-[N-(3-pyridinesulfonyl)-L-3,3-dimethyl-4-thiaprolyl]-O-[1-methylpiperzain-4-ylcarbonyl]-L-tyrosine isopropyl ester-treated animals and animals 10 days following withdrawal of N-[N-(3-pyridinesulfonyl)-L-3,3-dimethyl-4-thiaprolyl]-O-[1-methylpiperzain-4-ylcarbonyl]-L-tyrosine isopropyl ester. Samples were exposed to antibody against $\alpha_4$ integrin, then examined on a flow cytometer, gating on different cell populations by light scatter. Treatment of animals with N-[N-(3-pyridinesulfonyl)-L-3,3-dimethyl-4-thiaprolyl]-O-[1-methylpiperzain-4-ylcarbonyl]-L-tyrosine isopropyl ester caused a large increase in $\beta_4$ integrin bright lymphocytes in the circulation compared to saline-treated animals. These results indicate the number of alpha-4 expressing cells. There are more alpha-4 expressing cells when the compound is present then in the saline-control treated animals. The x-axis represents alpha-4 expression; the y-axis represents cell number assessed by FACS.

FIG. 7. Expression of $\alpha_4$ integrin on lymphocytes and monocytes in the circulation at day 80 post-immunization. Heparinized blood samples were collected from all groups of animals on day 80 post-immunization, exposed to antibody against $\alpha_4$ integrin, and sorted by flow cytometry. Panel A shows that Treatment with N-[N-(3-pyridinesulfonyl)-L-3,3-dimethyl-4-thiaprolyl]-O-[1-methylpiperzain-4-ylcarbonyl]-L-tyrosine isopropyl ester caused a large increase in the percentage of $\alpha_4$ integrin bright lymphocytes in the circulation compared to non-EAE and saline-treated animals, suggesting that activated peripheral lymphocytes were unable to enter the CNS in the presence of the inhibitor. Consistent with this idea, the percentage of these cells in the circulation returned to saline-treated levels when N-[N-(3-pyridinesulfonyl)-L-3,3-dimethyl-4-thiaprolyl]-O-[1-methylpiperzain-4-ylcarbonyl]-L-tyrosine isopropyl ester was removed and CNS inflammation returned as shown in Panel B. The general expression of $\beta_4$ integrin on circulating monocytes was increased in all EAE animals, although there were no discernable subpopulations. This monocytic increase in $\alpha_4$ integrin expression was not affected by N-[N-(3-pyridinesulfonyl)-L-3,3-dimethyl-4-thiaprolyl]-O-[1-methylpiperzain-4-ylcarbonyl]-L-tyrosine isopropyl ester, suggesting that the inhibitor did not affect the peripheral immune reaction.

Figure 8:
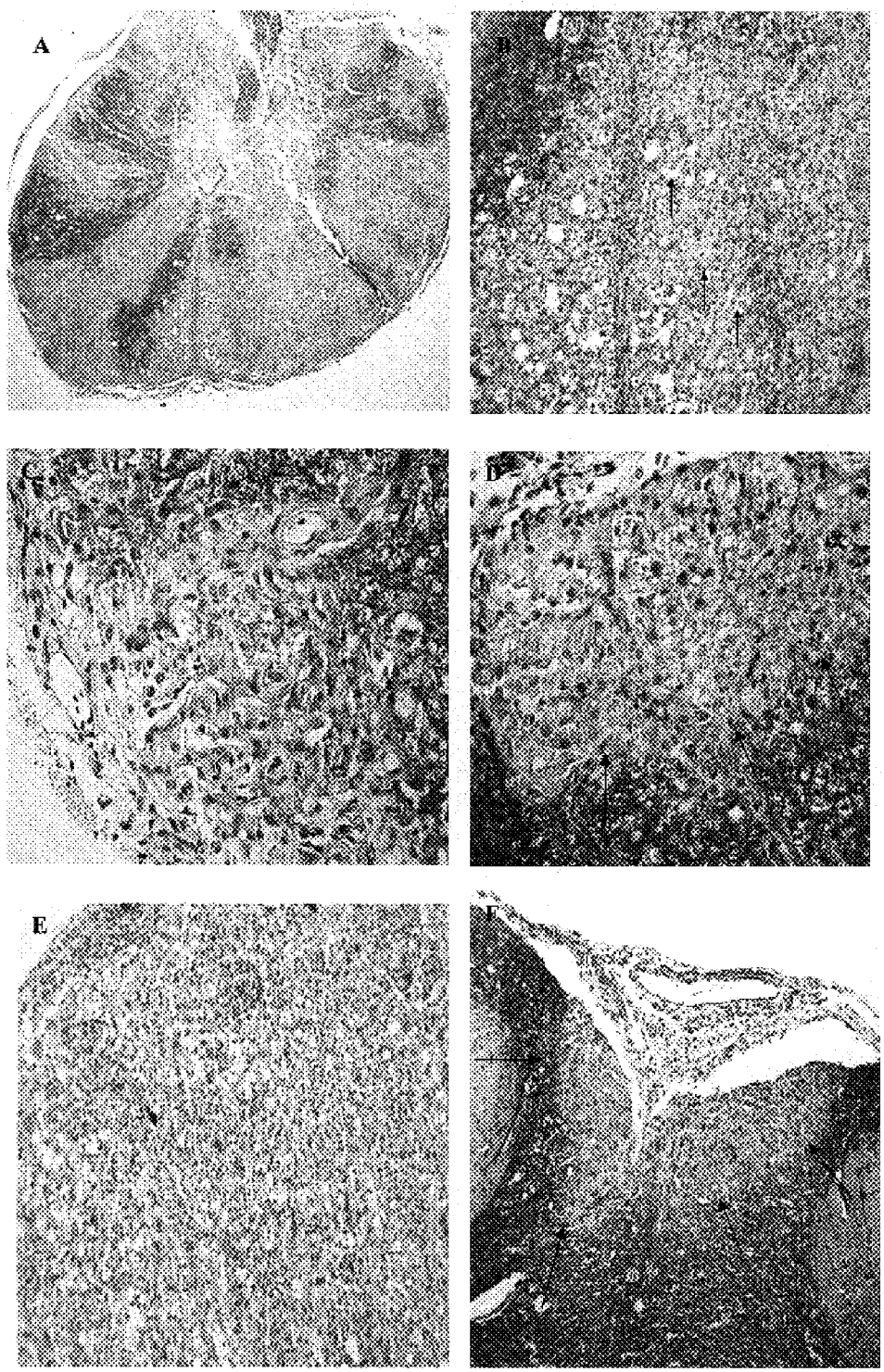

FIG. 8. Shadow plaques are observed in N-[N-(3-pyridinesulfonyl)-L-3,3-dimethyl-4-thiaprolyl]-O-[1-methylpiperzain-4-ylcarbonyl]-L-tyrosine isopropyl ester treated animals. Images 8A-F are representative solochrome-R-cyanin stained spinal cord sections from separate animals within the treatment groups. (8A) A low power image (40×) shows the extent of demyelination in the spinal cord. (8B) A high power image (100×) of a demyelinated lesion in a "day 0" (day 0 is at least measured 40 days post disease induction wherein the animal achieves a clinical score of 2 or greater) control animal shows dense cellular infiltration and foamy macrophages containing phagocytosed myelin debris (arrows). (8C) A lesion from an animal that received 20 days of saline treatment remains completely devoid of myelin (250×). (8D) In contrast, animals that received 20 days of N-[N-(3-pyridinesulfonyl)-L-3,3-dimethyl-4-thiaprolyl]-O-[1-methylpiperzain-4-ylcarbonyl]-L-tyrosine isopropyl ester treatment presented lesions with a diffuse blue stain covering the plaque (250×). (8E) Severe demyelination was evident in the spinal cord after 40 days of vehicle treatment (100×). (8F) After 40 days of N-[N-(3-pyridinesulfonyl)-L-3,3-dimethyl-4-thiaprolyl]-O-[1-methylpiperzain-4-ylcarbonyl]-L-tyrosine isopropyl ester therapy, however, the majority of lesions showed clear myelin pallor (100×).

Figure 9:
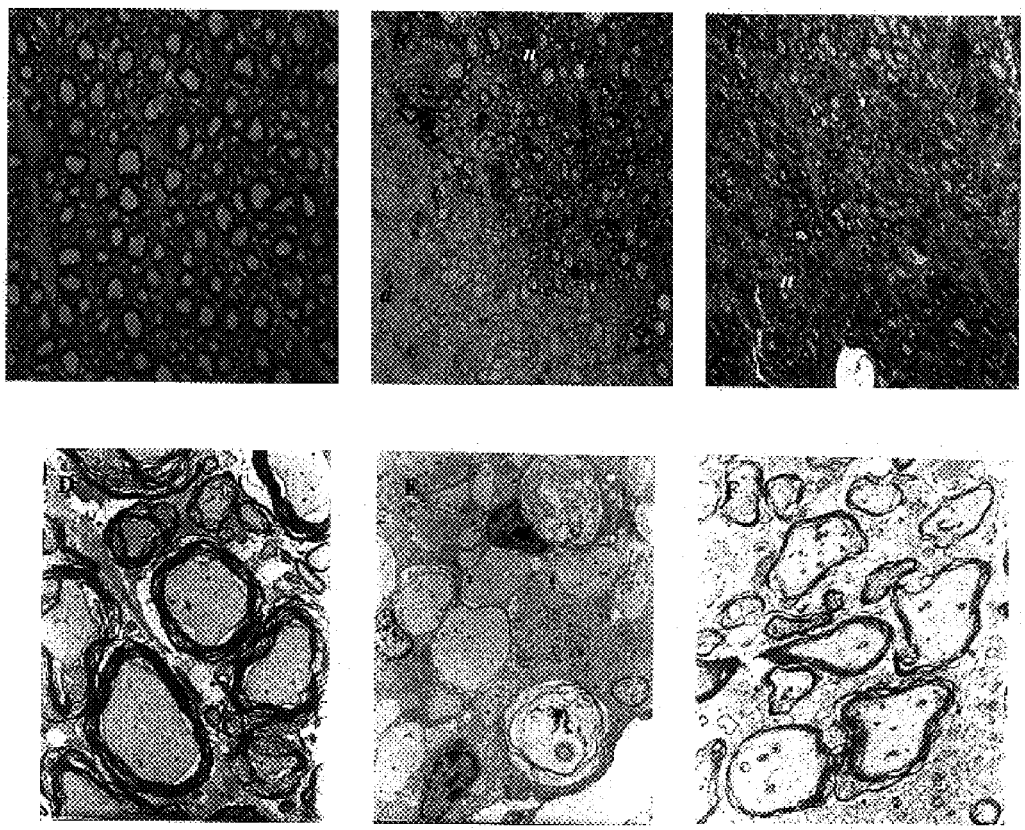

FIG. 9. Semithin and EM sections confirm remyelination with N-[N-(3-pyridinesulfonyl)-L-3,3-dimethyl-4-thiaprolyl]-O-[1-methylpiperzain-4-ylcarbonyl]-L-tyrosine isopropyl ester treatments. Toluidine blue semi-thin sections are shown in panels 9A, 9B, and 9C (all 400×). Representative EM sections from the same animals are shown in panels 9D, 9E and 9F (9D and 9E, 1100×; 9F, 1300×). (FIG. 9A and 9D) Normal myelin. (9B and 9E) Day 30 of saline treatment. Some small caliber axons showed thinly myelinated sheaths (t), juxtaposed between complete demyelination (d) and normal myelin (n). Some axons are undergoing Wallerian degeneration (arrows). In this case, degenerating axons were observed within the normal appearing myelin (arrows, 9B). Electron microscopy confirmed with absence of myelin wrapping around large caliber axons (9E). (9C and 9F) Day 30 N-[N-(3-pyridinesulfonyl)-L-3,3-dimethyl-4-thiaprolyl]-O-[1-methylpiperzain-4-ylcarbonyl]-L-tyrosine isopropyl ester treatment. In animals that received N-[N-(3-pyridinesulfonyl)-L-3,3-dimethyl-4-thiaprolyl]-O-[1-methylpiperzain-4-ylcarbonyl]-L-tyrosine isopropyl ester, an area of normal appearing myelin at the left of the image (n) sits adjacent to a large area of thinly myelinated axons of similar caliber (t). The area of thinly myelinated axons was more extensive and consisted of large caliber axons (9C). EM confirms multiple layers of thin myelin wrappings around large diameter axons indicative of remyelination (9F).

Figure 10:
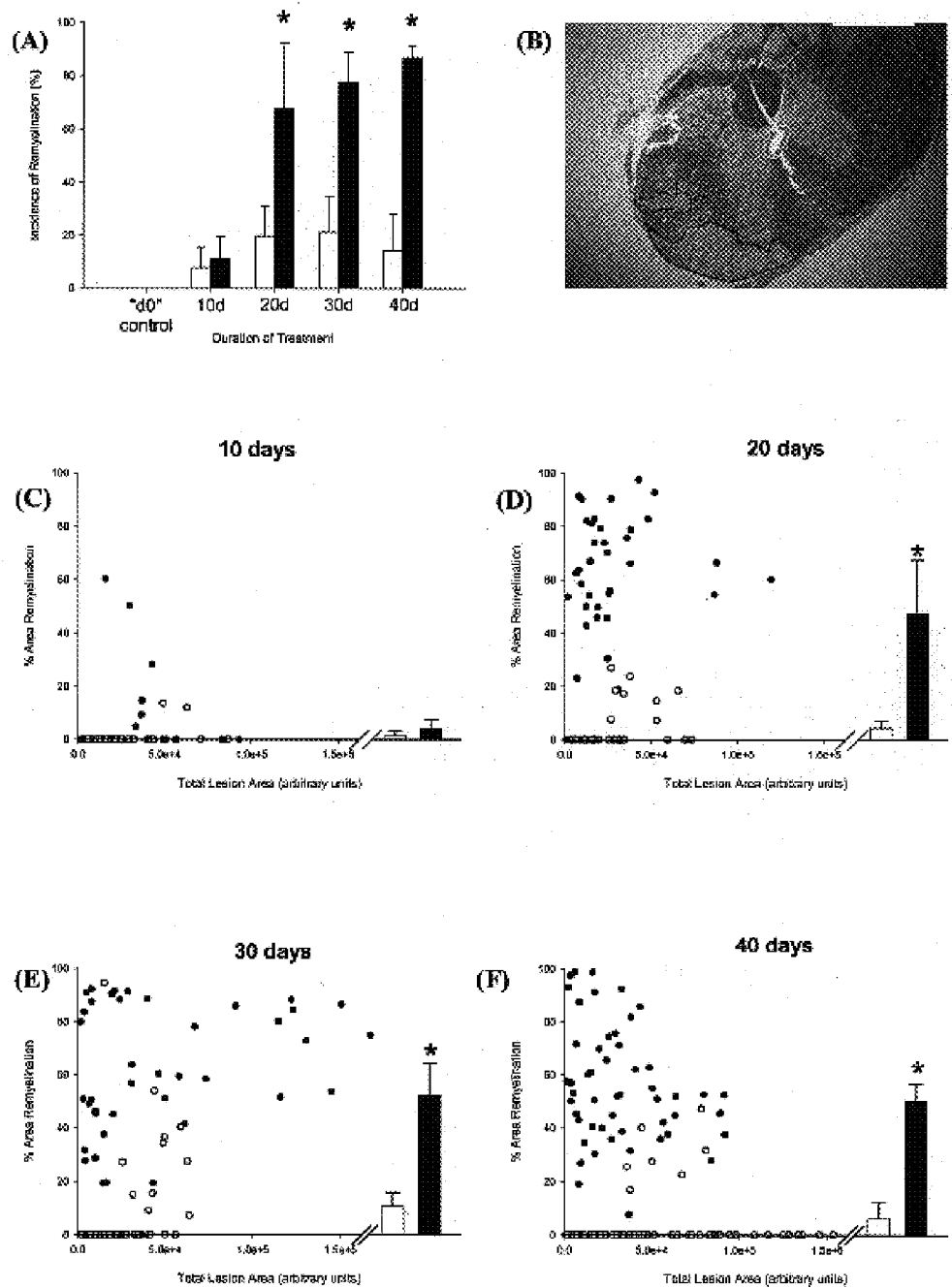

FIG. 10. N-[N-(3-pyridinesulfonyl)-L-3,3-dimethyl-4-thiaprolyl]-O-[1-methylpiperzain-4-ylcarbonyl]-L-tyrosine isopropyl ester increased both the incidence and area of remyelination within the spinal cord. (10A) The number of lesions showing myelin pallor was expressed as a percent of the total number of lesions within a mean of twelve spinal cord cross sections for each animal. N-[N-(3-pyridinesulfonyl)-L-3,3-dimethyl-4-thiaprolyl]-O-[1-methylpiperzain-4-ylcarbonyl]-L-tyrosine isopropyl ester (black bars) increased the incidence of remyelination with respect to saline-treated animals (white bars), and there was a time-dependent increase in the frequency of shadow plaques with N-[N-(3-pyridinesulfonyl)-L-3,3-dimethyl-4-thiaprolyl]-O-[1-methylpiperzain-4-ylcarbonyl]-L-tyrosine isopropyl ester treatment. (10B) Representation of methodology for determining the degree of remyelination. The shapes of all lesions within a spinal cord section were traced, and the area within the outline was calculated. Lesions showing myelin pallor were also traced to yield the total area of remyelination for each animal, and the degree of remyelination was expressed as a percent of the total lesion area. (10C-F) Each scatter plot shows the total lesion area along the x-axis, and the percentage of that lesion showing myelin pallor along the y-axis. Lesions in saline treated animals (white symbols) show little remyelination. In contrast, after 20, 30 or 40 days of N-[N-(3-pyridinesulfonyl)-L-3,3-dimethyl-4-thiaprolyl]-O-[1-methylpiperzain-4-ylcarbonyl]-L-tyrosine isopropyl ester treatment, most lesions in N-[N-(3-pyridinesulfonyl)-L-3,3-dimethyl-4-thiaprolyl]-O-[1-methylpiperzain-4-ylcarbonyl]-L-tyrosine isopropyl ester-treated animals (black symbols) showed variability in the degree of remyelination (0-100%). The mean percent areas are shown in the bar graphs at the right of each scatter plot (saline, white bar; N-[N-(3-pyridinesulfonyl)-L-3,3-dimethyl-4-thiaprolyl]-O-[1-methylpiperzain-4-ylcarbonyl]-L-tyrosine isopropyl ester, black bar). After 20, 30 or 40 days of therapy, N-[N-(3-pyridinesulfonyl)-L-3,3-dimethyl-4-thiaprolyl]-O-[1-methylpiperzain-4-ylcarbonyl]-L-tyrosine isopropyl ester-treated animals had significantly higher percentages of remyelination (50%) than after 10 days of treatment or all saline controls (<10%).

FIGS. 11A and 11B. DNA and amino acid sequences (SEQ ID NOS.: 51-52) of the mouse 21.6 light chain variable region respectively.

FIGS. 12A and 12B. DNA and amino acid sequences (SEQ ID NOS.: 53-54) of the mouse 21.6 heavy chain variable region, respectively.

FIG. 13. Comparisons of the amino acid sequences (SEQ ID NOS.: 55-58) of mouse and reshaped human 21.6 light chain variable regions. The amino acid residues that are part of the Chothia canonical sequences for the CDR loop structures are marked with an asterisk. RE1 shows the FRs and CDRs from the $V_L$ region of human RE1 light chain. La and Lb are the two versions of reshaped human 21.6 $V_L$ region. The residues in the FRs of La that differ from those in the RE1 sequence are underlined. In Lb, only the residues in the framework regions that differ from those of RE1 are shown.

FIG. 14. Comparisons of the amino acid sequences (SEQ ID NOS.: 59-63) of the mouse and reshaped human 21.6 heavy chain variable regions. The amino acid residues that are part of the canonical sequences for the Chothia CDR loop structures are marked with an asterisk. 2*CL shows the FRs and CORs from the $V_H$ region of human 21/28'CL antibody. Ha, Hb, and Hc are the three versions of reshaped human 21.6 $V_H$ region. The residues in the FRs of Ha that differ from those in the 21/28'CL sequence are underlined. In Hb and Hc, only the residues in the framework regions that differ from those of 21/28'CL are shown.

FIGS. 15A and 15B. cDNA and amino acid sequences (SEQ ID NOS.: 64-65) of the first version ("a") of reshaped human 21.6 light chain variable region.

FIGS. 16A and 16B. DNA and amino acid sequences (SEQ ID NOS.: 66-67) of the first version ("a") of reshaped human 21.6 heavy chain variable region.

FIGS. 17A and 17B. FIG. 17A is the 109 amino acid long sequence (SEQ ID NO.: 68) of mouse kappa $V_L$ regions from subgroup 5 used to design the reshaped human 21.6 light chain variable regions. FIG. 17B is the 114 amino acid long sequence (SEQ ID NO.: 69) of human $V_L$ regions from subgroup 1 used to design the reshaped human 21.6 light chain variable regions. The sequences are further described in Table 10 infra.

FIGS. 18A and 18B. FIG. 18A is the 125 amino acid long consensus sequence (SEQ ID NO.: 70) of mouse $V_H$ regions from subgroup 2c used to design the reshaped human 21.6 heavy chain variable regions. FIG. 18A is the 129 amino acid long consensus sequence (SEQ ID NO.: 71) of human $V_H$ regions from subgroup 1 used to design the reshaped human 21.6 heavy chain variable regions. The sequences are further described in Table 11 infra.

DETAILED DESCRIPTION OF THE INVENTION

Before the present methods and therapeutic agents are described, it is to be understood that this invention is not limited to particular methods and therapeutic agents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller, subject to any specifically excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

1. Abbreviations and Definitions

In accordance with this detailed description, the following abbreviations and definitions apply. It must be noted that as used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

1.1. Abbreviations

The following abbreviations have been used herein.

| | |
|---|---|
| AC | acid ceramidase |
| AcOH | acetic acid |
| ACTH | adrenocorticotropic hormone |
| ADEM | acute disseminated encephalomyelitis |
| ALD | adrenoleukodystrophy |
| AMN | adrenomyeloneuropathy |
| aq or aq. | aqueous |
| BBB | blood brain barrier |
| bd | broad doublet |
| bm | broad multiplet |
| Bn | benzyl |
| Boc | tert-butoxycarbonyl |
| $Boc_2O$ | di-tert-butyl dicarbonate |
| BOP | benzotriazol-1-yloxy-tris(dimethylamino)phosphonium hexafluorophosphate |
| bs | broad singlet |
| C | constant region of an immunoglobulin |
| CACH | childhood ataxia with central nervous system hypomyelination |
| CADASIL | cerebral autosomal dominant arteriopathy with subcortical infarcts and leukoencephalopathy |
| Cbz | carbobenzyloxy |
| cDNA | complementary deoxyribonucleic acid |
| CDR | complementarity determining region |
| CDR1 | complementarity determining region 1 |
| CDR2 | complementarity determining region 2 |
| CDR3 | complementarity determining region 3 |
| CFA | complete Freund's adjuvant |
| $CHCl_3$ | chloroform |
| $CH_2Cl_2$ | dichloromethane |
| CIDP | chronic immune demyelinating polyneuropathy |
| CJD | Creutzfeld-Jakob disease |
| CNS | central nervous system |
| $(COCl)_2$ | oxalyl chloride |
| COX-2 | cyclooxygenase-2 |
| CS | Cockayne's syndrome |
| CSF | colony stimulating factor |
| CTX | Cerebrotendinous xanthomatosis |
| d | doublet |
| DBU | 1,8-diazabicyclo[5.4.0]undec-7-ene |
| DCC | 1,3-dicyclohexylcarbodiimide |
| dd | doublet of doublets |
| DMAP | 4-N,N-dimethylaminopyridine |
| DME | ethylene glycol dimethyl ether |
| DMF | N,N-dimethylformamide |
| DMSO | dimethylsulfoxide |
| DNA | deoxyribonucleic acid |
| dt | doublet of triplets |
| EAE | experimental autoimmune encephalomyelitis |
| EBNA2 | Epstein-Barr virus nuclear antigen 2 |
| ECM | extracellular matrix |
| EDC | 1-(3-dimethylaminopropyl)-3-ethylcarbodiimide hydrochloride |
| EDTA | ethylenediaminetetraacetate |
| ELAMS | endothelial adhesion molecules |
| EM | electron microscopy |
| $Et_3N$ | triethylamine |
| $Et_2O$ | diethyl ether |
| EtOAc | ethyl acetate |
| EtOH | ethanol |
| eq or eq. | equivalent |
| FACS | fluorescence activated cell sorter |
| Fmoc | N-(9-fluorenylmethoxycarbonyl) |
| FmocONSu | N-(9-fluorenylmethoxycarbonyl)-Succinimide |
| FR | framework region |
| FR1 | framework region 1 |
| FR2 | framework region 2 |
| FR3 | framework region 3 |
| g | grams |
| GA | glatiramer acetate |
| GALOP | gait disorder, autoantibody, late-age, onset, polyneuropathy |
| GM-CSF | granulocyte monocyte colony stimulating factor |
| GSD | Gerstmann-Straussler disease |
| h or hr | hour |
| H | heavy chain of an immunoglobulin |
| HAMA | human anti-mouse antibody |
| HBr | hydrobromic acid |
| HCl | hydrochloric acid |
| H-E | hematoxylin-eosin |
| hex A | hexoaminidase A |
| HIC | Hydrophobic interaction chromatography |
| HIG | human immunoglobulin |
| HMSN IV | hereditary motor and sensory neuropathy IV (also known as heredopathia atactica polyneuritiformis) |
| $H_2O$ | water |
| HOBT | 1-hydroxybenzotriazole hydrate |
| HUVEC | human umbilical vascular endothelial cells |
| ICAM-1 | intercellular adhesion molecule 1 |
| Ig | immunoglobulin |
| IgG | immunoglobulin G |
| IgM | immunoglobulin M |
| IL | interleukin |
| IL-1 | interleukin-1 |
| IL-2 | interleukin-2 |
| IL-8 | interleukin-8 |
| $K_2CO_3$ | potassium carbonate |
| L | light chain of an immunoglobulin |
| LFA-1 | lymphocyte function-related antigen 1-(also known as $\beta_2$ integrin, CD11a/CD18 and $\alpha_L\beta_2$) |
| m | multiplet |
| MAbs | monoclonal antibodies |
| Mac-1 | $\alpha_M\beta_2$ integrin (also known as CD11b/CD18) |
| MAdCAM-1 | mucosal address in cell adhesion molecule |

-continued

| | |
|---|---|
| MALDI/TOF MS | matrix-assisted laser desorption ionization/time-of-flight mass spectrometry |
| MBP | myelin basic protein |
| MCP-1 | monocyte chemotactic protein 1 |
| MeOH | methanol |
| MES | 2-(N-morpholino)ethanesulfonic acid |
| mg | milligram |
| MgSO$_4$ | magnesium sulfate |
| min. | minute |
| MIP-1α | macrophage inflammatory protein 1 alpha |
| MIP-1β | macrophage inflammatory protein 1 beta |
| mL | milliliter |
| MLD | metachromatic leukodystrophy |
| mm | millimeter |
| mM | millimolar |
| mmol | millimol |
| MOG | myelin-oligodendrocyte glycoprotein |
| mp | melting point |
| MS | multiple sclerosis |
| N | normal |
| NaCl | sodium chloride |
| Na$_2$CO$_3$ | sodium carbonate |
| NaHCO$_3$ | sodium bicarbonate |
| NaOEt | sodium ethoxide |
| NaOH | sodium hydroxide |
| NH$_4$Cl | ammonium chloride |
| NMM | N-methylmorpholine |
| NSAID | nonsteroidal anti-inflammatory |
| PCR | polymerase chain reaction |
| PEG | polyethylene glycol |
| Phe | L-phenylalanine |
| PKU | phenylketonuria |
| PLP | proteolipid protein |
| PMSF | phenylmethylsulfonylfluoride |
| POEMS | polyneuropathy organomegaly endocrinopathy, M-protein and skin changes |
| Pro | L-proline |
| PRP | prion related protein |
| psi | pounds per square inch |
| PtO$_2$ | platinum oxide |
| q | quartet |
| quint. | quintet |
| RANTES | regulated upon activation, normal T-cell expressed and secreted chemokine (also known as small inducible cytokine A5) |
| RNA | ribonucleic acid |
| rt | room temperature |
| RT-PCR | reverse transcription polymerase chain reaction |
| s | singlet |
| SAMIs | selective adhesion molecule inhibitors |
| sat or sat. | saturated |
| scFv | single chain Fv fragment |
| SCR | solochrome-R-cyanlin |
| SDS | sodium dodecyl sulfate |
| SDS-PAGE | sodium dodecyl sulfate polyacrylamide gel electrophoresis |
| SP-MS | secondary progressive multiple sclerosis |
| t | triplet |
| t-BuOH | tert-butanol |
| TFA | trifluoroacetic acid |
| TGF-β | tumor growth factor beta |
| THF | tetrahydrofuran |
| TLC or tlc | thin layer chromatography |
| TNF | tumor necrosis factor |
| TNF-α | tumor necrosis factor alpha |
| TNF-β | tumor necrosis factor beta |
| Ts | tosyl |
| TsCl | tosyl chloride |
| TsOH | tosylate |
| UV | ultraviolet |
| VCAM-1 | vascular cell adhesion molecule 1 |
| V$_H$ | heavy chain of the variable domain |
| V$_L$ | light chain of the variable domain |
| VLA-4 | very late antigen 4 (also known as alpha-4 beta-1, α$_4$β$_1$) |
| μL | microliter |
| φ | phenyl |

1.2. Definitions

Abbreviations for the twenty naturally occurring amino acids follow conventional usage (IMMUNOLOGY-A SYNTHESIS (2nd ed., E. S. Golub & D. R. Gren, eds., Sinauer Associates, Sunderland, Mass., 1991)). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ωN-methylarginine, and other similar amino acids and imino acids (e.g., 4-hydroxyproline). Moreover, amino acids may be modified by glycosylation, phosphorylation and the like.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIGS. 11 or 12, or may comprise a complete DNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Natl. Acad. Sci. (USA) 85: 2444 (1988) (each of which is incorporated by reference in its entirety), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the term "sequence identity" means peptides share identical amino acids at corresponding positions. The term "sequence similarity" means peptides have identical or similar amino acids (i.e., conservative substitutions) at corresponding positions. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. The term "substantial similarity" means that two peptide sequences share corresponding percentages of sequence similarity.

The term "substantially similar" as used herein is intended to mean any polypeptide that has an alteration in the sequence such that a functionally equivalent amino acid is substituted for one or more amino acids in the polypeptide, thus producing a change that has no or relatively little effect on the binding properties of the polypeptide. For example, one or more amino acid residues within the sequence can be substituted by another amino acid of a similar polarity or similar size.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

For purposes of classifying amino acids substitutions as conservative or non-conservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for another.

Amino acids from the variable regions of the mature heavy and light chains of immunoglobulins are designated Hx and Lxx respectively, where "x" is a number designating the position of an amino acids according to the scheme of Kabat et al., SEQUENCES OF PROTEINS OF IMMUNOLOGICAL INTEREST (National Institutes of Health, Bethesda, Md. (1987) and (1991)) (hereinafter collectively referred to as "Kabat" incorporated by reference in their entirety). Kabat lists many amino acid sequences for antibodies for each subclass, and list the most commonly occurring amino acid for each residue position in that subclass. Kabat uses a method for assigning a residue number to each amino acid in a listed sequence, and this method for assigning residue numbers has become standard in the field. Kabat's scheme is extendible to other antibodies not included in the compendium by aligning the antibody in question with one of the consensus sequences in Kabat. The use of the Kabat numbering system readily identifies amino acids at equivalent positions in different antibodies. For example, an amino acid at the L50 position of a human antibody occupies the equivalence position to an amino acid position L50 of a mouse antibody.

The term "reagent" or "agent" is used to denote a biologically active molecule that binds to a ligand receptor. For example, antibodies or fragments thereof which immunoreact with the VLA-4 receptor or VCAM-1 can be useful to promote remyelination and/or reduces paralysis in a subject in a statistically significant amount. Peptides, or peptidomimetics or related compounds, which can act to bind the cell surface receptor, are also contemplated, and can be made synthetically by methods known in the art. Other reagents that react with a VLA-4 receptor as discussed herein or as apparent to those skilled in the art are also contemplated.

A "remyelinating agent" as used herein refers to any agent that promotes remyelination and/or reduces paralysis in a subject in a statistically significant amount. Preferably, such agents include immunoglobulins (e.g., antibodies, antibody fragments, and recombinantly produced antibodies or fragments), polypeptides (e.g., soluble forms of the ligand proteins for integrins) and small molecules, which when administered in an effective amount inhibits demyelination and/or promotes remyelination in a patient. Such may also result in the reduction of paralysis when administered in an effective amount to the patient. These agents can be selected from anti-alpha4 integrin agents (preferaply anti-alpha4 beta 1 antagonists) and anti-VCAM-1 agents. However, with reference to the present invention, such anti-alpha4 integrin and anti-VCAM-1 agents only include those which when administered in an effective amount inhibits demyelination and/or promotes remyelination and/or reduces paralysis.

The term "anti-alpha-4 integrin agent" as used herein refers to any agent that binds specifically to an integrin comprising an alpha-4 subunit and inhibits activity of the integrin. The term "integrin antagonist" includes any agent that inhibits alpha-4 subunit-containing integrins from binding with an integrin ligand and/or receptor. Preferably, the integrin antagonist inhibits the alpha-4 beta-1 dimer from binding to its cognate ligand(s). Such antagonists can include anti-integrin antibodies or antibody homolog-containing proteins, as well as other molecules such as soluble forms of the ligand proteins for integrins. Soluble forms of the ligand proteins for alpha-4 subunit-containing integrins include soluble VCAM-1, VCAM-1 fusion proteins, or bifunctional VCAM-1/Ig fusion proteins. For example, a soluble form of an integrin ligand or a fragment thereof may be administered to bind to integrin, and preferably compete for an integrin binding site on cells, thereby leading to effects similar to the administration of antagonists such as anti-integrin (e.g., VLA-4) antibodies. In particular, soluble integrin mutants that bind ligand but do not elicit integrin-dependent signaling are included within the scope of the invention.

By "natalizumab" or "ANTEGREN®" is meant a humanized antibody against VLA-4 as described in commonly owned U.S. Pat. Nos. 5,840,299 and 6,033,665, which are herein incorporated by reference in their entirety. Also contemplated herein are other VLA-4 specific antibodies. Such remyelinating antibodies and immunoglobulins. include but are not limited to those immunoglobulins described in U.S. Pat. Nos. 6,602,503 and 6,551,593, published U.S. Application No. 20020197233 (Relton et al.), and as further discussed herein.

The term "efficacy" as used herein in the context of a chronic dosage regime refers to the effectiveness of a particular treatment regime. Efficacy can be measured based on change the course of the disease in response to an agent of the present invention. For example, in the treatment of MS, efficacy can be measured by the frequency of relapses in relapsing-remitting MS, and by the presence or absence of new lesions in the central nervous system as detected using methods such as MRI.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce the most favorable patient outcome.

The terms "specifically binds" or "binds specifically" as used herein refer to the situation in which one member of a specific binding pair will not show any significant binding to molecules other than its specific binding partner (e.g., an affinity of about 1000× or more for its binding partner). In the present invention, the small compounds, such as N-[N-(3-pyridinesulfonyl)-L-3,3-dimethyl-4-thiaprolyl]-O-[1-methylpiperzain-4-ylcarbonyl]-L-tyrosine isopropyl ester, will not show significant binding to any polypeptide other than an alpha-4 integrin or a receptor comprising an alpha-4 integrin. For example, the small compounds used in the methods of the invention that bind to an alpha-4 integrin with a binding affinity of greater than 0.3 nM are said to bind specifically to an alpha-4 integrin.

The terms "elicits an immune response" and "elicits a host immune response" as used herein refer to the production of an immune response to a receptor comprising an alpha-4 integrin in a subject upon introduction of an agent of the invention to the subject. An immune response in the subject can be characterized by a serum reactivity with an alpha-4 integrin receptor that is at least twice that of an untreated subject, more preferably three times the reactivity of an untreated subject, and even more preferably at least four times the reactivity of an untreated subject, with serum immunoreactivity measured using a serum dilution of approximately 1:100.

The term "pharmaceutically acceptable carrier or excipient" is intended to mean any compound used in forming a part of the formulation that is intended to act merely as a carrier, i.e., not intended to have biological activity itself. The pharmaceutically acceptable carrier or excipient is generally safe, non-toxic and neither biologically nor otherwise undesirable. A pharmaceutically acceptable carrier or excipient as used in the specification and claims includes both one and more than one such carrier.

The terms "treating", and "treatment" and the like are used herein to generally mean obtaining a desired pharmacological and physiological effect. More specifically, the reagents described herein which are used to treat a subject with a demyelinating disease or condition to do one or more of the following: (1) prevent demyelination; (2) inhibit demyelination; (3) promote remyelination; (4) slow or halt paralysis; and (5) reduce/reverse paralysis. Thus, the effect may be prophylactic in terms of preventing or partially preventing a disease, symptom or condition thereof and/or may be therapeutic in terms of a partial or complete cure of a disease, condition, symptom or adverse effect attributed to the disease depending on the condition or disease being treated. The term "treatment", as used herein, covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease and/or its symptoms or conditions. The invention is directed towards treating a patient's suffering from disease related to pathological inflammation. The present invention is involved in preventing, inhibiting, or relieving adverse effects attributed to pathological inflammation and demyelination over long periods of time and/or are such caused by the physiological responses to inappropriate inflammation present in a biological system over long periods of time.

By "therapeutically effective amount" is meant an amount of agent, reagent, or combination of reagents disclosed herein that when administered to a mammal is sufficient to promote remyelination of mammalian cells and/or reduce paralysis in an animal in a statistically significant amount.

By the term "remyelinating effective amount" is meant an amount of an agent, reagent, or composition effective to inhibit demyelination and/or promote remyelination in a subject and/or reduce paralysis. The "remyelinating effective amount" will vary depending on the compound or composition, the specific disease to be treated and its severity, and the age, weight, etc., of the mammal to be treated.

By "chronic administration" is meant administration of an agent, reagent, or combination therapy of the invention in an amount and periodicity to result in one or more of the following: (1) reduce paralysis in a subject with a demyelinating disease or condition, (2) halt progression of paralysis in a subject with a demyelinating disease or condition; (3) promote remyelination in a subject with a demyelinating disease or condition; and (4) prevent demyelination in a subject with a demyelinating disease or condition. Administration is preferably biweekly, weekly, monthly, or every other month, but can be daily. More preferably the treatment is weekly or monthly and is administered for 6 months to several years or the remainder of the patient's life depending on the disease or condition being treated.

Additional definitions relevant to the compounds of Formulae I, IA, IB, IC, II, IIA, and IIB are as defined therein.

2. General Aspects of the Invention

The present invention is based on the surprising result that chronic administration of an emerging class of new compounds known as selective adhesion molecule inhibitors (SAMIs) provides appropriate control of the inflammatory response in such a manner as to promote remyelination. Existing inhibitors have not provided such control over the inflammatory response, and disease continues to progress. What the inventors have shown herein is that a class of small compounds, preferably exemplified by the compounds of formula I and II, preferably formula IB, IC, and IIB, is useful in treating such pathological inflammation. These small compounds can be administered using a chronic dosage regime or a short-term dosage regime. However, the chronic dosage regime is preferred to maintain the suppression of the pathological inflammation. Thus, in order to realize some of the more important advantages of the invention, the levels of remyelinating agents agent need to be maintained over a number of months or even years.

In a general sense, the method of the invention does not involve any particular mode of administration, since the mode of administration is dependent upon the form of the active agent and the formulation developed to administer the active agent. Modes of administration include oral, parenteral (e.g., subcutaneous, subdural, intravenous, intramuscular, intrathecal, intraperitoneal, intracerebral, intraarterial, or intralesional routes of administration), topical, localized (e.g., surgical application or surgical suppository), rectal, and pulmonary (e.g., aerosols, inhalation, or powder). Preferably, the route of administration is parenteral. The route of administration is based on the composition being administered (e.g., immunoglobulin being administered intravenously versus small compound being administered orally), tissue targeting (e.g., intrathecal administration to target the site of a spinal cord injury), and the like, as would be known to the artisan of ordinary skill.

Additionally, the remyleniating agents can be combined with other compounds or compositions used to treat, ameliorate or palliate symptoms associated with demyelination conditions or diseases. Furthermore, the compounds disclosed herein can be administered alone or in combination with other agents, such as other remyelinating agents, including antibodies and immunologically active fragments thereof (e.g., natalizumab). When administered in combination, the small compounds may be administered in the same formulation as these other compounds or compositions, or in a separate formulation. When administered in combination, the remyelinating agent antibodies are generally administered in a separate formulation than the small compound remyelinating agents, other compounds, and compositions. When administered in combinations, the remyelinating agents may be administered prior to, following, or concurrently with the other compounds and compositions used to treat, ameliorate, or palliate symptoms. The general concept of the invention relates to introducing relatively constant amounts of an active agent to a patient's circulatory system over a period of months or years. This chronic administration of a remyelinating agent is one that provides appropriate control over pathological inflammation being maintained at a constant level over a period of time. By maintaining therapeutic levels of an active agent for a period of time, pathological inflammation can be chronically suppressed in the patient.

In a very specific sense, the invention involves obtaining and maintaining a receptor saturation level in a human patient of a dimer comprising alpha-4 integrin in a range of from about 65% to 100%, more preferably between 75% and 100%, and even more preferably between 80-100%. These receptor saturation levels are maintained at these levels chronically (e.g., over a period of 6 months or so) to allow for continued suppression of pathological inflammation.

In general, the remyelinating agents may be selected from agents that specifically bind to an alpha-4-integrin or binds specifically an alpha-4-integrin. For example, the small compounds used in the methods of the invention may be selected from compounds that have a binding affinity for alpha-4-integrin of 0.3 to 3 nM. Also, antibodies such as natalizumab, which have a binding affinity for alpha-4-integrin of about 0.2 to about 0.4 nM, may also selected.

In another aspect of the invention, the compounds and compositions described herein can be used to inhibit immune cell migration from the bloodstream to the central nervous system in the instance of, for example, multiple sclerosis, or to areas which result in inflammatory-induced destruction of the myelin. Preferably, these agents or reagents inhibit immune cell migration in a manner that inhibits demyelination and that further may promote remyelination. The agents or reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

3. Indications for Treatment

Inflammatory diseases that are included for treatment by the compositions, compounds and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response. The compounds, compositions and methods disclosed herein are not directed towards diseases and conditions wherein there is, for example, a genetic defect leading to improper myelin formation, e.g., dysmyelination.

The compositions, compounds and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria, Tay-Sachs disease, Niemann-Pick disease, Gaucher's disease, Hurler's syndrome, Krabbe's disease and other leukodystrophies), neuropathies with abnormal myelination (e.g., Guillain Barré, chronic immune demyelinating polyneuropathy (CIDP), multifocal CIDP, anti-MAG syndrome, GALOP syndrome, anti-sulfatide antibody syndrome, anti-GM2 antibody syndrome, POEMS syndrome, perineuritis, IgM anti-GD1b antibody syndrome), drug related demyelination (e.g., caused by the administration of chloroquine, FK506, perhexiline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis or spinal cord injury) or diseases.

There are various disease models that can be used to study these diseases in vivo. For example, animal models include but are not limited to:

TABLE 1

| Disease Model | Species |
|---|---|
| EAE | Mouse, rat, guinea pig |
| Myelin-oligodendrocyte glycoprotein (MOG) induced EAE | Rat |
| TNF-α transgenic model of demyelination | Mouse |

3.1. Multiple Sclerosis

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high- but not low-frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include (1) treatment aimed at modification of the disease course, including treatment of acute exacerbation and directed to long-term suppression of the disease; (2) treatment of the symptoms of MS; (3) prevention and treatment of medical complications, and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and COPAXONE® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

3.2. Congenital Metabolic Disorders

Congenital metabolic disorders include phenylketonuria (PKU) and other aminoacidurias, Tay-Sachs disease, Niemann-Pick disease, Gaucher's disease, Hurler's syndrome, Krabbe's disease and other leukodystrophies that impact the developing sheath as described more fully below.

PKU is an inherited error of metabolism caused by a deficiency in the enzyme phenylalanine hydroxylase. Loss of this enzyme results in mental retardation, organ damage, unusual posture and can, in cases of maternal PKU, severely compromise pregnancy. A model for studying PKU has been discovered in mice. Preferably infants identified with PKU are sustained on a phenylalanine free or lowered diet. An aspect of the invention would be to combine such diets with the compounds and compositions disclosed herein to prevent demyelination and remyelinate cells damaged due to PKU.

Classical Tay-Sachs disease appears in the subject at about age 6 months and will eventually result in the death of the subject by age 5 years. The disease is due to the lack of the enzyme, hexoaminidase A (hex A), which is necessary for degrading certain fatty substances in the brain and nerve cells. The substances in the absence of the enzyme accumulate and lead to the destruction of nerve cells. Another form of hex A enzyme deficiency occurs later in life and is referred to as juvenile, chronic and adult onset forms of hex A deficiency.

Symptoms are similar to those that characterize classical Tay-Sachs disease. There is also an adult onset form of the enzyme deficiency. Currently there is no cure or treatment for the disease/deficiency, only the preventative measure of in utero testing of the fetus for the disease. Thus, the compounds and compositions disclosed herein may be useful in ameliorating or preventing the destruction of the cells.

Niemann-Pick disease falls into three categories: the acute infantile form, Type B is a less common, chronic, non-neurological form, and Type C is a biochemically and genetically distinct form of the disease. In a normal individual, cellular cholesterol is imported into lysosomes for processing, after which it is released. Cells taken from subjects with Niemann-Pick have been shown to be defective in releasing cholesterol from lysosomes. This leads to an excessive build-up of cholesterol inside lysosomes, causing processing errors. NPC1 was found to have known sterol-sensing regions similar to those in other proteins, which suggests it plays a role in regulating cholesterol traffic. No successful therapies have been identified for Types A and C forms of Neumann-Pick. For Type C, patients are recommended to follow a low-cholesterol diet. Thus, the compounds and compositions disclosed herein may be useful in ameliorating or preventing the destruction of the cells.

Gaucher's disease is an inherited illness caused by a gene mutation. Normally, this gene is responsible for an enzyme called glucocerebrosidase that the body needs to break down the fat, glucocerebroside. In patients with Gaucher's disease, the body is not able to properly produce this enzyme and the fat cannot be broken down. Like Tay-Sachs disease, Gaucher's disease is considerably more common in the descendants of Jewish people from Eastern Europe (Ashkenazi), although individuals from any ethnic group may be affected. Among the Ashkenazi Jewish population, Gaucher's disease is the most common genetic disorder, with an incidence of approximately 1 in 450 persons. In the general public, Gaucher's disease affects approximately 1 in 100,000 persons.

In 1991, enzyme replacement therapy became available as the first effective treatment for Gaucher's disease. The treatment consists of a modified form of the glucocerebrosidase enzyme given intravenously. It is contemplated that the compositions and compounds disclosed herein can be used alone or more preferably in combination with glycocerebrosidase administration to treat the disease in an afflicted subject.

Hurler's syndrome, also known as mucopolysaccharidosis type I, is a class of overlapping diseases. These genetic diseases share in common the cellular accumulation of mucopolysaccharides in fibroblasts. The diseases are genetically distinguishable. Fibroblast and bone marrow transplantation does not seem to be helpful, thus compounds and compositions useful in ameliorating disease severity and progression are needed. The compounds and compositions disclosed herein may be administered to a subject to ameliorate disease progression and/or severity.

Krabbe's disease (also known as Globoid cell leukodystrophy) is an autosomal recessive condition resulting from galactosylceramidase (or galactocerebrosidase) deficiency, a lysosomal enzyme that catabolises a major lipid component of myelin. Incidence in France is an estimated 1:150,000 births. The disease leads to demyelination of the central and peripheral nervous system. Onset generally occurs during the first year of life and the condition is rapidly progressive, but juvenile, adolescent or adult onset forms have also been reported, with a more variable rate of progression. Diagnosis is established from enzyme assay (galactosylceramidase deficiency). There are several natural animal models (mouse, dog, monkey). Krabbe's disease, like all leukodystrophies, has no known cures or effective treatments. One embodiment of the instant invention is to use the compositions and compounds disclosed herein to treat or ameliorate Krabbe's disease and other leukodystrophies.

Leukodystrophies are a group of genetically determined progressive disorders that affect the brain, spinal cord and peripheral nerves. They include adrenoleukodystrophy (ALD), adrenomyeloneuropathy (AMN), Aicardi-Goutiers syndrome, Alexander's disease, CACH (i.e., childhood ataxia with central nervous system hypomyelination or vanishing white matter disease), CADASIL (i.e., cerebral autosomal dominant arteriopathy with subcortical infarcts and leukoencephalopathy), Canavan disease (spongy degeneration), Cerebrotendinous Xanthomatosis (CTX), Krabbe's disease (discussed above), metachromatic leukodystrophy (MLD), neonatal adrenoleukodystrophy, ovarioleukodystrophy syndrome, Pelizaeus-Merzbacher disease (X-linked spastic paraglegia), Refsum disease, van der Knaap syndrome (vaculating leukodystrophy with subcortical cysts) and Zellweger syndrome. None of the diseases have effective treatments let alone cures. Consequently, means of treating or ameliorating the symptoms of the disease, such as by using the compositions and compounds disclosed herein, is needed.

3.3. Neuropathies with Abnormal Myelination

A variety of chronic immune polyneuropathies exist which result in demyelination in the patient. The age of onset for the conditions varies by condition. Standard treatments for these diseases exist and could be combined with the compositions and compounds disclosed herein. Alternatively, the compositions and compounds disclosed can be used alone. Existing standard therapies include the following:

TABLE 2

| Neuropathy | Clinical Features | Treatment |
| --- | --- | --- |
| Chronic Immune Demyelinating Polyneuropathy (CIDP) | Onset between 1-80 years. Characterized by weakness, sensory loss, and nerve hypertrophy. | T-cell immunosuppression with prednisone, cyclosporine A or methotrexate, HIG, plasma exchange |
| Multifocal CIDP | Onset between 28 to 58 years and characterized by asymmetric weakness, sensory loss with a course that is slowly progressive or relapsing-remitting. | T cell immunosuppression with prednisone Human immunoglobulin (HIG) |
| Multifocal Motor Neuropathy (MMN) | Onset ranges from 25 to 70 years, with twice as many men as women. Features include weakness, muscle atrophy, fasciculations, and cramps | HIG B cell immunosuppression with plasma exchange cyclophosphamide, |

TABLE 2-continued

| Neuropathy | Clinical Features | Treatment |
| --- | --- | --- |
| | which are progressive over 1-30 years. | Rituxan |
| Neuropathy with IgM binding to Myelin-Associated Glycoprotein (MAG) | Onset is usually over age 50 and is characterized by sensory loss (100%), weakness, gain disorder, tremor which is all slowly progressive. | B-cell immunosuppression plasma exchange cyclophosphamide Rituxan α-interferon cladribine or fludarabine prednisone |
| GALOP Syndrome (Gait disorder, Autoantibody, Late-age, Onset, Polyneuropathy) | A gait disorder with polyneuropathy | HIG Plasma exchange cyclophosphamide |
| POEMS Syndrome (Polyneuropathy, Organomegaly, Endocrinopathy, M-Protein and Skin changes) also known as Crow-Fukase Syndrome and Takatsuki disease | Onset occurs between 27 and 80 years with weakness, sensory loss, reduced or absent tendon reflexes, skin disorders and other features. | Osteosclerotic lesions are treated with irradiation. Widespread lesions with chemotherapy (Melphalan and prednisone). |

3.4. Drug and Radiation Induced Demyelination

Certain drugs and radiation can induce demyelination in subjects. Drugs that are responsible for demyelination include but are not limited to chloroquine, FK506, perhexiline, procainamide, and zimeldine.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 *Br. J. Cancer* 85: 1233-9. However, radiation exposure may also be an issue for astronauts (Hopewell, 1994 *Adv. Space Res.* 14: 433-42) as well as in the event of exposure to radioactive substances.

Patients who have received drugs or been exposed accidentally or intentionally to radiation may experience a benefit by administered one of the compounds or compositions disclosed herein to prevent demyelination or to promote remyelination.

3.5. Hereditary Conditions Involving Demyelination

Additional inherited syndromes/diseases that result in demyelination include Cockayne's syndrome, congenital hypomyelinating, Farber's disease, metachromatic leukodystrophy, Peliszaeus-Merzbacher disease, Refsum, prion related conditions and Salla disease.

Cockayne's syndrome (CS) is a rare inherited disorder in which people are sensitive to sunlight, have short stature and have the appearance of premature aging. In the classical form of Cockayne's syndrome (Type I), the symptoms are progressive and typically become apparent after the age of one year. An early onset or congenital form of Cockayne's syndrome (Type II) is apparent at birth. Interestingly, unlike other DNA repair diseases, Cockayne's syndrome is not linked to cancer. CS is a multi-system disorder that causes both profound growth failure of the soma and brain and progressive cachexia, retinal, cochlear, and neurologic degeneration, with a leukodystrophy and demyelinating neuropathy without an increase in cancer. After exposure to UV (e.g., sunlight), subjects with Cockayne's syndrome can no longer perform transcription-coupled repair. Two genes defective in Cockayne's syndrome, CSA and CSB, have been identified so far. The CSA gene is found on chromosome 5. Both genes code for proteins that interacts with components of the transcriptional machinery and with DNA repair proteins.

To date, no cures or effective treatments for patients with this disease have been identified. Thus, one aspect of the invention is treatment of this disease with the compounds and compositions disclosed herein.

Congenital hypomyelination has several names including congenital dysmyelinating neuropathy, congenital hypomyelinating polyneuropathy, congenital hypomyelination (Onion Bulb) polyneuropathy, congenital hypomyelination neuropathy, congenital neuropathy caused by hypomyelination, hypomyelination neuropathy and CHN. Hereditary peripheral neuropathies, among the most common genetic disorders in humans, are a complex, clinically and genetically heterogeneous group of disorders that produce progressive deterioration of the peripheral nerves. Congenital hypomyelination is one of a group of disorders. This group includes hereditary neuropathy with liability to pressure palsies, Charcot-Marie-Tooth disease, Dejerine-Sottas syndrome, and congenital hypomyelinating neuropathy. There are no known cures or effective treatments for any of these disorders.

Farber's disease has several names include: Farber lipogranulomatosis, ceremidase deficiency, acid ceramidase deficiency, AC deficiency, N-laurylsphingosine deacylase deficiency, and N-acylsphingosine amidohydrolase. As certain names reveal, the disease occurs due to a deficiency of acid ceramidase (also known as N-acylsphingosine amidohydrolase, ASAH). The lack of the enzyme results in an accumulation of non-sulfonated acid mucopolysaccharide in the neurons and glial cells. Patients with the disease usually die before the age of 2 years.

Metachromatic leukodystrophy (MLD) is a genetic disorder caused by a deficiency of the enzyme arylsulfatase A. It is one of a group of genetic disorders called the leukodystrophies that affect growth of the myelin sheath. There are three forms of MLD: late infantile, juvenile, and adult. In the late infantile form, which is the most common, onset of symptoms begins between ages 6 months and 2 years. The infant is usually normal at birth, but eventually loses previously gained abilities. Symptoms include hypotonia (low muscle tone), speech abnormalities, loss of mental abilities, blindness, rigidity (i.e., uncontrolled muscle tightness), convulsions, impaired swallowing, paralysis, and dementia. Symptoms of the juvenile form begin between ages 4 and 14, and include impaired school performance, mental deterioration, ataxia, seizures, and dementia. In the adult form, symptoms, which begin after age 16, may include impaired concentration, depression, psychiatric disturbances, ataxia, tremor, and dementia. Seizures may occur in the adult form, but are less common than in the other forms. In all three forms mental deterioration is usually the first sign.

Peliszaeus-Merzbacher disease (also known as perinatal sudanophilic leukodystrophy) is an X-linked genetic disorder that causes an abnormality of a proteolipid protein. The abnormality results in an infant's death typically before the age of one year. There are no known treatments or cures for the disease.

Refsum disease (also referred to as phytanic acid oxidase deficiency, heredopathia atactica polyneuritiformis or hereditary motor and sensory neuropathy IV, HMSN IV) is caused by mutations in the gene, which encodes phytanoyl-CoA hydroxylase (PAHX or PHYH). The major clinical features are retinitis pigmentosa, chronic polyneuropathy and cerebellar signs. Phytanic acid, an unusual branched chain fatty acid (3,7,11,15-tetramethyl-hexadecanoic acid) accumulates in the tissues and body fluids of patients with the disease and is unable to be metabolised due to the lack of PAHX. Plasmapheresis performed once or twice monthly effectively removes the acid from the body and permits liberalization of dietary restrictions limiting phytanic acid intake.

Prion related conditions include Gerstmann-Straussler disease (GSD), Creutzfeldt-Jakob disease (CJD), familial fatal insomnia and aberrant isoforms of the prion protein can act as infectious agents in these disorders as well as in kuru and scrapie (a disease found in sheep). The term prion derives from "protein infectious agent" (Prusiner, *Science* 216: 136-44, 1982). There is a proteolytic cleavage of the prion related protein (PRP) which results in an amyloidogenic peptide that polymerises into insoluble fibrils Salla disease and other types of sialurias are diseases involving problems with sialic acid storage. They are autosomal recessive neurodegenerative disorders that may present as a severe infantile form (i.e., ISSD) or as a slowly progressive adult form that is prevalent in Finland (i.e., Salla disease). The main symptoms are hypotonia, cerebellar ataxia and mental retardation. These conditions and diseases are also contemplated for palliative or ameliorating treatments.

3.6. Other Demyelinating Conditions

Other conditions that result in demyelination include post-infectious encephalitis (also known as acute disseminated encephalomyelitis, ADEM), meningitis and injuries to the spinal cord. The compositions and compounds disclosed herein are also contemplated for use in treating these other demyelinating conditions.

4. Remyelinating Agents

According to the present invention, the remyelinating agents can be selected from agents that specifically bind to alpha-4-integrins. Various types of agents with the ability to bind to and inhibit alpha-4 integrin may be remyelinating agents and thus may be used in the practice of the invention. Many such alpha-4-integrin antagonists have been identified and characterized, and specific agents are described below. These alpha-4-integrin antagonists may be screened for remyelination activity. Specifically, these agents may include both small compounds and polypeptides (e.g., immunoglobulins). Given the teachings disclosed herein, one skilled in the art will be able to identify other agents that will be able to inhibit the alpha-4-comprising integrin dimers in a manner that biologically mimics or is similar to the specifically described agents to inhibit demyelination and/or promote remyelination and/or reduce paralysis. The present invention is intended to include the chronic administration of such agents. As it is also contemplated to include combinations of agents, discussion of agents other than small compounds is also provided.

4.1. Compounds

Various compounds have been identified as agents, which interfere with VLA-4 and VCAM-1 binding. Certain of these compounds, when administered to a patient in an effective amount inhibit demyelination and/or promote remyelination and/or reduce paralysis. Compounds according to the present invention include compounds within formulae I, IA, IB, IC, II, IIA, and IIB described in section 4.1.1. below.

4.1.1. Compounds of Formula I and Formula II

In one aspect, the compounds that can be utilized as remyeleinating agents are compounds defined by formula I below. These compounds have a binding affinity to VLA-4 as expressed by an $IC_{50}$ of about 15 μM or less (measured as described in Example A below) and act as remyeleinating agents:

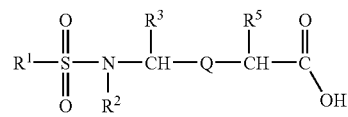

I wherein $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is —$(CH_2)_x$—Ar—$R^{5'}$ where $R^{5'}$ is selected from the group consisting of —O—Z—$NR^8R^{8'}$ and —O—Z—$R^{8''}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{8''}$ is selected from the group consisting of heterocycle and substituted heterocycle, and Z is selected from the group consisting of —C(O)— and —$SO_2$—;

Ar is aryl, heteroaryl, substituted aryl or substituted heteroaryl;

x is an integer of from 1 to 4;

Q is —C(X)$NR^7$— wherein $R^7$ is selected from the group consisting of hydrogen and alkyl; and X is selected from the group consisting of oxygen and sulfur;

and pharmaceutically acceptable salts thereof.

In another embodiment, the compounds can be provided as prodrugs which convert (e.g., hydrolyze, metabolize, etc.) in vivo to a compound of formula I above. In a preferred example of such an embodiment, the carboxylic acid group of the compound of formula I is modified into a group which, in vivo, will convert to a carboxylic acid group (including salts thereof). In a particularly preferred embodiment, such prodrugs are represented by compounds of formula IA:

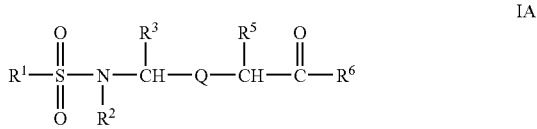

wherein:
$R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is —$(CH_2)_x$—Ar—$R^{5'}$ where $R^{5'}$ is selected from the group consisting of —O—Z—$NR^8R^{8'}$ and —O—Z—$R^{8''}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{8''}$ is selected from the group consisting of heterocycle and substituted heterocycle, and Z is selected from the group consisting of —C(O)— and —$SO_2$—;

Ar is aryl, heteroaryl, substituted aryl or substituted heteroaryl;

x is an integer of from 1 to 4;

$R^6$ is selected from the group consisting of 2,4-dioxotetrahydrofuran-3-yl (3,4-enol), amino, alkoxy, substituted alkoxy, cycloalkoxy, substituted cycloalkoxy, —O—(N-succinimidyl), —NH-adamantyl, —O-cholest-5-en-3-β-yl, —NHOY where Y is hydrogen, alkyl, substituted alkyl, aryl, and substituted aryl, —NH$(CH_2)_p$COOY where p is an integer of from 1 to 8 and Y is as defined above, —$OCH_2NR^9R^{10}$ where $R^9$ is selected from the group consisting of —C(O)-aryl and —C(O)-substituted aryl and $R^{10}$ is selected from the group consisting of hydrogen and —$CH_2COOR^{11}$ where $R^{11}$ is alkyl, and —$NHSO_2Z'$ where $Z'$ is alkyl, substituted alkyl, cycloalkyl, substituted cycloalkyl, aryl, substituted aryl, heteroaryl, substituted heteroaryl, heterocyclic and substituted heterocyclic;

Q is —$C(X)NR^7$— wherein $R^7$ is selected from the group consisting of hydrogen and alkyl; and X is selected from the group consisting of oxygen and sulfur;

and pharmaceutically acceptable salts thereof with the following provisos (A) when $R^1$ and $R^2$ together with the $SO_2$ group pendent to $R^1$ and the nitrogen pendent to $R^2$ form a saccharin-2-yl group, $R^3$ is —$CH_3$, $R^5$ is p-[$(CH_3)_2NC(O)O$—]benzyl and Q is —C(O)NH— then $R^6$ is not —$OC(CH_3)_3$;

(B) when $R^1$ is p-methylphenyl, $R^2$ and $R^3$ together with the nitrogen atom pendent to $R^2$ and the carbon atom pendent to $R^3$ form a pyrrodinyl ring derived from D-proline; $R^5$ is p-[(4-methylpiperazin-1-yl)NC(O)O—]benzyl derived from D-phenylalanine and Q is —C(O)NH— then $R^6$ is not —OC$(CH_3)_3$;

(C) when $R^1$ is pyrimidin-2-yl, $R^2$ and $R^3$ together with the nitrogen atom bound to $R^2$ and the carbon atom bound to $R^3$ form a pyrrolidinyl ring, $R^5$ is p-[$(CH_3)_2NC(O)O$—]benzyl and Q is —C(O)NH— then $R^6$ is not —$OC(CH_3)_3$; and (D) when $R^1$ is p-methylphenyl, $R^2$ and $R^3$ together with the nitrogen atom pendent to $R^2$ and the carbon atom pendent to $R^3$ form a (2S)-piperazin-2-carbonyl ring; $R^5$ is p-[$(CH_3)_2$NC(O)O—]benzyl and Q is —C(O)NH— then $R^6$ is not —$OC(CH_3)_3$.

Further description of the compounds of the above formulae I and IA and procedures and reaction conditions for preparing these compounds are described in U.S. Ser. Nos. 09/126,958 (filed Jul. 31, 1998 and issued as U.S. Pat. No. 6,489,300), herein incorporated by reference in their entirety.

Preferably, in the compounds of formula I and IA above, $R^1$ is selected from the group consisting of alkyl, substituted alkyl, aryl, substituted aryl, heterocyclic, substituted heterocylic, heteroaryl and substituted heteroaryl. More preferably $R^1$ is selected from the group consisting of aryl, substituted aryl, heteroaryl and substituted heteroaryl.

Preferably $R^1$, in the compounds of formula I and IA above is selected from the group consisting of phenyl, 4-methylphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl) phenyl, 4-($H_2NC(O)$—)phenyl, 4-($H_2NC(S)$—)phenyl, 4-cyanophenyl, 4-trifluoromethylphenyl, 4-trifluoromethoxyphenyl, 3,5-di-(trifluoromethyl)phenyl, 4-nitrophenyl, 4-aminophenyl, 4-($CH_3C(O)NH$—) phenyl, 4-(PhNHC(O)NH—)phenyl, 4-amidinophenyl, 4-methylamidinophenyl, 4-($CH_3SC(=NH)$—)phenyl, 4-chloro-3-($H_2NS(O)_2$—)phenyl, 1-naphthyl, 2-naphthyl, pyridin-2-yl, pyridin-3-yl, pyrimidin-2-yl, quinolin-8-yl, 2-(trifluoroacetyl)-1,2,3,4-tetrahydroisoquinolin-7-yl, morpholin-4-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

Preferably, $R^2$, in the compounds of formula I and IA above is selected from the group consisting of methyl, benzyl, —$(CH_2)_2$-2-thienyl, and —$(CH_2)_2$-φ.

In one preferred embodiment, $R^2$ and $R^3$, in the compounds of formula I and IA above together with the nitrogen atom bound to the $R^2$ substituent and the carbon bound to the $R^3$ substituent form a heterocyclic group or a substituted heterocyclic group of 4 to 6 ring atoms having 1 to 2 heteroatoms in the ring selected from the group consisting of nitrogen, oxygen and sulfur which ring is optionally substituted with 1 to 2 substituents selected from the group consisting of fluoro, methyl, hydroxy, oxo (=O), amino, phenyl, thiophenyl, thiobenzyl, (thiomorpholin-4-yl)C(O)O—, $CH_3S(O)_2$— and $CH_3S(O)_2O$—, or can be fused to another ring such as a phenyl or cycloalkyl ring to provide for a fused ring heterocycle of from 10 to 14 ring atoms having 1 to 2 heteroatoms in the ring selected from the group consisting of nitrogen, oxygen and sulfur. Such heterocyclic rings include azetidinyl (e.g., L-azetidinyl), thiazolidinyl (e.g., L-thiazolidinyl), piperidinyl (e.g., L-piperidinyl), piperazinyl (e.g., L-piperazinyl), dihydroindolyl (e.g., L-2,3-dihydroindol-2-yl), tetrahydroquinolinyl (e.g., L-1,2,3,4-tetrahydroquinolin-2-yl), thiomorpholinyl (e.g., L-thiomorpholin-3-yl), pyrrolidinyl (e.g., L-pyrrolidinyl), substituted pyrrolidinyl such as 4-hydroxypyrrolidinyl (e.g., 4-α-(or β-)hydroxy-L-pyrrolidinyl), 4-oxopyrrolidinyl (e.g., 4-oxo-L-pyrolidinyl), 4-fluoropyrrolidinyl (e.g., 4-α-(or β-)fluoro-L-pyrrolidinyl), 4,4-difluoropyrrolidinyl (e.g., 4,4-difluoro-L-pyrrolidinyl), 4-(thiomorpholin-4-ylC(O)O—)pyrrolidinyl (e.g., 4-α-(or β-)-(thiomorpholin-4-ylC(O)O—)-L-pyrrolidinyl, 4-($CH_3S(O)_2$O—)pyrrolidinyl (e.g., 4-α-(or β-)($CH_3S(O)_2$O—)-L-pyrrolidinyl, 3-phenylpyrrolidinyl (e.g., 3-α-(or β-)phenyl-L-pyrrolidinyl), 3-thiophenylpyrrolidinyl (e.g., 3-α-(or β-)thiophenyl-L-pyrrolidinyl), 4-aminopyrrolidinyl (e.g., 4-α-(or β-)amino-L-pyrrolidinyl), 3-methoxypyrrolidinyl (e.g., 3-α-(or β-)methoxy-L-pyrrolidinyl), 4,4-dimethylpyrrolidinyl, substituted piperazinyl such as 4-N-Cbz-piperazinyl and 4-($CH_3S(O)_2$—)piperazinyl, substituted thiazolidinyl such as 5,5-dimethylthiazolindin-4-yl, 1,1-dioxo-thiazolidinyl (e.g., L-1,1-dioxo-thiazolidin-2-yl), substituted 1,1-dioxo-thiazolidinyl such as L-1,1-dioxo-5,5-dimethylthiazolidin-2-yl, 1,1-dioxothiomorpholinyl (e.g., L-1,1-dioxo-thiomorpholin-3-yl) and the like.

Q, in the compounds of formula I and IA above, is preferably —C(O)NH— or —C(S)NH—.

In the compounds of formula I and IA above, Ar is preferably aryl or substituted aryl and, even more preferably, is phenyl or substituted phenyl. Preferably, x is 1.

In the compounds of formula I and IA above, $R^5$ is preferably selected from all possible isomers arising by substitution with the following groups:
3-[($CH_3)_2$NC(O)O—]benzyl,
4-[($CH_3)_2$NC(O)O—]benzyl,
4-[(piperidin-1'-yl)C(O)O—]benzyl,
4-[(piperidin-4'-yl)C(O)O—]benzyl,
4-[(1'-methylpiperidin-4'-yl)C(O)O—]benzyl,
4-[(4'-hydroxypiperidin-1'-yl)C(O)O—]benzyl,
4-[(4'-formyloxypiperidin-1'-yl)C(O)O—]benzyl,
4-[(4'-ethoxycarbonylpiperidin-1'-yl)C(O)O—]benzyl,
4-[(4'-carboxylpiperidin-1'-yl)C(O)O—]benzyl,
4-[(3'-hydroxymethylpiperidin-1'-yl)C(O)O—]benzyl,
4-[(4'-hydroxymethylpiperidin-1'-yl)C(O)O—]benzyl,
4-[(4'-phenyl-1'-Boc-piperidin-4'-yl)-C(O)O—]benzyl,
4-[(4'-piperidon-1'-yl ethylene ketal)C(O)O—]benzyl,
4-[(piperazin-4'-yl)-C(O)O—]benzyl,
4-[(1'-Boc-piperazin-4'-yl)-C(O)O—]benzyl,
4-[(4'-methylpiperazin-1'-yl)C(O)O—]benzyl,
4-[(4'-methylhomopiperazin-1'-yl)C(O)O—]benzyl,
4-[(4'-(2-hydroxyethyl)piperazin-1'-yl)C(O)O—]benzyl,
4-[(4'-phenylpiperazin-1'-yl)C(O)O—]benzyl,
4-[(4'-(pyridin-2-yl)piperazin-1'-yl)C(O)O—]benzyl,
4-[(4'-(4-trifluoromethylpyridin-2-yl)piperazin-1'-yl)C(O)O—]benzyl,
4-[(4'-(pyrimidin-2-yl)piperazin-1'-yl)C(O)O—]benzyl,
4-[(4'-acetylpiperazin-1'-yl)C(O)O—]benzyl,
4-[(4'-phenylC(O)—)piperazin-1'-yl)C(O)O—]benzyl,
4-[(4'-(pyridin-4-ylC(O)—)piperazin-1'-yl)C(O)O—]benzyl,
4-[(4'-phenylNHC(O)—)piperazin-1'-yl)C(O)O—]benzyl,
4-[(4'-phenylNHC(S)—)piperazin-1'-yl)C(O)O—]benzyl,
4-[(4'-methanesulfonylpiperazin-1'-yl-C(O)O—]benzyl,
4-[(4'-trifluoromethanesulfonylpiperazin-1'-yl-C(O)O—)benzyl,
4-[(morpholin-4'-yl)C(O)O—]benzyl,
3-nitro-4-[(morpholin-4'-yl)-C(O)O—]benzyl,
4-[(thiomorpholin-4'-yl)C(O)O—]benzyl,
4-[(thiomorpholin-4'-yl sulfone)-C(O)O—]benzyl (alternative nomenclature 4-[(1,1-dioxothiomorpholin-4-yl)-C(O)O—]benzyl),
4-[(pyrrolidin-1'-yl)C(O)O—]benzyl,
4-[(2'-methylpyrrolidin-1'-yl)C(O)O—]benzyl,
4-[(2'-(methoxycarbonyl)pyrrolidin-1'-yl)C(O)O—]benzyl,
4-[(2'-(hydroxymethyl)pyrrolidin-1'-yl)C(O)O—]benzyl,
4-[(2'-(N,N-dimethylamino)ethyl)($CH_3$)NC(O)O—]benzyl,
4-[(2'-(N-methyl-N-toluene-4-sulfonylamino)ethyl)($CH_3$)N—C(O)O—]benzyl,
4-[(2'-(morpholin-4'-yl)ethyl)($CH_3$)NC(O)O—]benzyl,
4-[(2'-(hydroxy)ethyl)($CH_3$)NC(O)O—]benzyl,
4-[bis(2'-(hydroxy)ethyl)NC(O)O—]benzyl,
4-[(2'-(formyloxy)ethyl)($CH_3$)NC(O)O—]benzyl,
4-[($CH_3$OC(O)$CH_2$)HNC(O)O—]benzyl,
4-[2'-(phenylNHC(O)—)ethyl-]HNC(O)O—]benzyl,
3-chloro-4-[($CH_3)_2$NC(O)O—]benzyl,
3-chloro-4-[(4'-methylpiperazin-1'-yl)C(O)O—]benzyl,
3-chloro-4-[(4'-(pyridin-2-yl)piperazin-1'-yl)C(O)O—]benzyl,
3-chloro-4-[(thiomorpholin-4'-yl)C(O)O—]benzyl, and
3-fluoro-4-[($CH_3)_2$NC(O)O—]benzyl.

In the compounds of formula IA, R is preferably 2,4-dioxotetrahydrofuran-3-yl (3,4-enol), methoxy, ethoxy, n-propoxy, isopropoxy, n-butoxy, t-butoxy, cyclopentoxy, cyclopropylmethoxy, neopentoxy, 2-α-isopropyl-4-β-methylcyclohexoxy, 2-β-isopropyl-4-β-methylcyclohexoxy, 2-methoxyphenoxy, 2-(morpholin-4-yl)ethoxy, —O($CH_2CH_2$O$)_2CH_3$, 2-(phenoxy)ethoxy, —O$CH_2$C($CH_3)_2$NHBoc, —$NH_2$, benzyloxy, —NH$CH_2$COOH, —NH$CH_2CH_2$COOH, —NH-adamantyl, —NHSO$_2$-p-$CH_3$-φ, —NH$CH_2CH_2$COOCH$_2CH_3$, —NHOY' where Y' is hydrogen, methyl, iso-propyl or benzyl, O—(N-succinimidyl), —O-cholest-5-en-3-β-yl, —O$CH_2$—OC(O)C($CH_3)_3$, —O($CH_2)_z$NHC(O)W where z is 1 or 2 and W is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or —$CH_2$C(O)O$CH_2CH_3$.

Even more preferably, $R^6$ in the compounds of formula IA is selected from the group consisting of methoxy, ethoxy, n-propoxy, isopropoxy, n-butoxy, t-butoxy, cyclopentoxy, cyclopropylmethoxy, neopentoxy, 2-α-isopropyl-4-β-methylcyclohexoxy, 2-β-isopropyl-4-β-methylcyclohexoxy, 2-methoxyphenoxy, 2-(morpholin-4-yl)ethoxy, —O($CH_2CH_2$O$)_2CH_3$, 2-(phenoxy)ethoxy, —O$CH_2$C($CH_3)_2$NHBoc, and benzyloxy.

Preferred compounds within the scope of formula I and IA above include by way of example:
N-(toluene-4-sulfonyl)-L-prolyl-L-4-(4-methylpiperazin-1-ylcarbonyloxy)phenylalanine ethyl ester
N-(toluene-4-sulfonyl)-L-prolyl-L-4-(N,N-dimethylcarbamyloxy)phenylalanine ethyl ester
N-(toluene-4-sulfonyl)-L-prolyl-L-4-(4-methylpiperazin-1-ylcarbonyloxy)phenylalanine isopropyl ester
N-(toluene-4-sulfonyl)-L-prolyl-L-4-(4-methylpiperazin-1-ylcarbonyloxy)phenylalanine n-butyl ester
N-(toluene-4-sulfonyl)-L-prolyl-L-4-(4-methylpiperazin-1-ylcarbonyloxy)phenylalanine cyclopentyl ester
N-(toluene-4-sulfonyl)-L-prolyl-L-4-(4-methylpiperazin-1-ylcarbonyloxy)phenylalanine tert-butyl ester N-(toluene-4-sulfonyl)-L-prolyl-L-4-(4-methylpiperazin-1-ylcarbonyloxy)phenylalanine
N-(toluene-4-sulfonyl)-L-prolyl-L-4-(N,N-dimethylcarbamyloxy)phenylalanine isopropyl ester
N-(toluene-4-sulfonyl)-L-prolyl-L-4-(N,N-dimethylcarbamyloxy)phenylalanine n-butyl ester
N-(toluene-4-sulfonyl)-L-prolyl-L-4-(N,N-dimethylcarbamyloxy)phenylalanine cyclopentyl ester
N-(toluene-4-sulfonyl)-L-prolyl-L-4-(N,N-dimethylcarbamyloxy)phenylalanine tert-butyl ester
N-(toluene-4-sulfonyl)-L-prolyl-L-4-(N,N-dimethylcarbamyloxy)phenylalanine
N-(toluene-4-sulfonyl)-L-prolyl-L-4-(isonipecotoyloxy)phenylalanine ethyl ester
N-(α-toluenesulfonyl)-L-prolyl-L-4-(N-methylisonipecotoyloxy)phenylalanine ethyl ester
N-(α-toluenesulfonyl)-L-prolyl-L-4-(4-methylpiperazin-1-ylcarbonyloxy)phenylalanine
N-(toluene-4-sulfonyl)-L-prolyl-L-3-(N,N-dimethylcarbamyloxy)phenylalanine ethyl ester
N-(toluene-4-sulfonyl)-L-prolyl-L-4-(1-tert-butylcarbonyloxy-4-phenylpiperidin-4-ylcarbonyloxy)phenylalanine ethyl ester
N-(toluene-4-sulfonyl)-L-(5,5-dimethyl)thiaprolyl-L-4-(N,N-dimethylcarbamyloxy)phenylalanine isopropyl ester
N-(toluene-4-sulfonyl)-L-(5,5-dimethyl)thiaprolyl-L-4-(N,N-dimethylcarbamyloxy)phenylalanine tert-butyl ester
N-(toluene-4-sulfonyl)-L-(5,5-dimethyl)thiaprolyl-L-4-(N,N-dimethylcarbamyloxy)phenylalanine
N-(toluene-4-sulfonyl)-L-[(1,1-dioxo)thiamorpholin-3-carbonyl]-L-4-(N,N-dimethylcarbamyloxy)phenylalanine tert-butyl ester
N-(toluene-4-sulfonyl)-L-[(1,1-dioxo)thiamorpholin-3-carbonyl]-L-4-(N,N-dimethylcarbamyloxy)phenylalanine
N-(toluene-4-sulfonyl)-L-(5,5-dimethyl)thiaprolyl-L-4-(4-methylpiperazin-1-ylcarbonyloxy)phenylalanine tert-butyl ester
N-(toluene-4-sulfonyl)-L-(5,5-dimethyl)thiaprolyl-L-4-(4-methylpiperazin-1-ylcarbonyloxy)phenylalanine
N-(toluene-4-sulfonyl)sarcosyl-L-4-(N,N-dimethylcarbamyloxy)phenylalanine isopropyl ester
N-(toluene-4-sulfonyl)sarcosyl-L-4-(N,N-dimethylcarbamyloxy)phenylalanine tert-butyl ester
N-(toluene-4-sulfonyl)sarcosyl-L-4-(N,N-dimethylcarbamyloxy)phenylalanine
N-(toluene-4-sulfonyl)-L-prolyl-L-4-(N,N-dimethylaminosulfonyloxy)phenylalanine tert-butyl ester
N-(toluene-4-sulfonyl)-L-prolyl-L-4-(N,N-dimethylaminosulfonyloxy)phenylalanine
N-(1-methylimidazole-4-sulfonyl)-L-prolyl-L-4-(N,N-dimethylcarbamyloxy)phenylalanine tert-butyl ester
N-(4-aminobenzenesulfonyl)-L-prolyl-L-4-(N,N-dimethylcarbamyloxy)phenylalanine tert-butyl ester
N-(toluene-4-sulfonyl)sarcosyl-L-4-(morpholin-4-ylcarbonyloxy)phenylalanine tert-butyl ester
N-(toluene-4-sulfonyl)-L-prolyl-L-4-(morpholin-4-ylcarbonyloxy)phenylalanine tert-butyl ester
N-(α-toluenesulfonyl)-L-(5,5-dimethyl)thiaprolyl-L-4-(N,N-dimethylcarbamyloxy)phenylalanine
N-(toluene-4-sulfonyl)-L-(piperazin-2-carbonyl)-L-4-(N,N-dimethylcarbamyloxy)phenylalanine
N-(α-toluenesulfonyl)-L-(5,5-dimethyl)thiaprolyl-L-4-(N,N-dimethylcarbamyloxy)phenylalanine tert-butyl ester
N-(toluene-4-sulfonyl)-L-prolyl-L-4-(N,N-dimethylcarbamyloxy)phenylalanine N-adamantyl amide
N-(toluene-4-sulfonyl)-L-prolyl-L-4-(N,N-dimethylcarbamyloxy)phenylalanylglycine
N-(toluene-4-sulfonyl)-L-prolyl-L-4-(N,N-dimethylaminosulfonyloxy)phenylalanine methyl ester
N-(toluene-4-sulfonyl)-L-(piperazin-2-carbonyl)-L-4-(N,N-dimethylcarbamyloxy)phenylalanine tert-butyl ester
N-(toluene-4-sulfonyl)-L-(4-benzyloxycarbonylpiperazin-2-carbonyl)-L-4-(N,N-dimethylcarbamyloxy)phenylalanine tert-butyl ester
N-(toluene-4-sulfonyl)sarcosyl-L-4-(isonipecotoyloxy)phenylalanine
N-(toluene-4-sulfonyl)-L-[(1,1-dioxo)thiamorpholin-3-carbonyl]-L-4-(morpholin-4-ylcarbonyloxy)phenylalanine tert-butyl ester
N-(toluene-4-sulfonyl)-L-[(1,1-dioxo)thiamorpholin-3-carbonyl]-L-4-(morpholin-4-ylcarbonyloxy)phenylalanine
N-(1-methylpyrazole-4-sulfonyl)-L-prolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(toluene-4-sulfonyl)sarcosyl-L-4-(4-methylpiperazin-1-ylcarbonyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine tert-butyl ester
N-(1-methylimidazole-4-sulfonyl)-L-prolyl-L-4-(N,N-dimethylcarbamyloxy)phenylalanine
2-(saccharin-2-yl)propionoyl-L-4-(N,N-dimethylcarbamyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine
N-(4-fluorobenzenesulfonyl)-L-prolyl-L-4-(N,N-dimethylcarbamyloxy)phenylalanine
N-(pyridine-3-sulfonyl)-L-prolyl-L-4-(N,N-dimethylcarbamyloxy)phenylalanine
N-(toluene-4-sulfonyl)-D-prolyl-L-4-(4-methylpiperazin-1-ylcarbonyloxy)phenylalanine tert-butyl ester
N-(toluene-4-sulfonyl)-L-N-methylalanyl-L-4-(4-methylpiperazin-1-ylcarbonyloxy)phenylalanine tert-butyl ester
N-(4-nitrobenzenesulfonyl)-L-prolyl-L-4-(N,N-dimethylcarbamyloxy)phenylalanine tert-butyl ester
N-(toluene-4-sulfonyl)-L-[(1,1-dioxo)thiamorpholin-3-carbonyl]-L-4-(N,N-dimethylaminosulfonyloxy)phenylalanine tert-butyl ester
N-(toluene-4-sulfonyl)sarcosyl-L-4-(thiomorpholin-4-ylcarbonyloxy)phenylalanine tert-butyl ester
N-(toluene-4-sulfonyl)-L-N-methylalanyl-L-4-(4-methylpiperazin-1-ylcarbonyloxy)phenylalanine
N-(toluene-4-sulfonyl)-L-prolyl-L-4-(1,1-dioxothiomorpholin-4-ylcarbonyloxy)phenylalanine
N-(toluene-4-sulfonyl)-L-prolyl-L-4-(thiomorpholin-4-ylcarbonyloxy)phenylalanine
N-(toluene-4-sulfonyl)-L-prolyl-L-4-(isonipecotoyloxy)phenylalanine
N-(toluene-4-sulfonyl)-L-prolyl-L-4-(pyrrolidin-1-ylcarbonyloxy)phenylalanine
N-(toluene-4-sulfonyl)-L-prolyl-L-4-(morpholin-4-ylcarbonyloxy)phenylalanine
N-(toluene-4-sulfonyl)-L-prolyl-L-4-(4-methylpiperazin-1-ylcarbonyloxy)phenylalanine neopentyl ester
N-(toluene-4-sulfonyl)-L-prolyl-L-4-(N,N-dimethylcarbamyloxy)phenylalanine neopentyl ester
N-(toluene-4-sulfonyl)-L-prolyl-L-4-(4-tert-butyloxycarbonylpiperazin-1-ylcarbonyloxy)phenylalanine ethyl ester
N-(toluene-4-sulfonyl)-L-prolyl-L-4-(morpholin-4-ylcarbonyloxy)phenylalanine ethyl ester
2-(saccharin-2-yl)propionoyl-L-4-(4-methylpiperazin-1-ylcarbonyloxy)phenylalanine tert-butyl ester 2-(saccharin-2-yl)propionoyl-L-4-(N,N-dimethylcarbamyloxy)phenylalanine
N-(toluene-4-sulfonyl)sarcosyl-L-4-(1,1-dioxothiomorpholin-4-ylcarbonyloxy)phenylalanine tert-butyl ester
N-(toluene-4-sulfonyl)sarcosyl-L-4-(thiomorpholin-4-ylcarbonyloxy)phenylalanine
N-(toluene-4-sulfonyl)-L-N-methylalanyl-L-4-(N,N-dimethylcarbamyloxy)phenylalanine tert-butyl ester
N-(toluene-4-sulfonyl)-L-(thiamorpholin-3-carbonyl)-L-4-(N,N-dimethylcarbamyloxy)phenylalanine tert-butyl ester
N-(toluene-4-sulfonyl)sarcosyl-L-4-(1,1-dioxothiomorpholin-4-ylcarbonyloxy)phenylalanine
N-(toluene-4-sulfonyl)-L-(1,1-dioxothiamorpholin-3-carbonyl)-L-4-(N,N-dimethylcarbamyloxy)phenylalanine tert-butyl ester
N-(toluene-4-sulfonyl)-L-(1,1-dioxothiamorpholin-3-carbonyl)-L-4-(morpholin-4-ylcarbonyloxy)phenylalanine tert-butyl ester
N-(toluene-4-sulfonyl)-L-N-methylalanyl-L-4-(N,N-dimethylcarbamyloxy)phenylalanine
N-(4-fluorobenzenesulfonyl)-L-(thiamorpholin-3-carbonyl)-L-4-(N,N-dimethylcarbamyloxy)phenylalanine tert-butyl ester
N-(4-fluorobenzenesulfonyl)-L-(1,1-dioxothiamorpholin-3-carbonyl)-L-4-(N,N-dimethylcarbamyloxy)phenylalanine tert-butyl ester
N-(pyridine-3-sulfonyl)-L-prolyl-L-4-(N,N-dimethylcarbamyloxy)phenylalanine tert-butyl ester
N-(pyrimidine-2-sulfonyl)-L-prolyl-L-4-(N,N-dimethylcarbamyloxy)phenylalanine tert-butyl ester
N-(4-nitrobenzenesulfonyl)-L-prolyl-L-4-(N,N-dimethylcarbamyloxy)phenylalanine
N-(4-cyanobenzenesulfonyl)-L-prolyl-L-4-(N,N-dimethylcarbamyloxy)phenylalanine tert-butyl ester
N-(toluene-4-sulfonyl)-L-(1,1-dioxothiamorpholin-3-carbonyl)-L-4-(N,N-dimethylaminosulfonyloxy)phenylalanine
N-(toluene-4-sulfonyl)-L-(1,1-dioxothiamorpholin-3-carbonyl)-L-4-(N,N-dimethylcarbamyloxy)phenylalanine
N-(toluene-4-sulfonyl)-L-(1,1-dioxo)thiaprolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(1-methylpyrazole-4-sulfonyl)-L-prolyl-L-4-(N,N-dimethylcarbamyloxy)phenylalanine
N-(toluene-4-sulfonyl)-L-(1,1-dioxo)thiaprolyl-L-4-(N,N-dimethylcarbamyloxy)phenylalanine
N-(4-fluorobenzenesulfonyl)-L-thiaprolyl-L-4-(N,N-dimethylcarbamyloxy)phenylalanine
N-(toluene-4-sulfonyl)-L-prolyl-L-4-(piperazin-1-ylcarbonyloxy)phenylalanine
N-(toluene-4-sulfonyl)-L-prolyl-L-4-(1-tert-butyloxycarbonylpiperazin-1-ylcarbonyloxy)phenylalanine tert-butyl ester
N-(toluene-4-sulfonyl)-L-prolyl-L-4-(piperazin-1-ylcarbonyloxy)phenylalanine ethyl ester
N-(toluene-4-sulfonyl)-L-prolyl-L-4-(4-acetylpiperazin-1-ylcarbonyloxy)phenylalanine ethyl ester
N-(toluene-4-sulfonyl)-L-prolyl-L-4-(4-methanesulfonylpiperazin-1-ylcarbonyloxy)phenylalanine ethyl ester
N-(toluene-4-sulfonyl)-L-prolyl-L-4-(morpholin-4-ylcarbonyloxy)-3-nitrophenylalanine
N-(toluene-4-sulfonyl)-L-prolyl-L-4-(1-tert-butyloxycarbonylpiperazin-1-ylcarbonyloxy)phenylalanine
N-(toluene-4-sulfonyl)-L-N-methyl-2-(tert-butyl)glycinyl-L-4-(4-methylpiperazin-1-ylcarbonyloxy)phenylalanine tert-butyl ester
N-(4-fluorobenzenesulfonyl)-L-(5,5-dimethyl)thiaprolyl-L-4-(N,N-dimethylcarbamyloxy)phenylalanine tert-butyl ester
N-(4-fluorobenzenesulfonyl)-L-(1,1-dioxothiamorpholin-3-carbonyl)-L-4-(1,1-dioxothiomorpholin-4-ylcarbonyloxy)phenylalanine tert-butyl ester
N-(toluene-4-sulfonyl)-L-(1,1-dioxothiamorpholin-3-carbonyl)-L-4-(1,1-dioxothiomorpholin-4-ylcarbonyloxy)phenylalanine tert-butyl ester
N-(4-fluorobenzenesulfonyl)-L-prolyl-L-4-(1,1-dioxothiomorpholin-4-ylcarbonyloxy)phenylalanine tert-butyl ester
N-(4-fluorobenzenesulfonyl)-L-prolyl-L-4-(thiomorpholin-4-ylcarbonyloxy)phenylalanine tert-butyl ester
N-(4-fluorobenzenesulfonyl)-L-prolyl-L-4-(morpholin-4-ylcarbonyloxy)phenylalanine tert-butyl ester
N-(4-fluorobenzenesulfonyl)-L-(5,5-dimethyl)thiaprolyl-L-4-(N,N-dimethylcarbamyloxy)phenylalanine
N-(4-fluorobenzenesulfonyl)-L-(1,1-dioxothiamorpholin-3-carbonyl)-L-4-(morpholin-4-ylcarbonyloxy)phenylalanine tert-butyl ester
N-(4-trifluoromethoxybenzenesulfonyl)-L-prolyl-L-4-(N,N-dimethylcarbamyloxy)phenylalanine tert-butyl ester
N-(toluene-4-sulfonyl)-L-(1,1-dioxothiamorpholin-3-carbonyl)-L-4-(N,N-dimethylcarbamyloxy)phenylalanine isopropyl ester
3-[N-(toluene-4-sulfonyl)-N-methylamino]-1-[1-tert-butyloxycarbonyl-2-(N,N-dimethylcarbamyloxy)phenylethyl]azetidin-2-one
N-(4-fluorobenzenesulfonyl)-L-(1,1-dioxo-5,5-dimethyl)thiaprolyl-L-4-(N,N-dimethylcarbamyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine isopropyl ester
N-(toluene-4-sulfonyl)-L-(1,1-dioxothiamorpholin-3-carbonyl)-L-4-(morpholin-4-ylcarbonyloxy)phenylalanine
N-(4-fluorobenzenesulfonyl)-L-(5,5-dimethyl)thiaprolyl-L-4-(N,N-dimethylcarbamyloxy)phenylalanine
N-(pyrimidine-2-sulfonyl)-L-prolyl-L-4-(N,N-dimethylcarbamyloxy)phenylalanine
N-(toluene-4-sulfonyl)-L-(1,1-dioxothiamorpholin-3-carbonyl)-L-4-(4-methylpiperazin-1-ylcarbonyloxy)phenylalanine tert-butyl ester
3-[N-(toluene-4-sulfonyl)-N-methylamino]-1-[1-carboxy-2-(N,N-dimethylcarbamyloxy)phenylethyl]azetidin-2-one
N-(1-methylpyrazole-4-sulfonyl)-L-prolyl-L-4-(4-methylpiperazin-1-ylcarbonyloxy)phenylalanine tert-butyl ester
N-(4-fluorobenzenesulfonyl)-L-(1,1-dioxo)thiaprolyl-L-4-(N,N-dimethylcarbamyloxy)phenylalanine
N-(toluene-4-sulfonyl)-L-prolyl-L-4-(isonipecotoyloxy)phenylalanine tert-butyl ester
N-(toluene-4-sulfonyl)-L-prolyl-L-4-(1,1-dioxothiomorpholin-4-ylcarbonyloxy)phenylalanine tert-butyl ester
N-(toluene-4-sulfonyl)-L-prolyl-L-4-(thiomorpholin-4-ylcarbonyloxy)phenylalanine tert-butyl ester
N-(toluene-4-sulfonyl)-L-prolyl-L-4-(pyrrolidin-1-ylcarbonyloxy)phenylalanine tert-butyl ester
N-(4-fluorobenzenesulfonyl)-L-thiaprolyl-L-4-(N,N-dimethylcarbamyloxy)phenylalanine tert-butyl ester
N-(4-fluorobenzenesulfonyl)-L-(1,1-dioxo)thiaprolyl-L-4-(N,N-dimethylcarbamyloxy)phenylalanine tert-butyl ester
N-(2,5-dichlorothiophene-3-sulfonyl)-L-prolyl-L-4-(N,N-dimethylcarbamyloxy)phenylalanine tert-butyl ester
N-(4-acetamidobenzenesulfonyl)-L-prolyl-L-4-(N,N-dimethylcarbamyloxy)phenylalanine tert-butyl ester N-(4-tert-butylbenzenesulfonyl)-L-(1,1-dioxothiamorpholin-3-carbonyl)-L-4-(N,N-dimethylcarbamyloxy)phenylalanine tert-butyl ester N-(pyridine-2-sulfonyl)-L-prolyl-L-4-(N,N-dimethylcarbamyloxy)phenylalanine N-(2-fluorobenzenesulfonyl)-L-(1,1-dioxothiamorpholin-3-carbonyl)-L-4-(N,N-dimethylcarbamyloxy)phenylalanine tert-butyl ester N-(3-fluorobenzenesulfonyl)-L-(1,1-dioxothiamorpholin-3-carbonyl)-L-4-(N,N-dimethylcarbamyloxy)phenylalanine tert-butyl ester N-(2,4-difluorobenzenesulfonyl)-L-(1,1-dioxothiamorpholin-3-carbonyl)-L-4-(N,N-dimethylcarbamyloxy)phenylalanine tert-butyl ester N-(4-acetamidobenzenesulfonyl)-L-prolyl-L-4-(N,N-dimethylcarbamyloxy)phenylalanine N-(4-trifluoromethoxybenzenesulfonyl)-L-prolyl-L-4-(N,N-dimethylcarbamyloxy)phenylalanine N-(4-fluorobenzenesulfonyl)-L-(5,5-dimethyl)thiaprolyl-L-4-(N,N-dimethylcarbamyloxy)phenylalanine tert-butyl ester N-(4-cyanobenzenesulfonyl)-L-prolyl-L-4-(N,N-dimethylcarbamyloxy)phenylalanine N-(toluene-4-sulfonyl)-L-(3,3-dimethyl)prolyl-L-4-(N,N-dimethylcarbamyloxy)phenylalanine tert-butyl ester N-(toluene-4-sulfonyl)-L-(3,3-dimethyl)prolyl-L-4-(N,N-dimethylcarbamyloxy)phenylalanine isopropyl ester N-(1-methylpyrazole-4-sulfonyl)-L-prolyl-L-4-(N,N-dimethylcarbamyloxy)phenylalanine iso-propyl ester N-(1-methylpyrazole-4-sulfonyl)-L-(5,5-dimethyl)thiaprolyl-L-4-(N,N-dimethylcarbamyloxy)phenylalanine tert-butyl ester N-(1-methylpyrazole-4-sulfonyl)-L-(5,5-dimethyl)thiaprolyl-L-4-(N,N-dimethylcarbamyloxy)phenylalanine N-(toluene-4-sulfonyl)-L-prolyl-L-4-(N-(1,4-dioxa-8-azaspiro[4.5]decan-8-yl)carbonyloxy)phenylalanine ethyl ester N-(toluene-4-sulfonyl)-L-prolyl-L-4-(N-(1,4-dioxa-8-azaspiro[4.5]decan-8-yl)carbonyloxy)phenylalanine N-(toluene-4-sulfonyl)-L-prolyl-L-4-(4'-acetylpiperazin-1-ylcarbonyloxy)phenylalanine N-(toluene-4-sulfonyl)-L-prolyl-L-4-(4'-methanesulfonylpiperazin-1-ylcarbonyloxy)phenylalanine N-(toluene-4-sulfonyl)-L-prolyl-L-4-(4'-phenylpiperazin-1-ylcarbonyloxy)phenylalanine N-(toluene-4-sulfonyl)-L-prolyl-L-4-(piperazin-1-ylcarbonyloxy)phenylalanine tert-butyl ester 2-(saccharin-2-yl)propionyl-L-4-(4'-methylpiperazin-1-ylcarbonyloxy)phenylalanine N-(toluene-4-sulfonyl)-L-prolyl-L-4-(4'-methanesulfonylpiperazin-1-ylcarbonyloxy)phenylalanine tert-butyl ester N-(toluene-4-sulfonyl)-L-prolyl-L-4-(N,N-dimethylcarbamyloxy)phenylalanine (N'-tert-butoxycarbonyl-2-amino-2-methylpropyl)ester N-(toluene-4-sulfonyl)-L-prolyl-L-4-(4'-acetylpiperazin-1-ylcarbonyloxy)phenylalanine tert-butyl ester N-(toluene-4-sulfonyl)-L-prolyl-L-4-(4'-hydroxypiperidin-1-ylcarbonyloxy)phenylalanine tert-butyl ester N-(toluene-4-sulfonyl)-L-prolyl-L-4-(N-(2'-(morpholin-4'-yl)ethyl)carbamyloxy)phenylalanine tert-butyl ester N-(toluene-4-sulfonyl)-L-prolyl-L-4-(N-(1,4-dioxa-8-azaspiro[4.5]decan-8-yl)carbonyloxy)phenylalanine tert-butyl ester N-(toluene-4-sulfonyl)-L-prolyl-L-4-(N-(2'-hydroxyethyl)-N-methylcarbamyloxy)phenylalanine tert-butyl ester N-(toluene-4-sulfonyl)-L-prolyl-4-(4'-(2-hydroxyethyl)piperazin-1-ylcarbonyloxy)-L-phenylalanine tert-butyl ester N-(toluene-4-sulfonyl)-L-prolyl-L-4-(N-(2'-formyloxyethyl)-N-methylcarbamyloxy)phenylalanine N-(toluene-4-sulfonyl)-L-prolyl-L-4-(N-(2'-hydroxyethyl)-N-methylcarbamyloxy)phenylalanine isopropyl ester N-(toulene-4-sulfonyl)-L-prolyl-L-4-(N-(methoxycarbonylmethyl)carbamyloxy)phenylalanine tert-butyl ester N-(1-methylpyrazole-4-sulfonyl)-L-(5,5-dimethyl)thiaprolyl-L-(4-N,N-dimethylcarbamyloxy)phenylalanine isopropyl ester N-(toluene-4-sulfonyl)-L-prolyl-L-4-(4'-methoxypiperidin-1-ylcarbonyloxy)phenylalanine isopropyl ester N-(toluene-4-sulfonyl)-L-prolyl-L-4-(4'-methoxypiperidin-1-ylcarbonyloxy)phenylalanine N-(toluene-4-sulfonyl)-L-4-oxoprolyl-L-4-(N,N-dimethylcarbamyloxy)phenylalanine tert-butyl ester N-(toluene-4-sulfonyl)-L-trans-4-hydroxyprolyl-L-4-(N,N-dimethylcarbamyloxy)phenylalanine tert-butyl ester N-(3-fluorobenzenesulfonyl)-L-prolyl-L-4-(N,N-dimethylcarbamyloxy)phenylalanine tert-butyl ester N-(morpholino-sulfonyl)-L-prolyl-L-(4-N,N-dimethylcarbamyloxy)phenylalanine tert-butyl ester N-(morpholino-sulfonyl)-L-prolyl-L-(4-N,N-dimethylcarbamyloxy)phenylalanine N-(1-methylpyrazole-4-sulfonyl)-L-(1,1-dioxothiamorpholin-3-carbonyl)-L-4-(N,N-dimethylcarbamyloxy)phenylalanine tert-butyl ester N-(2-fluorobenzenesulfonyl)-L-(1,1-dioxothiamorpholin-3-carbonyl)-L-4-(N,N-dimethylcarbamyloxy)phenylalanine N-(2,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine N-(pyridine-3-sulfonyl)-L-(5,5-dimethyl-thiaprolyl-L-4-(N,N-dimethylcarbamyloxy)phenylalanine isopropyl ester N-(3-fluorobenzenesulfonyl)-L-(1,1-dioxothiamorpholin-3-carbonyl)-L-4-(N,N-dimethylcarbamyloxy)phenylalanine N-(1-methylpyrazole-4-sulfonyl)-L-(1,1-dioxothiamorpholin-3-carbonyl)-L-4-(N,N-dimethylcarbamyloxy)phenylalanine N-(4-tert-butylbenzenesulfonyl)-L-(1,1-dioxothiamorpholin-3-carbonyl)-L-4-(N,N-dimethylcarbamyloxy)phenylalanine N-(toluene-4-sulfonyl)-(3,3-dimethyl)prolyl-L-4-(N,N-dimethylcarbamyloxy)phenylalanine N-(2,5-dichlorothiophene-3-sulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine isopropyl ester N-(toluene-4-sulfonyl)-L-(1-oxo-thiomorpholin-3-carbonyl)-L-4-(N,N-dimethylcarbamyloxy)phenylalanine N-(toluene-4-sulfonyl)-L-(1-oxo-thiomorpholin-3-carbonyl)-L-4-(N,N-dimethylcarbamyloxy)phenylalanine tert-butyl ester N-(3,4-difluorobenzenesulfonyl)-L-prolyl-4-(N,N-dimethylcarbamyloxy)phenylalanine isopropyl ester N-(3,4-difluorobenzenesulfonyl)-L-prolyl-4-(N,N-dimethylcarbamyloxy)phenylalanine N-(3,4-difluorobenzenesulfonyl)-L-(1,1-dioxothiamorpholin-3-carbonyl)-L-4-(N,N-dimethylcarbamyloxy)phenylalanine tert-butyl ester N-(3,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(5,5-dimethyl)thiaprolyl-L-(thiomorpholin-4-ylcarbonyloxy)phenylalanine tert-butyl ester N-(toluene-4-sulfonyl)-L-(5,5-dimethyl)thiaprolyl-L-(thiomorpholin-4-ylcarbonyloxy)phenylalanine N-(1-methylpyrazole-4-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine N-(pyridine-2-sulfonyl)-L-prolyl-L-4-(N,N-dimethylcarbamyloxy)phenylalanine isopropyl ester N-(pyridine-2-sulfonyl)-L-prolyl-L-4-(N,N-dimethylcarbamyloxy)phenylalanine N-(pyridine-2-sulfonyl)-L-(5,5-dimethyl)thiaprolyl-L-4-(N,N-dimethylcarbamyloxy)phenylalanine isopropyl ester N-(pyridine-2-sulfonyl)-L-(5,5-dimethyl)thiaprolyl-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine isopropyl ester N-(3-fluorobenzenesulfonyl)-L-(5,5-dimethyl)thiaprolyl-L-4-(N,N-dimethylcarbarnyloxy)phenylalanine isopropyl ester N-(2-fluorobenzenesulfonyl)-L-(5,5-dimethyl)thiaprolyl-L-4-(N,N-dimethylcarbamyloxy)phenylalanine isopropyl ester N-(3,4-difluorobenzenesulfonyl)-L-(5,5-dimethyl)thiaprolyl-L-4-(N,N-dimethylcarbamyloxy)phenylalanine isopropyl ester N-(3,5-difluorobenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(5,5-dimethyl)thiaprolyl-L-4-(N,N-dimethylcarbamyloxy)phenylalanine isopropyl ester N-(4-chlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(5,5-dimethyl)thiaprolyl-L-4-(N,N-dimethylcarbamyloxy)phenylalanine isopropyl ester N-(2-chlorobenzenesulfonyl)-L-(5,5-dimethyl)thiaprolyl-L-4-(N,N-dimethylcarbamyloxy)phenylalanine isopropyl ester N-(3,4-dichlorobenzenesulfonyl)-L-(5,5-dimethyl)thiaprolyl-L-4-(N,N-dimethylcarbamyloxy)phenylalanine isopropyl ester N-(3,5-dichlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(1,1-dioxothiamorpholin-3-carbonyl)-L-4-(N,N-dimethylcarbamyloxy)phenylalanine tert-butyl ester N-(3,4-dichlorobenzenesulfonyl)-L-(1,1-dioxothiamorpholin-3-carbonyl)-L-4-(N,N-dimethylcarbamyloxy)phenylalanine tert-butyl ester N-(4-methoxybenzenesulfonyl)-L-(5,5-dimethyl)thiaprolyl-L-4-(N,N-dimethylcarbamyloxy)phenylalanine isopropyl ester N-(3-methoxybenzenesulfonyl)-L-(5,5-dimethyl)thiaprolyl-L-4-(N,N-dimethylcarbamyloxy)phenylalanine isopropyl ester N-(2-methoxybenzenesulfonyl)-L-(5,5-dimethyl)thiaprolyl-L-4-(N,N-dimethylcarbamyloxy)phenylalanine isopropyl ester N-(3,4-dimethoxybenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(thiamorpholin-3-carbonyl)-L-4-(N,N-dimethylcarbamyloxy)phenylalanine isopropyl ester N-(3,4-dichlorobenzenesulfonyl)-L-(1,1-dioxothiamorpholin-3-carbonyl)-L-4-(N,N-dimethylcarbamyloxy)phenylalanine N-(3-chlorobenzenesulfonyl)-L-(1,1-dioxothiamorpholin-3-carbonyl)-L-4-(N,N-dimethylcarbamyloxy)phenylalanine N-(3-chloro-4-fluorobenzenesulfonyl)-L-(1,1-dioxothiamorpholin-3-carbonyl)-L-4-(N,N-dimethylcarbamyloxy)phenylalanine tert-butyl ester N-(1-methylpyrazole-4-sulfonyl)-L-(thiamorpholin-3-carbonyl)-L-4-(N,N-dimethylcarbamyloxy)phenylalanine tert-butyl ester N-(3,4-difluorobenzenesulfonyl)-L-(thiamorpholin-3-carbonyl)-L-4-(N,N-dimethylcarbamyloxy)phenylalanine tert-butyl ester N-(toluene-4-sulfonyl)-L-(5,5-dimethyl)thioprolyl-L-(thiomorpholin-4-ylcarbonyloxy)phenylalanine isopropyl ester N-(3,4-difluorobenzenesulfonyl)-L-(thiamorpholin-3-carbonyl)-L-4-(N,N-dimethylcarbamyloxy)phenylalanine N-(2,5-dichlorothiophene-3-sulfonyl)-L-(5,5-dimethyl)thiaprolyl-L-4-(N,N-dimethylcarbamyloxy)phenylalanine isopropyl ester N-(1-methylpyrazole-4-sulfonyl)-L-(5,5-dimethyl)thiaprolyl-L-4-(thiomorpholin-4-ylcarbonyloxy)phenylalanine isopropyl ester N-(8-quinolinesulfonyl)-L-prolyl-L-4-(N,N-dimethylcarbamyloxy)phenylalanine isopropyl ester N-(8-quinolinesulfonyl)-L-prolyl-L-4-(N,N-dimethylcarbamyloxy)phenylalanine N-(8-quinolinesulfonyl)-L-(5,5-dimethyl)thiaprolyl-L-4-(N,N-dimethylcarbamyloxy)phenylalanine isoproplyl ester N-(8-quinolinesulfonyl)-L-(5,5-dimethyl)thiaprolyl-L-4-(N,N-dimethylcarbamyloxy)phenylalanine N-(toluene-4-sulfonyl)-L-prolyl-L-4-(4-phenylpiperazin-1-ylcarbonyloxy)phenylalanine tert-butyl ester N-(toluene-4-sulfonyl)-L-prolyl-L-4-(4'-(ethoxycarbonyl)piperidin-1-ylcarbonyloxy)phenylalanine tert-butyl ester N-(pyridine-3-sulfonyl)-L-(5,5-dimethyl)thiaprolyl-L-4-(N,N-dimethylcarbamyloxy)phenylalanine tert-butyl ester N-(3-sulfonamido-4-chloro-benzenesulfonyl)-L-prolyl-L-4-(N,N-dimethylcarbamyloxy)phenylalanine isopropyl ester N-(toluene-4-sulfonyl)-L-(1-oxothiomorpholin-3-carbonyl)-L-4-(N,N-dimethylcarbamyloxy)phenylalanine isopropyl ester N-(2,4-difluorobenzenefulfonyl)-L-(1-oxothiomorpholin-3-carbonyl)-L-4-(N,N-dimethylcarbamyloxy)phenylalanine tert-butyl ester N-(1-methylpyrazole-4-sulfonyl)-L-(5,5-dimethyl)thiaprolyl-L-4-(N,N-dimethylcarbamyloxy)phenylalanine 2,2-dimethylpropyl ester N-(pyridine-3-sulfonyl)-L-(5,5-dimethyl)thiaprolyl-L-4-(N,N-dimethylcarbamyloxy)phenylalanine 2,2-dimethylpropyl ester N-(1-methylpyrazole-4-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine methyl ester N-(pyridine-3-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine 2-methoxyphenyl ester N-(1-methylpyrazole-4-sulfonyl)-L-(5,5-dimethyl)thiaprolyl-L-4-(N,N-dimethylcarbamyloxy)phenylalanine n-butyl ester N-(1-methylpyrazole-4-sulfonyl)-L-(5,5-dimethyl)thiaprolyl-L-4-(N,N-dimethylcarbamyloxy)phenylalanine n-propyl ester N-(1-methylpyrazole-4-sulfonyl)-L-(5,5-dimethyl)thiaprolyl-L-4-(N,N-dimethylcarbamyloxy)phenylalanine 2,2-dimethylpropionyloxymethyl ester N-(toluene-4-sulfonyl)-L-prolyl-L-4-(N-(4'-(2'-aminoethyl)morpholino)carbamyloxy)phenylalanine N-(toluene-4-sulfonyl)-L-prolyl-L-4-[4-(carboxy)piperidin-1-ylcarbonyloxy]phenylalanine N-(toluene-4-sulfonyl)-L-prolyl-L-4-(N,N-bis-(2-hydroxyethyl)carbamyloxy)phenylalanine isopropyl ester N-(toluene-4-sulfonyl)-L-prolyl-L-4-[3-(hydroxymethyl)piperidin-1-ylcarbonyloxy]phenylalanine isopropyl ester N-(toluene-4-sulfonyl)-L-prolyl-L-4-(4-trifluoromethanesulfonylpiperazin-1-ylcarbonyloxy)phenylalanine tert-butyl ester N-(4-(N-phenylurea)benzenesulfonyl)-L-prolyl-L-4-(N,N-dimethylcarbamyloxy)phenylalanine tert-butyl ester N-(2-trifluoroacetyl-1,2,3,4-tetrahydroisoquinolin-7-sulfonyl)-L-prolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine N-(pyridine-4-sulfonyl)-L-(5,5-dimethyl)thiaprolyl-L-4-(N,N-dimethylcarbamyloxy)phenylalanine isopropyl ester N-(pyridine-4-sulfonyl)-L-(5,5-dimethyl)thiaprolyl-L-4-(N,N-dimethylcarbamyloxy)phenylalanine N-(toluene-4-sulfonyl)-L-(5,5-dimethyl)thiaprolyl-L-4-(N-methyl-N-(2-dimethylaminoethyl)carbamyloxy)phenylalanine tert-butyl ester N-(toluene-4-sulfonyl)-L-prolyl-L-4-(N-methyl-N-(2-dimethylaminoethyl)carbamyloxy)phenylalanine tert-butyl ester N-(toluene-4-sulfonyl)-L-(5,5-dimethyl)thiapropyl-L-4-(N-methyl-N-(2-dimethylaminoethyl)carbamyloxy)phenylalanine N-(toluene-4-sulfonyl)-L-prolyl-L-4-(N-methyl-N-(2-dimethylaminoethyl)carbamyloxy)phenylalanine N-(4-fluorobenzenesulfonyl)-L-(5,5-dimethyl)thiaprolyl-L-3-chloro-4-(4-methylpiperazin-1-ylcarbonyloxy)phenylalanine tert-butyl ester N-(4-fluorobenzenesulfonyl)-L-(5,5-dimethyl)thiaprolyl-L-3-chloro-4-(N,N-dimethycarbamyloxy)phenylalanine N-(4-fluorobenzenesulfonyl)-L-(5,5-dimethyl)thiaprolyl-L-3-chloro-4-(thiomorpholin-4-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine isopropyl ester N-(4-fluorobenzenesulfonyl)-L-(5,5-dimethyl)thiaprolyl-L-3-chloro-4-(N,N-dimethylcarbamyloxy)]phenylalanine isopropyl ester N-(toluene-4-sulfonyl)-L-(5,5-dimethyl)thiaprolyl-L-3-chloro-4-(N,N-dimethylcarbamyloxy)phenylalanine isopropyl ester N-(4-fluorobenzenesulfonyl)-L-(5,5-dimethyl)thiaprolyl-L-3-chloro-4-(4-methylpiperazin-1-ylcarbonyloxy)]phenylalanine isopropyl ester N-(toluene-4-sulfonyl)-L-prolyl-L-3-chloro-4-(N,N-dimethylcarbamyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine tert-butyl ester N-(4-nitrobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine isopropyl ester N-(toluene-4-sulfonyl)-L-prolyl-L-4-(thiomorpholin-4-ylcarbonyloxy)phenylalanine isopropyl ester N-(toluene-4-sulfonyl)-L-prolyl-L-4-(4-phenylcarbamylpiperazin-1-ylcarbonyloxy)phenylalanine isopropyl ester N-(toluene-4-sulfonyl)-L-prolyl-L-4-(4-phenylcarbamylpiperazin-1-ylcarbonyloxy)phenylalanine N-(1-n-butylpyrazole-4-sulfonyl)-L-(5,5-dimethyl)thiaprolyl-L-4-(N,N-dimethylcarbamyloxy)phenylalanine isopropyl ester N-(toluene-4-sulfonyl)-L-prolyl-L-4-(pyridin-4-ylcarbonyl)piperazin-1-ylcarbonyloxy)phenylalanine isopropyl ester N-(toluene-4-sulfonyl)-L-4-oxoprolyl-L-4-(N,N-dimethylcarbamyloxy)phenylalanine N-(toluene-4-sulfonyl)-L-trans-4-hydroxyprolyl-L-4-(N,N-dimethylcarbamyloxy)phenylalanine N-(4-cyanobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine N-(toluene-4-sulfonyl)-L-4-oxoprolyl-L-4-(4-methylpiperazin-1-ylcarbonyloxy)phenylalanine tert-butyl ester N-(toluene-4-sulfonyl)-L-prolyl-L-4-[3-(hydroxymethyl)piperidin-1-ylcarbonyloxy]phenylalanine N-(toluene-4-sulfonyl)-L-(4,4-difluoro)prolyl-L-4-(N,N-dimethylcarbamyloxy)phenylalanine isopropyl ester N-(toluene-4-sulfonyl)-L-(4,4-difluoro)prolyl-L-4-(N,N-dimethylcarbamyloxy)phenylalanine N-(toluene-4-sulfonyl)-L-prolyl-L-4-(4-benzoylpiperazin-1-ylcarbonyloxy)phenylalanine isopropyl ester N-(1-methyl-1H-imidazole-4-sulfonyl)-L-prolyl-L-4-(N,N-dimethylcarbamyloxy)phenylalanine isopropyl ester N-(toluene-4-sulfonyl)-L-4-(thiomorpholin-4-ylcarbonyloxy)prolyl-L-4-(thiomorpholin-4-ylcarbonyloxy)phenylalanine N-(4-cyanobenzenesulfonyl)-L-prolyl-L-4-(thiomorpholin-4-ylcarbonyloxy)phenylalanine isopropyl ester N-(4-amidinobenzenesulfonyl)-L-prolyl-L-4-(N,N-dimethylcarbamyloxy)phenylalanine methyl ester N-(toluene-4-sulfonyl)-L-4-oxoprolyl-L-4-(thiomorpholin-4-ylcarbonyloxy)phenylalanine tert-butyl ester N-(toluene-4-sulfonyl)-L-4-hydroxyprolyl-L-4-(thiomorpholin-4-ylcarbonyloxy)phenylalanine N-(toluene-4-sulfonyl)-L-prolyl-L-(4-benzoylpiperazin-1-ylcarbonyloxy)phenylalanine N-(4-amidinobenzenesulfonyl)-L-prolyl-L-4-(thiomorpholin-4-ylcarbonyloxy)phenylalanine methyl ester
N-(3-fluorobenzenesulfonyl)-L-prolyl-L-4-(N,N-dimethylcarbonyloxy)phenylalanine
N-(toluene-4-sulfonyl)-L-prolyl-L-4-[N-methyl-N-(2-(N'-methyl-N'-toluenesulfonyl-amino)ethyl)carbamyloxy]phenylalanine isopropyl ester
N-(toluene-4-sulfonyl)-L-prolyl-L-4-[N-(2-(N'-phenylaminocarbonyloxy)ethyl)carbamyloxy)]phenylalanine isopropyl ester
N-(4-fluorobenzenesulfonyl)-L-4-(trans-hydroxy)prolyl-L-4-(N,N-dimethylcarbamyloxy)phenylalanine isopropyl ester
N-(4-fluorobenzenesulfonyl)-L-4-(trans-hydroxy)prolyl-L-4-(N,N-dimethylcarbamyloxy)phenylalanine tert-butyl ester
N-(4-amidinobenzenesulfonyl)-L-prolyl-L-4-(N,N-dimethylcarbamyloxy)phenylalanine
piperazine-1,4-dicarboxylic acid bis-{4-[(2S)-2-tert-butoxycarbonyl-2-((4R)-5,5-dimethyl-3-(toluene-4-sulfonyl)thiazolidine-4-carboxamido)ethyl]phenyl}ester
piperazine-1,4-dicarboxylic acid bis-{4-[(2S)-2-carboxy-2-((4R)-5,5-dimethyl-3-(toluene-4-sulfonyl)thiazolidine-4-carboxamido)ethyl]phenyl}ester
N-(toluene-4-sulfonyl)-L-(pyrazin-3-carbonyl)-L-4-(N,N-dimethylcarbamyloxy)phenylalanine tert-butyl ester
N-(4-fluorobenzenesulfonyl)-L-(5,5-dimethyl)thiaprolyl-L-4-(2-hydroxymethylpyrrolidin-1-ylcarbonyloxy)phenylalanine tert-butyl ester
N-(4-fluorobenzenesulfonyl)-L-(5,5-dimethyl)thiaprolyl-L-4-(2-hydroxymethylpyrrolidin-1-ylcarbonyloxy)phenylalanine
N-(toluene-4-sulfonyl)-L-prolyl-L-4-(2-methoxycarbonylpyrrolidin-1-ylcarbonyloxy)phenylalanine tert-butyl ester
N-(4-fluorobenzenesulfonyl)-L-(5,5-dimethyl)thiaprolyl-L-3-chloro-4-(thiomorpholin-4-ylcarbonyloxy)phenylalanine
N-(4-fluorobenzenesulfonyl)-L-(5,5-dimethyl)thiaprolyl-L-4-(4-(2-pyridyl)piperazin-1-ylcarbonyloxy)]phenylalanine
N-(4-fluorobenzenesulfonyl)-L-(5,5-dimethyl)thiaprolyl-L-4-(4-(2-pyridyl)piperazin-1-ylcarbonyloxy)]phenylalanine tert-butyl ester
piperazine-1,4-dicarboxylic acid bis-{4-[(2S)-2-isopropoxycarbonyl-2-((2R)-1-(toluene-4-sulfonyl)pyrrolidine-2-carboxamido)ethyl]phenyl}ester
N-(toluene-4-sulfonyl)-L-(4-hydroxy)prolyl-L-4-(thiomorpholin-4-ylcarbonyloxy)phenylalanine tert-butyl ester
N-(toluene-4-sulfonyl)-L-prolyl-L-4-(N,N-dimethylcarbamyloxy)phenylalanine 2-(2-methoxyethoxy)ethyl ester
N-(4-fluorobenzenesulfonyl)-L-(5,5-dimethyl)thiaprolyl-L-4-(4-(2-pyrimidyl)piperazin-1-ylcarbonyloxy)phenylalanine tert-butyl ester
N-(4-fluorobenzenesulfonyl)-L-(5,5-dimethyl)thiaprolyl-L-3-fluoro-4-(N,N-dimethylcarbamyloxy)phenylalanine isopropyl ester
N-(toluene-4-sulfonyl)-L-(1-methanesulfonylpyrazin-3-carbonyl)-L-4-(N,N-dimethylcarbamyloxy)phenylalanine tert-butyl ester
N-[2-(1,1-dioxo-2,3-dihydro-3,3-dimethyl-1,2-benzisothiazol-2-yl)acetyl]-L-4-(N,N-dimethylcarbamyloxy)phenylalanine
N-[2-(N-2,10-camphorsultamyl)acetyl]-L-4-(N,N-dimethylcarbamyloxy)phenylalanine tert-butyl ester
N-[2-(N-2,10-camphorsultamyl)acetyl]-L-4-(N,N-dimethylcarbamyloxy)phenylalanine
N-[2-(N-2,10-camphorsultamyl)acetyl]-L-3-chloro-4-(N,N-dimethylcarbamyloxy)phenylalanine isopropyl ester
N-(4-bromobenzenesulfonyl)-L-(5,5-dimethyl)thiaprolyl-L-4-(N,N-dimethylcarbamyloxy)phenylalanine tert-butyl ester
N-(4-bromobenzenesulfonyl)-L-(5,5-dimethyl)thiaprolyl-L-4-(N,N-dimethylcarbamyloxy)phenylalanine
N-(toluene-4-sulfonyl)-L-(4-hydroxy)prolyl-L-4-(4-methylpiperazin-1-ylcarbonyloxy)phenylalanine
N-(4-fluorobenzenesulfonyl)-L-(5,5-dimethyl)thiaprolyl-L-4-(4-(2-pyrimidyl)piperazin-1-ylcarbonyloxy)]phenylalanine
piperazine-1,4-dicarboxylic acid bis-{4-[(2S)-2-tert-butoxycarbonyl-2-((2R)-1-(toluene-4-sulfonyl)pyrrolidine-2-carboxamido)ethyl]phenyl}ester
N-(4-fluorobenzenesulfonyl)-L-(5,5-dimethyl)thiaprolyl-L-4-(4-(2-pyridyl)piperazin-1-ylcarbonyloxy)]phenylalanine isopropyl ester
N-(4-fluorobenzenesulfonyl)thiazolidinyl-2-carbonyl-L-4-(N,N-dimethylcarbamyloxy)phenylalanine
N-(4-fluorobenzenesulfonyl)thiazolidinyl-2-carbonyl-L-4-(N,N-dimethylcarbamyloxy)phenylalanine tert-butyl ester
N-(toluene-4-sulfonyl)-L-(4-oxo)prolyl-L-4-(thiomorpholin-4-ylcarbonyloxy)phenylalanine
N-(toluene-4-sulfonyl)-L-(4-oxo)prolyl-L-4-(4-methylpiperazin-1-ylcarbonyloxy)phenylalanine
N-(4-fluorobenzenesulfonyl)thiazolidinyl-2-carbonyl-L-4-(4-(2-pyridyl)piperazin-1-ylcarbonyloxy)]phenylalanine
N-(4-nitrobenzenesulfonyl)-L-prolyl-L-4-(4-(2-pyridyl)piperazin-1-ylcarbonyloxy)]phenylalanine tert-butyl ester
N-(4-fluorobenzenesulfonyl)thiazolidinyl-2-carbonyl-L-4-(4-(2-pyridyl)piperazin-1-ylcarbonyloxy)]phenylalanine tert-butyl ester
N-(4-bromobenzenesulfonyl)-L-(5,5-dimethyl)thiaprolyl-L-4-(4-(2-pyridyl)piperazin-1-ylcarbonyloxy)]phenylalanine
N-(toluene-4-sulfonyl)-L-prolyl-L-4-(4-(N-phenylthiocarbonyl)piperazin-1-ylcarbonyloxy)]phenylalanine isopropyl ester
N-(4-fluorobenzenesulfonyl)thiazolidinyl-2-carbonyl-L-4-(4-methylhomopiperazin-1-ylcarbonyloxy)phenylalanine tert-butyl ester
piperazine-1,4-dicarboxylic acid bis-{4-[(2S)-2-carboxyl-2-((2R)-1-(toluene-4-sulfonyl)pyrrolidine-2-carboxamido)ethyl]phenyl}ester
N-(toluene-4-sulfonyl)-L-4-(methanesulfonyloxy)prolyl-L-4-(N,N-dimethylcarbamyloxy)phenylalanine tert-butyl ester
N-(4-aminocarbonylbenzenesulfonyl)-L-prolyl-L-4-(N,N-dimethylcarbamyloxy)phenylalanine
N-(4-aminocarbonylbenzenesulfonyl)-L-prolyl-L-4-(thiomorpholin-4-ylcarbonyloxy)phenylalanine
N-(4-amidinobenzenesulfonyl)-L-prolyl-L-4-(thiomorpholin-4-ylcarbonyloxy)phenylalanine
N-(4-nitrobenzenesulfonyl)-L-prolyl-L-4-(4-(2-pyridyl)piperazin-1-ylcarbonyloxy)]phenylalanine
N-(4-fluorobenzenesulfonyl)-L-(5,5-dimethyl)thiaprolyl-L-3-chloro-4-(4-(2-pyridyl)piperazin-1-ylcarbonyloxy)]phenylalanine ethyl ester
N-(4-fluorobenzenesulfonyl)-L-(5,5-dimethyl)thiaprolyl-L-3-chloro-4-(4-(2-pyridyl)piperazin-1-ylcarbonyloxy)phenylalanine
N-(4-fluorobenzenesulfonyl)thiazolidinyl-2-carbonyl-L-4-(4-methylhomopiperazin-1-ylcarbonyloxy)phenylalanine
N-(1-methylpyrazole-3-sulfonyl)-L-(5,5-dimethyl)thiaprolyl-L-3-chloro-4-(N,N-dimethylcarbamyloxy)phenylalanine isopropyl ester N-(1-methylimidazole-4-sulfonyl)-L-prolyl-L-4-(4-(2-py-ridyl)piperazin-1-ylcarbonyloxy)phenylalanine isopropyl ester
N-(1-methylimidazole-4-sulfonyl)-L-prolyl-L-4-(4-(2-py-ridyl)piperazin 1-ylcarbonyloxy)phenylalanine tert-butyl ester
N-(toluene-4-sulfonyl)-L-prolyl-L-4-(4-(2-pyridyl)piper-azin-1-ylcarbonyloxy)phenylalanine
N-(toluene-4-sulfonyl)-L-prolyl-L-4-(4-(2-pyridyl)piper-azin-1-ylcarbonyloxy)phenylalanine tert-butyl ester
N-(toluene-4-sulfonyl)-L-prolyl-L-4-(4-(2-pyridyl)piper-azin-1-ylcarbonyloxy)phenylalanine isopropyl ester
N-(4-fluorobenzenesulfonyl)-L-prolyl-L-4-(4-(2-pyridyl)piperazin-1-ylcarbonyloxy)phenylalanine isopropyl ester
N-(4-fluorobenzenesulfonyl)-L-prolyl-L-4-(4-(2-pyridyl)piperazin-1-ylcarbonyloxy)phenylalanine tert-butyl ester
N-(toluene-4-sulfonyl)-L-(1-methanesulfonylpyrazin-3-car-bonyl)-L-4-(N,N-dimethylcarbamyloxy)phenylalanine
N-(toluene-4-sulfonyl)-L-4-(methanesulfonyloxy)prolyl-L-4-(N,N-dimethylcarbamyloxy)phenylalanine
N-(methanesulfonyl)-N-benzylglycinyl-L-4-(N,N-dimeth-ylcarbamyloxy)phenylalanine tert-butyl ester
N-(4-bromobenzenesulfonyl)-L-(5,5-dimethyl)thiaprolyl-L-4-(4-(2-pyridyl)piperazin-1-ylcarbonyloxy)phenylalanine tert-butyl ester
N-(4-trifluoromethoxybenzenesulfonyl)-L-(5,5-dimethyl)thiaprolyl-L-4-(N,N-dimethylcarbamyloxy)phenylala-nine
N-(4-trifluoromethoxybenzenesulfonyl)-L-(5,5-dimethyl)thiaprolyl-L-4-(N,N-dimethylcarbamyloxy)phenylala-nine tert-butyl ester
N-(4-trifluoromethoxybenzenesulfonyl)-L-(5,5-dimethyl)thiaprolyl-L-4-(4-(2-pyridyl)piperazin-1-ylcarbonyloxy)phenylalanine tert-butyl ester
N-(4-fluorobenzenesulfonyl)-L-prolyl-L-4-(4-(2-pyridyl)piperazin-1-ylcarbonyloxy)phenylalanine
N-(4-fluorobenzenesulfonyl)-L-(4-hydroxy)prolyl-L-4-(4-(2-pyridyl)piperazin-1-ylcarbonyloxy)phenylalanine
N-(4-trifluoromethoxybenzenesulfonyl)-L-(5,5-dimethyl)thiaprolyl-L-4-(4-(2-pyridyl)piperazin-1-ylcarbonyloxy)phenylalanine
N-(1-methylimidazole-4-sulfonyl)-L-prolyl-L-3-chloro-4-(N,N-dimethylcarbamyloxy)phenylalanine
N-(1-methylimidazole-4-sulfonyl)-L-prolyl-L-3-chloro-4-(N,N-dimethylcarbamyloxy)phenylalanine isopropyl ester
N-(1-methylimidazole-4-sulfonyl)-L-prolyl-L-4-(4-(2-py-ridyl)piperazin-1-ylcarbonyloxy)phenylalanine
N-(1-methylimidazole-4-sulfonyl)-L-(5,5-dimethyl)thiapro-lyl-L-4-(4-(2-pyridyl)piperazin-1-ylcarbonyloxy)pheny-lalanine
N-(1-methylpyrazole-3-sulfonyl)-L-prolyl-L-4-(4-(2-py-ridyl)piperazin-1-ylcarbonyloxy)phenylalanine
N-(1-methylpyrazole-3-sulfonyl)-L-prolyl-L-4-(4-(2-py-ridyl)piperazin-1-ylcarbonyloxy)phenylalanine isopropyl ester
N-(1-methylpyrazole-3-sulfonyl)-L-prolyl-L-4-(4-(2-py-ridyl)piperazin-1-ylcarbonyloxy)phenylalanine tert-butyl ester
N-(1-methylpyrazole-3-sulfonyl)-L-(5,5-dimethyl)thiapro-lyl-L-4-(4-(2-pyridyl)piperazin-1-ylcarbonyloxy)pheny-lalanine tert-butyl ester
N-(1-methylimidazole-4-sulfonyl)-L-prolyl-L-3-chloro-4-(4-(2-pyridyl)piperazin-1-ylcarbonyloxy)phenylalanine isopropyl ester
N-(1-methylpyrazole-3-sulfonyl)-L-(5,5-dimethyl)thiapro-lyl-L-4-(N,N-dimethylcarbamyloxy)phenylalanine 2-phe-noxyethyl ester
N-(1-methylpyrazole-3-sulfonyl)-L-(5,5-dimethyl)thiapro-lyl-L-3-chloro-4-(4-(2-pyridyl)piperazin-1-ylcarbony-loxy)phenylalanine
N-(1-methylpyrazole-3-sulfonyl)-L-(5,5-dimethyl)thiapro-lyl-L-3-chloro-4-(4-(2-pyridyl)piperazin-1-ylcarbony-loxy)phenylalanine ethyl ester
N-(3-chloro-1,5-dimethylpyrazole-3-sulfonyl)-L-(5,5-dim-ethyl)thiaprolyl-L-3-chloro-4-(4-(5-trifluoromethyl-2-py-ridyl)piperazin-1-ylcarbonyloxy)phenylalanine and pharmaceutically acceptable salts thereof as well as any of the ester compounds recited above wherein one ester is replaced with another ester selected from the group consist-ing of methyl ester, ethyl ester, n-propyl ester, isopropyl ester, n-butyl ester, isobutyl ester, sec-butyl ester, tert-butyl ester and neopentyl ester.

More preferred compounds within the scope of formula I, IA, and IIB include by way of example:
N-(toluene-4-sulfonyl)-L-prolyl-L-4-(4-methylpiperazin 1-ylcarbonyloxy)phenylalanine ethyl ester
N-(toluene-4-sulfonyl)-L-prolyl-L-4-(N,N-dimethylcar-bamyloxy)phenylalanine ethyl ester
N-(toluene-4-sulfonyl)-L-prolyl-L-4-(4-methylpiperazin-1-ylcarbonyloxy)phenylalanine isopropyl ester
N-(toluene-4-sulfonyl)-L-prolyl-L-4-(4-methylpiperazin-1-ylcarbonyloxy)phenylalanine n-butyl ester
N-(toluene-4-sulfonyl)-L-prolyl-L-4-(4-methylpiperazin-1-ylcarbonyloxy)phenylalanine cyclopentyl ester
N-(toluene-4-sulfonyl)-L-prolyl-L-4-(4-methylpiperazin-1-ylcarbonyloxy)phenylalanine tert-butyl ester
N-(toluene-4-sulfonyl)-L-prolyl-L-4-(4-methylpiperazin-1-ylcarbonyloxy)phenylalanine
N-(toluene-4-sulfonyl)-L-prolyl-L-4-(N,N-dimethylcar-bamyloxy)phenylalanine isopropyl ester
N-(toluene-4-sulfonyl)-L-prolyl-L-4-(N,N-dimethylcar-bamyloxy)phenylalanine n-butyl ester
N-(toluene-4-sulfonyl)-L-prolyl-L-4-(N,N-dimethylcar-bamyloxy)phenylalanine cyclopentyl ester
N-(toluene-4-sulfonyl)-L-prolyl-L-4-(N,N-dimethylcar-bamyloxy)phenylalanine tert-butyl ester
N-(toluene-4-sulfonyl)-L-prolyl-L-4-(N,N-dimethylcar-bamyloxy)phenylalanine
N-(toluene-4-sulfonyl)-L-prolyl-L-4-(isonipecotoyloxy)phenylalanine ethyl ester
N-(α-toluenesulfonyl)-L-prolyl-L-4-(N-methylisonipec-otoyloxy)phenylalanine ethyl ester
N-(α-toluenesulfonyl)-L-prolyl-L-4-(4-methylpiperazin-1-ylcarbonyloxy)phenylalanine
N-(toluene-4-sulfonyl)-L-prolyl-L-3-(N,N-dimethylcar-bamyloxy)phenylalanine ethyl ester
N-(toluene-4-sulfonyl)-L-prolyl-L-4-(1-tert-butylcarbony-loxy-4-phenylpiperidin-4-ylcarbonyloxy)phenylalanine ethyl ester
N-(toluene-4-sulfonyl)-L-(5,5-dimethyl)thiaprolyl-L-4-(N,N-dimethylcarbamyloxy)phenylalanine isopropyl ester
N-(toluene-4-sulfonyl)-L-(5,5-dimethyl)thiaprolyl-L-4-(N,N-dimethylcarbamyloxy)phenylalanine tert-butyl ester
N-(toluene-4-sulfonyl)-L-(5,5-dimethyl)thiaprolyl-L-4-(N,N-dimethylcarbamyloxy)phenylalanine
N-(toluene-4-sulfonyl)-L-[(1,1-dioxo)thiamorpholin-3-car-bonyl]-L-4-(N,N-dimethylcarbamyloxy)phenylalanine tert-butyl ester
N-(toluene-4-sulfonyl)-L-[(1,1-dioxo)thiamorpholin-3-car-bonyl]-L-4-(N,N-dimethylcarbamyloxy)phenylalanine N-(toluene-4-sulfonyl)-L-(5,5-dimethyl)thiaprolyl-L-4-(4-methylpiperazin-1-ylcarbonyloxy)phenylalanine tert-butyl ester
N-(toluene-4-sulfonyl)-L-(5,5-dimethyl)thiaprolyl-L-4-(4-methylpiperazin-1-ylcarbonyloxy)phenylalanine
N-(toluene-4-sulfonyl)sarcosyl-L-4-(N,N-dimethylcarbamyloxy)phenylalanine isopropyl ester
N-(toluene-4-sulfonyl)sarcosyl-L-4-(N,N-dimethylcarbamyloxy)phenylalanine tert-butyl ester
N-(toluene-4-sulfonyl)sarcosyl-L-4-(N,N-dimethylcarbamyloxy)phenylalanine
N-(1-methylimidazole-4-sulfonyl)-L-prolyl-L-4-(N,N-dimethylcarbamyloxy)phenylalanine tert-butyl ester
N-(4-aminobenzenesulfonyl)-L-prolyl-L-4-(N,N-dimethylcarbamyloxy)phenylalanine tert-butyl ester
N-(toluene-4-sulfonyl)sarcosyl-L-4-(morpholin-4-ylcarbonyloxy)phenylalanine tert-butyl ester
N-(toluene-4-sulfonyl)-L-prolyl-L-4-(morpholin-4-ylcarbonyloxy)phenylalanine tert-butyl ester
N-(α-toluenesulfonyl)-L-(5,5-dimethyl)thiaprolyl-L-4-(N,N-dimethylcarbamyloxy)phenylalanine
N-(toluene-4-sulfonyl)-L-(piperazin-2-carbonyl)-L-4-(N,N-dimethylcarbamyloxy)phenylalanine
N-(α-toluenesulfonyl)-L-(5,5-dimethyl)thiaprolyl-L-4-(N,N-dimethylcarbamyloxy)phenylalanine tert-butyl ester
N-(toluene-4-sulfonyl)-L-(piperazin-2-carbonyl)-L-4-(N,N-dimethylcarbamyloxy)phenylalanine tert-butyl ester
N-(toluene-4-sulfonyl)-L-(4-benzyloxycarbonylpiperazin-2-carbonyl)-L-4-(N,N-dimethylcarbamyloxy)phenylalanine tert-butyl ester
N-(toluene-4-sulfonyl)sarcosyl-L-4-(isonipecotoyloxy)phenylalanine
N-(toluene-4-sulfonyl)-L-[(1,1-dioxo)thiamorpholin-3-carbonyl]-L-4-(morpholin-4-ylcarbonyloxy)phenylalanine tert-butyl ester
N-(toluene-4-sulfonyl)-L-[(1,1-dioxo)thiamorpholin-3-carbonyl]-L-4-(morpholin-4-ylcarbonyloxy)phenylalanine
N-(1-methylpyrazole-4-sulfonyl)-L-prolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(toluene-4-sulfonyl)sarcosyl-L-4-(4-methylpiperazin-1-ylcarbonyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine tert-butyl ester
N-(1-methylimidazole-4-sulfonyl)-L-prolyl-L-4-(N,N-dimethylcarbamyloxy)phenylalanine
N-(toluene-4-sulfonyl)-L-(1,1-dioxo-5,5-dimethyl)thiaprolyl-L-4-(N,N-dimethylcarbamyloxy)phenylalanine
N-(4-fluorobenzenesulfonyl)-L-prolyl-L-4-(N,N-dimethylcarbamyloxy)phenylalanine
N-(pyridine-3-sulfonyl)-L-prolyl-L-4-(N,N-dimethylcarbamyloxy)phenylalanine
N-(toluene-4-sulfonyl)-D-prolyl-L-4-(4-methylpiperazin-1-ylcarbonyloxy)phenylalanine tert-butyl ester
N-(toluene-4-sulfonyl)-L-N-methylalanyl-L-4-(4-methylpiperazin-1-ylcarbonyloxy)phenylalanine tert-butyl ester
N-(4-nitrobenzenesulfonyl)-L-prolyl-L-4-(N,N-dimethylcarbamyloxy)phenylalanine tert-butyl ester
N-(toluene-4-sulfonyl)sarcosyl-L-4-(thiomorpholin-4-ylcarbonyloxy)phenylalanine tert-butyl ester
N-(toluene-4-sulfonyl)-L-N-methylalanyl-L-4-(4-methylpiperazin-1-ylcarbonyloxy)phenylalanine
N-(toluene-4-sulfonyl)-L-prolyl-L-4-(1,1-dioxothiomorpholin-4-ylcarbonyloxy)phenylalanine
N-(toluene-4-sulfonyl)-L-prolyl-L-4-(thiomorpholin-4-ylcarbonyloxy)phenylalanine
N-(toluene-4-sulfonyl)-L-prolyl-L-4-(isonipecotoyloxy)phenylalanine
N-(toluene-4-sulfonyl)-L-prolyl-L-4-(pyrrolidin-1-ylcarbonyloxy)phenylalanine
N-(toluene-4-sulfonyl)-L-prolyl-L-4-(morpholin-4-ylcarbonyloxy)phenylalanine
N-(toluene-4-sulfonyl)-L-prolyl-L-4-(4-methylpiperazin-1-ylcarbonyloxy)phenylalanine neopentyl ester
N-(toluene-4-sulfonyl)-L-prolyl-L-4-(N,N-dimethylcarbamyloxy)phenylalanine neopentyl ester
N-(toluene-4-sulfonyl)-L-prolyl-L-4-(4-tert-butyloxycarbonylpiperazin-1-ylcarbonyloxy)phenylalanine ethyl ester
N-(toluene-4-sulfonyl)-L-prolyl-L-4-(morpholin-4-ylcarbonyloxy)phenylalanine ethyl ester
N-(toluene-4-sulfonyl)sarcosyl-L-4-(1,1-dioxothiomorpholin-4-ylcarbonyloxy)phenylalanine tert-butyl ester
N-(toluene-4-sulfonyl)sarcosyl-L-4-(thiomorpholin-4-ylcarbonyloxy)phenylalanine
N-(toluene-4-sulfonyl)-L-N-methylalanyl-L-4-(N,N-dimethylcarbamyloxy)phenylalanine tert-butyl ester
N-(toluene-4-sulfonyl)-L-(thiamorpholin-3-carbonyl)-L-4-(N,N-dimethylcarbamyloxy)phenylalanine tert-butyl ester
N-(toluene-4-sulfonyl)sarcosyl-L-4-(1,1-dioxothiomorpholin-4-ylcarbonyloxy)phenylalanine
N-(toluene-4-sulfonyl)-L-(1,1-dioxothiamorpholin-3-carbonyl)-L-4-(N,N-dimethylcarbamyloxy)phenylalanine tert-butyl ester
N-(toluene-4-sulfonyl)-L-(1,1-dioxothiamorpholin-3-carbonyl)-L-4-(morpholin-4-ylcarbonyloxy)phenylalanine tert-butyl ester
N-(toluene-4-sulfonyl)-L-N-methylalanyl-L-4-(N,N-dimethylcarbamyloxy)phenylalanine
N-(4-fluorobenzenesulfonyl)-L-(thiamorpholin-3-carbonyl)-L-4-(N,N-dimethylcarbamyloxy)phenylalanine tert-butyl ester
N-(4-fluorobenzenesulfonyl)-L-(1,1-dioxothiamorpholin-3-carbonyl)-L-4-(N,N-dimethylcarbamyloxy)phenylalanine tert-butyl ester
N-(pyridine-3-sulfonyl)-L-prolyl-L-4-(N,N-dimethylcarbamyloxy)phenylalanine tert-butyl ester
N-(pyrimidine-2-sulfonyl)-L-prolyl-L-4-(N,N-dimethylcarbamyloxy)phenylalanine tert-butyl ester
N-(4-nitrobenzenesulfonyl)-L-prolyl-L-4-(N,N-dimethylcarbamyloxy)phenylalanine
N-(4-cyanobenzenesulfonyl)-L-prolyl-L-4-(N,N-dimethylcarbamyloxy)phenylalanine tert-butyl ester
N-(toluene-4-sulfonyl)-L-(1,1-dioxothiamorpholin-3-carbonyl)-L-4-(N,N-dimethylcarbamyloxy)phenylalanine
N-(toluene-4-sulfonyl)-L-(1,1-dioxo)thiaprolyl-L-4-(N,N-dimethylcarbamyloxy)phenylalanine tert-butyl ester
N-(4-fluorobenzenesulfonyl)-L-prolyl-L-4-(N,N-dimethylcarbamyloxy)phenylalanine tert-butyl ester
N-(1-methylpyrazole-4-sulfonyl)-L-prolyl-L-4-(N,N-dimethylcarbamyloxy)phenylalanine
N-(toluene-4-sulfonyl)-L-(1,1-dioxo)thiaprolyl-L-4-(N,N-dimethylcarbamyloxy)phenylalanine
N-(4-fluorobenzenesulfonyl)-L-thiaprolyl-L-4-(N,N-dimethylcarbamyloxy)phenylalanine
N-(toluene-4-sulfonyl)-L-prolyl-L-4-(piperazin-1-ylcarbonyloxy)phenylalanine
N-(toluene-4-sulfonyl)-L-prolyl-L-4-(1-tert-butyloxycarbonylpiperazin-1-ylcarbonyloxy)phenylalanine tert-butyl ester
N-(toluene-4-sulfonyl)-L-prolyl-L-4-(piperazin-1-ylcarbonyloxy)phenylalanine ethyl ester N-(toluene-4-sulfonyl)-L-prolyl-L-4-(4-acetylpiperazin-1-ylcarbonyloxy)phenylalanine ethyl ester
N-(toluene-4-sulfonyl)-L-prolyl-L-4-(4-methanesulfonylpiperazin-1-ylcarbonyloxy)phenylalanine ethyl ester
N-(toluene-4-sulfonyl)-L-prolyl-L-4-(morpholin-4-ylcarbonyloxy)-3-nitrophenylalanine
N-(toluene-4-sulfonyl)-L-prolyl-L-4-(1-tert-butyloxycarbonylpiperazin-1-ylcarbonyloxy)phenylalanine
N-(toluene-4-sulfonyl)-L-N-methyl-2-(tert-butyl)glycinyl-L-4-(4-methylpiperazin-1-ylcarbonyloxy)phenylalanine tert-butyl ester
N-(4-fluorobenzenesulfonyl)-L-(5,5-dimethyl)thiaprolyl-L-4-(N,N-dimethylcarbamyloxy)phenylalanine tert-butyl ester
N-(4-fluorobenzenesulfonyl)-L-(1,1-dioxothiamorpholin-3-carbonyl)-L-4-(1,1-dioxothiomorpholin-4-ylcarbonyloxy)phenylalanine tert-butyl ester
N-(toluene-4-sulfonyl)-L-(1,1-dioxothiamorpholin-3-carbonyl)-L-4-(1,1-dioxothiomorpholin-4-ylcarbonyloxy)phenylalanine tert-butyl ester
N-(4-fluorobenzenesulfonyl)-L-prolyl-L-4-(1,1-dioxothiomorpholin-4-ylcarbonyloxy)phenylalanine tert-butyl ester
N-(4-fluorobenzenesulfonyl)-L-prolyl-L-4-(thiomorpholin-4-ylcarbonyloxy)phenylalanine tert-butyl ester
N-(4-fluorobenzenesulfonyl)-L-prolyl-L-4-(morpholin-4-ylcarbonyloxy)phenylalanine tert-butyl ester
N-(4-fluorobenzenesulfonyl)-L-(5,5-dimethyl)thiaprolyl-L-4-(N,N-dimethylcarbamyloxy)phenylalanine
N-(4-fluorobenzenesulfonyl)-L-(1,1-dioxothiamorpholin-3-carbonyl)-L-4-(morpholin-4-ylcarbonyloxy)phenylalanine tert-butyl ester
N-(4-trifluoromethoxybenzenesulfonyl)-L-prolyl-L-4-(N,N-dimethylcarbamyloxy)phenylalanine tert-butyl ester
N-(toluene-4-sulfonyl)-L-(1,1-dioxothiamorpholin-3-carbonyl)-L-4-(N,N-dimethylcarbamyloxy)phenylalanine iso-propyl ester
3-[N-(toluene-4-sulfonyl)-N-methylamino]-1-[1-tert-butyloxycarbonyl-2-(N,N-dimethylcarbamyloxy)phenylethyl]azetidin-2-one
N-(4-fluorobenzenesulfonyl)-L-(1,1-dioxo-5,5-dimethyl)thiaprolyl-L-4-(N,N-dimethylcarbamyloxy)phenylalanine tert-butyl ester
N-(toluene-4-sulfonyl)-L-(1,1-dioxo-5,5-dimethyl)thiaprolyl-L-4-(N,N-dimethylcarbamyloxy)phenylalanine iso-propyl ester
N-(toluene-4-sulfonyl)-L-(1,1-dioxothiamorpholin-3-carbonyl)-L-4-(morpholin-4-ylcarbonyloxy)phenylalanine
N-(4-fluorobenzenesulfonyl)-L-(5,5-dimethyl)thiaprolyl-L-4-(N,N-dimethylcarbamyloxy)phenylalanine
N-(pyrimidine-2-sulfonyl)-L-prolyl-L-4-(N,N-dimethylcarbamyloxy)phenylalanine
N-(toluene-4-sulfonyl)-L-(1,1-dioxothiamorpholin-3-carbonyl)-L-4-(4-methylpiperazin-1-ylcarbonyloxy)phenylalanine tert-butyl ester
3-[N-(toluene-4-sulfonyl)-N-methylamino]-1-[1-carboxy-2-(N,N-dimethylcarbamyloxy)phenylethyl]azetidin-2-one
N-(1-methylpyrazole-4-sulfonyl)-L-prolyl-L-4-(4-methylpiperazin-1-ylcarbonyloxy)phenylalanine tert-butyl ester
N-(4-fluorobenzenesulfonyl)-L-(1,1-dioxo)thiaprolyl-L-4-(N,N-dimethylcarbamyloxy)phenylalanine
N-(toluene-4-sulfonyl)-L-prolyl-L-4-(isonipecotoyloxy)phenylalanine tert-butyl ester
N-(toluene-4-sulfonyl)-L-prolyl-L-4-(1,1-dioxothiomorpholin-4-ylcarbonyloxy)phenylalanine tert-butyl ester
N-(toluene-4-sulfonyl)-L-prolyl-L-4-(thiomorpholin-4-ylcarbonyloxy)phenylalanine tert-butyl ester
N-(toluene-4-sulfonyl)-L-prolyl-L-4-(pyrrolidin-1-ylcarbonyloxy)phenylalanine tert-butyl ester
N-(4-fluorobenzenesulfonyl)-L-thiaprolyl-L-4-(N,N-dimethylcarbamyloxy)phenylalanine tert-butyl ester
N-(4-fluorobenzenesulfonyl)-L-(1,1-dioxo)thiaprolyl-L-4-(N,N-dimethylcarbamyloxy)phenylalanine tert-butyl ester
N-(2,5-dichlorothiophene-3-sulfonyl)-L-prolyl-L-4-(N,N-dimethylcarbamyloxy)phenylalanine tert-butyl ester
N-(4-acetamidobenzenesulfonyl)-L-prolyl-L-4-(N,N-dimethylcarbamyloxy)phenylalanine tert-butyl ester
N-(4-tert-butylbenzenesulfonyl)-L-(1,1-dioxothiamorpholin-3-carbonyl)-L-4-(N,N-dimethylcarbamyloxy)phenylalanine tert-butyl ester
N-(pyridine-2-sulfonyl)-L-prolyl-L-4-(N,N-dimethylcarbamyloxy)phenylalanine
N-(2-fluorobenzenesulfonyl)-L-(1,1-dioxothiamorpholin-3-carbonyl)-L-4-(N,N-dimethylcarbamyloxy)phenylalanine tert-butyl ester
N-(3-fluorobenzenesulfonyl)-L-(1,1-dioxothiamorpholin-3-carbonyl)-L-4-(N,N-dimethylcarbamyloxy)phenylalanine tert-butyl ester
N-(2,4-difluorobenzenesulfonyl)-L-(1,1-dioxothiamorpholin-3-carbonyl)-L-4-(N,N-dimethylcarbamyloxy)phenylalanine tert-butyl ester
N-(4-acetamidobenzenesulfonyl)-L-prolyl-L-4-(N,N-dimethylcarbamyloxy)phenylalanine
N-(4-trifluoromethoxybenzenesulfonyl)-L-prolyl-L-4-(N,N-dimethylcarbamyloxy)phenylalanine
N-(4-fluorobenzenesulfonyl)-L-(5,5-dimethyl)thiaprolyl-L-4-(N,N-dimethylcarbamyloxy)phenylalanine tert-butyl ester
N-(4-cyanobenzenesulfonyl)-L-prolyl-L-4-(N,N-dimethylcarbamyloxy)phenylalanine
N-(toluene-4-sulfonyl)-L-(3,3-dimethyl)prolyl-L-4-(N,N-dimethylcarbamyloxy)phenylalanine tert-butyl ester
N-(toluene-4-sulfonyl)-L-(3,3-dimethyl)prolyl-L-4-(N,N-dimethylcarbamyloxy)phenylalanine isopropyl ester
N-(1-methylpyrazole-4-sulfonyl)-L-prolyl-L-4-(N,N-dimethylcarbamyloxy)phenylalanine iso-propyl ester
N-(1-methylpyrazole-4-sulfonyl)-L-(5,5-dimethyl)thiaprolyl-L-4-(N,N-dimethylcarbamyloxy)phenylalanine tert-butyl ester
N-(1-methylpyrazole-4-sulfonyl)-L-(5,5-dimethyl)thiaprolyl-L-4-(N,N-dimethylcarbamyloxy)phenylalanine
N-(toluene-4-sulfonyl)-L-prolyl-L-4-(N-(1,4-dioxa-8-azaspiro[4.5]decan-8-yl)carbonyloxy)phenylalanine ethyl ester
N-(toluene-4-sulfonyl)-L-prolyl-L-4-(N-(1,4-dioxa-8-azaspiro[4.5]decan-8-yl)carbonyloxy)phenylalanine
N-(toluene-4-sulfonyl)-L-prolyl-L-4-(4'-acetylpiperazin-1-ylcarbonyloxy)phenylalanine
N-(toluene-4-sulfonyl)-L-prolyl-L-4-(4'-methanesulfonylpiperazin-1-ylcarbonyloxy)phenylalanine
N-(toluene-4-sulfonyl)-L-prolyl-L-4-(4'-phenylpiperazin-1-ylcarbonyloxy)phenylalanine
N-(toluene-4-sulfonyl)-L-prolyl-L-4-(piperazin-1-ylcarbonyloxy)phenylalanine tert-butyl ester
N-(toluene-4-sulfonyl)-L-prolyl-L-4-(4'-methanesulfonylpiperazin-1-ylcarbonyloxy)phenylalanine tert-butyl ester
N-(toluene-4-sulfonyl)-L-prolyl-L-4-(N,N-dimethylcarbamyloxy)phenylalanine (N'-tert-butoxycarbonyl-2-amino-2-methylpropyl)ester
N-(toluene-4-sulfonyl)-L-prolyl-L-4-(4'-acetylpiperazin-1-ylcarbonyloxy)phenylalanine tert-butyl ester
N-(toluene-4-sulfonyl)-L-prolyl-L-4-(4'-hydroxypiperidin-1-ylcarbonyloxy)phenylalanine tert-butyl ester N-(toluene-4-sulfonyl)-L-prolyl-L-4-(N-(2'-(morpholin-4'-yl)ethyl)carbamyloxy)phenylalanine tert-butyl ester
N-(toluene-4-sulfonyl)-L-prolyl-L-4-(N-(1,4-dioxa-8-azaspiro[4.5]decan-8-yl)carbonyloxy)phenylalanine tert-butyl ester
N-(toluene-4-sulfonyl)-L-prolyl-L-4-(N-(2'-hydroxyethyl)-N-methylcarbamyloxy)phenylalanine tert-butyl ester
N-(toluene-4-sulfonyl)-L-prolyl-4-(4'-(2-hydroxyethyl)piperazin-1-ylcarbonyloxy)-L-phenylalanine tert-butyl ester
N-(toluene-4-sulfonyl)-L-prolyl-L-4-(N-(2'-formyloxyethyl)-N-methylcarbamyloxy)phenylalanine
N-(toluene-4-sulfonyl)-L-prolyl-L-4-(N-(2'-hydroxyethyl)-N-methylcarbamyloxy)phenylalanine isopropyl ester
N-(toulene-4-sulfonyl)-L-prolyl-L-4-(N-(methoxycarbonylmethyl)carbamyloxy)phenylalanine tert-butyl ester
N-(1-methylpyrazole-4-sulfonyl)-L-(5,5-dimethyl)thiaprolyl-L-(4-N,N-dimethylcarbamyloxy)phenylalanine isopropyl ester
N-(toluene-4-sulfonyl)-L-prolyl-L-4-(4'-methoxypiperidin-1-ylcarbonyloxy)phenylalanine isopropyl ester
N-(toluene-4-sulfonyl)-L-prolyl-L-4-(4'-methoxypiperidin-1-ylcarbonyloxy)phenylalanine
N-(toluene-4-sulfonyl)-L-4-oxoprolyl-L-4-(N,N-dimethylcarbamyloxy)phenylalanine tert-butyl ester
N-(toluene-4-sulfonyl)-L-trans-4-hydroxyprolyl-L-4-(N,N-dimethylcarbamyloxy)phenylalanine tert-butyl ester
N-(3-fluorobenzenesulfonyl)-L-prolyl-L-4-(N,N-dimethylcarbamyloxy)phenylalanine tert-butyl ester
N-(morpholino-sulfonyl)-L-prolyl-L-(4-N,N-dimethylcarbamyloxy)phenylalanine tert-butyl ester
N-(morpholino-sulfonyl)-L-prolyl-L-(4-N,N-dimethylcarbamyloxy)phenylalanine
N-(1-methylpyrazole-4-sulfonyl)-L-(1,1-dioxothiamorpholin-3-carbonyl)-L-4-(N,N-dimethylcarbamyloxy)phenylalanine tert-butyl ester
N-(2-fluorobenzenesulfonyl)-L-(1,1-dioxothiamorpholin-3-carbonyl)-L-4-(N,N-dimethylcarbamyloxy)phenylalanine
N-(2,4-difluorobenzenesulfonyl)-L-(1,1-dioxothiamorpholin-3-carbonyl)-L-4-(N,N-dimethylcarbamyloxy)phenylalanine
N-(toluene-4-sulfonyl)-L-(thiamorpholin-3-carbonyl)-L-4-(N,N-dimethylcarbamyloxy)phenylalanine
N-(pyridine-3-sulfonyl)-L-(5,5-dimethyl-thiaprolyl-L-4-(N,N-dimethylcarbamyloxy)phenylalanine isopropyl ester
N-(3-fluorobenzenesulfonyl)-L-(1,1-dioxothiamorpholin-3-carbonyl)-L-4-(N,N-dimethylcarbamyloxy)phenylalanine
N-(1-methylpyrazole-4-sulfonyl)-L-(1,1-dioxothiamorpholin-3-carbonyl)-L-4-(N,N-dimethylcarbamyloxy)phenylalanine
N-(4-tert-butylbenzenesulfonyl)-L-(1,1-dioxothiamorpholin-3-carbonyl)-L-4-(N,N-dimethylcarbamyloxy)phenylalanine
N-(toluene-4-sulfonyl)-(3,3-dimethyl)prolyl-L-4-(N,N-dimethylcarbamyloxy)phenylalanine
N-(2,5-dichlorothiophene-3-sulfonyl)-L-prolyl-L-4-(N,N-dimethylcarbamyloxy)phenylalanine
N-(4-methoxybenzenesulfonyl)-L-prolyl-L-4-(N,N-dimethylcarbamyloxy)phenylalanine
N-(4-methoxybenzenesulfonyl)-L-prolyl-L-4-(N,N-dimethylcarbamyloxy)phenylalanine isopropyl ester
N-(toluene-4-sulfonyl)-L-(1-oxo-thiomorpholin-3-carbonyl)-L-4-(N,N-dimethylcarbamyloxy)phenylalanine
N-(toluene-4-sulfonyl)-L-(1-oxo-thiomorpholin-3-carbonyl)-L-4-(N,N-dimethylcarbamyloxy)phenylalanine tert-butyl ester
N-(3,4-difluorobenzenesulfonyl)-L-prolyl-4-(N,N-dimethylcarbamyloxy)phenylalanine isopropyl ester
N-(3,4-difluorobenzenesulfonyl)-L-prolyl-4-(N,N-dimethylcarbamyloxy)phenylalanine
N-(3,4-difluorobenzenesulfonyl)-L-(1,1-dioxothiamorpholin-3-carbonyl)-L-4-(N,N-dimethylcarbamyloxy)phenylalanine tert-butyl ester
N-(3,4-difluorobenzenesulfonyl)-L-(1,1-dioxothiamorpholin-3-carbonyl)-L-4-(N,N-dimethylcarbamyloxy)phenylalanine
N-(toluene-4-sulfonyl)-L-(5,5-dimethyl)thiaprolyl-L-(thiomorpholin-4-ylcarbonyloxy)phenylalanine tert-butyl ester
N-(toluene-4-sulfonyl)-L-(5,5-dimethyl)thiaprolyl-L-(thiomorpholin-4-ylcarbonyloxy)phenylalanine
N-(1-methylpyrazole-4-sulfonyl)-L-(5,5-dimethyl)thiaprolyl-L-4-(N,N-dimethylcarbamyloxy)phenylalanine ethyl ester
N-(pyridine-3-sulfonyl)-L-(5,5-dimethyl)thiaprolyl-L-4-(N,N-dimethylcarbamyloxy)phenylalanine
N-(pyridine-2-sulfonyl)-L-prolyl-L-4-(N,N-dimethylcarbamyloxy)phenylalanine isopropyl ester
N-(pyridine-2-sulfonyl)-L-prolyl-L-4-(N,N-dimethylcarbamyloxy)phenylalanine
N-(pyridine-2-sulfonyl)-L-(5,5-dimethyl)thiaprolyl-L-4-(N,N-dimethylcarbamyloxy)phenylalanine isopropyl ester
N-(pyridine-2-sulfonyl)-L-(5,5-dimethyl)thiaprolyl-L-4-(N,N-dimethylcarbamyloxy)phenylalanine
N-(toluene-4-sulfonyl)-L-(thiamorpholin-3-carbonyl)-L-4-(N,N-dimethylcarbamyloxy)phenylalanine isopropyl ester
N-(3-fluorobenzenesulfonyl)-L-(5,5-dimethyl)thiaprolyl-L-4-(N,N-dimethylcarbamyloxy)phenylalanine isopropyl ester
N-(2-fluorobenzenesulfonyl)-L-(5,5-dimethyl)thiaprolyl-L-4-(N,N-dimethylcarbamyloxy)phenylalanine isopropyl ester
N-(3,4-difluorobenzenesulfonyl)-L-(5,5-dimethyl)thiaprolyl-L-4-(N,N-dimethylcarbamyloxy)phenylalanine isopropyl ester
N-(3,5-difluorobenzenesulfonyl)-L-(5,5-dimethyl)thiaprolyl-L-4-(N,N-dimethylcarbamyloxy)phenylalanine isopropyl ester
N-(2,4-difluorobenzenesulfonyl)-L-(5,5-dimethyl)thiaprolyl-L-4-(N,N-dimethylcarbamyloxy)phenylalanine isopropyl ester
N-(4-chlorobenzenesulfonyl)-L-(5,5-dimethyl)thiaprolyl-L-4-(N,N-dimethylcarbamyloxy)phenylalanine isopropyl ester
N-(3-chlorobenzenesulfonyl)-L-(5,5-dimethyl)thiaprolyl-L-4-(N,N-dimethylcarbamyloxy)phenylalanine isopropyl ester
N-(2-chlorobenzenesulfonyl)-L-(5,5-dimethyl)thiaprolyl-L-4-(N,N-dimethylcarbamyloxy)phenylalanine isopropyl ester
N-(3,4-dichlorobenzenesulfonyl)-L-(5,5-dimethyl)thiaprolyl-L-4-(N,N-dimethylcarbamyloxy)phenylalanine isopropyl ester
N-(3,5-dichlorobenzenesulfonyl)-L-(5,5-dimethyl)thiaprolyl-L-4-(N,N-dimethylcarbamyloxy)phenylalanine isopropyl ester
N-(3-chlorobenzenesulfonyl)-L-(1,1-dioxothiamorpholin-3-carbonyl)-L-4-(N,N-dimethylcarbamyloxy)phenylalanine tert-butyl ester
N-(3,4-dichlorobenzenesulfonyl)-L-(1,1-dioxothiamorpholin-3-carbonyl)-L-4-(N,N-dimethylcarbamyloxy)phenylalanine tert-butyl ester
N-(4-methoxybenzenesulfonyl)-L-(5,5-dimethyl)thiaprolyl-L-4-(N,N-dimethylcarbamyloxy)phenylalanine isopropyl ester N-(3-methoxybenzenesulfonyl)-L-(5,5-dimethyl)thiaprolyl-L-4-(N,N-dimethylcarbamyloxy)phenylalanine isopropyl ester
N-(2-methoxybenzenesulfonyl)-L-(5,5-dimethyl)thiaprolyl-L-4-(N,N-dimethylcarbamyloxy)phenylalanine isopropyl ester
N-(3,4-dimethoxybenzenesulfonyl)-L-(5,5-dimethyl)thiaprolyl-L-4-(N,N-dimethylcarbamyloxy)phenylalanine isopropyl ester
N-(2,4-difluorobenzenesulfonyl)-L-(thiamorpholin-3-carbonyl)-L-4-(N,N-dimethylcarbamyloxy)phenylalanine isopropyl ester
N-(3,4-dichlorobenzenesulfonyl)-L-(1,1-dioxothiamorpholin-3-carbonyl)-L-4-(N,N-dimethylcarbamyloxy)phenylalanine
N-(3-chlorobenzenesulfonyl)-L-(1,1-dioxothiamorpholin-3-carbonyl)-L-4-(N,N-dimethylcarbamyloxy)phenylalanine
N-(3-chloro-4-fluorobenzenesulfonyl)-L-(1,1-dioxothiamorpholin-3-carbonyl)-L-4-(N,N-dimethylcarbamyloxy)phenylalanine tert-butyl ester
N-(1-methylpyrazole-4-sulfonyl)-L-(thiamorpholin-3-carbonyl)-L-4-(N,N-dimethylcarbamyloxy)phenylalanine tert-butyl ester
N-(3,4-difluorobenzenesulfonyl)-L-(thiamorpholin-3-carbonyl)-L-4-(N,N-dimethylcarbamyloxy)phenylalanine tert-butyl ester
N-(toluene-4-sulfonyl)-L-(5,5-dimethyl)thioprolyl-L-(thiomorpholin-4-ylcarbonyloxy)phenylalanine isopropyl ester
N-(3,4-difluorobenzenesulfonyl)-L-(thiamorpholin-3-carbonyl)-L-4-(N,N-dimethylcarbamyloxy)phenylalanine
N-(2,5-dichlorothiophene-3-sulfonyl)-L-(5,5-dimethyl)thiaprolyl-L-4-(N,N-dimethylcarbamyloxy)phenylalanine isopropyl ester
N-(1-methylpyrazole-4-sulfonyl)-L-(5,5-dimethyl)thiaprolyl-L-4-(thiomorpholin-4-ylcarbonyloxy)phenylalanine isopropyl ester
N-(8-quinolinesulfonyl)-L-prolyl-L-4-(N,N-dimethylcarbamyloxy)phenylalanine isopropyl ester
N-(8-quinolinesulfonyl)-L-prolyl-L-4-(N,N-dimethylcarbamyloxy)phenylalanine
N-(8-quinolinesulfonyl)-L-(5,5-dimethyl)thiaprolyl-L-4-(N,N-dimethylcarbamyloxy)phenylalanine isoproplyl ester
N-(8-quinolinesulfonyl)-L-(5,5-dimethyl)thiaprolyl-L-4-(N,N-dimethylcarbamyloxy)phenylalanine
N-(toluene-4-sulfonyl)-L-prolyl-L-4-(4-phenylpiperazin-1-ylcarbonyloxy)phenylalanine tert-butyl ester
N-(toluene-4-sulfonyl)-L-prolyl-L-4-(4'-(ethoxycarbonyl)piperidin-1-ylcarbonyloxy)phenylalanine tert-butyl ester
N-(pyridine-3-sulfonyl)-L-(5,5-dimethyl)thiaprolyl-L-4-(N,N-dimethylcarbamyloxy)phenylalanine tert-butyl ester
N-(3-sulfonamido-4-chloro-benzenesulfonyl)-L-prolyl-L-4-(N,N-dimethylcarbamyloxy)phenylalanine isopropyl ester
N-(toluene-4-sulfonyl)-L-(1-oxothiomorpholin-3-carbonyl)-L-4-(N,N-dimethylcarbamyloxy)phenylalanine isopropyl ester
N-(2,4-difluorobenzenefulfonyl)-L-(1-oxothiomorpholin-3-carbonyl)-L-4-(N,N-dimethylcarbamyloxy)phenylalanine tert-butyl ester
N-(1-methylpyrazole-4-sulfonyl)-L-(5,5-dimethyl)thiaprolyl-L-4-(N,N-dimethylcarbamyloxy)phenylalanine 2,2-dimethylpropyl ester
N-(pyridine-3-sulfonyl)-L-(5,5-dimethyl)thiaprolyl-L-4-(N,N-dimethylcarbamyloxy)phenylalanine 2,2-dimethylpropyl ester
N-(1-methylpyrazole-4-sulfonyl)-L-(5,5-dimethyl)thiaprolyl-L-4-(N,N-dimethylcarbamyloxy)phenylalanine cyclopropylmethyl ester
N-(1-methylpyrazole-4-sulfonyl)-L-(5,5-dimethyl)thiaprolyl-L-4-(N,N-dimethylcarbamyloxy)phenylalanine methyl ester
N-(pyridine-3-sulfonyl)-L-(5,5-dimethyl)thiaprolyl-L-4-(N,N-dimethylcarbamyloxy)phenylalanine ethyl ester
N-(pyridine-3-sulfonyl)-L-(5,5-dimethyl)thiaprolyl-L-4-(N,N-dimethylcarbamyloxy)phenylalanine cyclopropylmethyl ester
N-(1-methylpyrazole-4-sulfonyl)-L-(5,5-dimethyl)thiaprolyl-L-4-(N,N-dimethylcarbamyloxy)phenylalanine 2-methoxyphenyl ester
N-(1-methylpyrazole-4-sulfonyl)-L-(5,5-dimethyl)thiaprolyl-L-4-(N,N-dimethylcarbamyloxy)phenylalanine n-butyl ester
N-(1-methylpyrazole-4-sulfonyl)-L-(5,5-dimethyl)thiaprolyl-L-4-(N,N-dimethylcarbamyloxy)phenylalanine n-propyl ester
N-(1-methylpyrazole-4-sulfonyl)-L-(5,5-dimethyl)thiaprolyl-L-4-(N,N-dimethylcarbamyloxy)phenylalanine 2,2-dimethylpropionyloxymethyl ester
N-(toluene-4-sulfonyl)-L-prolyl-L-4-(N-(4'-(2'-aminoethyl)morpholino)carbamyloxy)phenylalanine
N-(toluene-4-sulfonyl)-L-prolyl-L-4-[4-(carboxy)piperidin-1-ylcarbonyloxy]phenylalanine
N-(toluene-4-sulfonyl)-L-prolyl-L-4-(N,N-bis-(2-hydroxyethyl)carbamyloxy)phenylalanine isopropyl ester
N-(toluene-4-sulfonyl)-L-prolyl-L-4-[3-(hydroxymethyl)piperidin-1-ylcarbonyloxy]phenylalanine isopropyl ester
N-(toluene-4-sulfonyl)-L-prolyl-L-4-(4-trifluoromethanesulfonylpiperazin-1-ylcarbonyloxy)phenylalanine tert-butyl ester
N-(4-(N-phenylurea)benzenesulfonyl)-L-prolyl-L-4-(N,N-dimethylcarbamyloxy)phenylalanine tert-butyl ester
N-(2-trifluoroacetyl-1,2,3,4-tetrahydroisoquinolin-7-sulfonyl)-L-prolyl-L-4-(N,N-dimethylcarbamyloxy)phenylalanine isopropyl ester
N-(1-methylpyrazole-3-sulfonyl)-L-(5,5-dimethyl)thiaprolyl-L-4-(N,N-dimethylcarbamyloxy)phenylalanine isopropyl ester
N-(1-methylpyrazole-3-sulfonyl)-L-(5,5-dimethyl)thiaprolyl-L-4-(N,N-dimethylcarbamyloxy)phenylalanine
N-(pyridine-4-sulfonyl)-L-(5,5-dimethyl)thiaprolyl-L-4-(N,N-dimethylcarbamyloxy)phenylalanine isopropyl ester
N-(pyridine-4-sulfonyl)-L-(5,5-dimethyl)thiaprolyl-L-4-(N,N-dimethylcarbamyloxy)phenylalanine
N-(toluene-4-sulfonyl)-L-(5,5-dimethyl)thiaprolyl-L-4-(N-methyl-N-(2-dimethylaminoethyl)carbamyloxy)phenylalanine tert-butyl ester
N-(toluene-4-sulfonyl)-L-prolyl-L-4-(N-methyl-N-(2-dimethylaminoethyl)carbamyloxy)phenylalanine tert-butyl ester
N-(toluene-4-sulfonyl)-L-(5,5-dimethyl)thiapropyl-L-4-(N-methyl-N-(2-dimethylaminoethyl)carbamyloxy)phenylalanine
N-(toluene-4-sulfonyl)-L-prolyl-L-4-(N-methyl-N-(2-dimethylaminoethyl)carbamyloxy)phenylalanine
N-(4-fluorobenzenesulfonyl)-L-(5,5-dimethyl)thiaprolyl-L-3-chloro-4-(4-methylpiperazin-1-ylcarbonyloxy)phenylalanine tert-butyl ester
N-(4-fluorobenzenesulfonyl)-L-(5,5-dimethyl)thiaprolyl-L-3-chloro-4-(N,N-dimethycarbamyloxy)phenylalanine
N-(4-fluorobenzenesulfonyl)-L-(5,5-dimethyl)thiaprolyl-L-3-chloro-4-(thiomorpholin-4-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine isopropyl ester N-(4-fluorobenzenesulfonyl)-L-(5,5-dimethyl)thiaprolyl-L-3-chloro-4-(N,N-dimethylcarbamyloxy)]phenylalanine isopropyl ester N-(toluene-4-sulfonyl)-L-(5,5-dimethyl)thiaprolyl-L-3-chloro-4-(N,N-dimethylcarbamyloxy)phenylalanine isopropyl ester N-(4-fluorobenzenesulfonyl)-L-(5,5-dimethyl)thiaprolyl-L-3-chloro-4-(4-methylpiperazin-1-ylcarbonyloxy)]phenylalanine isopropyl ester N-(toluene-4-sulfonyl)-L-prolyl-L-3-chloro-4-(N,N-dimethylcarbamyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine tert-butyl ester N-(4-nitrobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine isopropyl ester N-(toluene-4-sulfonyl)-L-prolyl-L-4-(thiomorpholin-4-ylcarbonyloxy)phenylalanine isopropyl ester N-(toluene-4-sulfonyl)-L-prolyl-L-4-(4-phenylcarbamylpiperazin-1-ylcarbonyloxy)phenylalanine isopropyl ester N-(toluene-4-sulfonyl)-L-prolyl-L-4-(4-phenylcarbamylpiperazin-1-ylcarbonyloxy)phenylalanine N-(1-n-butylpyrazole-4-sulfonyl)-L-(5,5-dimethyl)thiaprolyl-L-4-(N,N-dimethylcarbamyloxy)phenylalanine isopropyl ester N-(toluene-4-sulfonyl)-L-prolyl-L-4-(pyridin-4-ylcarbonyl)piperazin 1-ylcarbonyloxy)phenylalanine isopropyl ester N-(toluene-4-sulfonyl)-L-4-oxoprolyl-L-4-(N,N-dimethylcarbamyloxy)phenylalanine N-(toluene-4-sulfonyl)-L-trans-4-hydroxyprolyl-L-4-(N,N-dimethylcarbamyloxy)phenylalanine N-(4-cyanobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine N-(toluene-4-sulfonyl)-L-4-oxoprolyl-L-4-(4-methylpiperazin-1-ylcarbonyloxy)phenylalanine tert-butyl ester N-(toluene-4-sulfonyl)-L-prolyl-L-4-[3-(hydroxymethyl)piperidin-1-ylcarbonyloxy]phenylalanine N-(toluene-4-sulfonyl)-L-(4,4-difluoro)prolyl-L-4-(N,N-dimethylcarbamyloxy)phenylalanine isopropyl ester N-(toluene-4-sulfonyl)-L-(4,4-difluoro)prolyl-L-4-(N,N-dimethylcarbamyloxy)phenylalanine N-(toluene-4-sulfonyl)-L-prolyl-L-(4-benzoylpiperazin-1-ylcarbonyloxy)phenylalanine isopropyl ester N-(1-methyl-1H-imidazole-4-sulfonyl)-L-prolyl-L-4-(N,N-dimethylcarbamyloxy)phenylalanine isopropyl ester N-(toluene-4-sulfonyl)-L-4-(thiomorpholin-4-ylcarbonyloxy)prolyl-L-4-(thiomorpholin-4-ylcarbonyloxy)phenylalanine N-(4-cyanobenzenesulfonyl)-L-prolyl-L-4-(thiomorpholin-4-ylcarbonyloxy)phenylalanine isopropyl ester N-(4-amidinobenzenesulfonyl)-L-prolyl-L-4-(N,N-dimethylcarbamyloxy)phenylalanine methyl ester N-(toluene-4-sulfonyl)-L-4-oxoprolyl-L-4-(thiomorpholin-4-ylcarbonyloxy)phenylalanine tert-butyl ester N-(toluene-4-sulfonyl)-L-4-hydroxyprolyl-L-4-(thiomorpholin-4-ylcarbonyloxy)phenylalanine N-(toluene-4-sulfonyl)-L-prolyl-L-(4-benzoylpiperazin-1-ylcarbonyloxy)phenylalanine N-(4-amidinobenzenesulfonyl)-L-prolyl-L-4-(thiomorpholin-4-ylcarbonyloxy)phenylalanine methyl ester N-(3-fluorobenzenesulfonyl)-L-prolyl-L-4-(N,N-dimethylcarbonyloxy)phenylalanine N-(toluene-4-sulfonyl)-L-prolyl-L-4-[N-methyl-N-(2-(N'-methyl-N'-toluenesulfonyl-amino)ethyl)carbamyloxy]phenylalanine isopropyl ester N-(toluene-4-sulfonyl)-L-prolyl-L-4-[N-(2-(N'-phenylaminocarbonyloxy)ethyl)carbamyloxy)]phenylalanine isopropyl ester N-(4-fluorobenzenesulfonyl)-L-4-(trans-hydroxy)prolyl-L-4-(N,N-dimethylcarbamyloxy)phenylalanine isopropyl ester N-(4-fluorobenzenesulfonyl)-L-4-(trans-hydroxy)prolyl-L-4-(N,N-dimethylcarbamyloxy)phenylalanine tert-butyl ester N-(4-amidinobenzenesulfonyl)-L-prolyl-L-4-(N,N-dimethylcarbamyloxy)phenylalanine N-(toluene-4-sulfonyl)-L-(pyrazin-3-carbonyl)-L-4-(N,N-dimethylcarbamyloxy)phenylalanine tert-butyl ester N-(4-fluorobenzenesulfonyl)-L-(5,5-dimethyl)thiaprolyl-L-4-(2-hydroxymethylpyrrolidin-1-ylcarbonyloxy)phenylalanine tert-butyl ester N-(4-fluorobenzenesulfonyl)-L-(5,5-dimethyl)thiaprolyl-L-4-(2-hydroxymethylpyrrolidin-1-ylcarbonyloxy)phenylalanine N-(toluene-4-sulfonyl)-L-prolyl-L-4-(2-methoxycarbonylpyrrolidin-1-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine N-(4-fluorobenzenesulfonyl)-L-(5,5-dimethyl)thiaprolyl-L-4-(4-(2-pyridyl)piperazin-1-ylcarbonyloxy)]phenylalanine N-(4-fluorobenzenesulfonyl)-L-(5,5-dimethyl)thiaprolyl-L-4-(4-(2-pyridyl)piperazin-1-ylcarbonyloxy)]phenylalanine tert-butyl ester N-(toluene-4-sulfonyl)-L-(4-hydroxy)prolyl-L-4-(thiomorpholin-4-ylcarbonyloxy)phenylalanine tert-butyl ester N-(toluene-4-sulfonyl)-L-prolyl-L-4-(N,N-dimethylcarbamyloxy)phenylalanine 2-(2-methoxyethoxy)ethyl ester N-(4-fluorobenzenesulfonyl)-L-(5,5-dimethyl)thiaprolyl-L-4-(4-(2-pyrimidyl)piperazin-1-ylcarbonyloxy)]phenylalanine tert-butyl ester N-(4-fluorobenzenesulfonyl)-L-(5,5-dimethyl)thiaprolyl-L-3-fluoro-4-(N,N-dimethylcarbamyloxy)phenylalanine isopropyl ester N-(toluene-4-sulfonyl)-L-(1-methanesulfonylpyrazin-3-carbonyl)-L-4-(N,N-dimethylcarbamyloxy)phenylalanine tert-butyl ester N-(4-bromobenzenesulfonyl)-L-(5,5-dimethyl)thiaprolyl-L-4-(N,N-dimethylcarbamyloxy)phenylalanine tert-butyl ester N-(4-bromobenzenesulfonyl)-L-(5,5-dimethyl)thiaprolyl-L-4-(N,N-dimethylcarbamyloxy)phenylalanine N-(toluene-4-sulfonyl)-L-(4-hydroxy)prolyl-L-4-(4-methylpiperazin-1-ylcarbonyloxy)phenylalanine N-(4-fluorobenzenesulfonyl)-L-(5,5-dimethyl)thiaprolyl-L-4-(4-(2-pyrimidyl)piperazin-1-ylcarbonyloxy)]phenylalanine N-(4-fluorobenzenesulfonyl)-L-(5,5-dimethyl)thiaprolyl-L-4-(4-(2-pyridyl)piperazin-1-ylcarbonyloxy)]phenylalanine isopropyl ester N-(4-fluorobenzenesulfonyl)thiazolidinyl-2-carbonyl-L-4-(N,N-dimethylcarbamyloxy)phenylalanine N-(4-fluorobenzenesulfonyl)thiazolidinyl-2-carbonyl-L-4-(N,N-dimethylcarbamyloxy)phenylalanine tert-butyl ester N-(toluene-4-sulfonyl)-L-(4-oxo)prolyl-L-4-(thiomorpholin-4-ylcarbonyloxy)phenylalanine N-(toluene-4-sulfonyl)-L-(4-oxo)prolyl-L-4-(4-methylpiperazin-1-ylcarbonyloxy)phenylalanine N-(4-fluorobenzenesulfonyl)thiazolidinyl-2-carbonyl-L-4-(4-(2-pyridyl)piperazin-1-ylcarbonyloxy)]phenylalanine N-(4-nitrobenzenesulfonyl)-L-prolyl-L-4-(4-(2-pyridyl)piperazin-1-ylcarbonyloxy)]phenylalanine tert-butyl ester N-(4-fluorobenzenesulfonyl)thiazolidinyl-2-carbonyl-L-4-(4-(2-pyridyl)piperazin-1-ylcarbonyloxy)]phenylalanine tert-butyl ester N-(4-bromobenzenesulfonyl)-L-(5,5-dimethyl)thiaprolyl-L-4-(4-(2-pyridyl)piperazin-1-ylcarbonyloxy)]phenylalanine N-(toluene-4-sulfonyl)-L-prolyl-L-4-(4-(N-phenylthiocarbonyl)piperazin-1-ylcarbonyloxy)]phenylalanine isopropyl ester N-(4-fluorobenzenesulfonyl)thiazolidinyl-2-carbonyl-L-4-(4-methylhomopiperazin-1-ylcarbonyloxy)phenylalanine tert-butyl ester N-(toluene-4-sulfonyl)-L-4-(methanesulfonyloxy)prolyl-L-4-(N,N-dimethylcarbamyloxy)phenylalanine tert-butyl ester N-(4-aminocarbonylbenzenesulfonyl)-L-prolyl-L-4-(N,N-dimethylcarbamyloxy)phenylalanine N-(4-aminocarbonylbenzenesulfonyl)-L-prolyl-L-4-(thiomorpholin-4-ylcarbonyloxy)phenylalanine N-(4-amidinobenzenesulfonyl)-L-prolyl-L-4-(thiomorpholin-4-ylcarbonyloxy)phenylalanine N-(4-nitrobenzenesulfonyl)-L-prolyl-L-4-(4-(2-pyridyl)piperazin-1-ylcarbonyloxy)]phenylalanine N-(4-fluorobenzenesulfonyl)-L-(5,5-dimethyl)thiaprolyl-L-3-chloro-4-(4-(2-pyridyl)piperazin-1-ylcarbonyloxy)]phenylalanine ethyl ester N-(4-fluorobenzenesulfonyl)-L-(5,5-dimethyl)thiaprolyl-L-3-chloro-4-(4-(2-pyridyl)piperazin-1-ylcarbonyloxy)phenylalanine N-(4-fluorobenzenesulfonyl)thiazolidinyl-2-carbonyl-L-4-(4-methylhomopiperazin-1-ylcarbonyloxy)phenylalanine N-(1-methylpyrazole-3-sulfonyl)-L-(5,5-dimethyl)thiaprolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine isopropyl ester N-(-methylimidazole-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine N-(toluene-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin 1-ylcarbonyloxy)phenylalanine isopropyl ester N-(4-fluorobenzenesulfonyl)-L-prolyl-L-4-(4-(2-pyridyl)piperazin-1-ylcarbonyloxy)phenylalanine isopropyl ester N-(4-fluorobenzenesulfonyl)-L-prolyl-L-4-(4-(2-pyridyl)piperazin-1-ylcarbonyloxy)phenylalanine tert-butyl ester N-(toluene-4-sulfonyl)-L-(1-methanesulfonylpyrazin-3-carbonyl)-L-4-(N,N-dimethylcarbamyloxy)phenylalanine N-(toluene-4-sulfonyl)-L-4-(methanesulfonyloxy)prolyl-L-4-(N,N-dimethylcarbamyloxy)phenylalanine N-(4-bromobenzenesulfonyl)-L-(5,5-dimethyl)thiaprolyl-L-4-(4-(2-pyridyl)piperazin-1-ylcarbonyloxy)phenylalanine tert-butyl ester N-(4-trifluoromethoxybenzenesulfonyl)-L-(5,5-dimethyl)thiaprolyl-L-4-(N,N-dimethylcarbamyloxy)phenylalanine N-(4-trifluoromethoxybenzenesulfonyl)-L-(5,5-dimethyl)thiaprolyl-L-4-(N,N-dimethylcarbamyloxy)phenylalanine tert-butyl ester N-(4-trifluoromethoxybenzenesulfonyl)-L-(5,5-dimethyl)thiaprolyl-L-4-(4-(2-pyridyl)piperazin-1-ylcarbonyloxy)phenylalanine tert-butyl ester N-(4-fluorobenzenesulfonyl)-L-prolyl-L-4-(4-(2-pyridyl)piperazin-1-ylcarbonyloxy)phenylalanine N-(4-fluorobenzenesulfonyl)-L-(4-hydroxy)prolyl-L-4-(4-(2-pyridyl)piperazin-1-ylcarbonyloxy)phenylalanine N-(4-trifluoromethoxybenzenesulfonyl)-L-(5,5-dimethyl)thiaprolyl-L-4-(4-(2-pyridyl)piperazin-1-ylcarbonyloxy)phenylalanine N-(1-methylimidazole-4-sulfonyl)-L-prolyl-L-3-chloro-4-(N,N-dimethylcarbamyloxy)phenylalanine N-(1-methylimidazole-4-sulfonyl)-L-prolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine N-(1-methylimidazole-4-sulfonyl)-L-(5,5-dimethyl)thiaprolyl-L-4-(4-(2-pyridyl)piperazin-1-ylcarbonyloxy)phenylalanine N-(1-methylpyrazole-3-sulfonyl)-L-prolyl-L-4-(4-(2-pyridyl)piperazin-1-ylcarbonyloxy)phenylalanine N-(-methylpyrazole-3-sulfonyl)-L-prolyl-L-4-(4-(2-pyridyl)piperazin-1-ylcarbonyloxy)phenylalanine isopropyl ester N-(1-methylpyrazole-3-sulfonyl)-L-prolyl-L-4-(4-(2-pyridyl)piperazin-1-ylcarbonyloxy)phenylalanine tert-butyl ester N-(1-methylpyrazole-3-sulfonyl)-L-(5,5-dimethyl)thiaprolyl-L-4-(4-(2-pyridyl)piperazin-1-ylcarbonyloxy)phenylalanine tert-butyl ester N-(1-methylimidazole-4-sulfonyl)-L-prolyl-L-3-chloro-4-(4-(2-pyridyl)piperazin-1-ylcarbonyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine 2-phenoxyethyl ester N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine ethyl ester N-(3-chloro-1,5-dimethylpyrazole-3-sulfonyl)-L-(5,5-dimethyl)thiaprolyl-L-3-chloro-4-(4-(5-trifluoromethyl-2-pyridyl)piperazin-1-ylcarbonyloxy)phenylalanine and pharmaceutically acceptable salts thereof.

Preferred compounds of formula I and IA above include those set forth in Table 3 below:

TABLE 3

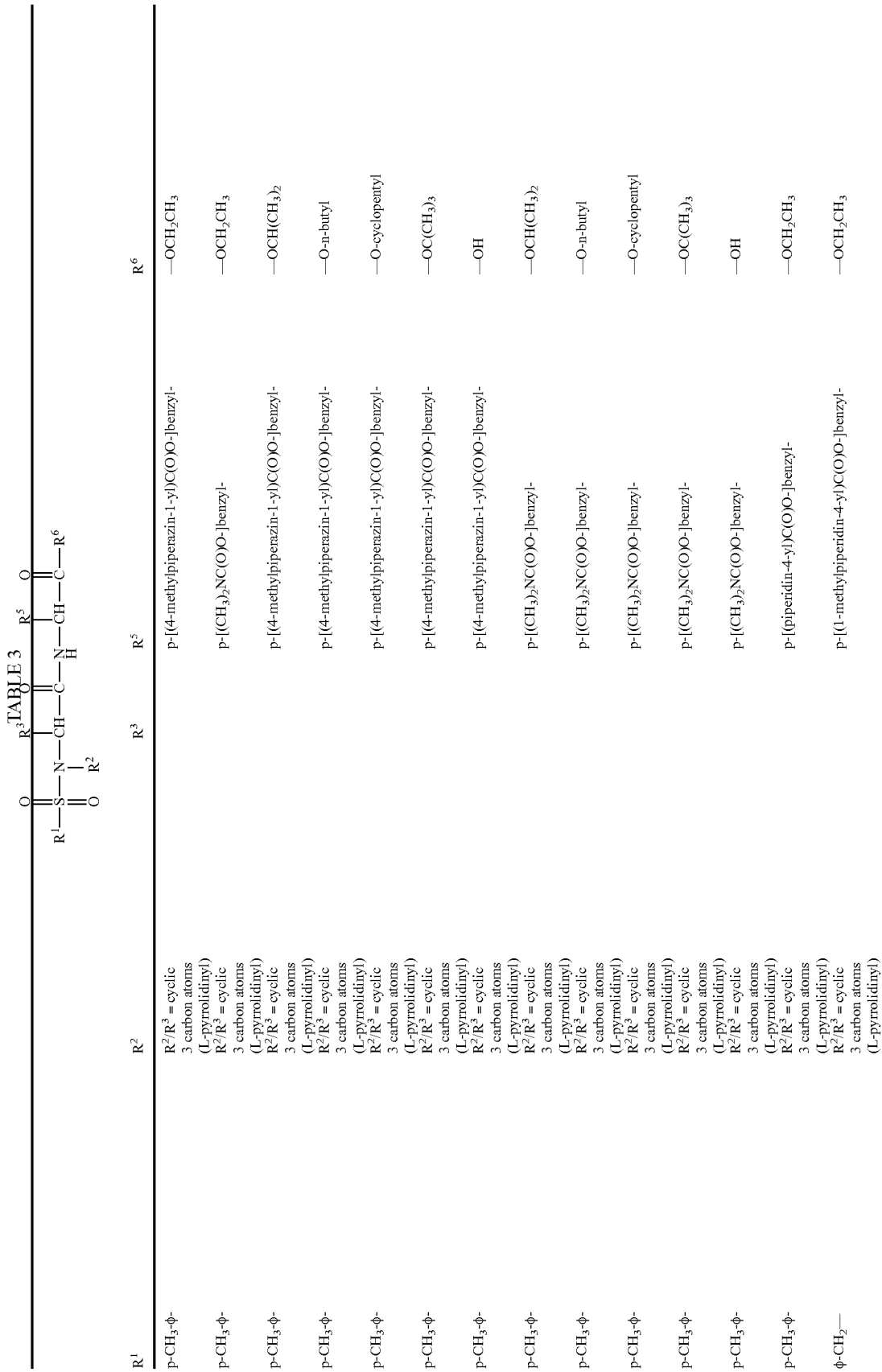

| R¹ | R² | R³ | R⁵ | R⁶ |
|---|---|---|---|---|
| p-CH₃-φ- | R²/R³ = cyclic 3 carbon atoms (L-pyrrolidinyl) | | p-[(4-methylpiperazin-1-yl)C(O)O-]benzyl- | —OCH₂CH₃ |
| p-CH₃-φ- | R²/R³ = cyclic 3 carbon atoms (L-pyrrolidinyl) | | p-[(CH₃)₂NC(O)O-]benzyl- | —OCH₂CH₃ |
| p-CH₃-φ- | R²/R³ = cyclic 3 carbon atoms (L-pyrrolidinyl) | | p-[(4-methylpiperazin-1-yl)C(O)O-]benzyl- | —OCH(CH₃)₂ |
| p-CH₃-φ- | R²/R³ = cyclic 3 carbon atoms (L-pyrrolidinyl) | | p-[(4-methylpiperazin-1-yl)C(O)O-]benzyl- | —O-n-butyl |
| p-CH₃-φ- | R²/R³ = cyclic 3 carbon atoms (L-pyrrolidinyl) | | p-[(4-methylpiperazin-1-yl)C(O)O-]benzyl- | —O-cyclopentyl |
| p-CH₃-φ- | R²/R³ = cyclic 3 carbon atoms (L-pyrrolidinyl) | | p-[(4-methylpiperazin-1-yl)C(O)O-]benzyl- | —OC(CH₃)₃ |
| p-CH₃-φ- | R²/R³ = cyclic 3 carbon atoms (L-pyrrolidinyl) | | p-[(4-methylpiperazin-1-yl)C(O)O-]benzyl- | —OH |
| p-CH₃-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(CH₃)₂NC(O)O-]benzyl- | —O-n-butyl |
| p-CH₃-φ- | R²/R³ = cyclic 3 carbon atoms (L-pyrrolidinyl) | | p-[(CH₃)₂NC(O)O-]benzyl- | —O-cyclopentyl |
| p-CH₃-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic 3 carbon atoms (L-pyrrolidinyl) | | p-[(piperidin-4-yl)C(O)O-]benzyl- | —OCH₂CH₃ |
| φ-CH₂— | R²/R³ = cyclic 3 carbon atoms (L-pyrrolidinyl) | | p-[(1-methylpiperidin-4-yl)C(O)O-]benzyl- | —OCH₂CH₃ |

TABLE 3-continued $$R^1-\underset{\underset{O}{\|}}{S}-\underset{\underset{R^2}{|}}{N}-CH-\underset{\underset{O}{\|}}{C}-N-CH-\underset{\underset{O}{\|}}{C}-R^6$$
$$\phantom{R^1-S-N-CH-C-N-}\phantom{xx}R^3\phantom{xx}H\phantom{xxxx}R^5$$

| R¹ | R² | R³ | R⁵ | R⁶ |
|---|---|---|---|---|
| φ-CH₂— | R²/R³ = cyclic 3 carbon atoms (L-pyrrolidinyl) | | p-[(4-methylpiperazin-1-yl)C(O)O-]benzyl- | —OH |
| p-CH₃-φ- | R²/R³ = cyclic 3 carbon atoms (L-pyrrolidinyl) | | m-[(CH₃)₂NC(O)O-]benzyl- | —OCH₂CH₃ |
| p-CH₃-φ- | R²/R³ = cyclic 3 carbon atoms (L-pyrrolidinyl) | | p-[(1-Boc-4-phenylpiperidin-4-yl)-C(O)O-]benzyl- | —OCH₂CH₃ |
| p-CH₃-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-CH₃-φ- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | | p-[(CH₃)₂NC(O)O-]benzyl- | —OH |
| p-CH₃-φ- | R²/R³ = cyclic —CH₂CH₂—SO₂—CH₂— (L-1,1-dioxothiomorpholin-3-yl) | | p-[(CH₃)₂NC(O)O-]benzyl- | —OH |
| p-CH₃-φ- | R²/R³ = cyclic —CH₂—S—C(CH₃)₂— (L-5,5-dimethylthiazolidin-4-yl) | | p-[(4-methylpiperazin-1-yl)C(O)O-]benzyl- | —OC(CH₃)₃ |
| p-CH₃-φ- | R²/R³ = cyclic —CH₂CH₂—SO₂—CH₂— (L-1,1-dioxothiomorpholin-3-yl) | | p-[(4-methylpiperazin-1-yl)C(O)O-]benzyl- | —OH |
| p-CH₃-φ- | CH₃— | H | p-[(CH₃)₂NC(O)O-]benzyl- | —OCH(CH₃)₂ |
| p-CH₃-φ- | CH₃— | H | p-[(CH₃)₂NC(O)O-]benzyl- | —OC(CH₃)₃ |
| p-CH₃-φ- | CH₃— | H | p-[(CH₃)₂NC(O)O-]benzyl- | —OH |
| 1-methylimidazol-4-yl | R²/R³ = cyclic 3 carbon atoms (L-pyrrolidinyl) | | p-[(CH₃)₂NC(O)O-]benzyl- | —OC(CH₃)₃ |
| p-NH₂-φ- | CH₃— | H | p-[(CH₃)₂NC(O)O-]benzyl- | —OC(CH₃)₃ |
| p-CH₃-φ- | R²/R³ = cyclic 3 carbon atoms (L-pyrrolidinyl) | | p-[(morpholin-4-yl)C(O)O-]benzyl- | —OC(CH₃)₃ |
| p-CH₃-φ- | | | p-[(morpholin-4-yl)C(O)O-]benzyl- | —OC(CH₃)₃ |

TABLE 3-continued $$R^1-\overset{O}{\underset{O}{S}}-\overset{}{\underset{R^2}{N}}-CH-\overset{O}{C}-\overset{}{\underset{H}{N}}-CH-\overset{O}{C}-R^6$$
$$\phantom{xxxxxxxxxxxxxxxxxxx}R^3\phantom{xxxx}R^5$$

| R¹ | R² | R³ | R⁵ | R⁶ |
|---|---|---|---|---|
| φ-CH₂— | R²/R³ = cyclic —CH₂—S—C(CH₃)₂— (L-5,5-dimethylthiazolidin-4-yl) | | p-[(CH₃)₂NC(O)O-]benzyl- | —OH |
| p-CH₃-φ- | R²/R³ = cyclic —CH₂CH₂—NH—CH₂— (L-piperazinyl) | | p-[(CH₃)₂NC(O)O-]benzyl- | —OH |
| φ-CH₂— | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| p-CH₃-φ- | R²/R³ = cyclic —CH₂CH₂—NH—CH₂— (L-piperazinyl) | | p-[(CH₃)₂NC(O)O-]benzyl- | —OC(CH₃)₃ |
| p-CH₃-φ- | R²/R³ = cyclic —CH₂CH₂—(Cbz)NHCH₂— [L-4-N—(Cbz)-piperazinyl] | | p-[(CH₃)₂NC(O)O-]benzyl- | —OC(CH₃)₃ |
| p-CH₃-φ- | CH₃— | H | p-[(piperidin-1-yl)C(O)O-]benzyl- | —OH |
| p-CH₃-φ- | R²/R³ = cyclic —CH₂CH₂—SO₂—CH₂— (L-1,1-dioxothiomorpholin-3-yl) | | p-[(morpholin-4-yl)C(O)O-]benzyl- | —OC(CH₃)₃ |
| p-CH₃-φ- | R²/R³ = cyclic —CH₂CH₂—SO₂—CH₂— (L-1,1-dioxothiomorpholin-3-yl) | | p-[(morpholin-4-yl)C(O)O-]benzyl- | —OH |
| 1-methylpyrazol-4-yl | R²/R³ = cyclic 3 carbon atoms (L-pyrrolidinyl) | | p-[(CH₃)₂NC(O)O-]benzyl- | —OC(CH₃)₃ |
| p-F-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | —CH₃ | H | p-[(4-methylpiperazin-1-yl)C(O)O-]benzyl- | —OC(CH₃)₃ |
| p-CH₃-φ- | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OC(CH₃)₃ |
| 1-methylpyrazol-4-yl | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—SO₂—C(CH₃)₂— (L-1,1-dioxo-5,5-dimethylthiazolidin-4-yl) | | p-[(CH₃)₂NC(O)O-]benzyl- | —OH |
| p-F-φ- | R²/R³ = cyclic 3 carbon atoms (L-pyrrolidinyl) | | p-[(CH₃)₂NC(O)O-]benzyl- | —OH |

TABLE 3-continued $$R^1-\overset{O}{\underset{O}{S}}-\overset{R^2}{\underset{}{N}}-CH-\overset{O}{C}-\overset{H}{N}-CH-\overset{O}{C}-R^6$$
$$\phantom{R^1-S-N-}\;\;\;\;\;\;\;\;\;\;\;\;\;R^3\;\;\;\;\;\;\;\;\;\;\;\;\;R^5$$

| R¹ | R² | R³ | R⁵ | R⁶ |
|---|---|---|---|---|
| 3-pyridyl | R²/R³ = cyclic 3 carbon atoms (L-pyrrolidinyl) | | p-[(CH₃)₂NC(O)O-]benzyl- | —OH |
| p-CH₃-φ | R²/R³ = cyclic 3 carbon atoms (D-pyrrolidinyl) | | p-[(4-methylpiperazin-1-yl)C(O)O-]benzyl- | —OC(CH₃)₃ |
| p-CH₃-φ | —CH₃ | —CH₃ | p-[(4-methylpiperazin-1-yl)C(O)O-]benzyl- | —OC(CH₃)₃ |
| p-nitro-φ | R²/R³ = cyclic 3 carbon atoms (L-pyrrolidinyl) | | p-[(CH₃)₂NC(O)O-]benzyl- | —OC(CH₃)₃ |
| p-CH₃-φ | —CH₃ | H | p-[(thiomorpholin-4-yl)C(O)O-]benzyl- | —OC(CH₃)₃ |
| p-CH₃-φ | —CH₃ | —CH₃ | p-[(4-methylpiperazin-1-yl)C(O)O-]benzyl- | —OH |
| p-CH₃-φ | R²/R³ = cyclic 3 carbon atoms (L-pyrrolidinyl) | | p-[(thiomorpholin-4-yl sulfone)-C(O)O-]benzyl- | —OH |
| p-CH₃-φ | R²/R³ = cyclic 3 carbon atoms (L-pyrrolidinyl) | | p-[(piperidin-1-yl)C(O)O-]benzyl- | —OH |
| p-CH₃-φ | R²/R³ = cyclic 3 carbon atoms (L-pyrrolidinyl) | | p-[(pyrrolidin-1-yl)C(O)O-]benzyl- | —OH |
| p-CH₃-φ | R²/R³ = cyclic 3 carbon atoms (L-pyrrolidinyl) | | p-[(morpholin-4-yl)C(O)O-]benzyl- | —OH |
| p-CH₃-φ | R²/R³ = cyclic 3 carbon atoms (L-pyrrolidinyl) | | p-[(4-methylpiperazin-1-yl)C(O)O-]benzyl- | —OCH₂C(CH₃)₃ |
| p-CH₃-φ | R²/R³ = cyclic 3 carbon atoms (L-pyrrolidinyl) | | p-[(CH₃)₂NC(O)O-]benzyl- | —OCH₂C(CH₃)₃ |
| p-CH₃-φ | R²/R³ = cyclic 3 carbon atoms (L-pyrrolidinyl) | | p-[(1-Boc-piperazin-4-yl)C(O)O-]benzyl- | —OCH₂CH₃ |
| p-CH₃-φ | R²/R³ = cyclic 3 carbon atoms (L-pyrrolidinyl) | | p-[(morpholin-4-yl)C(O)O-]benzyl- | —OCH₂CH₃ |
| p-CH₃-φ | —CH₃ | H | p-[(thiomorpholin-4-yl sulfone)-C(O)O-]benzyl- | —OC(CH₃)₃ |
| p-CH₃-φ | —CH₃ | H | p-[(thiomorpholin-4-yl)C(O)O-]benzyl- | —OH |
| p-CH₃-φ | —CH₃ | —CH₃ | p-[(CH₃)₂NC(O)O-]benzyl- | —OC(CH₃)₃ |
| p-CH₃-φ | —CH₂—CH₂—S—CH₂— (L-thiomorpholin-3-yl) | | p-[(CH₃)₂NC(O)O-]benzyl- | —OC(CH₃)₃ |

TABLE 3-continued $$R^1-\underset{\underset{O}{\overset{O}{\|}}}{S}-\underset{\underset{R^2}{|}}{N}-CH-\overset{O}{\overset{\|}{C}}-\underset{H}{N}-CH-\overset{O}{\overset{\|}{C}}-R^6$$

| R¹ | R² | R³ | R⁵ | R⁶ |
|---|---|---|---|---|
| p-CH₃-φ | —CH₃ | H | p-[(thiomorpholin-4-yl sulfone)-C(O)O-]benzyl- | —OH |
| p-CH₃-φ | R²/R³ = cyclic | | p-[(CH₃)₂NC(O)O-]benzyl- | —OC(CH₃)₃ |
| | —CH₂—CH₂—SO₂—CH₂— | | | |
| | (L-1,1-dioxothiomorpholin-3-yl) | | | |
| p-CH₃-φ | R²/R³ = cyclic | | p-[(morpholin-4-yl)C(O)O-]benzyl- | —OC(CH₃)₃ |
| | —CH₂—CH₂—SO₂—CH₂— | | | |
| | (L-1,1-dioxothiomorpholin-3-yl) | | | |
| p-CH₃-φ | —CH₃ | —CH₃ | p-[(CH₃)₂NC(O)O-]benzyl- | —OH |
| p-F-φ | R²/R³ = cyclic | | p-[(CH₃)₂NC(O)O-]benzyl- | —OC(CH₃)₃ |
| | —CH₂—CH₂—S—CH₂— | | | |
| | (L-thiomorpholin-3-yl) | | | |
| p-F-φ | R²/R³ = cyclic | | p-[(CH₃)₂NC(O)O-]benzyl- | —OC(CH₃)₃ |
| | —CH₂—CH₂—SO₂—CH₂— | | | |
| | (L-1,1-dioxothiomorpholin-3-yl) | | | |
| pyridin-3-yl | R²/R³ = cyclic | | p-[(CH₃)₂NC(O)O-]benzyl- | —OH |
| | 3 carbon atoms | | | |
| | (L-pyrrolidinyl) | | | |
| p-nitro-φ | R²/R³ = cyclic | | p-[(CH₃)₂NC(O)O-]benzyl- | —OC(CH₃)₃ |
| | 3 carbon atoms | | | |
| | (L-pyrrolidinyl) | | | |
| p-N≡C-φ | R²/R³ = cyclic | | p-[(CH₃)₂NC(O)O-]benzyl- | —OH |
| | —CH₂—CH₂—SO₂—CH₂— | | | |
| | (L-1,1-dioxothiomorpholin-3-yl) | | | |
| p-CH₃-φ | R²/R³ = cyclic | | p-[(CH₃)₂NC(O)O-]benzyl- | —OC(CH₃)₃ |
| | 3 carbon atoms | | | |
| | (L-pyrrolidinyl) | | | |
| p-CH₃-φ | R²/R³ = cyclic | | p-[(CH₃)₂NC(O)O-]benzyl- | —OC(CH₃)₃ |
| | —CH₂—SO₂—CH₂ | | | |
| | (L-1,1-dioxothiazolidin-4-yl) | | | |
| p-F₃C-φ | R²/R³ = cyclic | | p-[(CH₃)₂NC(O)O-]benzyl- | —OC(CH₃)₃ |
| | 3 carbon atoms | | | |
| | (L-pyrrolidinyl) | | | |
| 1-methylpyrazol-4-yl | R²/R³ = cyclic | | p-[(CH₃)₂NC(O)O-]benzyl- | —OH |
| | 3 carbon atoms | | | |
| | (L-pyrrolidinyl) | | | |
| p-CH₃-φ | R²/R³ = cyclic | | p-[(CH₃)₂NC(O)O-]benzyl- | —OH |
| | —CH₂—SO₂—CH₂ | | | |
| | (L-1,1-dioxothiazolidin-4-yl) | | | |
| p-F-φ | R²/R³ = cyclic | | p-[(CH₃)₂NC(O)O-]benzyl- | —OH |
| | —CH₂—S—CH₂ | | | |
| | (L-thiazolidin-4-yl) | | | |
| p-CH₃-φ | R²/R³ = cyclic | | p-[(CH₃)₂NC(O)O-]benzyl- | 2,4-dioxo-tetrahydrofuran-3-yl(3,4-enol) |
| | 3 carbon atoms | | | |
| | (L-pyrrolidinyl) | | | |

TABLE 3-continued $$R^1-\overset{O}{\underset{O}{S}}-N-CH-\overset{O}{C}-N-CH-\overset{O}{C}-R^6$$
$$\phantom{R^1-S-}\underset{R^2}{|}\phantom{-CH-C-}\underset{H}{|}\underset{R^3}{|}$$

| R¹ | R² | R³ | R⁵ | R⁶ |
|---|---|---|---|---|
| p-CH₃-φ | R²/R³ = cyclic 3 carbon atoms (L-pyrrolidinyl) | | p-[(piperazin-4-yl)C(O)O-]benzyl- | —OH |
| p-CH₃-φ | R²/R³ = cyclic 3 carbon atoms (L-pyrrolidinyl) | | p-[(1-Boc-piperazin-4-yl)C(O)O-]benzyl- | —OC(CH₃)₃ |
| p-CH₃-φ | R²/R³ = cyclic 3 carbon atoms (L-pyrrolidinyl) | | p-[(piperazin-4-yl)C(O)O-]benzyl- | —OCH₂CH₃ |
| p-CH₃-φ | R²/R³ = cyclic 3 carbon atoms (L-pyrrolidinyl) | | p-[(4-acetylpiperazin-1-yl)C(O)O-]benzyl- | —OCH₂CH₃ |
| p-CH₃-φ | R²/R³ = cyclic 3 carbon atoms (L-pyrrolidinyl) | | p-[(4-methanesulfonylpiperazin-1-yl)-C(O)O-]benzyl- | —OCH₂CH₃ |
| p-CH₃-φ | R²/R³ = cyclic 3 carbon atoms (L-pyrrolidinyl) | | 3-nitro-4-[(morpholin-4-yl)-C(O)O-]benzyl- | —OH |
| p-CH₃-φ | R²/R³ = cyclic 3 carbon atoms (L-pyrrolidinyl) | | p-[(1-Boc-piperazin-4-yl)C(O)O-]benzyl- | —OH |
| p-CH₃-φ | —CH₃ | —C(CH₃)₃ | p-[(4-methylpiperazin-1-yl)C(O)O-]benzyl- | —OC(CH₃)₃ |
| p-F-φ | —CH₂—S—C(CH₃)₂— (L-5,5-dimethylthiazolidin-4-yl) | | p-[(CH₃)₂NC(O)O-]benzyl- | —OC(CH₃)₃ |
| p-F-φ | —CH₂—CH₂—SO₂—CH₂— (L-1,1-dioxothiomorpholin-3-yl) | | p-[(1,1-dioxothiomorpholin-4-yl)-C(O)O-]benzyl- | —OC(CH₃)₃ |
| p-F-φ | R²/R³ = cyclic 3 carbon atoms (L-pyrrolidinyl) | | p-[(1,1-dioxothiomorpholin-4-yl)-C(O)O-]benzyl- | —OC(CH₃)₃ |
| p-F-φ | —CH₂—CH₂—SO₂—CH₂— (L-1,1-dioxothiomorpholin-3-yl) | | p-[(1,1-dioxothiomorpholin-4-yl)-C(O)O-]benzyl- | —OC(CH₃)₃ |
| p-F-φ | R²/R³ = cyclic 3 carbon atoms (L-pyrrolidinyl) | | p-[(thiomorpholin-4-yl)C(O)O-]benzyl- | —OC(CH₃)₃ |
| p-F-φ | R²/R³ = cyclic 3 carbon atoms (L-pyrrolidinyl) | | p-[(morpholin-4-yl)C(O)O-]benzyl- | —OC(CH₃)₃ |
| p-F-φ | —CH₂—S—C(CH₃)₂— (L-5,5-dimethylthiazolidin-4-yl) | | p-[(CH₃)₂NC(O)O-]benzyl- | —OH |

TABLE 3-continued

| R¹ | R² | R³ | R⁵ | R⁶ |
|---|---|---|---|---|
| p-F-φ | R²/R³ = cyclic —CH₂—CH₂—SO₂—CH₂— (L-1,1-dioxothiomorpholin-3-yl) | | p-[(morpholin-4-yl)C(O)O-]benzyl- | —OC(CH₃)₃ |
| p-F₃CO-φ | R²/R³ = cyclic 3 carbon atoms (L-pyrrolidinyl) | | p-[(CH₃)₂NC(O)O-]benzyl- | —OC(CH₃)₃ |
| p-CH₃-φ | R²/R³ = cyclic —CH₂—CH₂—SO₂—CH₂— (L-1,1-dioxothiomorpholin-3-yl) | | p-[(CH₃)₂NC(O)O-]benzyl- | —OCH(CH₃)₂ |
| p-F-φ | R²/R³ = cyclic —CH₂—SO₂—C(CH₃)₂— (L-1,1-dioxo-5,5-di-methylthiazolidin-4-yl) | | p-[(CH₃)₂NC(O)O-]benzyl- | —OC(CH₃)₃ |
| p-CH₃-φ | R²/R³ = cyclic —CH₂—SO₂—C(CH₃)₂— (L-1,1-dioxo-5,5-di-methylthiazolidin-4-yl) | | p-[(CH₃)₂NC(O)O-]benzyl- | —OCH(CH₃)₂ |
| p-CH₃-φ | R²/R³ = cyclic —CH₂—CH₂—SO₂—CH₂— (L-1,1-dioxothiomorpholin-3-yl) | | p-[(morpholin-4-yl)C(O)O-]benzyl- | —OH |
| p-F-φ | R²/R³ = cyclic —CH₂—SO₂—C(CH₃)₂— (L-1,1-dioxo-5,5-di-methylthiazolidin-4-yl) | | p-[(CH₃)₂NC(O)O-]benzyl- | —OH |
| pyrimidin-2-yl | R²/R³ = cyclic 3 carbon atoms (L-pyrrolidinyl) | | p-[(CH₃)₂NC(O)O-]benzyl- | —OH |
| p-CH₃-φ | R²/R³ = cyclic —CH₂—CH₂—SO₂—CH₂— (L-1,1-dioxothiomorpholin-3-yl) | | p-[(4-methylpiperazin-1-yl)C(O)O-]benzyl- | —OC(CH₃)₃ |
| p-F-φ | R²/R³ = cyclic 3 carbon atoms (L-pyrrolidinyl) | | p-[(CH₃)₂NC(O)O-]benzyl- | —OC(CH₃)₃ |
| 2,5-dichlorothien-3-yl | R²/R³ = cyclic —CH₂—CH₂—SO₂—CH₂— (L-1,1-dioxothiazolidin-4-yl) | | p-[(CH₃)₂NC(O)O-]benzyl- | —OC(CH₃)₃ |
| p-CH₃C(O)NH-φ | R²/R³ = cyclic 3 carbon atoms (L-pyrrolidinyl) | | p-[(CH₃)₂NC(O)O-]benzyl- | —OC(CH₃)₃ |
| p-C(CH₃)₃-φ | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| pyridin-2-yl | R²/R³ = cyclic 3 carbon atoms (L-pyrrolidinyl) | | p-[(CH₃)₂NC(O)O-]benzyl- | —OH |

TABLE 3-continued

| R¹ | R² | R³ | R⁵ | R⁶ |
|---|---|---|---|---|
| o-F-φ | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| m-F-φ | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| 2,4-difluoro-φ | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| p-CH₃C(O)NH-φ | R²/R³ = cyclic 3 carbon atoms (L-pyrrolidinyl) | | p-[(CH₃)₂NC(O)O-]benzyl- | —OH |
| p-C(F)₃O-φ | R²/R³ = cyclic 3 carbon atoms (L-pyrrolidinyl) | | p-[(CH₃)₂NC(O)O-]benzyl- | —OH |
| p-F-φ | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-N≡C-φ | R²/R³ = cyclic 3 carbon atoms (L-pyrrolidinyl) | | p-[(CH₃)₂NC(O)O-]benzyl- | —OH |
| morpholin-4-yl | R²/R³ = cyclic 3 carbon atoms (L-pyrrolidinyl) | | p-[(CH₃)₂NC(O)O-]benzyl- | —OC(CH₃)₃ |
| p-CH₃-φ | R²/R³ = cyclic —CH₂—CH₂—C(CH₃)₂— (L-4,4-dimethyl pyrrolidinyl) | | p-[(CH₃)₂NC(O)O-]benzyl- | —OC(CH₃)₃ |
| p-CH₃-φ | R²/R³ = cyclic —CH₂—CH₂—C(CH₃)₂— (L-4,4-dimethyl pyrrolidinyl) | | p-[(CH₃)₂NC(O)O-]benzyl- | —OCH(CH₃)₂ |
| 1-methylpyrazol-4-yl | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂—S—C(CH₃)₂— (L-5,5-dimethylthiazolidin-4-yl) | | p-[(thiomorpholin-4-yl)C(O)O-]benzyl- | —OCH(CH₃)₂ |
| p-CH₃-φ- | R²/R³ = cyclic 3 carbon atoms (L-pyrrolidinyl) | | p-[(CH₃)₂NC(O)O-]benzyl- | —OC(CH₃)₃ |
| 1-methylimidazol-4-yl | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |

TABLE 3-continued $$R^1-\underset{\underset{O}{\|}}{S}-\underset{R^2}{N}-CH-\underset{\underset{O}{\|}}{C}-\underset{H}{N}-CH-\underset{\underset{O}{\|}}{C}-R^6$$
$$\phantom{R^1-S-N-}\phantom{xx}R^3\phantom{xxxxxx}R^5$$

| R¹ | R² | R³ | R⁵ | R⁶ |
|---|---|---|---|---|
| 1-methylpyrazol-4-yl | R²/R³ = cyclic —CH₂—S—C(CH₃)₂— L-5,5-dimethylthiazolidin-4-yl) | | p-[(CH₃)₂NC(O)O-]benzyl- | —OC(CH₃)₃ |
| p-CH₃C(O)NH-φ | R²/R³ = cyclic 3 carbon atoms (L-pyrrolidinyl) | | p-[(CH₃)₂NC(O)O-]benzyl- | —OC(CH₃)₃ |
| p-(CH₃)₃C-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| 1-methylpyrazol-4-yl | R²/R³ = cyclic —CH₂—S—C(CH₃)₂— (L-5,5-dimethylthiazolidin-4-yl) | | p-[(CH₃)₂NC(O)O-]benzyl- | —OH |
| pyridin-3-yl- | R²/R³ = cyclic 3 carbon atoms (L-pyrrolidinyl) | | p-[(CH₃)₂NC(O)O-]benzyl- | —OH |
| p-N≡C-φ- | R²/R³ = cyclic 3 carbon atoms (L-pyrrolidinyl) | | p-[(CH₃)₂NC(O)O-]benzyl- | —OH |
| p-F-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂—S—C(CH₃)₂— (L-5,5-dimethylthiazolidin-4-yl) | | p-[(1,4-dioxa-8-azaspiro[4.5]decan-8-yl]-C(O)O-]benzyl- | —OCH₂CH₃ |
| p-CH₃-φ- | R²/R³ = cyclic 3 carbon atoms (L-pyrrolidinyl) | | p-[(1,4-dioxa-8-azaspiro[4.5]decan-8-yl]-C(O)O-]benzyl- | —OH |
| p-CH₃-φ- | R²/R³ = cyclic 3 carbon atoms (L-pyrrolidinyl) | | p-[(4-acetylpiperazin-1-yl)C(O)O-]benzyl- | —OH |
| p-CH₃-φ- | R²/R³ = cyclic 3 carbon atoms (L-pyrrolidinyl) | | p-[(4-methanesulfonylpiperazin-1-yl)-C(O)O-]benzyl- | —OH |
| p-CH₃-φ- | R²/R³ = cyclic 3 carbon atoms (L-pyrrolidinyl) | | p-[(4-φ-piperazin-1-yl)C(O)(O)-]benzyl- | —OH |
| p-CH₃-φ- | R²/R³ = cyclic —CH₂CH₂—NH—CH₂— (L-piperazinyl) | | p-[piperazin-1-yl)C(O)O-]benzyl- | —OC(CH₃)₃ |
| p-CH₃-φ- | R²/R³ = cyclic 3 carbon atoms (L-pyrrolidinyl) | | p-[(CH₃)₂NC(O)O-]benzyl- | —OC(CH₃)₃ |
| p-F₃CO-φ- | R²/R³ = cyclic 3 carbon atoms (L-pyrrolidinyl) | | p-[(CH₃)₂NC(O)O-]benzyl- | —OH |

TABLE 3-continued $$R^1-\underset{\underset{O}{\|}}{S}-\underset{R^2}{N}-CH-\underset{\underset{O}{\|}}{C}-\underset{H}{N}-CH-\underset{\underset{O}{\|}}{C}-R^6$$

| R¹ | R² | R³ | R⁵ | R⁶ |
|---|---|---|---|---|
| p-CH₃-φ- | R²/R³ = cyclic —CH₂—CH₂—C(CH₃)₂— (4,4-dimethyl pyrrolidinyl) | | p-[(CH₃)₂NC(O)O-]benzyl- | —OC(CH₃)₃ |
| p-CH₃-φ- | R²/R³ = cyclic —CH₂—CH₂—C(CH₃)₂— (4,4-dimethyl pyrrolidinyl) | | p-[(CH₃)₂NC(O)O-]benzyl- | —OCH(CH₃)₂ |
| p-CH₃C(O)NH-φ- | R²/R³ = cyclic 3 carbon atoms (L-pyrrolidinyl) | | p-[(CH₃)₂NC(O)O-]benzyl- | —OH |
| o-F-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| morpholin-4-yl- | R²/R³ = cyclic 3 carbon atoms (L-pyrrolidinyl) | | p-[(CH₃)₂NC(O)O-]benzyl- | —OC(CH₃)₃ |
| m-F-φ- | R²/R³ = cyclic —CH₂—CH₂—SO₂—CH₂— (L-1,1-dioxothiomorpholin-3-yl) | | p-[(CH₃)₂NC(O)O-]benzyl- | —OC(CH₃)₃ |
| 2,4-difluoro-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| morpholin-4-yl- | R²/R³ = cyclic 3 carbon atoms (L-pyrrolidinyl) | | p-[(CH₃)₂NC(O)O-]benzyl- | —OC(CH₃)₃ |
| 1-methylpyrazol-4-yl- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| o-F-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| 2,4-difluoro-φ- | R²/R³ = cyclic —CH₂—CH₂—S—CH₂— (L-thiomorpholin-3-yl) | | p-[(CH₃)₂NC(O)O-]benzyl- | —OH |
| p-CH₃-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| pyridin-3-yl- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| m-F-φ- | R²/R³ = cyclic 3 carbon atoms (L-pyrrolidinyl) | | p-[(CH₃)₂NC(O)O-]benzyl- | —OCH(CH₃)₂ |
| pyridin-2-yl- | R²/R³ = cyclic —CH₂—CH₂—SO₂—CH₂— (L-1,1-dioxothiomorpholin-3-yl) | | p-[(CH₃)₂NC(O)O-]benzyl- | —OCH(CH₃)₂ |

TABLE 3-continued $$R^1-\overset{O}{\underset{O}{S}}-\overset{}{\underset{R^2}{N}}-CH-\overset{O}{C}-\overset{}{\underset{H}{N}}-CH-\overset{O}{C}-R^6$$

| R¹ | R² | R³ | R⁵ | R⁶ |
|---|---|---|---|---|
| 1-methylpyrazol-4-yl | R²/R³ = cyclic —CH₂—CH₂—SO₂—CH₂— (L-1,1-dioxothiomorpholin-3-yl) | | p-[(CH₃)₂NC(O)O-]benzyl- | —OH |
| p-CH₃-φ- | R²/R³ = cyclic 3 carbon atoms (L-pyrrolidinyl) | | p-[(4-methanesulfonylpiperazin-1-yl)-C(O)O-]benzyl- | —OC(CH₃)₃ |
| p-CH₃-φ- | R²/R³ = cyclic 3 carbon atoms (L-pyrrolidinyl) | | p-[(4-φ-piperazin-1-yl)C(O)(O)-]benzyl- | —OC(CH₃)₃ |
| p-CH₃-φ- | R²/R³ = cyclic 3 carbon atoms (L-pyrrolidinyl) | | p-[(CH₃)₂NC(O)O-]benzyl- | —O—CH₂C(CH₃)₂—NHC(O)OC(CH₃)₃ |
| p-CH₃-φ- | R²/R³ = cyclic 3 carbon atoms (L-pyrrolidinyl) | | p-[(CH₃)₂NC(O)O-]benzyl- | —O—CH₂CH₂—(morpholin-4-yl) |
| p-CH₃-φ- | R²/R³ = cyclic 3 carbon atoms (L-pyrrolidinyl) | | p-[(4-acetylpiperazin-1-yl)C(O)O-]benzyl- | —OC(CH₃)₃ |
| p-CH₃-φ- | R²/R³ = cyclic 3 carbon atoms (L-pyrrolidinyl) | | p-[(CH₃)₂NCH₂CH₂N(CH₃)C(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | | p-[(CH₃)₂NCH₂CH₂N(CH₃)C(O)O-]benzyl- | —OC(CH₃)₃ |
| p-CH₃-φ- | R²/R³ = cyclic 3 carbon atoms (L-pyrrolidinyl) | | p-[(CH₃)₂NCH₂CH₂N(CH₃)C(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | | p-[(CH₃)₂NC(O)O-]benzyl- | —OH |
| p-CH₃-φ- | R²/R³ = cyclic 3 carbon atoms (L-pyrrolidinyl) | | p-[(4-hydroxypiperidin-1-yl)C(O)O-]benzyl- | —OH |
| p-CH₃-φ- | R²/R³ = cyclic 3 carbon atoms (L-pyrrolidinyl) | | p-[(CH₃)₂NC(O)O-]benzyl- | —OH |
| p-(CH₃)₃C-φ- | R²/R³ = cyclic —CH₂—CH₂—SO₂—CH₂— (L-1,1-dioxothiomorpholin-3-yl) | | p-[(CH₃)₂NC(O)O-]benzyl- | —OH |
| p-CH₃-φ- | R²/R³ = cyclic —CH₂—S—C(CH₃)₂— (L-5,5-dimethylthiazolidin-4-yl) | | p-[(thiomorpholin-4-yl)C(O)O-]benzyl- | —OC(CH₃)₃ |
| 2,5-dichlorothien-3-yl- | R²/R³ = cyclic 3 carbon atoms (L-pyrrolidinyl) | | p-[(CH₃)₂NC(O)O-]benzyl- | —OH |
| p-CH₃O-φ- | R²/R³ = cyclic 3 carbon atoms (L-pyrrolidinyl) | | p-[(CH₃)₂NC(O)O-]benzyl- | —OCH(CH₃)₂ |

TABLE 3-continued

| R¹ | R² | R³ | R⁵ | R⁶ |
|---|---|---|---|---|
| p-CH₃-ϕ- | R²/R³ = cyclic —CH₂—CH₂—C(CH₃)₂— (4,4-dimethyl pyrrolidinyl) | | p-[(CH₃)₂NC(O)O-]benzyl- | —OH |
| p-F-ϕ- | R²/R³ = cyclic —CH₂—S—C(CH₃)₂— (L-5,5-dimethylthiazolidin-4-yl) | | 3-chloro-4-[(4-methylpiperazin-1-yl)C(O)O-]benzyl- | —OC(CH₃)₃ |
| p-F-ϕ- | R²/R³ = cyclic —CH₂—S—C(CH₃)₂— (L-5,5-dimethylthiazolidin-4-yl) | | 3-chloro-4-[(CH₃)₂NC(O)O-]benzyl- | —OH |
| p-F-ϕ- | R²/R³ = cyclic —CH₂—S—C(CH₃)₂— (L-5,5-dimethylthiazolidin-4-yl) | | 3-chloro-4-[(thiomorpholin-4-yl)C(O)O-]benzyl- | —OC(CH₃)₃ |
| p-CH₃-ϕ- | R²/R³ = cyclic 3 carbon atoms (L-pyrrolidinyl) | | p-[(morpholin-4-yl)-CH₂CH₂NHC(O)O-]benzyl- | —OC(CH₃)₃ |
| p-CH₃-ϕ- | R²/R³ = cyclic 3 carbon atoms (L-pyrrolidinyl) | | p-[(1,4-dioxa-8-azaspiro[4.5]decan-8-yl)-C(O)O-]benzyl- | —OC(CH₃)₃ |
| p-F-ϕ- | R²/R³ = cyclic —CH₂—S—C(CH₃)₂— (L-5,5-dimethylthiazolidin-4-yl) | | 3-chloro-4-[(CH₃)₂NC(O)O-]benzyl- | —OC(CH₃)₃ |
| p-CH₃-ϕ- | R²/R³ = cyclic —CH₂—S—C(CH₃)₂— (L-5,5-dimethylthiazolidin-4-yl) | | p-[(thiomorpholin-4-yl)C(O)O-]benzyl- | —OH |
| pyridin-2-yl- | R²/R³ = cyclic 3 carbon atoms (L-pyrrolidinyl) | | p-[(CH₃)₂NC(O)O-]benzyl- | —OH |
| p-CH₃-ϕ- | R²/R³ = cyclic —CH₂—CH₂—(O)—CH₂— (L-1-oxothiomorpholin-4-yl) | | p-[(CH₃)₂NC(O)O-]benzyl- | —OCH(CH₃)₂ |
| 4-Cl-3-(NH₂—SO₂)ϕ- | R²/R³ = cyclic 3 carbon atoms (L-pyrrolidinyl) | | p-[(CH₃)₂NC(O)O-]benzyl- | —OCH(CH₃)₂ |
| p-F-ϕ- | R²/R³ = cyclic —CH₂—S—C(CH₃)₂— (L-5,5-dimethylthiazolidin-4-yl) | | 3-chloro-4-[(thiomorpholin-4-yl)C(O)O-]benzyl- | —OCH(CH₃)₂ |
| p-F-ϕ- | R²/R³ = cyclic —CH₂—S—C(CH₃)₂— (L-5,5-dimethylthiazolidin-4-yl) | | 3-chloro-4-[(CH₃)₂NC(O)O-]benzyl- | —OCH(CH₃)₂ |
| p-CH₃-ϕ- | R²/R³ = cyclic 3 carbon atoms (L-pyrrolidinyl) | | p-[HOCH₂CH₂N(CH₃)C(O)O-]benzyl- | —OC(CH₃)₃ |
| p-F-ϕ- | R²/R³ = cyclic —CH₂—S—C(CH₃)₂— (L-5,5-dimethylthiazolidin-4-yl) | | p-[(2-(hydroxymethyl)pyrrolidin-1-yl)-C(O)O-]benzyl- | —OC(CH₃)₃ |

TABLE 3-continued $$R^1-\overset{O}{\underset{O}{S}}-\underset{R^2}{N}-CH-\overset{O}{C}-\underset{H}{N}-CH-\overset{O}{C}-R^6$$

| R¹ | R²/R³ | R⁵ | R⁶ |
|---|---|---|---|
| p-F-φ- | R²/R³ = cyclic —CH₂—S—C(CH₃)₂— (L-5,5-dimethylthiazolidin-4-yl) | p-[2-(hydroxymethyl)pyrrolidin-1-yl)-C(O)O-]benzyl- | —OH |
| p-CH₃-φ- | R²/R³ = cyclic 3 carbon atoms (L-pyrrolidinyl) | p-[2-(CH₃OC(O)-)pyrrolidin-1-yl)-C(O)O-]benzyl- | —OC(CH₃)₃ |
| p-CH₃-φ- | R²/R³ = cyclic 3 carbon atoms (L-pyrrolidinyl) | p-[4-(HC(O)O—piperidin-1-yl)-C(O)O-]benzyl- | —OH |
| p-CH₃-φ- | R²/R³ = cyclic 3 carbon atoms (L-pyrrolidinyl) | p-[4-(hydroxy)piperidin-1-yl)-C(O)O-]benzyl- | —OCH(CH₃)₂ |
| p-F-φ- | R²/R³ = cyclic —CH₂—S—C(CH₃)₂— (L-5,5-dimethylthiazolidin-4-yl) | 3-chloro-4-[(thiomorpholin-4-yl)C(O)O-]benzyl- | —OH |
| p-CH₃-φ- | R²/R³ = cyclic 3 carbon atoms (L-pyrrolidinyl) | p-[(4-(CH₃CH₂OC(O)-)piperidin-1-yl)NC(O)O-]benzyl- | —OC(CH₃)₃ |
| p-CH₃-φ- | R²/R³ = cyclic 3 carbon atoms (L-pyrrolidinyl) | p-[(4-(HOCH₂CH₂-)piperazin-1-yl)-C(O)O—]benzyl- | —OC(CH₃)₃ |
| p-F-φ- | R²/R³ = cyclic 3 carbon atoms (L-pyrrolidinyl) | p-[(4-(pyridin-2-yl)piperazin-1-yl)-C(O)O-]benzyl- | —OH |
| p-F-φ- | R²/R³ = cyclic 3 carbon atoms (L-pyrrolidinyl) | p-[(4-(pyridin-2-yl)piperazin-1-yl)-C(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | p-[HC(O)OCH₂CH₂N(CH₃)C(O)O-]benzyl- | —OH |
| p-CH₃-φ- | R²/R³ = cyclic 3 carbon atoms (L-pyrrolidinyl) | p-[HOCH₂CH₂N(CH₃)C(O)O-]benzyl- | —OCH(CH₃)₂ |
| p-CH₃-φ- | R²/R³ = cyclic 3 carbon atoms (L-pyrrolidinyl) | p-[CH₃OC(O)CH₂NHC(O)O-]benzyl- | —OC(CH₃)₃ |
| quinolin-8-yl- | R²/R³ = cyclic 3 carbon atoms (L-pyrrolidinyl) | p-[(CH₃)₂NC(O)O-]benzyl- | —OCH(CH₃)₂ |
| 3,4-difluoro-φ- | R²/R³ = cyclic 3 carbon atoms (L-pyrrolidinyl) | p-[(CH₃)₂NC(O)O-]benzyl- | —OCH(CH₃)₂ |
| p-CH₃-φ- | R²/R³ = cyclic 3 carbon atoms (L-pyrrolidinyl) | p-[(thiomorpholin-4-yl)-C(O)O-]benzyl- | —OCH(CH₃)₂ |

TABLE 3-continued $$R^1-\underset{\underset{O}{\|}}{S}-\underset{R^2}{N}-CH-\underset{\underset{O}{\|}}{C}-\underset{H}{N}-CH-\underset{\underset{O}{\|}}{C}-R^6$$
$$\phantom{R^1-S-N-}\phantom{R^2}\phantom{-C-N-}R^3\phantom{-C-}R^5$$

| R¹ | R² | R³ | R⁵ | R⁶ |
|---|---|---|---|---|
| p-CH₃O-φ- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—(O)—CH₂— (L-1-oxothiomorpholin-4-yl) | | p-[(CH₃)₂NC(O)O-]benzyl- | —OH |
| 3,4-difluoro-φ- | R²/R³ = cyclic —CH₂CH₂—SO₂—CH₂— (L-1,1-dioxothiomorpholin-3-yl) | | p-[(CH₃)₂NC(O)O-]benzyl- | —OC(CH₃)₃ |
| p-H₂N-φ- | R²/R³ = cyclic 3 carbon atoms (L-pyrrolidinyl) | | p-[(CH₃)₂NC(O)O-]benzyl- | —OCH(CH₃)₂ |
| 3,4-difluoro-φ- | R²/R³ = cyclic —CH₂CH₂—SO₂—CH₂— (L-1,1-dioxothiomorpholin-3-yl) | | p-[(CH₃)₂NC(O)O-]benzyl- | —OH |
| 3,4-difluoro-φ- | R²/R³ = cyclic 3 carbon atoms (L-pyrrolidinyl) | | p-[(CH₃)₂NC(O)O-]benzyl- | —OH |
| quinolin-8-yl- | R²/R³ = cyclic 3 carbon atoms (L-pyrrolidinyl) | | p-[(CH₃)₂NC(O)O-]benzyl- | —OH |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-CH₃-φ- | R²/R³ = cyclic —CH₂—CH₂—(O)—CH₂— (L-1-oxothiomorpholin-4-yl) | | p-[(CH₃)₂NC(O)O-]benzyl- | —OC(CH₃)₃ |
| 1-n-butylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 1-methylpyrazol-3-yl | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 2-(CF₃C(O))H-2,3,4-tetra-hydro-isoquinolin-7-yl | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(4-(φNHC(O)piperazin-1-yl)-C(O)O-]benzyl- | —OH |
| p-CH₃-φ- | R²/R³ = cyclic 3 carbon atoms (L-pyrrolidinyl) | | p-[(4-methoxypiperidin-1-yl)C(O)O-]benzyl- | —OH |
| p-CH₃-φ- | R²/R³ = cyclic 3 carbon atoms (L-pyrrolidinyl) | | p-[(4-(pyridin-4-yl)C(O)piperazin-1-yl)-C(O)O-]benzyl- | —OCH(CH₃)₂ |

TABLE 3-continued $$R^1-\overset{O}{\underset{O}{S}}-N(R^2)-CH(R^3)-C(O)-N(H)-CH-C(O)-R^6$$

| R¹ | R² | R³ | R⁵ | R⁶ |
|---|---|---|---|---|
| p-CH₃-φ- | R²/R³ = cyclic —CH₂—C(O)—CH₂— (L-4-oxopyrrolidinyl) | | p-[(CH₃)₂NC(O)O-]benzyl- | —OC(CH₃)₃ |
| p-CH₃-φ- | R²/R³ = cyclic —CH₂—CH(OH)CH₂— (L-4-hydroxopyrrolidinyl) | | p-[(CH₃)₂NC(O)O-]benzyl- | —OC(CH₃)₃ |
| m-F-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic 3 carbon atoms (L-pyrrolidinyl) | | p-[(4-methoxypiperidin-1-yl)(O)O-]benzyl- | —OCH(CH₃)₂ |
| p-CH₃-φ- | R²/R³ = cyclic 3 carbon atoms (L-pyrrolidinyl) | | p-[(4-(φNHC(O)-)piperazin-1-yl)-C(O)O-]benzyl- | —OCH(CH₃)₂ |
| p-(φNHC(O)NH)φ- | R²/R³ = cyclic 3 carbon atoms (L-pyrrolidinyl) | | p-[(CH₃)₂NC(O)O-]benzyl- | —OC(CH₃)₃ |
| p-F-φ- | R²/R³ = cyclic —CH₂—S—C(CH₃)₂— (L-5,5-dimethylthiazolidin-4-yl) | | 3-chloro-4-[(4-methylpiperidin-1-yl)-C(O)O-]benzyl- | —OCH(CH₃)₂ |
| p-CH₃-φ- | R²/R³ = cyclic —CH₂—S—C(CH₃)₂— (L-5,5-dimethylthiazolidin-4-yl) | | 3-chloro-4-[(CH₃)₂NC(O)O-]benzyl | —OC(CH₃)₃ |
| p-CH₃-φ- | R²/R³ = cyclic 3 carbon atoms (L-pyrrolidinyl) | | p-[(4-(CH₃SO₂—)piperazin-1-yl)-C(O)O]benzyl- | —OCH(CH₃)₂ |
| p-CH₃-φ- | R²/R³ = cyclic 3 carbon atoms (L-pyrrolidinyl) | | p-[(morpholin-4-yl)CH₂CH₂NHC(O)O-]benzyl- | —OH |
| p-CH₃-φ- | R²/R³ = cyclic 3 carbon atoms (L-pyrrolidinyl) | | p-[(4-(HO(O)-)piperidin-1-yl)C(O)O-]benzyl- | —OH |
| p-CH₃-φ- | R²/R³ = cyclic 3 carbon atoms (L-pyrrolidinyl) | | p-[(HOCH₂CH₂)₂NC(O)O-]benzyl- | —OCH(CH₃)₂ |
| p-O₂N-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(4-(HOCH₂-)piperidin-1-yl)-C(O)O-]benzyl- | —OCH(CH₃)₂ |
| p-CH₃-φ- | R²/R³ = cyclic 3 carbon atoms (L-pyrrolidinyl) | | 3-chloro-4-[(CH₃)₂NC(O)O-]benzyl- | —OCH(CH₃)₂ |

TABLE 3-continued $$R^1-\underset{\underset{O}{\overset{O}{\|}}}{S}-\underset{\underset{R^2}{|}}{N}-CH-\underset{\underset{O}{\overset{O}{\|}}}{C}-\underset{\underset{H}{|}}{N}-CH-\underset{\underset{O}{\overset{O}{\|}}}{C}-R^6$$

| R¹ | R² | R³ | R⁵ | R⁶ |
|---|---|---|---|---|
| p-CH₃-φ- | R²/R³ = cyclic —CH₂—CH₂—S—CH₂— (L-thiomorpholin-3-yl) | | p-[(CH₃)₂NC(O)O-]benzyl- | —OCH(CH₃)₂ |
| 1-methylpyrazol-3-yl- | R²/R³ = cyclic —CH₂—S—C(CH₃)₂— (L-5,5-dimethylthiazolidin-4-yl) | | p-[(CH₃)₂NC(O)O-]benzyl- | —OH |
| m-F-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| o-F-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,4-difluoro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,5-difluoro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 2,4-difluoro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-NH₂-φ- | R²/R³ = cyclic 3 carbon atoms (L-pyrrolidinyl) | | p-[(CH₃)₂NC(O)O-]benzyl- | —OH |
| p-N≡C-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂CH(OH)CH₂— (L-4-hydroxypyrrolidinyl) | | p-[(CH₃)₂NC(O)O-]benzyl- | —OH |
| p-CH₃-φ- | R²/R³ = cyclic —CH₂C(O)CH₂— (L-4-oxypyrrolidinyl) | | p-[(CH₃)₂NC(O)O-]benzyl- | —OH |
| pyridin-2-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-Cl-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| m-Cl-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| o-Cl-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |

TABLE 3-continued $$R^1-\underset{\underset{O}{\|}}{S}-\underset{R^2}{N}-CH-\underset{R^3}{C}-\underset{H}{N}-CH-\underset{\|}{C}-R^6$$

| R¹ | R² | R³ | R⁵ | R⁶ |
|---|---|---|---|---|
| 3,4-dichloro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,5-dichloro-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 1-methylpyraozl-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂CH₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OH |
| 1-methylpyrazol-4-yl- | R²/R³ = cyclic —CH₂—S—C(CH₃)₂— (L-5,5-dimethylthiazolidin-4-yl) | | p-[(thiomorpholin-4-yl)-C(O)O-]benzyl- | —OCH(CH₃)₂ |
| quinolin-8-yl | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| m-Cl-φ- | R²/R³ = cyclic —CH₂CH₂—SO₂—CH₂— (L-1,1-dioxothiomorpholin-3-yl) | | p-[(CH₃)₂NC(O)O-]benzyl- | —OC(CH₃)₃ |
| pyridin-2-yl- | R²/R³ = cyclic —CH₂—S—C(CH₃)₂— (L-5,5-dimethylthiazolidin-4-yl) | | p-[(CH₃)₂NC(O)O-]benzyl- | —OH |
| 3,4-dichloro-φ- | R²/R³ = cyclic —CH₂CH₂—SO₂—CH₂— (L-1,1-dioxothiomorpholin-3-yl) | | p-[(CH₃)₂NC(O)O-]benzyl- | —OCH(CH₃)₂ |
| 2,5-dichlorothien-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| p-CH₃O-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| m-CH₃O-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| o-CH₃O-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 3,4-dimethoxy-φ- | R²/R³ = cyclic —CH₂—S—C(CH₃)₂— (L-5,5-dimethylthiazolidin-4-yl) | | p-[(CH₃)₂NC(O)O-]benzyl- | —OCH(CH₃)₂ |
| 2,4-difluoro-φ- | R²/R³ = cyclic —CH₂—CH₂—S—CH₂— (L-thiomorpholin-3-yl) | | p-[(CH₃)₂NC(O)O-]benzyl- | —OC(CH₃)₃ |

TABLE 3-continued

| R¹ | R² R³ | R⁵ | R⁶ |
|---|---|---|---|
| 3,4-dichloro-φ- | R²/R³ = cyclic —CH₂CH₂—SO₂—CH₂— (L-1,1-dioxothiomorpholin-3-yl) | p-[(CH₃)₂NC(O)O-]benzyl- | —OH |
| m-Cl-φ- | R²/R³ = cyclic —CH₂CH₂—SO₂—CH₂— (L-1,1-dioxothiomorpholin-3-yl) | p-[(CH₃)₂NC(O)O-]benzyl- | —OH |
| 2,4-difluoro-φ- | R²/R³ = cyclic —CH₂—CH₂—S(O)—CH₂— (L-1-oxothiomorpholin-4-yl) | p-[(CH₃)₂NC(O)O-]benzyl- | —OC(CH₃)₃ |
| p-CH₃-φ- | R²/R³ = cyclic —CH₂—C(O)—CH₂— (L-4-oxopyrrolidinyl) | p-[4-methylpiperzin-1-yl)C(O)O-]benzyl- | —OCH(CH₃)₂ |
| p-CH₃-φ- | R²/R³ = cyclic —CH₂CH(OH)CH₂— (L-4-hydroxypyrrolidinyl) | p-[(thiomorpholin-4-yl)-C(O)O-]benzyl- | —OC(CH₃)₃ |
| p-CH₃-φ- | R²/R³ = cyclic 3 carbon atoms (L-pyrrolidinyl) | p-[(3-(HOCH₂-(piperidin-1-yl)-C(O)O-]benzyl- | —OH |
| p-CH₃-φ- | R²/R³ = cyclic —CH₂—CF₂—CH₂— (L-4,4-difluoro-pyrrolidinyl) | p-[(CH₃)₂NC(O)O-]benzyl- | —OCH(CH₃)₂ |
| p-CH₃-φ- | R²/R³ = cyclic 3 carbon atoms (L-pyrrolidinyl) | p-[(CH₃)₂NC(O)O-]benzyl- | —O(CH₂CH₂O)₂CH₃ |
| p-CH₃-φ- | R²/R³ = cyclic —CH₂CH(—O—C(O)thiomorpholin-4-yl-CH₂— (L-4-(thiomorpholin-4-yl)C(O)O-pyrrolidinyl) | p-[(thiomorpholin-4-yl)-C(O)O-]benzyl- | —OC(CH₃)₃ |
| p-CH₃-φ- | R²/R³ = cyclic —CH₂—CF₂—CH₂— (L-4,4-difluoro-pyrrolidinyl) | p-[(CH₃)₂NC(O)O-]benzyl- | —OH |
| p-F-φ- | R²/R³ = cyclic —CH₂—S—C(CH₃)₂— (L-5,5-dimethylthiazolidin-4-yl) | p-[4-(pyrimidin-2-yl)piperazin-1-yl)-C(O)O-]benzyl- | —OC(CH₃)₃ |
| p-CH₃-φ- | R²/R³ = cyclic —CH₂—S—C(CH₃)₂— (L-5,5-dimethylthiazolidin-4-yl) | p-[4-(φC(O)-)piperazin-1-yl)-C(O)O]benzyl- | —OCH(CH₃)₂ |
| p-F-φ- | R²/R³ = cyclic —CH₂—S—C(CH₃)₂— (L-5,5-dimethylthiazolidin-4-yl) | 3-fluoro-4-[(CH₃)₂NC(O)]-benzyl- | —OCH(CH₃)₂ |
| p-F-φ- | R²/R³ = cyclic —CH₂—S—C(CH₃)₂— (L-5,5-dimethylthiazolidin-4-yl) | 3-chloro-4-[(4-(pyridin-2-yl)piperazin-1-yl)C(O)O]-benzyl- | —OCH(CH₃)₂ |
| p-F-φ- | R²/R³ = cyclic —CH₂—S—C(CH₃)₂— (L-5,5-dimethylthiazolidin-4-yl) | 3-chloro-4-[(4-(pyridin-2-yl)piperazin-1-yl)C(O)O]-benzyl- | —OC(CH₃)₃ |

TABLE 3-continued $$R^1-\underset{\underset{O}{\parallel}}{\overset{\overset{O}{\parallel}}{S}}-N-CH-\underset{\underset{H}{\parallel}}{\overset{\overset{O}{\parallel}}{C}}-N-CH-\overset{\overset{O}{\parallel}}{C}-R^6$$
$$\phantom{R^1-S-N-CH-C-N-}R^2\phantom{-CH-}R^5$$

| R$^1$ | R$^2$ | R$^3$ | R$^5$ | R$^6$ |
|---|---|---|---|---|
| p-CH$_3$-φ- | R$^2$/R$^3$ = cyclic —CH$_2$CH$_2$N(SO$_2$CH$_3$)—CH$_2$— (L-4-methanesulfonyl-piperazinyl) | | p-[(CH$_3$)$_2$NC(O)O-]benzyl- | —OC(CH$_3$)$_3$ |
| 1-methylimidazol-4-yl- | R$^2$/R$^3$ = cyclic 3 carbon atoms (L-pyrrolidinyl) | | p-[(CH$_3$)$_2$NC(O)O-]benzyl- | —OCH(CH$_3$)$_2$ |
| p-Br-φ- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OC(CH$_3$)$_3$ |
| p-Br-φ- | R$^2$/R$^3$ = cyclic —CH$_2$S—C(CH$_3$)$_2$— (L-5,5-dimethylthiazolidin-4-yl) | | p-[(CH$_3$)$_2$NC(O)O-]benzyl- | —OH |
| p-NH$_2$C(═N)-φ- | R$^2$/R$^3$ = cyclic 3 carbon atoms (L-pyrrolidinyl) | | p-[(CH$_3$)$_2$NC(O)O-]benzyl- | —OCH$_3$ |
| p-N═C-φ- | R$^2$/R$^3$ = cyclic 3 carbon atoms (L-pyrrolidinyl) | | p-[(thiomorpholin-4-yl)-C(O)O-]benzyl- | —OCH(CH$_3$)$_2$ |
| p-CH$_3$-φ- | R$^2$/R$^3$ = cyclic —CH$_2$CH(—O—C(O)thiomorpholin-4-yl)-CH$_2$— (L-4-(thiomorpholin-4-yl)C(O)O-pyrrolidinyl) | | p-[(thiomorpholin-4-yl)-C(O)O-]benzyl- | —OH |
| p-CH$_3$-φ- | R$^2$/R$^3$ = cyclic —CH$_2$—C(O)—CH$_2$— (L-4-oxopyrrolidinyl) | | p-[(thiomorpholin-4-yl)-C(O)O-]benzyl- | —OC(CH$_3$)$_3$ |
| p-CH$_3$-φ- | R$^2$/R$^3$ = cyclic —CH$_2$—C(O)—CH$_2$— (L-4-oxopyrrolidinyl) | | p-[(thiomorpholin-4-yl)-C(O)O-]benzyl- | —OH |
| p-CH$_3$-φ- | R$^2$/R$^3$ = cyclic —CH$_2$—C(O)—CH$_2$— (L-4-oxopyrrolidinyl) | | p-[(4-methylpiperazin-1-yl)-C(O)O-]benzyl- | —OH |
| p-F-φ- | R$^2$/R$^3$ = cyclic —CH$_2$—S—C(CH$_3$)$_2$— (L-5,5-dimethylthiazolidin-4-yl) | | p-[(4-(pyrimidin-2-yl)piperazin-1-yl)-C(O)O-]benzyl- | —OH |
| quinolin-8-yl- | R$^2$/R$^3$ = cyclic —CH$_2$—S—C(CH$_3$)$_2$— (L-5,5-dimethylthiazolidin-4-yl) | | p-[(CH$_3$)$_2$NC(O)O-]benzyl- | —OH |
| pyridin-4-yl- | R$^2$/R$^3$ = cyclic —CH$_2$—S—C(CH$_3$)$_2$— (L-5,5-dimethylthiazolidin-4-yl) | | p-[(4-(pyridin-2-yl)piperazin-1-yl)C(O)O-]benzyl- | —OCH(CH$_3$)$_2$ |
| p-F-φ- | R$^2$/R$^3$ = cyclic —CH$_2$—S—C(CH$_3$)$_2$— (L-5,5-dimethylthiazolidin-4-yl) | | p-[(4-(pyridin-2-yl)piperazin-1-yl)C(O)O-]benzyl- | —OCH(CH$_3$)$_2$ |
| m-F-φ- | R$^2$/R$^3$ = cyclic 3 carbon atoms (L-pyrrolidinyl) | | p-[(CH$_3$)$_2$NC(O)O-]benzyl- | —OH |

TABLE 3-continued $$R^1-\underset{\underset{O}{\|}}{S}-N-CH-C-N-CH-C-R^6$$

| R¹ | R² | R³ | R⁵ | R⁶ |
|---|---|---|---|---|
| p-F-φ- | R²/R³ = cyclic —CH₂—CH₂—S— (thiazolidin-2-yl) | | p-[(CH₃)₂NC(O)O-]benzyl- | —OH |
| p-F-φ- | R²/R³ = cyclic —CH₂—CH₂—S— (thiazolidin-2-yl) | | p-[(CH₃)₂NC(O)O-]benzyl- | —OC(CH₃)₃ |
| p-CH₃-φ- | R²/R³ = cyclic —CH₂—C(O)—CH₂— (L-4-oxopyrrolidinyl) | | p-[(thiomorpholin-4-yl)C(O)O-]benzyl- | —OH |
| p-NH₂—C(=N)-φ- | R²/R³ = cyclic 3 carbon atoms (L-pyrrolidinyl) | | p-[(thiomorpholin-4-yl)C(O)O-]benzyl- | —OCH₃ |
| p-CH₃-φ- | R²/R³ = cyclic —CH₂—C(O)—CH₂— (L-4-oxopyrrolidinyl) | | p-[(4-methylpiperazin-1-yl)-C(O)O-]benzyl- | —OH |
| p-F-φ- | R²/R³ = cyclic —CH₂—CH₂—S— (thiazolidin-2-yl) | | p-[(4-pyridin-2-yl)piperazin-1-yl)-C(O)O-]benzyl- | —OH |
| p-NO₂-φ- | R²/R³ = cyclic 3 carbon atoms (L-pyrrolidinyl) | | p-[(4-pyridin-2-yl)piperazin-1-yl)-C(O)O-]benzyl- | —OC(CH₃)₃ |
| p-F-φ- | R²/R³ = cyclic —CH₂—CH₂—S— (thiazolidin-2-yl) | | p-[(4-pyridin-2-yl)piperazin-1-yl)-C(O)O-]benzyl- | —OC(CH₃)₃ |
| p-Br-φ- | R²/R³ = cyclic —CH₂—S—C(CH₃)₂— (L-5,5-dimethylthiazolidin-4-yl) | | p-[(4-pyridin-2-yl)piperazin-1-yl)-C(O)O-]benzyl- | —OH |
| p-CH₃-φ- | R²/R³ = cyclic 3 carbon atoms (L-pyrrolidinyl) | | p-[(4-(φC(O)-)piperazin-1-yl)C(O)O-]benzyl- | —OH |
| p-CH₃-φ- | R²/R³ = cyclic 3 carbon atoms (L-pyrrolidinyl) | | p-[(4-(φNHC(S)-)piperazin-1-yl)C(O)O-]benzyl- | —OCH(CH₃)₂ |
| p-F-φ- | R²/R³ = cyclic —CH₂—CH₂—S— (thiazolidin-2-yl) | | p-[(4-CH₃-homopiperazin-1-yl)C(O)O-]benzyl- | —OC(CH₃)₃ |
| p-CH₃-φ- | R²/R³ = cyclic 3 carbon atoms (L-pyrrolidinyl) | | p-[p-CH₃-φ-SO₂N(CH₃)CH₂CH₂N(CH₃)—C(O)O-]benzyl- | —OCH(CH₃)₂ |
| p-CH₃-φ- | R²/R³ = cyclic —CH₂—CH₂—S— (thiazolidin-2-yl) | | p-[φNHC(O)O—CH₂CH₂NHC(O)O-]benzyl- | —OCH(CH₃)₂ |
| 3-Cl-4-F-φ- | R²/R³ = cyclic —CH₂CH₂—SO₂—CH₂— (L-1,1-dioxothiomorpholin-3-yl) | | p-[(CH₃)₂NC(O)O-]benzyl- | —OC(CH₃)₃ |

TABLE 3-continued $$R^1-\underset{\underset{O}{\overset{O}{\|}}}{S}-\underset{\underset{R^2}{\|}}{N}-CH-\underset{\overset{O}{\|}}{C}-\underset{\overset{H}{\|}}{N}-CH-\overset{O}{\overset{\|}{C}}-R^6$$

| R¹ | R² | R³ | R⁵ | R⁶ |
|---|---|---|---|---|
| 1-methylpyrazol-4-yl- | R²/R³ = cyclic —CH₂CH₂—S—CH₂— (L-thiomorpholin-3-yl) | | p-[(CH₃)₂NC(O)O-]benzyl- | —OC(CH₃)₃ |
| p-CH₃-φ- | R²/R³ = cyclic —CH₂CH(—OSO₂CH₃)—CH₂— (L-4-methanesulfoxy-pyrrolidinyl) | | p-[(CH₃)₂NC(O)O-]benzyl- | —OC(CH₃)₃ |
| p-H₂NC(O)-φ- | R²/R³ = cyclic 3 carbon atoms (L-pyrrolidinyl) | | p-[(CH₃)₂NC(O)O-]benzyl- | —OH |
| p-H₂N—C(=N)-φ- | R²/R³ = cyclic 3 carbon atoms (L-pyrrolidinyl) | | p-[(CH₃)₂NC(O)O-]benzyl- | —OH |
| p-H₂NC(O)-φ- | R²/R³ = cyclic 3 carbon atoms (L-pyrrolidinyl) | | p-[(thiomorpholin-4-yl)C(O)O-]benzyl- | —OH |
| p-H₂N—C(=N)-φ- | R²/R³ = cyclic 3 carbon atoms (L-pyrrolidinyl) | | p-[(thiomorpholin-4-yl)C(O)O-]benzyl- | —OH |
| p-NO₂-φ- | R²/R³ = cyclic 3 carbon atoms (L-pyrrolidinyl) | | p-[(4-(pyridin-2-yl)piperazin-1-yl)-C(O)O-]benzyl- | —OH |
| p-F-φ- | R²/R³ = cyclic —CH₂—S—C(CH₃)₂— (L-5,5-dimethylthiazolidin-4-yl) | | 3-chloro-4-[(4-(pyridin-2-yl)piperazin-1-yl)C(O)O-]benzyl- | —OCH₂CH₃ |
| p-F-φ- | R²/R³ = cyclic —CH₂—S—C(CH₃)₂— (L-5,5-dimethylthiazolidin-4-yl) | | 3-chloro-4-[(4-(pyridin-2-yl)piperazin-1-yl)C(O)O-]benzyl- | —OH |
| p-F-φ- | R²/R³ = cyclic —CH₂—CH₂—S— (thiazolidin-2-yl) | | p-[(4-CH₃-homopiperazin-1-yl)C(O)O-]benzyl- | —OH |
| 1-methylimidazol-4-yl- | R²/R³ = cyclic —CH₂—S—C(CH₃)₂— (L-5,5-dimethylthiazolidin-4-yl) | | 3-chloro-4-[(CH₃)₂NC(O)O-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OH |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |

TABLE 3-continued $$R^1-\underset{\underset{O}{\overset{O}{\|}}}{\overset{O}{\|}}S-N-CH-C-N-CH-C-R^6$$
$$\phantom{R^1-S-}\underset{R^2}{|}\phantom{CH-}\underset{H}{|}\phantom{CH-C-R^6}$$
$$\phantom{R^1-S-N-CH-C-N-CH-C-R^6}R^3\phantom{xxxxx}R^5$$

| R¹ | R² | R³ | R⁵ | R⁶ |
|---|---|---|---|---|
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-F-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-F-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-CH₃-φ- | —CH₂CH₂N(—SO₂—CH₃)CH₂— (4-methanesulfonyl-piperazin-2-yl) | | p-[(CH₃)₂NC(O)O-]benzyl- | —OH |
| p-CH₃-φ- | —CH₂CH(—OSO₂—CH₃)CH₂— (L-4-methanesulfoxy-pyrrolidinyl) | | p-[(CH₃)₂NC(O)O-]benzyl- | —OH |
| 3,4-difluoro-φ- | R²/R³ = cyclic —CH₂—CH₂—S—CH₂— (L-thiomorpholin-3-yl) | | p-[(CH₃)₂NC(O)O-]benzyl- | —OC(CH₃)₃ |
| pyridin-3-yl | R²/R³ = cyclic —CH₂—S—C(CH₃)₂— (L-5,5-dimethylthiazolidin-4-yl) | | p-[(thiomorpholin-4-yl)C(O)O-]benzyl- | —OCH(CH₃)₂ |
| 3,4-difluoro-φ- | R²/R³ = cyclic —CH₂—CH₂—S—CH₂— (L-thiomorpholin-3-yl) | | p-[(CH₃)₂NC(O)O-]benzyl- | —OH |
| p-F-φ- | R²/R³ = cyclic —CH₂CH(OH)CH₂— (L-4-hydroxypyrrolidinyl) | | p-[(4-(pyridin-2-yl)piperazin-1-yl)C(O)O-]benzyl- | —OCH(CH₃)₂ |
| p-Br-φ- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| p-CF₃O-φ- | R²/R³ = cyclic —CH₂—S—C(CH₃)₂— (L-5,5-dimethylthiazolidin-4-yl) | | p-[(CH₃)₂NC(O)O-]benzyl- | —OH |
| p-CF₃O-φ- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| p-CF₃O-φ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OC(CH₃)₃ |
| p-F-φ- | R²/R³ = cyclic 3 carbon atoms (L-pyrrolidinyl) | | p-[(4-(pyridin-2-yl)piperazin-1-yl)C(O)O-]benzyl- | —OH |
| p-F-φ- | —CH₂CH(OH)CH₂— (L-4-hydroxypyrrolidinyl) | | p-[(4-(pyridin-2-yl)piperazin-1-yl)C(O)O-]benzyl- | —OH |

TABLE 3-continued $$R^1-\underset{\underset{O}{\overset{O}{\|}}}{S}-N-CH-C-N-CH-C-R^6$$

| R¹ | R² | R³ | R⁵ | R⁶ |
|---|---|---|---|---|
| p-CF₃O-φ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OH |
| 1-methylimidazol-4-yl- | R²/R³ = cyclic 3 carbon atoms (L-pyrrolidinyl) | | 3-chloro-4-[(CH₃)₂NC(O)O-]benzyl- | —OH |
| 1-methylimidazol-4-yl- | R²/R³ = cyclic 3 carbon atoms (L-pyrrolidinyl) | | 3-chloro-4-[(CH₃)₂NC(O)O-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OH |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OH |
| 1-methylimidazol-4-yl- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OH |
| 1-methylpyrazol-4-yl- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 1-methylpyrazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| 1-methylpyrazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| 1-methylpyrazol-4-yl- | R²/R³ = cyclic —CH₂—S—C(CH₃)₂— (L-5,5-dimethylthiazolidin-4-yl) | | 3-chloro-4-[(4-(pyridin-2-yl)piperazin-1-yl)C(O)O-]benzyl- | —OCH(CH₃)₂ |
| 1-methylpyrazol-4-yl- | R²/R³ = cyclic 3 carbon atoms (L-pyrrolidinyl) | | p-[(CH₃)₂NC(O)O-]benzyl- | —OCH₂CH₂Oφ |
| 1-methylpyrazol-4-yl- | R²/R³ = cyclic —CH₂—S—C(CH₃)₂— (L-5,5-diemthylthiazolidin-4-yl) | | 3-chloro-4-[(4-(pyridin-2-yl)piperazin-1-yl)C(O)O-]benzyl- | —OH |
| 1-methylpyrazol-4-yl- | R²/R³ = cyclic 3 carbon atoms (L-pyrrolidinyl) | | 3-chloro-4-[(4-(pyridin-2-yl)piperazin-1-yl)C(O)O-]benzyl- | —OCH₂CH₃ |
| 1,5-dimethyl-3-chloropyrazol-4-yl- | R²/R³ = cyclic —CH₂—S—C(CH₃)₂— (L-5,5-dimethylthiazolidin-4-yl) | | p-[4-[5-CF₃-pyridin-2-yl]piperazin-1yl)-C(O)O-]benzyl- | —OH |
| p-F-φ- | R²/R³ = cyclic —CH₂CH(OH)CH₂— (L-4-hydroxypyrrolidinyl) | | p-[(CH₃)₂NC(O)O-]benzyl- | —OC(CH₃)₃ |

TABLE 3-continued $$R^1-S(O)_2-N(R^2)-CH(R^3)-C(O)-N(H)-CH(R^5)-C(O)-R^6$$

| R¹ | R² | R³ | R⁵ | R⁶ |
|---|---|---|---|---|
| pyridin-4-yl- | R²/R³ = cyclic —CH₂—S—C(CH₃)₂— (L-5,5-dimethylthiazolidin-4-yl) | | p-[(CH₃)₂NC(O)O-]benzyl- | —OH |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂C(CH₃)₃ |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂O—C(O)OC(C(CH₃)₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂C(CH₃)₃ |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | 2-CH₃O-φ-O— |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂cyclopropyl |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂CH₂CH₃ |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂CH₂CH₂CH₃ |
| 1-methylpyrazol-4-yl- | R²/R³ = cyclic —CH₂—S—C(CH₃)₂— (L-5,5-dimethylthiazolidin-4-yl) | | p-[(CH₃)₂NC(O)O-]benzyl- | —O—CH₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂CH₃ |
| pyridin-3-yl- | R²/R³ = cyclic —CH₂—S—C(CH₃)₂— (L-5,5-dimethylthiazolidin-4-yl) | | p-[(CH₃)₂NC(O)O-]benzyl- | —OCH₂cyclopropyl |

In a preferred embodiment of the compounds of formula I and IA, the compounds are defined by formula IB below:

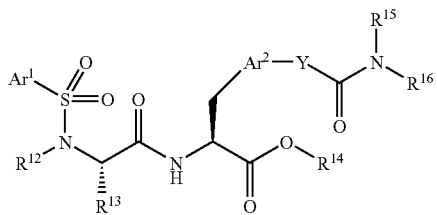

IB wherein:
Ar$^1$ is selected from the group consisting of aryl, substituted aryl, heteroaryl, and substituted heteroaryl;
Ar$^2$ is selected from the group consisting of aryl, substituted aryl, heteroaryl and substituted heteroaryl;
R$^{12}$ is selected from the group consisting of alkyl, substituted alkyl, cycloalkyl, and substituted cycloalkyl or R$^{12}$ and R$^{13}$ together with the nitrogen atom bound to R$^{12}$ and the carbon atom bound to R$^{13}$ form a heterocyclic or substituted heterocyclic group;
R$^{13}$ is selected from the group consisting of hydrogen, alkyl, and substituted alkyl, or R$^{12}$ and R$^{13}$ together with the nitrogen atom bound to R$^{12}$ and the carbon atom bound to R$^{13}$ form a heterocyclic or substituted heterocyclic group;
R$^{14}$ is selected from the group consisting of hydrogen, alkyl, substituted alkyl, cycloalkyl, substituted cycloalkyl, aryl, and substituted aryl;
R$^{15}$ is selected from the group consisting of alkyl, and substituted alkyl, or R$^{15}$ and R$^{16}$ together with the nitrogen atom to which they are bound form a heterocyclic or substituted heterocyclic group;
R$^{16}$ is selected from the group consisting of alkyl and substituted alkyl or R$^{15}$ and R$^{16}$ together with the nitrogen atom to which they are bound form a heterocyclic or substituted heterocyclic group; and
Y is selected from the group consisting of —O—, —NR$^{100}$—, and —CH$_2$— wherein R$^{100}$ is hydrogen or alkyl;
and pharmaceutically acceptable salts thereof.

Preferably, in the compounds of formula IB above, R$^{12}$ is alkyl, substituted alkyl, or R$^{12}$ and R$^{13}$ together with the nitrogen atom bound to R$^{12}$ and the carbon atom bound to R$^{13}$ form a heterocyclic or substituted heterocyclic group. Preferably, in the compounds of formula IB above, R$^{14}$ is hydrogen or alkyl.

Preferably, in the compounds of formula IB above, Ar$^1$ is selected from the group consisting of phenyl, 4-methylphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl)phenyl, 4-(H$_2$NC(O)—)phenyl, 4-(H$_2$NC(S)—)phenyl, 4-cyanophenyl, 4-trifluoromethylphenyl, 4-trifluoromethoxyphenyl, 3,5-di-(trifluoromethyl)phenyl, 4-nitrophenyl, 4-aminophenyl, 4-(CH$_3$C(O)NH—)phenyl, 4-(PhNHC(O)NH—)phenyl, 4-amidinophenyl, 4-methylamidinophenyl, 4-[CH$_3$SC(=NH)—]phenyl, 4-chloro-3-[H$_2$NS(O)$_2$—]phenyl, 1-naphthyl, 2-naphthyl, pyridin-2-yl, pyridin-3-yl, pyridine-4-yl, pyrimidin-2-yl, quinolin-8-yl, 2-(trifluoroacetyl)-1,2,3,4-tetrahydroisoquinolin-7-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

Preferably, in the compounds of formula IB above, R$^{12}$ and R$^{13}$ together with the nitrogen atom bound to R$^{12}$ and the carbon atom bound to R$^3$ form a heterocyclic or substituted heterocyclic of the formula:

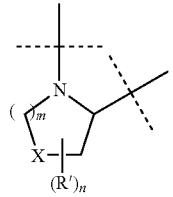

wherein
X is selected from the group consisting of —S—, —SO—, —SO$_2$, and optionally substituted —CH$_2$—;
m is an integer of 0 to 12;
n is an integer of 0 to 2; and
R' is selected from the group consisting of alkyl, substituted alkyl, and amino.

Preferably, m is 1, X is —S— or —CH$_2$—, R' is alkyl or substituted alkyl.

Even more preferably, R$^{12}$ and R$^{13}$ together with the nitrogen atom bound to R$^{12}$ and the carbon atom bound to R$^{13}$ form a heterocyclic or substituted heterocyclic selected from the group consisting of azetidinyl, thiazolidinyl, piperidinyl, piperazinyl, thiomorpholinyl, pyrrolidinyl, 4-hydroxypyrrolidinyl, 4-oxopyrrolidinyl, 4-fluoropyrrolidinyl, 4,4-difluoropyrrolidinyl, 4-(thiomorpholin-4-ylC(O)O—)pyrrolidinyl, 4-[CH$_3$S(O)$_2$O—]pyrrolidinyl, 3-phenylpyrrolidinyl, 3-thiophenylpyrrolidinyl, 4-aminopyrrolidinyl, 3-methoxypyrrolidinyl, 4,4-dimethylpyrrolidinyl, 4-N-Cbz-piperazinyl, 4-[CH$_3$S(O)$_2$—]piperazinyl, thiazolidin-3-yl, 5,5-dimethylthiazolidin-3-yl, 5,5-dimethylthiazolindin-4-yl, 1,1-dioxothiazolidinyl, 1,1-dioxo-5,5-dimethylthiazolidin-2-yl and 1,1-dioxothiomorpholinyl.

Preferably, in the compounds of formula IB, Ar$^2$ is selected from the group consisting of phenyl, 2-pyridyl, 3-pyridyl, 4-pyridyl, and 4-pyrid-2-onyl.

Preferably, in formula IB, Y is —O—, and when Y is —O—, the moiety —OC(O)NR$^{15}$R$^{16}$ is preferably selected from the group consisting of (CH$_3$)$_2$NC(O)O—, (piperidin-1-yl)C(O)O—, (4-hydroxypiperidin-1-yl)C(O)O—, (4-formyloxypiperidin-1-yl)C(O)O—, (4-ethoxycarbonylpiperidin-1-yl)C(O)O—, (4-carboxylpiperidin-1-yl)C(O)O—, (3-hydroxymethylpiperidin-1-yl)C(O)O—, (4-hydroxymethylpiperidin-1-yl)C(O)O—, (4-piperidon-1-yl ethylene ketal)C(O)O—, (piperazin-1-yl)-C(O)O—, (1-Boc-piperazin-4-yl)-C(O)O—, (4-methylpiperazin-1-yl)C(O)O—, (4-methylhomopiperazin-1-yl)C(O)O—, (4-(2-hydroxyethyl)piperazin-1-yl)C(O)O—, (4-phenylpiperazin-1-yl)C(O)O—, (4-(pyridin-2-yl)piperazin-1]-yl)C(O)O—, (4-(4-trifluoromethylpyridin-2-yl)piperazin-1-yl)C(O)O—, (4-(pyrimidin-2-yl)piperazin-1-yl)C(O)O—, (4-acetylpiperazin-1-yl)C(O)O—, (4-(phenylC(O)—)piperazin-1-yl)C(O)O—, (4-(pyridin-4'-ylC(O)—)piperazin-1-yl) C(O)O, (4-(phenylNHC(O)—)piperazin-1-yl)C(O)O—, (4-(phenylNHC(S)—)piperazin-1-yl)C(O)O—, (4-methanesulfonylpiperazin-1-yl-C(O)O—, (4-trifluoromethanesulfonylpiperazin-1-yl-C(O)O—, (morpholin-4-yl)C(O)O—, (thiomorpholin-4-yl)C(O)O—, (thiomorpholin-4'-yl sulfone)-C(O)O—, (pyrrolidin-1-yl)C(O)O—, (2-methylpyrrolidin-1-yl)C(O)O—, (2-(methoxycarbonyl)pyrrolidin-1-yl)C(O)O—, (2-(hydroxymethyl)pyrrolidin-1-yl)C(O)O—, (2-(N,N-dimethylamino)ethyl)(CH$_3$)NC(O)O—, (2-(N-methyl-N-toluene-4-sulfonylamino)ethyl)(CH$_3$)N—C(O)O—, (2-(morpholin-4-yl)ethyl)(CH$_3$)NC(O)O—, (2-(hydroxy)ethyl)(CH$_3$)NC(O)O—, bis(2-(hydroxy)ethyl)NC(O)O—, (2-(formyloxy)ethyl)(CH$_3$)NC(O)O—, (CH$_3$OC(O)CH$_2$)HNC(O)O—, and 2-[(phenylNHC(O)O—)ethyl-]HNC(O)O—.

In a preferred embodiment, the compounds are defined by formula IC below

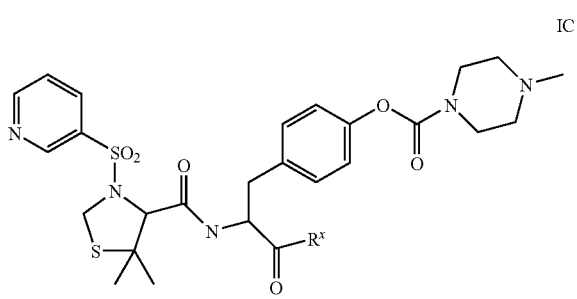

IC wherein R$^x$ is hydroxy or C$_{1-5}$ alkoxy and pharmaceutically acceptable salts thereof. Preferably, the compound is N-[N-(3-pyridinesulfonyl)-L-3,3-dimethyl-4-thiaprolyl]-O-[1-methylpiperazin-4-ylcarbonyl]-L-tyrosine isopropyl ester.

In another aspect, the compounds that can be utilized as remyleinating agents are compounds defined by formula II below. These compounds have a binding affinity to VLA-4 as expressed by an IC$_{50}$ of about 15 μM or less (measured as described in Example A below) and act as remyleinating agents:

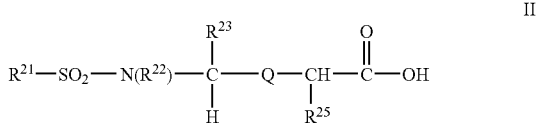

II wherein:

R$^{21}$ is selected from the group consisting of alkyl, substituted alkyl, aryl, substituted aryl, cycloalkyl, substituted cycloalkyl, heterocyclic, substituted heterocylic, heteroaryl and substituted heteroaryl;

R$^{22}$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and R$^{21}$ and R$^{22}$ together with the nitrogen atom bound to R$^{22}$ and the SO$_2$ group bound to R$^{21}$ can form a heterocyclic or a substituted heterocyclic group;

R$^{23}$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and where R$^{22}$ and R$^{23}$ together with the nitrogen atom bound to R$^{22}$ and the carbon atom bound to R$^{23}$ can form a saturated heterocyclic group or a saturated substituted heterocyclic group with the proviso that when monosubstituted, the substituent on said saturated substituted heterocyclic group is not carboxyl;

Q is —C(X)NR$^7$— wherein R$^7$ is selected from the group consisting of hydrogen and alkyl;

X is selected from the group consisting of oxygen and sulfur; and

R$^{25}$ is —CH$_2$Ar$^{22}$—R$^{25'}$ where Ar$^{22}$ is aryl or heteroaryl and R$^{25'}$ is selected from the group consisting of aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy, heterocyclic-O—, substituted heterocyclic-O—, heteroaralkoxy, and substituted heteroaralkoxy;

and pharmaceutically acceptable salts thereof.

In another embodiment, the compounds of this invention can also be provided as prodrugs which convert (e.g., hydrolyze, metabolize, etc.) in vivo to a compound of formula II above. In a preferred example of such an embodiment, the carboxylic acid in the compound of formula II is modified into a group which, in vivo, will convert to the carboxylic acid (including salts thereof). In a particularly preferred embodiment, such prodrugs are represented by compounds of formula IIA:

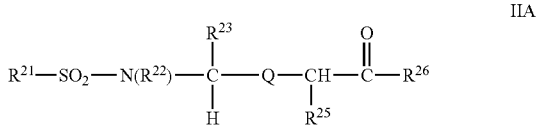

IIA where

R$^{21}$ is selected from the group consisting of alkyl, substituted alkyl, aryl, substituted aryl, cycloalkyl, substituted cycloalkyl, heterocyclic, substituted heterocylic, heteroaryl and substituted heteroaryl;

R$^{22}$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, and substituted heteroaryl, and R$^{21}$ and R$^{22}$ together with the nitrogen atom bound to R$^{22}$ and the SO$_2$ group bound to R$^{21}$ can form a heterocyclic or a substituted heterocyclic group;

R$^{23}$ is selected from the group consisting of hydrogen, alkyl, substituted alkyl, cycloalkyl, substituted cycloalkyl, aryl, substituted aryl, heteroaryl, substituted heteroaryl, heterocyclic, and substituted heterocyclic, and R$^{22}$ and R$^{23}$ together with the nitrogen atom bound to R$^{22}$ and the carbon atom bound to R$^{23}$ can form a saturated heterocyclic group or a saturated substituted heterocyclic group with the proviso that when monosubstituted, the substituent on said saturated substituted heterocyclic group is not carboxyl;

R$^{25}$ is —CH$_2$Ar$^{22}$—R$^{25'}$ where Ar$^{22}$ is aryl or heteroaryl and R$^{25'}$ is selected from the group consisting of aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy, heterocyclic-O—, substituted heterocyclic-O—, heteroaralkoxy, and substituted heteroaralkoxy;

R$^{26}$ is selected from the group consisting of 2,4-dioxotetrahydrofuran-3-yl (3,4-enol), amino, alkoxy, substituted alkoxy, cycloalkoxy, substituted cycloalkoxy, —O—(N-succinimidyl), —NH-adamantyl, —O-cholest-5-en-3-β-yl, —NHOY where Y is hydrogen, alkyl, substituted alkyl, aryl, and substituted aryl, —NH(CH$_2$)$_p$COOY where p is an integer of from 1 to 8 and Y is as defined above, —OCH$_2$NR$^{29}$R$^{30}$ where R$^{29}$ is selected from the group consisting of —C(O)-aryl and —C(O)-substituted aryl and R$^{30}$ is selected from the group consisting of hydrogen and —CH$_2$COOR$^{31}$ where R$^{31}$ is alkyl, and —NHSO$_2$Z' where Z' is alkyl, substituted alkyl, cycloalkyl, substituted cycloalkyl, aryl, substituted aryl, heteroaryl, substituted heteroaryl, heterocyclic or substituted heterocyclic;

Q is —C(X)NR$^7$— wherein R$^7$ is selected from the group consisting of hydrogen and alkyl; and X is selected from the group consisting of oxygen and sulfur;

and pharmaceutically acceptable salts thereof.

Further description of the compounds of the above formulae II and IIA and procedures and reaction conditions for preparing these compounds are described in U.S. Ser. No. 09/127,346 (filed Jul. 31, 1998), Ser. No. 09/688,820 (Continuation, filed Oct. 17, 200 and issued as U.S. Pat. No. 6,583,139) and Ser. No. 10/382,988 (Continuation, filed Mar. 7, 2003), all of which are herein incorporated by reference in their entirety.

Preferably, in the compounds of formula II and IIA above, R$^{21}$ is selected from the group consisting of alkyl, substituted alkyl, aryl, substituted aryl, heterocyclic, substituted heterocylic, heteroaryl and substituted heteroaryl. More preferably R$^{21}$ is selected from the group consisting of aryl, substituted aryl, heteroaryl and substituted heteroaryl.

Even more preferably, in the compounds of formula II and IIA above, R$^{21}$ is selected from the group consisting of 4-methylphenyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH$_3$C(O)NH—)phenyl, 4-trifluoromethoxyphenyl, 4-cyanophenyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, 1-N-methylimidazol-4-yl, 4-bromophenyl, 4-amidinophenyl, 4-methylamidinophenyl, 4-[CH$_3$SC(═NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H$_2$NC(S)]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl.

Preferably, R$^{22}$, in the compounds of formula II and IIA above, is hydrogen, methyl, phenyl, benzyl, —(CH$_2$)$_2$-2-thienyl, and —(CH$_2$)$_2$-ϕ.

In another preferred embodiment, R$^{22}$ and R$^{23}$, in the compounds of formula II and IIA above, and R$^{22}$ and R$^{32}$, in the compounds of formula IIB, together with the nitrogen atom bound to R$^{22}$ or R$^{32}$ and the carbon atom bound to R$^{23}$ or R$^{33}$ form a saturated heterocyclic group or a saturated substituted heterocyclic group with the proviso that when monosubstituted, the substituent on said saturated substituted heterocyclic group is not carboxyl.

Q, in the compounds of formula II and IIA above, is preferably —C(O)NH— or —C(S)NH—.

In the compounds of formula II and IIA, R$^{25}$ is preferably selected from the group consisting of all possible isomers arising by substitution with the following groups: 4-(2-carboxyphenoxy)benzyl, 4-(benzyloxy)benzyl, 4-[(1-methylpiperidin-4-yl)-O—]benzyl, 4-(imidazolid-2-one-1-yl)benzyl, and 4-(3-formylimidazolid-2-one-1-yl)benzyl.

In the compounds of formula IIA, R$^{26}$ is preferably 2,4-dioxo-tetrahydrofuran-3-yl (3,4-enol), methoxy, ethoxy, iso-propoxy, n-butoxy, t-butoxy, cyclopentoxy, neo-pentoxy, 2-α-iso-propyl-4-β-methylcyclohexoxy, 2-β-isopropyl-4-β-methylcyclohexoxy, —NH$_2$, benzyloxy, —NHCH$_2$COOH, —NHCH$_2$CH$_2$COOH, —NH-adamantyl, —NHCH$_2$CH$_2$COOCH$_2$CH$_3$, —NHSO$_2$-p-CH$_3$-ϕ, —NHOR$^8$ where R$^8$ is hydrogen, methyl, iso-propyl or benzyl, O—(N-succinimidyl), —O-cholest-5-en-3-β-yl, —OCH$_2$—OC(O)C(CH$_3$)$_3$, —O(CH$_2$)$_z$NHC(O)W where z is 1 or 2 and W is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R' is hydrogen or —CH$_2$C(O)OCH$_2$CH$_3$.

Preferred compounds within the scope of formulae II and IIA above include by way of example the following:

N-(Toluene-4-sulfonyl)-L-prolyl-4-(α-methylbenzyloxy)-L-phenylalanine

N-(Toluene-4-sulfonyl)-L-prolyl-4-(2-carboxyphenoxy)-L-phenylalanine

N-(Toluene-4-sulfonyl)-L-prolyl-O-(benzyl)-L-tyrosine and pharmaceutically acceptable salts thereof.

Preferred compounds of formula II and IIA above include those set forth in Table 4 below.

TABLE 4

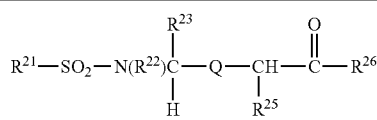

| R$^{21}$ | R$^{22}$ | R$^{23}$ | R$^{25}$ | R$^{26}$ | Q = —C(O)NR$^7$— wherein R$^7$ is: |
|---|---|---|---|---|---|
| p-CH$_3$-ϕ- | R$^{22}$/R$^{23}$ = cyclic 3 carbon atoms (L-pyrrolidinyl) | | p-[O-(o-carboxyphenyl)]-benzyl- | —OH | H |
| p-CH$_3$-ϕ- | R$^{22}$/R$^{23}$ = cyclic 3 carbon atoms (L-pyrrolidinyl) | | p-benzyloxybenzyl- | —OH | H |
| p-CH$_3$-ϕ- | R$^{22}$/R$^{23}$ = cyclic 3 carbon atoms (L-pyrrolidinyl) | | p-[(1-methylpiperidin-4-yl)-O-]benzyl- | —OCH$_2$CH$_3$ | H |
| p-CH$_3$-ϕ- | R$^{22}$/R$^{23}$ = cyclic 3 carbon atoms (L-pyrrolidinyl) | | p-[(imidazolid-2-one-1-yl)benzyl- | —OC(CH$_3$)$_3$ | H |

TABLE 4-continued $$R^{21}-SO_2-N(R^{22})\underset{H}{\overset{R^{23}}{C}}-Q-\underset{R^{25}}{CH}-\overset{O}{\underset{\|}{C}}-R^{26}$$

| $R^{21}$ | $R^{22}$ | $R^{23}$ | $R^{25}$ | $R^{26}$ | Q = —C(O)NR$^7$— wherein R$^7$ is: |
|---|---|---|---|---|---|
| p-CH$_3$-φ- | R$^{22}$/R$^{23}$ = cyclic 3 carbon atoms (L-pyrrolidinyl) | | p-[3-formylimidazolid-2-one-1-yl)benzyl- | —OH | H |
| p-CH$_3$-φ- | R$^{22}$/R$^{23}$ = cyclic 3 carbon atoms (L-pyrrolidinyl) | | p-[(imidazolid-2-one-1-yl)benzyl- | —OH | H |
| p-CH$_3$-φ- | R$^{22}$/R$^{23}$ = cyclic 3 carbon atoms (L-pyrrolidinyl) | | p-[1-H-2-oxo-3-methyl tetrahydro pyrimidin-1-yl]benzyl- | —Ot—Bu | H |
| p-CH$_3$-φ- | R$^{22}$/R$^{23}$ = cyclic 3 carbon atoms (L-pyrrolidinyl) | | p-[1-H-2-oxo-3-methyl tetrahydro pyrimidin-1-yl]benzyl- | —OH | H |
| p-CH$_3$-φ- | R$^{22}$/R$^{23}$ = cyclic 3 carbon atoms (L-pyrrolidinyl) | | 4-[2-methoxy phenyl]-benzyl- | —Ot—Bu | H |
| p-CH$_3$-φ- | R$^{22}$/R$^{23}$ = cyclic 3 carbon atoms (L-pyrrolidinyl) | | 4-[2-methoxy phenyl]-benzyl- | —OH | H |
| p-CH$_3$-φ- | R$^{22}$/R$^{23}$ = cyclic 3 carbon atoms (L-pyrrolidinyl) | | p-[2,4,5-trioxo-3-(3-chlorophenyl)-tetrahydroimidazol-1-yl]-benzyl- | —OBz | H |

In a preferred embodiment of the compounds of formula II and IIA, the compounds are defined by formula IIB below:

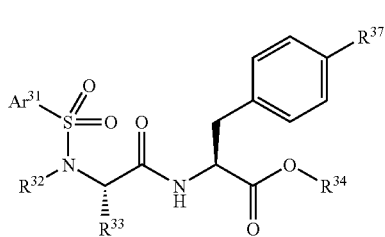

IIB wherein:

Ar$^{31}$ is selected from the group consisting of aryl, substituted aryl, heteroaryl, and substituted heteroaryl;

R$^{32}$ is selected from the group consisting of alkyl, substituted alkyl, cycloalkyl, and substituted cycloalkyl or R$^{32}$ and R$^{33}$ together with the nitrogen atom bound to R$^{32}$ and the carbon atom bound to R$^{33}$ form a heterocyclic or substituted heterocyclic group;

R$^{33}$ is selected from the group consisting of hydrogen, alkyl, and substituted alkyl, or R$^{32}$ and R$^{33}$ together with the nitrogen atom bound to R$^{32}$ and the carbon atom bound to R$^{33}$ form a heterocyclic or substituted heterocyclic group;

R$^{34}$ is selected from the group consisting of hydrogen, alkyl, substituted alkyl, cycloalkyl, substituted cycloalkyl, aryl, and substituted aryl; and R$^{37}$ is aryl, heteroaryl, substituted aryl, substituted heteroaryl, heterocyclic, substituted heterocyclic, aryloxy, substituted aryloxy, aralkoxy, substituted aralkoxy, heteroaryloxy, substituted heteroaryloxy;

and pharmaceutically acceptable salts thereof.

Preferably, in the compounds of formula IIB above, R$^{32}$ is alkyl, substituted alkyl, or R$^{32}$ and R$^{33}$ together with the nitrogen atom bound to R$^{32}$ and the carbon atom bound to R$^{33}$ form a heterocyclic or substituted heterocyclic group and R$^{34}$ is hydrogen or alkyl.

Preferably, in the compounds of formula IIB above, R$^{37}$ is aryl, substituted aryl, heteroaryl, substituted heteroaryl, heterocyclic, or substituted heterocyclic. In a preferred embodiment, R$^{37}$ is substituted aryl wherein the aryl is substituted with one to three substituents independently selected from the group consisting alkyl and alkoxy. In a preferred embodiment, R$^{37}$ is substituted heteroaryl wherein the heteroaryl is substituted with one to three substituents independently selected from the group consisting alkyl, alkoxy, and oxo. In another preferred embodiment R$^{37}$ is substituted aryl or heteroaryl wherein aryl or heteroaryl is 2,6-di-substituted. In yet another preferred embodiment R$^{37}$ is 2,6-di-substituted aryl wherein the substituents are independently selected from the group consisting of alkyl and alkoxy. In yet another preferred embodiment R$^{37}$ is 2,6-di-substituted heteroaryl wherein the substituents are independently selected from the group consisting of alkyl, oxo, and alkoxy. In another preferred embodiment, R$^{37}$ is selected from the group consisting of 2,6-dialkoxyaryl, 2,6-dialkoxyheteroaryl, 2-alkyl-6-alkoxyaryl, 2-alkyl-6-alkoxyheteroaryl, 2-oxo-6-alkoxyheteroaryl, 2-oxo-6-alkylheteroaryl, and optionally substituted imidazolidin-2,4-dion-3-yl.

Preferably in the compounds of formula IIB above, Ar$^{31}$ is selected from the group consisting of 4-methylphenyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH$_3$C(O)NH—)phenyl, 4-trifluoromethoxyphenyl, 4-cyanophenyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, 1-N-methylimidazol-4-yl, 4-bromophenyl, 4-amidinophenyl, 4-methylamidinophenyl, 4-[CH$_3$SC(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H₂NC(S)]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl.

When describing the compounds, compositions and methods of this invention, the following terms have the following meanings, unless otherwise indicated.

Definitions

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenoxy" refers to the group "alkenyl-O—".

"Substituted alkenoxy" refers to the group "substituted alkenyl-O—".

"Alkenyl" refers to alkenyl group preferably having from 2 to 10 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, cycloalkyloxy, substituted cycloalkyloxy, heteroaryloxy, substituted heteroaryloxy, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono-and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

Preferably, the substituents are independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, of from 1 to 10 carbon atoms, having from 1 to 5 substituents independently selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, cycloalkyloxy, substituted cycloalkyloxy, heteroaryloxy, substituted heteroaryloxy, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Preferably, the substituents are independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkylene" refers to linear and branched divalent alkyl groups having from 1 to 10 carbon atoms and more preferably 1 to 6 carbon atoms. This term is exemplified by groups such as methylene (—CH$_2$—), 1,6-heptylene, 1,8-octylene, ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents independently selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Amino" refers to the group —NH$_2$.

"Substituted amino" refers to the group —NRR, where each R group is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic, and substituted heterocyclic, provided that both R groups are not hydrogen; or where the R groups can be joined together with the nitrogen atom to form a heterocyclic or substituted heterocyclic ring.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like) provided that the point of attachment is through an aromatic ring atom. Preferred aryls include phenyl, naphthyl and 5,6,7,8-tetrahydronaphth-2-yl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$—substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

Preferred substituents are selected from the group consisting of hydroxy, acyl, acylamino, acyloxy, alkyl, substituted alkyl, alkoxy, substituted alkoxy, alkenyl, substituted alkenyl, amino, substituted amino, aminoacyl, aminocarbonyloxy, aminocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, cycloalkyl, substituted cycloalkyl, halo, nitro, heteroaryl, substituted heteroaryl, heterocyclic, substituted heterocyclic, and oxycarbonylamino.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aralkoxy" refers to aryl-alkylene-O— groups.

"Substituted aralkoxy" refers to substituted aryl-alkylene-O— groups.

"Carboxyl" refers to the group —COOH and pharmaceutically acceptable salts thereof.

"Carboxyl esters" refers —C(O)O-alkyl, —C(O)O-substituted alkyl, —C(O)O-alkenyl, —C(O)O-substituted alkenyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic.

"Cycloalkenyl" refers to cyclic alkenyl groups of frm 3 to 8 carbon atoms having a single cyclic ring.

"Cycloalkoxy" refers to —O-cycloalkyl groups.

"Substituted cycloalkoxy" refers to —O-substituted cycloalkyl groups.

"Cycloalkyl" refers to cyclic alkyl groups of from 3 to 12 carbon atoms having a single or multiple condensed rings including, by way of example, adamantyl, cyclopropyl, cyclobutyl, cyclopentyl, cyclohexyl, cyclooctyl and the like. Preferably "cycloalkyl" refers to cyclic alkyl groups of from 3 to 8 carbon atoms having a single cyclic ring.

"Substituted cycloalkyl" and "substituted cycloalkenyl" refers to an cycloalkyl or cycloalkenyl group, preferably of from 3 to 8 carbon atoms, having from 1 to 5 substituents independently selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Preferred substituents are selected from the group consisting of oxo (=O), thioxo (=S), alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is fluoro, chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (=O). Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S (O)₂-cycloalkyl, —S(O)₂-substituted cycloalkyl, —S(O)₂-alkenyl, —S(O)₂-substituted alkenyl, —S(O)₂-aryl, —S(O)₂-substituted aryl, —S(O)₂-heteroaryl, —S(O)₂-substituted heteroaryl, —S(O)₂-heterocyclic, —S(O)₂-substituted heterocyclic, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

Preferably the substituents are selected from the group consisting of those defined above as preferred for substituted aryl.

"Heteroaryloxy" refers to the group —O-heteroaryl and "substituted heteroaryloxy" refers to the group -O-substituted heteroaryl.

"Heteroaralkoxy" refers to the group heteroaryl-alkylene-O—.

"Substituted heteroaralkoxy" refers to the group substituted heteroaryl-alkylene-O—.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

Preferably, the substituents are selected from the group consisting of the preferred substitutents defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, morpholinyl, thiomorpholino, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group -O-substituted heterocyclic.

"N,N-Dimethylcarbamyloxy" refers to the group —OC(O)N(CH₃)₂.

"Oxo" refers to (=O).

"Oxyalkylene" refers to —OCH₂CHR$^d$— where R$^d$ is alkyl.

"Oxycarbonylamino" refers to the groups —OC(O)NH₂, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioalkyl" refers to the groups —S-alkyl.

"Substituted thioalkyl" refers to the group —S-substituted alkyl.

"Thioamidino" refers to the group RSC(=NH)— where R is hydrogen or alkyl.

"Thioaryl" refers to the group —S-aryl and "substituted thioaryl" refers to the group —S-substituted aryl.

"Thiocarbonylamino" refers to the group —C(S)NRR where each R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocycloalkyl" refers to the groups —S-cycloalkyl.

"Substituted thiocycloalkyl" refers to the group —S-substituted cycloalkyl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Thiol" refers to the group —SH.

"Optionally subsituted" means that the recited group may be unsubstituted or the recited group may be substituted.

"Pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl) amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl)amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

According to the following compound preparation, $R^1$, $R^2$, $R^3$, $R^5$, $R^6$, and $R^7$ are as defined herein for formulae I, IA, II, and IIA. In addition, according to the following compound preparation, $R^1$ is equivalent to:
- $Ar^1$ as herein defined for formula IB,
- $R^{21}$ as herein defined for formulae II and IIA, and
- $Ar^{21}$ as herein defined for formula IIB;

$R^2$ is equivalent to:
- $R^{12}$ as herein defined for formula IIB,
- $R^{22}$ as herein defined for formulae II and IIA, and
- $R^{32}$ as herein defined for formula IIB;

$R^3$ is equivalent to:
- $R^{13}$ as herein defined for formula IIB,
- $R^{23}$ as herein defined for formulae II and IIA, and
- $R^{33}$ as herein defined for formula IIB;

$R^5$ is equivalent to:
- $R^{25}$ as herein defined for formulae II and IIA; and $R^6$ is equivalent to:
- OH for formulae I and II,
- $OR^{14}$ as herein defined for formula IIB,
- $R^{26}$ as herein defined for formula IIA, and
- $OR^{34}$ as herein defined for formula IIB.

In a preferred method of synthesis, the compounds of formulae I, IA, II, and IIA, wherein Q is —C(O)NR$^7$—, and compounds of formulae IB, IC, and IIB are prepared by first coupling an amino acid of formula III:

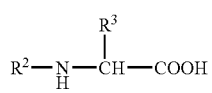

III with a sulfonyl chloride of formula IV:

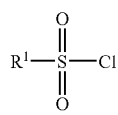

IV to provide an N-sulfonyl amino acid of formula V:

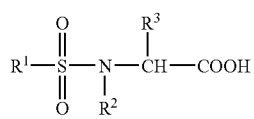

V

This reaction is typically conducted by reacting the amino acid of formula III with at least one equivalent, preferably about 1.1 to about 2 equivalents, of sulfonyl chloride IV in an inert diluent such as dichloromethane and the like. Generally, the reaction is conducted at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting N-sulfonyl amino acid V is recovered by conventional methods including neutralization, extraction, precipitation, chromatography, filtration, and the like.

The amino acids of formula III employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-indoline-2-carboxylic acid, L-1,2,3,4-tetrahydroisoquinoline-3-carboxylic acid, L-thiazolidine-4-carboxylic acid, L-(5,5-dimethyl)thiazolidine-4-carboxylic acid, L-thiamorpholine-3-carboxylic acid, glycine, 2-tert-butylglycine, D,L-phenylglycine, L-alanine, α-methylalanine, N-methyl-L-phenylalanine, L-diphenylalanine, sarcosine, D,L-phenylsarcosine, L-aspartic acid γ-tert-butyl ester, L-glutamic acid β-tert-butyl ester, L-(O-benzyl)serine, 1-aminocyclopropanecarboxylic acid, 1-aminocyclobutanecarboxylic acid, 1-aminocyclopentanecarboxylic acid (cycloleucine) 1-aminocyclohexanecarboxylic acid, L-serine and the like. If desired, the corresponding carboxylic acid esters of the amino acids of formula III, such as the methyl esters, ethyl esters and the like, can be employed in the above reaction with the sulfonyl chloride IV. Subsequent hydrolysis of the ester group to the carboxylic acid using conventional reagents and conditions, i.e., treatment with an alkali metal hydroxide in an inert diluent such as methanol/water, then provides the N-sulfonyl amino acid V.

Similarly, the sulfonyl chlorides of formula IV employed in the above reaction are either known compounds or compounds that can be prepared from known compounds by conventional synthetic procedures. Such compounds are typically prepared from the corresponding sulfonic acid, i.e., from compounds of the formula $R^1$—$SO_3H$, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chlorides of formula IV can be prepared from the corresponding thiol compound, i.e., from compounds of the formula $R^1$—SH, by treating the thiol with chlorine ($Cl_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acids of formula V.

The intermediate N-sulfonyl amino acids of formula V can also be prepared by reacting a sulfonamide of formula VI:

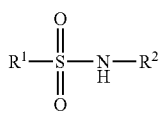

VI with a carboxylic acid derivative of the formula $L(R^3)CHCOOR^y$ where L is a leaving group, such as chloro, bromo, iodo, mesylate, tosylate and the like, and $R^y$ is hydrogen or an alkyl group. This reaction is typically conducted by contacting the sulfonamide VI with at least one equivalent, preferably 1.1 to 2 equivalents, of the carboxylic acid derivative in the presence of a suitable base, such as triethylamine, in an inert diluent, such as DMF, at a temperature ranging from about 24° C. to about 37° C. for about 0.5 to about 4 hours. This reaction is further described in Zuckermann et al., *J. Am. Chem. Soc.*, 1992, 114, 10646-10647. Preferred carboxylic acid derivatives for use in this reaction are α-chloro and α-bromocarboxylic acid esters such as tert-butyl bromoacetate and the like. When a carboxylic acid ester is employed in this reaction, the ester group is subsequently hydrolyzed using conventional procedures to afford an N-sulfonyl amino acid of formula V.

The compounds of the present invention are then prepared by coupling the intermediate N-sulfonyl amino acid of formula V with an amino acid derivative of formula VII:

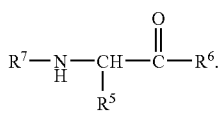

VII

This coupling reaction is typically conducted using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethylamino-propyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid V with about 1 to about 2 equivalents of the coupling reagent and at least one equivalent, preferably about 1 to about 1.2 equivalents, of amino acid derivative VII in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound of the present invention is recovered by conventional methods including neutralization, extraction, precipitation, chromatography, filtration, and the like.

Alternatively, the N-sulfonyl amino acid V can be converted into an acid halide and the acid halide coupled with amino acid derivative VII to provide compounds of the present invention. The acid halide of V can be prepared by contacting V with an inorganic acid halide, such as thionyl chloride, phosphorous trichloride, phosphorous tribromide or phosphorous penta-chloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide of N-sulfonyl amino acid V is then contacted with at least one equivalent, preferably about 1.1 to about 1.5 equivalents, of amino acid derivative VII in an inert diluent, such as dichloromethane, at a temperature ranging from about –70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of the present invention is recovered by conventional methods including neutralization, extraction, precipitation, chromatography, filtration, and the like.

Alternatively, the compounds of the present invention can be prepared by first forming a diamino acid derivative of formula VIII:

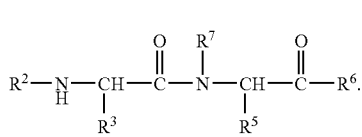

VIII

The diamino acid derivatives of formula III can be readily prepared by coupling an amino acid of formula III with an amino acid derivative of formula VII using conventional amino acid coupling techniques and reagents, such carbodiimides, BOP reagent and the like, as described above. Diamino acid VIII can then be sulfonated using a sulfonyl chloride of formula IV and using the synthetic procedures described above to provide a compound of the present invention.

The amino acid derivatives of formula VII employed in the above reactions are either known compounds or compounds that can be prepared from known compounds by conventional synthetic procedures. For example, amino acid derivatives of formula VII can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives of formula VII suitable for use in the above reactions include, but are not limited to, L-tyrosine methyl ester, L-3,5-diiodotyrosine methyl ester, L-3-iodotyrosine methyl ester, β(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

For ease of synthesis, the compounds of the present invention are typically prepared as an ester, i.e., where $R^6$ is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 10 hours. Alternatively, benzyl esters may be removed by hydrogenolysis using a palladium catalyst, such as palladium on carbon. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

As will be apparent to those skilled in the art, other functional groups present on any of the substituents of the compounds of the present invention can be readily modified or derivatized either before or after the above-described coupling reactions using well-known synthetic procedures. For example, a nitro group present on a substituent of a compound of the present invention or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on, e.g., the $R^3$ substituent, can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid. Compounds having a pyridyl group can be readily prepared by using, for example, β(2-pyridyl)-, β-(3-pyridyl)- or β-(4-pyridyl)-L-alanine derivatives in the above-described coupling reactions.

Additionally, when a substituent of a compound of the present invention or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on such a substituent may be prepared, for example, by reduction of the corresponding nitro compound as described above. Alternatively, such compounds can be prepared by using an amino acid derivative of formula VII derived from lysine, 4-aminophenylalanine and the like in the above-described coupling reactions.

By way of illustration, a compound of the present invention or an intermediate thereof having a substituent containing a primary or secondary amino group can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris (dimethylamino)-phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxybenzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of the present invention or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about of about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoromethylbenzoyl chloride, isonicotinoyl chloride, nicotinoyl chloride, picolinoyl chloride, acetic anhydride, succinic anhydride and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of the present invention or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride and the like. Similarly, sulfamoyl chlorides, such as dimethylsulfamoyl chloride, can be used to provide sulfamides (e.g., >N—SO$_2$—N<).

Additionally, a primary and secondary amino group present on a substituent of a compound of the present invention or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino) propyl thioisocyanate, phenyl thioisocyanate, benzyl thioisocyanate, 3-pyridyl thioisocyanate, fluorescein isothiocyanate (isomer L), and the like.

Furthermore, when a compound of the present invention or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of the present invention or an intermediate thereof has a substituent containing a hydroxyl group, the hydroxyl group can be further modified or derivatized either before or after the above coupling reactions to provide, by way of example, ethers, carbamates and the like. Compounds of formulae I and II having a hydroxyl group on the R$^5$ substituent, for example, can be prepared using an amino acid derivative of formula VII derived from tyrosine and the like in the above-described reactions.

By way of example, a compound of the present invention or an intermediate thereof having a substituent containing a hydroxyl group can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino) propyl chloride, N-(2-chloroethyl)morpholine, 2-(hexamethyleneimino)ethyl chloride, 3-(N-methylpiperazine)propyl chloride, 1-(3-chlorophenyl)-4-(3-chloropropyl) piperazine, 2-(4-hydroxy-4-phenylpiperidine)ethyl chloride, N-tert-butyloxycarbonyl-3-piperidinemethyl tosylate and the like.

Alternatively, a hydroxyl group present on a substituent of a compound of the present invention or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of the present invention or an intermediate thereof containing a aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of the present invention or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of the present invention or an intermediate thereof contains a primary or secondary hydroxyl group, such hydroxyl groups can be readily converted into a leaving group and displaced to form, for example, amines, sulfides and fluorides. For example, derivatives of 4-hydroxy-L-proline can be converted into the corresponding 4-amino, 4-thio or 4-fluoro-L-proline derivatives via nucleophilic displacement of the derivatized hydroxyl group. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino (—$NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of the present invention or an intermediate thereof having a substituent containing an iodoaryl group, for example, when $R^5$, of formula I or II, is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra(triphenylphosphine), in an inert diluent, such as tetrahydrofuran, at a temperature ranging from about 24° C. to about 30° C. until the reaction is complete. This reaction is further described, for example, in Rieke, *J. Org. Chem.* 1991, 56, 1445.

In some cases, the compounds of the present invention or intermediates thereof may contain substituents having one or more sulfur atoms. Such sulfur atoms will be present, for example, when the amino acid of formula III employed in the above reactions is derived from L-thiazolidine-4-carboxylic acid, L-(5,5-dimethyl)thiazolidine-4-carboxylic acid, L-thiamorpholine-3-carboxylic acid and the like. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about °50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, *"Advanced Organic Chemistry"*, 4th Ed., pp. 1202-1202, Wiley Publishers, (1992).

As described above, the compounds of the present invention having an $R^2$ substituent other an hydrogen can be prepared using an N-substituted amino acid of formula III, such as sarcosine, N-methyl-L-phenylalanine and the like, in the above-described coupling reactions. Alternatively, such compounds can be prepared by N-alkylation of a sulfonamide of formula I or V (where $R^2$ is hydrogen) using conventional synthetic procedures. Typically, this N-alkylation reaction is conducted by contacting the sulfonamide with at least one equivalent, preferably 1.1 to 2 equivalents, of an alkyl or substituted alkyl halide in the presence of a suitable base, such as potassium carbonate, in an inert diluent, such as acetone, 2-butanone and the like, at a temperature ranging from about 25° C. to about 70° C. for about 2 to about 48 hours. Examples of alkyl or substituted alkyl halides suitable for use in this reaction include, but are not limited to, methyl iodide, and the like.

Additionally, the sulfonamides of formula I or V wherein $R^2$ is hydrogen and $R^1$ is a 2-alkoxycarbonylaryl group can be intramolecularly cyclized to form 1,2-benzisothiazol-3-one derivatives or analogues thereof. This reaction is typically conducted by treating a sulfonamide, such as N-(2-methoxycarbonylphenylsulfonyl)glycine-L-phenylalanine benzyl ester, with about 1.0 to 1.5 equivalents of a suitable base, such as an alkali metal hydride, in a inert diluent, such as tetrahydrofuran, at a temperature ranging from about 0° C. to about 30° C. for about 2 to about 48 hours to afford the cyclized 1,2-benzisothiazol-3-one derivative.

Lastly, the compounds of formula I or II where Q is —C(S) NR$^7$— are prepared by using an amino thionoacid derivative in place of amino acid III in the above described synthetic procedures. Such amino thionoacid derivatives can be prepared by the procedures described in Shalaky et al., *J. Org. Chem.*, 61:9045-9048 (1996) and Brain et al., *J. Org. Chem.*, 62:3808-3809 (1997) and references cited therein.

4.1.2. Pharmaceutical Formulations of the Compounds

In general, the compounds of the subject invention will be administered in a therapeutically effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection. Preferably, the compounds are administered by parenteral routes. More preferably, the compounds are administered by intravenous routes. Such compositions are prepared in a manner well known in the pharmaceutical art.

The actual amount of the compound of the subject invention, i.e., the active ingredient, will depend on a number of factors, such as the severity of the disease, i.e., the condition or disease associated with demyelination or the paralysis associated with demyelination to be treated, the age and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. The effective blood level of the compounds of the subject invention is preferably greater than or equal to 10 ng/ml.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The active compound is effective over a wide dosage range and is generally administered in a pharmaceutically or therapeutically effective amount. The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds of the subject invention are usually administered in the form of pharmaceutical compositions. This invention also includes pharmaceutical compositions, which contain as the active ingredient, one or more of the compounds of the subject invention above, associated with one or more pharmaceutically acceptable carriers or excipients. The excipient employed is typically one suitable for administration to human subjects or other mammals. In making the compositions of this invention, the active ingredient is usually mixed with an excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The concentration of therapeutically active compound may vary from about 1 mg/ml to 1 g/ml.

Preferably, the compound can be formulated for parenteral administration in a suitable inert carrier, such as a sterile physiological saline solution. For example, the concentration of compound in the carrier solution is typically between about 1-100 mg/ml. The dose administered will be determined by route of administration. Preferred routes of administration include parenteral or intravenous administration. A therapeutically effective dose is a dose effective to produce a significant decrease in demyelination and a notable increase in remyelination. Preferably, the amount is sufficient to produce a statistically significant amount of remyelination in a subject.

By way of example, for preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions may be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The compounds of this invention can be administered in a sustained release form. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e. injectable microspheres composed of lactic acid-glycolic acid copolymer and leuprolide acetate), and poly-D-(-)-3-hydroxybutyric acid (EP 133,988).

The compounds of this invention can be administered in a sustained release form, for example a depot injection, implant preparation, or osmotic pump, which can be formulated in such a manner as to permit a sustained release of the active ingredient. Implants for sustained release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

The following formulation examples illustrate pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/capsule) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water | to 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Hard gelatin tablets, each containing 15 mg of active ingredient are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

FORMULATION EXAMPLE 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

According to one aspect of the invention, the compound may be administered alone, as a combination of compounds, in combination with remyelinating and/or anti-alpha-4-antibodies, or in combination with an anti-inflammatory agent, which is typically used to treat conditions and diseases associated with demyelination. When administered in combination, the small compounds may be administered in the same formulation as these other compounds or compositions, or in a separate formulation. When administered in combinations, the remyelinating agents may be administered prior to, following, or concurrently with the other compounds and compositions. Pharmaceutical compositions of the invention are suitable for use in a variety of drug delivery systems. Suitable formulations for use in the present invention are found in *Remington's Pharmaceutical Sciences,* Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Polymer Conjugates

Compounds of the present invention may be formulated and administered as polymer conjugates. Polymer conjugates may exhibit benefits over non-conjugated polymers, such as improved solubility and stability.

As such, single polymer molecules may be employed for conjugation with the compounds of the present invention, although it is also contemplated that more than one polymer molecule can be attached as well. The conjugated compounds of the present invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive and enable it to cross-link to a drug molecule and to enhance various properties or characteristics of the overall conjugated material. Accordingly, the polymer may contain any functionality, repeating groups, linkages, or other constitutent structures which do not preclude the efficacy of the conjugated the compounds of the present invention composition for its intended purpose.

Illustrative polymers that may usefully be employed to achieve these desirable characteristics are described supra, as well as in PCT WO 01/54690 (to Zheng et al.) incorporated by reference herein in its entirety. The polymer may be coupled to the compounds of the present invention (preferably via a linker moiety) to form stable bonds that are not significantly cleavable by human enzymes. Generally, for a bond to be not "significantly" cleavable requires that no more than about 20% of the bonds connecting the polymer and the compounds of the present invention to which the polymer is linked, are cleaved within a 24 hour period, as measured by standard techniques in the art including, but not limited to, high pressure liquid chromatography (HPLC).

The compounds of the present inventions are conjugated most preferably via a terminal reactive group on the polymer although conjugations can also be branched from non-terminal reactive groups. The polymer with the reactive group(s) is designated herein as "activated polymer". The reactive group selectively reacts with reactive groups on the compounds of the present invention. The activated polymer(s) is reacted so that attachment may occur at any available functional group on compounds of the present invention. Amino, carbon, free carboxylic groups, suitably activated carbonyl groups, hydroxyl, guanidyl, oxidized carbohydrate moieties, amino, carbon and mercapto groups of the compounds of the present invention (if available) can be used as attachment sites.

Generally, about 1.0 to about 10 moles of activated polymer per mole of the compounds of the present invention, depending on concentration, is employed. The final amount is a balance between maximizing the extent of the reaction while minimizing non-specific modifications of the product and, at the same time, defining chemistries that will maintain optimum activity, while at the same time optimizing the half-life of the compounds of the present invention. Preferably, at least about 50% of the biological activity of the compounds of the present invention is retained, and most preferably 100% is retained.

The reactions may take place by any suitable art-recognized method used for reacting biologically active materials with inert polymers. Generally, the process involves preparing an activated polymer and thereafter reacting the compounds of the present invention with the activated polymer to produce a soluble compound suitable for formulation. This modification reaction can be performed by several methods, which may involve one or more steps. The polymeric substances included herein are preferably water-soluble at room temperature. A non-limiting list of such polymers includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In the preferred practice of the present invention, polyalkylene glycol residues of $C_1$-$C_4$ alkyl polyalkylene glycols, preferably polyethylene glycol (PEG), or poly(oxy)alkylene glycol residues of such glycols are advantageously incorporated in the polymer systems of interest. Thus, the polymer to which the compounds of the present invention are attached may be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained.

Examples of polyoxyethylated polyols include, but are not limited to, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

Those of ordinary skill in the art will recognize that the foregoing list is merely illustrative and that all polymer materials having the qualities described herein are contemplated. The polymer need not have any particular molecular weight, but it is preferred that the molecular weight be between about 300 and 100,000, more preferably between 10,000 and 40,000. In particular, sizes of 20,000 or more are most effective at preventing loss of the product due to filtration in the kidneys.

Polyethylene glycol (PEG) and related polyalkylene oxides (PAO's) are known in the art as being usefull adjuncts for the preparation of drugs. See for example, PCT WO 93/24476. PEG has also been conjugated to proteins, peptides and enzymes to increase aqueous solubility and circulating life in vivo as well as reduce antigenicity. See, for example, U.S. Pat. Nos. 5,298,643 and 5,321,095, both to Greenwald et al. PCT WO 93/24476 discloses using an ester linkage to covalently bind an organic molecule to water-soluble polyethylene glycols. Thus, the compounds of the invention are preferably administered as polyethylene glycol (PEG) derivatives.

As such, the compounds or conjugates of this invention may contain one or more polyethylene glycol (PEG) substituents covalently attached thereto. Such conjugates demonstrate improved serum half-life, as compared to compounds lacking polyethylene glycol substituents. Without being limited to any theory, the improved serum half-life is believed to be associated with the covalent conjugation of at least one polyethylene glycol entity onto the structure of the compound.

The term "PEG" refers to polymers comprising multiple oxyalkylene units. Such polymers are optionally mono-capped with a substituent preferably selected from alkyl, aryl, substituted alkyl, and substituted aryl. Inclusive of such polymers are those diamino capped polyoxyalkylene polymers which are known in the art as Jeffamines®. Still further, such polymers can optionally contain one or more non-oxyalkylene units such as the commercially available poly[di(ethylene glycol)adipates, poly[di(ethylene glycol)phthalate diols, and the like.

By PEG derivative is meant a polyethylene glycol polymer in which one or both of the terminal hydroxyl groups found in polyethylene glycol itself has been modified. Examples of suitable modifications include replacing one or both hydroxyl group(s) with alternative functional groups, which may be protected or unprotected, with low molecular weight ligands, or with another macromolecule or polymer. Modification of the terminal hydroxyl groups in the polyethylene glycol may be achieved by reacting the polyethylene glycol with compounds comprising complementary reactive functional groups, including functional groups which are able to undergo a reaction with the hydroxyl groups in polyethylene glycol. The PEG derivatives of the compounds of this invention may contain one or more polyethylene glycol (PEG) substituents covalently attached thereto by a linking group.

"Linking group" or "linker" refers to a group or groups that covalently links a non-PEG substituted compound of the present invention with one or more PEG groups. Each linker may be chiral or achiral, linear, branched or cyclic and may be homogenous or heterogeneous in its atom content (e.g., linkers containing only carbon atoms or linkers containing carbon atoms as well as one or more heteroatoms present on the linker.

The PEG group or groups are covalently attached to the linker using conventional chemical techniques providing for covalent linkage of the PEG group to the linker. The linker, in turn, may be covalently attached to the otherwise, non-PEG substituted compounds of the present invention. Reaction chemistries resulting in such linkages are well known in the art. Such reaction chemistries involve the use of complementary functional groups on the linker, the non-PEG substituted compound of the present invention and the PEG groups. Preferably, the complementary functional groups on the linker are selected relative to the functional groups available on the PEG group for bonding or which can be introduced onto the PEG group for bonding. Again, such complementary functional groups are well known in the art.

Such polymers have a number average molecular weight of from about 100 to 100,000; preferably from about 1,000 to 50,000; more preferably from about 10,000 to about 40,000.

5. Immunoglobulins

In one specific embodiment, the agents of the invention are immunoglobulins the when administered to a patient inhibit demyelination and/or promote remyelination and/or reduce paralysis. These immunoglobulins may be selected from immunoglobulins that selectively bind to an alpha-4 integrin or a dimer comprising alpha-4 integrin, such as alpha-4 beta-1, or bind VCAM-1. Preferably, the immunoglobulins bind alpha-4 beta-1 and inhibits alpha-4 beta-1 activity. The immunoglobulins are preferably antibodies or fragments thereof.

By "antibodies" is meant to include complete immunoglobulins such as IgG1 (or any IgG subclass) or IgM, or inhibitors derived from antibodies, such as natalizumab (ANTEGREN®).

By "antibody homolog" is meant to include intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens (i.e., integrin or integrin ligand). The component polypeptides of an antibody homolog composed of more than one polypeptide may optionally be disulfide-bound or otherwise covalently crosslinked. Accordingly, therefore, "antibody homologs" include intact immunoglobulins of types IgA, IgG, IgE, IgD, IgM (as well as subtypes thereof, e.g., IgG1), wherein the light chains of the immunoglobulin may be of types kappa or lambda. "Antibody homologs" also includes portions of intact antibodies that retain antigen-binding specificity, for example Fab fragments, Fab' fragments, F(ab')$_2$ fragments, Fv fragments, scFv fragments, heavy and light chain monomers or dimers or mixtures thereof.

When the agent of the invention is an antibody, a monoclonal antibody is the preferred antibody. In contrast to polyclonal antibody preparations, which typically include different antibodies directed against different epitopes, each monoclonal antibody is directed against a single epitope on the antigen. A second advantage of monoclonal antibodies is that they are synthesized by means that are uncontaminated by other immunoglobulins, e.g., by phage display or isolation from a hybridoma. Although the present invention intends to encompass both polyclonal and monoclonal antibodies as agents of the invention, monoclonal antibodies are preferred as they are highly specific, and the invention is thus discussed primarily in terms of monoclonal antibodies.

"Native antibodies and immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., 1985, *J. Mol. Biol.*, 186: 651-63; Novotny et al., 1985, *Proc. Natl. Acad. Sci. USA*, 82: 4592-6).

In addition, other antibodies can be identified using techniques available in the art. For example, monoclonal antibodies of the present invention can be produced using phage display technology. Antibody fragments, which selectively bind to an alpha-4 integrin or a dimer comprising an alpha-4 integrin, are then isolated. Exemplary preferred methods for producing such antibodies via phage display are disclosed in U.S. Pat. Nos. 6,225,447; 6,180,336; 6,172,197; 6,140,471; 5,969,108; 5,885,793; 5,872,215; 5,871,907; 5,858,657; 5,837,242; 5,733,743 and 5,565,332.

A "variant" antibody refers herein to an immunoglobulin molecule that differs in amino acid sequence from a "parent" antibody amino acid sequence by virtue of addition, deletion and/or substitution of one or more amino acid residue(s) in the parent antibody sequence. The parent antibody or immunoglobulin can be a polyclonal antibody, monoclonal antibody, humanized antibody, primatized® antibody or any antibody fragment. In the preferred embodiment, the variant comprises one or more amino acid substitution(s) in one or more hypervariable region(s) of the parent antibody. For example, the variant may comprise at least one, e.g., from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. No N-terminal, C-terminal, or internal extensions, deletions, or insertions into the antibody sequence shall be construed as affecting sequence identity or homology. The variant retains the ability to bind the receptor and preferably has properties that are superior to those of the parent antibody. For example, the variant may have a stronger binding affinity, enhanced ability to activate the receptor, etc. To analyze such properties, one should compare a Fab form of the variant to a Fab form of the parent antibody or a full-length form of the variant to a full-length form of the parent antibody. The variant antibody of particular interest herein is one which displays at least about 10 fold, preferably at least about 20 fold, and most preferably at least about 50 fold, enhancement in biological activity when compared to the parent antibody. The "parent" antibody herein is one that is encoded by an amino acid sequence used for the preparation of the variant. Preferably, the parent antibody has a human framework region and has human antibody constant region(s). For example, the parent antibody may be a humanized or human antibody. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibodies will be prepared by at least one purification step.

5.1. Monoclonal Antibodies

Monoclonal antibodies can also be produced using the conventional hybridoma methods or genetically engineered. These methods have been widely applied to produce hybrid cell lines that secrete high levels of monoclonal antibodies against many specific antigens, and can also be used to produce monoclonal antibodies of the present invention. For example, mice (e.g., Balb/c mice) can be immunized with an antigenic alpha-4 epitope by intraperitoneal injection. After sufficient time has passed to allow for an immune response, the mice are sacrificed and the spleen cells obtained and fused with myeloma cells, using techniques well known in the art. The resulting fused cells, hybridomas, are then grown in a selective medium, and the surviving cells grown in such medium using limiting dilution conditions. After cloning and recloning, hybridomas can be isolated that secrete antibodies (for example, of the IgG or IgM class or IgG1 subclass) that selectively bind to the target, alpha-4 or a dimer comprising an alpha-4 integrin. To produce agents specific for human use, the isolated monoclonal can then be used to produce chimeric and humanized antibodies. Antibodies can also be prepared that are anti-peptide antibodies. Such anti-peptide antibodies would be prepared against peptides of alpha-4 integrin.

The term "chimeric", when referring to an agent of the invention, means that the agent is comprised of a linkage (chemical cross-linkage or covalent or other type) of two or more proteins having disparate structures and/or having disparate sources of origin. Thus, a chimeric alpha-4 integrin antagonist may include one moiety that is an alpha-4 integrin antagonist or fragment and another moiety that is not an alpha-4 integrin antagonist.

A species of "chimeric" protein is a "fusion" or "fusion protein" refers to a co-linear, covalent linkage of two or more proteins or fragments thereof via their individual peptide backbones, most preferably through genetic expression of a polynucleotide molecule encoding those proteins. Thus, preferred fusion proteins are chimeric proteins that include a remyelinating antibody or fragment thereof covalently linked to a second moiety that is not original to the remyelinating antibody (i.e., which derives from another immuoglobulin or polypeptide). Preferred fusion proteins of the invention may include portions of intact antibodies that retain antigen-binding specificity, for example, Fab fragments, Fab' fragments, F(ab')$_2$ fragments, Fv fragments, scFv fragments, heavy chain monomers or dimers, light chain monomers or dimers, dimers consisting of one heavy and one light chain, and the like.

The most preferred fusion proteins are chimeric and comprise a remyelinating moiety fused or otherwise linked to all or part of the hinge and constant regions of an immunoglobulin light chain, heavy chain, or both. Thus, this invention features a molecule which includes: (1) remyelinating moiety, (2) a second peptide, e.g., one which increases solubility or in vivo life time of the remyelinating moiety, e.g., a member of the immunoglobulin super family or fragment or portion thereof, e.g., a portion or a fragment of IgG, e.g., the human IgG1 heavy chain constant region, e.g., CH2, CH3, and hinge regions. Specifically, a "remyelinating moiety/Ig fusion" is a protein comprising a biologically active remyclinating moiety of the invention. A species of remyelinating agents is an "integrin/Fc fusion" which is a protein comprising an remyelinating immunoglobulin of the invention linked to at least a part of the constant domain of an immunoglobulin. A preferred Fc fusion comprises an remyelinating immunoglobulin of the invention linked to a fragment of an antibody containing the C terminal domain of the heavy immunoglobulin chains.

The term "fusion protein" also means a remyelinating moiety that is chemically linked via a mono- or hetero-functional molecule to a second moiety that is not a remyelinating moiety (resulting in a "chimeric" molecule) and is made de novo from purified protein as described below. Thus, one example of a chemically linked, as opposed to recombinantly linked, chimeric molecule that is a fusion protein may comprise: (1) an alpha-4 integrin subunit targeting moiety, e.g., a VCAM-1 moiety capable of binding to VLA-4) on the surface of VLA-4 bearing cells; (2) a second molecule which increases solubility or in vivo life time of the targeting moiety, e.g., a polyalkylene glycol polymer such as polyethylene glycol (PEG). The alpha-4 targeting moiety can be any naturally occurring alpha-4 ligand or fragment thereof, e.g., a VCAM-1 peptide or a similar conservatively substituted amino acid sequence.

Chimeric, primatized® and humanized antibodies can be produced from non-human antibodies, and can have the same or similar binding affinity as the antibody from which they are produced. Techniques developed for the production of chimeric antibodies (Morrison et al., 1984 *Proc. Natl. Acad. Sci.* 81: 6851; Neuberger et al., 1984 *Nature* 312: 604; Takeda et al., 1985 *Nature* 314: 452) by splicing the genes from a mouse antibody molecule of appropriate antigen specificity together with genes from, for example, a human antibody molecule of appropriate biological activity can be used; such antibodies are within the scope of this invention. For example, a nucleic acid encoding a variable (V) region of a mouse monoclonal antibody can be joined to a nucleic acid encoding a human constant (C) region, e.g., IgG1 or IgG4. The resulting antibody is thus a species hybrid, generally with the antigen binding domain from the non-human antibody and the C or effector domain from a human antibody.

Humanized antibodies are antibodies with variable regions that are primarily from a human antibody (the acceptor antibody), but which have complementarity determining regions substantially from a non-human antibody (the donor antibody). See, e.g., Queen et al., 1989 *Proc. Natl Acad. Sci. USA* 86: 10029-33; WO 90/07861; and U.S. Pat. Nos. 6,054,297; 5,693,761; 5,585,089; 5,530,101 and 5,224,539. The constant region or regions of these antibodies are generally also from a human antibody. The human variable domains are typically chosen from human antibodies having sequences displaying a high homology with the desired non-human variable region binding domains. The heavy and light chain variable residues can be derived from the same antibody, or a different human antibody. In addition, the sequences can be chosen as a consensus of several human antibodies, such as described in WO 92/22653.

Specific amino acids within the human variable region are selected for substitution based on the predicted conformation and antigen binding properties. This can be determined using techniques such as computer modeling, prediction of the behavior and binding properties of amino acids at certain locations within the variable region, and observation of effects of substitution. For example, when an amino acid differs between a non-human variable region and a human variable region, the human variable region can be altered to reflect the amino acid composition of the non-human variable region. Several examples of humanizing anti-alpha-4 antibodies are described herein.

By "humanized antibody homolog" is meant an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain. A "human antibody homolog" is an antibody homolog in which all the amino acids of an immunoglobulin light or heavy chain (regardless of whether or not they are required for antigen binding) are derived from a human source.

In a specific embodiment, the antibodies used in the chronic dosage regime of the present invention are humanized antibodies as disclosed in U.S. Pat. No. 5,840,299, which is incorporated herein by reference.

In another embodiment, transgenic mice containing human antibody genes can be immunized with an antigenic alpha-4 structure and hybridoma technology can be used to generate human antibodies that selectively bind to alpha-4.

Chimeric, human and/or humanized antibodies can be produced by recombinant expression, e.g., expression in human hybridomas (Cole et al., *Monoclonal Antibodies and Cancer Therapy*, Alan R. Liss, p. 77 (1985)), in myeloma cells or in Chinese Hamster Ovary (CHO) cells. Alternatively, antibody-coding sequences can be incorporated into vectors suitable for introducing into the genome of animal thereby producing a transgenic animal. One example would be to produce such antibodies in the milk of a transgenic animal such as a bovine. See e.g., U.S. Pat. Nos. 5,849,992 and 5,304,489. Suitable transgenes include trangenes having a promoter and/or enhancer from a mammary gland specific gene, for example casein or β-lactoglobulin.

5.1.1. Humanized and Primatized® Antibodies

In one embodiment of the invention, humanized (and primatized®) immunoglobulins (or antibodies) specific for the alpha-4 subunit of VLA-4 are provided, which when administered in an effective amount inhibit demyelination and/or promote remyelination and/or reduce paralysis. Humanized and primatized® antibodies are antibodies of animal (typically mammalian) origin that have been modified using genetic engineering techniques. The techniques are used to replace constant region and/or variable region framework sequences with juman sequences, while retaining the original antigen specificity of the antibody. Humanized and primatized® antibodies are commonly derived from rodent (e.g., mouse and hamster) antibodies with specificity for human antigens (e.g., human VCAM-1 or human VLA-4). By reshaping the donor antibody (the antibody from the animal to which the antigen was administered) to have sequences from the animal to which the antibody will be administered for therapeutic purposes, there will be a reduced host response in the animal upon administration of the antibody. Only the Fc regions or all but the complementarity determining regions (CDRs) can be replaced with acceptor domains, wherein the acceptor is the animal to whom the reshaped antibody is to be administered (e.g., mammals such as humans, domesticated animals, agricultural animals and the like).

Antibodies that bind to the alpha-4 subunit of VLA-4 which when administered to a patient in an effective amount inhibit demylination are preferred. More preferred are those antibodies which when administered in an effective amount induce remyelination and/or reduce paralysis in a subject wherein the subject is suffering from a demyelinating disease or condition.

Typically, CDRs of a murine antibody are transplanted onto the corresponding regions in a human antibody, since it is the CDRs (i.e., three in antibody heavy chains, three in light chains) that are the regions of the mouse antibody (or any other animal antibody), which bind to a specific antigen. Transplantation of CDRs is achieved by genetic engineering, whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in, e.g., Jones et al., 1986, *Nature* 321: 522-5; Riechmann et al., 1988, *Nature* 332: 323-7; Queen et al., 1989, *Proc. Nat. Acad. Sci. USA* 86: 10029; and Orlandi et al., 1989, *Proc. Nat. Acad. Sci. USA* 86: 3833.

Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity. In several cases, it appears to be critical to alter residues in the framework regions of the acceptor antibody (e.g., human antibody) in order to obtain binding activity.

Queen et al., 1989 (supra) and WO 90/07861 (Protein Design Labs) have described the preparation of a humanized antibody that contains modified residues in the framework regions of the acceptor antibody by combining the CDRs of a murine MAb (anti-Tac) with human immunoglobulin framework and constant regions. One solution to solve the problem of the loss of binding affinity without any modifications of the human V region framework residues involves two key steps. First, the human V framework regions are chosen by computer analysts for optimal protein sequence homology to the V region framework of the original murine antibody. In the second step, the tertiary structure of the murine V region is modeled by computer in order to visualize framework amino acid residues that are likely to interact with the murine CDRs. These murine amino acid residues are then superimposed on the homologous human framework. For additional detail, see U.S. Pat. Nos. 5,693,762; 5,693,761; 5,585,089; and 5,530,101 (Protein Design Labs).

Certain alpha-4 subunit-containing integrin antagonists useful in the present invention include chimeric and humanized recombinant antibody homologs (i.e., intact immunoglobulins and portions thereof) with B epitope specificity that have been prepared and are described in U.S. Pat. No. 5,932, 214 (MAb HP1/2). The starting material for the preparation of chimeric (mouse Variable-human Constant) and humanized anti-integrin antibody homologs may be a murine monoclonal anti-integrin antibody as previously described, a monoclonal anti-integrin antibody commercially available (e.g., HP2/1, Amae International, Inc., Westbrook, Me.). Other preferred humanized anti-VLA-4 antibody homologs are described by Athena Neurosciences, Inc. in PCT/US95/01219 (Jul. 27, 1995), U.S. Pat. Nos. 5,840,299 and 6,033,665. The content of the U.S. Pat. Nos. 5,932,214, 5,840,299 and 6,033,665 patents are incorporated by reference in their entirety herein.

These humanized anti-VLA-4 antibodies comprise a humanized light chain and a humanized heavy chain. The humanized light chain comprises three complementarity determining regions (CDR1, CDR2 and CDR3) having amino acid sequences from the corresponding complementarity determining regions of a mouse 21.6 immunoglobulin light chain, and a variable region framework from a human kappa light chain variable region framework sequence except in at least position the amino acid position is occupied by the same amino acid present in the equivalent position of the mouse 21.6 immunoglobulin light chain variable region framework. The humanized heavy chain comprises three complementarity determining regions (CDR1, CDR2 and CDR3) having amino acid sequences from the corresponding complementarity determining regions of a mouse 21.6 immunoglobulin heavy chain, and a variable region framework from a human heavy chain variable region framework sequence except in at least one position the amino acid position is occupied by the same amino acid present in the equivalent position of the mouse 21.6 immunoglobulin heavy chain variable region framework. See, U.S. Pat. Nos. 5,840,299 and 6,033,665

Fragments of an isolated alpha-4 integrin antagonist (e.g., fragments of antibody homologs described herein) can also be produced efficiently by recombinant methods, by proteolytic digestion, or by chemical synthesis using methods known to those of skill in the art. In recombinant methods, internal or terminal fragments of a polypeptide can be generated by removing one or more nucleotides from one end (for a terminal fragment) or both ends (for an internal fragment) of a DNA sequence which encodes for the isolated hedgehog polypeptide. Expression of the mutagenized DNA produces polypeptide fragments. Digestion with certain endonucleases can also generate DNAs, which encode an array of fragments. DNAs that encode fragments of a protein can also be generated by random shearing, restriction digestion, or a combination thereof. Protein fragments can be generated directly from intact proteins. Peptides can be cleaved specifically by proteolytic enzymes, including, but not limited to plasmin, thrombin, trypsin, chymotrypsin, or pepsin. Each of these enzymes is specific for the type of peptide bond it attacks. Trypsin catalyzes the hydrolysis of peptide bonds in which the carbonyl group is from a basic amino acid, usually arginine or lysine. Pepsin and chymotrypsin catalyze the hydrolysis of peptide bonds from aromatic amino acids, such as tryptophan, tyrosine, and phenylalanine. Alternative sets of cleaved protein fragments are generated by preventing cleavage at a site which is susceptible to a proteolytic enzyme. For instance, reaction of the ε-amino acid group of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with β-haloethylamines yields peptide linkages that are hydrolyzed by trypsin (Lindley, 1956, *Nature* 178: 647). In addition, chemical reagents that cleave peptide chains at specific residues can be used. For example, cyanogen bromide cleaves peptides at methionine residues (Gross et al., 1961, *J. Am. Chem. Soc.* 83: 1510). Thus, by treating proteins with various combinations of modifiers, proteolytic enzymes and/or chemical reagents, the proteins may be divided into fragments of a desired length with no overlap of the fragments, or divided into overlapping fragments of a desired length.

5.1.1.1. Natalizumab And Related Humanized Antibodies

The invention provides for a method of using humanized immunoglobulins that specifically bind to a VLA-4 ligand either alone or in combination to promote remyelination. One preferred antibody for use in such methods of treatment and in medicaments includes that described in U.S. Pat. No. 5,840,299 assigned to Elan Pharmaceuticals, which is herein incorporated in its entirety. Another aspect contemplates the use of fragments of these antibodies with remyelinating activity as assessed in vivo.

The humanized antibodies comprise a humanized light chain and a humanized heavy chain. In one aspect, the humanized light chain can comprise three complementarity determining regions (i.e., CDR1, CDR2 and CDR3) having amino acid sequences from the corresponding complementarity determining regions of a mouse 21-6 immunoglobulin light chain, and a variable region framework from a human kappa light chain variable region framework sequence except in at least one position selected from a first group consisting of positions L45, L49, L58 and L69, wherein the amino acid position is occupied by the same amino acid present in the equivalent position of the mouse 21.6 immunoglobulin light chain variable region framework.

The humanized heavy chain comprises three complementarity determining regions (i.e., CDR1, CDR2 and CDR3) having amino acid sequences from the corresponding complementarity determining regions of a mouse 21-6 immunoglobulin heavy chain, and a variable region framework from a human heavy chain variable region framework sequence except in at least one position selected from a group consisting of H27, H28, H29, H30, H44, H71, wherein the amino acid position is occupied by the same amino acid present in the equivalent position of the mouse 21-6 immunoglobulin heavy chain variable region framework. The immunoglobulins specifically bind to VLA-4 with an affinity having a lower limit of about $10^7$ $M^{-1}$ and an upper limit of about five times the affinity of the mouse 21-6 immunoglobulin.

Usually, the humanized light and heavy chain variable region frameworks are from RE1 and 21/28'CL variable region framework sequences respectively. When the humanized light chain variable region framework is from RE1, at least two framework amino acids are replaced. One amino acid is from the first group of positions described supra. The other amino acids are from a third group consisting of positions L104, L105 and L107. This position is occupied by the same amino acid present in the equivalent position of a kappa light chain from a human immunoglobulin other than RE1.

Some humanized immunoglobulins have a mature light chain variable region sequence designated La or Lb, or a mature heavy chain variable region sequence designated Ha, Hb or Hc (FIG. 13). Preferred humanized immunoglobulins include those having a La light chain and an Ha, Hb or Hc heavy chain (FIG. 14).

The humanized immunoglobulins have variable framework regions substantially from a human immunoglobulin (termed an acceptor immunoglobulin) and complementarity determining regions substantially from a mouse immunoglobulin termed mu MAb 21.6 (referred to as the donor immunoglobulin). The constant region(s), if present, are also substantially from a human immunoglobulin. The humanized antibodies exhibit a specific binding affinity for VLA-4 of at least $10^7$, $10^8$, $10^9$, or $10^{10}$ $M^{-1}$. Usually the upper limit of binding affinity of the humanized antibodies for VLA-4 is within a factor of three or five of that of mu MAb 21.6 (about $10^9$ $M^{-1}$). Often the lower limit of binding affinity is also within a factor of three or five of that of mu MAb 21.6.

Humanized antibodies can be produced as exemplified, for example, with the mouse MAb 21.6 monoclonal antibody. The starting material for production of humanized antibodies is mu MAb 21.6. The isolation and properties of this antibody are described in U.S. Pat. No. 6,033,655 (assigned to Elan Pharmaceuticals, Inc.), which is herein incorporated by reference in its entirety. Briefly, mu MAb 21.6 is specific for the alpha-4 subunit of VLA-4 and has been shown to inhibit human lymphocyte binding to tissue cultures of rat brain cells stimulated with tumor necrosis factor. From N-terminal to C-terminal, both light and heavy chains comprise the domains FR1, CDR1, FR2, CDR2, FR3, CDR3 and FR4. The assignment of amino acids to each domain is in accordance with the numbering convention of Kabat.

The next step involved selecting human antibodies to supply framework residues. The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4: 773 (1991); Kolbinger et al., *Protein Engineering* 6: 971 (1993).

Suitable human antibody sequences are identified by computer comparisons of the amino acid sequences of the mouse variable regions with the sequences of known human antibodies. The comparison is performed separately for heavy and light chains but the principles are similar for each. This comparison reveals that the mu 21.6 light chain shows greatest sequence identity to human light chains of subtype kappa 1; the mu 21.6 heavy chain shows greatest sequence identity to human heavy chains of subtype one, as defined by Kabat, supra. Thus, light and heavy human framework regions are usually derived from human antibodies of these subtypes, or from consensus sequences of such subtypes. The preferred light and heavy chain human variable regions showing greatest sequence identity to the corresponding regions from mu MAb 21.6 are from antibodies RE1 and 21/28'CL respectively.

Computer modeling can then be used to further enhance the humanized antibody's ability to bind to its cognate antigen. The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. For example, for the light chain of mu MAb 21.6, the starting point for modeling the framework regions, CDR1 and CDR2 regions, was the human light chain RE1. For the CDR3 region, the starting point was the CDR3 region from the light chain of a different human antibody HyHEL-5. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

As noted supra, the humanized antibodies of the invention comprise variable framework regions substantially from a human immunoglobulin and complementarity determining regions substantially from a mouse immunoglobulin termed mu MAb 21.6. Having identified the complementarity determining regions (CDRs) of mu MAb 21.6 and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

When an amino acid differs between a mu MAb 21.6 variable framework region and an equivalent human variable framework region, the human framework amino acid should usually be substituted by the equivalent mouse amino acid if it is reasonably expected that the amino acid:

(1) non-covalently binds antigen directly (e.g., amino acids at positions L49, L69 of mu MAb 21.6), (2) is adjacent to a CDR region, is part of a CDR region under the alternative definition proposed by Chothia et al., supra, or otherwise interacts with a CDR region (e.g., is within about 3 Å of a CDR region) (e.g., amino acids at positions L45, L58, H27, H28, H29, H30 and H71 of mu MAb 21.6), or (3) participates in the $V_L$-$V_H$ interface (e.g., amino acids at position H44 of mu MAb 21.6).

Other candidates for substitution are acceptor human framework amino acids that are unusual for a human immunoglobulin at that position (e.g., amino acids at positions L104, L105 and L107 of mu MAb 21.6). These amino acids can be substituted with amino acids from the equivalent position of more typical human immunoglobulins. Alternatively, amino acids from equivalent positions in the mouse MAb 21.6 can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, and alternative variant immunoglobulins are produced, one of which has that particular substitution, the other of which does not. The humanized antibodies will usually contain a substitution of a human light chain framework residue with a corresponding mu MAb 21.6 residue in at least 1, 2 or 3, and more usually 4, of the following positions: L45, L49, L58 and L69. The humanized antibodies also usually contain a substitution of a human heavy chain framework residue in at least 1, 2, 3, 4, or 5, and sometimes 6, of the following positions: H27, H28, H29, H30, H44 and H71. Optionally, H36 may also be substituted. In preferred embodiments when the human light chain acceptor immunoglobulin is RE1, the light chain also contains substitutions in at least 1 or 2, and more usually 3, of the following positions: L104, L105 and L107. These positions are substituted with the amino acid from the equivalent position of a human immunoglobulin having a more typical amino acid residues. Appropriate amino acids to substitute are shown in FIGS. 13 and 14.

Usually the CDR regions in humanized antibodies are substantially identical, and more usually, identical to the corresponding CDR regions in the mu MAb 21.6 antibody. Occasionally, however, it is desirable to change one of the residues in a CDR region. For example, Example 4 identifies an amino acid similarity between the mu MAb 21.6 CDR3 and the VCAM-1 ligand. This observation suggests that the binding affinity of humanized antibodies might be improved by redesigning the heavy chain CDR3 region to resemble VCAM-1 even more closely. Accordingly, one or more amino acids from the CDR3 domain can be substituted with amino acids from the VCAM-1 binding domain. Although not usually desirable, it is sometimes possible to make one or more conservative amino acid substitutions of CDR residues without appreciably affecting the binding affinity of the resulting humanized immunoglobulin.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

Production of Variable Regions. Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., *DNA* 2: 183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Selection of Constant Region. The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see Kabat et al., supra, and WO 87/02671) (each of which is incorporated by reference in its entirety). Ordinarily, the antibody will contain both light chain and heavy chain constant regions. The heavy chain constant region usually includes CH1, hinge, CH2, CH3, and CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

5.1.1.2. Other Anti-VLA-4 Antibodies

Other anti-VLA-4 antibodies include but are not limited to HP1/2, HP-2/1, HP2/4, L25, and P4C2. These antibodies may also be administered in an effective amount to inhibit demylination and/or promote remyelination and/or reduce paralysis in a patient as one skilled in the art as discussed herein and as generally known in the art would readily appreciate.

Frequently, monoclonal antibodies created in mice are later humanized to avoid the human anti-mouse antibody (HAMA) immune response in a human subject injected with a mouse antibody. This occurs by CDR grafting or reshaping. Thus, typically the antibodies are first mouse monoclonal antibodies that through CDR grafting or reshaping become humanized, as discussed above for the 21.6 antibody.

Specifically, the humanized antibodies have specificity for VLA-4 and have the ability to promote remyelination, prevent demyelination and/or reduce paralysis. These antibodies are derived from sources (e.g., mouse typically) that at least one or more of the complementarity determining regions (CDRs) of the variable domains are derived from a donor non-human anti-VLA-4 antibody, and in which there may or may not have been minimal alteration of the acceptor antibody heavy and/or light variable framework region in order to retain donor antibody binding specificity. Preferably, the antigen binding regions of the CDR-grafted heavy chain variable domain comprise the CDRs corresponding to positions 31-35 (CDR1), 50-65 (CDR2) and 95-102 (CDR3). In a preferred embodiment, the heavy chain further includes non-human residues at framework positions 27-30 (Kabat numbering). The heavy chain can further include non-human residues at framework position 75 (Kabat numbering). The heavy chain can further include non-human residues at framework position(s) 77-79 or 66-67 and 69-71 or 84-85 or 38 and 40 or 24 (Kabat numbering). Preferably, the antigen binding regions of the CDR-grafted light chain variable domain comprise CDRs corresponding to positions 24-34 (CDR1), 50-56 (CDR2) and 89-97 (CDR3). In a preferred embodiment, the light chain further includes non-human residues at framework positions 60 and 67 (Kabat numbering). These residue designations are numbered according to the Kabat numbering (Kabat et al., $5^{th}$ ed. 4 vol. SEQUENCES OF PROTEINS OF IMMUNOLOGICAL INTEREST, U.S. Department of Health Human Services, NIH, USA (1991)).

Synthesis and Humanization of Mouse Antibody HP1/2. HP1/2 is another antibody that is directed against VLA-4. The method of preparing a humanized version of this antibody for use in human subjects is described herein and is further described in U.S. Pat. No. 6,602,503 assigned to Biogen, Inc., and hereby incorporated by reference in its entirety. The sequences of the humanized antibodies are provided as follows. The HP1/2 $V_H$ DNA sequence (SEQ ID NO.: 1) and its translated amino acid sequence (SEQ ID NO.: 2) are:

```
5'-gtc aaa ctg cag cag tct ggg gca gag ctt gtg aag cca ggg gcc tca
48
   H-Val Lys Leu Gln Gln Ser Gly Ala Glu Leu Val Lys Pro Gly Ala Ser
       1               5                  10                  15 gtc aag ttg ttc tgc aca gct tct ggc ttc aac att aaa gac acc tat
96
     Val Lys Leu Phe Cys Thr Ala Ser Gly Phe Asn Ile Lys Asp Thr Tyr
                     20                  25                  30 atg cac tgg gtg aag cag agg cct caa cag ggc ctg gag tgg att gga
144
     Met His Trp Val Lys Gln Arg Pro Gln Gln Gly Leu Glu Trp Ile Gly
                 35                  40                  45 agg att gat cct gcg agt ggc gat act aaa tat gac ccg aag ttc cag
192
     Arg Ile Asp Pro Ala Ser Gly Asp Thr Lys Tyr Asp Pro Lys Phe Gln
             50                  55                  60 gtc aag gcc act att aca gcg gac acg tcc tcc aac aca gcc tgg ctg
240
     Val Lys Ala Thr Ile Thr Ala Asp Thr Ser Ser Asn Thr Ala Trp Leu
         65                  70                  75                  80 cag ctc agc agc ctg aca tct gag gac act gcc gtc tac tac tgt gca
288
     Gln Leu Ser Ser Leu Thr Ser Glu Asp Thr Ala Val Tyr Tyr Cys Ala
                     85                  90                  95 gac gga atg tgg gta tca acg gga tat gct ctg gac ttc tgg ggc caa
336
     Asp Gly Met Trp Val Ser Thr Gly Tyr Ala Leu Asp Phe Trp Gly Gln
                 100                 105                 110 ggg acc acg gtc acc gtc tcc tca-3'
360
     Gly Thr Thr Val Thr Val Ser Ser-C
                 115                 120
```

A comparison between HP1/2 $V_H$ the two sequences and a consensus sequence of family IIC revealed that the only unusual residues are at amino acid positions 80, 98 and 121 (i.e., 79, 94 and 121 in Kabat numbering). Although Tyr-80 is invariant in subgroup IIC other sequenced murine $V_H$ regions have other aromatic amino acids at this position, although none have Trp. The majority of human and murine $V_H$s have an arginine residue at Kabat position 94. The presence of Asp-94 in HP1/2 $V_H$ is extremely rare; there is only one reported example of a negatively charged residue at this position. Proline at Kabat position 113 is also unusual but is unlikely to be important in the conformation of the CDRs because of its distance from them. The amino acids making up CDR1 have been found in three other sequenced murine $V_H$ regions. However, CDR2 and CDR3 are unique to HP1/2 and are not found in any other reported murine $V_H$.

The HP1/2 $V_K$ DNA sequence (SEQ ID NO.: 3) and its translated amino acid sequence (SEQ ID NO.: 4) are as follows:

```
5'-agt att gtg atg acc cag act ccc aaa ttc ctg ctt gtt tca gca gga
48
   N-Ser Ile Val Met Thr Gln Thr Pro Lys Phe Leu Leu Val Ser Ala Gly
       1               5                  10                  15 gac agg gtt acc ata acc tgc aag gcc agt cag agt gtg act aat gat
96
     Asp Arg Val Thr Ile Thr Cys Lys Ala Ser Gln Ser Val Thr Asn Asp
                     20                  25                  30 gta gct tgg tac caa cag aag cca ggg cag tct cct aaa ctg ctg ata
144
     Val Ala Trp Tyr Gln Gln Lys Pro Gly Gln Ser Pro Lys Leu Leu Ile
                 35                  40                  45 tat tat gca tcc aat cgc tac act gga gtc cct gat cgc ttc act ggc
192
     Tyr Tyr Ala Ser Asn Arg Tyr Thr Gly Val Pro Asp Arg Phe Thr Gly
             50                  55                  60 agt gga tat ggg acg gat ttc act ttc acc atc agc act gtg cag gct
240
     Ser Gly Tyr Gly Thr Asp Phe Thr Phe Thr Ile Ser Thr Val Gln Ala
         65                  70                  75                  80
```

-continued

```
    gaa gac ctg gca gtt tat ttc tgt cag cag gat tat agc tct ccg tac
288
    Glu Asp Leu Ala Val Tyr Phe Cys Gln Gln Asp Tyr Ser Ser Pro Tyr
                    85                  90              95 acg ttc gga ggg ggg acc aag ctg gag atc-3'
318
    Thr Phe Gly Gly Gly Thr Lys Leu Glu Ile-C
                100             105
```

HP1/2 $V_K$ is a member of Kabat family V (Kabat et al., 5$^{th}$ ed., 4 vol., SEQUENCES OF PROTEINS OF IMMUNOLOGICAL INTEREST, U.S. Department of Health Human Services (1991)) and has no unusual residues. The amino acids of CDR1 and CDR3 are unique. The amino acids making up CDR2 have been reported in one other murine $V_K$.

Design of a CDR-grafted Anti-VLA-4 Antibody. To design a CDR-grafted anti-VLA-4 antibody, it was necessary to determine which residues of murine HP1/2 comprise the CDRs of the light and heavy chains. Three regions of hypervariability amid the less variable framework sequences are found on both light and heavy chains (Wu and Kabat, *J. Exp. Med.* 132: 211-250 (1970); Kabat et al., (1991)). In most cases these hypervariable regions correspond to, but may extend beyond, the CDR. CDRs of murine HP1/2 were elucidated in accordance with Kabat et al., (1991) by alignment with other $V_H$ and $V_K$ sequences. The CDRs of murine HP1/2 $V_H$ were identified and correspond to the residues identified in the humanized $V_H$ sequences as follows:

| CDR1 | $AA_{31}$-$AA_{35}$ |
|------|---------------------|
| CDR2 | $AA_{50}$-$AA_{66}$ |
| CDR3 | $AA_{99}$-$AA_{110}$ |

These correspond to $AA_{31}$-$AA_{35}$, $AA_{50}$-$AA_{65}$, and $AA_{95}$-$AA_{102}$, respectively, in Kabat numbering. The CDRs of murine HP1/2 $V_K$ were identified and correspond to the residues identified in the humanized $V_K$ sequences as follows:

| CDR1 | $AA_{24}$-$AA_{34}$ |
|------|---------------------|
| CDR2 | $AA_{50}$-$AA_{56}$ |
| CDR3 | $AA_{89}$-$AA_{97}$ |

These correspond to the same numbered amino acids in Kabat numbering. Thus, only the boundaries of the $V_K$, but not $V_H$, CDRs corresponded to the Kabat CDR residues. The human frameworks chosen to accept the HP1/2 (donor) CDRs were NEWM and RE1 for the heavy and light chains, respectively. The NEWM and the RE1 sequences have been published in Kabat et al., (1991).

The DNA and corresponding amino acid sequence (SEQ ID NOS.: 5 and 6) of the humanized heavy chain variable region of the humanized HP1/2 antibody is:

```
    5'-atg gac tgg acc tgg agg gtc ttc tgc ttg ctg gct gta gca cca ggt
 48
    N-Met Asp Trp Thr Trp Arg Val Phe Cys Leu Leu Ala Val Ala Pro Gly
        1               5                   10                  15 gcc cac tcc cag gtc caa ctg cag gag tcc ggt gct gaa gtt gtt aaa
 96
    Ala His Ser Gln Val Gln Leu Gln Glu Ser Gly Ala Glu Val Val Lys
                    20                  25                  30 ccg ggt tcc tcc gtt aaa ctg tcc tgc aaa gct tcc ggt ttc aac atc
144
    Pro Gly Ser Ser Val Lys Leu Ser Cys Lys Ala Ser Gly Phe Asn Ile
                35                  40                  45 aaa gac acc tac atg cac tgg gtt aaa cag cgt ccg ggt cag ggt ctg
192
    Lys Asp Thr Tyr Met His Trp Val Lys Gln Arg Pro Gly Gln Gly Leu
            50                  55                  60 gaa tgg atc ggt cgt atc gac ccg gct tcc ggt gac acc aaa tac gac
240
    Glu Trp Ile Gly Arg Ile Asp Pro Ala Ser Gly Asp Thr Lys Tyr Asp
        65                  70                  75              80 ccg aaa ttc cag gtt aaa gct acc atc acc gct gac gaa tcc acc tcc
288
    Pro Lys Phe Gln Val Lys Ala Thr Ile Thr Ala Asp Glu Ser Thr Ser
                    85                  90                  95 acc gct tac ctg gaa ctg tcc tcc ctg cgt tcc gaa gac acc gct gtt
336
```

```
                Thr Ala Tyr Leu Glu Leu Ser Ser Leu Arg Ser Glu Asp Thr Ala Val
                            100                 105                 110 tac tac tgc gct gac ggt atg tgg gtt tcc acc ggt tac gct ctg gac
384
          Tyr Tyr Cys Ala Asp Gly Met Trp Val Ser Thr Gly Tyr Ala Leu Asp
                      115                 120                 125 ttc tgg ggt cag ggt acc acg gtc acc gtc tca ggt gag tcc-3'
429
          Phe Trp Gly Gln Gly Thr Thr Val Thr Val Ser Ser Gly Glu Ser-C
              130                 135                 140
```

The DNA and corresponding amino acid sequence (SEQ ID NOS.: 7 and 8) of the humanized light chain variable region of the humanized HP1/2 antibody

```
      5'-atg ggt tgg tcc tgc atc atc ctg ttc ctg gtt gct acc gct acc ggt
48
        N-Met Gly Trp Ser Cys Ile Ile Leu Phe Leu Val Ala Thr Ala Thr Gly
              1               5                   10                  15 gtt cac tcc atc gtt atg acc cag tcc ccg gac tcc ctg gct gtt tcc
96
          Val His Ser Ile Val Met Thr Gln Ser Pro Asp Ser Leu Ala Val Ser
                              20                  25                  30 ctg ggt gaa cgt gtt acc atc aac tgc aaa gct tcc cag tcc gtt acc
144
          Leu Gly Glu Arg Val Thr Ile Asn Cys Lys Ala Ser Gln Ser Val Thr
                      35                  40                  45 aac gac gtt gct tgg tac cag cag aaa ccg ggt cag tcc ccg aaa ctg
192
          Asn Asp Val Ala Trp Tyr Gln Gln Lys Pro Gly Gln Ser Pro Lys Leu
              50                  55                  60 ctg atc tac tac gct tcc aac cgt tac acc ggt gtt ccg gac cgt ttc
240
          Leu Ile Tyr Tyr Ala Ser Asn Arg Tyr Thr Gly Val Pro Asp Arg Phe
          65                  70                  75                  80 tcc ggt tcc ggt tac ggt acc gac ttc acc ttc acc atc tcc tcc gtt
288
          Ser Gly Ser Gly Tyr Gly Thr Asp Phe Thr Phe Thr Ile Ser Ser Val
                              85                  90                  95 cag gct gaa gac gtt gct gtt tac tac tgc cag cag gac tac tcc tcc
336
          Gln Ala Glu Asp Val Ala Val Tyr Tyr Cys Gln Gln Asp Tyr Ser Ser
                      100                 105                 110 ccg tac acc ttc ggt ggt ggt acc aaa ctg gag atc taa ggatcctc-3'
383
          Pro Tyr Thr Phe Gly Gly Gly Thr Lys Leu Glu Ile-C
              115                 120
```

In addition to the above humanized HP1/2 antibody light and heavy chains, other acceptor heavy and light chains regions can also be utilized for insertion of the donor HP1/2 regions. All the following constructs contain Ser-75 (Kabat numbering). The STAW construct further contains Gln to Thr at position 77, Phe to Ala at position 78, and Ser to Trp at position 79 (Kabat numbering). The $V_H$ DNA sequence (SEQ ID NO.: 9) and its translated amino acid sequence (SEQ ID NO.: 10) are set forth below:

```
5'-atg gac tgg acc tgg agg gtc ttc tgc ttg ctg gct gta gca cca ggt
48
  N-Met Asp Trp Thr Trp Arg Val Phe Cys Leu Leu Ala Val Ala Pro Gly
      1               5                  10                 15 gcc cac tcc cag gtc caa ctg cag gag agc ggt cca ggt ctt gtg aga
96
    Ala His Ser Gln Val Gln Leu Gln Glu Ser Gly Pro Gly Leu Val Arg
                    20                  25                 30 cct agc cag acc ctg agc ctg acc tgc acc gtg tct ggc ttc aac att
144
    Pro Ser Gln Thr Leu Ser Leu Thr Cys Thr Val Ser Gly Phe Asn Ile
                    35                  40                 45 aaa gac acc tat atg cac tgg gtg aga cag cca cct gga cga ggt ctt
192
    Lys Asp Thr Tyr Met His Trp Val Arg Gln Pro Pro Gly Arg Gly Leu
            50                  55                 60 gag tgg att gga agg att gat cct gcg agt ggc gat act aaa tat gac
240
    Glu Trp Ile Gly Arg Ile Asp Pro Ala Ser Gly Asp Thr Lys Tyr Asp
        65                  70                 75                 80 ccg aag ttc cag gtc aga gtg aca atg ctg gta gac acc agc agc aac
288
    Pro Lys Phe Gln Val Arg Val Thr Met Leu Val Asp Thr Ser Ser Asn
                    85                  90                 95 aca gcc tgg ctg aga ctc agc agc gtg aca gcc gcc gac acc gcg gtc
336
    Thr Ala Trp Leu Arg Leu Ser Ser Val Thr Ala Ala Asp Thr Ala Val
                    100                 105                110 tat tat tgt gca gac gga atg tgg gta tca acg gga tat gct ctg gac
384
    Tyr Tyr Cys Ala Asp Gly Met Trp Val Ser Thr Gly Tyr Ala Leu Asp
                115                 120                125 ttc tgg ggc caa ggg acc acg gtc acc gtc tcc tca ggt gag tcc-3'
429
    Phe Trp Gly Gln Gly Thr Thr Val Thr Val Ser Ser Gly Glu Ser-C
        130                 135                140
```

The KAITAS construct contains the additional changes of Arg to Lys (position 66), Val to Ala (position 67), Met to Ile (position 69), Leu to Thr (position 70) and Val to Ala (position 71) (Kabat numbering. The KAITAS V$_H$ DNA sequence (SEQ ID NO.: 11) and its translated amino acid sequence (SEQ ID NO.: 12) are set forth below:

```
5'-atg gac tgg acc tgg agg gtc ttc tgc ttg ctg gct gta gca cca ggt
48
  N-Met Asp Trp Thr Trp Arg Val Phe Cys Leu Leu Ala Val Ala Pro Gly
      1               5                  10                 15 gcc cac tcc cag gtc caa ctg cag gag agc ggt cca ggt ctt gtg aga
96
    Ala His Ser Gln Val Gln Leu Gln Glu Ser Gly Pro Gly Leu Val Arg
                    20                  25                 30 cct agc cag acc ctg agc ctg acc tgc acc gtg tct ggc ttc aac att
144
    Pro Ser Gln Thr Leu Ser Leu Thr Cys Thr Val Ser Gly Phe Asn Ile
                    35                  40                 45 aaa gac acc tat atg cac tgg gtg aga cag cca cct gga cga ggt ctt
192
    Lys Asp Thr Tyr Met His Trp Val Arg Gln Pro Pro Gly Arg Gly Leu
            50                  55                 60 gag tgg att gga agg att gat cct gcg agt ggc gat act aaa tat gac
240
    Glu Trp Ile Gly Arg Ile Asp Pro Ala Ser Gly Asp Thr Lys Tyr Asp
        65                  70                 75                 80 ccg aag ttc cag gtc aaa gcg aca att acg gca gac acc agc agc aac
288
```

```
                                     -continued
    Pro Lys Phe Gln Val Lys Ala Thr Ile Thr Ala Asp Thr Ser Ser Asn
                        85              90                  95 cag ttc agc ctg aga ctc agc agc gtg aca gcc gcc gac acc gcg gtc
336
    Gln Phe Ser Leu Arg Leu Ser Ser Val Thr Ala Ala Asp Thr Ala Val
                100                 105                 110 tat tat tgt gca gac gga atg tgg gta tca acg gga tat gct ctg gac
384
    Tyr Tyr Cys Ala Asp Gly Met Trp Val Ser Thr Gly Tyr Ala Leu Asp
                115                 120                 125 ttc tgg ggc caa ggg acc acg gtc acc gtc tcc tca ggt gag tcc-3'
429
    Phe Trp Gly Gln Gly Thr Thr Val Thr Val Ser Ser Gly Glu Ser-C
            130                 135                 140
```

The SSE construct comprises the additional changes of Ala to Ser (position 84) and Ala to Glu (position 85) (Kabat numbering). The SSE $V_H$ DNA sequence (SEQ ID NO.: 13) and its translated amino acid sequence (SEQ ID NO.: 14) are set forth below:

```
    5'-cag gtc caa ctg cag gag agc ggt cca ggt ctt gtg aga cct agc cag
48
    N-Gln Val Gln Leu Gln Glu Ser Gly Pro Gly Leu Val Arg Pro Ser Gln
        1               5                   10                  15 acc ctg agc ctg acc tgc acc gtg tct ggc ttc aac att aaa gac acc
96
    Thr Leu Ser Leu Thr Cys Thr Val Ser Gly Phe Asn Ile Lys Asp Thr
                    20                  25                  30 tat atg cac tgg gtg aga cag cca cct gga cga ggt ctt gag tgg att
144
    Tyr Met His Trp Val Arg Gln Pro Pro Gly Arg Gly Leu Glu Trp Ile
                35                  40                  45 gga agg att gat cct gcg agt ggc gat act aaa tat gac ccg aag ttc
192
    Gly Arg Ile Asp Pro Ala Ser Gly Asp Thr Lys Tyr Asp Pro Lys Phe
            50                  55                  60 cag gtc aga gtg aca atg ctg gta gac acc agc agc aac cag ttc agc
240
    Gln Val Arg Val Thr Met Leu Val Asp Thr Ser Ser Asn Gln Phe Ser
        65                  70                  75                  80 ctg aga ctc agc agc gtg aca tct gag gac acc gcg gtc tat tat tgt
288
    Leu Arg Leu Ser Ser Val Thr Ser Glu Asp Thr Ala Val Tyr Tyr Cys
                    85                  90                  95 gca gac gga atg tgg gta tca acg gga tat gct ctg gac ttc tgg ggc
336
    Ala Asp Gly Met Trp Val Ser Thr Gly Tyr Ala Leu Asp Phe Trp Gly
                100                 105                 110 caa ggg acc acg gtc acc gtc tcc tca ggt gag tcc-3'
372
    Gln Gly Thr Thr Val Thr Val Ser Ser Gly Glu Ser-C
            115                 120
```

The KRS construct comprises the additional changes of Arg to Lys (position 38) and Pro to Arg (position 40) (Kabat numbering). The KRS $V_H$ DNA sequence (SEQ ID NO.: 15) and its translated amino acid sequence (SEQ ID NO.: 16) are set forth below:

```
   5'-atg gac tgg acc tgg agg gtc ttc tgc ttg ctg gct gta gca cca ggt
48
    N-Met Asp Trp Thr Trp Arg Val Phe Cys Leu Leu Ala Val Ala Pro Gly
        1                5                  10                 15 gcc cac tcc cag gtc caa ctg cag gag agc ggt cca ggt ctt gtg aga
96
    Ala His Ser Gln Val Gln Leu Gln Glu Ser Gly Pro Gly Leu Val Arg
                     20                  25                  30 cct agc cag acc ctg agc ctg acc tgc acc gtg tct ggc ttc aac att
144
    Pro Ser Gln Thr Leu Ser Leu Thr Cys Thr Val Ser Gly Phe Asn Ile
                 35                  40                  45 aaa gac acc tat atg cac tgg gtg aaa cag cga cct gga cga ggt ctt
192
    Lys Asp Thr Tyr Met His Trp Val Lys Gln Arg Pro Gly Arg Gly Leu
            50                  55                  60 gag tgg att gga agg att gat cct gcg agt ggc gat act aaa tat gac
240
    Glu Trp Ile Gly Arg Ile Asp Pro Ala Ser Gly Asp Thr Lys Tyr Asp
        65                  70                  75                  80 ccg aag ttc cag gtc aga gtg aca atg ctg gta gac acc agc agc aac
288
    Pro Lys Phe Gln Val Arg Val Thr Met Leu Val Asp Thr Ser Ser Asn
                     85                  90                  95 cag ttc agc ctg aga ctc agc agc gtg aca gcc gcc gac acc gcg gtc
336
    Gln Phe Ser Leu Arg Leu Ser Ser Val Thr Ala Ala Asp Thr Ala Val
                 100                 105                 110 tat tat tgt gca gac gga atg tgg gta tca acg gga tat gct ctg gac
384
    Tyr Tyr Cys Ala Asp Gly Met Trp Val Ser Thr Gly Tyr Ala Leu Asp
             115                 120                 125 ttc tgg ggc caa ggg acc acg gtc acc gtc tcc tca ggt gag tcc-3'
429
    Phe Trp Gly Gln Gly Thr Thr Val Thr Val Ser Ser Gly Glu Ser-C
         130                 135                 140
```

The AS construct comprises the change Val to Ala at position 24 (Kabat numbering). The AS $V_H$ DNA sequence (SEQ ID NO.: 17) and its translated amino acid sequence (SEQ ID NO.: 18) are:

```
   5'-atg gac tgg acc tgg agg gtc ttc tgc ttg ctg gct gta gca cca ggt
48
    N-Met Asp Trp Thr Trp Arg Val Phe Cys Leu Leu Ala Val Ala Pro Gly
        1                5                  10                 15 gcc cac tcc cag gtc caa ctg cag gag agc ggt cca ggt ctt gtg aga
96
    Ala His Ser Gln Val Gln Leu Gln Glu Ser Gly Pro Gly Leu Val Arg
                     20                  25                  30 cct agc cag acc ctg agc ctg acc tgc acc gcg tct ggc ttc aac att
144
    Pro Ser Gln Thr Leu Ser Leu Thr Cys Thr Ala Ser Gly Phe Asn Ile
                 35                  40                  45 aaa gac acc tat atg cac tgg gtg aga cag cca cct gga cga ggt ctt
192
    Lys Asp Thr Tyr Met His Trp Val Arg Gln Pro Pro Gly Arg Gly Leu
            50                  55                  60 gag tgg att gga agg att gat cct gcg agt ggc gat act aaa tat gac
240
    Glu Trp Ile Gly Arg Ile Asp Pro Ala Ser Gly Asp Thr Lys Tyr Asp
        65                  70                  75                  80
```

```
                                   -continued
    ccg aag ttc cag gtc aga gtg aca atg ctg gta gac acc agc agc aac
288
    Pro Lys Phe Gln Val Arg Val Thr Met Leu Val Asp Thr Ser Ser Asn
                        85                  90                  95 cag ttc agc ctg aga ctc agc agc gtg aca gcc gcc gac acc gcg gtc
336
    Gln Phe Ser Leu Arg Leu Ser Ser Val Thr Ala Ala Asp Thr Ala Val
                    100                 105                 110 tat tat tgt gca gac gga atg tgg gta tca acg gga tat gct ctg gac
384
    Tyr Tyr Cys Ala Asp Gly Met Trp Val Ser Thr Gly Tyr Ala Leu Asp
                115                 120                 125 ttc tgg ggc caa ggg acc acg gtc acc gtc tcc tca ggt gag tcc-3'
429
    Phe Trp Gly Gln Gly Thr Thr Val Thr Val Ser Ser Gly Glu Ser-C
            130                 135                 140
```

The humanized light chain generally requires few, if any, modifications. However, in the preparation of humanized anti-VLA-4 antibodies, several empirical changes did improve the immunological activity of the antibody towards its ligand. For example, the humanized heavy chain with the Ser mutation with the murine light chain was about 2.5 fold lower potency than murine HP1/2. The same humanized heavy chain with a humanized light chain was about 4-fold lower potency.

A humanized $V_K$ construct (VK1) comprises a Ser to Asp substitution at position 60, and a Ser for a Tyr at position 67. The DNA sequence (SEQ ID NO.: 19) and its translated amino acid sequence (SEQ ID NO.: 20) are set forth below:

```
    5'-atg ggt tgg tcc tgc atc atc ctg ttc ctg gtt gct acc gct acc ggt
48
    N-Met Gly Trp Ser Cys Ile Ile Leu Phe Leu Val Ala Thr Ala Thr Gly
         1               5                   10                  15 gtt cac tcc gac atc cag ctg acc cag agc cca agc agc ctg agc gcc
96
    Val His Ser Asp Ile Gln Leu Thr Gln Ser Pro Ser Ser Leu Ser Ala
                    20                  25                  30 agc gtg ggt gac aga gtg acc atc acc tgt aag gcc agt cag agt gtg
144
    Ser Val Gly Asp Arg Val Thr Ile Thr Cys Lys Ala Ser Gln Ser Val
                35                  40                  45 act aat gat gta gct tgg tac cag cag aag cca ggt aag gct cca aag
192
    Thr Asn Asp Val Ala Trp Tyr Gln Gln Lys Pro Gly Lys Ala Pro Lys
            50                  55                  60 ctg ctg atc tac tat gca tcc aat cgc tac act ggt gtg cca agc aga
240
    Leu Leu Ile Tyr Tyr Ala Ser Asn Arg Tyr Thr Gly Val Pro Ser Arg
        65                  70                  75                  80 ttc agc ggt agc ggt agc ggt acc gac ttc acc ttc acc atc agc agc
288
    Phe Ser Gly Ser Gly Ser Gly Thr Asp Phe Thr Phe Thr Ile Ser Ser
                        85                  90                  95 ctc cag cca gag gac atc gcc acc tac tac tgc cag cag gat tat agc
336
    Leu Gln Pro Glu Asp Ile Ala Thr Tyr Tyr Cys Gln Gln Asp Tyr Ser
                    100                 105                 110 tct ccg tac acg ttc ggc caa ggg acc aag gtg gaa atc aaa cgt aag tg-3'
386
    Ser Pro Tyr Thr Phe Gly Gln Gly Thr Lys Val Glu Ile Lys Arg Lys Lye-C
                115                 120                 125
```

Another V$_K$ construct (i.e., VK2) has the DQMDY sequences of the original RE1 framework restored. The DNA and corresponding amino acid sequence (SEQ ID NOS.: 21 and 22) are provided below:

```
     5'-atg ggt tgg tcc tgc atc atc ctg ttc ctg gtt gct acc gct acc ggt
 48
       N-Met Gly Trp Ser Cys Ile Ile Leu Phe Leu Val Ala Thr Ala Thr Gly
            1               5                  10                  15 gtc cac tcc agc atc gtg atg acc cag agc cca agc agc ctg agc gcc
 96
       Val His Ser Ser Ile Val Met Thr Gln Ser Pro Ser Ser Leu Ser Ala
                      20                  25                  30 agc gtg ggt gac aga gtg acc atc acc tgt aag gcc agt cag agt gtg
144
       Ser Val Gly Asp Arg Val Thr Ile Thr Cys Lys Ala Ser Gln Ser Val
                  35                  40                  45 act aat gat gta gct tgg tac cag cag aag cca ggt aag gct cca aag
192
       Thr Asn Asp Val Ala Trp Tyr Gln Gln Lys Pro Gly Lys Ala Pro Lys
              50                  55                  60 ctg ctg atc tac tat gca tcc aat cgc tac act ggt gtg cca gat aga
240
       Leu Leu Ile Tyr Tyr Ala Ser Asn Arg Tyr Thr Gly Val Pro Asp Arg
          65                  70                  75                  80 ttc agc ggt agc ggt tat ggt acc gac ttc acc ttc acc atc agc agc
288
       Phe Ser Gly Ser Gly Tyr Gly Thr Asp Phe Thr Phe Thr Ile Ser Ser
                      85                  90                  95 ctc cag cca gag gac atc gcc acc tac tac tgc cag cag gat tat agc
336
       Leu Gln Pro Glu Asp Ile Ala Thr Tyr Tyr Cys Gln Gln Asp Tyr Ser
                  100                 105                 110 tct ccg tac acg ttc ggc caa ggg acc aag gtg gaa atc aaa cgt aag tg-3'
386
       Ser Pro Tyr Thr Phe Gly Gln Gly Thr Lys Val Glu Ile Lys Arg Lys-C
              115                 120                 125
```

A third V$_K$ construct is VK3 has SVM versus DQM in the amino terminus and two other residue changes. The DNA and corresponding amino acid sequence (SEQ ID NOS.: 23 and 24) are:

```
     5'-atg ggt tgg tcc tgc atc atc ctg ttc ctg gtt gct acc gct acc ggt
 48
       N-Met Gly Trp Ser Cys Ile Ile Leu Phe Leu Val Ala Thr Ala Thr Gly
            1               5                  10                  15 gtc cac tcc gac atc cag atg acc cag agc cca agc agc ctg agc gcc
 96
       Val His Ser Asp Ile Gln Met Thr Gln Ser Pro Ser Ser Leu Ser Ala
                      20                  25                  30 agc gtg ggt gac aga gtg acc atc acc tgt aag gcc agt cag agt gtg
144
       Ser Val Gly Asp Arg Val Thr Ile Thr Cys Lys Ala Ser Gln Ser Val
                  35                  40                  45 act aat gat gta gct tgg tac cag cag aag cca ggt aag gct cca aag
192
       Thr Asn Asp Val Ala Trp Tyr Gln Gln Lys Pro Gly Lys Ala Pro Lys
              50                  55                  60 ctg ctg atc tac tat gca tcc aat cgc tac act ggt gtg cca gat aga
240
       Leu Leu Ile Tyr Tyr Ala Ser Asn Arg Tyr Thr Gly Val Pro Asp Arg
          65                  70                  75                  80
```

```
                                    -continued
        ttc agc ggt agc ggt tat ggt acc gac ttc acc ttc acc atc agc agc
288
        Phe Ser Gly Ser Gly Tyr Gly Thr Asp Phe Thr Phe Thr Ile Ser Ser
                         85              90              95 ctc cag cca gag gac atc gcc acc tac tac tgc cag cag gat tat agc
336
        Leu Gln Pro Glu Asp Ile Ala Thr Tyr Tyr Cys Gln Gln Asp Tyr Ser
                    100             105             110 tct ccg tac acg ttc ggc caa ggg acc aag gtg gaa atc aaa cgt aag tg-3'
386
        Ser Pro Tyr Thr Phe Gly Gln Gly Thr Lys Val Glu Ile Lys Arg Lys-C
                    115             120             125
```

Details regarding how each of these light and heavy chain sequences were prepared are provided in U.S. Pat. No. 6,602,503, which is hereby incorporated by reference in its entirety for all purposes. Various combinations of the above light and heavy chains can be prepared based on computer modeling as known in the art.

Additional antibodies that recognize and bind to alpha-4 integrin are known in the art. These include but are not limited to GG5/3 (Keszthelyi et al., *Neurology* 47(4): 1053-1059 (1996)), FW3-218-1 (ATCC No.: HB-261; an IgG2b antibody against sheep alpha 4 integrin), and R1-2 (ATCC No.: HB-227; IgG2b antibody developed in *Rattus norvegicus*). Whether the antibodies are developed in mouse or other animals, each of the sequences can be genetically engineered such that they are humanized based on what is known in the art and with the aid of computer modeling. The anti-alpha-4 integrin humanized antibodies can then be assessed for their ability to promote remyelination and/or inhibit demyelination and/or reduce paralysis based on the in vitro and in vivo assays disclosed herein.

5.2. Antibody Fragments

Also contemplated for use in treating disorders and conditions involving demyelination are antibody fragments of antibodies that bind to anti-alpha-4 or VCAM-1 such that they inhibit VLA-4 and VCAM-1 interaction. Antibody fragments include Fab, F(ab')$_2$, scFv and Fv fragments which can be used in the compositions disclosed herein.

The term "Fab fragment" as used herein refers to a partial antibody molecule containing a single antigen-binding region, which consists of a portion of both the heavy and light chains of the molecule.

The term "F(ab')$_2$ fragment" as used herein refers to a partial antibody molecule containing both antigen binding regions, and which consists of the light chains and a portion of the heavy chains of the molecule.

The term "Fv fragment" as used herein refers to the portion of the antibody molecule involved in antigen recognition and binding.

The term "scFv" as used herein refers to single chain Fv (scFv) fragments. These scFv fragments are recombinant antibody derivatives that consist only of the variable domains of antibody heavy and light chains connected by a flexible linker. scFv antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scfv to form the desired structure for antigen binding. For a review of scFv see Pluckthun in *The Pharmacology of Monoclonal Antibodies,* vol. 113, 269-315 (Rosenburg and Moore eds., Springer-Verlag, New York 1994).

Also included in antibody fragments are diabodies. The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., 1993 *Proc. Natl. Acad. Sci. USA* 90: 6444-8.

Antibody fragments also include linear antibodies. The expression "linear antibodies" when used throughout this application refers to the antibodies described in, e.g., Zapata et al., 1995 *Protein Eng.* 8(10): 1057-62. Briefly, these antibodies comprise a pair of tandem Fd segments ($V_H$-$C_H$1-$V_H$-$C_H$1), which form a pair of antigen binding regions. Linear antibodies can be bispecific or monospecific.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

Several mouse anti-VLA-4 monoclonal antibodies have been previously described. See, e.g., U.S. Pat. Nos. 6,602,503, 6,033,665, and 5,840,299, as further discussed herein and which are herein incorporated by reference in their entirety; Sanchez-Madrid et al., 1986, *Eur. J. Immunol.* 16: 1343-9; Hemler et al., 1987, *J. Biol. Chem.* 262: 11478-85; Pulido et al., 1991, *J. Biol. Chem.*, 266: 10241-45; Issekutz et al., 1991, *J. Immunol.,* 147: 109 (TA-2 MAb)). These anti-VLA-4 monoclonal antibodies and other anti-VLA-4 antibodies (e.g., U.S. Pat. No. 5,888,507—Biogen, Inc. and references cited therein) capable of recognizing the alpha and/or beta chain of VLA-4 will be useful in the methods of treatment according to the present invention. AntiVLA-4 antibodies that will recognize the VLA-4 alpha-4 chain epitopes involved in binding to VCAM-1 and fibronectin ligands (i.e., antibodies which can bind to VLA-4 at a site involved in ligand recognition and block VCAM-1 and fibronectin binding) are preferred. Such antibodies have been defined as B epitope-specific antibodies (B1 or B2) (Pulido et al., 1991, supra) and are also anti-VLA-4 antibodies according to the present invention.

Fully human monoclonal antibody homologs against VLA-4 are another preferred binding agent that may block or coat VLA-4 ligands in the method of the invention. In their intact form these may be prepared using in vitro-primed human splenocytes, as described by Boerner et al., 1991, *J. Immunol.,* 147: 86-95. Alternatively, they may be prepared by repertoire cloning as described by Persson et al., 1991, *Proc.*

Nat. Acad. Sci. USA, 88: 2432-36 or by Huang et al., 1991, J. Immunol. Meth., 141: 227-236. U.S. Pat. No. 5,798,230 (Aug. 25, 1998, "Process for the preparation of human monoclonal antibodies and their use") describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production. Additional methods are known in the art.

For yet another method for producing fully human antibodies, see, e.g., U.S. Pat. No. 5,789,650, which describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells, which are thereafter immortalized, e.g., by fusing with an immortalizing cell line such as a myeloma or by manipulating such B-cells by other techniques to perpetuate a cell line capable of producing a monoclonal, heterologous, fully human antibody homolog. Large non-immunized human phage display libraries may also be used to isolate high affinity antibodies that can be developed as human therapeutics using standard phage technology.

Following the early methods for the preparation of true "chimeric antibodies" (i.e., where the entire constant and entire variable regions are derived from different sources), a new approach was described in EP 0239400 (Winter et al.) whereby antibodies are altered by substitution (within a given variable region) of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies, which are totally human in composition except for the substituted murine CDRs. Such CDR-substituted antibodies would be predicted to be less likely to elicit an immune response in humans compared to true chimeric antibodies, because the CDR-substituted antibodies contain considerably less non-human components. The process for humanizing monoclonal antibodies via CDR "grafting" has been termed "reshaping" (Riechmann et al., 1988, Nature 332: 323-7; and Verhoeyen et al., 1988, Science 239: 1534-6).

5.3. Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., BioTechnology 10: 163-7 (1992) describe a procedure for isolating antibodies, which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. In instances when the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells is preferably subjected to at least one purification step prior to LPHIC. Examples of suitable purification steps include hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., 1983 J. Immunol. Meth. 62: 1-13). Protein G is recommended for all mouse isotypes and for human $\gamma 3$ (Guss et al., 1986 EMBO J. 5: 1567-75). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminant(s) is subjected to LPHIC. Often, the antibody composition to be purified will be present in a buffer from the previous purification step. However, it may be necessary to add a buffer to the antibody composition prior to the LPHIC step. Many buffers are available and can be selected by routine experimentation. The pH of the mixture comprising the antibody to be purified and at least one contaminant in a loading buffer is adjusted to a pH of about 2.5-4.5 using either an acid or base, depending on the starting pH. Preferably, the loading buffer has a low salt concentration (i.e., less than about 0.25 M salt).

The mixture is loaded on the HIC column. HIC columns normally comprise a base matrix (e.g., cross-linked agarose or synthetic copolymer material) to which hydrophobic ligands (e.g., alkyl or aryl groups) are coupled. A preferred HIC column comprises an agarose resin substituted with phenyl groups (e.g., a Phenyl SEPHAROSE™ column). Many HIC columns are available commercially. Examples include, but are not limited to, Phenyl SEPHAROSE 6 FAST FLOW™ column with low or high substitution (Pharmacia LKB Biotechnology, AB, Sweden); Phenyl SEPHAROSE™ High Performance column (Pharmacia LKB Biotechnology, AB, Sweden); Octyl SEPHAROSE™ High Performance column (Pharmacia LKB Biotechnology, AB, Sweden); FRACTOGEL™ EMD Propyl or FRACTOGEL™ EMD Phenyl columns (E. Merck, Germany); MACRO-PREP™ Methyl or MACRO-PREP™ t-Butyl Supports (Bio-Rad, California);

WP HI-Propyl (C₃)™ column (J. T. Baker, New Jersey); and TOYOPEARL™ ether, phenyl or butyl columns (TosoHaas, Pa.).

The antibody is eluted from the column using an elution buffer, which is normally the same as the loading buffer. The elution buffer can be selected using routine experimentation. The pH of the elution buffer is between about 2.5-4.5 and has a low salt concentration (i.e., less than about 0.25 M salt). It has been discovered that it is not necessary to use a salt gradient to elute the antibody of interest; the desired product is recovered in the flow through fraction, which does not bind significantly to the column.

The LPHIC step provides a way to remove a correctly folded and disulfide bonded antibody from unwanted contaminants (e.g., incorrectly associated light and heavy fragments). In particular, the method provides a means to substantially remove an impurity characterized herein as a correctly folded antibody fragment whose light and heavy chains fail to associate through disulfide bonding.

Diagnostic or therapeutic formulations of the purified protein can be made by providing the antibody composition in the form of a physiologically acceptable carrier, examples of which are provided below.

To remove contaminants (e.g., unfolded antibody and incorrectly associated light and heavy fragments) from the HIC column so that it can be re-used, a composition including urea (e.g., 6.0 M urea, 1% MES buffer pH 6.0, 4 mM ammonium sulfate) can be flowed through the column. Other methods are known in the art.

5.4. Immunoglobulin Formulations

Antibodies and immunoglobulins having the desired therapeutic effect may be administered in a physiologically acceptable carrier to a subject. The antibodies may be administered in a variety of ways including but not limited to parenteral administration, including subcutaneous, subdural, intravenous, intramuscular, intrathecal, intraperitoneal, intracerebral, intraarterial, or intralesional routes of administration, localized (e.g., surgical application or surgical suppository), and pulmonary (e.g., aerosols, inhalation, or powder) and as described further below.

Depending upon the manner of introduction, the immunoglobulins may be formulated in a variety of ways. The concentration of therapeutically active immunoglobulin in the formulation (i.e., a formulation sufficient to inhibit demyelination and/or promote remyelination) may vary from about 1 mg/ml to 1 g/ml. Preferably, the immunoglobulin composition, when administered to a subject in need thereof, reaches a blood level of immunoglobulin in the subject of about 10 ng/ml or more.

Preferably, the immunoglobulin is formulated for parenteral administration in a suitable inert carrier, such as a sterile physiological saline solution. For example, the concentration of immunoglobulin in the carrier solution is typically between about 1-100 mg/ml. The dose administered will be determined by route of administration. Preferred routes of administration include parenteral or intravenous administration.

For parenteral administration, the antibodies of the invention can be administered as injectionable dosages of a solution or suspension of the substance in a physiologically acceptable diluent with a pharmaceutical carrier which can be a sterile liquid such as water and oils with or without the addition of a surfactant and other pharmaceutically preparations are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. The antibodies of this invention can be administered in the form of a depot injection or implant preparation, which can be formulated in such a manner as to permit a sustained release of the active ingredient. A preferred composition comprises monoclonal antibody at 5 mg/mL, formulated in aqueous buffer consisting of 50 mM L-histidine, 150 mM NaCl, adjusted to pH 6.0 with HCl.

A therapeutically effective dose is a dose effective to produce a significant decrease in demyelination and a notable increase in remyelination. Preferably, the amount is sufficient to produce a statistically significant amount of remyelination in a subject.

According to an important feature of the invention, an immunoglobulin that recognizes and binds to VLA-4 may be administered alone, or in combination with an anti-inflammatory agent, which is typically used to treat conditions and diseases associated with demyelination. Administration of anti-inflammatory agents can occur prior to, concurrent with or after administration with the immunoglobulin.

A therapeutically effective amount of a remyelinating antibody or immunoglobulin, e.g., natalizumab, can be estimated by comparison with established effective doses for known antibodies, taken together with data obtained for natalizumab in both in vivo and in vitro models. Preferably the data is from inhibition of demyelination studies. As is known in the art, adjustments in the dose may be necessary due to immunoglobulin degeneration or metabolism, systemic versus localized delivery, as well as the age, body weight, general health, sex, diet, time of administration, drug interactions and the severity of the condition of the subject to whom the immunoglobulin is administered. Such adjustments may be made and appropriate doses determined by one of skill in the art through routine experimentation.

Therapeutic formulations of the immunoglobulin are prepared for storage by mixing the immunoglobulin having the desired degree of purity with optional physiologically acceptable carriers, excipients, or stabilizers (*Remington's Pharmaceutical Sciences*, 16th ed., A. Osol, Ed., 1980 and more recent editions), in the form of lyophilized cake or aqueous solutions. Acceptable immunoglobulin carriers, excipients or stabilizers are nontoxic, nontherapeutic and/or non-immunogenic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG). Specific examples of carrier molecules include but are not limited to glycosaminoglycans (e.g., heparin sulfate), hyaluronic acid, keratan-sulfate, chondroitin 4-sulfate, chondroitin 6-sulfate, heparan sulfate and dermatin sulfate, perlecan and pentopolysulfate.

Pharmaceutical compositions comprising immunoglobulins can also include if desired, pharmaceutically acceptable, non-toxic carriers or diluents, which are vehicles commonly used to formulated pharmaceutical compositions for animal or human administration. The diluent is selected so as not to affect the biological activity of the combination. Examples include but are not limited to distilled water, physiological phosphate-buffered saline, Ringer's solutions, dextrose solution, and Hank's solution.

The agents of the invention can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol. The formulations may also contain conventional additives, such as solubilizers, isotonic agents, suspending agents, emulsifying agents, stabilizers and preservatives.

The immunoglobulins may also be utilized in aerosol formulation to be administered via inhalation or pulmonary delivery. The agents of the present invention can be formulated into pressurized acceptable propellants such as dichlorodifluoromethane, propane, nitrogen and the like.

The immunoglobulin also may be entrapped in microcapsules prepared, for example, by coacervation techniques or by interfacial polymerization (e.g., hydroxymethylcellulose or gelatin-microcapsules and poly-methylmethacylate microcapsules), in colloidal drug delivery systems (e.g., liposomes, albumin microspheres, microemulsions, nano-particles and nanocapsules), or in macroemulsions. Such techniques are disclosed in Remington's Pharmaceutical Sciences, supra.

The immunoglobulin to be used for in vivo administration must be sterile. This is readily accomplished by filtration through sterile filtration membranes, prior to or following lyophilization and reconstitution. The immunoglobulin ordinarily will be stored in lyophilized form or in solution.

Therapeutic immunoglobulin compositions generally are placed into a container having a sterile access port, for example, an intravenous solution bag or vial having a stopper pierceable by a hypodermic injection needle or similar sharp instrument.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinylalcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(–)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for immunoglobulin stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, developing specific polymer matrix compositions, and the like.

Sustained-release immunoglobulin compositions also include liposomally entrapped immunoglobulin. Liposomes containing the immunoglobulin are prepared by methods known per se. See, e.g., Epstein et al., *Proc. Natl. Acad. Sci. USA* 82: 3688-92 (1985); Hwang et al., *Proc. Natl. Acad. Sci. USA* 77: 4030-4 (1980); U.S. Pat. Nos. 4,485,045; 4,544,545; 6,139,869; and 6,027,726. Ordinarily, the liposomes are of the small (about 200 to about 800 Angstroms), unilamellar type in which the lipid content is greater than about 30 mole percent (mol. %) cholesterol; the selected proportion being adjusted for the optimal immunoglobulin therapy.

The immunoglobulins of this invention can be administered in a sustained release form, for example a depot injection, implant preparation, or osmotic pump, which can be formulated in such a manner as to permit a sustained release of the active ingredient. Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

In addition, immunoglobulins which prevent demyelination and/or induce remyelination may be provided by administering a polynucleotide encoding a whole or partial antibody (e.g., a single chain Fv) to a subject. The polynucleotide is administered to a subject in an appropriate vehicle to allow the expression of the immunoglobulin in the subject in a therapeutically effective amount.

A typical daily dosage might range for immunoglobulins ranges from about 1 µg/kg to up to about 10 mg/kg or more, depending on the factors mentioned herein. Typically, the clinician will administer immunoglobulin until a dosage is reached that achieves the desired effect. The progress of this therapy is easily monitored by conventional assays.

A "stable" antibody or antibody fragment formulation is one in which the protein therein essentially retains its physical stability and/or chemical stability and/or biological activity upon storage. Various analytical techniques for measuring protein stability are available in the art and are reviewed in *Peptide and Protein Drug Delivery*, 247-301, (Vincent Lee Ed., Marcel Dekker, Inc., New York, N.Y., Pubs. 1991) and A. Jones, *Adv. Drug Delivery Rev.* 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year for at least about 2 years. Furthermore, the formulation is preferably stable following freezing (to, e.g., –70° C.) and thawing of the formulation.

A protein "retains its physical stability" in a pharmaceutical formulation if it shows no signs of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g., clipping) that can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g., occurring as a result of deamidation) that can be evaluated by, e.g., ion-exchange chromatography.

An immunoglobulin "retains its biological activity" in a pharmaceutical formulation, if the biological activity of the immunoglobulin at a given time is within about 10% (within the errors of the assay) of the biological activity exhibited at the time the pharmaceutical formulation was prepared as determined in an antigen-binding assay, for example.

5.5. Routes of Administration of Immunoglobulin Compositions

As discussed briefly above, the pharmaceutical compositions discussed supra can be administered for prophylactic and/or therapeutic treatments of multiple sclerosis or other demyelination related disorders. In therapeutic applications, compositions are administered to a patient suspected of, or already suffering from a disease such as multiple sclerosis, in an amount sufficient to promote remyelination. An amount adequate to accomplish this is defined as a therapeutically- or pharmaceutically-effective dose.

The pharmaceutical compositions will be administered by parenteral, topical, intravenous, oral, or subcutaneous, intramuscular local administration, such as by aerosol or transdermally, for prophylactic and/or therapeutic treatment. Although the proteinaceous substances of this invention may survive passage through the gut following oral administration (p.o.), subcutaneous (s.c.), intravenous (i.v.), intramuscular (i.m.), intraperitoneal administration by depot injection; or by implant preparation are preferred.

The pharmaceutical compositions can be administered in a variety of unit dosage forms depending upon the method of administration. For example, unit dosage forms suitable for oral administration include powder, tablets, pills, capsules, and lozenges.

Effective doses of the compositions of the present invention, for the treatment of the above described conditions will vary depending upon many different factors, including means of administration, target site, physiological state of the patient, and other medicaments administered. Thus, treatment dosages will need to be titrated to optimize safety and efficacy. These compositions may be administered to mammals for veterinary use and for clinical use in humans in a manner similar to other therapeutic agents, i.e., in a physiologically acceptable carrier. In general, the administration dosage will range from about 0.0001 to 100 mg/kg, and more usually 0.01 to 0.5 mg/kg of the host body weight.

In a preferred treatment regime, the antibody is administered by intravenous infusion or subcutaneous injection at a dose from 1 to 5 mg antibody per kilo of patient bodyweight. The dose is repeated at interval from 2 to 8 weeks. Within this range, the preferred treatment regimen is 3 mg antibody per kilo of bodyweight repeated at a 4-week interval.

6. Drug Combinations

As stated previously, no previously described drug or drug combination was identified as stopping the progressive loss of neurologic function for demyelinating diseases. Some drugs existed which suppressed immune-mediated inflammation and can also decrease the relapse rate of multiple sclerosis. These and other drugs used to treat symptoms associated with multiple sclerosis and demyelination-associated conditions and diseases are also contemplated for use in combination with the compounds and compositions disclosed herein. Selection of one or more agent to be utilized in a cocktail and/or combination with the compounds and compositions disclosed herein will be dependent on the management of the disease. For example, in MS, disease management can be categorized into two groups: (1) treatment designed to arrest the disease process, and (2) symptomatic management. Various combinations of drugs can be used in category (D). For example, the compounds and compositions disclosed herein can be administered with immunosuppressant agents to further inhibit the influx of immune cells and thereby demyelinating activity. For example, immunosuppressants such as corticosteroids maybe used.

The remyelinating agents (e.g., anti-alpha-4 integrin antibodies, small compound alpha-4 integrin antagonists and the like) can be combined with other compounds or compositions used to treat, ameliorate or palliate symptoms associated with demyelinating conditions or diseases.

Other agents utilized to treat, ameliorate or palliate symptoms associated with demyelination conditions or diseases, including multiple sclerosis, include but are not limited to: muscle relaxants (e.g., diazepam, cyclobenzaprine, clonazepam, clonidine, primidone, and the like), anticholinergics (e.g., propantheline, dicyclomine, and the like), central nervous system stimulants (e.g., pemoline), non-steroidal anti-inflammatory agents (NSAIDs such as ibuprofen, naproxen and ketoprofen), interferons, immune globulin, glatiramer (COPAXONE®), mitoxantrone (NOVANTRONE®), misoprostol, tumor necrosis factor-alpha inhibitors (e.g., pirfenidone, infliximab and the like) and corticosteroids (e.g., glucocorticoids and mineralocorticoids).

Common agents for treating multiple sclerosis include interferon beta-1b (BETASERON®), interferon beta-1a (AVONEX®) high-dose interferon beta-1a (REBIF®), glatiramer (COPAXONE®), immune globulin, mitoxantrone (NOVANTRONE®), corticosteroids (e.g., prednisone, methylprednisolone, dexamethasone and the like). Other corticosteroids may also be used and include but are not limited to cortisol, cortisone, fludrocortisone, prednisolone, 6α-methylprednisolone, triamcinolone, and betamethasone.

Dosage forms of the agents to be used in combination with the compounds and compositions disclosed herein would vary depending on the subject and drug combination being utilized. For example, interferons are typically administered as follows: Interferon beta-1a (Avonex®) is administered 30 μg once a week; interferon beta-1a is administered at about 22 μg or 44 μg three times a week; and interferon beta-1b (Betaseron®) is administered at 250 μg on alternate days (Durelli et al., Lancet 359: 1453-60, 2002). Typically the interferons are administered for relapsing or remitting multiple sclerosis. Thus, in combination with the remyelinating agents disclosed herein, preferred ranges of interferons may include about 0.1 μg to about 250 μg and more preferably about 0.5 μg to about 50 μg, depending on the manner in which the agent is administered in conjunction with the other remyelinating compounds and compositions disclosed herein.

Non-steroidal anti-inflammatories (NSAIDs) contemplated for use with this invention include but are not limited to non-selective COX inhibitors and selective COX-2 inhibitors. Non-selective COX inhibitors include but are not limited to salicylic acid derivatives (e.g., aspirin, sodium salicylates, choline magnesium trisalicylate, salsalate, diflunisal, sulfasalazine, and olsalazine), para-aminophenol derivatives (e.g., acetaminophen), indole and indene acetic acids (e.g., tolmetin, diclofenac, and ketorolac), heteroaryl acetic acids (e.g., abuprofen, naproxen, flurbiprofen, ketoprofen, fenprofen, and oxaprozin), anthranilic acids or fenamates (e.g., mefenamic acid and meclofenamic acid), enolic acids (e.g., oxicams such as piroxicam and meloxicam), and alkanones (e.g., nabumetone). Selective COX-2 inhibitors include diaryl-substituted furanones (e.g., rofecoxib), diaryl-substituted pyrazoles (e.g., celecoxib), indole acetic acids (e.g., etodolac), and sulfonanilides (e.g., nimesulide). NS are oftentimes administered in combination with interferon to lessen the flu-like symptoms experienced by patients receiving, for example, Avonex®. Common NS include naproxen, ibuprofen and ketoprofen. Paracetamol is also frequently administered to patients. See, Reess et al., 2002 *Mult. Scler.* 8: 15-8.

Glatiramer acetate (COPAXONE®) is a synthetic molecule that inhibits activation of myelin basic protein-reactive T cells and induces a T-cell repertoire characterized by anti-inflammatory effects. Moreover, glatiramer can access the central nervous system (CNS), whereas interferon-beta cannot (Dhib-Jalbut, 2002 *Neurology* 58: S3-9; Weinstock-Guttman et al., 2000 *Drugs* 59: 401-10).

Mitoxantrone is an anthracenedione synthetic agent, which has been shown to be effective for treating secondary progressive multiple sclerosis (SP-MS). However, use of this drug is again limited by its cumulative cardiotoxicity (Weinstock-Guttman et al., 2000).

Tumor necrosis factor-alpha (TNF-α) may be a key cytokine in demyelination (Walker et al., 2001 *Mult. Scler.* 7: 305-12). Thus use of agents that antagonize TNF-α function or inhibit its synthesis may be useful in combination with the agents and compounds disclosed herein. This can include anti-TNF-α antibodies (e.g., infliximab) as well as agents such as pirfenidone. Pirfenidone is a non-peptide drug, which has been shown to decrease synthesis of TNF-α and to block receptors for TNF-α. Id.

The long mainstay in most demyelinating conditions and diseases has been the use of ACTH, glucocorticoids and corticoid steroids. These agents are used for their anti-edema and anti-inflammatory effects. ACTH is commonly administered to a subject at 80 U given intravenously in 500 mL of 5% dextrose and water over 6-8 hours for 3 days. It may also be administered at 40 U/ml intramuscularly at a dose of 40 U every 12 hours for 7 days, with the dose then reduced every 3 days. See, S. Hauser, "Multiple sclerosis and other demyelinating diseases," in *Harrison's Principles of Internal Medicine* 2287-95 (13th ed., Isselbacher et al., ed. 1994). Methylprednisolone is typically administered slowly in 500 ml D5W over 6 hours, preferably in the morning. Common dosages include 1000 mg daily for 3 days, 500 mg daily for 3 days and 250 mg daily for 3 days. Id. A methylprednisolone-prednisone combination is also commonly administered. Typically 1000 mg of intravenous methylprednisolone is administered over three days followed by oral prednisone at 1 mg/kg per day for 14 days. Thus, for use in combination with the compounds and compositions disclosed herein, the steroids may be administered in amounts ranging from about 1 to about 1000 mg/kg over about 1 to 14 days, as needed.

A side effect in demyelinating conditions such as MS, is fatigue and decreased cognitive function. Agents such as amantadine hydrochloride and pemoline have been frequently used to treat fatigue associated with MS (Geisler et al., 1996 *Arch. Neurol.* 53: 185-8).

The benefit of such combination therapies is that it may lessen the class-specific and agent-specific side effects currently encountered with some of the drugs. Class-specific side effects of interferon-beta include fever, chills, myalgias, arthralgias and other flu-like symptoms beginning 2-6 hours after injection and typically resolving 24 hours post injection. Occasionally interferon-beta also induces transient worsening of preexisting MS symptoms. Agent specific side effects include injection-site reactions with interferon beta-1b. Management of these effects can be accomplished by tailoring the dose and time of administration, prescribing appropriate combinations of acetaminophen, non-steroidal anti-inflammatory drugs (NSAIDs) and steroids. See, Munschauer et al., 1997 *Clin. Ther.* 19: 883-93.

Thus, combinations of drugs that can lessen the quantity of a particular drug administered may reduce adverse side effects experienced by a patient.

When administered in combination, the small compound remyelinating agents may be administered in the same formulation as these other compounds or compositions, or in a separate formulation. When administered in combination, the remyelinating immunoglobulins are generally administered in a separate formulation than the other compounds and compositions. When administered in combinations, the remyelinating agents may be administered prior to, following, or concurrently with the other compounds and compositions used to treat, ameliorate, or palliate symptoms.

7. Chronic Administration Dosage Regimens

The chronic treatment regimen of the present invention provides that an alpha-4 integrin agent (e.g., small molecule or immunoglobulin) at a level that will maintain sufficient receptor saturation to suppress pathological inflammation in a patient in need of such. The methods of the invention entails administration once per every two weeks or once a month to once every two months, with repeated dosings taking place over a period of at least six months, and more preferably for a year or longer. The methods of the invention involve obtaining and maintaining a receptor saturation level in a human patient of a dimer comprising alpha-4 integrin (e.g., VLA-4) in a range of from about 65% to 100%, more preferably between 75%, to 100%, and even more preferably between 80-100%. These receptor saturation levels are maintained at these levels chronically (e.g., over a period of 6 months or so) to allow for continued suppression of pathological inflammation.

In a specific embodiment, the remyelinating agent is an antibody, preferably a humanized or human antibody, and the dosing is on a monthly basis. In another specific embodiment, the remyelinating agent is a compound of formula I, IA, IB, IC, II, IIA, or IIB as defined above. Levels of receptor saturation can be monitored to determine the efficacy of the dosing regime, and physiological markers measured to confirm the success of the dosage regime. As a confirmation, serum levels of the antibody can be monitored to identify clearance of the antibody and to determine the potential effect of half-life on the efficacy of the treatment.

For treatment with an agent of the invention, the dosage ranges from about 0.0001 to 100 mg/kg, and more usually 0.01 to 5 mg/kg, of the host body weight. For example dosages can be 1 mg/kg body weight or 10 mg/kg body weight. Dosage and frequency vary depending on the half-life of the agent in the patient. The dosage and frequency of administration can vary depending on whether the treatment is prophylactic or therapeutic. For immunoglobulin administration, each dosing injection is generally between 2.0 to 8.0 mg/kg dosage. For a compound administration, each dosing injection is generally between 1.0 to 50.0 mg/kg dosage. In accordance with the teachings provided herein, effective dosages can be monitored by obtaining a fluid sample from a patient. For this, generally a blood serum or cerebrospinal fluid sample is taken and integrin receptor saturation is determined using methods well known in the art. Ideally, a sample is taken prior to initial dosing; subsequent samples are taken and measured prior to and/or after each treatment.

As an alternative to chronic administration comprised of repeated individual dosings, a remyelinating agent can be administered as a sustained release formulation, provided the dosage is such that the levels of receptor saturation remain sufficient to suppress inflammation. For example, controlled release systems can be used to chronically administer a remyelinating agent within the scope of this invention. Discussions of appropriate controlled release dosage forms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems. Physical systems include, but not limited to, reservoir systems with rate-controlling membranes, such as microencapsulation, macroencapsulation, and membrane systems; reservoir systems without rate- controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

The methods of the invention can be used to treat a patient that is affected with a disorder involving or arising from pathological inflammation, or to prophylactically treat a patient at risk for a particular disorder. The dosage regimens necessary for prophylactic versus therapeutic treatment can vary, and will need to be designed for the specific use and disorder treated.

In some methods, two or more agents (e.g., monoclonal antibodies with different binding specificities, a monoclonal antibody and a compound as disclosed herein) are administered concurrently, in which case the dosage of each agent administered falls within the ranges indicated. Combination therapies can also occur where the agents are administered consecutively to the patient with a desired time interval been periods of administration. Intervals can also be irregular as indicated by measuring receptor saturation levels or by following other indicia of the disease process.

Those of skill will readily appreciate that dose levels can vary as a function of the specific agent, the severity of the symptoms and the susceptibility of the subject to side effects. Some of the specific agents are more potent than others. Preferred dosages for a given agent are readily determinable by those of skill in the art by a variety of means. A preferred means is to measure the physiological potency of a given agent.

In prophylactic applications, pharmaceutical compositions are chronically administered to a patient susceptible to, or otherwise at risk of, a particular disease in an amount sufficient to eliminate or reduce the risk or delay the outset of the disease. Such an amount is defined to be a prophylactically effective dose. In patients with multiple sclerosis in remission, risk may be assessed by NMR imaging or, in some cases, by pre-symptomatic indications observed by the patient.

Effective dosage regimes of the compositions of the present invention, for the treatment of the above described conditions will vary depending upon many different factors, including means of administration, target site, physiological state of the patient, and other medicaments administered. Thus, treatment dosages will need to be titrated to optimize safety and efficacy. In general, each administration of the dosage regimen will range from about 0.0001 to about 100 mg/kg, usually about 0.01 to about 50, and more usually from about 0.1 to about 30 mg/kg of the host body weight.

The remyelinating agents of the invention can be used with effective amounts of other therapeutic agents against acute and chronic inflammation. Such agents include other antagonists of adhesion molecules (e.g., other integrins, selectins, and immunoglobulin (Ig) superfamily members (see Springer, *Nature* (1990) 346:425-433; Osborn (1990) *Cell* 62:3; and Hynes (1992) *Cell* 9:11)). Integrins are heterodimeric transmembrane glycoproteins consisting of an α chain (120-180 kDa) and a β chain (90-110 kDa), generally having short cytoplasmic domains. For example, three important integrins, LFA-1, Mac-1 and P150,95, have different alpha subunits, designated CD11a, CD11b and CD11c, and a common beta subunit designated CD18. LFA-1 ($\alpha_L\beta_2$) is expressed on lymphocytes, granulocyte and monocytes, and binds predominantly to an Ig-family member counter-receptor termed ICAM-1 and related ligands. ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1. The third $\beta_2$ integrin, P150,95 ($\alpha_X\beta_2$), is also found on neutrophils and monocytes. The selectins consist of L-selectin, E-selectin and P-selectin.

Other anti-inflammatory agents that can be used in combination with the remyelinating agents include antibodies and other antagonists of cytokines, such as interleukins IL-1 through IL-13, tumor necrosis factors α and β (TNF-α and TNF-β), interferons α, β and γ, tumor growth factor Beta (TGF-β), colony stimulating factor (CSF) and granulocyte monocyte colony stimulating factor (GM-CSF). Other anti-inflammatory agents include antibodies and other antagonists of chemokines such as MCP-1, MIP-1α, MIP-1β, RANTES, exotaxin and IL-8. Other anti-inflammatory agents include NS, steroids and other small molecule inhibitors of inflammation. Timing and sequence of administration, formulations, routes of administration and effective concentrations of agents for combined therapies are as described above for the humanized antibodies against alpha-4 integrin, the small compounds against alpha-4 integrin, and the drug combinations.

8. Testing Reagents

Reagents can be tested in vitro and in vivo. Many in vitro models exist to test whether a reagent binds to the alpha-4 subunit, as would be known in the art. Testing whether the reagent has activity in vivo at promoting remyelination and inhibiting demyelination can be performed using the experimental autoimmune encephalomyelitis (EAE) animal model. EAE is an inflammatory condition of the central nervous system with similarities to multiple sclerosis (Paterson, IN TEXTBOOK OF IMMUNOPATHOLOGY, eds. Miescher and Mueller-Eberhard, 179-213, Grune and Stratton, N.Y. 1976).

EAE may be induced in rats by a single intraperitoneal injection of a CD4-positive T-cell clone specific for myelin basic protein. Inflammation is initiated within 4 to 12 hours; endogenous monocytes and lymphocytes infiltrate inflamed vessels in the brain stem and spinal cord, leading to paralysis of the tail and hind limbs by day 4 or 5.

Sections of EAE brain can be tested for their ability to support leukocyte attachment using, for example, an in vitro binding assay described in Stamper and Woodruff, *J. Exp. Med.* 144: 828-833 (1976). Reagents against leukocyte adhesion receptors can be examined for inhibitory activity in the in vitro section assay described in Example 4. As shown in Tables 12 and 13, the attachment of U937 cells (a human monocytic cell line) was almost completely blocked by antibodies against human VLA-4 integrin. The remyelinating antibodies produced significantly greater blocking effect as compared to antibodies against other adhesion molecules.

Surprisingly, antibodies that selectively inhibit the fibronectin binding activity of $\alpha_4$ integrin (P4G9 and HP1/7) enhanced U937 attachment to the EAE vessels. These results suggest that fibronectin-binding activity of $\alpha_4$ integrin is not directly involved in U937 adhesion to EAE vessels in vitro. Tables 12 and 13 also show that antibodies against many other leukocyte adhesion receptors were without effect on U937 or lymphocyte binding to EAE vessels.

Given the in vitro results using the $\alpha_4\beta_1$ reagents described above, the effect of these antibodies on the progression of EAE can also be tested in vivo by measuring the delay in the onset of paralysis or reduction in severity of the paralysis. The protective effect of one of the antibodies useful in the present invention, HP2/1, is provided in Example 4.

Additional reagents effective for inhibiting leukocyte binding to brain endothelial cells and thereby potentially that inhibit demyelination or promote remyelination can be identified by use of adhesion assays. Using HP2/1 or N-[N-(3-pyridinesulfonyl)-L-3,3-dimethyl-4-thiaprolyl]-O-[1-methylpiperazin-4-ylcarbonyl]-L-tyrosine isopropyl ester as a control for example, other antibodies or reagents can be screened for their ability to inhibit the binding of lymphocytes to a known ligand for $\alpha_4\beta_1$ integrin. Several additional reagents can be identified that inhibit adhesion by targeting the $\alpha_4$ subunit of the VLA-4 leukocyte cell surface receptor.

Monoclonal antibodies useful in the methods and compositions of the present invention include for example HP2/1, TY21.6, TY21.12, and L25 as discussed in U.S. Pat. No. 6,033,665, which is herein incorporated by reference in its entirety. These antibodies react with the a chain of VLA-4 and block binding to VCAM-1, fibronectin and inflamed brain endothelial cells, but do not affect the activity of the other members of the $\beta_1$ integrin family.

Other reagents which selectively react against the VLA-4/VCAM-1 target can also be used. For example, an antibody which interacts with the VCAM-1 binding domain VLA-4 ($\alpha_4$) in conjunction with the $\beta_1$ chain that blocks only lymphocyte migration into sites of inflammation, such as the brain during multiple sclerosis, can be used to promote remyelination. This reagent further would not affect matrix interactions (mediated by all members of the $\beta_1$ integrins) nor would it affect normal intestinal immunity (mediated by $\alpha_4\beta_7$). The production of this and other such reagents are well within the skill of the art.

9. Examples

The following examples are put forth so as to provide those of ordinary skill in the art with a complete disclosure and description of how to make and use the present invention, and is not intended to limit the scope of what the inventors regard as their invention nor is it intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

9.1. Synthesis of Compounds

In the examples below, if an abbreviation is not defined above, it has its generally accepted meaning. Further, all temperatures are in degrees Celsius (unless otherwise indicated). The following Methods were used to prepare the compounds set forth below as indicated.

Method 1

N-Tosylation Procedure

N-Tosylation of the appropriate amino acid was conducted via the method of Cupps, Boutin and Rapoport *J. Org. Chem.* 1985, 50, 3972.

Method 2

Methyl Ester Preparation Procedure

Amino acid methyl esters were prepared using the method of Brenner and Huber *Helv. Chim. Acta* 1953, 36, 1109.

Method 3

BOP Coupling Procedure

The desired dipeptide ester was prepared by the reaction of a suitable N-protected amino acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method 4

Hydrogenation Procedure I

Hydrogenation was performed using 10% palladium on carbon (10% by weight) in methanol at 30 psi overnight. The mixture was filtered through a pad of Celite and the filtrate concentrated to yield the desired amino compound.

Method 5

Hydrolysis Procedure I

To a chilled (0° C.) THF/$H_2O$ solution (2:1, 5-10 mL) of the appropriate ester was added LiOH (or NaOH) (0.95 equivalents). The temperature was maintained at 0° C. and the reaction was complete in 1-3 hours. The reaction mixture was extracted with ethyl acetate and the aqueous phase was lyophilized resulting in the desired carboxylate salt.

Method 6

Ester Hydrolysis Procedure II

To a chilled (0° C.) THF/$H_2O$ solution (2:1, 5-10 mL) of the appropriate ester was added LiOH (1.1 equivalents). The temperature was maintained at 0° C. and the reaction was complete in 1-3 hours. The reaction mixture was concentrated and the residue was taken up into $H_2O$ and the pH adjusted to 2-3 with aqueous HCl. The product was extracted with ethyl acetate and the combined organic phase was washed with brine, dried over $MgSO_4$, filtered and concentrated to yield the desired acid.

Method 7

Ester Hydrolysis Procedure III

The appropriate ester was dissolved in dioxane/$H_2O$ (1:1) and 0.9 equivalents of 0.5 N NaOH was added. The reaction was stirred for 3-16 hours and than concentrated. The resulting residue was dissolved in $H_2O$ and extracted with ethyl acetate. The aqueous phase was lyophilized to yield the desired carboxylate sodium salt.

Method 8

Sulfonylation Procedure I

To the appropriately protected aminophenylalanine analog (11.2 mmol), dissolved in methylene chloride (25 ml) and cooled to −78° C. was added the desired sulfonyl chloride (12 mmol) followed by dropwise addition of pyridine (2 mL). The solution was allowed to warm to room temperature and was stirred for 48 hr. The reaction solution was transferred to a 250 mL separatory funnel with methylene chloride (100 mL) and extracted with 1N HCl (50 mL×3), brine (50 mL), and water (100 mL). The organic phase was dried ($MgSO_4$) and the solvent concentrated to yield the desired product.

Method 9

Reductive Amination Procedure

Reductive amination of Tos-Pro-p-NH2-Phe with the appropriate aldehyde was conducted using acetic acid, sodium triacetoxyborohydride, methylene chloride and the combined mixture was stirred at room temperature overnight. The crude product was purified by flash chromatography.

Method 10

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in $Et_2O$ and reconcentrated. This procedure was repeated and the resulting solid was placed under high vacuum overnight.

Method 11 tert-Butyl Ester Hydrolysis Procedure I

The tert-butyl ester was dissolved in $CH_2Cl_2$ and treated with TFA. The reaction was complete in 1-3 hr at which time the reaction mixture was concentrated and the residue dissolved in $H_2O$ and lyophilized to yield the desired acid.

Method 12

EDC Coupling Procedure I

To a $CH_2Cl_2$ solution (5-20 mL) of N-(toluene-4-sulfonyl)-L-proline (1 equivalent), the appropriate amino acid ester hydrochloride (1 equivalent), N-methylmorpholine (1.1-2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into $H_2O$ and the organic phase was washed with sat. $NaHCO_3$, brine, dried ($MgSO_4$ or $Na_2SO_4$), filtered and concentrated. The crude product was purified by column chromatography.

Method 13

EDC Coupling Procedure II

To a DMF solution (5-20 mL) of the appropriate N-protected amino acid (1 equivalent), the appropriated amino acid ester hydrochloride (1 equivalent), $Et_3N$ (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and $H_2O$ and the organic phase washed with 0.2 N citric acid, $H_2O$, sat. $NaHCO_3$, brine, dried ($MgSO_4$ or $Na_2SO_4$), filtered and concentrated. The crude product was purified by column chromatography or preparative TLC.

Method 14

Sulfonylation Procedure II

The appropriate sulfonyl chloride was dissolved in $CH_2Cl_2$ and placed in an ice bath. L-Pro-L-Phe-OMe.HCl (1 equivalent) and $Et_3N$ (1.1 equivalent) was added and the reaction allowed to warm to room temperature and stirred overnight under an atmosphere of nitrogen. The reaction mixture was concentrated and the residue partitioned between EtOAc and $H_2O$ and the organic phase washed with sat. $NaHCO_3$, brine, dried ($MgSO_4$ or $Na_2SO_4$), filtered and concentrated. The crude product was purified by column chromatography or preparative TLC.

Method 15

Sulfonylation Procedure III

To a solution of L-Pro-L-4-(3-dimethylaminopropyloxy)-Phe-OMe [prepared using the procedure described in Method 10] (1 equivalent) in $CH_2Cl_2$ was added $Et_3N$ (5 equivalents) followed by the appropriate sulfonyl chloride (1.1 equivalent). The reaction was allowed to warm to room temperature and stirred overnite under an atmosphere of nitrogen. The mixture was concentrated, dissolved in EtOAc, washed with sat. $NaHCO_3$ and 0.2 N citric acid. The aqueous phase was made basic with solid $NaHCO_3$ and the product extracted with EtOAc. The organic phase was washed with brine, dried ($MgSO_4$ or $Na_2SO_4$), filtered and concentrated. The crude methyl ester was purified by preparative TLC. The corresponding acid was prepared using the procedure described in Method 7.

Method 16

Hydrogenation Procedure II

To a methanol (10-15 mL) solution of the azlactone was added NaOAc (1 equivalent) and 10% Pd/C. This mixture was placed on the hydrogenator at 40 psi $H_2$. After 8-16 hours, the reaction mixture was filtered through a pad of Celite and the filtrate concentrated to yield the dehydrodipeptide methyl ester. The ester was dissolved in dioxane/$H_2O$ (5-10 mL), to which was added 0.5 N NaOH (1.05 equivalents). After stirring for 1-3 hours, the reaction mix was concentrated and the residue was redissolved in $H_2O$ and washed with EtOAc. The aqueous phase was made acidic with 0.2 N HCl and the product was extracted with EtOAc. The combined organic phase was washed with brine (1×5 mL), dried (MgSO$_4$ or Na$_2$SO$_4$), filtered and concentrated to yield the acid as approximately a 1:1 mixture of diastereomers.

Method 17 tert-Butyl Ester Hydrolysis Procedure II

The tert-butyl ester was dissolved in $CH_2Cl_2$ (5 mL) and treated with TFA (5 mL). The reaction was complete in 1-3 hours at which time the reaction mixture was concentrated and the residue dissolved in $H_2O$ and concentrated. The residue was redissolved in $H_2O$ and lyophilized to yield the desired product.

EXAMPLE 1

Synthesis of N-(Toluene-4-sulfonyl)-L-prolyl-L-4-(4-methylpiperazin-1-ylcarbonyloxy)phenylalanine Ethyl Ester The title compound was prepared following the procedure outlined for the preparation of Example 4 and substitution of appropriate starting materials.

NMR data was as follows:

$^1$H NMR (CD$_3$)$_2$SO): δ=8.33 (d, 1H), 7.70 (d, 2H), 7.41 (d, 2H), 7.24 (d, 2H), 7.00 (d, 2H), 4.52-4.44 (m, 1H), 4.09-4.00 (m, 3H), 3.53 (bs, 2H), 3.38-3.31 (m, 3H), 3.11-3.01 (m, 3H), 2.39 (s, 3H), 2.32 (bs, 4H), 2.19 (s, 3H), 1.61-1.50 (m, 3H), 1.43-1.38 (m, 1H), 1.13 (t, 3H).

$^{13}$C NMR (CD$_3$)$_2$SO): δ=171.1, 171.1, 153.9, 149.8, 143.6, 134.1, 133.9, 130.0, 129.8, 127.4, 121.5, 61.2, 60.7, 54.2, 54.1, 53.3, 49.0, 45.7, 44.0, 43.4, 35.8, 30.5, 23.8, 21.0, 14.0.

EXAMPLE 2

Synthesis of N-(Toluene-4-sulfonyl)-L-prolyl-L-4-(N,N-dimethylcarbamyloxy)phenylalanine Ethyl Ester Into a reaction vial were combined 7.00 g (15.2 mmol, 1.0 eq) Ts-Pro-Tyr(H)-OEt and 1.86 g (15.2 mmol, 1.0 eq) DMAP. Methylene chloride (50 mL), triethylamine (2.12 mL—1.54 g, 15.2 mmol, 1.0 eq), and dimethylcarbamyl chloride (1.68 mL—1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The workup of the reaction solution was as follows: add 50 mL EtOAc and 50 mL hexanes to the reaction mixture, and wash with 3×50 mL 0.5 mL hexanes to the reaction mixture, and wash with 3×50 mL 0.5 M citric acid, 2×50 mL water, 2×50 mL 10% K$_2$CO$_3$, and 1×50 mL sat. NaCl. Dry with MgSO$_4$. Filter. Evaporate to obtain 8.00 g (99%) of the title compound as a clear oil, which solidifies upon standing. Recrystallize from 5:3:2 heptane/EtOAc/CH$_2$Cl$_2$.

NMR data was as follows:

$^1$H NMR (CD$_3$)$_2$SO): δ=8.32 (d, 1H), 7.70 (d, 2H), 7.41 (d, 2H), 7.23 (d, 2H), 7.00 (d, 2H), 4.52-4.44 (m, 1H), 4.09-4.02 (m, 3H), 3.37-3.31 (m, 1H), 3.11-2.96 (m, 3H), 3.00 (s, 3H), 2.87 (s, 3H), 2.39 (s, 3H), 1.61-1.50 (m, 3H), 1.43-1.38 (m, 1H), 1.13 (t, 3H).

$^{13}$C NMR(CD$_3$)$_2$SO): δ=171.1, 171.1, 154.0, 150.0, 143.6, 133.9, 133.9, 130.0, 129.8, 127.4, 121.5, 61.2, 60.6, 53.3, 49.0, 36.3, 36.1, 35.8, 30.5, 23.8, 21.0, 14.0.

EXAMPLE 3

Synthesis of N-(Toluene-4-sulfonyl)-L-prolyl-L-4-(4-methylpiperazin-1-ylcarbonyloxy)phenylalanine Isopropyl Ester The title compound was prepared following the procedure outlined for the preparation of Example 4 and substitution of appropriate starting materials.

NMR data was as follows:

$^1$H NMR (CDCl$_3$): δ=7.72 (d, 2H), 7.36 (d, 1H), 7.33 (d, 2H), 7.16 (d, 2H), 7.03 (d, 2H), 5.07 (Sept., 1H), 4.78 (dt, 1H), 4.08-4.05 (m, 1H), 3.67 (bs, 2H), 3.57 (bs, 2H), 3.41-3.35 (m, 1H), 3.24 (dd, 1H), 3.15-3.07 (m, 1H), 3.04 (dd, 1H), 3.46-2.43 (m, 7H), 2.34 (s, 3H), 2.05-2.02 (m, 1H).

$^{13}$C NMR (CDCl$_3$): δ=170.9, 170.4, 153.6, 150.5, 144.3, 133.2, 133.1, 130.2, 130.0, 127.9, 121.7, 69.5, 62.2, 54.7, 53.4, 49.6, 46.1, 44.3, 43.7, 37.2, 29.7, 24.1, 21.6, 21.6, 21.4.

EXAMPLE 4

Synthesis of N-(Toluene-4-sulfonyl)-L-prolyl-L-4-(4-methylpiperazin-1-ylcarbonyloxy)phenylalanine tert-Butyl Ester Combine 41.2 g (84.34 mmol, 1.0 eq) Ts-Pro-Tyr(H)-OtBu and 17.0 g (84.34 mmol, 1.0 eq) 4-nitrophenyl chloroformate. Add 700 mL CH$_2$Cl$_2$. Cap with a septum. Attach a N$_2$ line. Immerse the flask in a 4:1 water/EtOH+dry ice slurry, and stir to cool to −15° C. Add 29.38 mL (21.33 g, 210.81 mmol, 2.5 eq) Et$_3$N over five minutes with stirring. Stir at −10 to −15° C. for 1 h. Add 9.35 mL (8.45 g, 84.34 mmol, 1.0 eq) N-methyl piperazine over 3 minutes with stirring. Stir overnight while warming to room temperature. Dilute with 700 mL hexanes. Wash repeatedly with 10% K$_2$CO$_3$, until no yellow color (4-nitrophenol) is seen in the aqueous layer. Wash with sat. NaCl. Dry over anhydrous MgSO$_4$. Filter. Evaporate. Dissolve in 500 mL EtOH, and evaporate, to remove Et$_3$N. Repeat once. Dissolve in 400 mL EtOH, and add 600 mL water with stirring, to precipitate a solid or oil. If an oil, stir vigorously to solidify. Isolate the solid by filtration. Repeat dissolution, precipitation, and filtration, once. Rinse with water to remove traces of yellow color. High vacuum to constant mass yields the title compound as a white solid.

NMR data was as follows:

$^1$H NMR (CDCl$_3$): δ=7.72 (d, 2H), 7.33 (d, 3H), 7.17 (d, 2H), 7.02 (d, 2H), 4.71 (q, 1H), 4.09-4.06 (m, 1H), 3.67 (bs,

2H), 3.57 (bs, 2H), 3.41-3.34 (m, 1H), 3.22 (dd, 1H), 3.16-3.09 (m, 1H), 3.03 (dd, 1H), 2.46-2.43 (m, 7H), 2.34 (s, 3H), 2.05-2.02 (m, 1H), 1.57-1.43 (m, 3H), 1.47 (s, 9H).

$^{13}$C NMR (CDCl$_3$): δ=171.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

EXAMPLE 5

Synthesis of N-(Toluene-4-sulfonyl)-L-prolyl-L-4-(4-methylpiperazin-1-ylcarbonyloxy)phenylalanine The title compound was prepared from the product of Example 1 using the procedure described in Method 7.

NMR data was as follows:

$^1$H NMR (CD$_3$OD): δ=7.74 (d, 2H), 7.42 (d, 2H), 7.26 (d, 2H), 7.04 (d, 2H), 4.58-4.54 (m, 1H), 4.16-4.12 (m, 1H), 3.70 (bs, 2H) 3.53 (bs, 2H), 3.43-3.31 (m, 1H), 3.26-3.13 (m, 7H), 2.82 (s, 3H), 2.43 (s, 3H), 1.98-1.94 (m, 1H), 1.76-1.51 (m, 3H).

$^{13}$C NMR (CD$_3$OD): δ=175.7, 173.6, 154.8, 151.6, 146.1, 136.3, 134.8, 131.9, 131.3, 129.1, 122.7, 63.6, 55.9, 53.9, 50.7, 43.5, 37.6, 31.3, 25.5, 21.5.

EXAMPLE 6

Synthesis of N-(Toluene-4-sulfonyl)-L-prolyl-L-4-(N,N-dimethylcarbamyloxy)phenylalanine n-Butyl Ester The title compound was prepared following the procedure outlined for the preparation of Example 2 and substitution of appropriate starting materials.

NMR data was as follows:

$^1$H NMR (CD$_3$)$_2$SO: δ=8.31 (d, 1H), 7.70 (d, 2H), 7.41 (d, 2H), 7.23 (d, 2H), 6.99 (d, 2H), 4.53-4.46 (m, 1H), 4.10-4.01 (m, 1H), 3.63-3.30 (m, 1H), 3.10-2.96 (m, 3H), 3.00 (s, 3H), 2.88 (s, 3H), 2.39 (s, 3H), 1.59-1.30 (m, 6H), 1.33-1.20 (m, 2H), 0.85 (t, 3H).

$^{13}$C NMR (CD$_3$)$_2$SO: δ=171.4, 171.3, 154.2, 150.2, 143.7, 134.0, 130.1, 130.0, 127.6, 121.7, 64.3, 61.2, 59.2, 53.4, 49.0, 36.2, 36.0, 35.8, 30.0, 23.8, 21.0, 18.5, 13.5.

EXAMPLE 7

Synthesis of N-(Toluene-4-sulfonyl)-L-prolyl-L-4-(N,N-dimethylcarbamyloxy)phenylalanine Cyclopentyl Ester The title compound was prepared following the procedure outlined for the preparation of Example 2 and substitution of appropriate starting materials.

NMR data was as follows:

$^1$H NMR (CD$_3$)$_2$SO: δ=8.27 (d, 1H), 7.70 (d, 2H), 7.41 (d, 2H), 7.22 (d, 2H), 6.99 (d, 2H), 5.04 (bs, 1H), 4.48-4.40 (m, 1H), 4.08-4.05 (m, 1H), 3.34-3.30 (m, 1H), 3.09-2.95 (m, 3H), 3.00 (s, 3H), 2.88 (s, 3H), 2.39 (s, 3H), 1.76-1.74 (m, 2H), 1.57-1.40 (m, 1OH).

$^{13}$C NMR (CD$_3$)$_2$SO: δ=171.3, 171.0, 154.2, 150.2, 432.7, 134.1, 130.1, 130.0, 127.6, 121.6, 77.4, 61.2, 53.4, 49.0, 36.2, 36.1, 35.7, 32.0, 30.5, 23.8, 23.2, 21.0.

EXAMPLE 8

Synthesis of N-(Toluene-4-sulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CD$_3$)$_2$SO: δ=8.18 (d, 1H), 7.71 (d, 2H), 7.41 (d, 2H), 7.23 (d, 2H), 6.99 (d, 2H), 4.42-4.38 (m, 1H), 4.10-4.07 (m, 1H), 3.37-3.30 (m, 1H), 3.09-2.95 (m, 3H), 3.00 (s, 3H), 2.88 (s, 3H), 2.39 (s, 3H), 1.58-1.50 (m, 3H), 1.40-1.30 (m, 1H), 1.36 (s, 9H).

$^{13}$C NMR (CD$_3$)$_2$SO: δ=171.1, 170.3, 154.2, 150.2, 143.8, 134.2, 134.1, 130.2, 130.0, 127.6, 121.6, 81.0, 61.3, 53.8, 49.0, 36.3, 36.0, 35.9, 30.5, 27.5, 23.8, 21.0.

EXAMPLE 9

Synthesis of N-(Toluene-4-sulfonyl)-L-prolyl-L-4-(N,N-dimethylcarbamyloxy)phenylalanine The title compound was prepared from the product of Example 2 using the procedure described in Method 7.

NMR data was as follows:

$^1$H NMR (CD$_3$)$_2$SO: δ=8.13 (d, 1H), 7.70 (d, 2H), 7.41 (d, 2H), 7.23 (d, 2H), 6.99 (d, 2H), 4.51-4.44 (m, 1H), 4.11-4.09 (m, 1H), 3.40-3.34 (m, 2H), 3.11-2.94 (m, 3H), 3.00 (s, 3H), 2.87 (s, 3H), 2.39 (s, 3H), 1.59-1.36 (m, 4H).

$^{13}$C NMR (CD$_3$)$_2$SO: δ=172.7, 171.2, 153.6, 150.2, 143.8, 134.3, 134.0, 130.2, 130.0, 127.6, 121.6, 61.3, 53.2, 49.0, 36.3, 36.1, 35.9, 30.4, 23.8, 21.0.

EXAMPLE 10

Synthesis of N-(Toluene-4-sulfonyl)-L-prolyl-L-3-(N,N-dimethylcarbamyloxy)phenylalanine Ethyl Ester The title compound was prepared following the procedure outlined for the preparation of Example 2 and substitution of appropriate starting materials.

NMR data was as follows:

$^1$H NMR (CDCl$_3$): δ=7.74 (m, 2H), 7.70-7.36 (m, 4H), 7.24-7.14 (m, 3H), 6.93-4.90 (m, 1H), 4.78-4.27 (m, 3H), 4.05-3.55 (m, .5H), 3.48-3.43 (m, 1.5H), 3.37-3.30 (m, 3H), 3.02-3.08 (bs, 3H), 2.99 (bs, 3H), 2.45 (s, 1.5H), 2.43 (s, 1.5H), 2.12 (m, 1H), 198, 1.80 (m, 0.5M), 1.62-1.44 (m, 2.5H), 1.29 (t, 1.5H), 1.24 (t, 1.5H).

$^{13}$C NMR (CDCl$_3$): δ=171.1, 171.0, 170.9, 154.9, 154.8, 151.8, 151.6, 144.4, 144.3, 137.6, 137.1, 133.1, 132.9, 130.0, 129.9, 129.5, 129.2, 127.9, 127.9, 126.5, 126.1, 122.9, 122.7, 120.7, 120.5.

EXAMPLE 11

Synthesis of N-(Toluene-4-sulfonyl)-L-(5,5-dimethyl)thiaprolyl-L-4-(N,N-dimethylcarbamyloxy)phenylalanine Isopropyl Ester The title compound was prepared following the procedure outlined for the preparation of Example 2 and substitution of appropriate starting materials.

NMR data was as follows:

$^1$H NMR (CDCl$_3$): δ=7.76 (d, 2H), 7.35 (d, 2H), 7.22 (d, 2H), 7.01 (m, 3H), 5.05 (m, 1H), 4.85 (m, 1H), 4.57 (d, 1H), 4.38 (d, 1H), 3.86 (s, 1H), 3.19-3.00 (m, 2H), 3.09 (s, 3H), 3.01 (s, 3H), 2.45 (s, 3H), 1.24 (t, 6H), 1.16 (s, 3H), 1.09 (s, 3H).
$^{13}$C NMR (CDCl$_3$): δ=170.3, 168.4, 154.9, 150.6, 144.8, 132.9, 132.8, 130.3, 130.0, 128.2, 121.7, 73.4, 69.5, 54.5, 53.2, 50.4, 37.7, 36.5, 36.3, 29.0, 23.8, 21.5, 21.4.

EXAMPLE 12

Synthesis of N-(Toluene-4-sulfonyl)-L-(5,5-dimethyl)thiaprolyl-L-4-(N,N-dimethylcarbamyloxy)phenylalanine tert-Butyl Ester The title compound was prepared following the procedure outlined for the preparation of Example 2 and substitution of appropriate starting materials.
NMR data was as follows:
$^1$H NMR (CDCl$_3$): δ=7.75 (d, 2H), 7.34 (d, 2H), 7.23 (d, 2H), 7.05-6.98 (m, 3H), 4.76 (m, 1H), 4.56 (d, 1H), 4.40 (d, 1H), 3.85 (s, 1H), 3.09-3.00 (m, 8H), 2.44 (s, 3H), 1.43 (s, 3H), 1.16 (s, 3H), 1.09 (s, 3H).
$^{13}$C NMR (CDCl$_3$): δ=169.8, 168.3, 154.9, 150.6, 144.8, 133.2, 132.9, 130.4, 130.0, 128.2, 121.6, 82.6, 73.4, 54.6, 53.8, 50.4, 37.8, 36.5, 36.3, 29.0, 27.7, 23.8, 21.5.

EXAMPLE 13

Synthesis of N-(Toluene-4-sulfonyl)-L-(5,5-dimethyl)thiaprolyl-L-4-(N,N-dimethylcarbamyloxy)phenylalanine The title compound was prepared from the product of Example 11 using the procedure described in Method 7.
NMR data was as follows:
$^1$H NMR (CDCl$_3$): δ=7.76 (d, 2H), 7.35 (d, 2H), 7.25 (d, 2H), 7.14 (d, 1H), 7.02 (d, 2H), 5.17 (br s, 1H), 4.89 (m, 1H), 4.56 (d, 1H), 4.40 (d, 1H), 3.90 (s, 1H), 3.30-3.00 (m, 8H), 2.43 (s, 3H), 1.09 (s, 6H).
$^{13}$C NMR (CDCl$_3$): δ=172.7, 169.3, 155.2, 150.6, 144.9, 133.1, 132.7, 130.5, 130.1, 128.1, 121.9, 73.3, 54.5, 53.3, 50.5, 36.9, 36.6, 36.4, 29.0, 23.7, 21.5.

EXAMPLE 14

Synthesis of N-(Toluene-4-sulfonyl)-L-[(1,1-dioxo)thiamorpholin-3-carbonyl]-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517-525). N-(Toluene-4-sulfonyl)-L-thiamorpholine-5-carboxylic acid was prepared using the procedure described in Method 1 and was then coupled to t-butyl tyrosine in DMF in the presence of BOP and NMM, to give after aqueous workup and flash chromatography N-(Toluene-4-sulfonyl)-L-[thiamorpholin-3-carbonyl]-L-4-phenylalanine tert-butyl ester.
Formation of the 4-(N,N-dimethylcarbamyloxy) group was per Example 2 above and oxidation of the thiamorpholino group to the 1,1-dioxo-thiamorpholino group was per Larsson and Carlson (*Acta Chemica Scan.* 1994, 48, 522).
NMR data was as follows:
$^1$H NMR (CDCl$_3$): δ=7.68 (d, 2H), 7.37 (d, 2H), 7.08 (m, 4H), 6.73 (d, 1H), 5.11 (m, 1H), 4.62 (m, 1H), 4.23 (m, 1H), 4.00 (m, 1H), 3.82 (m, 1H), 3.14 (s, 3H), 3.03 (s, 3H), 2.80 (m, 5H), 2.44 (s, 3H), 1.48 (s, 9H).
$^{13}$C NMR (CDCl$_3$): δ=171.3, 169.9, 164.4, 145.6, 135.4, 132.6, 130.8, 130.4, 127.3, 121.9, 83.0, 56.1, 53.8, 49.4, 48.7, 44.5, 42.0, 36.9, 36.6, 36.4, 27.8, 21.5.

EXAMPLE 15

Synthesis of N-(Toluene-4-sulfonyl)-L-[(1,1-dioxo)thiamorpholin-3-carbonyl]-L-4-(N,N-dimethylcarbamyloxy)phenylalanine The title compound was prepared from the product of Example 14 using the procedure described in Method 11.
NMR data was as follows:
$^1$H NMR (CD$_3$OD): δ=7.77 (d, 2H), 7.40 (d, 2H), 7.22 (d, 2H), 7.00 (d, 2H), 5.19 (m, 1H), 4.65 (m, 1H), 4.30 (m, 1H), 3.95 (m, 1H), 3.61 (m, 1H), 3.20 (m, 5H), 3.09 (s, 3H), 2.97 (s, 3H), 2.43 (s, 3H).
$^{13}$C NMR (CD$_3$OD): δ=174.1, 168.0, 157.0,152.0, 146.4, 137.7, 135.3, 131.7, 131.6, 128.8, 123.0, 57.1, 54.8, 51.1, 50.9, 48.0, 47.7, 43.2, 37.4, 36.8, 36.7, 21.5.

EXAMPLE 16

Synthesis of N-(Toluene-4-sulfonyl)-L-(5,5-dimethyl)thiaprolyl-L-4-(4-methylpiperazin-1-ylcarbonyloxy)phenylalanine tert-Butyl Ester The title compound was prepared following the procedure outlined for the preparation of Example 4 and substitution of appropriate starting materials.
NMR data was as follows:
$^1$H NMR (CDCl$_3$): δ=7.74 (d, 2H), 7.33 (d, 2H), 7.25 (d, 2H), 7.20-7.00 (m, 3H), 4.74 (m, 1H), 4.55 (d, 1H), 4.38 (d, 1H), 3.83 (s, 1H), 3.66 (br m, 2H), 3.57 (br m, 2H), 3.08-3.05 (m, 2H), 2.45-2.42 (m, 7H), 2.33 (s, 3H), 1.42 (s, 9H), 1.15 (s, 3H), 1.08 (s, 3H).
$^{13}$C NMR (CDCl$_3$): δ=169.7, 168.2, 153.6, 150.3, 144.7, 133.3, 132.7, 130.4, 129.9, 128.1, 121.5, 82.6, 73.4, 54.5, 53.7, 50.4, 46.0, 44.2, 43.6, 37.7, 28.9, 27.7, 23.8, 21.4.

EXAMPLE 17

Synthesis of N-(Toluene-4-sulfonyl)-L-(5,5-dimethyl)thiaprolyl-L-4-(4-methylpiperazin-1-ylcarbonyloxy)phenylalanine The title compound was prepared from the product Example 16 using the procedure described in Method 11.
NMR data was as follows:
$^1$H NMR (CDCl$_3$): δ=8.31 (d, 1H), 7.72 (d, 2H), 7.42-7.35 (m, 4H), 7.08 (d, 2H), 4.90-4.68 (m, 1H), 4.64-4.61 (m, 1H), 4.47-4.44 (m, 1H), 4.01 (s, 1H), 3.36-3.32 (br m, 4H), 3.27-3.25 (m, 1H), 3.22-3.10 (m, 1H), 2.94 (s, 3H), 2.43 (s, 3H), 1.14 (s, 3H), 1.07 (s, 3H).

EXAMPLE 18

Synthesis of N-(Toluene-4-sulfonyl)sarcosyl-L-4-(N,N-dimethylcarbamyloxy)phenylalanine Isopropyl Ester The title compound was prepared following the procedure outlined for the preparation of Example 2 and substitution of appropriate starting materials.
NMR data was as follows:
$^1$H NMR (CDCl$_3$): δ=7.66 (d, 2H), 7.34 (d, 2H), 7.18 (d, 2H), 7.07 (d, 2H), 6.98 (d, 1H), 5.03 (m, 1H), 4.81 (m, 1H), 3.69 (d, 1H), 3.49 (d, 1H), 3.08 (m, 2H), 3.04 (s, 3H), 2.99 (s, 3H), 2.63 (s, 3H), 2.43 (s, 3H).
$^{13}$C NMR (CDCl$_3$): δ=167.4, 154.9, 150.8, 144.4, 132.6, 130.2, 130.1, 127.7, 122.0, 110.9, 69.5, 57.3, 53.9, 53.0, 37.1, 36.6, 21.6, 21.4.

EXAMPLE 19

Synthesis of N-(Toluene-4-sulfonyl)sarcosyl-L-4-(N,N-dimethylcarbamyloxy)phenylalanine tert-Butyl Ester The title compound was prepared following the procedure for the preparation of Example 2 and substitution of appropriate starting materials.
NMR data was as follows:
$^1$H NMR (CDCl$_3$): δ=7.67 (d, 2H), 7.34 (d, 2H), 7.19 (d, 2H), 7.03 (d, 2H), 6.98 (d, 1H), 4.76 (m, 1H), 3.67 (q, 1H), 3.06 (m, 2H), 3.16 (s, 3H), 2.99 (s, 3H), 2.64 (s, 3H), 2.43 (s, 3H), 1.42 (s, 9H).
$^{13}$CNMR(CDCl$_3$): δ=170.0, 137.2, 154.9, 150.7, 144.3, 133.2, 132.9, 130.3, 130.0, 127.7, 121.9, 82.6, 83.9, 53.3, 37.2, 36.6, 36.4, 27.9, 21.4.

EXAMPLE 20

Synthesis of N-(Toluene-4-sulfonyl)sarcosyl-L-4-(N,N-dimethylcarbamyloxy)phenylalanine The title compound was prepared from the product of Example 18 using the procedure described in Method 7.
NMR data was as follows:
$^1$H NMR (CDCl$_3$): δ=7.41 (d, 2H), 7.10 (d, 2H), 6.98 (d, 2H), 6.75 (d, 2H), 4.42 (m, 1H), 3.43 (m, 2H), 3.04 (m, 2H), 2.80 (s, 3H), 2.69 (s, 3H), 2.33 (s, 3H), 2.14 (s, 3H).
$^{13}$CNMR(CDCl$_3$): δ=174.2, 170.2, 156.9, 151.9, 145.6, 135.5, 135.2, 131.4, 131.1, 128.9, 123.0, 54.6, 54.0, 37.4, 36.8, 36.7, 21.4.

EXAMPLE 21

Synthesis of N-(Toluene-4-sulfonyl)-L-prolyl-L-4-(N,N-dimethylaminosulfonyloxy)phenylalanine tert-Butyl Ester Substituting dimethysulfamoyl chloride for dimethylcarbamyl chloride, and following the method for the preparation of Example 2, gave the title compound.
NMR data was as follows:
$^1$H NMR (CDCl$_3$): δ=7.72 (d, 2H), 7.34 (d, 2H), 7.21 (s, 4H), 4.69 (m, 1H), 4.04 (m, 1H), 3.4 (m, 1H), 3.24 (m, 3H), 2.96 (s, 6H), 2.42 (s, 3H), 2.02 (m, 1H), 1.45 (m, 13H).
$^{13}$C NMR (CDCl$_3$): δ=166.3, 165.3, 144.8, 140.0, 130.9, 126.4, 125.6, 123.5, 117.3, 95.5, 78.3, 57.8, 49.2, 45.2, 34.2, 32.9, 25.0, 23.4, 19.7, 17.1.

EXAMPLE 22

Synthesis of N-(Toluene-4-sulfonyl)-L-prolyl-L-4-(N,N-dimethylaminosulfonyloxy)phenylalanine The title compound was prepared from the product of Example 21 using the procedure described in method 11.
NMR data was as follows:
$^1$H NMR (CD$_3$OD): δ=7.73 (d, 2H), 7.41 (d, 2H), 7.38 (d, 2H), 7.22 (d, 2H), 4.69 (m, 1H), 4.11 (m, 1H), 3.41 (m, 2H), 3.19 (m, 2H), 2.94 (s, 6H), 2.41 (s, 3A), 1.78 (m, 1H), 1.61 (m, 3H).
$^{13}$C NMR (CD$_3$OD): δ=174.3, 174.0, 150.8, 145.9, 137.3, 135.1, 132.1, 131.2, 129.1, 123.1, 63.3, 54.6, 50.6, 39.1, 37.5, 31.6, 25.3, 21.5.

EXAMPLE 23

Synthesis of N-(Toluene-4-sulfonyl)-sarcosyl-L-(4-morpholinecarbamyloxy)phenylalanine t-butyl ester Substituting sacrosine for L-proline in the preparation of Ts-Pro-Tyr(H)-O-t-butyl ester and substitution of 4-morpholinecarbonyl chloride for dimethylcarbamyl chloride, and following the method for the preparation of Example 2, gave the title compound as a white solid.
NMR data was as follows:
$^1$H NMR (CDCl$_3$): δ7.61 (d, 2H), 7.28 (d, 2H), 7.16 (d, 2H), 7.02 (d, 2H), 4.69 (m, 1H), 3.67 (m, 8H), 3.58 (m, 1H), 3.48 (m, 1H), 3.06 (m, 2H), 2.59 (s, 3H), 2.36 (s, 3H), 1.26 (s, 9H).
$^{13}$C NMR (CDCl$_3$): δ 169.7, 167.1, 153.5, 150.1, 144.1, 133.1, 133.0, 133.0, 130.1, 129.8, 127.4, 121.6, 82.6, 66.3, 53.6, 53.1, 44.5, 43.7, 36.9, 36.4, 27.6, 21.2.

EXAMPLE 24

Synthesis of N-(Toluene-4-sulfonyl)sarcosyl-L-4-(isonipecotoyloxy)phenylalanine

The title compound was prepared from the product of Example 23 using the procedure described in Method 11.
NMR data was as follows:
$^1$H NMR (CD$_3$OD): δ=7.30 (d, 2H), 7.02 (d, 2H), 6.88 (d, 2H), 6.67 (d, 2H), 4.33 (m, 1H), 3.32 (m, 3H), 3.25 (m, 2H), 3.12 (m, 3H), 2.89 (m, 1H), 2.70 (m, 3H), 2.22 (s, 3H), 2.03 (s, 3H).
$^{13}$C NMR (CD$_3$OD): δ=174.2, 170.3, 155.6, 151.7, 145.6, 135.8, 135.2, 131.5, 131.1, 128.9, 123.0, 67.5, 54.6, 54.0, 37.4, 36.8, 21.5.

EXAMPLE 25

Synthesis of N-(Toluene-4-sulfonyl)-L-[(1,1-dioxo)thiamorpholin-3-carbonyl]-L-4-(morpholin-4-ylcarbonyloxy)phenylalanine tert-Butyl Ester Substitution of 4-morpholinecarbonyl chloride for dimethylcarbamyl chloride, and following the methods for the preparation of Example 2 and 14, gave the title compound as a white solid.
NMR data was as follows:
$^1$H NMR (CDCl$_3$): δ=7.76 (d, 1H), 7.68 (d, 1H), 7.37 (m, 2H), 7.14 (m, 2H), 7.05 (m, 1H), 6.97 (d, 1H), 6.80 (d, 0.5H), 6.57 (d, 0.5H), 5.09 (m, 0.5H), 4.91 (m, 0.5H), 4.75 (m, 0.5H), 4.62 (m, 0.5H), 4.25 (m, 0.5H), 4.09 (m, 2H), 3.79 (m, 4H), 3.65 (m, 4H), 2.91 (s, 3H), 2.44 (s, 3H), 1.69 (s, 4H), 1.44 (s, 5H).
$^{13}$CNMR(CDCl$_3$): δ=170.0, 169.8, 164.8, 164.4, 153.7, 150.4, 145.6, 145.4, 135.4, 135.3, 132.9, 130.8, 130.7, 130.5, 130.4, 127.5, 127.2, 122.1, 121.8, 83.01, 82.8, 66.4, 56.1, 56.1, 53.7, 53.6, 49.5, 49.3, 48.6, 44.7, 43.9, 42.0, 41.6, 36.9, 36.3, 27.8, 21.5.

EXAMPLE 26

Synthesis of N-(Toluene-4-sulfonyl)-L-[(1,1-dioxo)thiamorpholin-3-carbonyl]-L-4-(morpholin-4-ylcarbonyloxy)phenylalanine The title compound was prepared from the product of Example 25 using the procedure described in Method 11.

NMR data was as follows:

$^1$H NMR (CD$_3$OD): δ=7.67 (m, 2H), 7.32 (m, 2H), 7.08 (m, 2H), 6.93 (m, 2H), 5.09 (m, 1H), 4.54 (m, 1H), 4.19 (m, 0.5H), 4.02 (m, 0.5H), 3.81 (m, 0.5H), 3.66 (m, 8H), 2.99 (m, 7H), 2.32 (s, 3H).

$^{13}$CNMR(CD$_3$OD): δ=174.0, 168.0, 155.7, 151.9, 151.8, 146.6, 146.4, 137.5, 135.5, 135.3, 131.7, 131.6, 131.6, 128.8, 123.3, 122.9, 67.6, 57.3, 57.1, 54.8, 51.1, 50.9, 50.6, 46.0, 45.3, 45.2, 43.0, 37.4, 37.0, 21.5.

EXAMPLE 27

Synthesis of N-(4-Fluorobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^{13}$C NMR (CDCl$_3$): δ=7.87-7.83 (m, 2H), 7.26-7.13 (m, 5H), 4.74-4.69 (m, 1H), 4.05 (m, 1H), 3.36 (m, 1H), 3.24-3.17 (m, 1H), 3.11-3.01 (m, 4H), 2.97 (s, 3H), 2.05-2.02 (m, 1H), 1.60-1.47 (m, 3H), 1.46 (s, 9H).

$^{13}$C NMR (CDCl$_3$): δ=170.6, 170.0, 165.7, 154.9, 150.6, 133.2, 132.4, 130.7, 130.2, 121.7, 116.7, 82.7, 62.3, 53.7, 49.6, 37.2, 36.6, 36.4, 29.9, 27.9, 24.2.

EXAMPLE 28

Synthesis of N-(Toluene-4-sulfonyl)sarcosyl-L-4-(4-methylpiperazin-1-ylcarbonyloxy)phenylalanine tert-Butyl Ester The title compound was prepared following the procedure outlined for the preparation of Example 4 and substitution of appropriate starting materials.

NMR data was as follows:

$^1$H NMR (CDCl$_3$): δ=8.17 (d, 1H), 7.59 (d, 2H), 7.26 (d, 2H), 7.13 (d, 2H), 7.00 (d, 2H), 4.66 (m, 1H), 3.60 (m, 6H), 3.04 (m, 2H), 2.56 (s, 3H), 2.40 (m, 7H), 2.34 (s, 3H), 1.41 (s, 9H).

$^{13}$C NMR (CDCl$_3$): δ=169.7, 167.0, 153.4, 150.2, 144.0, 133.0, 132.9, 130.1, 129.8, 127.4, 121.6, 82.2, 54.3, 53.5, 53.1, 45.8, 44.2, 43.5, 36.9, 27.6, 21.2.

EXAMPLE 29

Synthesis of N-(Toluene-4-sulfonyl)-L-(1,1-dioxo-5,5-dimethyl)-thiaprolyl-L-4-(N,N-dimethylcarbamyloxy)phenylalanine tert-Butyl Ester The product of Example 12 was oxidized by the method of Larsson and Carlson (*Acta Chemica Scan.* 1994, 48, 517-525), yielding the title compound as a white solid.

NMR data was as follows:

$^1$H NMR (CDCl$_3$): δ=7.73 (d, 2H), 7.36 (d, 2H), 7.21 (d, 2H), 7.06-6.95 (m, 3H), 4.79 (m, 1H), 4.38 (dd, 2H), 4.10 (s, 1H), 3.18-2.95 (m, 8H), 2.43 (s, 3H), 1.45 (s, 9H), 1.33 (s, 3H), 1.08 (s, 3H).

$^{13}$C NMR (CDCl$_3$): δ=169.8, 166.2, 154.9, 120.7, 145.8, 133.0, 131.9, 130.2, 128.5, 121.9, 82.9, 68.0, 60.9, 59.3, 53.9, 37.5, 36.6, 36.3, 27.7, 21.6, 19.3, 18.5.

EXAMPLE 30

Synthesis of N-(1-Methylimidazolyl-4-sulfonyl)-L-prolyl-L-4-(N,N-dimethylcarbamyloxy)phenylalanine The title compound was prepared from the product of Example 106 using the procedure described in Method 11.

NMR data was as follows:

$^1$H NMR (CDCl$_3$): δ=8.07 (d, 1H), 7.75 (s, 1H), 7.71 (s, 1H), 7.25 (d, 2H), 7.01 (d, 2H), 4.71-4.66 (m, 1H), 4.28-4.24 (m, 1H), 3.77 (s, 3H), 3.42-3.05 (m, 3H), 3.09 (s, 3H), 2.96 (s, 3H), 1.84-1.69 (m, 2H), 1.61-1.54 (m, 2H).

$^{13}$C NMR (CDCl$_3$): δ=174.4, 174.1, 156.9, 151.9, 141.8, 137.7, 135.6, 131.6, s 127.6, 122.9, 63.7, 54.7, 50.8, 37.4, 36.8, 36.7, 34.3, 31.6, 25.4.

PREPARATIVE EXAMPLE A

Synthesis of 2-(Saccharin-2-yl)propionoyl-L-4-(N,N-dimethylcarbamyloxy)phenylalanine tert-Butyl Ester N-(Benzisothiazolone)-L-alanyl-L-tyrosine t-butyl ester was prepared by first combining sodium hydride (washed free of mineral oil) in THF chilled to 0° C., and a solution of N-(2-methoxycarbonyl)sulfonyl-L-alanine-L-tyrosine t-butyl ester in THF which was added dropwise. The reaction was stirred at 0° C. for one hour and then at room temperature for two hours. The reaction mixture was extracted with EtOAc and 0.2 N HCl, the combined EtOAc layers were washed successively with 0.2 N HCl, sat. NaHCO$_3$, and sat. NaCl. The organic layer was dried over MgSO$_4$, filtered and concentrated. The residue was filtered by silica gel chromatography to afford N-(benzisothiazolone)-L-alanyl-L-tyrosine t-butyl ester.

The title compound was then prepared following the procedure described in Example 2.

NMR data was as follows:

$^1$H NMR (DMSO-d$_6$, 400 MHz) (1:1 mixture of diastereomers) δ=8.15 (m, 2H); 8.5 (m, 3H); 7.20 (m, 2H); 6.95 (m, 2H); 4.75 (m, 1H); 4.30 (m, 1H); 3.05 (s, 3H); 2.95 (m, 2H); 2.90 (s, 3H); 1.75 and 1.65 (two d, 3H); 1.30 and 1.35 (two s, 9H).

EXAMPLE 31

Synthesis of N-(Toluene-4-sulfonyl)-L-(1,1-dioxo-5,5-dimethyl)-thiaprolyl-L-4-(N,N-dimethylcarbamyloxy)phenylalanine The title compound was prepared from the product of Example 29 using the procedure described in Method 11.

NMR data was as follows:

$^1$H NMR (CDCl$_3$): δ=7.75 (m, 3H), 7.29 (m, 4H), 7.08 (d, 2H), 4.95 (m, 1H), 4.46-4.20 (m, 3H), 3.17 (s, 3H), 3.30-3.10 (m, 2H), 3.02 (s, 3H), 2.43 (s, 3H), 1.15 (s, 3H), 0.88 (s, 3H).

$^{13}$C NMR (CDCl$_3$): δ=127.2, 167.5, 155.8, 150.3, 145.4, 133.6, 132.6, 130.8, 130.2, 128.3, 121.9, 67.9, 65.8, 60.8, 53.9, 36.8, 36.6, 35.8, 21.6, 18.8, 15.0.

EXAMPLE 32

Synthesis of N-(4-Fluorobenzenesulfonyl)-L-prolyl-L-4-(N,N-dimethylcarbamyloxy)phenylalanine The title compound was prepared from the product of Example 27 using the procedure described in Method 11.

NMR data was as follows:

$^{13}$C NMR (CDCl$_3$): δ=7.88-7.84 (m, 2H), 7.54 (d, 1H), 7.26-7.18 (m, 4H), 7.01 (d, 2H), 6.92 (s, 3H), 4.88-4.83 (m, 1H), 4.14-4.11 (m, 1H), 3.39-3.29 (m, 2H), 3.13 (m, 2H), 3.00 (s, 3H), 2.99 (s, 3H), 1.92-1.89 (m, 1H), 1.59-1.43 (m, 3H).

$^{13}$C NMR (CDCl$_3$): δ=173.1, 172.4, 165.6, 155.5, 150.4, 133.2, 131.9, 130.6, 130.3, 121.8, 116.6, 61.9, 53.1, 49.6, 36.6, 36.3, 30.2, 23.9.

EXAMPLE 33

Synthesis of N-(Toluene-4-sulfonyl)-D-prolyl-L-4-(4-methylpiperazin-1-yl)phenylalanine t-butyl Ester The title compound was prepared following the procedure outlined for the preparation of Example 4 and substitution of appropriate starting materials.

NMR data was as follows:

$^{13}$C NMR (CDCl$_3$): δ=7.72 (d, 2H), 7.33 (d, 3H), 7.17 (d, 2H), 7.02 (d, 2H), 4.71 (q, 1H), 4.09-4.06 (m, 1H), 3.67 (bs, 2H), 3.57 (bs, 2H), 3.41-3.34 (m, 1H), 3.22 (dd, 1H), 3.16-3.09 (m, 1H), 3.03 (dd, 1H), 2.46-2.43 (m, 7H), 2.05-2.02 (m, 1H), 1.57-1.43 (m, 3H), 1.47 (s, 9H).

$^{13}$C NMR (CDCl$_3$): δ=170.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

EXAMPLE 34

Synthesis of N-(Toluene-4-sulfonyl)-N-methyl-L-alanyl-L-4-(4-methylpiperazin-1-ylcarbonyloxy) phenylalanine t-butyl ester The title compound was prepared following the procedure outlined for the preparation of Example 4 and substitution of appropriate starting materials.

NMR data was as follows:

$^1$H NMR (CDCl$_3$): δ=7.68 (d, 2H), 7.31 (d, 2H), 7.17 (d, 2H), 7.04 (d, 2H), 6.86 (d, 1H), 4.65 (m, 1H), 4.47 (q, 1H), 3.71-3.53 (m, 4H), 3.24-2.92 (m, 2H), 2.50-2.40 (m, 10H), 2.35 (s, 3H), 1.45 (s, 9H), 0.92 (d, 3H).

$^{13}$C NMR (CDCl$_3$): δ=170.1, 169.9, 153.6, 150.4, 143.9, 135.6, 133.3, 130.2, 129.9, 127.2, 121.8, 82.4, 55.4, 54.6, 53.6, 46.0, 44.2, 43.7, 37.2, 29.6, 27.8, 21.4, 11.5.

EXAMPLE 35

Synthesis of N-(4-Nitrobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CDCl$_3$): δ=8.38-8.34 (m, 2H), 8.05-8.00 (m, 2H), 7.16-2.12 (m, 2H), 7.03-6.94 (m, 3H), 4.74-4.68 (m, 1H), 4.15-4.14 (m, 1H), 3.41-3.32 (m, 1H), 3,23-3.14 (m, 2H), 3.08 (s, 3H), 3.03 (m, 1H), 2.98 (s, 3H), 2.05 (m, 1H), 1.66-1.48 (m, 3H), 1.47 (s, 9H).

$^{13}$C NMR (CDCl$_3$): δ=170.0, 169.9, 154.8, 150.6, 150.4, 142.4, 132.9, 130.2, 129.0, 124.5, 121.6, 82.7, 62.2, 53.4, 49.4, 37.0, 36.5, 36.2, 30.1, 27.7, 24.1.

EXAMPLE 36

Synthesis of N-(Toluene-4-sulfonyl)-L-[(1,1-dioxo)-thiamorpholin-3-carbonyl]-L-4-(N,N-dimethylaminosulfonyloxy)phenylalanine tert-Butyl Ester The title compound was prepared using the procedure described for the preparation of Example 21 and substitution of appropriate starting materials.

NMR data was as follows:

$^1$H NMR (CDCl$_3$): δ=7.73 (d, 1H), 7.67 (d, 1H), 7.35 (m, 2H), 7.27 (m, 2H), 6.88 (d, 1H), 6.66 (d, 1H), 5.08 (m, 0.5H), 4.97 (m, 0.5H), 4.71 (m, 0.5H), 4.61 (m, 0.5H), 4.25 (m, 0.5H), 4.03 (m, 1H), 3.21-3.04 (m, 4H), 2.89 (s, 3H), 2.83 (s, 3H), 2.78 (m, 3H), 2.42 (s, 3H), 1.44 (s, 4.5H), 1.38 (s, 4.5H).

$^{13}$C NMR (CDCl$_3$): δ=169.8, 169.6, 164.9, 164.5, 149.3, 149.1, 145.6, 145.4, 135.4, 135.0, 134.6, 130.9, 130.6, 130.5, 127.4, 127.2, 122.0, 121.8, 83.0, 83.0, 56.0, 53.7, 49.2, 49.1, 48.5, 41.9, 41.4, 38.6, 36.8, 36.2, 27.7, 21.5.

EXAMPLE 37

Synthesis of N-(Toluene-4-sulfonyl)sarcosyl-L-4-(thiomorpholin-4-ylcarbonyloxy)phenylalanine tert-Butyl Ester Substituting thiomorpholine for N-methylpiperazine, and following the method for the preparation of Example 4, gave the title compound.

NMR data was as follows:

$^1$H NMR (CDCl$_3$): δ=7.65 (d, 2H), 7.33 (d, 2H), 7.20 (d, 2H), 7.04 (d, 2H), 4.76 (m, 1H), 3.89 (m, 4H), 3.68 (d, 1H), 3.48 (d, 1H), 3.10 (m, 2H), 2.66 (m, 7H), 2.41 (s, 3H), 1.43 (s, 9H).

$^{13}$C NMR (CDCl$_3$): δ=169.9, 167.2, 153.5, 150.3, 144.3, 133.1, 130.3, 130.0, 127.6, 121.8, 82.5, 53.8, 53.3, 47.0, 36.4, 37.2, 36.6, 27.8, 27.3, 27.0, 21.4.

EXAMPLE 38

Synthesis of N-(Toluene-4-sulfonyl)-L-N-methylalanyl-L-4-(4-methylpiperazin-1-ylcarbonyloxy)phenylalanine The title compound was prepared from the product of Example 34 using the procedure described in Method 11.

NMR data was as follows:

$^1$H NMR (CDCl$_3$): δ=7.65 (d, 2H), 7.34 (d, 2H), 7.27 (d, 2H), 7.09 (d, 2H), 4.64-4.50 (m, 2H), 4.48-4.23 (m, 2H), 3.60-2.96 (m, 8H), 2.92 (s, 3H), 2.55 (s, 3H), 2.40 (s, 3H), 0.93 (d, 3H).

$^{13}$C NMR (CDCl$_3$): δ=174.3, 173.1, 154.9, 151.6, 145.5, 137.0, 136.1, 131.6, 131.2, 128.5, 123.1, 56.4, 54.8, 54.0, 43.8, 37.3, 30.2, 21.5, 13.2.

EXAMPLE 39

Synthesis of N-(Toluene-4-sulfonyl)-L-prolyl-L-4-(1,1-dioxothiomorpholin-4-ylcarbonyloxy)phenylalanine The title compound was prepared from the product of Example 81 using the procedure described in Method 11.

NMR data was as follows:
¹H NMR (CD₃OD): δ=8.03 (m, 1H), 7.73 (d, 2H), 7.41 (d, 2H), 7.28 (d, 2H), 7.08 (d, 2H), 4.70-4.65 (m, 1H), 4.12-4.00 (m, 5H), 3.38-3.36 (m, 1H), 3.31-3.06 (m, 7H), 2.43 (s, 3H), 1.77-1.48 (m, 5H).
¹³C NMR (CD₃OD): δ=168.4, 159.1, 130.0, 129.1, 125.6, 125.1, 123.0, 116.9, 57.2, 48.8, 46.3, 44.5, 31.5, 25.6, 19.3, 15.4.

EXAMPLE 40

Synthesis of N-(Toluene-4-sulfonyl)-L-prolyl-L-4-(thiomorpholin-4-ylcarbonyloxy)phenylalanine The title compound was prepared from the product of Example 82 using the procedure described in Method 11.
NMR data was as follows:
¹H NMR (CD₃OD): δ=7.73 (d, 2H), 7.41 (d, 2H), 7.27 (d, 2H), 7.04 (d, 2H), 4.68-4.65 (m, 1H), 4.10-4.07 (m, 1H), 3.90 (t, 2H), 3.77 (t, 2H), 3.38-3.11 (m, 4H), 2.66 (m, 4H), 2.43 (s, 3H), 1.80-1.48 (m, 5H).
¹³C NMR (CD₃OD): δ=168.4, 168.2, 149.4, 145.7, 139.8, 129.7, 129.0, 125.6, 125.1, 123.1, 116.9, 57.2, 48.8, 44.6, 42.1, 36.0, 31.4, 25.7, 22.1, 21.8, 19.3, 15.4.

EXAMPLE 41

Synthesis of N-(Toluene-4-sulfonyl)-L-prolyl-L-4-(isonipecotoyloxy)phenylalanine The title compound was prepared from the product of Example 80 using the procedure described in Method 11.
NMR data was as follows:
¹H NMR (CD₃OD): δ=8.08 (m, 1H), 7.73 (d, 2H), 7.41 (d, 2H), 7.27 (d, 2H), 7.03 (d, 2H), 4.71 (m, 1H), 4.11-4.08 (m, 1H), 3.61 (t, 2H), 3.47-3.38 (m, 3H), 3.31-3.11 (m, 4H), 2.43 (s, 3H), 1.77-1.47 (m, 10H).
¹³C NMR (CD₃OD): δ=168.3, 168.1, 158.8, 149.6, 145.9, 139.8, 129.5, 129.0, 125.6, 125.1, 123.1, 116.9, 57.2, 48.6, 44.6, 40.6, 40.1, 36.0, 31.4, 25.7, 20.9, 20.6, 19.3.

EXAMPLE 42

Synthesis of N-(Toluene-4-sulfonyl)-L-prolyl-L-4-(pyrrolidin-1-ylcarbonyloxy)phenylalanine The title compound was prepared from the product of Example 83 using the procedure described in Method 11.
NMR data was as follows:
¹H NMR (CD₃OD): δ=8.08 (m, 1H), 7.73 (d, 2H), 7.41 (d, 2H), 7.04 (d, 2H), 7.27 (d, 2H), 4.72-4.68 (m, 1H), 4.11-4.08 (m, 1H), 3.57-3.53 (t, 2H), 3.43-3.28 (m, 3H), 3.25-3.06 (m, 4H), 2.43 (s, 3H), 1.99-1.80 (m, 4H), 1.78-1.49 (m, 5H).
¹³C NMR (CD₃OD): δ=168.2, 158.3, 149.2, 145.8, 139.8, 129.4, 129.1, 125.6, 125.1, 123.1, 116.9, 57.2, 48.7, 44.5, 41.5, 31.4, 25.7, 20.6, 19.8, 19.3, 15.4.

EXAMPLE 43

Synthesis of N-(Toluene-4-sulfonyl)-L-prolyl-L-4-(morpholin-4-ylcarbonyloxy)phenylalanine The title compound was prepared from the product of Example 108 using the procedure described in Method 11.
NMR data was as follows:
¹H NMR (CD₃OD): δ=7.73 (d, 2H), 7.41 (d, 2H), 7.27 (d, 2H), 7.04 (d, 2H), 4.95-4.93 (m, 1H), 4.10-4.07 (m, 1H), 3.71-3.65 (m, 6H), 3.50 (t, 2H), 3.40-3.10 (m, 4H), 2.43 (s, 3H), 1.78-1.48 (m, 4H).
¹³C NMR (CD₃OD): δ=168.4, 168.2, 149.6, 145.7, 139.8, 129.1, 125.6, 125.1, 123.1, 116.8, 61.5, 57.2, 44.5, 36.0, 31.4, 25.6, 19.3, 15.4.

EXAMPLE 44

Synthesis of N-(Toluene-4-sulfonyl)-L-prolyl-L-4-(4-methylpiperazin-1-ylcarbonyloxy)phenylalanine Neopentyl Ester Titanium isopropoxide (0.3 equivalents) was added to Tos-Pro-Tyr ethyl ester (1 equivalent) and an excess of neopentyl alcohol. The mixture was heated to reflux under an argon atmosphere overnight. Excess neopentyl alcohol was removed under reduced pressure and the residue purified by flash column chromatography (silica, hexane: EtOAc 2:1) to give the neopentyl ester a white solid (0.9 g, 85%). The title compound was prepared following the procedure described in Example 4.
NMR data was as follows:
¹H NMR (DMSO-d₆, 400 MHz) δ=8.29 (d, 1H, J=7.91 Hz); 7.68 (d, 2H, J=8.45 Hz); 7.40 (d, 2H, J=8.34 Hz); 7.24 (d, 2H, J=8.57 Hz); 7.00 (d, 2H, J=8.57 Hz); 4.56 (m, 1H); 4.07 (m, 1H); 3.73 (s, 2H); 3.55 (br s, 2H); 3.40 (m, 3H); 3.10 (m, 3H); 2.40 (s, 3H); 2.35 (br s, 4H); 2.20 (s, 3H); 1.55 (m, 3H); 1.37 (m, 1H); 0.85 (s, 9H).

EXAMPLE 45

Synthesis of N-(Toluene-4-sulfonyl)-L-prolyl-L-4-(N,N-dimethylcarbamyloxy)phenylalanine Neopentyl Ester Titanium isopropoxide (0.3 equivalents) was added to Tos-Pro-Tyr ethyl ester (1 equivalent) and an excess of neopentyl alcohol. The mixture was heated to reflux under an argon atmosphere overnight. Excess neopentyl alcohol was removed under reduced pressure and the residue purified by flash column chromatography (silica, hexane: EtOAc 2:1) to give the neopentyl ester a white solid (0.9 g, 85%). The title compound was prepared following the procedure described in Example 2.
NMR data was as follows:
¹H NMR (DMSO-d₆, 400 MHz) δ=8.28 (d, 1H, J=8.13 Hz); 7.68 (d, 2H, J=8.4 Hz); 7.40 (d, 2H, J=7.9 Hz); 7.23 (d, 2H, J=8.56 Hz), 6.99 (d, 2H, J=8.35 Hz); 4.57 (m, 3H); 2.40 (s, 3H); 1.55 (m, 3H); 1.38 (m, 1H); 0.85 (s, 9H).

EXAMPLE 46

Synthesis of 2-(Saccharin-2-yl)propionoyl-L-4-(4-methylpiperazin-1-ylcarbonyloxy)phenylalanine tert-Butyl Ester The title compound was prepared following the procedure described in Preparative Example A and Example 4.
NMR data was as follows:
¹H NMR (DMSO-d₆, 400 MHz) (1:1 mixture of diastereomers) δ=8.31 (m, 1H); 8.26 (m, 1H); 8.03 (m, 3H); 7.20 (m, 2H); 7.00 (m, 2H); 4.73 (m, 1H); 4.30 (m, 1H); 3.58 (br s, 2H); 3.40 (br s, 2H); 3.02 (m, 1H); 2.95 (m, 1H); 2.35 (br s, 4H); 2.20 (s, 3H); 2.75 and 2.65 (two d, 3H); 1.35 and 1.32 (two s, 9H).

EXAMPLE 47

Synthesis of 2-(Saccharin-2-yl)propionoyl-L-4-(N,N-dimethylcarbamyloxy)phenylalanine The title compound was prepared from the product of Preparative Example A using the procedure described in Method 11.

NMR data was as follows:

$^1$H NMR (DMSO-d$_6$, 400 MHz) (1:1 mixture of diastereomers) δ=12.75 (br s, 1H); 8.28 (m, 2H); 8.05 (m, 3H); 7.20 (m, 2H); 7.00 and 9.95 (two d, 2H); 4.75 (m, 1H); 4.40 (m, 1H); 3.10 (m, 1H); 3.05 (s, 3H); 2.95 (m, 1H); 2.90 (s, 3H); 2.75 and 2.60 (two d, 3H).

EXAMPLE 48

Synthesis of N-(Toluene-4-sulfonyl)-L-N-methylalanyl-L-4-(N,N-dimethylcarbamyloxy)phenylalanine tert-Butyl Ester The title compound was prepared following the procedure for the synthesis of Example 2 with the substitution of appropriate starting materials.

NMR data was as follows:

$^1$H NMR (CDCl$_3$): δ=7.68 (d, 2H), 7.31 (d, 2H), 7.17 (d, 2H), 7.04 (d, 2H), 6.87 (d, 2H), 4.67 (m, 1H), 4.48 (q, 1H), 3.09 (s, 3H), 3.00 (s, 3H), 3.14-2.92 (m, 2H), 2.46 (s, 3H), 2.43 (s, 3H), 1.45 (s, 9H), 0.92 (d, 3H).

$^{13}$C NMR (CDCl$_3$): δ=170.2, 169.9, 154.9, 150.6, 143.9, 135.6, 133.2, 130.2, 130.0, 127.3, 121.9, 82.5, 55.5, 53.7, 37.2, 36.6, 36.4, 29.7, 27.8, 21.4, 11.5.

EXAMPLE 49

Synthesis of N-(Toluene-4-sulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517-525). N-(Toluene-4-sulfonyl)-L-thiamorpholine-3-carboxylic acid was prepared using the procedure described in Method 1. The title compound was prepared following the procedure for the synthesis of Example 2 with substitution of appropriate starting materials.

NMR data was as follows:

$^1$H NMR (CDCl$_3$): δ=7.69 (d, 2H), 7.31 (d, 2H), 7.16 (d, 2H), 6.98 (d, 2H), 6.86 (d, 1H), 4.71 (m, 1H), 4.62 (m, 1H), 3.94 (m, 1H), 3.31 (m, 1H), 3.09 (m, 4H), 2.98 (s, 3H), 2.67 (m, 1H), 2.50 (m, 1H), 2.40 (s, 3H), 2.31 (m, 1H), 2.10 (m, 1H), 1.49 (s, 9H).

$^{13}$C NMR (CDCl$_3$): δ=169.9, 167.4, 154.8, 150.6, 144.2, 136.8, 132.8, 130.4, 130.2, 127.3, 121.8, 82.6, 55.2, 54.0, 43.3, 36.5, 36.3, 27.8, 25.2, 24.6, 21.4.

EXAMPLE 50

Synthesis of N-(Toluene-4-sulfonyl)sarcosyl-L-4-(1,1-dioxothiomorpholin-4-ylcarbonyloxy)phenylalanine The title compound was prepared from the product of Example 121 using the procedure described in Method 11.

NMR data was as follows:

$^1$H NMR (CD$_3$OD): δ=7.67 (d, 2H), 7.40 (d, 2H), 7.27 (d, 2H), 7.09 (d, 2H), 4.61 (m, 1H), 4.12 (m, 2H), 3.99 (m, 2H), 3.60 (m, 2H), 3.23 (m, 8H), 2.58 (s, 3H), 2.42 (s, 3H).

$^{13}$C NMR (CD$_3$OD): δ=174.2, 170.3, 155.0, 151.6, 145.6, 136.1, 135.2, 131.5, 131.1, 128.9, 123.0, 54.6, 54.0, 52.4, 52.2, 44.4, 44.0, 37.4, 36.8, 21.4.

EXAMPLE 51

Synthesis of N-(Toluene-4-sulfonyl)-L-(1,1-dioxothiamorpholin-3-carbonyl)-L-4-(N,N-dimethylcarbamyloxy)phenylalanine tert-Butyl Ester The title compound was prepared from the product of Example 49 following the procedure described by Larsson and Carlson (*Acta Chemica Scan.* 1994, 48, 522).

NMR data was as follows:

$^1$H NMR (CDCl$_3$): δ=7.76 (d, 2H), 7.37 (d, 2H), 7.08 (d, 2H), 6.98 (d, 2H), 6.56 (d, 1H), 4.95 (m, 1H), 4.62 (m, 1H), 3.99 (m, 2H), 3.25 (m, 1H), 3.07 (s, 3H), 2.97 (m, 8H), 2.44 (s, 3H), 1.48 (s, 9H).

$^{13}$C NMR (CDCl$_3$): δ=170.0, 164.8, 154.9, 150.7, 145.4, 135.3, 132.6, 130.7, 130.3, 127.5, 122.3, 82.8, 56.1, 53.6, 49.5, 48.6, 41.6, 36.6, 36.4, 27.9, 21.6.

EXAMPLE 52

Synthesis of N-(Toluene-4-sulfonyl)-L-(1,1-dioxothiamorpholin-3-carbonyl)-L-4-(morpholin-4-ylcarbonyloxy)phenylalanine tert-Butyl Ester The title compound was prepared following the procedure described for the preparation of Example 71.

NMR data was as follows:

$^1$H NMR (CDCl$_3$): δ=7.75 (d, 2H), 7.36 (d, 2H), 7.12 (d, 2H), 6.98 (d, 2H), 6.58 (d, 1H), 4.93 (m, 1H), 4.63 (m, 1H), 4.09 (m, 2H), 3.72 (m, 4H), 3.63 (m, 2H), 3.51 (m, 2H), 3.24 (m, 1H), 2.96 (m, 4H), 2.43 (s, 3H), 1.46 (s, 9H).

$^{13}$C NMR (CDCl$_3$): δ=170.0, 164.8, 153.7, 150.4, 145.4, 135.2, 132.9, 130.7, 130.4, 127.5, 122.1, 82.9, 66.4, 56.1, 53.6, 49.4, 48.5, 44.7, 43.9, 41.6, 36.3, 27.8, 21.6.

EXAMPLE 53

Synthesis of N-(Toluene-4-sulfonyl)-L-N-methylalanyl-L-4-(N,N-dimethylcarbamyloxy)phenylalanine The title compound was prepared from the product of Example 48 using the procedure described in Method 11.

NMR data was as follows:

$^1$H NMR (CDCl$_3$): δ=7.68 (d, 2H), 7.31 (d, 2H), 7.20 (d, 2H), 7.11-7.04 (m, 3H), 6.35 (br s, 1H), 4.81 (m, 1H), 4.52 (q, 1H), 3.35-2.98 (m, 2H), 3.09 (s, 3H), 3.00 (s, 3H), 2.45 (s, 3H), 2.43 (s, 3H), 0.91 (d, 3H).

$^{13}$C NMR (CDCl$_3$): δ=173.7, 170.8, 155.2, 150.6, 144.0, 135.4, 133.2, 130.2, 130.0, 127.3, 122.1, 55.5, 53.2, 36.6, 36.5, 36.4, 29.8, 21.4, 11.6.

EXAMPLE 54

Synthesis of N-(4-Fluorobenzenesulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517-525). N-(Toluene-4-sulfonyl)-L-thiamorpholine-3-carboxylic acid was prepared using the procedure described in Method 1.

The title compound was then prepared following the procedure for the synthesis of Example 2.

NMR data was as follows:

¹H NMR (CDCl₃): δ=7.87-7.82 (m, 2H), 7.20 (t, 2H), 7.16 (d, 2H), 7.00 (d, 2H), 6.76 (d, 1H), 4.74 (t, 1H), 4.65 (q, 1H), 3.92 (d, 1H), 3.32 (dd, 1H), 3.17-3.00 (m, 2H), 3.09 (s, 3H), 2.99 (s, 3H), 2.76-2.66 (m, 1H), 2.62 (dd, 1H), 2.46 (dt, 1H), 2.22 (d, 1H), 1.49 (s, 9H).

¹³C NMR (CDCl₃): δ=170.0, 167.2, 165.5, 154.8, 150.7, 135.8, 132.7, 130.5, 130.1, 121.9, 116.9, 82.8, 55.3, 53.9, 43.4, 36.6, 36.4, 36.3, 27.9, 25.8, 25.0.

EXAMPLE 55

Synthesis of N-(4-Fluorobenzenesulfonyl)-L-(1,1-dioxothiamorpholin-3-carbonyl)-L-4-(N,N-dimethylcarbamyloxy)phenylalanine tert-Butyl Ester The title compound was prepared from the product of Example 54 following the procedure described by Larsson and Carlson (*Acta Chemica Scan.* 1994, 48, 522).

NMR data was as follows:

¹H NMR (CDCl₃): δ=7.92-7.88 (m, 2H), 7.24 (t, 2H), 7.09 (d, 2H), 6.97 (d, 2H), 6.41 (d, 1H), 4.96 (d, 1H), 4.62 (d, 1H), 4.03 (d, 1H), 3.26 (dd, 1H), 3.13-2.92 (m, 6H), 3.09 (s, 3H), 2.97 (s, 3H), 1.49 (s, 9H).

¹³C NMR (CDCl₃): δ=170.1, 165.9, 164.5, 154.9, 150.7, 134.0, 132.4, 130.5, 130.4, 122.2, 117.3, 83.0, 56.1, 53.4, 50.0, 49.1, 41.7, 36.6, 36.3, 36.1, 27.9.

EXAMPLE 56

Synthesis of N-(Pyridine-3-sulfonyl)-L-prolyl-L-4-(N,N-dimethylcarbamyloxy)phenylalanine tert-Butyl Ester N-Benzyl-L-proline was coupled to L-tyrosine t-butyl ester using the procedure described in Method 12. N-Benzyl-L-prolyl-L-(N,N-dimethylcarbamyloxy)phenylalanine t-butyl ester was prepared following the procedure described for the preparation of Example 2. L-Prolyl-L-(4-N,N-dimethylcarbamyloxy)phenylalanine t-butyl ester was prepared from the product of the previous reaction using the procedure described in Method 4. The title compound was prepared using the procedure described for the preparation of 3-pyridine sulfonyl chloride (see Crowell et al., *J. Med. Chem.*, 1989, 32, 2436-2442) and the product of the last reaction.

NMR data was as follows:

¹H NMR (CDCl₃): δ=9.95 (d, 1H), 8.83 (dd, 1H), 8.14-8.10 (m, 1H), 7.51-7.47 (m, 1H), 7.16-7.13 (m, 3H), 7.02-6.99 (m, 2H), 4.72-4.69 (m, 1H), 4.09-4.06 (m, 1H), 3.41-3.39 (m, 1H), 3.23-3.17 (m, 1H), 3.13-2.98 (m, 1H), 3.07 (s, 3H), 2.97 (s, 3H), 2.04 (m, 1H), 1.59-1.47 (m, 3H), 1.45 (s, 9H).

¹³C NMR (CDCl₃): δ=170.1, 169.9, 154.8, 153.9, 150.5, 148.4, 135.5, 133.0, 130.1, 123.9, 121.6, 82.6, 52.2, 53.6, 49.5, 37.1, 36.5, 36.3, 29.9, 27.8, 24.0.

PREPARATIVE EXAMPLE B

Synthesis of N-(Pyrimidine-2-sulfonyl)-L-prolyl-L-4-(N,N-dimethylcarbamyloxy)phenylalanine tert-Butyl Ester The title compound was prepared by substituting 2-pyrimidine sulfonyl chloride (see Skulnick et al., *J. Med. Chem.*, 1997, 40, 1149-1164) and following the method for the preparation of Example 56.

NMR data was as follows:

¹H NMR (CDCl₃): δ=8.28 (d, 2H), 7.39 (d, 1H), 7.02 (d, 2H), 6.88 (d, 2H), 6.54 (m, 1H), 4.76-4.69 (m, 1H), 4.57-4.55 (m, 1H), 3.64 (m, 1H), 3.55-3.52 (m, 1H), 3.09-3.03 (m, 1H), 3.08 (s, 3H), 2.99-2.95 (m, 1H), 2.98 (s, 3H), 2.32 (m, 1H), 2.01-1.97 (m, 3H), 1.37 (s, 9H).

¹³C NMR (CDCl₃): δ=172.1, 170.4, 160.6, 157.7, 154.8, 150.3, 133.0, 130.1, 121.3, 110.5, 82.0, 60.7, 53.3, 47.5, 37.1, 36.5, 36.3, 28.9, 27.7, 24.1.

EXAMPLE 57

Synthesis of N-(4-Nitrobenzenesulfonyl)-L-prolyl-L-4-(N,N-dimethylcarbamyloxy)phenylalanine The title compound was prepared from the product of Example 35 using the procedure described in method 11.

NMR data was as follows:

¹H NMR (CDCl₃): δ=8.36 (d, 2H), 8.02 (d, 2H), 7.42 (d, 1H), 7.20 (d, 2H), 7.01 (d, 2H), 4.86 (m, 1H), 4.18-4.15 (m, 1H), 3.46-3.43 (m, 1H), 3.32-3.26 (m, 1H), 3.19-3.11 (m, 2H), 3.09 (s, 3H), 3.01 (s, 3H), 1.91 (m, 1H), 1.65-1.54 (m, 3H).

¹³C NMR (CDCl₃): δ=172.9, 171.7, 155.5, 150.4, 150.4, 142.1, 133.2, 130.5, 129.1, 124.6, 121.8, 61.9, 52.9, 49.6, 36.6, 36.3, 36.3, 30.6, 24.1.

EXAMPLE 58

Synthesis of N-(4-Cyanobenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

¹H NMR (CDCl₃): δ=7.94 (d, 2H), 7.82 (d, 2H), 7.13 (d, 2H), 7.05-6.99 (m, 3H), 4.71-4.66 (m, 1H), 4.12-4.09 (m, 1H), 3.36-3.35 (m, 1H), 3.22-3.11 (m, 2H), 3.07 (s, 3H), 3.06-3.01 (m, 1H), 2.97 (s, 3H), 2.05 (m, 1H), 1.63-1.37 (m, 3H), 1.46 (s, 9H).

¹³C NMR (CDCl₃): δ=170.1, 169.9, 154.8, 150.6, 140.8, 133.1, 132.9, 130.2, 128.4, 121.7, 117.1, 116.9, 82.7, 62.2, 53.4, 49.4, 37.0, 36.5, 36.3, 30.1, 27.8, 24.1.

EXAMPLE 59

Synthesis of N-(Toluene-4-sulfonyl)-L-(1,1-dioxothiamorpholin-3-carbonyl)-L-4-(N,N-dimethylaminosulfonyloxy)phenylalanine The title compound was prepared from the product of Example 36 using the procedure described in Method 11.

NMR data was as follows:

¹H NMR (CD₃OD): δ=7.79 (m, 2H), 7.44 (m, 2H), 7.27 (m, 2H), 7.17 (m, 2H), 5.21 (m, 1H), 4.64 (m, 1H), 4.14 (m, 1H), 3.61 (m, 2H), 3.24 (m, 2H), 3.08 (m, 2H), 2.89 (s, 6H), 2.80 (m, 2H), 2.43 (s, 3H).

¹³C NMR (CD₃OD): δ=173.9, 168.1, 168.0, 150.8, 150.8, 146.7, 146.5, 137.6, 137.5, 137.1, 136.9, 132.2, 132.1, 131.7, 131.6, 128.8, 123.3, 123.1, 57.3, 54.8, 51.0, 50.8, 50.5, 47.9, 47.8, 43.2, 43.0, 39.0, 39.0, 37.4, 37.0, 21.5.

EXAMPLE 60

Synthesis of N-(Toluene-4-sulfonyl)-L-(1,1-dioxothiamorpholin-3-carbonyl)-L-4-(N,N-dimethylcarbamyloxy)phenylalanine The title compound was prepared from the product of Example 51 using the procedure described in Method 11.

NMR data was as follows:

$^1$H NMR (CDCl$_3$): δ=7.79 (d, 2H), 7.43 (d, 2H), 7.20 (d, 2H), 7.00 (d, 2H), 5.21 (m, 1H), 4.65 (m, 1H), 4.12 (m, 1H), 3.75 (m, 1H), 3.29 (m, 3H), 3.08 (s, 3H), 3.00 (m, 1H), 3.00 (m, 1H), 2.97 (s, 3H), 2.80 (m, 3H), 2.44 (s, 3H).

$^{13}$C NMR (CDCl$_3$): δ=165.1,159.0,147.9, 143.1,137.6,128.6, 126.1,122.7, 122.6, 119.8, 114.3, 48.3, 45.8, 41.6, 34.0, 28.0, 27.8, 27.7, 12.5.

EXAMPLE 61

Synthesis of N-(Toluene-4-sulfonyl)-L-(1,1-dioxo)thiaprolyl-L-4-(N,N-dimethylcarbamyloxy)phenylalanine tert-Butyl Ester The title compound was prepared from N-(toluene-4-sulfonyl)-L-thiaprolyl-L-4-(N,N-dimethylcarbamyloxy)phenylalanine tert-butyl ester, prepared as per the examples herein, following the procedure described by by Larsson and Carlson (*Acta Chemica Scan.* 1994, 48, 522).

NMR data was as follows:

$^1$H NMR (CDCl$_3$): δ=7.77 (d, 2H), 7.38 (d, 2H), 7.18 (m, 3H), 7.09 (d, 2H), 4.83-4.57 (m, 3.H), 3.77-3.60 (m, 2H), 3.36-3.23 (m, 1H), 3.15-3.00 (m, 7H), 2.85-2.73 (m, 1H), 2.46 (s, 3H), 1.50 (s, 9H).

EXAMPLE 62

Synthesis of N-(4-Fluorobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CDCl$_3$): δ=7.96 (d, 2H), 7.80 (d, 2H), 7.26-7.13 (m, 3H), 7.01 (d, 2H), 4.72-4.70 (m, 1H), 4.11-4.08 (m, 1H), 3.40-3.37 (m, 1H), 3.25-3.10 (m, 2H), 3.07 (s, 3H), 3.04-3.02 (m, 1H), 2.98 (s, 3H), 2.06 (m, 1H), 2.06-2.04 (m, 1H), 1.61-1.52 (m, 3H), 1.46 (s, 9H).

$^{13}$C NMR (CDCl$_3$): δ=170.3, 169.9, 154.9, 150.6, 139.9, 134.9, 133.1, 130.2, 128.4, 126.5, 121.7, 82.7, 62.3, 5.35, 49.6, 37.2, 36.6, 36.3, 30.0, 27.8 24.1.

EXAMPLE 63

Synthesis of N-(1-Methylpyrazolyl-4-sulfonyl)-L-prolyl-L-4-(N,N-dimethylcarbamyloxy)phenylalanine The title compound was prepared from the product of Example 117 using the procedure described in Method 11.

NMR data was as follows:

$^1$H NMR (CDCl$_3$): δ=8.84 (br s, 1H), 7.93 (s, 1H), 7.79 (s, 1H), 7.68-7.65 (m, 1H), 7.18 (d, 2H), 6.99 (d, 2H), 4.88-4.81 (m, 1H), 4.08-4.06 (m, 1H), 3.92 (s, 3H), 3.45-3.40 (m, 1H), 3.34-3.27 (m, 1H), 3.11-3.01 (m, 5H), 2.97 (s, 3H), 1.82 (m, 1H), 1.66-1.57 (m, 2H), 1.45 (m, 1H).

$^{13}$C NMR (CDCl$_3$): δ=173.1, 172.9, 159.1, 158.6, 150.4, 138.8, 133.4, 133.2, 130.3, 121.9, 117.3, 62.0, 53.1, 49.7, 39.4, 36.6, 36.5, 36.4, 30.4, 23.9.

EXAMPLE 64

Synthesis of N-(Toluene-4-sulfonyl)-L-(1,1-dioxo)thiaprolyl-L-4-(N,N-dimethylcarbamyloxy)phenylalanine The title compound was prepared from the product of Example 61 using the procedure described in Method 11.

NMR data was as follows:

$^1$H NMR (CDCl$_3$): δ=8.34 (d, 1H), 7.70 (d, 2H), 7.33 (d, 2H), 7.14 (d, 2H), 7.01 (d, 2H), 5.07 (m, 1H), 4.93 (m, 1H), 4.43 (d, 1H), 4.01 (d, 1H), 3.68 (m, 1H), 3.37 (m, 1H), 3.17 (s, 3H), 3.14 (m, 1H), 3.09 (s, 3H), 2.54 (m, 1H), 2.43 (s, 3H).

$^{13}$C NMR (CDCl$_3$): δ=171.5, 166.4, 156.4, 150.5, 145.5, 134.2, 134.1, 131.4, 130.3, 128.1, 121.8, 64.3, 59.2, 53.7, 50.5, 36.9, 36.5, 35.8, 21.6.

EXAMPLE 65

Synthesis of N-(4-Fluorobenzenesulfonyl)-L-thiaprolyl-L-4-(N,N-dimethylcarbamyloxy)phenylalanine The title compound was prepared from the product of Example 84 using the procedure described in Method 11.

NMR data was as follows:

$^1$H NMR (CDCl$_3$): δ=7.83 (m, 2H), 7.73 (d, 1H), 7.16 (m, 4H), 6.99 (d, 2H), 5.57 (br s, 1H), 4.87 (m, 1H), 4.76 (m, 1H), 4.53 (d, 1H), 4.10 (d, 1H), 3.34 (m, 1H), 3.22 (d, 2H), 3.12 (s, 3H), 3.04 (s, 3H), 2.43 (m, 1H).

$^{13}$C NMR (CDCl$_3$): δ=172.1, 168.7, 155.7, 150.5, 133.6, 133.1, 130.8, 130.7, 121.7, 116.9, 116.6, 65.3, 53.3, 51.3, 36.8, 36.4, 36.1, 33.4.

EXAMPLE 66

Synthesis of N-(4-Fluorobenzenesulfonyl)-L-(5,5-dimethyl)-thiaprolyl-L-4-(N,N-dimethylcarbamyloxy)phenylalanine tert-Butyl Ester The title compound was prepared following the procedure described for the preparation of Example 2 with the substitution of appropriate starting materials.

NMR data was as follows:

$^1$H NMR (CDCl$_3$): δ=7.91 (m, 2H), 7.26 (m, 4H), 7.02 (d, 2H), 6.96 (d, 1H), 4.75 (m, 1H), 4.55 (d, 1H), 4.42 (d, 1H), 3.86 (s, 1H), 3.08 (s, 3H), 3.05 (m, 2H), 3.00 (s, 3H), 1.43 (s, 9H), 1.17 (s, 3H), 1.16 (s, 3H).

$^{13}$C NMR (CDCl$_3$): δ=169.9, 168.1, 167.6, 164.2, 154.9, 150.6, 133.1, 132.2, 131.0, 130.9, 130.4, 121.7, 116.9, 116.6, 82.7, 73.5, 54.7, 53.7, 50.5, 37.8, 36.6, 36.4, 29.1, 27.8, 23.8.

EXAMPLE 67

Synthesis of N-(4-Fluorobenzenesulfonyl)-L-(1,1-dioxothiamorpholin-3-carbonyl)-L-4-(1,1-dioxothiomorpholin-4-ylcarbonyloxy)phenylalanine tert-Butyl Ester The title compound was prepared following the procedure described for the preparation of Example 68.

NMR data was as follows:

$^1$H NMR (CDCl$_3$): δ=7.91-7.87 (m, 2H), 7.27-7.25 (m, 2H), 7.15 (d, 2H), 6.51 (d, 1H), 4.93-4.90 (m, 1H), 4.64-4.58 (m, 1H), 4.14-3.99 (m, 7H), 3.28-2.90 (m, 10H), 1.47 (s, 9H).

$^{13}$C NMR (CDCl$_3$): δ=170.1, 167.6,164.5, 153.1, 149.8, 133.9, 133.4, 130.7, 130.5, 121.7, 117.4, 117.1, 83.1, 56.1, 53.4, 51.6, 49.9, 48.9, 43.1, 41.6, 36.2, 27.8.

EXAMPLE 68

Synthesis of N-(Toluene-4-sulfonyl)-L-(1,1-di-oxothiamorpholin-3-carbonyl)-L-4-(1,1-dioxothio-morpholin-4-ylcarbonyloxy)phenylalanine tert-Butyl Ester Substituting thiomorpholine for N-methylpiperazine, and following the method for the preparation of Example 4 and oxidation of the sulfur group in the thiomorpholino ring per by Larsson and Carlson (*Acta Chemica Scan.* 1994, 48, 522) gave the title compound as a white solid.
NMR data was as follows:
$^1$H NMR (CDCl$_3$): δ=7.75 (d, 2H), 7.35 (d, 2H), 7.17 (d, 2H), 6.99 (d, 2H), 6.65 (d, 1H), 4.92-4.90 (m, 1H), 4.63-4.60 (m, 1H), 4.15-3.95 (m, 7H), 3.30-3.23 (m, 1H), 3.14 (t, 4H), 3.07-2.80 (m, 6H), 2.45 (s, 3H), 1.48 (s, 9H).
$^{13}$C NMR (CDCl$_3$): δ=169.9, 164.8, 153.1, 149.8, 145.5, 135.1, 133.6, 130.7, 127.5, 121.8, 82.9, 60.3, 56.1, 53.7, 51.8, 49.3, 48.4, 43.1, 42.7, 41.5, 36.3, 27.8, 21.5.

EXAMPLE 69

Synthesis of N-(4-Fluorobenzenesulfonyl)-L-prolyl-L-4-(thiomorpholin-4-ylcarbonyloxy)phenylalanine tert-Butyl Ester The title compound was prepared following the procedure described in Example 37 and substitution of appropriate starting materials.
NMR data was as follows:
1H NMR (CDCl$_3$): δ=7.88-7.83 (m, 2H), 7.26-7.15 (m, 5H), 7.01 (d, 2H), 4.74-4.67 (m, 1H), 4.08-4.05 (m, 1H), 3.91-3.80 (m, 4H), 3.41-3.35 (m, 1H), 3.24-3.00 (m, 3H), 2.70-2.65 (t, 4H), 2.06-2.04 (m, 1H). 1.60-1.46 (m, 12H).
$^3$C NMR (CDCl$_3$): δ=170.5, 169.8, 153.4, 150.2, 133.5, 130.7, 130.5, 130.3, 121.6, 116.8, 116.5, 82.6, 62.2, 53.6, 49.6, 47.0, 46.4, 37.2, 29.8, 27.8, 27.3, 27.0, 24.1.

EXAMPLE 70

Synthesis of N-(4-Fluorobenzenesulfonyl)-L-(5,5-dimethyl)-thiaprolyl-L-4-(N,N-dimethylcarbamy-loxy)phenylalanine The title compound was prepared from the product of Example 66 using the procedure described in Method 11.
NMR data was as follows:
$^1$H NMR (CDCl$_3$): δ=7.90 (m, 2H), 7.30-7.14 (m, 5H), 7.02 (d, 2H), 5.83 (br s, 1H), 4.90 (m, 1H), 4.57 (d, 1H), 4.40 (d, 1H), 3.96 (s, 1H), 3.09 (s, 3H), 3.28-3.02 (m, 2H), 3.00 (s, 3H), 1.13 (s, 6H).
$^{13}$C NMR (CDCl$_3$): δ=173.2, 169.2, 164.2, 163.9, 155.3, 150.6, 133.1, 132.0, 131.0, 130.9, 130.6, 122.0, 117.0, 116.7, 73.3, 54.6, 53.3, 50.5, 37.0, 36.7, 36.4, 29.0, 23.7.

EXAMPLE 71

Synthesis of N-(4-Fluorobenzenesulfonyl)-L-(1,1-dioxothiamorpholin-3-carbonyl)-L-4-(morpholin-4-ylcarbonyloxy)phenylalanine tert-Butyl Ester Substituting 4-morpholinecarbamyl chloride for dimethyl-carbamyl chloride, and following the methods for the preparation of Example 2, gave the title compound as a white solid.

NMR data was as follows:
$^1$H NMR (CDCl$_3$): δ=7.91-7.87 (m, 2H), 7.26-7.20 (m, 2H), 7.11 (d, 2H), 6.98 (d, 2H), 6.43 (d, 1H), 4.95-4.92 (m, 1H), 4.62-4.60 (m, 1H), 4.05-4.00 (m, 2H), 3.74 (t, 4H), 3.66-3.52 (m, 4H), 3.30-2.92 (m, 6H), 1.48 (s, 9H).
$^{13}$C NMR (CDCl$_3$): δ=170.1, 164.5, 150.4, 134.6, 132.7, 130.5, 122.0, 117.4, 1.17.1, 83.1, 66.5, 56.1, 53.4, 49.9, 49.0, 44.7, 44.0, 41.6, 36.2, 27.8.

EXAMPLE 72

Synthesis of N-(4-Trifluoromethoxybenzenesulfo-nyl)-L-prolyl-L-4-(N,N-dimethylcarbamyloxy)phe-nylalanine tert-Butyl Ester The title compound was prepared following the procedure described for the preparation of Example 2 and substitution of appropriate starting materials.
NMR data was as follows:
$^1$H NMR (CDCl$_3$): δ=7.89 (d, 2H), 7.35 (d, 2H), 7.25-7.13 (m, 3H), 7.01 (d, 2H), 4.70 (m, 1H), 4.09-4.06 (m, 1H), 3.39-3.36 (m, 1H), 3.24-3.01 (m, 5H), 2.98 (s, 3H), 2.05 (m, 1H), 1.62-1.47 (m, 3H), 1.46 (s, 9H).
$^{13}$C NMR (CDCl$_3$): δ=170.4, 169.9, 154.9, 152.7, 150.6, 134.6, 113.2, 130.2, 130.1, 121.7, 120.2, 82.7, 62.2, 53.6, 49.6, 37.2, 36.6, 36.3, 29.9, 27.8, 24.1.

EXAMPLE 73

Synthesis of N-(Toluene-4-sulfonyl)-L-(1,1-di-oxothiamorpholin-3-carbonyl)-L-4-(N,N-dimethyl-carbamyloxy)phenylalanine Isopropyl Ester Following the method for the preparation of Example 2 and oxidation of the sulfur group in the thiomorpholino ring per by Larsson and Carlson (*Acta Chemica Scan.* 1994, 48, 522) gave the title compound.
NMR data was as follows:
$^1$H NMR (CDCl$_3$): δ=7.70 (d, 2H), 7.31 (d, 2H), 7.04 (d, 2H), 6.93 (d, 2H), 6.59 (d, 1H), 5.01 (m, 2H), 4.65 (m, 1H), 4.01 (d, 1H), 3.90 (d, 1H), 3.25 (m, 1H), 3.00 (s, 3H), 2.82 (m, 8H), 2.37 (s, 3H), 1.22 (s, 3H), 1.20 (s, 3H).
$^{13}$C NMR (CDCl$_3$): δ=170.3, 165.0, 154.6, 150.5, 145.1, 135.2, 132.3, 130.4, 130.0, 127.2, 122.1, 69.5, 55.9, 53.1, 49.1, 48.5, 41.4, 36.3, 36.1, 35.9, 21.4.

EXAMPLE 74

Synthesis of N-(4-Fluorobenzenesulfonyl)-L-(1,1-dioxo-5,5-dimethyl)thiaprolyl-L-4-(N,N-dimethyl-carbamyloxy)phenylalanine tert-Butyl Ester The title compound was prepared from the product of Example 66 following the procedure described by Larsson and Carlson (*Acta Chemica Scan.* 1994, 48, 522).
NMR data was as follows:
$^1$H NMR (CDCl$_3$): δ=7.88 (m, 2H), 7.24 (m, 4H), 7.05 (d, 2H), 6.95 (d, 1H), 4.80 (m, 1H), 4.40 (m, 2H), 4.10 (s, 1H), 3.17-3.03 (m, 2H), 3.10 (s, 3H), 3.01 (s, 3H), 1.47 (s, 9H), 1.36 (s, 3H), 1.11 (s, 3H).
$^{13}$C NMR (CDCl$_3$): δ=169.8, 168.6, 166.0, 154.5, 150.8, 139.7, 133.0, 131.5, 131.4, 130.3, 122.0, 117.1, 116.8, 83.0, 68.0, 60.9, 59.3, 53.8, 37.4, 36.6, 36.4, 27.8, 18.9, 18.8.

EXAMPLE 75

Synthesis of N-(Toluene-4-sulfonyl)-L-(1,1-dioxo-5,5-dimethyl)thiaprolyl-L-4-(N,N-dimethylcarbamyloxy)phenylalanine Isopropyl Ester The title compound was prepared from the product of Example 11 following the procedure described by Larsson and Carlson (*Acta Chemica Scan.* 1994, 48, 522).
NMR data was as follows:
$^1$H NMR (CDCl$_3$): δ=7.75 (d, 2H), 7.38 (d, 2H), 7.21 (d, 2H), 7.03 (m, 3H), 5.08 (m, 1H), 4.89 (m, 1H), 4.38 (m, 2H), 4.10 (s, 1H), 3.22-3.04 (m, 2H), 3.10 (s, 3H), 3.00 (s, 3H), 2.43 (s, 3H), 1.26 (m, 9H), 1.09 (s, 3H).
$^{13}$C NMR (CDCl$_3$): δ=170.3, 166.3, 150.8, 145.9, 132.8, 131.9, 130.3, 128.6, 122.0, 69.8, 68.0, 60.9, 59.4, 53.4, 37.4, 36.6, 36.4, 21.6, 21.5, 19.2, 18.6.

EXAMPLE 76

Synthesis of N-(4-Fluorobenzenesulfonyl)-L-(5,5-dimethyl)thiaprolyl-L-4-(N,N-dimethylcarbamyloxy)phenylalanine The title compound was prepared from the product of Example 74 using the procedure described in Method 11.
NMR data was as follows:
$^{13}$C NMR (CDCl$_3$): δ=171.7, 167.9, 137.3, 164.5, 155.9, 150.4, 133.6, 131.8, 131.3, 131.2, 130.8, 121.9, 117.1, 116.8, 67.8, 60.9, 59.9, 53.8, 36.8, 36.6, 36.0, 19.1, 19.0.

EXAMPLE 77

Synthesis of N-(Pyrimidine-2-sulfonyl)-L-prolyl-L-4-(N,N-dimethylcarbamyloxy)phenylalanine The title compound was prepared from the product of Preparative Example B using the procedure described in Method 11.
NMR data was as follows:
$^1$H NMR (CDCl$_3$): δ=8.45 (br m, 2H), 8.22 (br s, 1H), 7.55 (d, 1H), 7.11 (d, 2H), 6.95 (d, 2H), 6.81 (m, 1H), 4.80-4.74 (m, 2H), 3.70 (m, 1H), 3.55 (m, 1H), 3.20-3.08 (m, 4H), 2.98 (s, 3H), 2.89-2.76 (m, 1H), 2.13-1.96 (m, 3H), 1.60 (m, 1H).
$^{13}$C NMR (CDCl$_3$): δ=190.0, 173.6, 171.0, 155.2, 153.9, 150.6, 133.2, 130.1, 121.9, 110.3, 62.0, 55.1, 48.2, 36.6, 36.6, 36.3, 30.2, 23.4.

EXAMPLE 78

Synthesis of N-(Toluene-4-sulfonyl)-L-(1,1-dioxothiamorpholin-3-carbonyl)-L-4-(4-methylpiperazin-1-ylcarbonyloxy)phenylalanine tert-Butyl Ester Following the method for the preparation of Example 4 and oxidation of the sulfur group in the thiamorpholino ring per Larsson and Carlson (*Acta Chemica Scan.* 1994, 48, 522) gave the title compound.
NMR data was as follows:
$^1$H NMR (CDCl$_3$): δ=7.76 (d, 2H), 7.37 (d, 2H), 7.12 (d, 2H), 6.96 (d, 2H), 6.57 (d, 1H), 4.95 (m, 1H), 4.62 (m, 1H), 4.03 (m, 2H), 3.67 (m, 4H), 3.25 (m, 1H), 2,89 (m, 4H), 2.45 (m, 6H), 2.35 (s, 3H), 1.48 (s, 9H).
$^{13}$C NMR (CDCl$_3$): δ=170.0, 164.8, 153.7, 150.5, 145.4, 135.3, 132.8, 130.7, 130.4, 127.5, 122.2, 82.9, 56.2, 54.6, 54.5, 53.6, 49.5, 48.6, 46.0, 44.2, 43.7, 41.6, 36.3, 27.9, 21.6.

EXAMPLE. 79

Synthesis of N-(4-Fluorobenzenesulfonyl)-L-(1,1-dioxo)thiaprolyl-L-4-(N,N-dimethylcarbamyloxy)phenylalanine The title compound was prepared from the product of Example 85 using the procedure described in Method 11.
NMR data was as follows:
$^1$H NMR (CDCl$_3$): δ=4.98, (m, 1H), 4.90 (m, 1H), 4.44 (d, 1H), 4.03 (d, 1H), 3.67 (m, 1H), 3.37(m, 1H), 3.25-3.02 (m, 1H), 3.20 (s, 3H), 3.11 (s, 3H), 2.68 (m, 1H).
$^{13}$C NMR (CDCl$_3$): δ=171.7, 167.9, 166.3, 164.4, 157.0, 156.4, 150.5, 139.6, 134.0, 133.1, 131.3, 131.1, 130.9, 121.9, 117.2, 116.9, 64.1, 58.8, 53.7, 50.6, 36.9, 36.5, 35.6.

EXAMPLE 80

Synthesis of N-(Toluene-4-sulfonyl)-L-prolyl-L-4-(isonipecotoyloxy)phenylalanine tert-Butyl Ester Substituting piperazine for N-methylpiperazine, and following the methods for the preparation of Example 4, gave the title compound as a white solid.
NMR data was as follows:
$^{13}$C NMR (CDCl$_3$): δ=7.70 (d, 2H), 7.32-7.26 (m, 2H), 7.14 (d, 2H), 7.01 (d, 2H), 4.72-4.68 (m, 1H), 4.07-4.05 (m, 1H), 3.60-3.49 (m, 4H), 3.37-3.31 (m, 1H), 3.22-2.98 (m, 3H), 2.42 (s, 3H), 2.02 (m, 2H), 1.61-1.55 (m, 6H), 1.50-1.45 (m, 13H).
$^{13}$C NMR (CDCl$_3$): δ=177.3, 170.7, 169.8, 150.6, 144.3, 133.1, 130.1, 129.9, 127.9, 121.6, 110.8, 82.5, 62.2, 57.2, 53.7, 49.5, 44.9, 37.2, 29.7, 27.8, 25.7, 24.1, 21.4.

EXAMPLE 81

Synthesis of N-(Toluene-4-sulfonyl)-L-prolyl-L-4-(1,1-dioxothiomorpholin-4-ylcarbonyloxy)phenylalanine tert-Butyl Ester The product of Example 82 was oxidized by the method of Larsson and Carlson (*Acta Chemica Scan.* 1994, 48, 517-525), yielding the title compound as a white solid.
NMR data was as follows:
$^1$H NMR (CDCl$_3$): δ=7.69 (d, 2H), 7.33-7.29 (m, 3H), 7.20 (d, 2H), 7.00 (d, 2H), 4.71-4.66 (m, 1H), 4.13-4.04 (m, 5H), 3.37-3.32 (m, 1H), 3.21-3.00 (m, 7H), 2.41 (s, 3H), 2.05-2.01 (m, 1H), 1.52-1.44 (m, 12H).
$^{13}$C NMR (CDCl$_3$): δ=170.7, 169.7, 149.8, 144.3, 134.4, 133.3, 130,6, 130.0, 127.9, 121.4, 82.7, 62.4, 54.0, 52.1, 49.7, 43.2, 37.6, 29.7, 28.1, 24.4, 21.7.

EXAMPLE 82

Synthesis of N-(Toluene-4-sulfonyl)-L-prolyl-L-4-(thiomorpholin-4-ylcarbonyloxy)phenylalanine tert-Butyl Ester Substituting thiomorpholine for N-methylpiperazine, and following the methods for the preparation of Example 4, gave the title compound as a white solid.
NMR data was as follows:
$^{13}$C NMR (CDCl$_3$): δ=7.70 (d, 2H), 7.31-7.26 (m, 2H), 7.16 (d, 2H), 7.00 (d, 2H), 4.72-4.66 (m, 1H), 4.07-4.04 (m, 1H), 3.89-3.79 (m, 4H), 3.37-3.32 (m, 1H), 3.22-2.99 (m, 3H), 2.67 (t, 4H), 2.42 (s, 3H), 2.02 (m, 2H), 1.50-1.45 (m, 12H).

¹³C NMR (CDCl₃): δ=177.2, 170.7, 169.8, 153.5, 150.2, 144.3, 133.6, 132.9, 130.3, 129.9, 127.9, 121.5, 82.5, 62.4, 53.7, 49.5, 47.0, 46.4, 37.2, 29.6, 27.8, 27.3, 24.1, 21.4.

EXAMPLE 83

Synthesis of N-(Toluene-4-sulfonyl)-L-prolyl-L-4-(pyrrolidin-1-ylcarbonyloxy)phenylalanine tert-Butyl Ester Substituting pyrrolidinecarbonyl chloride for dimethylcarbamyl chloride, and following the methods for the preparation of Example 2, gave the title compound as a white solid.

NMR data was as follows:

¹H NMR (CDCl₃): δ=7.71 (d, 2H), 7.32 (d, 2H), 7.15 (d, 2H), 7.04 (d, 2H), 4.73-4.67 (m, 1H), 4.07-4.04 (m, 1H), 3.53 (t, 2H), 3.45 (t, 2H), 3.36-3.32 (m, 1H), 3.24-2.98 (m, 3H), 2.42 (s, 3H), 2.03-1.88 (m, 5H), 1.75 (s, 1H), 1.52 (1.24 (m, 12H).

¹³C NMR (CDCl₃): δ=170.7, 169.8, 153.1, 150.4, 144.3, 133.1, 130.1, 129.9, 127.9, 121.6, 110.8, 99.8, 82.5, 62.2, 53.7, 49.5, 46.3, 37.2, 29.7, 27.8, 25.6, 24.8, 24.0, 21.4.

EXAMPLE 84

Synthesis of N-(4-Fluorobenzenesulfonyl)-L-thiaprolyl-L-4-(N,N-dimethylcarbamyloxy)phenylalanine tert-Butyl Ester The title compound was prepared following the procedures described for the preparation of Example 2 and substitution of appropriate starting materials.

NMR data was as follows:

¹H NMR (CDCl₃): δ=7.87 (m, 2H), 7.28-7.13 (m, 5H), 7.02 (d, 2H), 4.70-4.60 (m, 2H), 4.58 (d, 1H), 4.06 (d, 1H), 3.38-3.01 (m, 3H), 3.09 (s, 3H), 3.00 (s, 3H), 2.58 (m, 1H), 1.47 (s, 9H).

¹³C NMR (CDCl₃): δ=169.7, 167.8, 154.9, 150.7, 132.7, 130.9, 130.7, 130.4, 121.8, 117.1, 116.8, 82.9, 65.1, 53.9, 51.4, 36.8, 36.6, 36.4, 33.1, 27.9.

EXAMPLE 85

Synthesis of N-(4-Fluorobenzenesulfonyl)-L-(1,1-dioxo)thiaprolyl-L-4-(N,N-dimethylcarbamyloxy)phenylalanine tert-Butyl Ester The title compound was prepared from the product of Example 84 following the procedure oxidation procedure of Larsson and Carlson (*Acta Chemica Scan.* 1994, 48, 517-525).

NMR data was as follows:

¹H NMR (CDCl₃): δ=7.90 (m, 2H), 7.30-7.04 (m, 7H), 4.83-4.58 (m, 3H), 3.66 (m, 2H), 3.32-3.24 (m, 1H), 3.09-2.85 (m, 2H), 3.10 (s, 3H), 3.01 (s, 3H), 1.50 (s, 9H).

¹³C NMR (CDCl₃): δ=173.1, 169.8, 168.0, 165.6, 154.9, 150.9, 132.6, 131.1, 131.0, 130.3, 122.3, 117.3, 117.0, 83.2, 62.8, 57.8, 53.9, 49.0, 36.8, 36.6, 36.4, 27.9.

EXAMPLE 86

Synthesis of N-(2,5-Dichlorothiophene-3-sulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

¹H NMR (CDCl₃): δ=7.14 (d, 2H), 7.09 (s, 1H), 7.07 (d, 1H), 7.01 (d, 2H), 4.73-4.66 (m, 1H), 4.32-4.28 (m, 1H), 3.42-3.17 (m, 3H), 3.08 (s, 3H), 3.06-3.01 (m, 1H), 2.98 (s, 3H), 2.17-2.04 (m, 1H), 1.84-1.60 (m, 2H), 1.60-1.46 (m, 1H), 1.45 (s, 9H).

¹³C NMR (CDCl₃): δ=170.2, 169.9, 154.9, 150.6, 133.4, 133.1, 131.2, 130.2, 127.9, 127.0, 121.7, 82.7, 62.2, 53.6, 49.3, 37.2, 36.6, 36.4, 30.1, 27.8, 24.2.

EXAMPLE 87

Synthesis of N-(4-Acetamidobenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

¹H NMR (CDCl₃): δ=8.58 (s, 1H), 7.70-7.67 (m, 4H), 7.32 (d, 1H), 7.14 (d, 2H), 7.01 (d, 2H), 4.68 (m, 1H), 3.99 (m, 1H), 3.37-3.34 (m, 1H), 3.23-3.16 (m, 1H), 3.11-3.01 (m, 1H), 3.08 (s, 3H), 2.98 (s, 3H), 2.13 (s, 3H), 1.97-1.94 (m, 1H), 1.55-1.47 (m, 3H), 1.44 (s, 9H).

¹³C NMR (CDCl₃): δ=171.1, 169.9, 169.4, 155.0, 150.6, 143.3, 133.3, 130.2, 130.0, 128.9, 121.7, 119.4, 82.7, 62.2, 53.8, 49.6, 37.2, 36.6, 36.4, 29.9, 27.8, 24.4, 24.1.

EXAMPLE 88

Synthesis of N-(4-tert-Butylbenzenesulfonyl)-L-(1,1-dioxothiamorpholin-3-carbonyl)-L-4-(N,N-dimethylcarbamyloxy)phenylalanine tert-Butyl Ester The title compound was prepared following the procedure outlined for the preparation of Example 73 and substitution of appropriate starting materials.

NMR data was as follows:

¹H NMR (CDCl₃): δ=7.81 (d, 2H), 7.59 (d, 2H), 7.07 (d, 2H), 6.97 (d, 2H), 6.46 (d, 1H), 4.95 (m, 1H), 4.62 (m, 1H), 4.06 (m, 2H), 3.23 (m, 1H), 3.07 (m, 4H), 2.97 (m, 4H), 2.81 (m, 4H), 1.55 (s, 9H), 1.37 (s, 9H).

¹³C NMR (CDCl₃): δ=170.0, 164.9, 158.2, 154.8, 150.6, 135.0, 132.6, 130.2, 127.4, 126.9, 122.2, 82.7, 56.1, 53.5, 49.7, 48.8, 41.5, 36.5, 36.3, 36.1, 35.2, 30.8, 27.8.

EXAMPLE 89

Synthesis of N-(Pyridine-3-sulfonyl)-L-prolyl-L-4-(N,N-dimethylcarbamyloxy)phenylalanine The title compound was prepared from the product of Example 56 using the procedure described in Method 11.

NMR data was as follows:

¹H NMR (CD₃OD): δ=8.95 (s, 1H), 8.83 (d, 1H), 8.28-8.24 (m, 1H), 7.73-7.69 (m, 1H), 7.30 (d, 2H), 7.05 (d, 2H), 4.68-4.63 (m, 1H), 4.29-4.25 (m, 1H), 3.47-3.41 (m, 1H), 3.38-3.22 (m, 2H), 3.09 (s, 3H), 3.06-3.02 (m, 1H), 2.96 (s, 3H), 1.92-1.66 (m, 4H).

¹³C NMR (CD₃OD): δ=174.2, 173.9, 160.6, 160.0, 156.9, 152.9, 152.0, 147.9, 139.1, 136.9, 135.7, 131.6, 126.5, 123.1, 63.1, 54.8, 50.4, 37.5, 36.8, 36.7, 32.2, 25.5.

EXAMPLE 90

Synthesis of N-(2-Fluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517-525). N-(2-fluorobenzene-4-sulfonyl)-L-thiamorpholine-3-carboxylic acid was prepared using the procedure described in Method 1. The title compound was prepared according to the procedures set forth above using suitable starting materials.

NMR data was as follows:

$^1$H NMR (CDCl$_3$): δ=7.92 (m, 1H), 7.69 (m, 1H), 7.34 (m, 2H), 7.16 (m, 2H), 6.99 (m, 2H), 6.60 (d, 1H), 5.01 (m, 1H), 4.64 (m, 1H), 4.03 (m, 2H), 3.29 (m, 1H), 3.06 (m, 6H), 2.90 (m, 7H), 1.49 (d, 9H).

$^{13}$C NMR (CDCl$_3$): δ=169.9, 164.8, 160.3, 156.9, 154.9, 150.7, 136.6, 136.4, 132.7, 131.0, 130.3, 128.8, 126.4, 126.2, 125.1, 122.2, 118.1, 117.8, 82.7, 56.3, 56.7, 50.2, 49.5, 41.8, 36.5, 36.3, 27.8.

EXAMPLE 91

Synthesis of N-(3-Fluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517-525). N-(3-fluorobenzene-4-sulfonyl)-L-thiamorpholine-5-carboxylic acid was prepared using the procedure described in Method 1. The title compound was prepared according to the procedures set forth above using suitable starting materials.

NMR data was as follows:

$^1$H NMR (CDCl$_3$): δ=7.66 (m, 1H), 7.58 (m, 2H), 7.34 (m, 1H), 7.07 (d, 1H), 6.92 (d, 1H), 6.42 (d, 1H), 5.00 (m, 1H), 4.58 (m, 1H), 4.02 (m, 2H), 3.22 (m, 1H), 3.05 (s, 3H), 2.98 (m, 6H), 1.45 (s, 9H).

$^{13}$C NMR (CDCl$_3$): δ=170.0, 164.5, 164.4, 161.0, 154.9, 150.6, 140.3, 140.2, 132.5, 131.9, 131.8, 130.2, 123.2, 123.1, 122.2, 121.4, 121.2, 115.0, 114.7, 82.9, 56.1, 53.4, 49.9, 49.1, 41.7, 36.5, 36.3, 36.0, 27.8.

EXAMPLE 92

Synthesis of N-(2,4-Difluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517-525). N-(2,4-difluorobenzene-4-sulfonyl)-L-thiamorpholine-5-carboxylic acid was prepared using the procedure described in Method 1. The title compound was prepared according to the procedures set forth above using suitable starting materials.

NMR data was as follows:

$^1$H NMR (CDCl$_3$): δ=7.93 (m, 1H), 7.15 (m, 2H), 7.04 (m, 4H), 6.53 (d, 1H), 4.97 (m, 1H), 4.64 (m, 1H), 4.05 (m, 2H), 3.21 (m, 3H), 3.17 (s, 3H), 2.97 (m, 5H), 1.43 (s, 9H).

$^{13}$C NMR (CDCl$_3$): δ=170.0, 164.6, 154.9, 150.7, 132.6, 132.6, 130.3, 122.6, 122.1, 112.6, 112.3, 107.0, 106.7, 106.3, 82.8, 56.3, 53.5, 50.5, 49.8, 42.0, 36.5, 36.3, 27.8.

EXAMPLE 93

Synthesis of N-(4-Acetamidobenzenesulfonyl)-L-prolyl-L-4-(N,N-dimethylcarbamyloxy)phenylalanine The title compound was prepared from the product of Example 87 using the procedure described in Method 11.

NMR data was as follows:

$^1$H NMR (CD$_3$OD): δ=8.05 (d, 1H), 7.78 (m, 4H), 7.26 (d, 2H), 7.02 (d, 2H), 4.94 (m, 1H), 4.72-4.67 (m, 1H), 4.13-4.09 (m, 1H), 3.40-3.36 (m, 1H), 3.30-3.05 (m, 3H), 3.08 (s, 3H), 2.97 (s, 3H), 2.15 (s, 3H), 1.81-1.51 (m, 4H).

$^{13}$C NMR (CD$_3$OD): δ=174.3, 174.2, 172.3, 156.9, 152.0, 144.9, 135.5, 132.4, 131.6, 130.2, 122.9, 120.7, 63.2, 54.7, 50.6, 37.5, 36.8, 36.7, 31.7, 25.4, 24.0.

EXAMPLE 94

Synthesis of N-(4-Trifluoromethoxybenzenesulfonyl)-L-prolyl-L-4-(N,N-dimethylcarbamyloxy)phenylalanine The title compound was prepared from the product of Example 72 using the procedure described in Method 11.

NMR data was as follows:

$^1$H NMR (CD$_3$OD): δ=7.93 (d, 2H), 7.48 (d, 2H), 7.28 (d, 2H), 7.03 (d, 2H), 4.72-4.68 (m, 1H), 4.17-4.13 (m, 1H), 3.45-3.42 (m, 1H), 3.28-3.11 (m, 2H), 3.14-3.07 (m, 1H), 3.09 (s, 3H), 2.97 (s, 3H), 1.85-1.69 (m, 3H), 1.59 (m, 1H).

$^{13}$C NMR (CD$_3$OD): δ=174.2, 174.1, 157.0, 153.9, 152.0, 137.3, 135.6, 131.7, 131.5, 123.0, 122.5, 121.8, 63.1, 54.7, 50.6, 37.4, 36.8, 36.6, 31.9, 25.4.

EXAMPLE 95

Synthesis of N-(4-Fluorobenzenesulfonyl)-L-(5,5-dimethyl)thiaprolyl-L-4-(N,N-dimethylcarbamyloxy)phenylalanine tert-Butyl Ester The title compound was prepared using the procedure described in Example 2 and substitution of appropriate starting materials.

NMR data was as follows:

$^1$H NMR (CDCl$_3$): δ=7.90 (m, 2H), 7.22 (m, 4H), 7.00 (m, 3H), 5.08 (m, 1H), 4.84 (m, 1H), 4.56 (d, 1H), 4.42 (d, 1H), 3.88 (s, 1H), 3.15-2.99 (m, 2H), 3.09 (s, 3H), 3.00 (s, 3H), 1.26-1.16 (m, 12H).

$^{13}$C NMR (CDCl$_3$): δ=170.4, 168.2, 167.5, 164.1, 154.9, 150.7, 132.8, 132.2, 132.1, 131.0, 130.8, 130.3, 121.8, 116.9, 116.6, 73.5, 69.6, 54.6, 53.2, 50.5, 37.6, 36.6, 36.3, 29.1, 23.8, 21.6, 21.5.

EXAMPLE 96

Synthesis of N-(4-Cyanobenzenesulfonyl)-L-prolyl-L-4-(N,N-dimethylcarbamyloxy)phenylalanine The title compound was prepared from the product of Example 58 using the procedure described in Method 11.

NMR data was as follows:

$^1$H NMR (CD$_3$OD): δ=8.14 (d, 1H), 7.94-7.89 (m, 4H), 7.29 (d, 2H), 7.03 (d, 2H), 4.70-4.66 (m, 1H), 4.21-4.17 (m, 1H), 3.47-3.40 (m, 1H), 3.31-3.21 (m, 2H), 3.11-3.04 (m, 1H), 3.09 (s, 3H), 2.97 (s, 3H), 1.87-1.72 (m, 3H), 1.70-1.61 (m, 1H).

EXAMPLE 97

Synthesis of N-(Toluene-4-sulfonyl)-L-(3,3-dimethyl)prolyl-L-4-(N,N-dimethylcarbamyloxy)phenylalanine tert-Butyl Ester The title compound was prepared using the procedure described for the preparation of Example 98.

NMR data was as follows:

$^1$H NMR (CDCl$_3$): δ=7.76 (d, 1H), 7.75 (d, 1H), 7.35 (d, 1H), 7.34 (d, 1H), 7.33 (d, 1H), 7.20 (d, 1H), 7.10 (d, 1H), 7.03 (d, 0.5H), 6.91 (d, 0.5H), 6.08 (d, 0.5H), 4.86 (ddd, 0.5H), 4.77 (q, 0.5H), 3.61-3.47 (m, 2H), 3.27-3.02 (m, 3H), 3.09 (s, 3H), 3.00 (s, 3H), 2.45 (s, 1.5H), 2.43 (s, 1.5H), 1.75-1.68 (m, 0.5H), 1.61-1.51 (m, 0.5H), 1.45 (s, 4.5H), 1.40 (s, 4.5H), 1.48-1.25 (m, 3H); 0.95 (s, 1.5H), 0.80 (s, 1.5H); 0.61 (s, 1.5H).

$^{13}$C NMR (CDCl$_3$): δ=170.4, 170.1, 170.0, 169.6, 155.0, 154.9, 150.7, 150.6, 144.3, 144.2, 133.4, 133.1, 132.8, 132.6, 130.7, 130.2, 129.9, 129.8, 128.0, 121.8, 121.7, 82.6, 82.2, 71.5, 71.2, 53.6, 52.7, 47.3, 47.2, 42.7, 42.5, 38.2, 38.1, 37.7, 37.5, 36.6, 36.3, 27.8, 27.8, 27.2, 23.4, 23.2, 21.5.

EXAMPLE 98

Synthesis of N-(Toluene-4-sulfonyl)-L-(3,3-dimethyl)prolyl-L-4-(N,N-dimethylcarbamyloxy)phenylalanine Isopropyl Ester 3,3-Dimethyl proline (see Sharma and Lubell, *J. Org. Chem.* 1996, 61, 202-209) was N-tosylated using the procedure described in Method 1. The title compound was then prepared following the procedure described for the preparation of Example 2.

NMR data was as follows:

$^1$H NMR (CDCl$_3$): δ=7.76 (d, 1H), 7.74 (d, 1H), 7.36 (d, 1H), 7.33 (d, 2H), 7.19 (d, 1H), 7.10 (d, 1H), 7.03 (d, 1H), 6.91 (d, 0.5H), 6.89 (d, 0.5H), 5.06 (sept., 0.5H), 4.96 (sept., 0.5H), 4.98-4.83 (m, 1H), 3.59-3.48 (m, 2H), 3.31-3.03 (m, 3H), 3.09 (s, 3H), 3.00 (s, 3H), 2.45 (s, 1.5H), 2.43 (s, 1.5H), 1.75-1.66 (m, 0.5), 1.62-1.52 (m, 0.5H), 1.34-1.22 (m, 3H), 1.27 (s, 1.5H), 1.25 (s, 1.5H), 1.22 (s, 1.5H), 1.20 (s, 1.5H), 0.95 (s, 1.5H), 0.78 (s, 1.5H), 0.60 (s, 1.5H), 0.57 (s, 1.5H).

$^{13}$C NMR (CDCl$_3$): δ=170.8, 170.6, 170.0, 169.7, 154.9, 150.8, 150.6, 144.4, 144.2, 133.2, 132.5, 132.5, 130.7, 130.2, 129.9, 129.8, 128.0, 122.0, 121.8, 71.5, 17.2, 69.5, 69.3, 53.0, 52.2, 47.3, 47.2, 42.8, 42.5, 38.2, 38.1, 37.6, 37.2, 36.6, 36.3, 27.1, 23.4, 23.2, 21.6, 21.6, 21.5, 21.5.

Other compounds prepared by the methods described above include those set forth in Examples 99-137 in Table II below. In addition, Examples 101, 109, 111, 117, 132 and 137 found in Table II are exemplified as follows:

EXAMPLE 101

Synthesis of N-(Toluene-4-sulfonyl)-L-prolyl-4-(N,N-dimethylcarbamyloxy)-L-phenylalanine Isopropyl Ester The title compound was prepared following the procedure outlined for the preparation of Example 2.

NMR data was as follows:

$^1$H NMR (CD$_3$)$_2$SO: δ=8.28 (d, 1H), 7.70 (d, 2H), 7.41 (d, 2H), 7.23 (d, 2H), 6.99 (d, 2H), 4.86 (sept, 1H), 4.47 (m, 1H), 4.40 (m, 1H), 4.10 (m, 1H), 4.07 (m, 1H), 3.38 (m, 1H), 3.30 (m, 1H), 3.09 (m, 3H), 2.95 (s, 3H), 3.00 (s, 3H), 2.88 (s, 3H), 2.39 (s, 3H), 1.63 (m, 3H), 1.51 (m, 3H), 1.44 (m, 1H), 1.39 (m, 1H), 1.16 (d, 3H), 1.11 (d, 3H).

$^{13}$C NMR (CD$_3$)$_2$SO: δ=171.3, 170.8, 154.2, 150.2, 143.7, 134.1, 130.2, 130, 127.6, 121.6, 68.2, 61.2, 53.5, 49, 36.3, 36.1, 35.7, 30.5, 23.8, 21.4, 21.4, 21.

EXAMPLE 109

Synthesis of N-(Benzylsulfonyl)-L-(5,5-dimethyl)thiaprolyl-L-(4-N,N-dimethylcarbamyloxy)phenylalanine The title compound was prepared from the product of Example 111 using the procedure described in Method 11.

Physical data was as follows:

MS (FAB) (M+H)$^+$ 550.

Calcd. for: C$_{25}$H$_{31}$N$_3$O$_7$S$_2$; C, 54.62; H, 5.68; N 7.64.

Found: C 54.51; H 5.60; N 7.63.

EXAMPLE 111

Synthesis of N-(Benzylsulfonyl)-L-(5,5-dimethyl)thiaprolyl-L-(4-N,N-dimethylcarbamyloxy)phenylalanine tert-Butyl Ester The title compound was prepared following the procedure outlined for the preparation of Example 2 and by substituting the appropriate starting materials.

Physical data was as follows:

MS [M+H]$^+$ 550.

Calcd. for: C$_{29}$H$_{39}$N$_3$O$_7$S$_2$; C, 57.52; H, 6.45; N, 6.94.

Found: C, 57.32; H, 6.52; N, 6.81.

EXAMPLE 117

Synthesis of N-(Methyl-pyrazole-4-sulfonyl)-L-prolyl-L-(4-N,N-dimethylcarbamyloxy)phenylalanine tert-Butyl Ester Substituting N-methyl-pyrazole sulfonyl chloride (see Dickson, U.S. Pat. No. 3,665,009 (May 23, 1972) and following the method for the preparation of Example 56, gave the title compound.

NMR data was as follows:

$^1$H NMR (CDCl$_3$): δ=7.83 (s, 1H), 7.76 (s, 1H), 7.26 (m, 1H), 7.15 (m, 2H), 7.00 (m, 2H), 4.69 (m, 1H), 3.95 (m, 1H), 3.93 (s, 3H), 3.38 (m, 1H), 3.23-3.11 (m, 1H), 3.10-2.99 (m, 4H), 2.99 (s, 3H), 2.05 (m, 1H), 1.66-1.46 (m, 3H), 1.44 (s, 9H).

$^{13}$C NMR (CDCl$_3$): δ 170.7, 169.9, 154.9, 150.6, 138.9, 133.2, 132.5, 130.2, 121.7, 117.9, 82.6, 62.4, 53.7, 49.7, 39.6, 37.7, 36.6, 36.4, 29.9, 27.9, 24.2.

EXAMPLE 132

Synthesis of N-(4-Fluorobenzenesulfonyl)-L-prolyl-L-4-(1,1-dioxothiomorpholin-4-ylcarbonyloxy)-phenylalanine tert-Butyl Ester Substituting thiamorpholine for N-methylpiperazine, and following the method for the preparation of Example 4 and 14, gave the title compound.

NMR data was as follows:

$^1$H NMR (CDCl$_3$): δ=7.87-7.82 (m, 2H), 7.28-7.17 (m, 5H), 7.01 (d, 2H), 4.71-4.69 (m, 1H), 4.14-4.05 (m, 5H), 3.39-3.36 (m, 1H), 3.23-3.01 (m, 7H), 2.05-2.03 (m, 1H), 1.58-1.44 (m, 12H).

$^{13}$C NMR (CDCl$_3$): δ=170.4, 169.8, 153.0, 149.7, 134.2, 130.6, 130.5, 121.3, 116.8, 116.5, 82.6, 62.1, 53.6, 51.8, 49.5, 43.1, 42.7, 37.2, 29.7, 27.8, 24.2.

EXAMPLE 137

Synthesis of N-(Methyl-pyrazole-4-sulfonyl)-L-prolyl-L-(4-N,N-dimethylcarbamyloxy)-phenylalanine Isopropyl Ester The title compound was prepared following the procedure described for the preparation of Example 117.

NMR data was as follows:

$^1$H NMR (CDCl$_3$): δ 7.83 (s, 1H), 7.76 (s, 1H), 7.27 (d, 1H), 7.13 (d, 2H), 7.01 (d, 2H), 5.06-5.02 (m, 1H), 4.80-4.73 (m, 1H), 3.97-3.94 (m, 1H), 3.93 (s, 3H), 3.44-3.37 (m, 1H), 3.25-3.19 (m, 1H), 3.09-3.00 (m, 5H), 2.97 (s, 3H), 2.06-2.02 (m, 1H), 1.66-1.48 (m, 3H), 1.23 (d, 6H).

$^{13}$C NMR (CDCl$_3$): δ 170.8, 170.5, 154.9, 150.6, 138.9, 132.9, 32.5, 130.2, 121.7, 117.8, 69.5, 62.3, 53.2, 49.7, 39.6, 37.1, 36.6, 36.3, 29.9, 24.1, 21.6, 21.5.

TABLE 4

$$R^1-\underset{\underset{O}{\|}}{\overset{\overset{O}{\|}}{S}}-\underset{R^2}{N}-\underset{R^3}{CH}-\overset{\overset{O}{\|}}{C}-\underset{H}{N}-\underset{R^5}{CH}-\overset{\overset{O}{\|}}{C}-R^6$$

| R$^1$ | R$^2$ | R$^3$ | R$^5$ | R$^6$ | Ex. No. |
|---|---|---|---|---|---|
| p-CH$_3$-ϕ- | R$^2$/R$^3$ = cyclic 3 carbon atoms (L-pyrrolidinyl) | | p-[(4-methylpiperazin-1-yl)C(O)O-]benzyl- | —O-n-butyl | 99 |
| p-CH$_3$-ϕ- | R$^2$/R$^3$ = cyclic 3 carbon atoms (L-pyrrolidinyl) | | p-[(4-methylpiperazin-1-yl)C(O)O-]benzyl- | —O-cyclopentyl | 100 |
| p-CH$_3$-ϕ- | R$^2$/R$^3$ = cyclic 3 carbon atoms (L-pyrrolidinyl) | | p-[(CH$_3$)$_2$NC(O)O-]benzyl- | —OCH(CH$_3$)$_2$ | 101 |
| p-CH$_3$-ϕ- | R$^2$/R$^3$ = cyclic 3 carbon atoms (L-pyrrolidinyl) | | p-[(piperidin-4-yl)C(O)O-]benzyl- | —OCH$_2$CH$_3$ | 102 |
| ϕ-CH$_2$— | R$^2$/R$^3$ = cyclic 3 carbon atoms (L-pyrrolidinyl) | | p-[(1-methylpiperidin-4-yl)C(O)O-]benzyl- | —OCH$_2$CH$_3$ | 103 |
| ϕ-CH$_2$— | R$^2$/R$^3$ = cyclic 3 carbon atoms (L-pyrrolidinyl) | | p-[(4-methylpiperazin-1-yl)C(O)O-]benzyl- | —OH | 104 |
| p-CH$_3$-ϕ- | R$^2$/R$^3$ = cyclic 3 carbon atoms (L-pyrrolidinyl) | | p-[(1-Boc-4-phenylpiperidin-4-yl)-C(O)O-]benzyl- | —OCH$_2$CH$_3$ | 105 |
| 1-methyl-imidazol-4-yl | R$^2$/R$^3$ = cyclic 3 carbon atoms (L-pyrrolidinyl) | | p-[(CH$_3$)$_2$NC(O)O-]benzyl- | —OC(CH$_3$)$_3$ | 106 |
| p-NH$_2$-ϕ- | R$^2$/R$^3$ = cyclic 3 carbon atoms (L-pyrrolidinyl) | | p-[(CH$_3$)$_2$NC(O)O-]benzyl- | —OC(CH$_3$)$_3$ | 107 |
| p-CH$_3$-ϕ- | R$^2$/R$^3$ = cyclic 3 carbon atoms (L-pyrrolidinyl) | | p-[(morpholin-4-yl)C(O)O-]benzyl- | —OC(CH$_3$)$_3$ | 108 |
| ϕ-CH$_2$— | R$^2$/R$^3$ = cyclic —CH$_2$—S—C(CH$_3$)$_2$— (L-5,5-dimethyl-thiazolidin-4-yl) | | p-[(CH$_3$)$_2$NC(O)O-]benzyl- | —OH | 109 |
| p-CH$_3$-ϕ- | R$^2$/R$^3$ = cyclic —CH$_2$CH$_2$—NH—CH$_2$— (L-piperazinyl) | | p-[(CH$_3$)$_2$NC(O)O-]benzyl- | —OH | 110 |
| ϕ-CH$_2$— | R$^2$/R$^3$ = cyclic —CH$_2$—S—C(CH$_3$)$_2$— (L-5,5-dimethyl-thiazolidin-4-yl) | | p-[(CH$_3$)$_2$NC(O)O-]benzyl- | —OC(CH$_3$)$_3$ | 111 |
| p-CH$_3$-ϕ- | R$^2$/R$^3$ = cyclic 3 carbon atoms (L-pyrrolidinyl) | | p-[(CH$_3$)$_2$NC(O)O-]benzyl- | —NH-adamantyl | 112 |
| p-CH$_3$-ϕ- | R$^2$/R$^3$ = cyclic 3 carbon atoms (L-pyrrolidinyl) | | p-[(CH$_3$)$_2$NC(O)O-]benzyl- | —NHCH$_2$C(O)OH | 113 |
| p-CH$_3$-ϕ- | R$^2$/R$^3$ = cyclic 3 carbon atoms (L-pyrrolidinyl) | | p-[(CH$_3$)$_2$NS(O)$_2$O-]benzyl- | —OCH$_3$ | 114 |
| p-CH$_3$-ϕ- | R$^2$/R$^3$ = cyclic —CH$_2$CH$_2$—NH—CH$_2$— (L-piperazinyl) | | p-[(CH$_3$)$_2$NC(O)O-]benzyl- | —OC(CH$_3$)$_3$ | 115 |

TABLE 4-continued $$R^1-\underset{\underset{O}{\overset{O}{\|}}}{S}-\underset{R^2}{N}-\underset{\underset{}{\overset{R^3}{|}}}{CH}-\overset{O}{\overset{\|}{C}}-\underset{H}{N}-\underset{\underset{}{\overset{R^5}{|}}}{CH}-\overset{O}{\overset{\|}{C}}-R^6$$

| R¹ | R² | R³ | R⁵ | R⁶ | Ex. No. |
|---|---|---|---|---|---|
| p-CH₃-φ- | R²/R³ = cyclic —CH₂CH₂—(Cbz)NHCH₂— [L-4-N—(Cbz)-piperazinyl] | | p-[(CH₃)₂NC(O)O-]benzyl- | —OC(CH₃)₃ | 116 |
| 1-methyl-pyrazol-4-yl | R²/R³ = cyclic 3 carbon atoms (L-pyrrolidinyl) | | p-[(CH₃)₂NC(O)O-]benzyl- | —OC(CH₃)₃ | 117 |
| 3-pyridyl | R²/R³ = cyclic 3 carbon atoms (L-pyrrolidinyl) | | p-[(CH₃)₂NC(O)O-]benzyl- | —OH | 118 |
| p-CH₃-φ | R²/R³ = cyclic 3 carbon atoms (L-pyrrolidinyl) | | p-[(1-Boc-piperazin-4-yl)C(O)O-]benzyl- | —OCH₂CH₃ | 119 |
| p-CH₃-φ | R²/R³ = cyclic 3 carbon atoms (L-pyrrolidinyl) | | p-[(morpholin-4-yl)C(O)O-]benzyl- | —OCH₂CH₃ | 120 |
| p-CH₃-φ | —CH₃ | H | p-[(thiomorpholin-4-yl sulfone)-C(O)O-]benzyl- | —OC(CH₃)₃ | 121 |
| p-CH₃-φ | —CH₃ | H | p-[(thiomorpholin-4-yl)C(O)O-]benzyl- | —OH | 122 |
| p-CH₃-φ | R²/R³ = cyclic 3 carbon atoms (L-pyrrolidinyl) | | p-[(CH₃)₂NC(O)O-]benzyl- | 2,4-dioxo-tetrahydro-furan-3-yl(3,4-enol) | 123 |
| p-CH₃-φ | R²/R³ = cyclic 3 carbon atoms (L-pyrrolidinyl) | | p-[(piperazin-4-yl)C(O)O-]benzyl- | —OH | 124 |
| p-CH₃-φ | R²/R³ = cyclic 3 carbon atoms (L-pyrrolidinyl) | | p-[(1-Boc-piperazin-4-yl)C(O)O-]benzyl- | —OC(CH₃)₃ | 125 |
| p-CH₃-φ | R²/R³ = cyclic 3 carbon atoms (L-pyrrolidinyl) | | p-[(piperazin-4-yl)C(O)O-]benzyl- | —OCH₂CH₃ | 126 |
| p-CH₃-φ | R²/R³ = cyclic 3 carbon atoms (L-pyrrolidinyl) | | p-[(4-acetylpiperazin-1-yl)C(O)O-]benzyl- | —OCH₂CH₃ | 127 |
| p-CH₃-φ | R²/R³ = cyclic 3 carbon atoms (L-pyrrolidinyl) | | p-[(4-methanesulfonyl-piperazin-1-yl)-C(O)O-]benzyl- | —OCH₂CH₃ | 128 |
| p-CH₃-φ | R²/R³ = cyclic 3 carbon atoms (L-pyrrolidinyl) | | 3-nitro-4-[(morpholin-4-yl)-C(O)O-]benzyl- | —OH | 129 |
| p-CH₃-φ | R²/R³ = cyclic 3 carbon atoms (L-pyrrolidinyl) | | p-[(1-Boc-piperazin-4-yl)C(O)O-]benzyl- | —OH | 130 |
| p-CH₃-φ | —CH₃ | —C(CH₃)₃ | p-[(4-methylpiperazin-1-yl)C(O)O-]benzyl- | —OC(CH₃)₃ | 131 |
| p-F-φ | R²/R³ = cyclic 3 carbon atoms (L-pyrrolidinyl) | | p-[(1,1-dioxothiomorpholin-4-yl)-C(O)O-]benzyl- | —OC(CH₃)₃ | 132 |
| p-F-φ | R²/R³ = cyclic 3 carbon atoms (L-pyrrolidinyl) | | p-[(morpholin-4-yl)C(O)O-]benzyl- | —OC(CH₃)₃ | 133 |
| p-CH₃-φ | R²/R³ = cyclic —CH₂—CH₂—SO₂—CH₂— (L-1,1-dioxothio-morpholin-3-yl) | | p-[(morpholin-4-yl)C(O)O-]benzyl- | —OH | 134 |
| 1-methyl-pyrazol-4-yl | R²/R³ = cyclic 3 carbon atoms (L-pyrrolidinyl) | | p-[(4-methylpiperazin-1-yl)C(O)O-]benzyl- | —OC(CH₃)₃ | 135 |
| morpholin-4-yl | R²/R³ = cyclic 3 carbon atoms (L-pyrrolidinyl) | | p-[(CH₃)₂NC(O)O-]benzyl- | —OC(CH₃)₃ | 136 |
| 1-methyl-pyrazol-4-yl | R²/R³ = cyclic 3 carbon atoms (L-pyrrolidinyl) | | p-[(CH₃)₂NC(O)O-]benzyl- | —OCH(CH₃)₂ | 137 |

EXAMPLE 138

Synthesis of N-(1-Methylpyrazole-4-sulfonyl)-L-(5,5-dimethyl)thiaprolyl-L-4-(N,N-dimethylcarbamyloxy)phenylalanine tert-Butyl Ester The N-methylpyrazole sulfonyl chloride was prepared by adding N-methylpyrazole to chilled (0° C.) chlorosulfonic acid. The reaction mixture was allowed to warm to room temperature and then heated to 100° C. overnight under a stream of $N_2$. The reaction mixture was then cooled to room temperature and chilled to 0° C. To this solution was added thionyl chloride (2.5 eq.) and the reaction was stirred at room temperature for 30 min., then warmed to 70° C. for two hours. The reaction was cooled to room temperature and then chilled in an ice bath. Water and ice were slowly added to the reaction mixture to precipitate a white solid which was collected by filtration. The desired sulfonyl chloride was washed with cold water and hexane.

The title compound was then prepared following the procedure outlined for the preparation of Example 2 by substitution of the appropriate starting materials, mp: 169-170° C.

EXAMPLE 139

Synthesis of N-(1-Methylpyrazole-4-sulfonyl)-L-(5,5-dimethyl)thiaprolyl-L-4-(N,N-dimethylcarbamyloxy)phenylalanine The title compound was prepared from the product of Example 138 using the procedure described in Method 11.

NMR data was as follows:

$^1$H NMR (CDCl$_3$): δ=7.94 (s, 1H); 7.79 (s, 1H); 7.25 (d, 2H, J=8.8 Hz); 7.0 (d, 2H, J=8.8 Hz); 5.15 (br s, 1H); 4.80 (m, 1H); 4.54 (d, 1H, J=9. HHz); 4.39 (d, 1H, J=9.3 Hz); 3.93 (s, 3H); 3.88 (s, 1H); 3.23-3.02 (m, 2H0; 3.07 (s, 3H); 2.98 (s, 3H); 1.27 (s, 3H); 1.14 (s, 3H).

$^{13}$C NMR (CDCl$_3$): 173.86, 169.05, 155.23, 150.47, 139.21, 133.59, 133.15, 130.53, 121.84, 117.57, 73,58, 54,71, 53.75, 50.42, 39.60, 37.18, 36.60, 36.36, 35.11, 28.97, 23.95.

EXAMPLE 140

Synthesis of N-(Toluene-4-sulfonyl)-L-prolyl-L-4-(N-(1,4-dioxa-8-aza-spiro[4.5]decan-8-yl)carbonyloxy)phenylalanine Ethyl Ester The title compound was prepared following the procedure outlined for Example 4 by substitution of the appropriate starting materials.

Physical data was as follows:
MS (+ESI): 630 [M+H]$^+$.
Anal. Calcd. for $C_{31}H_{39}N_3O_9S \cdot 0.2\ CH_2Cl_2$: C, 57.94; H, 6.14; N, 6.50.
Found: C, 57.73; H, 5.90; N, 6.47.

EXAMPLE 141

Synthesis of N-(Toluene-4-sulfonyl)-L-prolyl-L-4-(N-(1,4-dioxa-8-aza-spiro[4.5]decan-8-yl)carbonyloxy)phenylalanine The product of Example 140 was hydrolyzed using the procedure described in Method 5 but employing methanol as the solvent and running the reaction at 25° C. for 24 h. The solvent was then evaporated, the residue taken up in $H_2O$, washed with methylene chloride and lyophilized to afford the title compound.

Physical data was as follows:
MS (+ESI): 619 [M+H]$^+$.
Anal. Calcd. for $C_{29}H_{35}N_3O_9SLi \cdot 1.5\ H_2O$: C, 53.37; H, 6.02; N, 6.44.
Found: C, 53.40; H, 5.58; N, 6.48.

EXAMPLE 142

Synthesis of N-(Toluene-4-sulfonyl)-L-prolyl-L-4-(4'-acetylpiperazin-1-ylcarbonyloxy)phenylalanine The product of Example 127 was hydrolyzed using the procedure described in Method 5 but employing methanol as the solvent and running the reaction at 25° C. for 24 h. The solvent was then evaporated, the residue taken up in $H_2O$, washed with methylene chloride and lyophilized to afford the title compound.

Physical data was as follows:
MS (+ESI): 587 [M+H]$^+$.
Anal. Calcd. for $C_{28}H_{33}N_4O_8SLi \cdot 3H_2O$: C, 52.01; H, 6.08; N, 8.66.
Found: C, 52.03; H, 5.36; N, 8.04.

EXAMPLE 143

Synthesis of N-(Toluene-4-sulfonyl)-L-prolyl-L-4-(4'-methanesulfonylpiperazin-1-ylcarbonyloxy)phenylalanine The product of Example 128 was hydrolyzed using the procedure described in Example 142.

Physical data was as follows:
MS (+ESI): 623 [M+H]$^+$.
Anal. Calcd. for $C_{27}H_{33}N_4O_9S_2Li \cdot 2\ H_2O$: C, 48.79; H, 5.61; N, 8.43.
Found: C, 48.66; H, 5.14; N, 8.04.

EXAMPLE 144

Synthesis of N-(Toluene-4-sulfonyl)-L-prolyl-L-4-(4'-phenylpiperazin-1-ylcarbonyloxy)phenylalanine The ethyl ester of the title compound was prepared following the procedure outlined for Example 4 by substitution of the appropriate starting materials. The ethyl ester was then hydrolyzed using the procedure described in Example 142.

Physical data was as follows:
MS (-ESI): 619 [M-H]$^-$.
Anal. Calcd. for $C_{32}H_{36}N_4O_7SLi \cdot 2H_2O$: C, 58.00; H, 5.93; N, 8.45.
Found: C, 57.65; H, 5.49; N, 8.13.

EXAMPLE 145

Synthesis of N-(Toluene-4-sulfonyl)-L-prolyl-L-4-(piperazin-1-ylcarbonyloxy)phenylalanine tert-Butyl Ester The product of Example 125 (0.7 g, 1 mmol) was dissolved in methylene chloride (9 mL). The solution was cooled to 0° C. and trifluoroacetic acid (1.0 mL) was added and the resulting clear solution was stirred for 4 h. The reaction solution was then diluted with additional methylene chloride (50 mL), washed with saturated sodium bicarbonate solution (3×50 mL), dried ($K_2CO_3$) and the solvent stripped off to give a white solid (0.465 g). Flash chromatography (9:1 $CH_2Cl_2$:

EtOH) of this material gave a clear oil which was washed several times with hexane to give a white solid (0.289 g, 48%).
Physical data was as follows:
MS (+ESI): 601.7 [M+1]$^+$. Anal. Calcd. for $C_{30}H_{40}N_4O_7S.0.25$ $CH_2Cl_2$: C, 58.42; H, 6.56; N, 9.01.
Found: C, 58.79; H, 6.51; N, 8.74.

EXAMPLE 146

Synthesis of 2-(Saccharin-2-yl)propionyl-L-4-(4'-methylpiperazin-1-ylcarbonyloxy)phenylalanine The title compound was prepared from the product of Example 46 using the procedure described in Method 11, mp=117-122° C. (with foaming).
Physical data was as follows:
Anal. Calcd. for $C_{25}H_{28}N_4O_8S.1.5$ $H_2O$: C, 52.53; H, 5.47; N, 9.80.
Found: C, 52.26; H, 5.36; N, 9.23.

EXAMPLE 147

Synthesis of N-(Toluene-4-sulfonyl)-L-prolyl-L-4-(4'-methanesulfonyl piperazin-1-ylcarbonyloxy)phenylalanine tert-Butyl Ester The title compound was prepared following the procedure outlined for Example 128 by substitution of the appropriate starting materials.
Physical data was as follows:
MS (+ESI): 696 [M+NH$_4$]$^+$.
Anal. Calcd. for $C_{31}H_{42}N_4O_9S_2.0.5$ $CH_2Cl_2$: C, 51.62; H, 6.00; N, 7.76.
Found: C, 51.55; H, 6.21; N, 7.60.

EXAMPLE 148

Synthesis of N-(Toluene-4-sulfonyl)-L-prolyl-L-4-(N,N-dimethylcarbamyloxy)phenylalanine (N'-tert-butoxycarbonyl-2-amino-2-methylpropyl) Ester (BOC)$_2$O (96 mg, 0.44 mmol) was added to a solution of the product from Example 9 (200 mg, 0.4 mmol.), N-Boc-2-amino-2-methyl-1-propanol (965 mg, 0.5 mmol) and a catalytic amount of DMAP in THF (92 mL) containing pyridine (50 µl). The mixture was stirred at room temperature under argon for 48 h. The mixture was poured into 1N HCl and extracted with ethyl acetate. The organic phase was washed (1N HCl), dried (MgSO$_4$) and the solvent was removed under reduced pressure. The residue was purified by flash chromatography (EtOAc:hexanes 2:1) to give the desired compound as an amorphous white foam (150 mg., 55%).
Physical data was as follows:
MS: [M+H]$^+$ at 675.
MS (+ESI): [M+NH$_4$]$^+$ at 692 (100%).

EXAMPLE 149

Synthesis of N-(Toluene-4-sulfonyl)-L-prolyl-L-4-(N,N-dimethylcarbamyloxy)phenylalanine 2-(Morpholin-4-yl)ethyl Ester The title compound was prepared following the procedure outlined for Example 148 by substituting 2-morpholinoethanol for N-Boc-2-amino-2-methyl-1-propanol.

Physical data was as follows: Anal. Calcd. for $C_{30}H_{40}N_4O_8S.0.5$ $H_2O$: C, 57.58; H, 6.60; N, 8.95.
Found: C, 57.26; H, 6.29; N, 8.82.

EXAMPLE 150

Synthesis of N-(Toluene-4-sulfonyl)-L-prolyl-L-4-(4'-acetylpiperazin-1-ylcarbonyloxy)phenylalanine tert-Butyl Ester The title compound was prepared following the procedure outlined for Example 127 by substitution of the appropriate starting materials.
Physical data was as follows:
MS (+ESI): 660.4 [M+NH$_4$]$^+$.
Anal. Calcd. for $C_{32}N_{42}N_4O_8S.0.15$ $CH_2Cl_2$: C, 58.91; H, 6.50; N, 8.55.
Found: C, 58.64; H, 6.36; N, 8.40.

EXAMPLE 151

Synthesis of N-(Toluene-4-sulfonyl)-L-prolyl-L-4-(4'-hydroxypiperidin-1-ylcarbonyloxy)phenylalanine tert-Butyl Ester The title compound was prepared following the procedure outlined for Example 4 by substituting 4-piperidinol for N-methyl piperazine.
Physical data was as follows:
Anal. Calcd. for $C_{31}H_{41}N_3O_8S.0.6$ $H_2O.0.22$ EtOAc: C, 59.28; H, 6.86; N, 6.51
Found: C, 58.92; H, 6.37; N, 6.47.

EXAMPLE 152

Synthesis of N-(Toluene-4-sulfonyl)-L-prolyl-L-4-(N-(2'-(morpholin-4'-yl)ethyl)carbamyloxy)phenylalanine tert-Butyl Ester The title compound was prepared following the procedure outlined for Example 4 by substituting 4-(2-aminoethyl)morpholine for N-methyl piperazine.
Physical data was as follows:
Anal. Calcd. for $C_{32}H_{44}N_4O_8S.0.25$ $H_2O$: C, 59.20; H, 6.91; N, 8.63
Found: C, 59.01; H, 6.54; N, 8.38.

EXAMPLE 153

Synthesis of N-(Toluene-4-sulfonyl)-L-prolyl-L-4-(N-(1,4-dioxa-8-aza-spiro [4.5]decan-8-yl)carbonyloxy)phenylalanine tert-Butyl Ester The title compound was prepared following the procedure outlined for Example 4 by substitution of the appropriate starting materials.
Physical data was as follows:
MS (-ESI): 656 [M-H]$^-$.
Anal. Calcd. for $C_{33}H_{43}N_3O_9S.0.1$ $CH_2Cl_2$: C, 59.67; H, 6.54; N, 6.31.
Found: C, 59.83; H, 6.63; N, 6.66.

EXAMPLE 154

Synthesis of N-(Toluene-4-sulfonyl)-L-prolyl-L-4-(N-(2'-hydroxyethyl)-N-methylcarbamyloxy)phenylalanine tert-Butyl Ester The title compound was prepared following the procedure outlined for Example 4 by substituting 2-(methylamino)ethanol for N-methyl piperazine.

Physical data was as follows:
Anal. Calcd. for $C_{29}H_{39}N_3O_8S \cdot 0.5 H_2O$: C, 58.18; H, 6.73; N, 7.02.
Found: C, 57.95; H, 6.5; N, 6.9.

EXAMPLE 155

Synthesis of N-(Toluene-4-sulfonyl)-L-prolyl-L-4-(4'-formyloxypiperidin-1-ylcarbonyloxy)phenylalanine The title compound was prepared by treating the product of Example 151 with formic acid overnight with stirring. The title compound was obtained as a white foam (130 mg., 94%), following removal of excess formic acid.

NMR data was as follows:
$^1$H NMR (DMSO-$d_6$, 400 MHZ) δ12.8 (s, 1H); 8.23 (s, 1H); 8.09 (d, 1H); 7.69 (d, 2H); 7.4 (d, 2H); 7.23 (d, 2H), 7.02 (d, 2H); 5.00 (m, 1H); 4.45 (m, 1H); 4.10 (m, 1H); 3.6-3.8 (br, 2H); 3.4 (br s, 1H); 3.25 (m, 2H); 3.10 (m, 2H); 2.95 (m, 1H); 2.35 (s, 3H); 1.95 (m, 2H); 1.56-1.75 (m, 5H); 1.4 (m, 1H).
IR (KBr,cm$^{-1}$) 3400, 2950, 1720, 1680, 1510, 1430, 1325, 1250, 1150, 1010, 650, 75, 540.
MS ((+)ESI, m/z (%)) 605 (100 [M+NH, 1$^+$).
Anal. Calcd. for $C_{28}H_{33}N_3O_9S \cdot 0.66H_2O$: C, 56.09; H, 5.77; N, 7.01.
Found: C, 56.14; H, 5.83; N, 6.78.

EXAMPLE 156

Synthesis of N-(Toluene-4-sulfonyl)-L-prolyl-L-4-(4'-hydroxypiperidin-1-ylcarbonyloxy)phenylalanine Isopropyl Ester The title compound was prepared following the procedure outlined for Example 4 by substitution of the appropriate starting materials, mp. 64-67° C. (with foaming).

Physical data was as follows:
Anal. Calcd. for $C_{30}H_{39}N_3O_8S \cdot 0.75 H_2O \cdot 0.1$ EtOAc: C, 58.51; H, 6.67; N, 6.73.
Found: C, 58.55; H, 6.09; N, 6.78.

EXAMPLE 157

Synthesis of N-(Toluene-4-sulfonyl)-L-prolyl-L-4-(4'-(2-hydroxyethyl)piperazin-1-ylcarbonyloxy)phenylalanine tert-Butyl Ester The carbonate was prepared by treatment of Tos-Pro-Tyr-t-butyl ester with 4-nitrophenyl chloroformate, followed by addition of N-(2-hydroxyl ethyl)piperazine (triethylamine, methylene chloride, chilled to 0° C., then stirred at room temperature overnight). The crude product was purified by flash chromatography (silica, 95:5 EtOAc:EtOH) to afford a white solid, mp.158-160° C. (0.387 g, 58%).

NMR data was as follows:
$^1$H NMR (DMSO-$d_6$, 400 MHZ) δ 8.15 (d, 1H, J=7.90 Hz); 7.70(d, 2H, J=6.59 Hz); 7.40 (d, 2H, J=7.90 Hz); 7.23(d, 2H, J=8.56 Hz); 7.00 (d, 2H, J=8.56 Hz); 4.42 (m, 1H); 4.38 (m, 1H); 4.08 (m, 1H); 3.51 (m, 4H); 3.34 (m, 3H); 3.09 (m, 1H); 2.99 (m, 2H); 2.43 (m, 6H); 2.39 (s, 3H); 1.59 (m, 3H); 1.39 (m, 1H); 1.35 (s, 9H).
IR (KBr,cm$^{-1}$) 3505, 3400, 2990, 2930, 2890, 1730, 1700, 1670, 1510, 1430, 1350, 1220, 1200, 1160, 670, 590, 545.
MS ((-)ESI, m/z (%)) 643 (98 [M-NH$_4$]).
Anal. Calcd. for $C_{32}H_{44}N_4O_8S$: C, 59.61; H, 6.88; N, 8.69.
Found: C, 59.06; H, 6.95; N, 8.43.

EXAMPLE 158

Synthesis of N-(Toluene-4-sulfonyl)-L-prolyl-L-4-(N-(2'-formyloxyethyl)-N-methylcarbamyloxy)phenylalanine The title compound was prepared by treating the product of Example 154 with formic acid overnight with stirring. The title compound was obtained as a white foam (110 mg., 77%), following removal of excess formic acid.

NMR data was as follows:
$^1$H NMR (DMSO-$d_6$, 400 MHz) δ 12.8 (s, 1H); 8.25 (d, 1H); 8.08 (d, 1H); 7.69 (d, 2H), 7.40 (d, 2H); 7.22 (d, 2H), 6.98 (dd, 2H); 4.47 (m, 1H); 4.35 (m, 1H); 4.27 (m, 1H); 4.10 (m, 1H); 3.65 (m, 1H); 3.55 (m, 1H); 2.85-3.15 (overlapping m, 7H); 2.40 (s, 3H); 1.55 (m, 3H); 1.40 (m, 1H).
IR (KBr,cm$^{-1}$) 3420, 2910, 1725, 1510, 1400, 1340, 1270, 1150, 675, 590, 550.
MS ((+)ESI, m/z (%)) 579 (100 [M+NH, 1$^+$).
Anal. Calcd. for $C_{26}H_{31}N_3O_9S \cdot 0.66H_2O$: C, 54.45; H, 5.68; N, 7.33
Found: C, 54.41; H, 5.60; N, 7.24.

EXAMPLE 159

Synthesis of N-(Toluene-4-sulfonyl)-L-prolyl-L-4-(N-(2'-hydroxyethyl)-N-methylcarbamyloxy)phenylalanine Isopropyl Ester The title compound was prepared following the procedure outlined for Example 4 by substitution of the appropriate starting materials, mp. 49-52° C.

Physical data was as follows:
Anal Calcd. for $C_{28}H_{37}N_3O_8S \cdot 0.5 H_2O$: C, 57.52; H, 6.55; N, 7.19.
Found: C, 57.56; H, 6.38; N, 7.14.

EXAMPLE 160

Synthesis of N-(Toluene-4-sulfonyl)-L-prolyl-4-(N-(methoxycarbonylmethyl)carbamyloxy)phenylalanine tert-Butyl Ester The carbonate was prepared by treatment of Tos-Pro-Tyr-t-butyl ester with 4-nitrophenyl chloroformate, followed by addition of glycine methyl ester (triethylamine, methylene chloride, chilled to 0°, then stirred at room temperature overnight). The crude product was purified by flash chromatography (silica, 3:2 EtOAc:hexane) to afford a white foam (0.640 g, 35%).

NMR data was as follows:
$^1$H NMR (DMSO-$d_6$, 400 MHz) δ 8.15 (d, 1H, J=8.12 Hz); 8.12 (d, 2H, J=6.15 Hz); 7.73 (d, 2H, J=8.34 Hz); 7.40 (d, 2H, J=7.90 Hz); 7.24 (d, 2H, J=8.56 Hz); 6.98 (d, 2H, J=8.34 Hz); 4.25 (m, 1H); 4.07 (m, 1H); 3.83 (d, 2H, J=6.15 Hz); 3.64 (s, 3H); 3.32 (m, 1H); 3.02 (m, 3H); 2.39 (s, 3H); 1.56 (m, 3H); 1.41 (m, 1H); 1.35 (s, 9H).

IR (KBr,CM$^{-1}$) 3400, 2990, 1745, 1680, 1500, 1370, 1350, 1200, 1160, 670, 600.

MS ((+)ESI, m/z (%)) 621 (100[M+NH$_4$]$^+$).

Anal. Calcd. for C$_{29}$H$_{37}$N$_3$O$_9$S: c, 57.70; H, 6.18; N, 6.96. Found: C, 57.63; H, 6.11; N, 6.74.

EXAMPLE 161

Synthesis of N-(1-Methylpyrazole-4-sulfonyl)-L-(5,5-dimethyl)thiaprolyl-L-4-(N,N-dimethylcarbamyloxy)phenylalanine Isopropyl Ester The title compound was prepared following the procedure outlined for Example 138 by substitution of the appropriate starting materials.

NMR data was as follows:

$^1$H NMR (CDCl$_3$): δ 7.91 (s, 1H), 7.81 (s, 1H), 7.21 (d, 2H, J=8.2 Hz), 7.03 (m, 3H); 5.03 (m, 1H), 4.84 (m, 1H), 4.55 (d, 1H), 4.42 (d, 1H), 3.96 (s, 3H), 3.83 (s, 1H), 3.18-3.01 (m, 2H), 3.10 (s, 3H), 3.01 (s, 3H), 1.28 (s, 3H), 1.24 (m, 6H), 1.17 (s, 3H).

$^{13}$C NMR (CDCl$_3$): δ 170.43, 166.31, 154.92, 150.68, 132.91, 132.88, 130.34, 121.78, 117.69, 73.76, 69.61, 54,79, 53.2, 50.52, 39.61, 37.62, 36.58, 36.35, 28.96, 24.02, 21.57, 21.49.

EXAMPLE 162

Synthesis of N-(Toluene-4-sulfonyl)-L-prolyl-L-4-(4'-methoxypiperidin-1-ylcarbonyloxy)phenylalanine Isopropyl Ester The title compound was prepared following the procedure outlined for Example 156 by substitution of the appropriate starting materials.

NMR data was as follows:

$^1$H NMR (DSMO-d$_6$, 400 MHz) δ 8.10 (d, 1H); 7.72 (d, 2H); 7.41(d, 2H); 7.24 (d, 2H); 7.02 (d, 2H); 4.92 (m, 1H); 4.45 (m, 1H); 4.10 (m, 1H); 3.8 (br s, 1H); 3.65 (br s, 1H); 3.40 (M, 2H); 3.25 (s, 3H); 2.95-3.15 (overlapping m, 5H); 2.40 (s, 3H); 1.85 (br, 2H); 1.4-1.6 (m, 6H); 1.18 (d, 3H); 1.12 (d, 3H).

IR (KBr,cm$^{-1}$) 3400, 2950, 1720, 1520, 1425, 1340, 1210, 1160, 1100, 625, 590, 540.

MS ((+) ESI, m/z (%)) 633 [M+NH]$^+$).

EXAMPLE 163

Synthesis of N-(Toluene-4-sulfonyl)-L-prolyl-L-4-(4'-methoxypiperidin-1-ylcarbonyloxy)phenylalanine The title compound was prepared from the product of Example 162 using the procedure described in Method 5.

NMR data was as follows:

$^1$H NMR (DMSO-d$_6$, 400 MHz) δ 12.8 (s, 1H); 8.10 (d, 1H); 7.72 (d, 2H); 7.41 (d, 2H); 7.24 (d, 2H); 7.02 (d, 2H); 4.45 (m, 1H); 4.10 (m, 1H); 3.8 (br s, 1H); 3.65 (br s, 1H); 3.40 (m, 2H); 3.25 (s, 3H); 2.95-3.15 (overlapping m, 5H); 2.40 (s, 3H); 1.85(br, 2H); 1.4-1.6 (m, 6H).

IR(KBr, cm$^{-1}$) 3400, 2950, 1720, 1520, 1425, 1340, 1210, 1160, 1100, 625, 590, 540.

MS ((−)ESI, m/z (%)) 572 (100 [M−H]$^-$).

Anal. Calcd. for C$_{28}$H$_{35}$N$_3$O$_8$S.0.33EtOAc.1H$_2$O: C, 56.73; H, 6.44; N, 6.77.

Found: C, 56.96; H, 6.01; N, 6.76.

EXAMPLE 164

Synthesis of N-(Toluene-4-sulfonyl)-L-4-oxoprolyl-L-4-(N,N-dimethylcarbamyloxy)phenylalanine tert-Butyl Ester Dichloromethane (7 mL) was cooled to −60° C. (chloroform/dry ice bath). Oxalyl chloride (0.15 mL) was added. The product from Example 165 (870 mg) and dry DMSO (0.26 mL) were dissolved in dichloromethane (8 mL) and added slowly to the above solution. The reaction was stirred at −60° C. for 30 minutes under dry conditions. Triethylamine (1.05 mL) was added. After 5 minutes, the dry ice bath was removed. The reaction was stirred at room temperature for 1 hour. The solvent was evaporated in vacuo. Ethyl acetate (30 mL) was added to the residue. The mixture was washed with citric acid solution (5%, 2×30 mL) and saturated NaHCO$_3$ solution (2×30 mL); and finally with brine. The solution was dried over MgSO$_4$. The solvent was evaporated in vacuo, and the residue was flushed on a silica gel column to give 440 mg of the desired product, mp: 78-80° C.

EXAMPLE 165

Synthesis of N-(Toluene-4-sulfonyl)-L-trans-4-hydroxyprolyl-L-4-(N,N-dimethylcarbamyloxy)phenylalanine tert-Butyl Ester N-(Toluene-4-sulfonyl)-L-trans-4-hydroxyprolyl-L-4-(hydroxy)phenylalanine tert-butyl ester (1.60 g) and dimethylcarbamyl chloride (0.30 mL) were dissolved in DMF at 0° C. in an ice bath. Potassium carbonate powder (2.03 g) was added to the solution. The ice bath was removed after 5 minutes. The reaction was stirred at room temperature for 6 hours. The solid was filtered. Ethyl acetate (40 mL) was added to the solution. The solution was washed with citric acid solution (5%, 40 mL) 2 times, and saturated NaHCO$_3$ solution (40 mL) 1 time. The solution was then washed with brine and dried with MgSO$_4$. The solvent was evaporated in vacuo to give 1.07 g of the title compound, mp: 170-172° C.

EXAMPLE 166

Synthesis of N-(3-Fluorobenzenesulfonyl)-L-prolyl-L-4-(N,N-dimethylcarbamyloxy)phenylalanine tert-Butyl Ester N-(3-Fluorobenzenesulfonyl)-L-prolyl-L-4-(hydroxy) phenylalanine tert-butyl ester (700 mg) and dimethylcarbamyl chloride (0.2 mL) were dissolved in DMF (15 mL) at 0° C. in an ice bath. Potassium carbonate powder (1.375 g) was added to the solution. The ice bath was removed after 5 minutes. The reaction was stirred at room temperature for 6 hours. The solid was filtered. Ethyl acetate (20 mL) was added to the solution. The solution was washed with citric acid solution (5%, 30 mL, 2×), and saturated NaHCO$_3$ solution. The solution was then washed with brine and dried with MgSO$_4$. The solvent was evaporated in vacuo to give 890 mg of the title compound, mp: 107-109° C.

EXAMPLE 167

Synthesis of N-(Morpholino-sulfonyl)-L-prolyl-L-(4-N,N-dimethylcarbamyloxy)phenylalanine tert-Butyl Ester N-(Morpholino-sulfonyl)-L-proline was prepared using the procedure described by Cheeseright et al., *J. Chem. Soc. Perkin Trans.* 1 1994, 12, 1595-1600. The title compound was prepared following the procedure described for the preparation of Example 2.

NMR data was as follows:

$^1$H NMR (CDCl$_3$): δ 7.13 (d, 2H), 7.03 (d, 2H), 6.92 (d, 1H), 4.71 (q, 1H), 4.25 (t, 1H), 3.67 (t, 4H), 3.39 (dt, 1H), 3.28-3.19 (m, 1H), 3.23 (t, 4H), 3.18 (dd, 1H), 3.08 (dd, 1H), 3.09 (s, 3H), 3.00 (s, 3H), 2.16-2.08 (m, 2H), 1.98-1.86 (m, 1H), 1.78-1.66 (m, 1H), 1.45 (s, 9H).

$^{13}$C NMR (CDCl$_3$): δ 171.2, 170.4, 154.8, 150.7, 132.9, 130.3, 121.7, 82.7, 66.3, 62.6, 53.3, 49.6, 46.2, 37.0, 36.6, 36.3, 30.5, 27.8, 24.7.

EXAMPLE 168

Synthesis of N-(Morpholino-sulfonyl)-L-prolyl-L-(4-N,N-dimethylcarbamyloxy)phenylalanine The title compound was prepared from the product of Example 167 using the procedure described in Method 11.

NMR data was as follows:

$^1$H NMR (CD$_3$OD): δ 8.04 (d, 1H), 7.25 (d, 2H), 7.01 (d, 2H), 4.71-4.64 (m, 1H), 4.22 (dd, 1H), 3.62-3.50 (m, 4H), 3.43-3.31 (m, 2H), 3.24 (dd, 1H), 3.11 (t, 4H), 3.09 (s, 3H), 3.03 (dd, 1H), 2.97 (s, 3H), 2.22-2.11 (m, 1H), 1.98-1.80 (m, 3H).

$^{13}$C NMR (CD$_3$OD): δ 174.65, 174.58, 174.00, 156.60, 151.70, 135.30, 131.20, 122.70, 67.10, 63.10, 54.59, 54.50, 50.6, 47.10, 37.10, 36.50, 36.40, 32.0, 25.60.

EXAMPLE 169

Synthesis of N-(1-Methylpyrazole-4-sulfonyl)-L-(1,1-dioxothiamorpholin-3-carbonyl)-L-4-(N,N-dimethylcarbamyloxy)phenylalanine tert-Butyl Ester The title compound was prepared following the procedures described for the preparation of Examples 14 and 117.

NMR data was as follows:

$^1$H NMR (CDCl$_3$): δ 7.93 (s, 1H), 7.80 (s, 1H), 7.12 (d, 2H), 6.98 (d, 2H), 6.44 (d, 1H0HH), 4.95 (m, 1H), 4.66 (m, 1H), 4.04 (m, 2H), 3.98 (s, 3H), 3.19 (m, 2H), 3.06 (m, 6H), 2.98 (m, 4H), 1.42 (m, 9H).

$^{13}$C NMR (CDCl$_3$): δ 170.58, 164.75, 154.91, 150.75, 139.33, 132.73, 132.43, 130.43, 122.18, 119.66, 83.07, 56.02, 53.23, 50.03, 49.03, 41.49, 39.63, 36.56, 36.31, 36.16, 27.87.

EXAMPLE 170

Synthesis of N-(2-Fluorobenzenesulfonyl)-L-(1,1-dioxothiamorpholin-3-carbonyl)-L-4-(N,N-dimethylcarbamyloxy)phenylalanine The title compound was prepared from the product of Example 90 using the procedure described in Method 11.

NMR data was as follows:

$^1$H NMR (CD$_3$OD): δ 7.90 (m, 1H), 7.72 (m, 1H), 7.56 (d, 1H), 7.37 (m, 2H), 7.20 (d, 2H), 7.07 (d, 2H), 5.18 (m, 1H), 4.59 (m, 1H), 4.26 (m, 1H), 3.76 (m, 2H), 3.36 (m, 1H), 3.21 (m, 2H), 3.08 (m, 6H), 2.96 (s, 3H).

$^{13}$C NMR (CD$_3$OD): δ 173.85, 168.04, 162.06, 158.69, 156.92, 152.06, 137.69, 135.05, 131.83, 131.59, 129.77, 128.44, 128.26, 126.21, 123.17, 119.04, 118.75, 57.04, 54.99, 52.08, 51.66, 43.36, 37.24, 36.83, 36.66.

EXAMPLE 171

Synthesis of N-(2,4-Difluorobenzenesulfonyl)-L-(1,1-dioxothiamorpholin-3-carbonyl)-L-4-(N,N-dimethylcarbamyloxy)phenylalanine The title compound was prepared from the product of Example 92 using the procedure described in Method 11.

NMR data was as follows:

$^1$H NMR (CD$_3$OD): δ 8.88 (m, 1/2H), 8.14 (m, 1/2H), 7.90 (m, 1H), 7.64 (m, 1H), 7.20 (m, 2H), 7.10 (m, 1H), 7.03 (m, 2H), 5.16 (m, 1H), 4.63 (m, 1H), 4.28 (m, 1H), 3.75 (m, 2H), 3.41 (m, 1H), 3.15 (m, 5H), 3.02 (m, 4H).

$^{13}$C NMR (CD$_3$OD): δ 173.91, 168.04, 156.93, 152.05, 135.15, 133.81, 133.67, 131.60, 123.13, 113.48, 113.18, 107.38, 107.02, 57.02, 55.02, 52.29, 51.84, 43.45, 37.34, 36.83, 36.66.

EXAMPLE 172

Synthesis of N-(Toluene-4-sulfonyl)-L-(thiamorpholin-3-carbonyl)-L-4-(N,N-dimethylcarbamyloxy)phenylalanine The title compound was prepared from the product of Example 49 using the procedure described in Method 11.

NMR data was as follows:

$^1$H NMR (CDCl$_3$): δ 7.67 (d, 2H), 7.32 (d, 2H), 7.21 (d, 2H), 7.10 (d, 1H), 7.00 (d, 2H), 5.40 (bs, >1H), 4.85 (m, 2H), 3.95 (m, 1H), 3.41 (m, 1H), 3.07 (m, 6H), 2.98 (m, 4H), 2.62 (m, 1H), 2.41 (m, 5H), 2.13 (m, 1H).

$^{13}$C NMR (CDCl$_3$): δ 173.40, 168.49, 155.26, 144.44, 136.88, 132.95, 130.51, 130.30, 127.28, 122.08, 55.34, 53.45, 43.43, 36.62, 36.38, 35.85, 25.25, 24.54, 21.43.

EXAMPLE 173

Synthesis of N-(Pyridine-3-sulfonyl)-L-(5,5-dimethyl-thiaprolyl-L-4-(N,N-dimethylcarbamyloxy)phenylalanine Isopropyl Ester The title compound was prepared following the procedure outlined for the preparation of Example 56 by substitution of the appropriate starting materials.

NMR data was as follows:

$^1$H NMR (CDCl$_3$): δ 9.13 (m, 1H), 8.90 (m, 1H), 8.19 (m, 1H), 7.56 (m, 1H), 7.23 (d, 2H), 7.04 (d, 2H), 6.93 (d, 1H), 5.07 (m, 1H), 4.85 (m, 1H), 4.62 (d, 1H), 4.48 (d, 1H), 3.92 (s, 1H), 3.20-3.05 (m, 2H), 3.12 (s, 3H), 3.03 (s, 3H), 1.32-1.16 (m, 12H).

$^{13}$C NMR (CDCl$_3$): δ170.30, 167.75, 154.19, 150.67, 148.59, 135.72, 132.94, 132.72, 130.27, 123.91, 121.78, 73.62, 69.64, 54.69, 53.12, 50.48, 37.50, 36.53, 36.29, 29.05, 23.73, 21.54, 21.46.

EXAMPLE 174

Synthesis of N-(3-Fluorobenzenesulfonyl)-L-(1,1-dioxothiamorpholin-3-carbonyl)-L-4-(N,N-dimethylcarbamyloxy)phenylalanine The title compound was prepared from the product of Example 91 using the procedure described in Method 11.
NMR data was as follows:
$^1$H NMR (CD$_3$OD): δ 7.68 (m, 3H), 7.44 (m, 1H), 7.20 (m, 2H), 7.01 (m, 2H), 5.21 (m, 1H), 4.60 (m, 1H), 4.20 (m, 1H), 3.75 (m, 1H), 3.43 (m, 1H), 3.21 (m, 3H), 3.02 (m, 4H), 2.96 (m, 4H).
$^{13}$C NMR (CD$_3$OD): δ 173.98, 167.98, 165.89, 162.56, 156.94, 152.06, 142.70, 142.61, 135.11, 133.30, 133.19, 131.57, 124.71, 123.25, 122.21, 121.93, 116.05, 115.71, 57.27, 54.87, 54.79, 51.29, 51.06, 43.24, 37.11, 36.83.

EXAMPLE 175

Synthesis of N-(1-Methylpyrazole-4-sulfonyl)-L-(1,1-dioxothiamorpholin-3-carbonyl)-L-4-(N,N-dimethylcarbamyloxy)phenylalanine The title compound was prepared from the product of Example 169 using the procedure described in Method 11.
NMR data was as follows:
$^1$H NMR (CD$_3$OD): δ 8.11 (s, 1H), 7.83 (s, 1H), 7.36 (d, 1H), 7.24 (d, 2H), 7.02 (d, 2H), 5.16 (m, 1H), 4.69 (m, 1H), 4.19 (m, 1H), 3.90 (s, 3H), 3.81 (m, 2H), 3.33 (m, 3H), 3.10 (s, 3H), 3.02 (m, 4H).
$^{13}$C NMR (CD$_3$OD): δ 174.07, 168.11, 156.93, 152.08, 140.12, 135.05, 134.90, 131.67, 123.28, 121.82, 57.33, 54.77, 50.83, 50.64, 42.94, 39.80, 37.02, 36.84, 36.76.

EXAMPLE 176

Synthesis of N-(4-tert-Butylbenzenesulfonyl)-L-(1,1-dioxothiamorpholin-3-carbonyl)-L-4-(N,N-dimethylcarbamyloxy)phenylalanine The title compound was prepared from the product of Example 88 using the procedure described in Method 11.
NMR data was as follows:
$^1$H NMR (CD$_3$OD): δ 7.70 (d, 2H), 7.53 (d, 2H), 7.04 (d, 2H), 6.87 (d, 2H), 5.09 (m, 1H), 4.48 (m, 1H), 3.99 (m, 1H), 3.60 (m, 1H), 2.90 (m, 5H), 2.80 (m, 5H), 1.15 (s, 9H).
$^{13}$C NMR (CD$_3$OD): δ 173.95, 168.09, 159.33, 156.88, 152.09, 137.52, 135.03, 131.54, 128.68, 128.15, 123.32, 57.27, 54.81, 50.75, 43.04, 36.97, 36.82, 36.65, 36.16, 31.35.

EXAMPLE 177

Synthesis of N-(Toluene-4-sulfonyl)-(3,3-dimethyl)prolyl-L4-(N,N-dimethylcarbamyloxy)phenylalanine The title compound was prepared from the product of Example 97 using the procedure described in Method 11.
NMR data was as follows:
$^1$H NMR (CDCl$_3$): δ 7.77 (d, 1H), 7.75 (d, 1H), 7.42-7.33 (m, 3.5H), 7.27 (d, 1H), 7.19 (d, 0.5H), 7.10 (d, 1H), 7.03 (d, 1H), 5.07-5.00 (m, 0.5H), 4.94-4.87 (m, 0.5), 3.67 (d, 1H), 3.58-3.52 (m, 1H), 3.35-3.25 (m, 1H), 3.19-3.08 (m, 2H), 3.11 (s, 3H), 3.02 (s, 3H), 2.45 (s, 1.5 H), 2.43 (s, 1.5H), 1.70-1.57 (m, 1H), 1.34-1.27 (m, 1H), 0.94 (s, 1.5H), 0.75 (s, 1.5H), 0.54 (s, 6H).

$^{13}$C NMR (CDCl$_3$): δ 174.6, 174.4, 171.8, 171.4, 155.7, 150.5, 150.4, 144.5, 144.4, 133.5, 132.6, 130.9, 130.6, 130.0, 129.9, 128.0, 127.9, 122.2, 122.0, 71.2, 70.9, 53.3, 52.2, 47.3, 47.1, 43.0, 42.7, 38.1, 37.9, 36.6, 36.4, 27.0, 26.8, 23.3, 23.0.

EXAMPLE 178

Synthesis of N-(2,5-Dichlorothiophene-3-sulfonyl)-L-prolyl-L-4-(N,N-dimethylcarbamyloxy)phenylalanine The title compound was prepared from the product of Example 86 using the procedure described in Method 11.
NMR data was as follows:
$^1$H NMR (CD$_3$OD): δ 8.10 (d, 1H), 7.25 (d, 2H), 7.20 (s, 1H), 7.0 (d, 2H), 4.65 (m, 1H), 4.35 (m, 1H), 3.55-3.35 (m, 2H), 3.30-3.20 (m, 2H), 3.15-3.00 (m, 4H), 2.95 (s, 3H), 2.05-1.80 (m, 2H), 1.80-1.65 (m, 2H).
$^{13}$C NMR (CD$_3$OD): δ 174.2, 173.9, 156.9, 151.9, 135.9, 135.5, 132.3, 131.6, 128.9, 128.6, 122.9, 63.1, 54.8, 54.7, 50.3, 37.4, 36.8, 36.7, 32.1, 25.5.

EXAMPLE 179

Synthesis of N-(4-Methoxybenzenesulfonyl)-L-prolyl-L-4-(N,N-dimethylcarbamyloxy)phenylalanine The title compound was prepared from the product of Example 180 using the procedure described in Method 7.
NMR data was as follows:
$^1$H NMR (CD$_3$OD): δ 7.78 (d, 2H), 7.27 (d, 2H), 7.09 (d, 2H), 7.02 (d, 2H), 4.71-4.67 (m, 1H), 4.10-4.06 (m, 1H), 3.88 (s, 3H), 3.41-3.31 (m, 1H), 3.28-3.07 (m, 6H), 2.97 (s, 3H), 1.81-1.50 (m, 4H).
$^{13}$C NMR (CD$_3$OD): δ 168.3, 168.2, 159.2, 150.9, 145.9, 129.5, 125.6, 125.3, 123.5, 116.9, 109.6, 57.2, 50.2, 48.7, 44.6, 31.4, 30.8, 30.6, 25.7, 19.3.

EXAMPLE 180

Synthesis of N-(4-Methoxybenzenesulfonyl)-L-prolyl-L-4-(N,N-dimethylcarbamyloxy)phenylalanine Isopropyl Ester The title compound was prepared using the procedure described in Example 2 by substitution of the appropriate starting materials.
NMR data was as follows:
$^1$H NMR (CDCl$_3$): δ 7.76 (d, 2H), 7.34 (d, 1H), 7.14 (d, 2H), 7.03-6.97 (m, 4H), 5.08-5.04 (m, 1H), 4.77 (m, 1H), 4.05-4.03 (m, 1H), 3.86 (s, 3H), 3.37-3.34 (m, 1H), 3.26-3.19 (m, 1H), 3.10-3.01 (m, 4H), 2.98 (s, 3H), 2.02 (m, 1H), 1.56-1.46 (m, 3H), 1.25 (d, 6H).
$^{13}$C NMR (CDCl$_3$): δ 170.8, 170.3, 163.4, 154.8, 150.5, 132.9, 130.1, 129.9, 127.6, 121.6, 114.3, 69.4, 62.1, 55.4, 53.2, 49.5, 37.1, 36.5, 36.2, 29.7, 24.0, 21.5, 21.4.

EXAMPLE 181

Synthesis of N-(Toluene-4-sulfonyl)-L-(1-oxo-thiomorpholin-3-carbonyl)thiaprolyl-L-4-(N,N-dimethylcarbamyloxy)phenylalanine The title compound was prepared from the product of Example 182 using the procedure described in Method 11.

NMR data was as follows:

¹H NMR (CD₃OD): δ 7.90 (m, 1H), 7.78 (m, 2H), 7.40 (m, 2H), 7.26 (m, 2H), 7.03 (m, 2H), 5.14 (m, 1H), 4.64 (m, 2H), 3.81 (m, 1H), 3.71 (m, 2H), 3.19 (m, 1H), 3.14 (m, 3H), 3.02 (m, 4H), 2.84 (m, 1H), 2.60 (m, 1H), 2.42 (m, 4H), 2.21 (m, 1H).

¹³C NMR (CD₃OD): δ 174.22, 173.93, 169.59, 156.88, 152.08, 152.05, 146.44, 146.26, 137.75, 137.63, 135.61, 134.96, 131.79, 131.64, 131.55, 131.39, 128.75, 128.66, 123.35, 123.06, 57.03, 54.88, 54.66, 51.64, 42.69, 42.51, 40.34, 37.12, 36.83, 36.66, 32.76, 21.51.

EXAMPLE 182

Synthesis of N-(Toluene-4-sulfonyl)-L-(1-oxo-thiomorpholin-3-carbonyl)-L-4-(N,N-dimethylcarbamyloxy)phenylalanine tert-Butyl Ester The title compound was prepared following the procedure described for the preparation of Example 49. The oxidation of the thiomorpholine group to the 1-oxo-thiomorpholine group was per Larsson and Carlson (*Acta Chemica Scan.* 1994, 48, 517-525).

NMR data was as follows:

¹H NMR (CDCl₃): δ 7.72 (m, 2H), 7.69 (m, 2H), 7.31 (m, 2H), 7.11 (m, 2H), 7.07 (m, 2H), 6.96 (m, 2H), 4.79 (m, 1H), 4.54 (m, 1H), 3.80 (m, 4H), 3.04 (4H), 2.92 (m, 3H), 2.64 (m, 1H), 2.43 (m, 4H), 1.44 (s, 3H), 1.36 (s, 6H).

¹³C NMR (CDCl₃): δ 169.8, 166.5, 166.,3 154.6, 150.5, 150.4, 144.9, 144.4, 135.7, 135.3, 132.8, 130.5, 130.1, 29.9, 127.4, 126.9, 122.1, 121.4, 82.6, 82.2, 55.6, 53.9, 53.1, 50.6, 48.1, 47.8, 41.7, 40.5, 38.3, 36.4, 36.1, 31.1, 27.5, 21.2.

EXAMPLE 183

Synthesis of N-(3,4-Difluorobenzenesulfonyl)-L-prolyl-4-(N,N-dimethylcarbamyloxy)phenylalanine Isopropyl Ester The title compound was prepared following the procedure described for the preparation of Example 2 by substitution of the appropriate starting materials.

NMR data was as follows:

¹H NMR (CDCl₃): δ 7.72-7.60 (m, 2H), 7.87-7.37 (m, 1H), 7.13-7.11 (m, 3H), 7.01 (d, 2H), 5.08-5.04 (m, 1H), 4.81-4.74 (m, 1H), 4.09-4.06 (m, 1H), 3.39

¹³C NMR (CDCl₃):δ 170.07, 169.45, 164.42, 155.06, 155.44,154.81, 152.21, 152.17, 150.58, 148.81, 148.64, 134.90, 134.85, 132.41, 130.29, 124.82, 124.71, 124.66, 121.97, 119.07, 118.76, 117.52, 117.23, 82.92, 55.98, 53.20, 50.10, 49.40, 41.76, 36.41, 36.16, 35.99, 27.64.

EXAMPLE 186

Synthesis of N-(3,4-Difluorobenzenesulfonyl)-L-(1,1-dioxothiamorpholin-3-carbonyl)-L-4-(N,N-dimethylcarbamyloxy)phenylalanine The title compound was prepared from the product of Example 185 using the procedure described in Method 11.

NMR data was as follows:

¹H NMR (CD₃OD): δ 6.22 (m, 1H), 6.03 (m, 1H), 5.84 (m, 1H), 5.58 (m, 2H), 5.38 (m, 2H), 3.33 (m, 1H), 3.01 (m, 1H), 2.57 (m, 1H), 2.14 (m, 1H), 1.91 (m, 1H), 1.66 (m, 3H), 1.44 (s, 3H), 1.35 (m, 3H), 1.32 (s, 3H).

¹³C NMR (CD₃OD): δ 173.97, 167.89, 156.94, 153.53, 152.07, 150.00, 137.48, 135.17, 131.63, 126.54, 126.43, 123.20, 120.21, 119.96, 118.84, 118.57, 57.25, 54.82, 51.29, 49.86, 43.29, 37.21, 36.85, 36.67.

EXAMPLE 187

Synthesis of N-(Toluene-4-sulfonyl)-L-(5,5-dimethyl)thiaprolyl-L-(thiomorpholin-4-ylcarbonyloxy)phenylalanine tert-Butyl Ester The title compound was prepared using the procedure described in Example 82 by substitution of the appropriate starting materials.

NMR data was as follows:

¹H NMR (CDCl₃): δ 7.64 (d, 2H), 7.33 (d, 2H), 7.25 (d, 2H), 7.08-6.97 (m, 3H), 4.76 (m, 1H), 4.57 (d, 1H), 4.38 (d, 1H), 3.83 (s, 1H), 3.95-3.78 (m, 4H), 3.09 (m, 2H), 2.69 (m, 4H), 2.43 (s, 3H), 1.44 (s, 9H), 1.16 (s, 3H), 1.08 (s, 3H).

¹³C NMR (CDCl₃): δ 169.78, 168.36, 153.53, 150.28, 144.84, 133.53, 132.76, 130.51, 130.03, 128.19, 121.58, 82.69, 73.42, 54.56, 53.78, 50.46, 47.05, 46.40, 37.80, 29.06, 27.76, 27.37, 27.04, 23.86, 21.52.

EXAMPLE 188

Synthesis of N-(Toluene-4-sulfonyl)-L-(5,5-dimethyl)thiaprolyl-L-(thiomorpholin-4-ylcarbonyloxy)phenylalanine The title compound was prepared from the product of Example 187 using the procedures described in Method 11.

NMR data was as follows:

¹H NMR (CDCl₃): δ 7.77 (d, 2H), 7.37 (d, 2H), 7.28 (d, 2H), 7.22 (d, 1H), 7.03 (d, 2H), 5.35 (brs, 1H), 4.91 (m, 1H), 4.60 (d, 1H), 4.39 (d, 1H), 3.91 (s, 1H), 3.96-3.28 (m, 4H), 3.30-3.07 (m, 2H), 2.67 (m, 4H), 2.45 (s, 3H), 1.10 (s, 3H), 1.08 (s, 3H).

¹³C NMR (CDCl₃): δ 173.09, 169.45, 153.81, 150.28, 145.02, 133.42, 132.61, 130.60, 130.12, 128.13, 121.86, 73.28, 54.51, 53.31, 50.48, 47.08, 46.47, 36.97, 28.97, 27.35, 27.03, 23.70, 21.52.

EXAMPLE 189

Synthesis of N-(1-Methylpyrazole-4-sulfonyl)-L-(5,5-dimethyl)thiaprolyl-L-4-(N,N-dimethylcarbamyloxy)phenylalanine Ethyl Ester The title compound was prepared following the procedure described for the preparation of Example 117 by substitution of the appropriate starting materials.

NMR data was as follows:

¹H NMR (CDCl₃): δ 7.89 (s, 1H), 7.81 (s, 1H), 7.19 (d, 2H), 7.00 (m, 3H), 4.87 (m, 1H), 4.54 (d, 1H), 4.42 (d, 1H), 4.18 (q, 2H), 3.95 (s, 3H), 3.81 (s, 1H), 3.11 (m, 2H), 3.08 (s, 3H), 2.99 (s, 3H), 1.30 (s, 3H), 1.25 (t, 3H), 1.16 (s, 3H).

¹³C NMR (CDCl₃): δ 170.98, 168.34, 154.91, 150.71, 139.62, 132.88, 130.28, 121.85, 117.71, 73.77, 61.66, 54.80, 53.16, 50.53, 39.64, 37.63, 36.60, 36.36, 28.98, 24.00, 13.92.

EXAMPLE 190

Synthesis of N-(Pyridine-3-sulfonyl)-L-(5,5-dimethyl)thiaprolyl-4-(N,N-dimethylcarbamyloxy)phenylalanine The title compound was prepared from the product of Example 191 using the procedure described in Method 11.

NMR data was as follows:

1H NMR (CDCl$_3$): δ 9.09 (s, 1H), 8.82 (m, 1H), 8.20 (m, 1H), 7.56 (m, 1H), 7.23 (d, 2H), 7.07 (d, 1H), 5.58 (brs, 1H), 4.83 (m, 1H), 4.56 (m, 2H), 4.07 (s, 1H), 3.14 (m, 2H), 3.07 (s, 3H), 2.99 (s, 3H), 1.26 (s, 3H), 1.18 (s, 3H).

$^{13}$C NMR (CDCl$_3$): δ 173.04, 168.29, 155.16, 153.39, 150.60, 147.96, 136.43, 133.91, 133.06, 130.66, 130.50, 124.65, 122.14, 121.91, 73.43, 54.58, 53.21, 50.38, 37.18, 36.64, 36.38,.29.25, 23.64.

EXAMPLE 191

Synthesis of N-(Pyridine-3-sulfonyl)-L-(5,5-dimethyl)thiaprolyl-L-4-(N,N-dimethylcarbamyloxy) phenylalanine tert-Butyl Ester The title compound was prepared following the procedure described for the preparation of Example 56 and substitution of appropriate starting materials.

Physical data was as follows:

MS: [M+H]$^+$ 593

Anal. Calcd. for C$_{27}$H$_{36}$N$_4$O$_7$S$_2$.0.5 H$_2$O: C, 53.88; H, 6.07; N, 9.27.

Found: C, 53.98; H, 6.07; N, 9.27.

EXAMPLE 192

Synthesis of N-(Pyridine-2-sulfonyl)-L-prolyl-L4-(N,N-dimethylcarbamyloxy)phenylalanine Isopropyl Ester Substituting 2-pyridinesulfonyl chloride (see Corey et al., *J. Org. Chem.* 1989, 54, 389-393) and following the method for the preparation of Example 56, gave the title compound.

NMR data was as follows:

$^1$H NMR (CDCl$_3$): δ 8.59 (d, 1H), 8.00-7.89 (m, 2H), 7.78 (d, 1H), 7.53-7.49 (m, 1H), 7.16 (d, 2H), 7.01 (d, 2H), 5.05-4.99 (m, 1H), 4.85-4.78 (m, 1H), 4.60-4.57 (m, 1H), 3.44-3.35 (m, 2H), 3.25-3.19 (m, 1H), 3.07 (s, 3H), 3.06-3.01 (m, 1H), 2.97 (s, 3H), 2.19-2.13 (m, 1H), 1.88-1.71 (m, 2H), 1.55 (m, 1H), 1.22-1.19 (m, 6H).

$^{13}$C NMR (CDCl$_3$): δ 170.90, 170.30, 156.20, 154.80, 150.50, 150.00, 138.00, 133.10, 130.10, 127.00, 123.40, 121.60, 69.20, 62.80, 53.30, 49.60, 37.20, 36.40, 36.20, 29.80, 24.30, 21.42, 21.40.

EXAMPLE 193

Synthesis of N-(Pyridine-2-sulfonyl)-L-prolyl-L-4-(N,N-dimethylcarbamyloxy)phenylalanine The title compound was prepared from the product of Example 192 using the procedure described in Method 7.

NMR data was as follows:

$^1$H NMR (CD$_3$OD): δ 8.67 (d, 1H), 8.27 (d, 1H), 8.07-8.02 (m, 1H), 7.96-7.91 (m, 1H), 7.65-7.61 (m, 1H), 7.27 (d, 2H), 7.01 (d, 2H), 4.72-4.69 (m, 1H), 4.58-4.54 (m, 1H), 3.44-3.37 (m, 2H), 3.28-3.24 (m, 1H), 3.13-3.05 (m, 4H), 2.96 (s, 3H), 1.94-1.89 (m, 2H), 1.70-1.63 (m, 2H).

$^{13}$C NMR (CD$_3$OD): δ 174.5, 174.4, 174.2, 157.7, 156.9, 151.9, 139.9, 135.6, 131.6, 128.8, 124.7, 122.9, 64.1, 54.8, 54.7, 50.9, 37.5, 36.8, 36.7, 31.9, 25.6.

EXAMPLE 194

Synthesis of N-(Pyridine-2-sulfonyl)-L-(5,5-dimethyl)thiaprolyl-L-4-(N,N-dimethylcarbamyloxy) phenylalanine Isopropyl Ester The title compound was prepared following the procedure described for the preparation of Example 192 by substitution of the appropriate starting materials.

NMR data was as follows:

$^1$H NMR (CDCl$_3$): δ 8.64-8.62 (m, 1H), 7.98-7.92 (m, 2H), 7.56-7.51 (m, 1H), 7.28-7.21 (m, 3H), 7.01 (d, 2H), 5.01-4.97 (m, 1H), 4.88-4.85 (m, 2H), 4.80 (d, 1H), 4.63 (d, 1H), 4.19 (s, 1H), 3.11-3.07 (m, 5H), 2.98 (s, 3H), 1.28 (s, 3H), 1.26-1.18 (m, 9H).

$^{13}$C NMR (CDCl$_3$): δ 170.3, 168.4, 155.5, 154.9, 150.7, 150.4, 138.2, 133.0, 130.4, 127.5, 123.5, 121.8, 73.5, 69.5, 54.7, 53.3, 51.0, 37.6, 36.6, 36.4, 29.3, 23.9, 21.52, 21.50.

EXAMPLE 195

Synthesis of N-(Pyridine-2-sulfonyl)-L-(5,5-dimethyl)thiaprolyl-L-4-(N,N-dimethylcarbamyloxy) phenylalanine The title compound was prepared from the product of Example 194 using the procedure described in Method 7.

NMR data was as follows:

$^1$H NMR (CD$_3$OD): δ 8.70-8.69 (m, 1H), 8.07-8.01 (m, 1H), 7.92-7.89 (m, 1H), 7.67-7.63 (m, 1H), 4.77-4.67 (m, 3H), 4.30 (s, 1H), 3.23-3.06 (m, 5H), 2.97 (s, 3H), 1.27-1.18 (m, 6H).

$^{13}$C NMR (CD$_3$OD): δ 174.1, 171.2, 157.0, 151.9, 151.6, 139.9, 135.7, 131.8, 131.7, 129.0, 124.6, 122.9, 74.3, 61.6, 55.7, 54.9, 51.9, 37.6, 36.8, 36.7, 30.1, 24.9.

EXAMPLE 196

Synthesis of N-(Toluene-4-sulfonyl)-L-(thiamorpholin-3-carbonyl)-L-4-(N,N-dimethylcarbamyloxy) phenylalanine Isopropyl Ester The title compound was prepared following the procedure described for the preparation of Example 49 by substitution of the appropriate starting materials.

NMR data was as follows:

$^1$H NMR (CDCl$_3$): δ 7.67 (d, 2H), 7.30 (d, 2H), 7.12 (d, 2H), 6.97 (d, 2H), 6.86 (d, 1H), 5.05 (m, 1H), 4.70 (m, 2H), 3.90 (m, 1H), 3.31 (m, 1H), 3.06 (m, 4H), 2.97 (s, 3H), 2.68 (m, 1H), 2.50 (m, 1H), 2.44 (s, 3H), 2.29 (m, 1H), 2.13 (m, 1H), 1.24 (s, 3H), 1.22 (s, 3H).

$^{13}$C NMR (CDCl$_3$): δ 170.35, 167.55, 155.00, 150.61, 144.20, 136.80, 132.51, 130.24, 130.14, 127.20, 121.82, 69.48, 55.14, 53.55, 43.26, 36.43, 36.16, 25.21, 24.56, 21.48, 21.31.

EXAMPLE 197

Synthesis of N-(3-Fluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:
¹H NMR (CDCl₃): δ 7.68 (d, 1H), 7.61-7.52 (m, 2H), 7.36 (dt, 1H), 7.21 (d, 2H), 7.02 (d, 2H), 6.94 (d, 1H), 5.05 (sept, 1H), 4.85 (q, 1H), 4.59 (d, 1H), 4.41 (d, 1H), 3.88 (s, 1H), 3.17-3.03 (m, 2H), 3.09 (s, 3H), 3.00 (s, 3H), 1.25 (d, 3H), 1.23 (d, 3H), 1.16 (s, 3H), 1.12 (s, 3H).
¹³C NMR (CDCl₃): δ 170.3, 168.1, 162.6, 154.9, 150.7, 137.9, 132.8, 131.3, 130.4, 123.9, 121.8, 121.0, 115.4, 73.5, 69.6, 54.5, 53.2, 50.5, 37.6, 36.6, 36.3, 29.0, 23.7, 21.6, 21.5.

EXAMPLE 198

Synthesis of N-(2-Fluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.92-7.87 (m, 1H), 7.67-7.59 (m, 1H), 7.33-7.24 (m, 2H), 7.21 (d, 2H), 7.03 (d, 2H), 6.93 (d, 1H), 5.03 (Sept, 1H), 4.83 (q, 1H), 4.67 (d, 1H), 4.63 (d, 1H), 4.03 (s, 1H), 3.16-3.03 (m, 2H), 3.09 (s, 3H), 3.00 (s, 3H), 1.31 (s, 3H), 1.24 (d, 3H), 1.22 (d, 3H), 1.19 (s, 3H).
¹³C NMR (CDCl₃): δ 170.3, 168.1, 159.2, 154.9, 150.7, 136.0, 132.9, 132.0, 130.3, 124.6, 121.8, 117.6, 73.3, 69.6, 54.8, 53.2, 50.3, 37.6, 36.6, 36.3, 29.1, 23.9, 21.6, 21.5.

EXAMPLE 199

Synthesis of N-(3,4-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.77-7.71 (m, 1H), 7.70-7.65 (m, 1H), 7.40-7.31 (m, 1H), 7.20 (d, 2H), 7.02 (d, 2H), 6.87 (d, 1H), 5.05 (Sept, 1H), 4.88-4.82 (m, 1H), 4.55 (d, 1H), 4.44 (d, 1H), 3.91 (s, 1H), 3.17-3.03 (m, 2H), 3.09 (s, 3H), 3.00 (s, 3H), 1.25 (d, 3H), 1.23 (d, 3H), 1.23 (s, 3H), 1.18 (s, 3H).
¹³C NMR (CDCl₃): δ 170.4, 167.9, 154.9, 150.7, 133.1, 132.7, 130.4, 124.4, 121.8, 118.5, 118.0, 73.6, 69.7, 54.6, 53.1, 50.5, 37.6, 36.6, 36.3, 29.2, 23.7, 21.6, 21.5.

EXAMPLE 200

Synthesis of N-(3,5-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.77-7.71 (m, 1H), 7.70-7.65 (m, 1H), 7.40-7.31 (m, 1H), 7.20 (d, 2H), 7.02 (d, 2H), 6.87 (d, 1H), 5.05 (Sept, 1H), 4.88-4.82 (m, 1H), 4.55 (d, 1H), 4.44 (d, 1H), 3.91 (s, 1H), 3.17-3.03 (m, 2H), 3.09 (s, 3H), 3.00 (s, 3H), 1.25 (d, 3H), 1.23 (d, 3H), 1.23 (s, 3H), 1.18 (s, 3H).
¹³C NMR (CDCl₃): δ 170.4, 167.9, 154.9, 150.7, 133.1, 132.7, 130.4, 124.4, 121.8, 118.5, 118.0, 73.6, 69.7, 54.6, 53.1, 50.5, 37.6, 36.6, 36.3, 29.2, 23.7, 21.6, 21.5.

EXAMPLE 201

Synthesis of N-(2,4-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.94-7.86 (m, 1H), 7.20 (d, 2H), 7.03 (d, 2H), 7.02-6.95 (m, 2H), 6.88 (d, 1H), 5.03 (Sept, 1H), 4.82 (q, 1H), 4.67 (d, 1H), 4.61 (d, 1H), 4.01 (s, 1H), 3.16-3.03 (m, 2H), 3.09 (s, 3H), 3.00 (s, 3H), 1.36 (s, 3H), 1.23 (d, 3H), 1.21 (d, 3H), 1.20 (s, 3H).
¹³C NMR (CDCl₃): δ 170.3, 167.9, 154.9, 150.7, 133.7, 132.8, 130.3, 121.8, 112.1, 106.1, 73.4, 69.6, 54.9, 53.2, 50.4, 37.6, 36.6, 36.3, 29.1, 23.9, 21.6, 21.5.

EXAMPLE 202

Synthesis of N-(4-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.82 (d, 2H), 7.53 (d, 2H), 7.21 (d, 2H), 7.02 (d, 2H), 6.93 (d, 1H), 5.05 (Sept, 1H), 4.89-4.82 (m, 1H), 4.55 (d, 1H), 4.41 (d, 1H), 3.87 (s, 1H), 3.17-3.03 (m, 2H), 3.09 (s, 3H), 3.00 (s, 3H), 1.25 (d, 3H), 1.23 (d, 3H), 1.16 (s, 6H).
¹³C NMR (CDCl₃): δ 170.3, 168.1, 154.9, 150.7, 140.4, 134.5, 132.8, 130.4, 129.7, 129.5, 121.8, 73.5, 69.6, 54.6, 53.1, 50.5, 37.6, 36.6, 36.3, 29.1, 23.8, 21.6, 21.0.

EXAMPLE 203

Synthesis of N-(3-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.88 (t, 1H), 7.78-7.75 (m, 1H), 7.64-7.61 (m, 1H), 7.51 (t, 1H), 7.21 (d, 2H), 7.02 (d, 2H), 6.92 (d, 1H), 5.05 (sept, 1H), 4.89-4.82 (m, 1H), 4.58 (d, 1H), 4.40 (d, 1H), 3.88 (s, 1H), 3.18-3.03 (m, 2H), 3.09 (s, 3H), 3.00 (s, 3H), 1.25 (d, 3H), 1.23 (d, 3H), 1.16 (s, 3H), 1.14 (s, 3H).
¹³C NMR (CDCl₃): δ 170.3, 168.0, 154.9, 150.7, 137.7, 135.7, 133.9, 132.8, 130.7, 130.3, 127.9, 126.2, 121.8, 73.6, 69.96, 54.5, 53.2, 50.5, 37.6, 36.6, 36.3, 29.1, 23.7, 21.6, 21.5.

EXAMPLE 204

Synthesis of N-(2-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:
¹H NMR (CDCl₃): δ 8.08 (dd, 1H), 7.54-7.52 (m, 2H), 7.45-7.39 (m, 1H), 7.19 (d, 2H), 7.02 (d, 2H), 6.79 (d, 1H), 5.00 (sept, 1H), 4.78 (d, 1H), 4.75-4.68 (m, 1H), 4.69 (d, 1H), 4.19 (s, 1H), 3.09 (s, 3H), 3.06 (d, 2H), 3.00 (s, 3H), 1.38 (s, 3H), 1.23 (s, 3H), 1.23 (d, 3H), 1.19 (d, 3H).
¹³C NMR (CDCl₃): δ 170.3, 168.1, 154.9, 150.7, 135.6, 134.4, 132.8, 132.7, 132.4, 130.3, 127.3, 121.8, 73.3, 69.5, 54.7, 53.3, 50.4, 37.6, 36.6, 36.3, 29.6, 23.7, 21.6, 21.5.

EXAMPLE 205

Synthesis of N-(3,4-Dichlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.97 (d, 1H), 7.70 (dd, 1H), 7.63 (d, 1H), 7.20 (d, 2H), 7.02 (d, 2H), 6.86 (d, 1H), 5.05 (sept, 1H), 4.89-4.82 (m, 1H), 4.55 (d, 1H), 4.43 (d, 1H), 3.92 (s, 1H), 3.17-3.03 (m, 2H), 3.09 (s, 3H), 3.00 (s, 3H), 1.26 (d, 3H), 1.22 (d, 3H), 1.23 (s, 3H), 1.18 (s, 3H).
¹³C NMR (CDCl₃): δ 170.3, 167.9, 154.9, 150.7, 138.7, 136.1, 134.2, 132.7, 131.4, 130.3, 129.8, 127.1, 121.8, 73.6, 69.7, 54.6, 53.1, 50.5, 37.5, 36.6, 36.3, 29.2, 23.7, 21.6, 21.5.

EXAMPLE 206

Synthesis of N-(3,5-Dichlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.
NMR data was as follows:
¹H NMR (CDCl₃): δ 7.76 (d, 2H), 7.62 (t, 1H), 7.20 (d, 2H), 7.03 (d, 2H), 6.85 (d, 1H), 5.05 (sept, 1H), 4.89-4.82 (m, 1H), 4.57 (d, 1H), 4.42 (d, 1H), 3.92 (s, 1H), 3.18-3.04 (m, 2H), 3.09 (s, 3H), 3.00 (s, 3H), 1.25 (d, 3H), 1.23 (d, 3H), 1.27 (s, 3H), 1.18 (s, 3H).
¹³C NMR (CDCl₃): δ 170.3, 167.8, 154.9, 150.7, 139.1, 136.5, 133.7, 132.7, 130.3, 126.2, 121.8, 73.7, 69.7, 54.6, 53.1, 50.5, 37.5, 36.6, 36.3, 29.2, 23.7, 21.6, 21.5.

EXAMPLE 207

Synthesis of N-(3-Chlorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.
NMR data was as follows:
¹H NMR (CDCl₃): δ 7.85 (m, 1H), 7.76 (m, 1H), 7.63 (m, 1H), 7.53 (m, 1H), 7.06 (d, 2H), 6.96 (d, 2H), 6.37 (m, 1H), 5.01 (m, 1H), 4.62 (m, 1H), 4.01 (m, 2H), 3.26 (m, 1H), 3.06 (s, 3H), 2.96 (m, 7H), 1.49 (s, 9H).
¹³C NMR (CDCl₃): δ 170.0, 164.5, 154.9, 150.6, 140.0, 136.1, 134.2, 132.5, 131.3, 130.2, 127.4, 125.5, 122.2, 82.8, 56.0, 53.3, 49.9, 49.2, 41.7, 36.5, 36.3, 36.0, 27.8.

EXAMPLE 208

Synthesis of N-(3,4-Dichlorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.
NMR data was as follows:
¹H NMR (CDCl₃): δ 7.91 (m, 1H), 7.66 (m, 2H), 7.06 (d, 2H), 6.94 (d, 2H), 6.33 (m, 1H), 4.98 (m, 1H), 4.60 (m, 1H), 3.49 (m, 3H), 3.12 (m, 2H), 3.04 (s, 3H), 3.00 (m, 2H), 2.94 (s, 3H), 1.44 (s, 9H).
¹³C NMR (CDCl₃): δ 170.0, 164.3, 154.8, 150.6, 138.8, 137.9, 134.3, 132.4 132.0, 130.3, 129.2, 126.4, 122.1, 83.0, 55.5, 53.1, 50.2, 49.5, 41.8, 36.5, 36.2, 36.0, 27.7.

EXAMPLE 209

Synthesis of N-(4-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.
NMR data was as follows:
¹H NMR (CDCl₃): δ 7.81 (d, 2H), 7.22 (d, 2H), 7.06-6.99 (m, 5H), 5.04 (sept, 1H), 4.89-4.82 (m, 1H), 4.56 (d, 1H), 4.39 (d), 3.88 (s, 3H), 3.83 (s, 1H), 3.17-3.03 (m, 2H), 3.09 (s, 3H), 3.00 (s, 3H), 1.25 (d, 3H), 1.22 (d, 3H), 1.15 (s, 3H), 1.12 (s, 3H).
¹³C NMR (CDCl₃): δ 170.3, 168.5, 163.8, 154.9, 150.7, 132.9, 130.4, 130.3, 127.4, 121.7, 114.5, 73.5, 69.5, 55.6, 54.6, 53.2, 50.5, 37.7, 36.6, 36.3, 29.1, 23.9, 21.6, 21.5.

EXAMPLE 210

Synthesis of N-(3-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.
NMR data was as follows:
¹H NMR (CDCl₃): δ 7.47-7.45 (m, 2H), 7.37-7.36 (m, 1H), 7.21 (d, 2H), 7.19-7.15 (m, 1H), 7.04-6.98 (m, 3H), 5.04 (sept, 1H), 4.88-4.82 (m, 1H), 4.58 (d, 1H), 4.40 (d, 1H), 3.89 (s, 1H), 3.87 (s, 3H), 3.17-3.03 (m, 2H), 3.09 (s, 3H), 3.00 (s, 3H), 1.25 (d, 3H), 1.23 (d, 3H), 1.15 (s, 3H), 1.08 (s, 3H).
¹³C NMR (CDCl₃): δ 170.3, 168.3, 160.2, 154.9, 150.7, 136.9, 132.9, 130.5, 130.4, 121.7, 120.2, 120.0, 112.6, 73.4, 69.6, 55.7, 54.5, 53.2, 50.4, 37.7, 36.6, 36.3, 29.1, 23.7, 21.6, 21.5.

EXAMPLE 211

Synthesis of N-(2-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.92 (dd, 1H), 7.54 (dd, 1H), 7.21 (d, 2H), 7.07-7.00 (m, 4H), 6.96 (d, 1H), 5.01 (sept, 1H), 4.83-4.76 (m, 1H), 4.73 (d, 1H), 4.61 (d, 1H), 4.17 (s, 1H), 3.93 (s, 3H), 3.14-3.03 (m, 2H), 3.09 (s, 3H), 3.00 (s, 3H), 1.36 (s, 3H), 1.22 (d, 3H), 1.21 (s, 3H), 1.19 (d, 3H).

$^{13}$C NMR (CDCl$_3$): δ 170.3, 168.7, 157.7, 154.9, 150.6, 135.4, 133.0, 132.5, 130.3, 125.2, 121.7, 120.5, 112.6, 73.3, 69.5, 56.0, 54.8, 53.3, 50.4, 37.7, 36.6, 36.3, 29.2, 24.1, 21.6, 21.5.

EXAMPLE 212

Synthesis of N-(3,4-Dimethoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.50 (dd, 1H), 7.31 (d, 1H), 7.21 (d, 2H), 7.05-7.01 (m, 3H), 6.97 (d, 1H), 5.04 (sept, 1H), 4.89-4.82 (m, 1H), 4.56 (d, 1H), 4.40 (d, 1H), 3.95 (s, 3H), 3.94 (s, 3H), 3.89 (s, 1H), 3.17-3.03 (m, 2H), 3.09 (s, 3H), 3.00 (s, 3H), 1.25 (d, 3H), 1.22 (d, 3H), 1.16 (s, 3H), 1.14 (s, 3H).

$^{13}$C NMR (CDCl$_3$): δ 170.3, 168.5, 154.9, 153.5, 150.7, 149.4, 132.9, 130.4, 127.6, 122.3, 121.7, 110.6, 110.3, 73.5, 69.6, 56.3, 56.1, 54.6, 53.2, 50.5, 37.7, 36.6, 36.3, 29.2, 23.8, 21.6, 21.5.

EXAMPLE 213

Synthesis of N-(2,4-Difluorobenzenesulfonyl)-L-(thiamorpholin-3-carbonyl)-L-4-(N,N-dimethylcarbamyloxy)phenylalanine Isopropyl Ester The title compound was prepared following the procedure described for the preparation of Example 49 by substitution of the appropriate starting material.

NMR data was as follows:

$^1$H NMR (CDCl$_3$): δ 7.89 (m, 1H), 7.16 (m, 2H), 6.97 (m, 4H), 6.77 (d, 1H), 4.72 (m, 1H), 4.60 (m, 1H), 3.92 (m, 1H), 3.29 (m, 1H), 3.09 (m, 5H), 2.93 (s, 3H), 2.70 (m, 2H), 2.55 (m, 1H), 2.10 (m, 1H), 1.42 (s, 9H).

$^{13}$C NMR (CDCl$_3$): δ 170.0, 168.0, 167.7, 137.1, 164.4, 164.3, 161.1, 160.9, 157.7, 157.5, 154.8, 150.5, 132.7, 132.6, 132.4, 130.4, 124.0, 123.8, 121.7, 112.2, 111.9, 106.5, 106.1, 105.8, 82.6, 55.4, 53.9, 43.5, 36.4, 36.2, 27.7, 26.8, 25.5.

EXAMPLE 214

Synthesis of N-(3,4-Dichlorobenzenesulfonyl)-L-(1,1-dioxothiamorpholin-3-carbonyl)-L-4-(N,N-dimethylcarbamyloxy)phenylalanine The title compound was prepared from the product of Example 208 using the procedure described in Method 11.

NMR data was as follows:

$^1$H NMR (CD$_3$OD): δ 8.04 (m, 1H), 7.68 (m, 2H), 7.52 (m, 1H), 7.21 (d, 2H), 7.02 (d, 2H), 5.22 (m, 1H), 4.63 (m, 1H), 4.22 (m, 1H), 3.71 (m, 1H), 3.57 (m, 1H), 3.30 (m, 3H), 3.08 (s, 3H), 3.02 (m, 3H), 2.97 (s, 3H).

$^{13}$C NMR (CD$_3$OD): δ 174.0, 168.0, 156.9, 152.1, 140.7, 139.3, 135.2, 133.2, 131.6, 130.7, 128.3, 123.2, 57.2, 54.9, 54.6, 51.7, 51.4, 43.3, 37.3, 36.9, 36.7.

EXAMPLE 215

Synthesis of N-(3-Chlorobenzenesulfonyl)-L-(1,1-dioxothiamorpholin-3-carbonyl)-L-4-(N,N-dimethylcarbamyloxy)phenylalanine The title compound was prepared from the product of Example 207 using the procedure described in Method 11.

NMR data was as follows:

$^1$H NMR (CD$_3$OD): δ 7.94 (m, 1H), 7.77 (m, 2H), 7.58 (m, 1H), 7.46 (d, 1H), 7.19 (d, 2H), 7.07 (d, 2H), 5.23 (m, 1H), 4.63 (m, 1H), 4.20 (m, 1H), 3.71 (m, 1H), 3.43 (m, 1H), 3.26 (m, 4H), 3.17 (s, 3H), 2.95 (m, 5H).

$^{13}$C NMR (CD$_3$OD): δ 168.0, 152.1, 142.5, 136.8, 135.0, 132.7, 131.6, 128.6, 127.1, 123.3, 57.2, 54.9, 51.4, 51.2, 43.2, 37.2, 36.8, 36.7.

EXAMPLE 216

Synthesis of N-(3-Chloro-4-fluorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

$^1$H NMR (CD$_3$OD): δ 7.93 (d), 7.90 (m), 7.29 (s), 7.27 (d), 7.04 (d), 4.60 (m), 4.46 (d), 3.90-3.40 (m), 3.10 (s), 2.98 (s), 1.43 (s).

$^{13}$C NMR (CD$_3$OD): δ 171.5, 166.5, 156.9, 151.9, 135.2, 131.3, 129.9, 127.9, 127.8, 123.1, 117.8, 117.5, 101.4, 83.7, 57.9, 56.0, 42.9, 37.3, 36.9, 36.7, 28.1.

EXAMPLE 217

Synthesis of N-(1-Methylpyrazole-4-sulfonyl)-L-(thiamorpholin-3-carbonyl)-L-4-(N,N-dimethylcarbamyloxy)phenylalanine tert-Butyl Ester The title compound was prepared following the procedures described for the preparation of Examples 49 and 117.

NMR data was as follows:

$^1$H NMR (CDCl$_3$): δ 7.77 (s), 7.63 (s), 7.08 (d), 6.93 (d), 6.76 (d), 6.71 (d), 5.50 (d), 5.22 (s), 4.82 (t), 4.61 (q), 3.83 (s), 3.25 (dt), 3.04 (m), 2.90 (s), 2.05 (dd), 1.34 (s).

$^{13}$C NMR (CDCl$_3$): δ 169.3, 166.8, 154.7, 150.4, 138.4, 132.4, 132.2, 130.2, 121.4, 118.3, 105.4, 82.5, 55.2, 53.6, 53.3, 39.5, 38.3, 36.6, 36.3, 36.1, 27.6, 23.5.

EXAMPLE 218

Synthesis of N-(3,4-Difluorobenzenesulfonyl)-L-(thiamorpholin-3-carbonyl)-L-4-(N,N-dimethylcarbamyloxy)phenylalanine tert-Butyl Ester The title compound was prepared following the procedure described for the preparation of Example 49 by substitution of the appropriate starting materials.

NMR data was as follows:

$^1$H NMR (CD$_3$OD): δ 7.88 (m, 1H), 7.70 (m, 1H), 7.57 (m, 1H), 7.23 (d, 2H), 7.03 (d, 2H), 6.83 (d, 1H), 5.63 (dd, 1H), 5.07 (t, 1H), 4.58 (m, 1H), 3.22-3.00 (m, 3H), 3.09 (s, 3H), 2.98 (s, 3H), 2.07 (dd, 1H), 1.44 (s, 9H).

$^{13}$C NMR (CD$_3$OD): δ 171.3, 169.3, 156.9, 152.0, 135.0, 131.6, 126.5, 122.9, 120.2, 119.9, 119.4, 118.7, 118.4, 106.4, 83.6, 56.5, 55.6, 37.1, 36.8, 36.6, 28.1, 25.2.

EXAMPLE 219

Synthesis of N-(Toluene-4-sulfonyl)-L-(5,5-dimethyl)thioprolyl-L-(thiomorpholin-4-ylcarbonyloxy)phenylalanine Isopropyl Ester The title compound was prepared using the procedure described in Example 82 by substitution of the appropriate starting materials.
NMR data was as follows:
$^1$H NMR (CDCl$_3$): δ 9.09 (s, 1H), 8.88 (m, 1H), 8.16 (m, 1H), 7.50 (m, 1H), 7.22 (d, 2H), 7.01 (d, 2H), 6.91 (d, 1H), 5.05 (m, 1H), 4.85 (m, 1H), 4.60 (d, 1H), 4.46 (d, 1H), 3.89 (s, 1H), 3.93-3.83 (m, 4H), 3.11 (m, 2H), 2.69 (m, 4H), 1.29-1.16 (m, 12H).
$^{13}$C NMR (CDCl$_3$): δ 170.3, 167.8, 154.3, 153.5, 150.4, 148.7, 135.8, 133.1, 132.9, 130.4, 124.0, 121.8, 73.7, 69.7, 54.7, 53.2, 50.5, 47.1, 46.4, 37.6, 29.1, 27.4, 27.0, 23.8, 21.6, 21.5.

EXAMPLE 220

Synthesis of N-(3,4-Difluorobenzenesulfonyl)-L-(thiamorpholin-3-carbonyl)-L-4-(N,N-dimethylcarbamyloxy)phenylalanine The title compound was prepared from the product of Example 218 using the procedure described in Method 11.
NMR data was as follows:
$^1$H NMR (CDCl$_3$): δ 7.89 (s, 1H), 7.57-7.46 (m, 2H), 7.35 (d, 1H), 7.32-7.22 (m, 1H), 7.09 (d, 2H), 6.91 (d, 2H), 6.64 (d, 1H), 5.50 (d, 1H), 4.89 (s, 1H), 4.88-4.79 (m, 1H), 3.17-3.02 (m, 3H), 3.02 (s, 3H), 2.93 (s, 3H), 1.75 (dd, 1H).
$^{13}$C NMR (CDCl$_3$): δ 173.6, 167.7, 155.5, 152.0, 151.8, 150.1, 148.4, 132.8, 130.4, 124.6, 121.5, 118.7, 118.5, 117.5, 117.3, 117.1, 106.9, 54.9, 53.0, 36.4, 36.2, 36.0, 23.4.

EXAMPLE 221

Synthesis of N-(2,5-Dichlorothiophene-3-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.
NMR data was as follows:
$^1$H NMR (CDCl$_3$): δ 7.18 (d, 2H), 7.11 (s, 1H), 7.00 (d, 2H), 6.87 (d, 1H), 5.03-4.99 (m, 1H), 4.84-4.81 (m, 1H), 4.65-4.56 (m, 2H), 4.07 (s, 1H), 3.10-3.01 (m, 5H), 2.98 (s, 3H), 1.37 (s, 3H), 1.22 (s, 3H), 1.21 (s, 3H), 1.18 (s, 3H).
$^{13}$C NMR (CDCl$_3$): δ 170.3, 167.7, 154.9, 150.7, 132.9, 132.8, 131.9, 130.3, 128.0, 127.0, 121.8, 73.4, 69.6, 54.8, 53.2, 50.5, 37.5, 36.6, 36.3, 29.1, 23.8, 21.6, 21.5.

EXAMPLE 222

Synthesis of N-(1-Methylpyrazole-4-sulfonyl)-L-(5,5-dimethyl)thiaprolyl-L-4-(thiomorpholin-4-ylcarbonyloxy)phenylalanine Isopropyl Ester The title compound was prepared using the procedure described in Example 82 by substitution of the appropriate starting materials.

NMR data was as follows:
$^1$H NMR (CDCl$_3$): δ 7.89 (s, 1H), 7.80 (s, 1H), 7.21 (d, 2H), 7.01 (m, 3H), 5.03 (m, 1H), 4.83 (m, 1H), 4.54 (d, 1H), 4.40 (d, 1H), 3.95 (s, 3H), 3.86 (m, 4H), 3.80 (s, 1H), 3.09 (m, 2H), 2.68 (m, 4H), 1.28 (s, 3H), 1.22 (m, 6H), 1.16 (s, 3H).
$^{13}$C NMR (CDCl$_3$): δ 170.4, 168.3, 153.5, 150.4, 139.3, 133.3, 132.9, 130.4, 121.7, 117.6, 73.8, 69.7, 54.8, 53.2, 50.5, 47.1, 46.4 39.6, 37.6, 29.0, 27.4, 27.1, 24.0, 21.6, 21.5.

EXAMPLE 223

Synthesis of N-(8-Quinolinesulfonyl)-L-prolyl-L-4-(N,N-dimethylcarbamyloxy)phenylalanine Isopropyl Ester The title compound was prepared following the procedure described for the preparation of Example 2 by substitution of the appropriate starting materials.
NMR data was as follows:
$^1$H NMR (CDCl$_3$): δ 9.01-8.99 (m, 1H), 8.56-8.53 (m, 1H), 8.27-8.23 (m, 1H), 8.07-8.04 (m, 1H), 7.66-7.61 (m, 2H), 7.55-7.51 (m, 1H), 7.17 (d, 2H), 7.01 (d, 2H), 5.27-5.23 (m, 1H), 5.07-4.98 (m, 1H), 4.84-4.76 (m, 1H), 3.34-3.20 (m, 3H), 3.06-2.98 (m, 4H), 2.97 (s, 3H), 2.15-2.09 (m, 1H), 1.64-1.51 (m, 3H), 1.23 (d, 6H).
$^{13}$C NMR (CDCl$_3$): δ 172.0, 170.5, 154.9, 151.5, 150.6, 143.9, 136.8, 135.6, 134.9, 134.1, 133.3, 130.2, 129.2, 125.6, 122.3, 121.7, 69.3, 62.8, 53.5, 48.7, 37.3, 36.5, 36.3, 29.7, 24.3, 21.6, 21.6.

EXAMPLE 224

Synthesis of N-(8-Quinolinesulfonyl)-L-prolyl-L-4-(N,N-dimethylcarbamyloxy)phenylalanine The title compound was prepared from the product of Example 223 using the procedure described in Method 7.
NMR data was as follows:
$^1$H NMR (CD$_3$OD): δ 9.03-9.01 (m, 1H), 8.49-8.42 (m, 2H), 8.23-8.20 (m, 1H), 8.09-8.07 (m, 1H), 7.73-7.61 (m, 2H), 7.25 (d, 2H), 7.00 (d, 2H), 5.30-5.27 (m, 1H), 4.73-4.69 (m, 1H), 3.38-3.21 (m, 3H), 3.09-3.02 (m, 4H), 2.95 (s, 3H), 1.86 (m, 1H), 1.78-1.73 (m, 1H), 1.58-1.50 (m, 2H).
$^{13}$C NMR (CD$_3$OD): δ 175.3, 174.2, 164.7, 156.9, 152.9, 145.2, 138.5, 136.9, 135.8, 135.6, 131.6, 130.9, 126.9, 123.8, 122.9, 63.9, 54.7, 50.0, 37.5, 36.8, 36.7, 31.6, 25.5.

EXAMPLE 225

Synthesis of N-(8-Quinolinesulfonyl)-L-(5,5-dimethyl)thiaprolyl-L-4-(N,N-dimethylcarbamyloxy)phenylalanine Isoproplyl Ester The title compound was prepared following the procedure described for the preparation of Example 2 by substitution of the appropriate starting materials.
NMR data was as follows:
$^1$H NMR (CDCl$_3$): δ 9.05-9.03 (m, 1H), 8.53-8.49 (m, 1H), 8.26-8.22 (m, 1H), 8.08-8.05 (m, 1H), 7.65-7.60 (m, 1H), 7.56-7.52 (m, 1H), 7.19 (d, 2H), 7.06 (d, 1H), 7.00 (d, 2H), 5.17 (d, 1H), 4.94 (m, 1H), 7.74-4.78 (m, 2H), 4.66 (s, 1H), 3.08-2.99 (m, 8H), 1.20-1.16 (m, 12H).
$^{13}$C NMR (CDCl$_3$): δ 170.2, 168.9, 154.9, 151.5, 150.6, 144.2, 136.7, 134.4, 134.4, 133.1, 130.3, 129.2, 125.5, 122.3, 121.7, 73.2, 69.3, 54.8, 53.3, 50.6, 37.6, 36.6, 36.3, 29.2, 24.1, 21.5, 21.4.

EXAMPLE 226

Synthesis of N-(8-Quinolinesulfonyl)-L-(5,5-dimethyl)thiaprolyl-L-4-(N,N-dimethylcarbamyloxy)phenylalanine The title compound was prepared from the product of Example 225 using the procedure described in Method 7.

NMR data was as follows:

$^1$H NMR (CD$_3$OD): δ 9.06-9.04 (m, 1H), 8.45-8.39 (m, 2H), 8.23-8.14 (m, 1H), 7.72-7.61 (m, 2H), 7.32 (d, 2H), 7.03 (d, 2H), 5.12 (d, 1H), 4.87 (d, 1H), 4.69-4.64 (m, 2H), 3.28-3.02 (m, 5H), 2.98 (s, 2H), 1.18 (s, 3H), 1.08 (s, 3H).

$^{13}$C NMR (CD$_3$OD): δ 174.1, 171.8, 157.1, 152.9, 152.0, 145.5, 138.4, 137.3, 135.8, 135.6, 135.1, 131.8, 130.9, 126.8, 123.8, 122.9, 73.7, 55.9, 54.8, 51.7, 37.6, 36.8, 36.7, 30.2, 25.0.

EXAMPLE 227

Synthesis of N-(3-Sulfonamido-4-chloro-benzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

NMR data was as follows:

$^1$H NMR (CDCl$_3$): δ 8.45 (d, 1H), 7.91 (d, 1H), 7.67 (d, 1H), 7.13 (d, 2H), 7.06 (d, 1H), 7.01 (d, 2H), 5.90 (brs, 2H), 5.06-5.02 (m, 1H), 4.79-4.72 (m, 1H), 4.14-4.10 (m, 1H), 3.42-3.39 (m, 1H), 3.25-3.14 (m, 2H), 3.07 (s, 3H), 3.04-2.97 (m, 1H), 2.96 (s, 3H), 1.98-1.96 (m, 1H), 1.72-1.62 (m, 3H), 1.28-1.25 (m, 6H).

$^{13}$C NMR (CDCl$_3$): δ 170.8, 170.7, 155.1, 150.6, 141.4, 136.9, 136.1, 132.9, 132.8, 131.9, 130.3, 128.7, 121.9, 69.8, 62.1, 53.3, 49.6, 36.9, 36.6, 36.4, 30.4, 24.3, 21.6, 21.6.

EXAMPLE 228

Synthesis of N-(Toluene-4-sulfonyl)-L-(1-oxothiomorpholin-3-carbonyl)-L-4-(N,N-dimethylcarbamyloxy)phenylalanine Isopropyl Ester The title compound was prepared following the procedure described for the preparation of Example 182 and substitution of appropriate starting materials.

NMR data was as follows:

$^1$H NMR (CDCl$_3$): δ 7.77 (d, 2H), 7.72 (d, 2H), 7.33 (m, 2H), 7.20 (m, 2H), 7.12 (d, 2H), 7.01 (m, 2H), 5.10 (m, 1H), 5.01 (m, 1H), 4.84 (m, 1H), 4.75 (m, 1H), 3.80 (m, 3H), 3.05 (m, 4H), 2.96 (m, 3H), 2.74 (m, 1H), 2.42 (m, 4H), 1.30-1.20 (m, 6H).

$^{13}$C NMR (CDCl$_3$): δ 170.6, 170.4, 166.8, 166.7, 154.9, 150.7, 150.6, 145.1, 144.8, 135.8, 135.5, 132.7, 130.6, 130.4, 130.3, 130.0, 127.7, 127.1, 122.4, 121.8, 69.8, 69.4, 55.8, 53.7, 52.9, 50.8, 48.2, 47.9, 42.0, 41.2, 38.4, 36.6, 36.5, 36.3, 31.2, 21.5, 21.5.

EXAMPLE 229

Synthesis of N-(2,4-Difluorobenzenesulfonyl)-L-(1-oxothiomorpholin-3-carbonyl)-L-4-(N,N-dimethylcarbamyloxy)phenylalanine tert-Butyl Ester The title compound was prepared following the procedure described for the preparation of Example 182 and substitution of appropriate starting materials.

NMR data was as follows:

$^1$H NMR (CDCl$_3$): δ 7.91 (m, 1H), 7.30 (m, 2H), 6.97 (m, 4H), 4.71 (m, 1H), 4.55 (m, 1H), 3.90 (m, 2H), 3.77 (m, 1H), 3.11 (m, 4H), 2.85 (m, 3H), 2.80 (m, 1H), 2.60 (m, 2H), 1.46 (s, 9H), 1.39 (s, 9H).

$^{13}$C NMR (CDCl$_3$): δ 170.0, 168.0, 167.9, 166.4, 166.2, 164.6, 164.4, 162.7, 161.4, 161.2, 157.9, 157.8, 154.8, 150.6, 150.4, 132.8, 132.5, 132.4, 130.9, 130.4, 130.1, 123.3, 123.1, 122.2, 121.6, 121.1, 122.6, 122.2, 111.9, 106.6, 106.3, 105.9, 82.8, 82.3, 55.8, 54.1, 53.2, 51.6, 49.2, 48.7, 43.1, 42.3, 38.7, 36.5, 36.2, 31.8, 27.7.

EXAMPLE 230

Synthesis of N-(1-Methylpyrazole-4-sulfonyl)-L-(5,5-dimethyl)thiaprolyl-L-4-(N,N-dimethylcarbamyloxy)phenylalanine 2,2-Dimethylpropyl Ester The product from Example 161 (1 g., 0.72 mmol) was dissolved in neopentyl alcohol (5 mL). Titanium (IV) isopropoxide (260 mg., 0.9 mmol) was added and the mixture heated at 100° C. under an inert atmosphere for 48 h. Excess neopentyl alcohol was removed under reduced pressure and the residue purified by flash column chromatography (silica, 1% MeOH in CHCl$_3$) to give the title compound as a white solid (1.02 g, 97%).

Physical data was as follows:

MS (+) ESI [M+H]$^+$ 610; [M+NH4]$^+$ 627 (100%).

Anal. Calcd. For C$_{29}$H$_{39}$N$_5$O$_7$S: C, 53.18; H, 6.45; N, 11.49.

Found: C, 53.46; H, 6.38; N, 11.06.

EXAMPLE 231

Synthesis of N-(Pyridine-3-sulfonyl)-L-(5,5-dimethyl)thiaprolyl-L-4-(N,N-dimethylcarbamyloxy)phenylalanine 2,2-Dimethylpropyl Ester The product from Example 173 was subjected to the transesterification procedure described for the preparation of Example 230. The compound was purfied by flash column chromatography (silica, 1% MeOH in CHCl$_3$) followed by recrystallization from ethyl acetate to give the title compound as a white solid (720 mg, 47%).

Physical data was as follows:

Anal. Calcd. For C$_{28}$H$_{38}$N$_4$O$_7$S$_2$: C, 55.43; H, 6.31; N, 9.23.

Found: C, 55.37; H, 6.32; N, 9.22.

EXAMPLE 232

Synthesis of N-(1-Methylpyrazole4-sulfonyl)-L-(5,5-dimethyl)thiaprolyl-L4-(N,N-dimethylcarbamyloxy)phenylalanine Cyclopropylmethyl Ester The product from Example 161 was subjected to the transesterification procedure described for the preparation of Example 230. The title compound was obtained as a white solid following flash column chromatography (silica, 1% MeOH in CHCl$_3$) (860 mg, 70%).

Physical data was as follows:

Anal. Calcd. For C$_{26}$H$_{35}$N$_5$O$_7$S$_2$: C, 52.6; H, 5.94; N, 11.8.

Found: C, 52.49; H, 5.93; N, 11.62.

EXAMPLE 233

Synthesis of N-(1-Methylpyrazole-4-sulfonyl)-L-(5,5-dimethyl)thiaprolyl-L-4-(N,N-dimethylcarbamyloxy)phenylalanine Methyl Ester The title compound was prepared following the procedure described for the preparation of Example 161 and substitution of appropriate starting materials.

Physical data was as follows:

MS (+) ESI [M+H]$^+$ 554; [M+NH$_4$]$^+$ 571 (100%).

Anal. Calcd. For C$_{23}$H$_{31}$N$_5$O$_7$S$_2$.0.2 EtOAc: C, 50.04; H, 5.75; N, 12.26.

Found: C, 50.12; H, 5.69; N, 12.19.

EXAMPLE 234

Synthesis of N-(Pyridine-3-sulfonyl)-L-(5,5-dimethyl)thiaprolyl-L-4-(N,N-dimethylcarbamyloxy)phenylalanine Ethyl Ester The product from Example 173 was subjected to the transesterification procedure described for the preparation of Example 230. The compound was purified by flash column chromatography (silica, 2% MeOH in CHCl$_3$), followed by recrystallization from ethyl acetate to give the title compound as a white solid (1.2 g, 61%).

Physical data was as follows:

Anal. Calcd. For C$_{25}$H$_{32}$N$_4$O$_7$S$_2$: C, 53.18; H, 5.71; N, 9.92.

Found: C, 53.14; H, 5.72; N, 9.57.

EXAMPLE 235

Synthesis of N-(Pyridine-3-sulfonyl)-L-(5,5-dimethyl)thiaprolyl-L-4-(N,N-dimethylcarbamyloxy)phenylalanine Cyclopropylmethyl Ester The product from Example 173 was subjected to the transesterification procedure described for the preparation of Example 230. The compound was isolated as a white solid following flash column chromatography (silica, 2% MeOH in CHCl$_3$) and recrystallization from EtOAc/hexanes (1 g, 65%).

Physical data was as follows:

Anal. Calcd. For C$_{27}$H$_{34}$N$_4$O$_4$S$_2$: C, 54.9; H, 5.8; N, 9.48.

Found: C, 54.77; H, 5.65; N, 9.46.

EXAMPLE 236

Synthesis of N-(1-Methylpyrazole-4-sulfonyl)-L-(5,5-dimethyl)thiaprolyl-L-4-(N,N-dimethylcarbamyloxy)phenylalanine 2-Methoxyphenyl Ester To a solution of the compound from Example 139 (1.79 g, 3.31 mmol), 2-methoxy-phenol (0.45 g, 3.64 mmol) and BOP (1.61 g, 3.64 mmol) in methylene chloride (25 mL) at 0° C. was added triethylamine (0.7 mL, 4.97 mmol). The reaction mixture was then slowly warmed to 25° C. where it was stirred, under nitrogen, for 24 h. The reaction was quenched by addition of 100 mL saturated brine and extracted with EtOAc. The organic extract was washed sequentially with 2N HCl (3 times), saturated sodium bicarbonate (3×) and saturated brine (2×), dried over MgSO$_4$, and evaporated to 2.1 g of crude product. Flash chromatography (eluant: 96-4 methylene chloride:EtOAc) afforded 1.85 g of a white solid which upon trituration with hexane gave 1.68 g (79%) of white crystals, mp 72-75° C.

Physical data was as follows:

Anal. Calcd. For C$_{29}$H$_{35}$N$_5$O$_8$S$_2$: C, 59.94; H, 5.46; N, 10.85.

Found: C, 53.45; H, 5.62; N, 10.31.

EXAMPLE 237

Synthesis of N-(1-Methylpyrazole-4-sulfonyl)-L-(5,5-dimethyl)thiaprolyl-L-4-(N,N-dimethylcarbamyloxy)phenylalanine n-Butyl Ester A solution of the compound of Example 139 (2 g) in n-butanol (50 mL) was saturated upon ice-cooling with HCl gas. The mixture was stirred at ambient temperature for 36 h, evaporated in vacuo to almost dryness, then partitioned between 5% NaHCO$_3$ and chloroform. The organic layer was dried and evaporated in vacuo to furnish 900 mg of the title compound.

Physical data was as follows:

MS: [(+)ESI], [M+H]$^+$ 596.

EXAMPLE 238

Synthesis of N-(1-Methylpyrazole-4-sulfonyl)-L-(5,5-dimethyl)thiaprolyl-L-4-(N,N-dimethylcarbamyloxy)phenylalanine n-Propyl Ester A solution of N-(1-methylpyrazole-4-sulfonyl)-L-(5,5-dimethyl)thiaprolyl-L-4-(N,N-dimethylcarbamyloxy)phenylalanine (2 g) in n-propanol (50 mL) was saturated upon ice-cooling with HCl gas. The mixture was stirred at ambient temperature for 36 hours, evaporated in vacuo to almost dryness, then partioned between 5% NaHCO$_3$ and chloroform. The organic layer was dried and evaporated in vacuo to provide 1500 mg of the title compound.

Physical data was as follows:

MS: [(+)ESI], [M+H]$^+$ 582.

EXAMPLE 239

Synthesis of N-(1-Methylpyrazole-4-sulfonyl)-L-(5,5-dimethyl)thiaprolyl-L4-(N,N-dimethylcarbamyloxy)phenylalanine 2,2-Dimethylpropionyloxymethyl Ester Potassium iodide (324 mg) was added at once to a mixture of the compound of Example 139 (1.08 g), chloromethylpivalate (294 mg) and powdered K$_2$CO$_3$ (222 mg) in DMF (5 mL). The reaction mixture was stirred at ambient temperature overnight, partitioned between water (12 mL) and ethyl acetate (60 mL). The separated organic layer was washed with ice cold 0.1 N sodium thiosulfate, water and brine, then dried over MgSO$_4$, filtered and evaporated in vacuo to yield 750 mg of the title compound.

Physical data was as follows:

MS: [(+)ESI], [M+H]$^+$ 654.

EXAMPLE 240

Synthesis of N-(Toluene-4-sulfonyl)-L-prolyl-L-4-(4-phenylpiperazin-1-ylcarbonyloxy)phenylalanine tert-Butyl Ester The title compound was prepared following the procedure outlined for Example 4 by substitution of the appropriate starting materials. A white solid was obtained, mp. 60-65° C.

Physical data was as follows:

MS (+ESI) 694.3 [M+NH$_4$]$^+$.

Anal. Calcd for $C_{36}H_{44}N_4O_7S \cdot 0.5 C_4H_8O_2$: C, 63,31; H, 6.71; N, 7.77.

Found: C, 63.12; H, 6.58; N, 7.69.

EXAMPLE 241

Synthesis of N-(Toluene-4-sulfonyl)-L-prolyl-L-4-(4'-(ethoxycarbonyl)piperidin-1-ylcarbonyloxy)phenylalanine tert-Butyl Ester The carbamate was prepared by treatment of Tos-Pro-Tyr-t-butyl ester with 4-nitrophenylchloroformate, followed by addition of ethylisonipecotate (triethylamine, methylene chloride, chilled to 0° C., then stirred at room temperature overnight). The crude product was purified by flash chromatography (silica, 95:5 EtoAc:Et$_3$N) to afford a white solid. (0.78 g, 39%).

NMR data was as follows:

$^1$H NMR (DMSO-d$_6$, 400 MHz): δ 8.15 (d, 1H, J=7.68 Hz); 7.70 (d, 2H, J=8.34 Hz); 7.40 (d, 2H, J=7.90 Hz); 7.22 (d, 2H, J=8.56 Hz); 7.00 (d, 2H, J=8.56 Hz); 4.37 (m, 1H), 4.07 (q, 2H, J=7.14, 14.08 Hz); 4.03 (m, 2H); 3.90 (m, 1H); 3.34 (m, 1H); 3.09 (m, 2H); 3.00 (m, 3H); 2.59 (m, 1H); 2.39 (s, 3H); 1.87 (m, 2H); 1.58 (m, 5H); 1.41 (m, 1H); 1.35 (s, 9H); 1.18 (t, 3H, 7.14 Hz).

IR (KBr, cm$^{-1}$): 3410, 2990, 2950, 1725, 1680, 1510, 1430, 1355, 1220, 1200, 1170, 1000, 675, 595.

MS ((+)ESI, m/z (%)) 689 (100[M+NH$_4$]$^+$); 691 (37[M+NH$_4$]$^+$).

Anal. Calc'd for $C_{34}H_{45}N_3O_9S$: C, 60.79; H, 6.75; N, 6.25.

Found: C, 60.59; H, 6.67; N, 6.22.

EXAMPLE 242

Synthesis of N-(Toluene-4-sulfonyl)-L-prolyl-L-4-(N-(4'-(2'-aminoethyl)morpholino)carbamyloxy)phenylalanine The title compound was prepared from the product of Example 152 using the procedure described in Method 11.

NMR data was as follows:

$^1$H NMR (DMSO-d$_6$, 400 MHz): δ 12.75 (s, 1H); 8.08 (d, 1H); 7.68 (d, 2H); 7.60 (t, 1H); 7.39 (d, 2H); 7.21 (d, 2H); 6.97 (d, 2H); 4.46 (m, 1H); 4.08 (m, 1H); 3.56 (m, 4H); 3.26 (m, 3H); 3.09 (m, 2H); 2.94 (m, 1H); 2.49 (s, 6H); 2.48 (s, 3H); 1.5 (m, 3H); 1.38 (m, 1H).

IR (KBr, cm$^{-1}$) 3400, 2975, 1725, 1650, 1500, 1350, 1150, 650, 575, 550.

MS ((−)ESI, m/z (%)) 587 (100[M−H]$^+$).

Anal. Calc'd for $C_{28}H_{36}N_4O_8S \cdot HCOOH \cdot 0.5 H_2O$: C, 54.11; H, 6.11; N, 8.70.

Found: C, 53.96; H, 6.02; N, 8.68.

EXAMPLE 243

Synthesis of N-(Toluene-4-sulfonyl)-L-prolyl-L-4-[4-(carboxy)piperidin-1-ylcarbonyloxy]phenylalanine The title compound was prepared from the product of Example 241 using the procedures described in Methods 6 and 11.

NMR data was as follows:

$^1$H NMR (DMSO-d$_6$, 400 MHz): δ 12.50 (bs, 2H); 8.08 (d, 1H, J=7.90 Hz); 7.69 (d, 2H, J=8.34 Hz); 7.39 (d, 2H, J=7.90 Hz); 7.22 (D, 2H, J=8.56 Hz); 6.99 (d, 2H, J=8.56 Hz); 4.46 (m, 1H); 4.09 (m, 1H); 4.00 (m, 1H); 3.90 (m, 1H); 3.30 (m, 1H); 3.09 (m, 3H); 2.95 (m, 2H); 2.49 (m, 1H); 2.38 (s, 3H); 1.86 (m, 2H); 1.36-1.61 (m, 6H).

IR (KBr, cm$^{-1}$) 3400, 2960, 1720, 1535, 1430, 1350, 1200, 1160, 670, 590, 550.

MS ((+)ESI, m/z (%)) 605 (100[M+NH$_4$]$^+$).

Anal. Calc'd for $C_{28}H_{33}N_3O_9S \cdot H_2O$: C, 55.53; H, 5.65; N, 6.94.

Found: C, 55.23; H, 5.82; N, 6.59.

EXAMPLE 244

Synthesis of N-(Toluene-4-sulfonyl)-L-prolyl-L-4-(N,N-bis-(2-hydroxyethyl)carbamyloxy)phenylalanine Isopropyl Ester The carbamate was prepared by treatment of Tos-Pro-Tyr-iPr ester with 4-nitrophenyl chloroformate, followed by addition of diethanol amine (triethylamine, methylene chloride, chilled to 0° C., stirred at room temperature overnight). The crude product was purified by flash chromatography (silica, 98:2 EtOAc:EtOH) to afford a white foam. (0.180 g, 28%).

NMR data was as follows:

$^1$H NMR (DMSO-d$_6$, 400 MHz): δ 8.26 (d, 1H, J=7.90 Hz); 7.69 (d, 2H, J=8.12 Hz); 7.40 (d, 2H, J=8.12 Hz); 7.23 (D, 2H, J=8.56 Hz); 6.99 (d, 2H, J=8.56 Hz); 4.87 (m, 1H); 4.83 (t, 1H, J=5.49 Hz); 4.76 (t, 1H, J=5.49 Hz); 4.42 (m, 1H); 4.08 (m, 1H); 3.58 (m, 2H); 3.51 (m, 2H); 3.44 (m, 2H); 3.34 (m, 3H); 2.99-3.09 (m, 3H); 2.39 (s, 3H); 1.59 (m, 3H); 1.41 (m, 1H); 1.16 (d, 3H, J=6.15 Hz); 1.12 (d, 3H, J=6.15 Hz).

IR (KBr, cm$^{-1}$) 3420, 2940, 1725, 1535, 1670, 1520, 1460, 1410, 1350, 1220, 1160, 1110, 670, 600, 550.

MS ((+)ESI, m/z (%)) 606 (15[M+H]$^+$); 623 (100[M+NH$_2$]$^+$).

Anal. Calc'd for $C_{29}H_{39}N_3O_9S \cdot H_2O$: C, 56.66; H, 6.56; N, 6.84.

Found: C, 56.66; H, 6.41; N, 6.72.

EXAMPLE 245

Synthesis of N-(Toluene-4-sulfonyl)-L-prolyl-L-4-[3-(hydroxymethyl)piperidin-1-ylcarbonyloxylphenylalanine Isopropyl Ester The carbamate was prepared by treatment of Tos-Pro-Tyr-iPr ester with 4-nitrophenyl chloroformate, followed by addition of 3-piperidine methanol (triethylamine, methylene chloride, chilled to 0° C., stirred at room temperature overnight). The crude product was purified by flash chromatography (silica, 3:2 EtOAc:Hex) to afford a white foam (0.519 g, 67%).

NMR data was as follows:

$^1$H NMR (DMSO-d$_6$, 400 MHz): δ 8.26 (d, 1H, J=7.90 Hz); 7.69 (d, 2H, J=8.12 Hz); 7.40 (d, 2H, J=8.12 Hz); 7.22 (d,

2H, J=8.56 Hz); 6.98 (d, 2H, J=8.34 Hz); 4.85 (M, 1H); 4.57 (bs, 1H); 4.42 (m, 1H); 3.99-4.09 (m, 3H); 3.85 (m, 1H); 3.31 (m, 1H); 3.22 (m, 1H); 2.91-3.10 (m, 4H); 2.80 (m, 1H); 2.55 (m, 1H); 2.39 (s, 3H); 1.51-1.72 (m, 6H); 1.42 (m, 2H); 1.16 (d, 3H, J=6.15 Hz); 1.11 (d, 3H), J=6.15 Hz).

IR (KBr, cm$^{-1}$) 3400, 2990, 2940, 2880, 1725, 1520, 1430, 1350, 1220, 1165, 1100, 660, 600, 550.

MS ((-)ESI, m/z (%)) 614 (30[M-H]).

Anal. Calc'd for $C_{31}H_{41}N_3O_8S$: C, 60.47; H, 6.71; N, 6.82. Found: C, 59.83; H, 6.61; N, 6.59.

EXAMPLE 246

Synthesis of N-(Toluene-4-sulfonyl)-L-prolyl-L-4-(4-trifluoromethanesulfonylpiperazin-1-ylcarbonyloxy)phenylalanine tert-Butyl Ester The title compound was prepared following the procedure outlined for Example 128 and substitution of appropriate starting materials.

Physical data was as follows:

MS (+ESI):733 [M+H]$^+$.

Anal. Calc'd for $C_{31}H_{39}F_3N_4O_9S_2 \cdot 0.10\ C_4H_8O_2$: C, 50.20; H, 5.40; N, 7.55.

Found: C, 50.25; H, 5.46; N, 7.07.

EXAMPLE 247

Synthesis of N-(4-(N-Phenylurea)benzenesulfonyl)-L-prolyl-L-4-(N,N-dimethylcarbamyloxy)phenylalanine tert-Butyl Ester A mixture of Example 107 (250 mg, 0.51 mmol), phenyl isocyanate (62 mg, 0.56 mmol) and triethylamine (76 μL, 0.56 mmol) was heated to reflux under argon. Reflux was continued overnight. Solvent was removed under reduced pressure and the residue purified by flash chromatography. (silica, hexanes: EtOAc 1:1 then EtOAc) to give the title compound as an off-white foam (160 mg, 46%), mp 112-115° C.

Physical data was as follows: MS (+ESI) [M+NH$_4$]$^+$ 697 (100%).

EXAMPLE 248

Synthesis of N-(2-Trifluoroacetyl-1,2,3,4-tetrahydroisoquinolin-7-sulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

NMR data was as follows:

$^1$H NMR (CDCl$_3$): δ 7.70-7.66 (m, 2H), 7.35-7.30 (m, 1H), 7.27-7.21 (m, 1H), 7.14-7.10 (m, 2H), 7.01 (d, 2H), 5.09-4.95 (m, 1H), 4.89-4.75 (m, 2H), 4.14-4.07 (m, 1H), 3.93-3.85 (m, 2H), 3.35-3.20 (m, 2H), 3.13-2.97 (m, 9H), 2.05-2.01 (m, 1H), 1.63 (1.50 (m, 3H), 1.20 (d, 6H).

$^{13}$C NMR (CDCl$_3$): δ 170.7, 170.6, 170.5, 156.3, 155.8, 154.9, 150.6, 140.1, 139.2, 135.1, 135.1, 13.2, 133.0, 133.0, 132.9, 130.2, 130.1, 129.9, 126.9, 126.4, 126.3, 125.8, 121.7, 118.3, 114.5, 69.6, 62.1, 62.0, 53.2, 49.6, 46.6, 46.5, 45.1, 42.7, 40.9, 37.1, 36.6, 36.3, 30.1, 30.0, 29.2, 27.8, 24.2, 24.2, 21.6, 21.6.

EXAMPLE 249

Synthesis of N-(1-Methylpyrazole-3-sulfonyl)-L-(5,5-dimethyl)thiaprolyl-L-4-(N,N-dimethylcarbamyloxy)phenylalanine Isopropyl Ester Substituting N-methylpyrazole-3-sulfonyl chloride (See European Patent Application, 095925) and following the method for the preparation of Example 56, gave the title compound.

NMR data was as follows:

$^1$H NMR (CDCl$_3$): δ 7.45 (d, 1H), 7.21 (d, 2H), 7.09 (d, 1H), 7.01 (d, 2H), 6.71 (d, 1H), 5.03-4.98 (m, 1H), 4.87-4.84 (m, 1H), 4.60-4.59 (m, 2H), 4.05 (s, 1H), 3.97 (s, 3H), 3.12-3.01 (m, 5H), 2.98 (s, 3H), 1.22-1.15 (m, 12H).

$^{13}$C NMR (CDCl$_3$): δ 170.3, 168.3, 154.9, 150.7, 146.7, 133.0, 131.9, 130.3, 121.7, 108.9, 73.5, 69.5, 54.7, 53.3, 50.7, 39.9, 37.7, 36.6, 36.3, 28.8, 24.1, 21.5, 21.5.

EXAMPLE 250

Synthesis of N-(1-Methylpyrazole-3-sulfonyl)-L-(5,5-dimethyl)thiaprolyl-L-4-(N,N-dimethylcarbamyloxy)phenylalanine The title compound was prepared from the product of Example 249 using the procedure described in Method 7.

NMR data was as follows:

$^1$H NMR (CD$_3$OD): δ 8.25 (d, 1H), 7.76 (d, 1H), 7.32 (d, 2H), 7.01 (d, 2H), 6.70 (d, 1H), 4.74-4.71 (m, 1H), 4.68 (d, 1H), 4.56 (d, 1H), 4.12 (s, 1H), 3.97 (s, 3H), 3.24-3.07 (m, 5H), 2.97 (s, 3H), 1.14 (s, 3H), 1.13 (s, 3H).

$^{13}$C NMR (CD$_3$OD): δ 174.1, 171.4, 157.0, 151.9, 148.2, 135.7, 134.2, 131.8, 122.9, 109.6, 74.4, 55.6, 55.0, 51.5, 40.0, 37.6, 36.8, 36.7, 29.6, 24.8.

EXAMPLE 251

Synthesis of N-(Pyridine-4-sulfonyl)-L-(5,5-dimethyl)thiaprolyl-L-4-(N,N-dimethylcarbamyloxy)phenylalanine Isopropyl Ester The title compound was prepared following the procedure outlined for the preparation of Example 56, where 4-pyridinesulfonyl chloride N-oxide was used in place of 3-pyridinesulfonyl chloride (see Marsais and coworkers, *J. Org. Chem.* 1987, 52, 1133-1136). Deoxygenation of the N-oxide was accomplished using the procedure of Aoyagi and coworkers, *Synthesis* 1997, 891.

NMR data was as follows:

$^1$H NMR (CDCl$_3$): δ 8.89-8.87 (m, 2H), 7.72-7.70 (m, 2H), 7.19 (d, 2H), 7.01 (d, 2H), 6.79 (d, 1H), 5.05-5.01 (m, 1H), 4.85-4.82 (m, 1H), 4.58 (d, 1H), 4.45 (d, 1H), 3.91 (s, 1H), 3.11-3.02 (m, 5H), 2.99 (s, 3H), 1.28-1.16 (m, 12H).

$^{13}$C NMR (CDCl$_3$): δ 170.3, 167.7, 154.9, 151.5, 150.7, 144.2, 132.7, 130.3, 121.8, 120.9, 73.6, 69.7, 54.6, 53.1, 50.4, 37.5, 36.6, 36.3, 29.1, 23.6, 21.6, 21.5.

EXAMPLE 252

Synthesis of N-(Pyridine-4-sulfonyl)-L-(5,5-dimethyl)thiaprolyl-L-4-(N,N-dimethylcarbamyloxy)phenylalanine The title compound was prepared from the product of Example 251 using the procedure described in Method 7.

NMR data was as follows:

$^1$H NMR (CD$_3$OD): δ 8.78 (d, 2H), 7.42 (d, 1H), 7.69 (d, 2H), 7.35 (d, 2H), 7.06 (d, 2H), 4.69-4.61 (m, 3H), 4.16 (s, 1H), 3.25-3.19 (m, 1H), 3.13-3.05 (m, 4H), 2.97 (s, 3H), 1.25 (s, 6H).

$^{13}$C NMR (CD$_3$OD): δ 174.1, 170.5, 157.0, 152.2, 152.0, 147.2, 135.8, 131.8, 123.1, 122.7, 73.9, 55.6, 54.9, 54.4, 37.5, 36.8, 36.7, 30.1, 24.8.

EXAMPLE 253

Synthesis of N-(Toluene-4-sulfonyl)-L-(5,5-dimethyl)thiaprolyl-L-4-(N-methyl-N-(2-dimethylaminoethyl)carbamyloxy)phenylalanine tert-Butyl Ester A solution of the starting acid (500 mg), (2S)-2-amino-3-{4-[(2-dimethylaminoethyl)-methylcarbamoyloxy]phenyl}propionic acid tert-butyl ester (730 mg), HOBt (235 mg), and 4-methylmorpholine (0.87 mL) in DMF (10 mL) was stirred in ice bath at 0° C. 1-[3-(Dimethylamino)propyl]-3-ethylcarbodiimide hydrochloride (360 mg) was added to the solution. The ice bath was removed after 10 minutes. The reaction was stirred at room temperature for 3 hours. Ethyl acetate (20 mg) was added. The solution was washed with saturated NaHCO$_3$ solution (30 mL) 2 times, then washed with brine. The solution was dried with MgSO$_4$. The solvent was evaporated in vacuo, and the residue flash chromatographed on silica gel to give 385 mg of the title compound.

Physical data was as follows:

MS: [(+)ESI], [M+H]$^+$ 663.

EXAMPLE 254

Synthesis of N-(Toluene-4-sulfonyl)-L-prolyl-L-4-(N-methyl-N-(2-dimethylaminoethyl)carbamyloxy)phenylalanine tert-Butyl Ester The title compound was prepared following the procedure described for the preparation of Example 253 and substitution of appropriate starting materials.

Physical data was as follows:

MS: [(+)ESI], [M+H]$^+$ 617.

EXAMPLE 255

Synthesis of N-(Toluene4-sulfonyl)-L-(5,5-dimethyl)thiapropyl-L-4-(N-methyl-N-(2-dimethylaminoethyl)carbamyloxy)phenylalanine The title compound was prepared from the product of Example 253 using the procedure described in Method 11.

Physical data was as follows:

MS: [(+)ESI], [M+H]$^+$ 607.

EXAMPLE 256

Synthesis of N-(Toluene-4-sulfonyl)-L-prolyl-L-4-(N-methyl-N-(2-dimethylaminoethyl)carbamyloxy)phenylalanine The title compound was prepared from the product of Example 254 using the procedure described in Method 11.

Physical data was as follows:

MS: [(+)ESI], [M+H]$^+$ 561.

EXAMPLE 257

Synthesis of N-(4-Fluorobenzenesulfonyl)-L-(5,5-dimethyl)thiaprolyl-L-3-chloro-4-(4-methylpiperazin-1-ylcarbonyloxy)phenylalanine tert-Butyl Ester The title compound was prepared following the procedure described for the preparation of Example 4 and substitution of appropriate starting materials, mp: 64-67° C.

Physical data was as follows:

MS: [M+H]$^+$ 699.

Anal. Calcd. for C$_{31}$H$_{40}$ClFN$_4$O$_7$S$_2$.H$_2$0: C, 51.90; H, 5.9; N, 7.8.

Found: C, 51.53; H, 5.50; N, 7.62.

EXAMPLE 259

Synthesis of N-(4-Fluorobenzenesulfonyl)-L-(5,5-dimethyl)thiaprolyl-L-3-chloro-4-(N,N-dimethycarbamyloxy)phenylalanine The title compound was prepared for the product of Example 258 using the procedure described in Method 11.

Physical data was as follows:

MS: [M+1] 603.

Anal. Calcd. for C$_{24}$H$_{27}$FN$_3$O$_7$S$_2$: C, 49.02; H, 4.63; N, 7.15.

Found: C, 49.25; H, 4.89; N, 6.73.

EXAMPLE 260

Synthesis of N-(4-Fluorobenzenesulfonyl)-L-(5,5-dimethyl)thiaprolyl-L-3-chloro-4-(thiomorpholin-4-ylcarbonyloxy)phenylalanine tert-Butyl Ester The title compound was prepared following the procedure described for the preparation of Example 82 and substitution of appropriate starting materials, mp. 111-114° C.

Physical data was as follows:

MS: +ESI [M+NH4]+ 719.

Anal. Calcd. for C$_{30}$H$_{37}$ClFN$_3$O$_7$S: C, 50.02; H, 5.46; N, 5.8.

Found: C, 50.23; H, 5.10; N, 5.50.

EXAMPLE 261

Synthesis of N-(4-Fluorobenzenesulfonyl)-L-(5,5-dimethyl)thiaprolyl-L-3-chloro-4-(thiomorpholin-4-ylcarbonyloxy)phenylalanine Isopropyl Ester The title compound was prepared following the procedure described for the preparation of Example 82 and substitution of appropriate starting materials, mp. 77-81° C.

Physical data was as follows:

MS: [M+NH$_4$]+ 705.

Anal. Calcd. for C$_{29}$H$_{35}$ClFN$_3$O$_7$S$_3$: C, 50.61; H, 5.13; N, 6.1.

Found: C, 50.33; H, 5.07; N, 5.94.

EXAMPLE 262

Synthesis of N-(4-Fluorobenzenesulfonyl)-L-(5,5-dimethyl)thiaprolyl-L-3-chloro-4-(N,N-dimethylcarbamyloxy)]phenylalanine Isopropyl Ester The title compound was prepared following the procedure described for the preparation of Example 2 and substitution of appropriate starting materials, mp. 65-69° C.

Physical data was as follows:

MS: $[M+NH_4]^+$ 647.

Anal. Calcd. for $C_{27}H_{33}ClFN_3O_7S_2$: C, 51.46; H, 5.28; N, 6.4.

Found: C, 51.29; H, 5.19; N, 6.50.

EXAMPLE 263

Synthesis of N-(Toluene-4-sulfonyl)-L-(5,5-dimethyl)thiaprolyl-L-3-chloro-4-(N,N-dimethylcarbamyloxy)phenylalanine Isopropyl Ester The title compound was prepared following the procedure described for the preparation of Example 2 and substitution of appropriate starting materials, mp. 68-72° C.

Physical data was as follows:

MS: $[M+H]^+$ 626.

Anal. Calcd. for $C_{28}H_{36}ClN_3O_7S_2$: C, 53.77; H, 5.80; N, 6.71.

Found: C, 53.26; H, 5.8; N, 6.63.

EXAMPLE 264

Synthesis of N-(4-Fluorobenzenesulfonyl)-L-(5,5-dimethyl)thiaprolyl-L-3-chloro-4-(4-methylpiperazin-1-ylcarbonyloxy)]phenylalanine Isopropyl Ester The title compound was prepared following the procedure described for the preparation of Example 4 and substitution of appropriate starting materials.

Physical data was as follows:

MS: $[M+H]^+$ 685.

Anal. Calcd. for $C_{30}H_{38}ClN_4O_7$: C, 52.59; H, 5.59; N, 8.18.

Found: C, 52.09; H, 5.48; N, 7.77.

EXAMPLE 265

Synthesis of N-(Toluene-4-sulfonyl)-L-prolyl-L-3-chloro-4-(N,N-dimethylcarbamyloxy)]phenylalanine Isopropyl Ester The title compound was prepared following the procedure described for the preparation of Example 2 and substitution of appropriate starting materials.

Physical data was as follows:

MS: $[M+H]^+$ 580.

Anal. Calcd. for $C_{27}H_{34}ClN_3O_7S.0.5\ H_2O$: C, 55.04; H, 6.00; N, 7.13.

Found: C, 55.06; H, 5.71; N, 6.93.

EXAMPLE 266

Synthesis of N-(4-Fluorobenzenesulfonyl)-L-(5,5-dimethyl)thiaprolyl-L-3-chloro4-(4-(2'-pyridyl)-piperazin-1-ylcarbonyloxy)]phenylalanine Isopropyl Ester The title compound was prepared following the procedure described for the preparation of Example 4 and substitution of appropriate starting materials.

Physical data was as follows: MS: $[M+H]^+$ 748.

Anal. Calcd. for $C_{34}H_{39}ClFN_5O_7S_2$: C, 54.57; H, 5.25; N, 9.3.

Found: C, 54.26; H, 5.10; N, 9.07.

EXAMPLE 267

Synthesis of N-(4-Fluorobenzenesulfonyl)-L-(5,5-dimethyl)thiaprolyl-L-3-chloro-4-(4-(2'-pyridyl)-piperazin-1-ylcarbonyloxy)]phenylalanine tert-Butyl Ester The title compound was prepared following the procedure described for the preparation of Example 4 and substitution of appropriate starting materials, mp. 80-86° C.

Physical data was as follows:

MS: $[M+H]^+$ 762.

Anal. Calcd. for $C_{35}H_{41}ClFN_5O_7S_2$: C, 55.14; H, 5.42; N, 9.19.

Found: C, 54.67; H, 5.40; N, 8.69.

EXAMPLE 268

Synthesis of N-(4-Nitrobenzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

Physical data was as follows:

Anal. Calcd. for $C_{26}H_{32}N_4O_9S$: C, 54.16; H, 5.59; N, 9.72.

Found: C, 53.69; H, 5.24; N, 9.52.

EXAMPLE 269

Synthesis of N-(4-Aminobenzenesulfonyl)-L-prolyl-L-4-(N,N-dimethylcarbamyloxy)phenylalanine Isopropyl Ester The title compound was prepared from the product of Example 268 using the procedure described in Method 4.

Physical data was as follows:

Anal. Calcd. for $C_{26}H_{34}N_4O_7S$: C, 57.13; H, 6.27; N, 10.25.

Found: C, 56.30; H, 6.12; N, 10.05.

EXAMPLE 270

Synthesis of N-(Toluene-4-sulfonyl)-L-prolyl-L-4-(thiomorpholin-4-ylcarbonyloxy)phenylalanine Isopropyl Ester The title compound was prepared following the procedure described for the preparation of Example 82 and substitution of appropriate starting materials.

Physical data was as follows:

Anal. Calcd. for $C_{29}H_{37}N_3O_7S_2$: C, 57.69; H, 6.18; N, 6.96.

Found: C, 57.36; H, 5.99; N, 6.76.

EXAMPLE 271

Synthesis of N-(Toluene-4-sulfonyl)-L-prolyl-L-4-(4-phenylcarbamylpiperazin-1-ylcarbonyloxy)phenylalanine Isopropyl Ester The title compound was prepared following the procedure described for the preparation of Example 4 and substitution of appropriate starting materials.

NMR data was as follows:

$^1$H NMR (DMSO-d$_6$, 400 MHz): δ 8.62 (s, 1H); 8.11 (d, 1H); 7.73 (d, 2H); 7.45 (m, 4H); 7.26 (m, 3H); 7.04 (m, 2H); 6.95 (m, 1H); 6.25 (d, 1H); 4.90 (m, 1H); 4.50 (m, 1H); 4.11 (m, 1H); 3.6 (br, 4H); 3.4 (br, 4H); 3.10 (m, 2H); 3.00 (m, 1H); 2.40 (s, 3H); 1.60 (m, 3H); 1.40 (m, 1H); 1.18 (d, 3H); 1.12 (d, 3H).

IR (KBr, cm$^{-1}$) 3400-3500(br), 2950, 2900, 1725, 1650, 1540, 1450, 1240, 1210, 1000, 760, 675, 580, 540.

MS ((+)ESI, m/z (%)) 706 (100 [M+H]$^+$).

Anal. Calcd. for $C_{36}H_{43}N_5O_8S.0.35$ EtOAc: C, 60.98; H, 6.27; N, 9.51.

Found: C, 50.31; H, 6.16; N, 9.33.

EXAMPLE 272

Synthesis of N-(Toluene-4-sulfonyl)-L-prolyl-L-4-(4-phenylcarbamylpiperazin-1-ylcarbonyloxy)phenylalanine The title compound was prepared from the product of Example 271 using the procedure described in Method 7.

NMR data was as follows:

$^1$H NMR (DMSO-d$_6$, 400 MHz): δ 12.8 (s, 1H); 8.62 (s, 1H); 8.11 (d, 1H); 7.73 (d, 2H); 7.45 (m, 4H); 7.26 (m, 3H); 7.04 (m, 2H); 6.95 (m, 1H); 6.25 (d, 1H); 4.50 (m, 1H); 4.11 (m, 1H); 3.6 (br, 4H); 3.4 (br, 4H); 3.10 (m, 2H); 3.00 (m, 1H); 2.40 (s, 3H); 1.60 (m, 3H); 1.40 (m, 1H).

IR (KBr, cm$^{-1}$) 3400, 1725, 1650, 1540, 1450, 1240, 1210, 1000, 760, 675, 580, 540.

MS ((−)ESI, m/z (%)) 662 (100 [M−H]$^+$).

EXAMPLE 273

Synthesis of N-(1-n-Butylpyrazole-4-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 137 and substitution of appropriate starting materials.

NMR data was as follows:

$^1$H NMR (CDCl$_3$): δ 7.89 (s, 1H), 7.83 (s, 1H), 7.21 (d, 2H), 7.06 (d, 1H), 7.02 (d, 2H), 5.04 (sept, 1H), 4.89-4.82 (m, 1H), 4.57 (d, 1H), 4.41 (d, 1H), 4.16 (t, 2H), 3.78 (s, 1H), 3.14 (dd, 1H), 3.06 (dd, 1H), 3.09 (s, 3H), 3.00 (s, 3H), 1.85 (pent, 2H), 1.36-1.23 (m, 2H), 1.27 (s, 3H), 1.24 (d, 3H), 1.21 (d, 3H), 1.16 (s, 3H).

$^{13}$C NMR (CDCl$_3$): δ 170.4, 168.3, 154.9, 150.7, 139.2, 131.8, 130.3, 121.8, 117.0, 73.8, 69.6, 54.8, 53.2, 52.7, 50.6, 37.7, 36.6, 36.3, 31.8, 28.9, 24.0, 21.6, 21.5, 19.4, 13.3.

EXAMPLE 274

Synthesis of N-(Toluene-4-sulfonyl)-L-prolyl-L4-(pyridin-4-ylcarbonyl)piperazin-1-ylcarbonyloxy)phenylalanine Isopropyl Ester The title compound was prepared following the procedure described for the preparation of Example 4 and substitution of appropriate starting materials.

NMR data was as follows:

$^1$H NMR (DMSO-d$_6$, 400 MHz): δ 8.69 (dd, 2H), 8.28 (d, 1H); 7.71 (d, 2H); 7.43 (m, 4H); 7.26 (d, 2H); 7.04 (d, 2H); 4.86 (m, 1H); 4.42 (m, 1H); 4.05 (m, 1H); 3.4-3.8 (brm, 9H); 3.05 (m, 3H); 2.40 (s, 3H); 1.60 (m, 3H); 1.40 (m, 1H); 1.18 (d, 3H); 1.15 (d, 3H).

IR(KBr, cm$^{-1}$) 3400, 1725, 1650, 1510, 1200, 1160, 1100, 1010, 650, 600, 550.

MS ((+)ESI, m/z (%)) 692 (100 [M+H]$^+$).

Anal. Calcd. for $C_{35}H_{41}N_5O_9S.0.75H_2O$: C, 59.60; H, 6.07; N, 9.93

Found: C, 59.45; H, 5.86; N, 9.88.

EXAMPLE 275

Synthesis of N-(Toluene-4-sulfonyl)-L-4-oxoprolyl-L-4-(N,N-dimethylcarbamyloxy)phenylalanine The title compound was prepared from the product of Example 164 using the procedure described in Method 11.

Physical data was as follows:

MS [(−)ESI][M−H]) 516.

EXAMPLE 276

Synthesis of N-(Toluene-4-sulfonyl)-L-trans-4-hydroxyprolyl-L-4-(N,N-dimethylcarbamyloxy)phenylalanine The title compound was prepared from the product of Example 165 using the procedure described in Method 11.

Physical data was as follows:

MS [(−)ESI][M−H]) 518.

EXAMPLE 277

Synthesis of N-(4-Cyanobenzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials, mp. 166-167° C.

EXAMPLE 278

Synthesis of N-(4-Aminobenzenesulfonyl)-L-prolyl-L-4-(N,N-dimethylcarbamyloxy)phenylalanine The title compound was prepared from the product of Example 107 using the procedure described in Method 11.

Physical data was as follows:

Anal. Calcd. For $C_{23}H_{28}N_4O_7S$: C, 47.34; H, 4.84; N, 9.60.

Found: C, 47.57; H, 5.20; N, 8.75.

EXAMPLE 279

Synthesis of N-(Toluene-4-sulfonyl)-L-4-oxoprolyl-L-4-(4-methylpiperazin-1-ylcarbonyloxy)phenylalanine tert-Butyl Ester Acetonitrile (3 mL) was cooled to −40° C. ($CH_3CN$/dry ice). Oxalyl chloride (0.10 mL) was added. N-(Toluene-4-sulfonyl)-L-4-hydroxyprolyl-L-4-(4-methylpiperazin-1-ylcarbonyloxy)phenylalanine tert-butyl ester (300 mg) and dry DMSO (0.008 mL) were dissolved in acetonitrile (4 mL) and were added to the above solution. The reaction was stirred at −40° C. for half an hour under dry conditions. Triethylamine (0.33 mL) was added to the solution. The dry ice bath was removed after 5 minutes. The reaction was stirred at room temperature for 1 hour. The solvent was evaporated in vacuo, and ethyl acetate (15 mL) was added. The mixture was washed with water (3×), then washed with brine. The solution was dried over $MgSO_4$. The solvent was evaporated in vacuo, and the residue was flushed on a silica gel column to give 150 mg of the title compound, mp. 84-85° C.

EXAMPLE 280

Synthesis of N-(Toluene-4-sulfonyl)-L-prolyl-L-4-[3-(hydroxymethyl)piperidin-1-ylcarbonyloxy]phenylalanine The title compound was prepared following the procedure described for the preparation of Example 4 and substitution of appropriate starting materials, mp. 84-85° C.

EXAMPLE 281

Synthesis of N-(Toluene-4-sulfonyl)-L-(4,4-difluoro)prolyl-L-4-(N,N-dimethylcarbamyloxy)phenylalanine Isopropyl Ester The title compound was prepared following the procedure described for the preparation of Example 2 and substitution of appropriate starting materials.
Physical data was as follows:
MS: [(+)ESI], $[M+NH_4]^+$ 599.

EXAMPLE 282

Synthesis of N-(Toluene4-sulfonyl)-L-(4,4-difluoro)prolyl-L-4-(N,N-dimethylcarbamyloxy)phenylalanine The title compound was prepared from the product of Example 281 using the procedure described in Method 7.
Physical data was as follows:
MS: [(+)ESI], $[M+NH_4]$ 557.

EXAMPLE 283

Synthesis of N-(Toluene-4-sulfonyl)-L-prolyl-L-(4-benzoylpiperazin-1-ylcarbonyloxy)phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 8.27 (d, 1H); 7.69 (d, 2H); 7.45 (m, 7H); 7.24 9d, 2H); 7.02 (d, 2H); 4.86 (m, 1H); 4.42 (m, 1H); 4.07 (m, 1H); 3.65 (br s, 4H); 3.45 (br s, 4H); 3.35 (m, 1H); 3.05 (m, 3H); 2.38 (s, 3H); 1.60 (m, 3H); 1.40 (m, 1H); 1.18 (d, 3H); 1.11 (d, 3H).
IR(KBr, $cm^{-1}$) 3400, 1725, 1675, 1625, 1510, 1425, 1350, 1250, 1175, 1110, 1010, 700, 660, 590, 550.
MS ((+)ESI, m/z (%)) 708 (100 $[M+NH_2]^+$).
Anal. Calcd. for $C_{36}H_{42}N_4O_8S.0.5H_2O$: C, 61.79; H, 6.19; N, 8.01.
Found: C, 61.64; H, 6.10; N, 7.72.

EXAMPLE 284

Synthesis of N-(1-Methyl-1H-imidazole-4-sulfonyl)-L-prolyl-L-4-(N,N-dimethylcarbamyloxy)phenylalanine Isopropyl Ester The carbamate was prepared by treatment of 1-methylimidazole-4-sulfonyl-Pro-Try-iPr ester with 4-nitrophenyl chloroformate, followed by addition of dimethylamine (triethylamine, methylene chloride, 0° C., stirred at room temperature overnight.) The crude product was purified by flash chromatography (silica, 95:3:2 EtOAc:EtOH;$Et_3N$), followed by recrystallization from EtOAc. A white solid was obtained, mp 162-164° C (8.7 g, 66%).
Physical data was as follows:
Anal. Calcd. for $C_{24}H_{33}N_5O_7S$: C, 53.82; H, 6.21; N, 13.08.
Found: C, 53.47; H, 6.13; N, 12.96.

EXAMPLE 286

Synthesis of N-(Toluene-4-sulfonyl)-L-4-(thiomorpholin-4-ylcarbonyloxy)prolyl-L-4-(thiomorpholin-4-ylcarbonyloxy)phenylalanine The title compound was prepared from the product of Example 285 using the procedure described in Method 11, mp.116-118° C.

EXAMPLE 287

Synthesis of N-(4-Cyanobenzenesulfonyl)-L-prolyl-L-4-(thiomorpholin-4-ylcarbonyloxy)phenylalanine Isopropyl Ester The title compound was prepared following the procedure described for the preparation of Example 4 and substitution of appropriate starting materials, mp. 70-71° C.

EXAMPLE 288

Synthesis of N-(4-Amidinobenzenesulfonyl)-L-prolyl-L-4-(N,N-dimethylcarbamyloxy)phenylalanine Methyl Ester Methanol (dry) was cooled to 0° C. HCl was bubbled in the solution for 15 minutes to make a saturated solution. Example 277 was added and the reaction mixture was stirred at 0° C. for 30 minutes then at room temperature for 24 hours. The solvent was evaporated. $NH_3$ in methanol (2M, 5 mL) was added. The reaction was stirred at room temperature for 24 hours. The solvent was evaporated. The residue was purified by reverse phase HPLC in $CH_3CN:H_2O$ (20:80). At a retention time of 12.45 minutes, the product was isolated and freeze-dried to provide the title compound.
NMR data was as follows:
$^1$H NMR (in DMSO) multiplet at 1.47-1.55 ppm (1H), 1.63-1.72 ppm (3H's), singlet at 2.87 ppm (3H's), singlet at 3.02 ppm (3H's), multiplet at 3.05-3.10 ppm (2H's), multiplet at 3.17-3.22 ppm (1H), multiplet at 3.37-3.42 ppm (1H), singlet at 3.62 ppm (3H's), multiplet at 4.21-4.23 ppm (1H), quartet at 4.48-4.56 ppm (1H), doublet at 7.00-7.03 ppm (2H's), doublet at 7.23-7.26 ppm (2H's), a broad peak at 7.20-7.50 ppm, doublet at 8.02-8.03 ppm (4H's), doublet at 8.48-8.52 ppm (1H).

EXAMPLE 289

Synthesis of N-(Toluene-4-sulfonyl)-L-4-hydroxyprolyl-L-4-(thiomorpholin-4-ylcarbonyloxy)phenylalanine tert-Butyl Ester The title compound was prepared following the procedure described for the preparation of Example 4 and substitution of appropriate starting materials, mp. 80-82° C.

EXAMPLE 290

Synthesis of N-(Toluene4-sulfonyl)-L-4-hydroxyprolyl-L-4-(thiomorpholin-4-ylcarbonyloxy)phenylalanine N-(Toluene-4-sulfonyl)-L-4-hydroxyprolyl-L-4-(thiomorpholin-4-ylcarbonyloxy)phenylalanine tert-butyl ester (160 mg) was dissolved in formic acid (7 mL). The reaction was stirred at room temperature for 6 hours. The solvent was evaporated and the residue purified using reverse phase HPLC in 20:80 $CH_3CN$/water. At a retention time of 5.85 minutes, 50 mg of the title compound was obtained, mp. 170-172° C.

EXAMPLE 291

Synthesis of N-(Toluene-4-sulfonyl)-L-prolyl-L-(4-benzoylpiperazin-1-ylcarbonyloxy)phenylalanine The title compound was prepared from the product of Example 283 using the procedure described in Method 11.
NMR data was as follows:
$^1$H NMR (DMSO-$d_6$, 400 MHz): δ 12.8 (s, 1H); 8.27 (d, 1H); 7.69 (d, 2H); 7.45 (m, 7H); 7.24 (d, 2H); 7.02 (d, 2H); 4.42 (m, 1H); 4.07 (m, 1H); 3.65 (br s, 4H); 3.45 (br s, 4H); 3.35 (m, 1H); 3.05 (m, 3H); 2.38 (s, 3H); 1.60 (m, 3H); 1.40 (m, 1H).
IR(KBr, $cm^{-1}$) 3400, 1725, 1675, 1625, 1510, 1425, 1350, 1260, 1175, 1110, 1010, 700, 660, 590, 550.
MS ((+)ESI, m/z (%)) 666 (100 $[M+NH_4]^+$).
Anal. Calcd. for $C_{33}H_{36}N_4O_8S.0.66H_2O$: C, 60.00; H, 5.69; N, 8.48
Found: C, 60.36; H, 5.70; N, 7.81.

EXAMPLE 292

Synthesis of N-(4-Amidinobenzenesulfonyl)-L-prolyl-L-4-(thiomorpholin-4-ylcarbonyloxy)phenylalanine Methyl Ester The title compound was prepared following the procedure described for the preparation of Examples 287 and 288.
Physical data was as follows:
MS: [(+)ESI][M+H] 604.

EXAMPLE 293

Synthesis of N-(3-Fluorobenzenesulfonyl)-L-prolyl-L-4-(N,N-dimethylcarbonyloxy)phenylalanine The title compound was prepared from the product of Example 166 using the procedure described in Method 11, mp. 82-83° C.

EXAMPLE 294

Synthesis of N-(Toluene-4-sulfonyl)-L-prolyl-L-4-[N-methyl-N-(2-(N'-methyl-N'-toluenesulfonyl-amino)ethyl)carbamyloxy]phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 8.27 (d, 1H); 7.71 (d, 2H); 7.69 (d, 2H); 7.40 (m, 4H); 7.24 (d, 2H); 6.99 (d, 2H); 4.86 (m, 1H); 4.43 (m, 1H); 4.06 (m, 1H); 3.51 (m, 1H); 3.2-3.35 (m, 3H); 2.9-3.2 (overlapping m, 7H); 2.67 (d, 3H); 2.38 (s, 6H); 1.60 (m, 3H); 1.40 (m, 1H); 1.20 (d, 3H); 1.15 (d, 3H).
IR (KBr, $cm^{-1}$) 3400, 2975, 2950, 1725, 1680, 1510, 1450, 1400, 1280, 1225, 1150, 1110, 800, 730, 675, 575, 550.
MS ((+)ESI, m/z (%)) 760 (100 $[M+NH_4]^+$).
Anal. Calcd. for $C_{36}H_{46}N_4O_9S_2$: C, 58.20; H, 6.24; N, 7.54.
Found: C, 57.90; H, 6.30; N, 7.34.

EXAMPLE 295

Synthesis of N-(Toluene-4-sulfonyl)-L-prolyl-L-4-[N-(2-(N'-phenylaminocarbonyloxy)ethyl)carbamyloxy)]phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 9.67 (s, 1H); 8.27 (d, 1H); 7.72 (d, 2H); 7.47 (d, 2H); 7.42 (d, 2H); 7.24 (m, 4H); 6.98 (m, 3H); 4.87 (m, 1h); 4.45 (m, 1H); 4.18 (m, 2H); 4.05 (m, 1H); 3.4 (m, 3H); 3.05 (m, 3H) 2.40 (s, 3H); 1.6 (m, 3H); 1.40 (m, 1H); 1.2 (d, 3H); 1.15 (d, 3H).
IR (KBr, $cm^{-1}$) 3350, 2950, 1725, 1675, 1600, 1550, 1500, 1325, 1200, 1150, 1100, 650, 575, 525.
MS ((+)ESI, m/z (%)) 698 (100 $[M+NH_4]^+$).
Anal. Calcd. for $C_{34}H_{40}N_4O_9S.0.21$ EtOAc. $0.5H_2O$: C, 59.08; H, 6.07; N, 7.91.
Found: C, 59.08; H, 6.02; N, 7.80.

EXAMPLE 296

Synthesis of N-(4-Fluorobenzenesulfonyl)-L4-(trans-hydroxy)prolyl-L-4-(N,N-dimethylcarbamyloxy) phenylalanine Isopropyl Ester The title compound was prepared following the procedure described in Example 2 and substitution of appropriate starting materials.
Physical data was as follows:
MS: [(+)ESI], $[M+NH_4]$ 583.

EXAMPLE 297

Synthesis of N-(4-Fluorobenzenesulfonyl)-L-4-(trans-hydroxy)prolyl-L-4-(N,N-dimethylcarbamyloxy)phenylalanine tert-Butyl Ester The title compound was prepared following the procedure described in Example 2 and substitution of appropriate starting materials.
Physical data was as follows:
MS: [(+)ESI], $[M+NH_4]$ 597.

EXAMPLE 298

Synthesis of N-(4-Amidinobenzenesulfonyl)-L-prolyl-L4-(N,N-dimethylcarbamyloxy)phenylalanine The title compound was prepared from the product of Example 288 using the procedure described in Method 5, mp.130-132° C.

EXAMPLE 299

Synthesis of Piperazine-1,4-dicarboxylic Acid Bis-{4-[(2S)-2-tert-butoxycarbonyl-2-((4R)-5,5-dimethyl-3-(toluene-4-sulfonyl)thiazolidine-4-carboxamido)ethyl phenyl}Ester The title compound was prepared following the procedure described in Example 4, except that 0.5 equivalents of piperazine were used.

Physical data was as follows:
Anal. Calcd. for $C_{58}H_{74}N_6O_{14}S_4$: C, 57.69; H, 6.18; N, 6.96.
Found: C, 58.01; H, 6.07; N, 6.68.

EXAMPLE 300

Synthesis of Piperazine-1,4-dicarboxylic Acid Bis-{4-[(2S)-2-carboxy-2-((4R)-5,5-dimethyl-3-(toluene-4-sulfonyl)thiazolidine-4-carboxamido)ethyl] phenyl}Ester The title compound was prepared by hydrolysis of the di-t-butyl ester from Example 299 with formic acid to give a white foam (300 mg, quantitative).

Physical data was as follows:
Anal. Calcd. for $C_{50}H_{58}N_6O_{14}S_4$: C, 54.83; H, 5.34; N, 7.67
Found: C, 55.10; H, 5.57; N, 7.37.

Other compounds of formulae I and Ia prepared by the methods described above include those set forth in Examples 301-370 in Table 5 below.

TABLE 5

$$R^1-\underset{\underset{O}{\overset{O}{\|}}}{S}-\underset{R^2}{N}-CH(R^3)-\overset{O}{\overset{\|}{C}}-\underset{H}{N}-CH(R^5)-\overset{O}{\overset{\|}{C}}-R^6$$

| Ex. No. | $R^1$ | $R^2$ | $R^3$ | $R^5$ | $R^6$ |
|---|---|---|---|---|---|
| 301 | p-CH$_3$-φ- | $R^2/R^3$ = cyclic —CH$_2$CH$_2$—NH—CH$_2$— (L-piperazinyl) | | p-[(CH$_3$)$_2$NC(O)O-]benzyl- | —OC(CH$_3$)$_3$ |
| 302 | p-F-φ- | $R^2/R^3$ = cyclic —CH$_2$—S—C(CH$_3$)$_2$— (L-5,5-dimethylthiazolidin-4-yl) | | p-[(2-(hydroxymethyl)pyrrolidin-1-yl-C(O)O-]benzyl- | —OC(CH$_3$)$_3$ |
| 303 | p-F-φ- | $R^2/R^3$ = cyclic —CH$_2$—S—C(CH$_3$)$_2$— (L-5,5-dimethylthiazolidin-4-yl) | | p-[(2-(hydroxymethyl)pyrrolidin-1-yl-C(O)O-]benzyl- | —OH |
| 304 | p-CH$_3$-φ- | $R^2/R^3$ = cyclic 3 carbon atoms (L-pyrrolidinyl) | | p-[(2-(CH$_3$OC(O)-)pyrrolidin-1-yl)-C(O)O-]benzyl- | —OC(CH$_3$)$_3$ |
| 305 | p-F-φ- | $R^2/R^3$ = cyclic —CH$_2$—S—C(CH$_3$)$_2$— (L-5,5-dimethylthiazolidin-4-yl) | | 3-chloro-4-[(thiomorpholin-4-yl)-C(O)O-]benzyl- | —OH |
| 306 | p-F-φ- | $R^2/R^3$ = cyclic —CH$_2$—S—C(CH$_3$)$_2$— (L-5,5-dimethylthiazolidin-4-yl) | | p-[(4-(pyridin-2-yl)piperazin-1-yl)-C(O)O-]benzyl- | —OH |
| 307 | p-F-φ- | $R^2/R^3$ = cyclic —CH$_2$—S—C(CH$_3$)$_2$— (L-5,5-dimethylthiazolidin-4-yl) | | p-[(4-(pyridin-2-yl)piperazin-1-yl)-C(O)O-]benzyl- | —OC(CH$_3$)$_3$ |
| 308 | p-CH$_3$-φ- | $R^2/R^3$ = cyclic —CH$_2$CH(OH)CH$_2$— (L-4-hydroxypyrrolidinyl) | | p-[(thiomorpholin-4-yl)-C(O)O-]benzyl- | —OC(CH$_3$)$_3$ |
| 309 | p-CH$_3$-φ- | $R^2/R^3$ = cyclic 3 carbon atoms (L-pyrrolidinyl) | | p-[(CH$_3$)$_2$NC(O)O-]benzyl- | —O(CH$_2$CH$_2$O)$_2$CH$_3$ |
| 310 | p-F-φ- | $R^2/R^3$ = cyclic —CH$_2$—S—C(CH$_3$)$_2$— (L-5,5-dimethylthiazolidin-4-yl) | | p-[(4-(pyrimidin-2-yl)piperazin-1-yl)-C(O)O-]benzyl- | —OC(CH$_3$)$_3$ |
| 311 | p-F-φ- | $R^2/R^3$ = cyclic —CH$_2$—S—C(CH$_3$)$_2$— (L-5,5-dimethylthiazolidin-4-yl) | | 3-fluoro-4-[(CH$_3$)$_2$NC(O)O-]benzyl- | —OCH(CH$_3$)$_2$ |
| 312 | p-CH$_3$-φ- | $R^2/R^3$ = cyclic —CH$_2$—CH$_2$N—(—SO$_2$CH$_3$)—CH$_2$— (L-4-methanesulfonyl-piperazinyl) | | p-[(CH$_3$)$_2$NC(O)O-]benzyl- | —OC(CH$_3$)$_3$ |
| 313 | $R^1/R^2$ = 1,1-dioxo-2,3-dihydro-3,3-dimethyl-1,2-benzisothiazol-2-yl- | | H | p-[(CH$_3$)$_2$NC(O)O-]benzyl- | —OH |

TABLE 5-continued $$R^1-\underset{\underset{O}{\overset{O}{\|}}}{\overset{\overset{O}{\|}}{S}}-\underset{R^2}{\overset{}{N}}-\underset{}{\overset{R^3}{\underset{}{CH}}}-\underset{}{\overset{O}{\underset{}{C}}}-\underset{H}{\overset{}{N}}-\underset{}{\overset{R^5}{\underset{}{CH}}}-\underset{}{\overset{O}{\underset{}{C}}}-R^6$$

| Ex. No. | R¹ | R² | R³ | R⁵ | R⁶ |
|---|---|---|---|---|---|
| 314 | R¹/R² = N-2,10-camphor-sultamyl- | | H | p-[(CH₃)₂NC(O)O-]benzyl- | —OC(CH₃)₃ |
| 315 | R¹/R² = N-2,10-camphor-sultamyl- | | H | p-[(CH₃)₂NC(O)O-]benzyl- | —OH |
| 316 | R¹/R² = N-2,10-camphor-sultamyl- | | H | 3-chloro-4-[(CH₃)₂NC(O)O-]benzyl- | —OCH(CH₃)₂ |
| 317 | p-Br-φ- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| 318 | p-Br-φ- | R²/R³ = cyclic —CH₂—S—C(CH₃)₂— (L-5,5-dimethylthiazolidin-4-yl) | | p-[(CH₃)₂NC(O)O-]benzyl- | —OH |
| 319 | p-CH₃-φ- | R²/R³ = cyclic —CH₂—CH(OH)—CH₂— (L-4 hydroxypyrrolidinyl) | | p-[(4-methylpiperazin-1-yl)-C(O)O-]benzyl- | —OH |
| 320 | p-F-φ- | R²/R³ = cyclic —CH₂—S—C(CH₃)₂— (L-5,5-dimethylthiazolidin-4-yl) | | p-[(4-pyrimidin-2-yl)piperazin-1-yl)-C(O)O-]benzyl- | —OH |
| 321 | p-F-φ- | R²/R³ = cyclic —CH₂—S—C(CH₃)₂— (L-5,5-dimethylthiazolidin-4-yl) | | p-[4-(pyridin-2-yl)piperazin-1-yl)C(O)O-]benzyl- | —OCH(CH₃)₂ |
| 322 | p-F-φ- | R²/R³ = cyclic —CH₂—CH₂—S— (thiazolidin-2-yl) | | p-[(CH₃)₂NC(O)O-]benzyl- | —OH |
| 323 | p-F-φ- | R²/R³ = cyclic —CH₂—CH₂—S— (thiazolidin-2-yl) | | p-[(CH₃)₂NC(O)O-]benzyl- | —OC(CH₃)₃ |
| 324 | p-CH₃-φ- | R²/R³ = cyclic —CH₂—C(O)—CH₂— (L-4-oxopyrrolidinyl) | | p-[(thiomorpholin-4-yl)C(O)O-]benzyl- | —OH |
| 325 | p-CH₃-φ- | R²/R³ = cyclic —CH₂—C(O)—CH₂— (L-4-oxopyrrolidinyl) | | p-[(4-methylpiperazin-1-yl)-C(O)O-]benzyl- | —OH |
| 326 | p-F-φ- | R²/R³ = cyclic —CH₂—CH₂—S— (thiazolidin-2-yl) | | p-[(4-(pyridin-2-yl)piperazin-1-yl)-C(O)O-]benzyl- | —OH |
| 327 | p-NO₂-φ- | R²/R³ = cyclic 3 carbon atoms (L-pyrrolidinyl) | | p-[(4-(pyridin-2-yl)piperazin-1-yl)-C(O)O-]benzyl- | —OC(CH₃)₃ |
| 328 | p-F-φ- | R²/R³ = cyclic —CH₂—CH₂—S— (thiazolidin-2-yl) | | p-[(4-(pyridin-2-yl)piperazin-1-yl)-C(O)O-]benzyl- | —OC(CH₃)₃ |
| 329 | p-Br-φ- | R²/R³ = cyclic —CH₂—S—C(CH₃)₂— (L-5,5-dimethylthiazolidin-4-yl) | | p-[(4-(pyridin-2-yl)piperazin-1-yl)-C(O)O-]benzyl- | —OH |
| 330 | p-CH₃-φ- | R²/R³ = cyclic 3 carbon atoms (L-pyrrolidinyl) | | p-[(4-(φNHC(S)-)piperazin-1-yl)-C(O)O-]benzyl- | —OCH(CH₃)₂ |
| 331 | p-F-φ- | R²/R³ = cyclic —CH₂—CH₂—S— (thiazolidin-2-yl) | | p-[(4-CH₃-homo-piperazin-1-yl)-C(O)O-]benzyl- | —OC(CH₃)₃ |
| 332 | p-CH₃-φ- | R²/R³ = cyclic —CH₂CH(—OSO₂HC₃)—CH₂— (L-4-methanesulfoxy-pyrrolidinyl) | | p-[(CH₃)₂NC(O)O-]benzyl- | —OC(CH₃)₃ |
| 333 | p-H₂NC(O)-φ- | R²/R³ = cyclic 3 carbon atoms (L-pyrrolidinyl) | | p-[(CH₃)₂NC(O)O-]benzyl- | —OH |
| 334 | p-H₂NC(O)-φ- | R²/R³ = cyclic 3 carbon atoms (L-pyrrolidinyl) | | p-[(thiomorpholin-4-yl)C(O)O-]benzyl- | —OH |
| 335 | p-H₂NC(=N)-φ- | R²/R³ = cyclic 3 carbon atoms (L-pyrrolidinyl) | | p-[(thiomorpholin-4-yl)C(O)O-]benzyl- | —OH |

TABLE 5-continued $$R^1-\underset{\underset{O}{\overset{O}{\|}}}{\overset{\overset{O}{\|}}{S}}-\underset{R^2}{N}-\underset{\underset{}{}}{\overset{R^3}{C}H}-\overset{O}{\overset{\|}{C}}-\underset{H}{N}-\underset{}{\overset{R^5}{C}H}-\overset{O}{\overset{\|}{C}}-R^6$$

| Ex. No. | R¹ | R² | R³ | R⁵ | R⁶ |
|---|---|---|---|---|---|
| 336 | p-NO₂-ϕ- | R²/R³ = cyclic 3 carbon atoms (L-pyrrolidinyl) | | p-[(4-(pyridin-2-yl)piperazin-1-yl)-C(O)O-]benzyl- | —OH |
| 337 | p-F-ϕ- | R²/R³ = cyclic —CH₂—S—C(CH₃)₂— (L-5,5-dimethylthiazolidin-4-yl) | | 3-chloro-4-[(4-pyridin-2-yl)piperazin-1-yl)C(O)O]-benzyl- | —OCH₂CH₃ |
| 338 | p-F-ϕ- | R²/R³ = cyclic —CH₂—S—C(CH₃)₂— (L-5,5-dimethylthiazolidin-4-yl) | | 3-chloro-4-[(4-pyridin-2-yl)piperazin-1-yl)C(O)O]-benzyl- | —OH |
| 339 | p-F-ϕ- | R²/R³ = cyclic —CH₂—CH₂—S— (thiazolidin-2-yl) | | p-[(4-CH₃-homopiperazin-1-yl-C(O)O-]benzyl- | —OH |
| 340 | 1-methylpyrazol-4-yl- | R²/R³ = cyclic —CH₂—S—C(CH₃)₂— (L-5,5-dimethylthiazolidin-4-yl) | | 3-chloro-4-[(CH₃)₂NC(O)O-]benzyl- | —OCH(CH₃)₂ |
| 341 | 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 342 | 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| 343 | p-CH₃-ϕ- | R²/R³ = cyclic 3 carbon atoms (L-pyrrolidinyl) | | p-[(4-(pyridin-2-yl)piperazin-1-yl)C(O)O-]benzyl- | —OH |
| 344 | p-CH₃-ϕ- | R²/R³ = cyclic 3 carbon atoms (L-pyrroldiinyl) | | p-[(4-(pyridin-2-yl)piperazin-1-yl)C(O)O-]benzyl- | —OC(CH₃)₃ |
| 345 | p-CH₃-ϕ- | R²/R³ = cyclic 3 carbon atoms (L-pyrrolidinyl) | | p-[(4-(pyridin-2-yl)piperazin-1-yl)-C(O)O-]benzyl- | —OCH(CH₃)₂ |
| 346 | p-F-ϕ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 347 | p-F-ϕ- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| 348 | p-CH₃-ϕ- | R²/R³ = cyclic —CH₂CH₂N(—SO₂—CH₃)CH₂— (4-methanesulfonyl-piperazin-2-yl) | | p-[(CH₃)₂NC(O)O-]benzyl- | —OH |
| 349 | p-CH₃ϕ- | R²/R³ = cyclic —CH₂CH(—OSO₂—CH₃)CH₂— (L-4-methanesulfoxy-pyrrolidinyl) | | p-[(CH₃)₂NC(O)O-]benzyl- | —OH |
| 350 | CH₃— | —CH₂ϕ | H | p-[(CH₃)₂NC(O)O-]benzyl- | —OC(CH₃)₃ |
| 351 | p-Br-ϕ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OC(CH₃)₃ |
| 352 | p-CF₃O-ϕ- | R²/R³ = cyclic —CH₂—S—C(CH₃)₂— (L-5,5-dimethylthiazolidin-4-yl) | | p-[(CH₃)₂NC(O)O-]benzyl- | —OH |
| 353 | p-CF₃O-ϕ- | R²/R³ = cyclic —CH₂—S—C(CH₃)₂— (L-5,5-dimethylthiazolidin-4-yl) | | p-[(CH₃)₂NC(O)O-]benzyl- | —OC(CH₃)₃ |
| 354 | p-CF₃O-ϕ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OC(CH₃)₃ |
| 355 | p-F-ϕ- | R²/R³ = cyclic 3 carbon atoms (L-pyrrolidinyl) | | p-[(4-(pyridin-2-yl)piperazin-1-yl)C(O)O-]benzyl- | —OH |
| 356 | p-F-ϕ- | R²/R³ = cyclic —CH₂CH(OH)CH₂— (L-4-hydroxypyrrolidinyl) | | p-[(4-(pyridin-2-yl)piperazin-1-yl)C(O)O-]benzyl- | —OH |
| 357 | p-CF₃O-ϕ- | R²/R³ = cyclic —CH₂—S—C(CH₃)₂— (L-5,5-dimethylthiazolidin-4-yl) | | p-[(4-(pyridin-2-yl)piperazin-1-yl)C(O)O-]benzyl- | —OH |
| 358 | 1-methylimidazol-4-l- | R²/R³ = cyclic 3 carbon atoms (L-pyrrolidinyl) | | 3-chloro-4-[(CH₃)₂NC(O)O]-benzyl- | —OH |

TABLE 5-continued $$R^1-\underset{\underset{O}{\|}}{\overset{\overset{O}{\|}}{S}}-\underset{R^2}{\overset{}{N}}-CH-\underset{}{\overset{\overset{O}{\|}}{C}}-\underset{H}{N}-CH-\overset{\overset{O}{\|}}{C}-R^6$$

with R³ on first CH and R⁵ on second CH

| Ex. No. | R¹ | R² | R³ R⁵ | R⁶ |
|---|---|---|---|---|
| 359 | 1-methylimidazol-4-yl- | R²/R³ = cyclic 3 carbon atoms (L-pyrrolidinyl) | 3-chloro-4-[(CH₃)₂NC(O)O-]benzyl- | —OCH(CH₃)₂ |
| 360 | 1-methylimidazol-4-yl- | R²/R³ = cyclic 3 carbon atoms (L-pyrrolidinyl) | p-[(4-(pyridin-2-yl)piperazin-1-yl)-C(O)O-]benzyl- | —OH |
| 361 | 1-methylimidazol-4-yl- | R²/R³ = cyclic —CH₂—S—C(CH₃)₂— (L-5,5-dimethylthiazolidin-4-yl) | p-[(4-(pyridin-2-yl)piperazin-1-yl)C(O)O-]benzyl- | —OH |
| 362 | 1-methylpyrazol-4-yl- | R²/R³ = cyclic 3 carbon atoms (L-pyrrolidinyl) | p-[(4-(pyridin-2-yl)piperazin-1-yl)C(O)O-]benzyl- | —OH |
| 363 | 1-methylpyrazol-4-yl- | R²/R³ = cyclic 3 carbon atoms (L-pyrrolidinyl) | p-[(4-(pyridin-2-yl)piperazin-1-yl)C(O)O-]benzyl- | —OCH(CH₃)₂ |
| 364 | 1-methylpyrazol-4-yl- | R²/R³ = cyclic 3 carbon atoms (L-pyrrolidinyl) | p-[(4-(pyridin-2-yl)piperazin-1-yl)C(O)O-]benzyl- | —OC(CH₃)₃ |
| 365 | 1-methylpyrazol-4-yl- | R²/R³ = cyclic —CH₂—S—C(CH₃)₂— (L-5,5-dimethylthiazolidin-4-yl) | p-[(4-(pyridin-2-yl)piperazin-1-yl)C(O)O-]benzyl- | —OC(CH₃)₃ |
| 366 | 1-methylpyrazol-4-yl- | R²/R³ = cyclic 3 carbon atoms (L-pyrrolidinyl) | 3-chloro-4-[(4-(pyridin-2-yl)piperazin-1-yl)C(O)O-]benzyl- | —OCH(CH₃)₂ |
| 367 | 1-methylpyrazol-4-yl- | R²/R³ = cyclic —CH₂—S—C(CH₃)₂— (L-5,5-dimethylthiazolidin-4-yl) | p-[(CH₃)₂NC(O)O-]benzyl- | —OCH₂CH₂Oφ |
| 368 | 1-methylpyrazol-4-yl- | R²/R³ = cyclic —CH₂—S—C(CH₃)₂— (L-5,5-dimethylthiazolidin-4-yl) | 3-chloro-4-[(4-pyridin-2-yl)piperazin-1-yl)C(O)O-]benzyl- | —OH |
| 369 | 1-methylpyrazol-4-yl- | R²/R³ = cyclic —CH₂—S—C(CH₃)₂— (L-5,5-dimethylthiazolidin-4-yl) | 3-chloro-4-[(4-pyridin-2-yl)piperazin-1-yl)C(O)O-]benzyl- | —OCH₂CH₃ |
| 370 | 1,5-dimethyl-3-chloro-pyrazol-4-yl- | R²/R³ = cyclic —CH₂—S—C(CH₃)₂— (L-5,5-dimethylthiazolidin-4-yl) | p-[4-[5-CF₃-pyridin-2-yl)piperazin-1 yl)-C(O)O-]benzyl- | —OH |

In addition, Examples 319, 324, 325, 332, 333, 334, 335 and 349 in Table 5 are exemplified as follows:

EXAMPLE 319

Synthesis of N-(Toluene-4-sulfonyl)-L-(4-hydroxy) prolyl-L-4-(4-methylpiperazin-1-ylcarbonyloxy) phenylalanine The starting N-(toluene-4-sulfonyl)-L-(4-hydroxy)prolyl-L-4-(4-methylpiperazin-1-ylcarbonyloxy)phenylalanine tert-butyl ester (300 mg) was dissolved in formic acid (15 mL). The reaction was stirred at room temperature for 72 hours. The solvent was evaporated and the residue was purified using HPLC, reverse phase, 20-80% CH₃CN/water. At a retention time of 10.75 minutes, 82 mg of the title compound was obtained, mp: 128-130° C.

EXAMPLE 324

Synthesis of N-(Toluene-4-sulfonyl)-L-(4-oxo)prolyl-L-4-(thiomorpholin-4-ylcarbonyloxy)phenylalanine The starting N-(toluene-4-sulfonyl)-L-(4-oxo)prolyl-L-4-(thiomorpholin-4-ylcarbonyloxy)phenylalanine tert-butyl ester (130 mg) was dissolved in formic acid (7 mL). The reaction was stirred at room temperature for 6 hours. The solvent was evaporated in vacuo to give 150 mg of the desired product, mp: 111-112° C.

EXAMPLE 325

Synthesis of N-(Toluene-4-sulfonyl)-L-(4-oxo)prolyl-L-4-(4-methylpiperazin-1-ylcarbonyloxy)phenylalanine The starting N-(toluene-4-sulfonyl)-L-(4-oxo)prolyl-L-4-(4-methylpiperazin-1-ylcarbonyloxy)phenylalanine tert-butyl ester (150 mg) was dissolved in formic acid (7 mL). The reaction was stirred at room temperature for 6 hours. The solvent was evaporated in vacuo, and the residue was purified using HPLC, reverse phase, 20-80% CH₃CH/water. The retention time was 10.34 minutes. The product was freeze dried to yield 82 mg of the title compound, mp: 99-101° C.

EXAMPLE 332

Synthesis of N-(Toluene-4-sulfonyl)-L-(4-methanesulfonyloxy)prolyl-L-4-(N,N-dimethylcarbamyloxy) phenylalanine tert-Butyl Ester The starting N-(toluene-4-sulfonyl)-L-(4-hydroxy)prolyl-L-4-(N,N-dimethylcarbamyloxy)phenylalanine tert-butyl ester (300 mg) and methylsulfonyl chloride was dissolved in THF (7 mL) at 0° C. in an ice bath. Triethylamine (0.21 mL) was added. The ice bath was removed after 10 minutes. The reaction mixture was stirred at room temperature for 24 hours. Ethyl acetate (20 mL) as added. The mixture was washed with citric acid (5%, 20 mL, 2×), and washed with saturated NaHCO$_3$ solution (20 mL), then with brine. The solution was dried over MgSO$_4$. The solvent was evaporated, and the residue was flushed on a silica gel column. The solvent was evaporated in vacuo to give 300 mg of the desired product, mp: 73-74° C.

EXAMPLE 333

Synthesis of N-(4-Aminobenzenesulfonyl)-L-prolyl-L-4-(N,N-dimethylcarbamyloxy)phenylalanine The starting N-(4-aminobenzenesulfonyl)-L-prolyl-L-4-(N,N-dimethylcarbamyloxy)phenylalanine methyl ester (300 mg) and LiOH solution (2M, 0.6 mL) were added to methanol (6 mL). The reaction was stirred at room temperature for 7 hours. The solvent was evaporated in vacuo, and the residue was purified using HPLC, reverse phase, 20-80% CH$_3$CN/water. At a retention time of 12.11 minutes, 27 mg of the desired product were obtained, mp: 130-132° C.

EXAMPLE 334

Synthesis of N-(4-Aminocarbonylbenzenesulfonyl)-L-prolyl-L-4-(thiomorpholin4-ylcarbonyloxy)phenylalanine The starting N-(4-aminocarbonylbenzenesulfonyl)-L-prolyl-L-4-(thiomorpholin-4-ylcarbonyloxy)phenylalanine methyl ester (300 mg) and LiOH solution (2M, 0.5 mL) were added to methanol (6 mL). The reaction was stirred at room temperature for 6 hours. The solvent was evaporated in vacuo, and the residue purified using HPLC, reverse phase, 20-80% CH$_3$CN/water. At a retention time of 12.69 minutes, 20 mg of the desired product was obtained, mp: 123-125° C.

EXAMPLE 335

Synthesis of N-(4-Amidinobenzenesulfonyl)-L-prolyl-L-4-(thiomorpholin-4-ylcarbonyloxy)phenylalanine The starting N-(4-amidinobenzenesulfonyl)-L-prolyl-L-4-(thiomorpholin-4-ylcarbonyloxy)phenylalanine methyl ester (300 mg) and LiOH solution (2M, 0.5 mL) were added to methanol (6 mL). The reaction was stirred at room temperature for 8 hours. The solvent was evaporated in vacuo, and the residue was purified using HPLC, reverse phase, 20-80% CH$_3$CN/water. At a retention time of 11.78 minutes, 25 mg of the desired product were obtained, mp: 123-125° C.

EXAMPLE 349

Synthesis of N-(Toluene-4-sulfonyl)-L-(4-methanesulfonyloxy)prolyl-L-4-(N,N-dimethylcarbamyloxy)phenylalanine The starting N-(toluene-4-sulfonyl)-L-(4-methanesulfonyloxy)prolyl-L-4-(N,N-dimethylcarbamyloxy)phenylalanine tert-butyl ester (200 mg) was dissolved in formic acid (5 mL). The reaction mixture was stirred at room temperature for 6 hours. The solvent was evaporated in vacuo to provide the desired product (195 mg), mp: 83-84° C.

EXAMPLE 371

Synthesis of N-(Toluene-4-sulfonyl)-L-prolyl-4-(α-methylbenzyloxy)-L-phenylalanine N-(Toluene-4-sulfonyl)-L-prolyl-L-tyrosine methyl ester (785 mg, 1.89 mmol) was dissolved in DMF (20 mL) at room temperature. To this was added K$_2$CO$_3$ (1.1 eq, 281 mg) and 1-bromoethyl benzene (1.1 eq, 284 µL). The reaction was stirred for 12 hours at room temperature. Ethyl acetate (100 mL) was added, and the organic layer washed several times with brine (5×50 mL). The organic layer was dried over MgSO$_4$. Upon filtration and evaporation of the solvents under reduced pressure, an oil was isolated. The crude material was purified by elution on silica gel (EtOAc/hexanes (1:4)). The desired material was isolated in 32% yield (330 mg, 0.6 mmol). The methyl ester (330 mg. 0.6 mmol) was then converted to the corresponding acid upon treatment with NaOH (1.1 eq, 27 mg), in MeOH:H$_2$O (1:1) (15 mL), for 4 hours at room temperature. EtOAc was added as well as water. The aqueous layer was collected and acidified with 1N HCl to pH 2.5, and reextracted with EtOAc. The organic layer was dried over MgSO$_4$. Upon filtration and evaporation of the solvents under reduced pressure, a foam was isolated in quantitative yields.

NMR data was as follows:

$^1$H NMR (300 MHz, CDCl$_3$): δ=7.71 (bd, 2H), 7.34 (m, 7H), 7.20 (m, 1H), 7.01 (m, 2H), 6.80 (d, 2H, J=8.37 Hz), 5.27 (m, 1H), 4.75 (m, 1H), 4.04 (m, 1H), 3.23-2.93 (m, 4H), 2.42 (s, 3H), 1.85 (m, 1H), 1.60 (d, 3H, J=6.09 Hz), 1.36-1.26 (m, 3H).

$^{13}$C NMR (75 MHz, CDCl$_3$): δ=174.74, 172.22, 157.53, 145.00, 143.77, 133.42, 130.76, 130.58, 129.14, 128.60, 128.48, 127.94, 126.15, 116.57, 76.39, 62.73, 53.90, 50.09, 37.09, 25.07, 24.52, 22.17.

Mass Spectroscopy: (FAB) 537 (M+H).

EXAMPLE 372

Synthesis of N-(Toluene-4-sulfonyl)-L-prolyl-4-(2-carboxyphenoxy)-L-phenylalanine N-(Toluene-4-sulfonyl)-L-prolyl-L-tyrosine methyl ester (2.14 g, 5.16 mmol) was added to a suspension of sodium hydride, 60% in oil (1.1 eq., 228 mg) in xylenes (50 mL) at 0° C. The reaction mixture was stirred for 5 minutes and cuprous bromidedimethyl sulfide complex (1.4 eq., 1.48 g) was added. The reaction mixture was stirred at 23° C. for 0.5 hr. To this was added sodium 2-iodobenzoate (1.5 eq., 8.06 mmol), and the reaction mixture was refluxed for 12 hours. EtOAc (100 mL) was added, and the organic layer washed with NH$_4$Cl, 10% HCl, and brine, then dried over MgSO$_4$. The crude material was eluted on column chromatography (silica gel), with CHCl$_3$:MeOH (9:1), and isolated as an oil. The acid was prepared by treatment with NaOH (1.1 eq), in MeOH:H$_2$O (1:1) for 4 hours at room temperature. The diacid was isolated as a foam.

NMR data was as follows:

$^1$H NMR (300 MHz, CDCl$_3$): δ=7.71 (m, 2H), 7.29 (m, 4H), 7.19 (m, 4H), 6.72 (m, 1H), 4.84 (m, 1H), 4.13 (m, 1H), 3.39 (m, 1H), 3.11 (m, 3H), 2.43 (s, 3H), 1.89 (m, 1H), 1.48 (m, 3H).

$^{13}$C NMR (75 MHz, CDCl$_3$): δ=172.67, 157.84, 155.89, 155.04, 145.17, 133.61, 133.19, 133.08, 131.69, 131.02, 130.64, 128.42, 127.87, 124.24, 120.04, 119.61, 116.12, 62.81, 50.31, 37.28, 30.69, 24.81, 22.15.

Mass Spectroscopy: (FAB) 553 (M+H).

EXAMPLE 373

Synthesis of N-(Toluene-4-sulfonyl)-L-prolyl-O-(benzyl)-L-tyrosine

N-(Toluene-4-sulfonyl)-L-Pro-OH was treated with $(COCl)_2$ and DMF in $CH_2Cl_2$ to give, after evaporation, N-(Toluene-4-sulfonyl)-L-Pro-Cl. This product was treated with L-Tyr(Bn)-OH and NaOH in THF and $H_2O$, to give, after acidification, extraction, drying with $MgSO_4$, and evaporation the title compound as a clear oil.

NMR data was as follows:

$^1$H NMR (DMSO-$d_6$, 300 MHz): δ=8.04 (d, J=8.2, 1H), 7.70 (d, J=8.1, 2H), 7.42-7.21 (m, 6H), 7.15 (d, J=8.5, 2H), 6.90 (d, J=8.5, 2H), 5.04 (s, 2H), 4.49-4.42 (m, 1H), 4.13-4.09 (m, 1H), 3.33-3.27 (m, 2H), 3.10-2.89 (m, 3H), 2.38 (s, 3H), 1.60-1.35 (m, 4H).

$^{13}$C NMR (DMSO-$d_6$, 75 MHz): δ=172.63, 170.8, 157.0, 143.6, 137.2, 133.8, 130.3, 129.8, 129.4, 128.9, 128.4, 127.6, 125.3, 114.4, 69.1, 61.3, 53.4, 49.0, 35.8, 30.4, 23.8, 21.0.

Mass Spectroscopy: (+FAB, 3-nitrobenzyl alcohol) 523 (M+H).

EXAMPLE 374

Synthesis of N-(Toluene-4-sulfonyl)-L-prolyl-4-(1-H, 2-oxo-3-methyltetrahydropyrimidin-1-yl)-L-phenylalanine The title compound was prepared from the corresponding t-butyl ester using the procedure described in Method 11.

NMR data was as follows:

$^1$H NMR (CDCl$_3$): δ=7.73 (d, 2H), 7.58 (d, 1H), 7.34 (d, 2H), 7.21 (d, 2H), 7.17 (d, 2H), 4.79 (q, 1H), 4.15-4.11 (m, 1H), 3.68-3.63 (m, 2H), 3.48-3.39 (m, 3H), 3.27 (dd, 1H), 3.17 (dd, 1H), 3.15-3.07 (m, 1H), 2.99 (s, 3H), 2.43 (s, 3H), 2.16-2.08 (m, 2H), 2.00-1.98 (m, 1H).

$^{13}$C NMR (CDCl$_3$):δ=173.4, 172.2, 164.2, 156.4, 144.4, 142.5, 134.1, 133.0, 130.2, 130.0, 127.9, 126.2, 62.1, 53.4, 49.5, 48.9, 47.9, 36.5, 35.9, 30.2, 24.2, 22.0, 21.4.

EXAMPLE 375

Synthesis of N-(Toluene-4-sulfonyl)-L-prolyl-4-(2-methoxyphenyl)-L-phenylalanine The title compound was prepared from the corresponding t-butyl ester using the procedure described in Method 11.

NMR data was as follows:

$^1$H NMR (CD$_3$OD):δ=7.70 (m, 2H), 7.36 (m, 4H), 7.22 (m, 4H), 6.98 (m, 2H), 4.75 (m, 1H), 4.10 (m, 1H), 3.71 (s, 3H), 3.29 (m, 2H), 3.11 (m, 2H), 2.39 (s, 3H), 1.75 (m, 1H), 1.53 (m, 3H).

$^{13}$C NMR (CD$_3$OD):δ=174.4, 174.2, 158.1, 145.9, 138.9, 136.7, 135.1, 131.2, 130.9, 130.8, 130.2, 129.9, 129.1, 122.0, 112.6, 63.3, 55.9, 54.6, 50.5, 37.9, 31.5, 25.2, 21.4.

EXAMPLE 376

Synthesis of N-(Toluene-4-sulfonyl)-L-prolyl-4-(2-methoxyphenyl)-L-phenylalanine The title compound was prepared from the corresponding t-butyl ester using the procedure described in Method 11.

NMR data was as follows:

$^1$H NMR (CDCl$_3$): δ 8.41 (d, 1H), 8.21 (s, 1H), 8.03 (d, 1H), 7.98 (s, 1H), 7.74 (d, 2H), 7.39 (d, 1H), 7.33 (d, 2H), 4.72-4.68 (m, 1H), 4.17-4.13 (m, 1H), 3.54-3.34 (m, 3H), 3.20-3.12 (m, 1H), 2.82 (s, 6H)m 2.43 (s, 3H), 2.09-2.04 (m, 1H), 1.79-1.59 (m, 3H).

$^{13}$C NMR (CDCl$_3$):δ=173.7, 171.8, 154.5, 147.2, 144.4, 137.8, 135.5, 133.2, 130.1, 127.9, 126.4, 62.2, 53.0, 49.5, 38.5, 36.0, 30.3, 24.4, 21.4.

EXAMPLE 377

Synthesis of N-(Toluene-4-sulfonyl)-L-prolyl-4-(2,4,5-trioxo-3-(3-chlorophenyl)-tetrahydroimidazol-1-yl)-L-phenylalanine benzyl ester The compound was prepared by treatment of N-(toluene-4-sulfonyl)-L-prolyl-4-[(3-chlorophenyl ureido)-tetrahydroimidazol-1-yl]-L-phenylalanine isopropyl ester with oxalyl chloride in methylene chloride. The crude product was purified by flash chromatography (silica, 3:2 Hex: EtOAc) to afford a white solid. (0.410 g, 50%).

MS ((+)ESI, m/z (%) 746 (100[M+H]+) (746/748 1Cl)

EXAMPLE 378

Synthesis of N-(Phenyl-sulfonyl)-D-prolyl-L-4-(2,6-dimethoxyphenyl)phenylalanine The title compound was prepared by coupling of 2,6-dimethoxyphenylboronic acid and 4'-iodophenylalanine derivates to provide dimethoxybiphenylalanines such as the title compound following procedures outlined in Hagmann et al., *Bioorganic & Medicinal Chemistry Letters*, 2001; 11(20): 2709-2713; Kamenecka et al., *Bioorganic & Medicinal Chemistry Letters*, 2002; 12(16): 2205-2208; and Doherty et al., *Bioorganic & Medicinal Chemistry Letters*, 2003; 13(11): 1891-1895.

EXAMPLE 379

Synthesis of N-(3,5-dichlorophenyl-sulfonyl)-D-prolyl-L-4-[4-(methylcarbonyl aminobutyl)-2,5-Di-oxo-imidazolidin-1-yl]phenylalanine The title compound was prepared following procedures outlined in WO 01/54690.

EXAMPLE 380

Synthesis of N-(2,6-dichlorophenyl-carbonyl)-L-4-(2,6-dimethoxyphenyl)phenylalanine The title compound was prepared by coupling of 2,6-dimethoxyphenylboronic acid and 4'-iodophenylalanine derivates to provide dimethoxybiphenylalanines such as the title compound following procedures outlined in WO 99/36393 and Sircar et al., *Bioorganic & Medicinal Chemistry*, 2002; 10(6): 2051-2066.

EXAMPLE 381

Synthesis of N-[N-(3-pyridinesulfonyl)-L-3,3-dimethyl-4-thiaprolyl]-O-[1-methylpiperazin4-ylcarbonyl]-L-tyrosine isopropyl ester 3-Pyridinesulfonyl Chloride The free base of the title compound may be prepared from 3-pyridinesulfonic acid (Aldrich) by a published procedure: Corey et al., *J. Org. Chem.* 1989, 54(2): 389. Alternatively, the hydrochloride of the title compound may be prepared from 3-pyridinesulfonic acid (Aldrich) by published procedures: Crowell et al., *J. Med. Chem.* 1989, 32(11): 2436; Karaman et al., *J. Am. Chem. Soc.* 1992, 114(12): 4889.

L-3,3-Dimethyl-4-thiaproline

The title compound may be prepared from L-penicillamine (Aldrich) by published procedures: Samanen et al., *J. Med. Chem.* 1989, 32(2): 466; Nagasawa et al., *J. Med. Chem.* 1984, 27(5): 591.

N-(3-pyridinesulfonyl)-L-3,3-dimethyl-4-thiaproline

A pH=7.4 buffer was prepared by dissolving disodium hydrogen phosphate (43.2 g, 0.304 mol) and potassium dihydrogen phosphate (11.8 g, 0.0870 mol) in $H_2O$ to give a volume of 1.0 L. To a 0° C. solution of L-3,3-dimethyl-4-thiaproline (25.4 g, 0.157 mol) in 700 mL pH=7.4 buffer was added with stirring a solution of 3-pyridinesulfonyl chloride (28.0 g, 0.157 mol) in 300 mL $CH_2Cl_2$. The mixture was stirred for 24 h while warming to room temperature, and was acidified to pH=2 by addition of 3 M $H_2SO_4$, precipitating a yellow solid. The yellow solid was isolated by filtration of both phases, and the $CH_2Cl_2$ layer was separated and evaporated to afford additional yellow solid. The combined yellow solids were stirred in 700 mL $H_2O$ for 1 h, to dissolve associated inorganic salts, and isolated again by filtration. The two aqueous layers were combined and extracted with EtOAc (3×500 mL). The EtOAc layers were washed with brine, treated with sodium sulfate, filtered, and evaporated to afford additional yellow solid. All aliquots of yellow solid were combined to afford 36.1 g (76%) N-(3-pyridinesulfonyl)-L-3,3-dimethyl-4-thiaproline.

N-[N-(3-pyridinesulfonyl)-L-3,3-dimethyl-4-thiaprolyl]-L-tyrosine isopropyl ester 1-(3-Dimethylaminopropyl)-3-ethylcarbodiimide hydrochloride (4.83 g, 0.0253 mol) was added to a 0° C. solution of N-(3-pyridinesulfonyl)-L-3,3-dimethyl-4-thiaproline (6.37 g, 0.0211 mol), L-tyrosine isopropyl ester hydrochloride (5.48 g, 0.0211 mol), 1-hydroxybenzotriazole (5.69 g, 0.0421 mol), and 4-methylmorpholine (2.32 mL, 2.13 g, 0.0211 mol) dissolved in 125 mL DMF. The mixture was stirred for 16 h while warming to room temperature, and 200 mL EtOAc and 200 mL $H_2O$ were added. The mixture was shaken, and the aqueous layer was separated, and the organic layer was washed with 0.2 M citric acid (2×100 mL), $H_2O$ (2×100 mL), sat. $NaHCO_3$ (2×100 mL), $H_2O$ (2×100 mL), and brine (2×100 mL). The organic layer was treated with sodium sulfate, filtered, and evaporated to afford 9.40 g (86%) N-[N-(3-pyridinesulfonyl)-L-3,3-dimethyl-4-thiaprolyl]-L-tyrosine isopropyl ester as a yellow foam. $^1$H NMR (CDCl$_3$, 300 MHz) δ 9.08 (bs, 1H), 8.86 (bs, 1H), 8.16 (dt, J$_d$=8.1 Hz, J$_t$=2.0 Hz, 1H), 7.51 (dd, J=8.0 Hz, J=4.6), 7.07 (d, J=8.1 Hz, 2H), 6.87 (d, J=8.1 Hz, 1H), 6.74 (d, J=8.1 Hz, 2H), 5.96 (bs, 1H), 5.06 (sept, J=6.3, 1H), 4.83 (dt, J$_d$=6.0 Hz, J$_t$=7.8 Hz, 1H), 4.57 (d, J=9.3 Hz, 1H), 4.46 (d, J=9.3 Hz, 1H), 3.91 (s, 1H), 3.09 (dd, J=14.1 Hz, J=5.4 Hz, 1H), 2.98 (dd, J=14.1 Hz, J=7.5 Hz, 1H), 1.25 (t, J=6.6 Hz, 6H), 1.18 (s, 3H), 1.13 (s, 3H). $^{13}$C NMR (CDCl$_3$, 75 MHz) δ 170.5, 168.0, 155.2, 154.2, 148.6, 135.9, 130.7, 127.6, 124.1, 115.5, 105.5, 73.7, 69.7, 54.7, 53.4, 50.5, 37.5, 29.2, 23.7, 21.62, 21.55.

N-[N-(3-pyridinesulfonyl)-L-3,3-dimethyl-4-thiaprolyl]-O-[1-methylpiperazin-4-ylcarbonyl]-L-tyrosine isopropyl ester N-[N-(3-pyridinesulfonyl)-L-3,3-dimethyl-4-thiaprolyl]-L-tyrosine isopropyl ester (1.51 g, 2.89 mmol) and 4-nitrophenyl chloroformate (0.58 g, 2.89 mmol) were dissolved in 40 mL $CH_2Cl_2$, and the solution was stirred for 15 min while cooling in a −15° C. slurry of 4:1 $H_2O$/EtOH and dry ice. To the solution was added Et$_3$N (1.00 mL, 0.73 g, 7.23 mol) with stirring over 2 min, and the solution was stirred for 1 h at −15° C. To the resulting suspension was added 1-methylpiperazine (0.32 mL, 0.289 g, 2.89 mmol) with stirring over 1 min, and the mixture was stirred for 16 h while warming to room temperature. The mixture was diluted with 40 mL hexanes, and washed with 10% (w/v) $K_2CO_3$ (4×50 mL) until no yellow color (4-nitrophenol) was seen in the aqueous layer. The organic layer was washed with brine (75 mL), treated with sodium sulfate, filtered, and evaporated to give a light yellow residue. The residue was purified by chromatography on silica gel using 70:25:5 $CH_2Cl_2$/EtOAc/EtOH to afford 1.53 g (84%) N-[N-(3-pyridinesulfonyl)-L-3,3-dimethyl-4-thiaprolyl]-O-[1-methylpiperazin-4-ylcarbonyl]-L-tyrosine isopropyl ester as a colorless foam. $^1$H NMR (CDCl$_3$, 300 MHz) δ 9.09 (d, J=2.1 Hz, 1H), 8.87 (dd, J=4.9 Hz, J=1.6 Hz, 1H), 8.16 (dt, J$_d$=8.4 Hz, J$_t$=2.0 Hz, 1H), 7.51 (dd, J=8.2 Hz, J=4.9 Hz, 1H), 7.21 (d, J=8.4 Hz, 2H), 7.02 (d, J=8.4 Hz, 2H), 6.89 (d, J=7.8 Hz, 1H), 5.05 (sept, J=6.4 Hz, 1H), 4.84 (q, J=7.0 Hz, 1H), 6.59 (d, J=9.9 Hz, 1H), 4.47 (d, J=9.9 Hz, 1H), 3.90 (s, 1H), 3.67 (bs, 2H), 3.58 (bs, 2H), 3.18-3.03 (m, 2H), 2.45 (t, J=10.2 Hz, 4H), 2.34 (s, 3H), 1.26 (d, J=6.0 Hz, 3H), 1.23 (d, J=6.6 Hz, 3H), 1.20 (s, 3H), 1.17 (s, 3H). $^{13}$C NMR (CDCl$_3$, 75 MHz) δ 170.4, 167.8, 154.3, 153.7, 150.6, 148.7, 135.8, 133.1, 133.0, 130.4, 133.0, 121.8, 73.7, 69.7, 54.8, 54.6, 54.5, 50.5, 46.1, 44.3, 43.8, 37.6, 29.1, 23.8, 21.6, 21.5.

9.2. In Vivo and In Vitro Screening of Agents

EXAMPLE A

In vitro Assay For Determining Binding of Candidate Compounds to VLA-4

An in vitro assay was used to assess binding of candidate compounds to $α_4β_1$ integrin. Compounds which bind in this assay can be used to assess VCAM-1 levels in biological samples by conventional assays (e.g., competitive binding assays). This assay is sensitive to IC$_{50}$ values as low as about 1 nM.

The activity of $α_4β_1$, integrin was measured by the interaction of soluble VCAM-1 with Jurkat cells (e.g., American Type Culture Collection Nos. TIB 152, TIB 153, and CRL 8163), a human T-cell line which expresses high levels of $α_4β_1$ integrin. VCAM-1 interacts with the cell surface in an $α_4β_1$ integrin-dependent fashion (Yednock et al., *J. Bio. Chem.*, 1995, 270:28740).

Recombinant soluble VCAM-1 was expressed as a chimeric fusion protein containing the seven extracellular domains of VCAM-1 on the N-terminus and the human IgG$_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM $MnCl_2$ and 5 µg/mL 15/7 antibody for 30 minutes on ice. $Mn^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock et al., supra. Antibodies similar to the 15/7 antibody have been prepared by other investigators (Luque et al., 1996, *J. Bio. Chem.*, 271:11067) and may be used in this assay.

Cells were then incubated for 30 minutes at room temperature with candidate compounds, in various concentrations ranging from 66 µg/mL to 0.01 µg/mL using a standard 5-point serial dilution. 15 µL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock et al., supra.

Compounds having an $IC_{50}$ of less than about 15 µM possess binding affinity to $\alpha_4\beta_1$.

When tested in this assay, each of the compounds of Examples 1-381 (or the corresponding carboxylic acids of the ester compounds, i.e., the prodrugs) has an $IC_{50}$ of 15 µM or less.

EXAMPLE B

In vitro Saturation Assay For Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µg/mL to 0.01 µg/mL, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter analysis as described in Yednock et al., *J. Bio. Chem.*, 1995, 270: 28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related to $\alpha_4\beta_1$ (Palmer et al., 1993, *J. Cell Bio.*, 123: 1289).

Accordingly, the above-described assay may be performed with a human colon carcinoma cell line, SW 480 (ATTC #CCL228) transfected with cDNA encoding $\alpha_9$ integrin (Yokosaki et al., 1994, *J. Bio. Chem.*, 269:26691), in place of the Jurkat cells, to measure the binding of the $\alpha_9\beta_1$ integrin. As a control, SW 480 cells which express other a and $\beta_1$ subunits may be used.

Using this assay, the plasma levels necessary to obtain efficacy in in vivo models for $\alpha_4\beta_1$ and $\alpha_9\beta_1$ have been established for compounds of the present invention tested in this assay.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

EXAMPLE 1

Clinical Reversal of Experimental Allergic Encephalomyelitis Using N-[N-(3-pyridinesulfonyl)-L-3,3-dimethyl-4-thiaprolyl]-O-[1-methylpiperazin-4-yl-carbonyl]-L-tyrosine isopropyl ester Experimental allergic encephalomyelitis is an experimentally induced, cell-mediated, autoimmune inflammatory disorder of the central nervous system (CNS) that serves as an animal model of multiple sclerosis. Infiltrates typically consist of lymphocytes and macrophages, although polymorphonuclear cells are occasionally observed (Traugott et al., 1985 *Cell. Immunol.* 91: 240-54; Traugott et al., 1986 *Cell. Immunol.* 99: 395-410). EAE is actively induced in susceptible animals by injection with homogenized CNS antigens in complete Freund's adjuvant (CFA). EAE can also be passively transferred by activated myelin-specific T cells from an actively immunized animal (Paterson, 1960, *J. Exp. Med.* 111: 119-36). Susceptibility to disease depends not only on the inducing antigen and animal species used, but it is also affected by age, sex and commercial source of the animals (Tsunoda et al., 1996, *J. Neuropath. Exp. Neurol.* 55: 673-86).

Just as in MS, clinical EAE can manifest in several different forms. In some models animals develop an acute, monophasic illness followed by spontaneous recovery. In other models, however, animals will develop a chronic relapsing disease, characterized by recurrent clinical attacks with intermittent periods of recovery (Tsunoda et al., 1996). A chronic progressive form of EAE can be induced in adult Hartley guinea pigs by immunization with whole CNS in adjuvant (Wisniewski et al., 1983, *J. Neuropath. & Exp. Neurol.* 42: 243-55; Karlik et al., 1986, *Neurology* 36: 1112-4; Karlik et al., 1993, *Magn. Reson. Med.* 30: 326-31), in which the animals show progressive worsening of clinical symptoms without periods of recovery or remission. Histologically, large confluent plaques of demyelination accompany continuous mononuclear CNS infiltration.

Materials & Methods: Animals and Induction of EAE. Female Hartley guinea pigs (Charles River Canada, St. Constant, Quebec) were maintained in a controlled light environment and allowed food and water ad libitum. EAE was induced in 50 animals (200-250 g) via nuchal, intradermal injection of 0.6 mL of a 1:1 mixture of homogenized, isologous CNS tissue and complete Freund's adjuvant, with an additional 10 mg/mL of *Mycobacterium tuberculosis* (Difco). Animals were assessed daily by a blinded observer using a 4-point clinical scale as follows: 0=no abnormality; 0.5=more than one consecutive day of weight loss; 1=ataxia and poor righting reflex; 2=hind limb paresis, urinary incontinence, fecal impaction; 3=paralysis; 4=terminal paralysis.

Treatment Regimes. N-[N-(3-pyridinesulfonyl)-L-3,3-dimethyl-4-thiaprolyl]-O-[1-methylpiperazin-4-ylcarbonyl]-L-tyrosine isopropyl ester is a small molecule that binds with high affinity to human and guinea pig 4 integrin ($IC_{50}$ for inhibition of cell adhesion to VCAM=1 nm). Disease in animals was considered chronic by day 40 post immunization, and thus the treatment period began at this time, and lasted for 10, 20, 30 or 40 days. Animals received either 0.5 mL saline (vehicle for N-[N-(3-pyridinesulfonyl)-L-3,3-dimethyl-4-thiaprolyl]-O-[1-methylpiperazin-4-ylcarbonyl]-L-tyrosine isopropyl ester; n=20) or 30 mg/kg N-[N-(3-pyridinesulfonyl)-L-3,3-dimethyl-4-thiaprolyl]-O-[1-methylpiperazin-4-ylcarbonyl]-L-tyrosine isopropyl ester (n=25) twice a day. With the dosing regimen, receptor saturation levels of N-[N-(3-pyridinesulfonyl)-L-3,3-dimethyl-4-thiaprolyl]-O-[1-methylpiperazin-4-ylcarbonyl]-L-tyrosine isopropyl ester (>10 nm) were maintained at all times. One subgroup of animals received N-[N-(3-pyridinesulfonyl)-L-3,3-dimethyl-4-thiaprolyl]-O-[1-methylpiperazin-4-ylcarbonyl]-L-tyrosine isopropyl ester for 30 days, and then treatment was withdrawn and the animals were maintained for an additional 10 days (n=5). All treatments were administered subcutaneously.

Animal Sacrifice and Histological Analysis. Untreated, chronic EAE animals (n=5) were sacrificed on day 40, as well as non-EAE controls (n=5). Following each 10-day treatment interval, 5 animals from each group were sacrificed (0.25 mL sodium pentobarbital), blood samples were collected for FACS analysis (see below), and the brain and spinal cord dissected and sectioned. Three spinal sections were used, corresponding to lumbar, thoracic and cervical regions of the cord. The brain was cut into five transverse sections. The first three proximal sections were combined in one block, and the last two distal sections in another. Tissues were fixed in 10% formalin and embedded in paraffin. Five nm sections were stained with hematoxylin-eosin (H-E) or solochrome-R-cyanlin (SCR) and evaluated by a blinded observer in each of four categories: (1) meningeal inflammation, (2) perivascular infiltration, (3) encephalitis or (4) myelitis and demyelination (Table 6). The combined pathological score represents the total score (out of a potential 20) from all 5 CNS sections in each animal.

TABLE 6

Pathological Scoring Scale

| | |
|---|---|
| M: | Inflammatory reaction in the meninges |
| 0: | no changes |
| 1: | perivascular and/or meningeal infiltration by mononuclear cells, 1-3 vessels involved |
| 2: | 4-6 vessels involved |
| 3: | 6+ vessels involved |
| 4: | dense infiltration of meninges with nearly all or all blood vessels involved |
| P: | Parenchymal perivascular infiltration |
| 0: | no changes |
| 1: | 1-3 parenchymal vessels infiltrated in Virchow-Robin spaces |
| 2: | 4-6 vessels involved |

TABLE 6-continued

Pathological Scoring Scale

| | |
|---|---|
| 3: | 6+ vessels involved |
| 4: | virtually all or all vessels involved |
| E: | Encephalitis or myelitis |
| 0: | no invasion of the neural parenchyma; microglial or inflammatory cells invading neural parenchyma |
| 1: | a few scattered cells |
| 2: | invasion by cells from several perivascular cuffs |
| 3: | large areas of neural parenchyma involved |
| 4: | virtually the entire section is infiltrated |
| D: | Demyelination, remyelination and myelin debris |
| 0: | no demyelination |
| 1: | single focus of subpial demyelination or myelin debris |
| 2: | several small foci of demyelination |
| 3: | one large confluent area of demyelination |
| 4: | several large confluent areas of demyelination |

To quantify the abnormalities observed in the spinal cord, sections stained with H-E were divided into 12 representative pie-shaped areas. In each area, the number of cells within a 0.12 mm² field of view was counted using Sigma Scan Pro image analysis software (SPSS Inc.), and the combined mean number of cells in all 12 areas was calculated for the whole spinal cord (36 fields of view per animal). Note that as all cell nuclei were counted, the number of cells may include neurons and glial cells in addition to infiltrates. Hence the cell count in non-EAE animals served as a baseline.

Quantitative Reverse Transcription-PCR: IL-2, IL-10, MCP-1. RNA was isolated from 30 mg of frozen guinea pig spinal cord using the S.N.A.P.™ (simple nucleic acid preparation) total RNA Isolation Kit (Invitrogen) according to manufacturer's instructions, modified to include a second DNAse treatment step followed by an additional purification over the S.N.A.P. column. By adding the second DNAse treatment, we found that DNA contamination is consistently undetectable for these samples and assays as measured using a reverse-transcriptase negative control RT-PCR assay.

Primer/probe sequences and concentrations for IL-2, IL-10, and MCP-1 are given in Table 7, as well as the standard RNA used for each gene. RT-PCR was carried out in triplicate using the ABI PRISM® 7700 Sequence Detection System. 50 µl reactions contained 10 to 800 ng of total RNA and primers and probes at the concentrations indicated above in reaction buffer consisting of 6.67% glycerol (Amresco); 5.5 mM MgCl; 300 µM dATP, dCTP, dGTP, and dUTP; 100 nM probe; 1.25 unit of AmpliTaq Gold® DNA Polymerase (Applied Biosystems); 1× TaqMan® Buffer A (TaqMan® PCR Core reagents kit, Applied Biosystems), 20 units of RNase Inhibitor (Roche); 1.25 unit of murine leukemia virus (MULV) Reverse Transcriptase (Applied Biosystems). Reverse-transcription of RNA was carried out at 48° C. for 30 min., followed by a 10 min. denaturing step at 95° C. PCR was carried out by 40 thermo-cycles consisting of 95° C. for 15 seconds followed by 60° C. for 1 minute. Each plate included a standard curve using the standard RNA listed in Table 7 and two additional control samples: 1) a positive control RNA sample used on all plates, 2) a non-template control (NTC).

TABLE 7

Mean Cell Counts in Spinal Cord

| Treatment Group | Mean # Cells/0.12 mm² |
|---|---|
| Non-EAE | 61 ± 3.2 |
| d40 control | 107 ± 6.1 |

TABLE 7-continued

Mean Cell Counts in Spinal Cord

| Treatment Group | Mean # Cells/0.12 mm² |
|---|---|
| d50 saline | 138 ± 8.3 |
| D60 saline | 137 ± 8.3 |
| D70 saline | 143 ± 6.7 |
| D80 saline | 113 ± 4.8 |
| D50 N-[N-(3-pyridinesulfonyl)-L-3,3-dimethyl-4-thiaprolyl]-O-[1-methylpiperazin-4-ylcarbonyl]-L-tyrosine isopropyl ester | 97 ± 3.9 |
| D60 N-[N-(3-pyridinesulfonyl)-L-3,3-dimethyl-4-thiaprolyl]-O-[1-methylpiperazin-4-ylcarbonyl]-L-tyrosine isopropyl ester | 86 ± 4.2 |
| D70 N-[N-(3-pyridinesulfonyl)-L-3,3-dimethyl-4-thiaprolyl]-O-[1-methylpiperazin-4-ylcarbonyl]-L-tyrosine isopropyl ester | 89 ± 8 |
| D80 N-[N-(3-pyridinesulfonyl)-L-3,3-dimethyl-4-thiaprolyl]-O-[1-methylpiperazin-4-ylcarbonyl]-L-tyrosine isopropyl ester | 70 ± 4 |

The correlation coefficients of the standard curves were greater than 0.990 for all data shown. The coefficients of variation for sample triplicates were less than 0.2. Since the RNA used for the standard curve is a heterogeneous mix of RNA containing a constant but unknown amount of the target message, the numbers calculated are relative.

FACS Analysis. On day 80 post-immunization, heparinized blood samples were collected from non-EAE animals, saline-treated animals, N-[N-(3-pyridinesulfonyl)-L-3,3-dimethyl-4-thiaprolyl]-O-[1-methylpiperazin-4-ylcarbonyl]-L-tyrosine isopropyl ester-treated animals and animals 10 days following withdrawal of N-[N-(3-pyridinesulfonyl)-L-3,3-dimethyl-4-thiaprolyl]-O-[1-methylpiperazin-4-ylcarbonyl]-L-tyrosine isopropyl ester. All samples were maintained at 4° C. for all procedures. 150 µl samples were exposed to primary antibody for 30 minutes, washed twice, and then incubated with PE-conjugated goat anti-mouse IgG Fc in the presence of 5% guinea pig serum (Beckman Coulter #PN EM055 1). Red blood cells were lysed with Becton-Dickinson lysing solution and the samples were examined on a FACScan flow cytometer (Becton Dickinson, Mountain View, Calif.) gating on different cell populations by light scatter.

Statistical Analysis. Statistical analysis was performed using SigmaStat v2 software (SPSS Inc.). Clinical scores were assessed using the Mann Whitney rank sum test, while pathological scores were assessed with a two-Way ANOVA. Quantitative abnormalities were compared using Kruskal-Wallis ANOVA on ranks. In each case, $p<0.05$ was considered significant. A linear regression was performed on the mean cell counts in the spinal cord.

RESULTS: Clinical Reversal. Animals began to show clinical signs of disease on day 9 post immunization, and continued through to day 40. At this point the disease was considered to be chronic. The treatment period began on day 40 and lasted a minimum of 10 days to a maximum of 40 days. While animals that received saline showed a continued clinical profession until the end of the experiment, animals treated with N-[N-(3-pyridinesulfonyl)-L-3,3-dimethyl-4-thiaprolyl]-O-[1-methylpiperazin-4-ylcarbonyl]-L-tyrosine isopropyl ester began to show a clinical reversal commencing 2-3 days following the initial treatment (FIG. 1A). In several animals that had an established clinical score of 2 before treatment began, N-[N-(3-pyridinesulfonyl)-L-3,3-dimethyl-4-thiaprolyl]-O-[1-methylpiperazin-4-ylcarbonyl]-L-tyrosine isopropyl ester reversed the paresis, and the animals were able to use their hind limbs throughout the treatment period (i.e., reversion to a clinical score of 1). Depending on the duration of treatment, some animals that had previously shown signs of disease appeared completely disease-free while receiving N-[N-(3-pyridinesulfonyl)-L-3,3-dimethyl-4-thiaprolyl]-O-[1-methylpiperazin-4-ylcarbonyl]-L-tyrosine isopropyl ester. Over the course of the treatment period, the mean clinical scores of N-[N-(3-pyridinesulfonyl)-L-3,3-dimethyl-4-thiaprolyl]-O-[1-methylpiperazin-4-ylcarbonyl]-L-tyrosine isopropyl ester-treated animals were significantly lower than that of saline-treated animals ($p<0.001$, Mann Whitney rank sum test).

N-[N-(3-pyridinesulfonyl)-L-3,3-dimethyl-4-thiaprolyl]-O-[1-methylpiperazin-4-ylcarbonyl]-L-tyrosine isopropyl ester-treated group, there was a small transient increase centered on day 54 post immunization (FIG. 1A). Two animals showed a moderate fluctuation in the degree of clinical symptoms; they wavered from a complete absence of clinical signs (score of 0) to a very slight ataxia (score of 1). None of the animals, however, escaped from treatment, as we have observed previously with antibodies to $\alpha_4$ integrin, where the animal stops responding to the therapy altogether due to guinea pig rejection of the murine or humanized antibody. There were no ancillary problems, (such as injection site inflammation), with treatment of animals for extended periods of time with N-[N-(3-pyridinesulfonyl)-L-3,3-dimethyl-4-thiaprolyl]-O-[1-methylpiperazin-4-ylcarbonyl]-L-tyrosine isopropyl ester.

In one subgroup of animals, N-[N-(3-pyridinesulfonyl)-L-3,3-dimethyl-4-thiaprolyl]-O-[1-methylpiperazin-4-ylcarbonyl]-L-tyrosine isopropyl ester was administered for 30 days, and then removed and the animals were maintained on saline injections for the final 10 days of the experiment. Once N-[N-(3-pyridinesulfonyl)-L-3,3-dimethyl-4-thiaprolyl]-O-[1-methylpiperazin-4-ylcarbonyl]-L-tyrosine isopropyl ester was withdrawn, clinical progression returned, similar to the clinical course of animals that received saline for the duration of the treatment period (FIG. 1B). Between day 70 and day 80 post immunization, the mean clinical score of post-N-[N-(3-pyridinesulfonyl)-L-3,3-dimethyl-4-thiaprolyl]-O-[1-methylpiperazin-4-ylcarbonyl]-L-tyrosine isopropyl ester-treated animals was significantly greater than that of animals which received N-[N-(3-pyridinesulfonyl)-L-3,3-dimethyl-4-thiaprolyl]-O-[1-methylpiperazin-4-ylcarbonyl]-L-tyrosine isopropyl ester throughout the treatment period ($p<0.05$, Mann Whitney rank sum test). In summary, N-[N-(3-pyridinesulfonyl)-L-3,3-dimethyl-4-thiaprolyl]-O-[1-methylpiperazin-4-ylcarbonyl]-L-tyrosine isopropyl ester was successfully administered for up to 40 days without any adverse side effects, and it maintained a reversal of the clinical deficits associated with chronic progressive EAE.

Figure 2C:
Figure 2D:
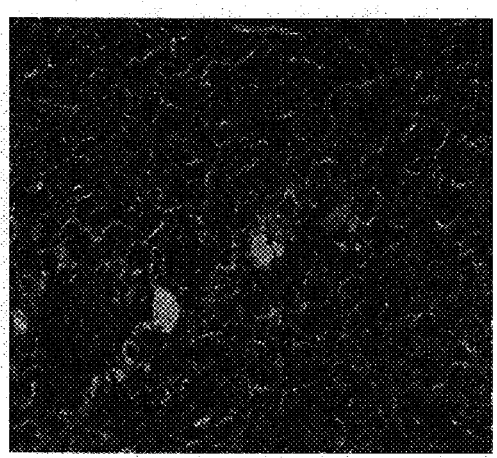
Figure 2E:
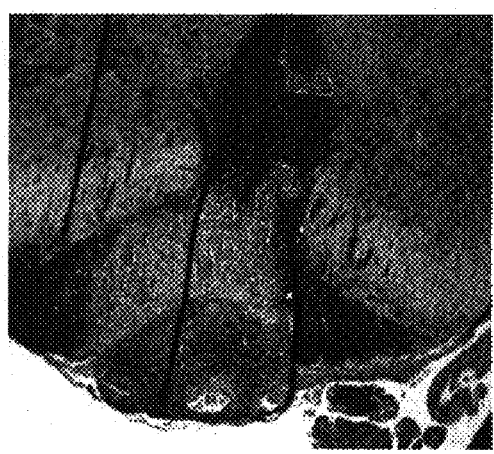
Figure 2F:
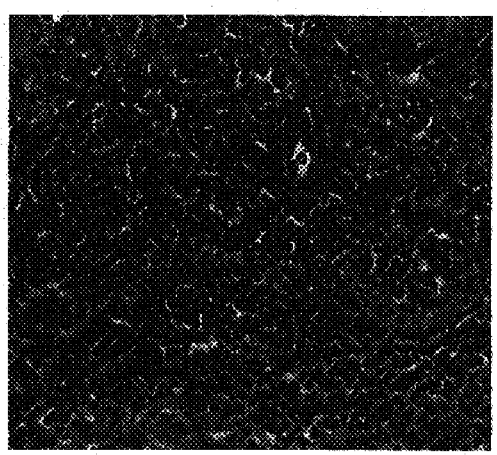
Figure 2G:
Figure 2H:
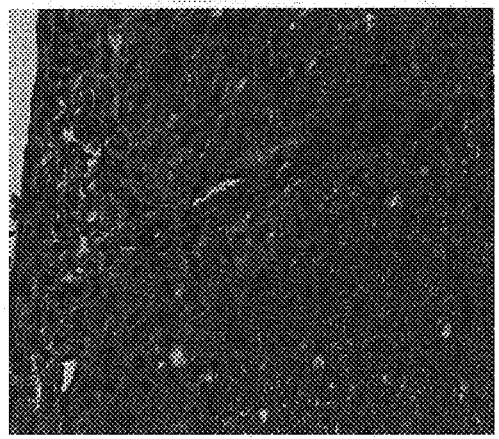
Figure 2I:
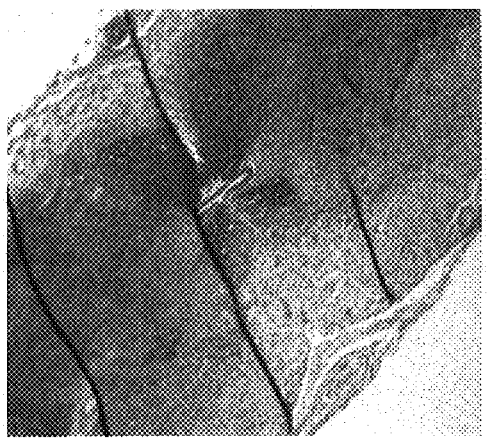
Figure 2J:
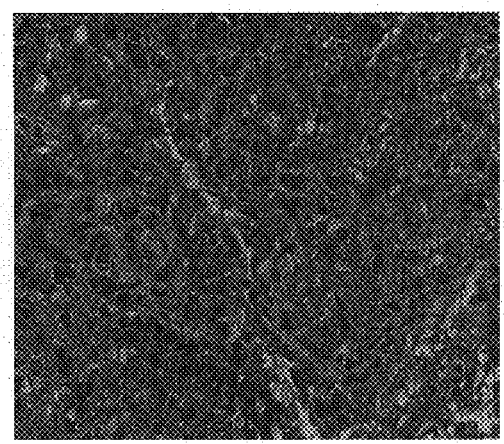
Figure 2K:
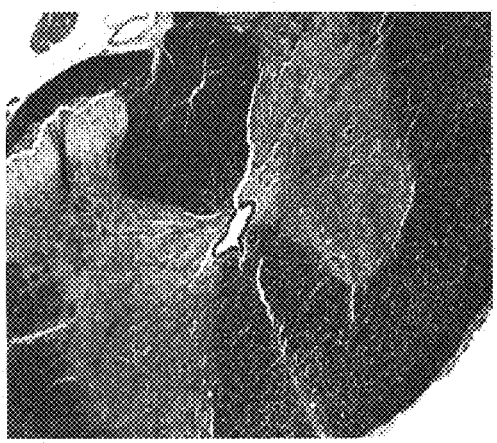
Figure 2L:
Figure 3A:
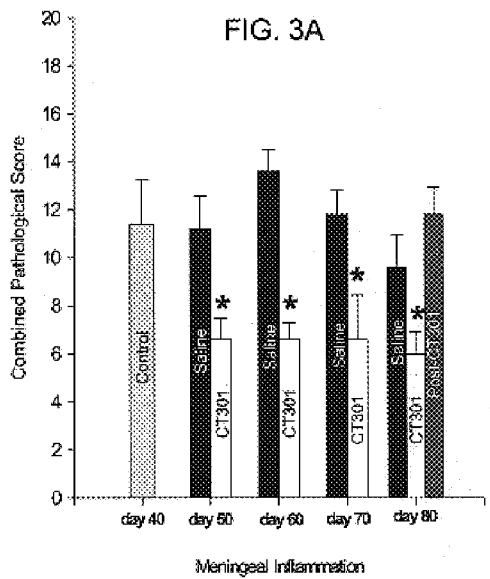
Figure 3B:
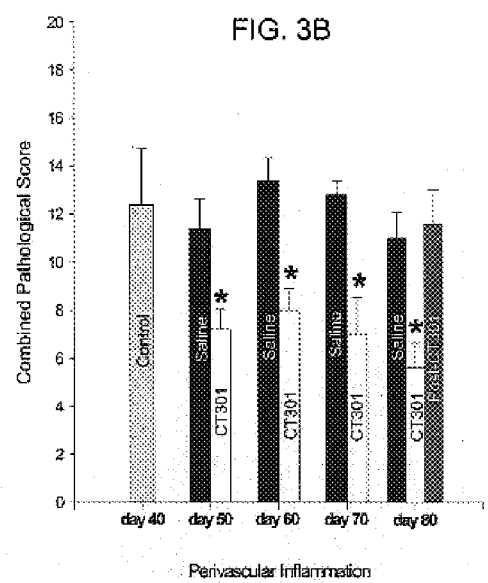
Figure 3C:
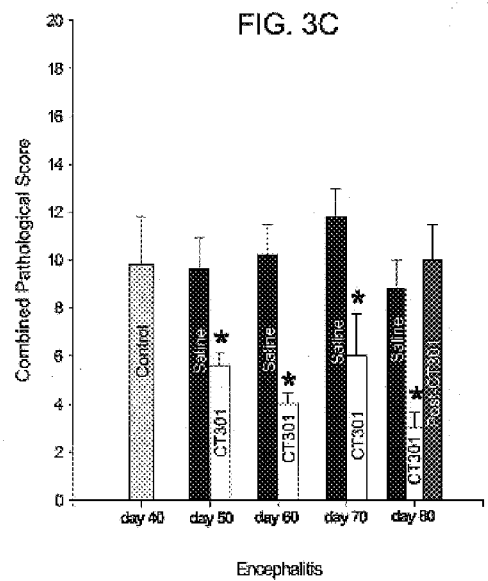
Figure 3D:
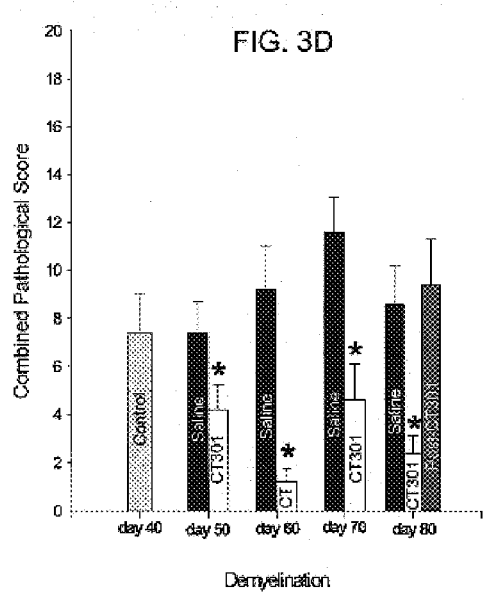

RESULTS: Reversal of Pathological Abnormalities. Pathological abnormalities were evaluated on H-E and SCR stained brain and spinal sections. In FIG. 2, panels on the left are SCR stained sections, which stains myelin blue (×40). Panels on the right are high magnification (×250) H-E stained sections taken from the dorsal medial region of the corresponding SCR photo (FIG. 2). The sections shown in panels A and B of FIG. 2 were taken from a normal guinea pig, and show neither inflammation nor demyelination. By day 40 post immunization, chronic animals had extensive meningeal and perivascular inflammation, as well as one or more large subpial plaques of demyelination (FIG. 2C). The density of infiltrating cells was markedly increased (FIG. 2D). The observed pathological abnormalities became more extreme as the disease progressed. At day 60 post-immunization, control animals that received 20 days of saline treatment had severe meningeal infiltration, large areas of myelitis, and focal demyelination (FIGS. 2E, F). By day 80 post-immunization, virtually the entire spinal sections were infiltrated and demyelinated, including invasion of some areas of gray matter (FIGS. 2I, J). In contrast, animals that received 20 days of N-[N-(3-pyridinesulfonyl)-L-3,3-dimethyl-4-thiaprolyl]-O-[1-methylpiperazin-4-ylcarbonyl]-L-tyrosine isopropyl ester treatment had much smaller areas of demyelination at day 60 post immunization, and there was a paucity of meningeal and perivascular cell invasion (FIGS. 2G, H). After 40 days of N-[N-(3-pyridinesulfonyl)-L-3,3-dimethyl-4-thiaprolyl]-O-[1-methylpiperazin-4-ylcarbonyl]-L-tyrosine isopropyl ester treatment, the pathological recovery was greater still; animals showed almost no meningeal and perivascular infiltration, and the myelin remained intact (FIGS. 2K, L).

A total of five blocks from each animal were scored by a blinded observer, and the combined pathological score represents the total score from all five sections in each of the four categories (meningeal inflammation, perivascular infiltration, myelitis and demyelination; FIG. 3). Over the course of the treatment period, animals that received N-[N-(3-pyridinesulfonyl)-L-3,3-dimethyl-4-thiaprolyl]-O-[1-methylpiperazin-4-ylcarbonyl]-L-tyrosine isopropyl ester showed a significant decrease in mean pathological score in all four categories with respect to saline-treated animals ($p<0.001$, two way ANOVA). When N-[N-(3-pyridinesulfonyl)-L-3,3-dimethyl-4-thiaprolyl]-O-[1-methylpiperazin-4-ylcarbonyl]-L-tyrosine isopropyl ester was removed, and animals were maintained for an additional 10 days without treatment, the mean combined pathological score in all four categories was significantly higher than animals that continued to receive the small molecule for the duration of the treatment period (FIG. 3; $p<0.05$, Kruskal Wallis ANOVA on ranks with SNK test).

RESULTS: Quantitation of Pathological Abnormalities. The pathological reversal scored qualitatively above was quantitatively confirmed in the spinal cord. The mean number of cells was calculated from 12 representative 0.12 mm areas on H-E stained sections of lumbar, thoracic and cervical cord, and combined to examine the whole spinal cord (FIG. 4). All untreated EAE animals had significantly higher cell counts than non-EAE animals, indicating that cellular infiltration increased during disease, as expected ($p<0.001$, two-way ANOVA). A significant reduction in cell number was observed after as little as 10 days of N-[N-(3-pyridinesulfonyl)-L-3,3-dimethyl-4-thiaprolyl]-O-[1-methylpiperazin-4-ylcarbonyl]-L-tyrosine isopropyl ester treatment, and was maintained through 20, 30 and 40 days of treatment with respect to saline-treated animals ($p<0.001$, two-way ANOVA). Furthermore, the mean cell counts of animals treated for 20, 30 or 40 days with N-[N-(3-pyridinesulfonyl)-L-3,3-dimethyl-4-thiaprolyl]-O-[1-methylpiperazin-4-ylcarbonyl]-L-tyrosine isopropyl ester were significantly lower than that of chronic control animals ($p<0.05$, Kruskal Wallis ANOVA on ranks with SNK test), and after 40 days of N-[N-(3-pyridinesulfonyl)-L-3,3-dimethyl-4-thiaprolyl]-O-[1-methylpiperazin-4-ylcarbonyl]-L-tyrosine isopropyl ester treatment, the mean cell count in the spinal cord was not different than that of non-EAE animals. A linear regression of these means demonstrates a progressive loss of inflammatory cells in the spinal cord ($r^2=0.90$). From the slope of this line, we can calculate a rate of cell loss of 8 cells/mm$^2$/day. After removal of N-[N-(3-pyridinesulfonyl)-L-3,3-dimethyl-4-thiaprolyl]-O-[1-methylpiperazin-4-ylcarbonyl]-L-tyrosine isopropyl ester, in animals that were maintained on saline for an additional 10 days, a significant increase in the mean number of cells was again observed ($p<0.05$, ANOVA on ranks with SNK test).

RESULTS: Quantitative PCR. Quantitative PCR was performed on lumbar sections of spinal cord to assess levels of IL-2, IL-10 and MCP-1, and the results compliment the pathological reversal already discussed. In saline-treated animals, the amount of IL-2 increased through the chronic phase of disease. In contrast, animals receiving N-[N-(3-pyridinesulfonyl)-L-3,3-dimethyl-4-thiaprolyl]-O-[1-methylpiperazin-4-ylcarbonyl]-L-tyrosine isopropyl ester had almost no detectable IL-2 RNA. Following the withdrawal of N-[N-(3-pyridinesulfonyl)-L-3,3-dimethyl-4-thiaprolyl]-O-[1-methylpiperazin-4-ylcarbonyl]-L-tyrosine isopropyl ester, the amount of IL-2 in the spinal cord returned to levels comparable to saline-treated animals. Similar results were seen regarding IL-10 and MCP-1. A significant reduction in cytokine RNA levels was evident during treatment, followed by a return to high levels after removal of the inhibitor (FIG. 5).

Figure 7A:
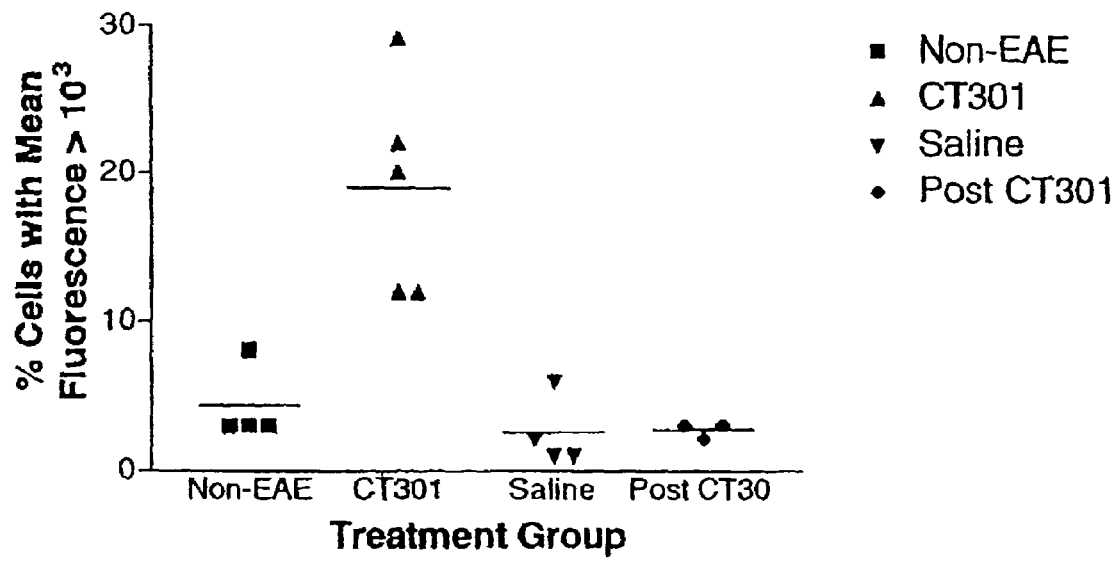
Figure 7B:
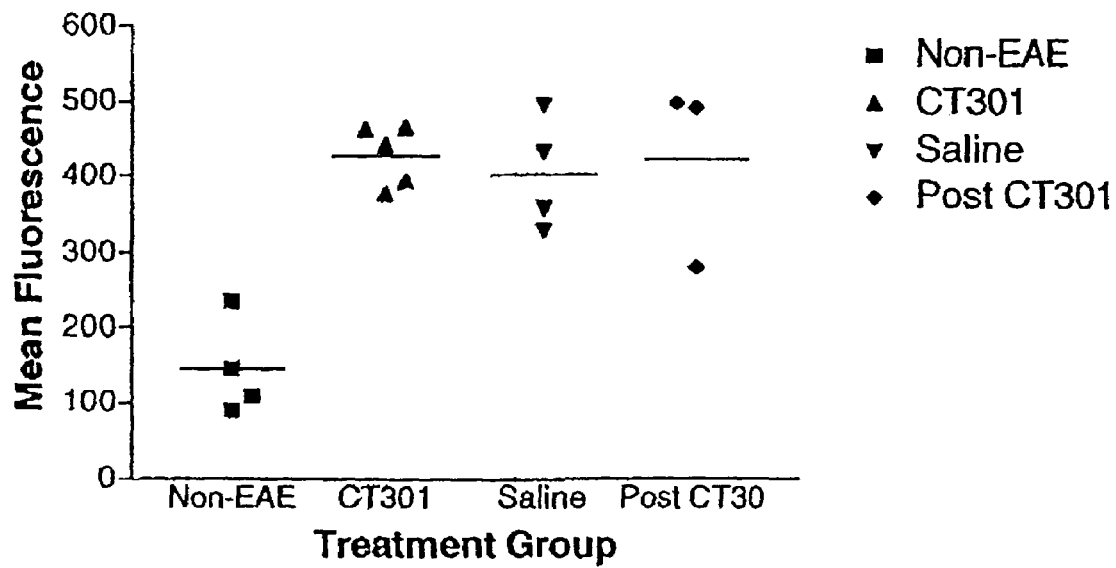

RESULTS: FACS Analysis. As determined by FACS analysis, treatment of EAE animals with N-[N-(3-pyridinesulfonyl)-L-3,3-dimethyl-4-thiaprolyl]-O-[1-methylpiperazin-4-ylcarbonyl]-L-tyrosine isopropyl ester caused a large increase in the percentage of $\alpha_4$ integrin bright lymphocytes in the circulation, compared to saline-treated animals. These results suggest that lymphocytes activated by peripheral immunization were unable to enter the CNS in the presence of N-[N-(3-pyridinesulfonyl)-L-3,3-dimethyl-4-thiaprolyl]-O-[1-methylpiperazin-4-ylcarbonyl]-L-tyrosine isopropyl ester, and accumulated in the circulation (FIGS. 6 and 7A). Consistent with this suggestion, the percentage of $\alpha_4$ integrin bright lymphocytes in the circulation returned to saline-treated levels when N-[N-(3-pyridinesulfonyl)-L-3,3-dimethyl-4-thiaprolyl]-O-[1-methylpiperazin-4-ylcarbonyl]-L-tyrosine isopropyl ester was removed and CNS inflammation returned (FIG. 7A). There were no discernable subpopulations of $\alpha_4$ integrin low and high monocytes; however, the general expression of $\alpha_4$ integrin on circulating monocytes increased in EAE animals (FIG. 7B). This increase was not affected by N-[N-(3-pyridinesulfonyl)-L-3,3-dimethyl-4-thiaprolyl]-O-[1-methylpiperazin-4-ylcarbonyl]-L-tyrosine isopropyl ester, further suggesting that the peripheral immune reaction was not inhibited by the treatment.

EXAMPLE 2

Spontaneous Remyelination Following Prolonged Inhibition of $\alpha_4$ Integrin in Chronic EAE The model of immune cell influx into the central nervous system being blocked by inhibiting alpha-4 beta-1 ($\alpha_4\beta_1$) integrin (VLA-4) blocks was studied to determine whether the presence of inflammatory cells suppresses spontaneous myelin repair in experimental autoimmune encephalomyelitis. Paralyzed guinea pigs were treated in an advanced, demyelinated stage of EAE with the $\alpha_4\beta_1$ specific inhibitor, N-[N-(3-pyridinesulfonyl)-L-3,3-dimethyl-4-thiaprolyl]-O-[1-methylpiperazin-4-ylcarbonyl]-L-tyrosine isopropyl ester (Piraino et al., *J. Neuroimmunol.* 2002, 131:147-159), and we found that: (1) 87% of plaques showed evidence of remyelination after 40 days of treatment; (2) myelin repair occurred in 50% of the total lesion area; and (3) 50% of the animals regained motor function. There was no significant repair or gain of motor function in vehicle treated animals. These results indicate that prolonged inhibition of CNS inflammation, in the absence of targeted myelin repair, can facilitate mechanisms of spontaneous remyelination.

Methods.

Animals and Disease Induction. Female Hartley guinea pigs (200-250 g, Charles River Canada, St. Constant, Quebec) were maintained in a light and temperature controlled environment and allowed food and water ad libitum. EAE was induced via nuchal, intradermal injection of 0.6 mL of a 1:1 mixture of homogenized, isologous CNS tissue and complete Freund's adjuvant (Difco, Detroit, Mich.), with an additional 10 mg/mL of *Mycobacterium tuberculosis* (Difco). Animals began to show clinical signs of disease on day 9, and were considered chronic by day 40 post immunization. Animals were weighed and assessed daily by a blinded observer using a 4-point clinical scale as follows: 0—no abnormality; 0.5—more than one consecutive day of weight loss; 1—ataxia and poor righting reflex; 2—hind limb paresis, urinary incontinence, fecal impaction; 3—paralysis; and 4—terminal paralysis.

Treatment Criteria. Animals were chosen for treatment based on severity of disease, according to two criteria: (1) animals must have been in the chronic stages of disease (i.e., at least day 40 post immunization); and (2) animals must have attained a clinical score of 2 before the start of the treatment period (i.e., hind limb paresis). In our past experience with this chronic progressive model of EAE, 95% of chronic animals with clinical scores of 2 showed moderate to severe demyelination in the spinal cord, ranging from several small foci of demyelination to one or more large confluent plaques. Adherence to these criteria optimized the potential for myelin loss before the treatment period began.

Treatment Regimes. Animals that met both treatment criteria were treated for intervals of 10, 20, 30 or 40 days. N-[N-(3-pyridinesulfon)-L-3,3-dimethyl-4-thiaprolyl]-O-[1-methylpiperazin-4-ylcarbonyl]-L-tyrosine isopropyl ester is a small molecule (molecular weight ~500 Da) that binds with high affinity to human and guinea pig $\alpha_4$ integrin ($IC_{50}$ for inhibition of cell adhesion to high density VCAM-1 in the presence of 100% serum=1-10 nm). Animals received either saline (n=16) or N-[N-(3-pyridinesulfon)-L-3,3-dimethyl-4-thiaprolyl]-O-[1-methylpiperazin-4-ylcarbonyl]-L-tyrosine isopropyl ester (30 mg/kg, n=12) twice daily during the treatment period. With this dosing regimen, receptor-saturating levels of N-[N-(3-pyridinesulfonyl)-L-3,3-dimethyl-4-thiaprolyl]-O-[1-methylpiperazin-4-ylcarbonyl]-L-tyrosine isopropyl ester (>10 nm) were maintained at all times. Both treatments were administered subcutaneously. Additionally, a cohort of animals was sacrificed within days of receiving a clinical score of 2 to serve as a baseline "d0" control.

Tissue Collection and Processing. Following sacrifice (0.25 mL sodium pentobarbital), animals were exsanguinated, and the CNS was dissected and sectioned. Three spinal cord sections were used, corresponding to lumbar, thoracic and cervical regions of the cord. Tissues were fixed in 10% formalin and embedded in paraffin. Five μm cross-sections were stained with solochrome-R-cyanin, a qualitative myelin stain, and examined by light microscopy for evidence of demyelination (absence of blue stain) and remyelination (areas of pale blue stain within lesions).

From each of the lumbar, thoracic and cervical sections, a 5 mm piece of spinal cord from the distal end was fixed in 2.5% glutaraldehyde at 4° C. A 0.5 mm slice from the center of each cross section was then divided into dorsal and ventral halves. These slices were post-fixed in osmium tetroxide and embedded in epoxy resin. One micron cross sections stained with toluidine blue were examined by light microscopy for evidence of demyelination and remyelination. Areas containing lesions were further sectioned for electron microscopy, and thin sections were stained with potassium permanganate and ethanolic uranyl acetate and examined in a Philips EM 300 microscope.

Histological Analysis. Spinal cord pathology was quantified using a method modified from McGavern et al., *J. Neurosci. Res.* 1999, 58: 492-504. Images from a mean of 12 cross-sections per animal were captured at 40× magnification using a Nikon Coolpix 995 digital camera. Sigma Scan Pro image analysis software (SPSS Inc.) was used to calculate both the total lesion area and the remyelinated lesion area within each cross section (in arbitrary units). These areas were summed to yield an overall estimation for the entire spinal cord, and the area of remyelination was expressed as a percentage of the total lesion area.

Results and Discussion. The primary aim in this study was to determine if extended inhibition of immune cell migration into the CNS would allow spontaneous remyelination of existing spinal cord lesions. The guinea pig model of EAE exhibits non-remitting, progressive disease following immunization with whole CNS homogenate (Wisniewski et al., *J. Neuropath. Exp. Neurol.* 1983, 42: 243-255; Karlik et al., 1986, *Neurology* 36: 1112-4; Karlik et al., 1993, *Magn. Res. Med.* 30: 326-331). Acute paralysis begins after approximately 10 days, with notable demyelination by day 20 (Karlik et al., 1986, *Neurology* 36: 1112-4; Karlik et al., 1993, *Magn. Res. Med.* 30: 326-331). After 40 days, 95% of animals exhibiting full bilateral hind limb paralysis have moderate to severe demyelination throughout the brainstem and spinal cord. It is important to note that animals at this stage of disease never relapse or remit, nor do they spontaneously recover. In the current study, treatment was only initiated when an animal reached this stage—at least 40 days post immunization and exhibiting full bilateral hind limb paralysis (clinical score 2). Animals then received either the small molecule inhibitor of $\alpha_4\beta_1$ integrin N-[N-(3-pyridinesulfonyl)-L-3,3-dimethyl-4-thiaprolyl]-O-[1-methylpiperazin-4-ylcarbonyl]-L-tyrosine isopropyl ester or vehicle (saline) for intervals of 10, 20, 30 or 40 days. FIG. 8 shows representative light micrographs of solochrome-R-cyanin stained spinal cord sections (FIGS. 8A-F). In controls (day "0" of treatment), extensive demyelination was evident in every animal; lesions were typically devoid of intact myelin, exhibiting dense immune cell infiltration with foamy macrophages containing phagocytosed myelin debris at their leading edge (FIGS. 8A, 8B). In the shortest treatment interval (10 days), saline- and N-[N-(3-pyridinesulfonyl)-L-3,3-dimethyl-4-thiaprolyl]-O-[1-methylpiperazin-4-ylcarbonyl]-L-tyrosine isopropyl ester-treated animals continued to show large areas of demyelination in the spinal cord, with minimal evidence of myelin pallor. In contrast, after 20 days of N-[N-(3-pyridinesulfonyl)-L-3,3-dimethyl-4-thiaprolyl]-O-[1-methylpiperazin-4-ylcarbonyl]-L-tyrosine isopropyl ester therapy, many lesions exhibited diffuse pale blue staining, analogous to classically described shadow plaques that are indicative of remyelination in MS patients (FIG. 8D). Plaques within saline control animals that remained devoid of myelin (FIG. 8C). By day 40 of treatment, a striking difference in the overall myelin appearance between the two treatment groups was observed. The majority of lesions in the N-[N-(3-pyridinesulfonyl)-L-3,3-dimethyl-4-thiaprolyl]-O-[1-methylpiperazin-4-ylcarbonyl]-L-tyrosine isopropyl ester-treated animals presented as shadow plaques (FIG. 8F), while lesions in control animals showed little, if any, blue staining (FIG. 8E).

To better define the change in histological appearance, tissue samples were examined with higher resolution, both by light and electron microscopy (EM) (FIG. 9). In 30-day saline-treated animals, toluidine blue-stained semithin sections showed areas of normal myelin (FIG. 9A), as well as areas of severe demyelination and axonal loss (FIG. 9B). Small transition zones between these two areas contained thinly sheathed axons of relatively small caliber (FIG. 9B), which may represent recently demyelinated axons attempting repair. There was also frequent evidence of axons undergoing Wallerian degeneration, both within lesions and within normally myelinated areas. In animals that received N-[N-(3-pyridinesulfonyl)-L-3,3-dimethyl-4-thiaprolyl]-O-[1-methylpiperazin-4-ylcarbonyl]-L-tyrosine isopropyl ester (FIG. 9C), the areas of thinly myelinated axons were greatly expanded, and the axons tended to be of larger caliber, indicating a more general reparative response, often throughout the lesioned area. Electron microscopy confirmed the observations. Thick wraps of myelin around large caliber axons, representative of "normal" compact myelin, are shown in FIG. 9D. In animals receiving 40 days of saline treatment, lesioned areas showed myelin paucity where large axons were fully demyelinated (FIG. 9E). In contrast, treatment with N-[N-(3-pyridinesulfonyl)-L-3,3-dimethyl-4-thiaprolyl]-O-[1-methylpiperazin-4-ylcarbonyl]-L-tyrosine isopropyl ester resulted in the appearance of the multiple thin myelin layers around large caliber axons, representing a state of remyelination (FIG. 9F). Therefore, it appears that prolonged administration of N-[N-(3-pyridinesulfonyl)-L-3,3-dimethyl-4-thiaprolyl]-O-[1-methylpiperazin-4-ylcarbonyl]-L-tyrosine isopropyl ester allowed for spontaneous remyelination in the spinal cord of animals with chronic progressive EAE.

In order to quantify the effect of N-[N-(3-pyridinesulfonyl)-L-3,3-dimethyl-4-thiaprolyl]-O-[1-methylpiperazin-4-ylcarbonyl]-L-tyrosine isopropyl ester, the percentage of plaques exhibiting evidence of remyelination was determined. The number of lesions showing myelin pallor was divided by the total number of lesions within cross sections of spinal cord taken throughout its length from each animal (FIG. 10) (for the method see Warrington et al., 2000, Proc. Nat'l Acad. Sci. USA 97: 6820-5). After 20, 30 and 40 days of saline treatment, the mean percentage of plaques exhibiting remyelination was between 10 and 20%; there was no significant change over time in the incidence of myelin pallor in these animals (FIG. 10A). In contrast, after 20 days of N-[N-(3-pyridinesulfonyl)-L-3,3-dimethyl-4-thiaprolyl]-O-[1-methylpiperazin-4-ylcarbonyl]-L-tyrosine isopropyl ester administration, the frequency of shadow plaques in the spinal cord was increased over saline-treated animals, reaching 68%; after 30 and 40 days, the incidence was 77% and 87%, respectively ($p<0.001$, 2-way ANOVA with Tukey test). These values are significantly higher than those at the initiation of treatment (day 0 and day 10) ($p<0.05$, 2-way ANOVA with Tukey test), indicating that the compound increased the incidence of remyelination in a time-dependent manner. Since the percentage of plaques showing evidence of remyelination did not significantly increase past day 20, it appears that remyelination was largely initiated in a synchronous manner between days 10 and 20 of treatment day (FIG. 10A).

The overall degree of plaque remyelination in the spinal cord was also measured. FIG. 10B shows a representative spinal cord section with a large demyelinated lesion in the ventral horn. Total lesion area was determined for each animal by tracing all lesions within all spinal cord sections and summing the areas. Likewise, the total area of remyelination was measured by tracing regions of myelin pallor. FIGS. 10C-F plot the total lesion area against the percentage of remyelination. In saline-treated animals, lesions rarely show any evidence of repair, with means ranging between 2 and 11%, and there were no significant differences over the 40-day treatment period (FIGS. 10C-F). In contrast, after 20, 30 or 40 days of N-[N-(3-pyridinesulfonyl)-L-3,3-dimethyl-4-thiaprolyl]-O-[1-methylpiperazin-4-ylcarbonyl]-L-tyrosine isopropyl ester treatment, the majority of lesions identified show a variable degree of remyelination ranged from 2 to 100% in the majority of lesions (mean area of remyelination approximately 50%) (FIGS. 10D-5). ($p<0.001$, 2-way ANOVA with Tukey test). Therefore while lesions were evident in all animals throughout the 40-day treatment period, N-[N-(3-pyridinesulfonyl)-L-3,3-dimethyl-4-thiaprolyl]-O-[1-methylpiperazin-4-ylcarbonyl]-L-tyrosine isopropyl ester increased the incidence and percentage of remyelination. Furthermore, evidence of remyelination in N-[N-(3-pyridinesulfonyl)-L-3,3-dimethyl-4-thiaprolyl]-O-[1-methylpiperazin-4-ylcarbonyl]-L-tyrosine isopropyl ester-treated animals is consistent with an observed regain of motor function. The starting point for treatment was a clinical score of 2, which denotes full bilateral hind limb paralysis. In 50% of N-[N-(3-pyridinesulfonyl)-L-3,3-dimethyl-4-thiaprolyl]-O-[1-methylpiperazin-4-ylcarbonyl]-L-tyrosine isopropyl ester-treated animals, paralysis was reversed to a clinical score of 1, indicating that animals regained significant use of their hind limbs ($p<0.05$, Mann Whitney rank sum test). Functional recovery was never observed in control animals.

Spontaneous remyelination, by definition, is myelin repair in the absence of therapeutic intervention specifically designed to stimulate remyelination (Miller et al., 1995, Microsc. Res. Tech. 32: 230-245). Spontaneous repair is well documented in animal models of demyelination involving acute toxic damage, as with cuprizone, lysolecithin or ethidium bromide (Dubois-Dalcq et al., 1990, Bioessays 12: 569-576), and in models of viral encephalitis (Miller et al., 1995, Microsc. Res. Tech. 32: 230-245) or in models with broad immunosuppression or immune cell depletion (Rodriguez et al., 1992, Neurol. 42: 348-57; and Murray et al., 2001, Brain 124: 1403-16). In these instances, remyelination can be complete within several weeks. N-[N-(3-pyridinesulfonyl)-L-3,3-dimethyl-4-thiaprolyl]-O-[1-methylpiperazin-4-ylcarbonyl]-L-tyrosine isopropyl ester is a small molecule that interferes with $\alpha_4\beta_1$ integrin activity on immune cells, and was designed as a disease-limiting agent to prevent inflammatory cell infiltration of the brain, rather than as an agent to directly promote myelin repair (Piraino et al., 2002, J. Neuroimmunol. 131:147-159). Since the guinea pig model of CP-EAE is a non-episodic disease that does not normally exhibit repair, the finding that a disease-limiting agent can, by itself, promote spontaneous remyelination is significant. These results indicate that the inflammatory environment itself suppresses or overwhelms normal repair mechanisms, and may eventually lead to their exhaust. Although there was microscopic evidence of remyelination in saline-treated animals, it did not attain significant levels, and was never accompanied by clinical remission. Thus, it appears that by suppressing immune cell infiltration, N-[N-(3-pyridinesulfonyl)-L-3,3-dimethyl-4-thiaprolyl]-O-[1-methylpiperazin-4-ylcarbonyl]-L-tyrosine isopropyl ester prevented attack of newly formed myelin and allowed repair.

Induced remyelination of the CNS has indeed been achieved by a number of means, including administration of myelin glycolipids (Raine et al., 1978, Acta. Neuropathol. (Berl). 43: 43-53; Traugott et al., 1982, J. Neurol. Sci. 56: 65-73), CNS-specific antiserum, purified immunoglobulins (Warrington et al., 2001, J. Allergy Clin. Immunol. 108:121-5), or growth factors (Yao et al., 1995, Proc. Nat'l Acad. Sci. USA 92: 6190-4). It has also recently been shown that serum-derived human monoclonal antibodies (IgM) can promote remyelination apparently through direct stimulation of oligodendrocytes (Warrington et al., 2000, *Proc. Nat'l Acad. Sci. USA* 97: 6820-6825; Bieber et al., 2002, *Glia* 37: 241-9; Mitsunaga et al., 2002, *FASEB J.* 16: 1325-1327). Transplantation of both embryonic and adult neural stem cells has also led to generation of oligodendrocytes and new myelin synthesis in deficient models (Halfpenny et al., 2002, *Lancet Neurol.* 1: 31-40). While these studies have shown that the CNS is capable of repair, it is important to note that therapeutically induced remyelination does not stop ongoing disease. The Notch pathway, for example, has recently been implicated as an inhibitor of myelination in MS, reflecting the interaction between oligodendrocytes, glial cells and on-going inflammation (John et al., 2002, *Nat. Med.* 8: 1115-21). In an inflammatory disorder such as MS, the CNS would still be vulnerable to attack.

Remyelinating antibodies, such as natalizumab, reverse disease pathology in EAE by inhibiting the otherwise continuous influx of new inflammatory cells. Cells that have already entered the CNS are cleared by normal apoptotic mechanisms (Hyduk et al., 1998, *J. Neuropath. Exp. Neurol.* 57: 602-614). Consistent with these observations, N-[N-(3-pyridinesulfonyl)-L-3,3-dimethyl-4-thiaprolyl]-O-[1-methylpiperazin-4-ylcarbonyl]-L-tyrosine isopropyl ester has been demonstrated to progressively reduce immune cell infiltrates and their associated inflammatory mediators with increasing duration of treatment (Piraino et al., 2002, *J. Neuroimmunol.* 131:147-159). In a controlled trial for relapsing MS, natalizumab demonstrated that treatment over a six-month period led to fewer inflammatory brain lesions and fewer relapses as compared with subjects treated with the placebo. Therapy was well tolerated during the trial, and there was an improved perception of well being among natalizumab-treated patients (Miller et al., 2003, *New Engl. J. Med.* 348: 15-23). Thus, agents such as anti-$\alpha_4$ integrin antibody therapy and compounds such as N-[N-(3-pyridinesulfonyl)-L-3,3-dimethyl-4-thiaprolyl]-O-[1-methylpiperzain-4-ylcarbonyl]-L-tyrosine isopropyl ester will not only serve as a disease-limiting factor in MS, but also as an agent permissive for CNS repair.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention.

EXAMPLE 3

Construction of Humanized 21.6 Antibody

Chimeric light and heavy chains were constructed by linking the PCR-cloned cDNAs of mouse 21.6 $V_L$ and $V_H$ regions to human constant regions. The 5'- and 3'-ends of the mouse cDNA sequences were modified using specially designed PCR primers. The 5'-end PCR-primers (Table 8), which hybridize to the DNA sequences coding for the beginnings of the leader sequences, were designed to create the DNA sequences essential for efficient translation (Kozak, *J. Mol. Biol.* 196: 947-950 (1987)), and to create a HindIII restriction sites for cloning into an expression vector. The 3'-end primers (Table 8), which hybridize to the DNA sequences coding for the ends of J regions, were designed to create the DNA sequences essential for splicing to the constant regions, and to create a BamHI site for cloning into an expression vector. The products of PCR amplification were digested with HindIII and BamHI, cloned into a pUC19 vector, and sequenced to confirm that no errors had occurred during PCR amplification. The adapted mouse 21.6 variable regions were then subcloned into mammalian cells expression vectors containing either the human kappa or gamma-1 constant regions.

TABLE 8

PCR Primers for the Construction of Chimeric 21.6 Antibody

A. Light Chain Variable Region

1. Primer for reconstruction of the 5'-end (37-mer)
(SEQ ID NOS.: 25 and 26)
5' C AGA <u>AAG CTT</u> GCC GCC ACC ATG AGA CCG TCT ATT CAG 3'
        HindIII Kozak      M   R   P   S   I   Q
               Consensus
               Sequence 2. Primer for reconstruction of the 3'-end (35-mer)
(SEQ ID NO.: 27)
5' CC G<u>AG GAT CC</u>A CTC ACG TTT GAT TTC CAG CTT GGT 3'
      BamHI    Splice donor site B. Heavy chain variable region 1. Primer for reconstruction of the 5'-end (37-mer)
(SEQ ID NOS.: 28 and 29)
5' C AGA <u>AAG CTT</u> GCC GCC ACC ATG AAA TGC AGC TGG GTC 3'
        HindIII Kozak      M   K   C   S   W   V
               Consensus
               Sequence 2. Primer for reconstruction of the 3'-end (33-mer)
(SEQ ID NO.: 30)
5' CC G<u>AG GAT CC</u>A CTC ACC TGA GGA GAC GGT GAC T 3'
      BamHI    Splice donor site Modeling the Structure of the Mouse 21.6 Variable Regions. A molecular model of the $V_L$ and $V_H$ regions of mouse 21.6 antibody was built. The model was built on a Silicon Graphics IRIS 4D workstation running under the UNIX operating system and using the molecular modeling package QUANTA (Polygen Corp., USA). The structure of the FRs of mouse 21.6 $V_L$ region was based on the solved structure of human Bence-Jones immunoglobulin RE1 (Epp et al., *Biochemistry* 14: 4943-4952 (1975)). The structure of the FRs of mouse 21.6 $V_H$ region was based on the solved structure of mouse antibody Gloop2. Identical residues in the FRs were retained; non-identical residues were substituted using the facilities within QUANTA. CDR1 and CDR2 of mouse 21.6 $V_L$ region were identified as belonging to canonical structure groups 2 and 1, respectively (Chothia et al., *J. Mol. Biol.* 196: 901-917 (1987)). Since CDR1 and CDR2 of RE1 belong to the same canonical groups, CDR1 and CDR2 of mouse 21.6, $V_L$ region were modeled on the structures of CDR1 and CDR2 of RE1. CDR3 of mouse 21.6 $V_L$ region did not appear to correspond to any of the canonical structure groups for CDR3s of $V_L$ regions. A database search revealed, however, that CDR3 in mouse 21.6 $V_L$ region was similar to CDR3 in mouse HyHEL-5 $V_L$ region (Sheriff et al., *Proc. Natl. Acad. Sci. USA* 84: 8075-8079 (1987)). Thus, the CDR3 of mouse 21.6 $V_L$ region was modeled on the structure of CDR3 in mouse HyHEL-5 $V_L$ region. CDR1 and CDR2 of mouse 21.6 $V_H$ region were identified as belonging to canonical structure groups 1 and 2, respectively. CDR1 of mouse 21.6 $V_H$ region was modeled on CDR1 of Gloop2 $V_H$ region, which closely resembles members of canonical group 1 for CDR1s of $V_H$ regions. CDR2 of mouse 21.6 $V_H$ region was modeled on CDR2 of mouse HyHEL-5 (Sheriff et al., supra), which is also a member of canonical group 2 for CDR2 for $V_H$ regions. For CDR3s of $V_H$ regions, there are no canonical structures. However, CDR3 in mouse 21.6 $V_H$ region was similar to CDR3 in mouse R19.9 $V_H$ region (Lascombe et al., *Proc. Natl. Acad. Sci. USA* 86: 607-611 (1989)) and was modeled on this CDR3 by removing an extra serine residue present at the apex of the CDR3 loop of mouse R19.9 $V_H$ region and annealing and refining the gap. The model was finally subjected to steepest descents and conjugate gradients energy minimization using the CHARMM potential (Brooks et al., *J. Comp. Chem.* 4: 187-217 (1983)), as implemented in QUANTA in order to relieve unfavorable atomic contacts and to optimize van der Waals and electrostatic interactions.

Design of Reshaped Human 21.6 Variable Regions—Selection of Homologous Human Antibodies for Framework Sequence. Human variable regions whose FRs showed a high percent identity to those of mouse 21.6 were identified by comparison of amino acid sequences. Tables 10 and 11 compare the mouse 21.6 variable regions to all known mouse variable regions and then to all known human variable regions. The mouse 21.6 $V_L$ region was identified as belonging to mouse kappa $V_L$ region subgroup 5 as defined by Kabat. Individual mouse kappa $V_L$ regions were identified that had as much as 93.4% identity to the mouse 21.6 kappa $V_L$ region (38C13V'CL and PC613'CL). Mouse 21.6 $V_L$ region was most similar to human kappa $V_L$ regions of subgroup 1, as defined by Kabat. Individual human kappa $V_L$ regions were identified that had as much as 72.4% identity to the mouse 21.6 kappa $V_L$ region. The framework regions (FRs) from one of the most similar human variable regions, RE1, were used in the design of reshaped human 21.6 $V_L$ region. Mouse 21.6 $V_H$ region was identified as belonging to mouse $V_H$ region subgroup 2c as defined by Kabat. Individual mouse heavy chain variable regions were identified that have as much as 93.3% identity to the mouse 21.6 $V_H$ region (17.2.25'CL and 87.92.6'CL). Mouse 21.6 $V_H$ region was most similar to human $V_H$ regions of subgroup 1 as defined by Kabat et al., supra. Individual human $V_H$ regions were identified that had as much as 64.7% identity to the mouse 21.6 $V_H$ region. The FRs from one of the most similar human variable regions, 21/28'CL, was used in the design of reshaped human 21.6 $V_H$ region.

Substitution of Amino Acids in Framework Regions.

(A) Light Chain. The next step in the design process for the reshaped human 21.6 $V_L$ region was to join the CDRs from mouse 21.6 $V_L$ region to the FRs from human RE1 (Palm et al., *Physiol. Chem.* 356: 167-191 (1975). In the first version of reshaped human 21.6 $V_L$ region (La), seven changes were made in the human FRs (Table 10, FIG. 13). At positions 104, 105, and 107 in FR4, amino acids from RE1 were substituted with more typical human J region amino acids from another human kappa light chain (Riechmann et al., *Nature* 332:323-327 (1988)).

At position 45 in FR2, the lysine normally present in RE1 was changed to an arginine as found at that position in mouse 21.6 $V_L$ region. The amino acid residue at this position was thought to be important in the supporting the CDR2 loop of the mouse 21.6 $V_L$ region.

At position 49 in FR2, the tyrosine normally present in RE1 was changed to a histidine as found at that position in mouse 21.6 $V_L$ region. The histidine at this position in mouse 21.6 $V_L$ region was observed in the model to be located in the middle of the binding site and could possibly make direct contact with antigen during antibody-antigen binding.

At position 58 in FR3, the valine normally present in RE1 was changed to an isoleucine as found at that position in mouse 21.6 $V_L$ region. The amino acid residue at this position was thought to be important in the supporting the CDR2 loop of the mouse 21.6 $V_L$ region.

At position 69 in FR3, the threonine normally present in RE1 was changed to an arginine as found at that position in mouse 21.6 $V_L$ region. The arginine at this position in mouse 21.6 $V_L$ region was observed in the model to be located adjacent to the CDR1 loop of mouse 21.6 $V_L$ region and could possibly make direct contact with the antigen during antibody-antigen binding.

A second version of reshaped human 21.6 $V_L$ region (termed Lb) was designed containing the same substitutions as above except that no change was made at position 49 in FR2 of RE1. (FIG. 13).

(B) Heavy Chain. The next step in the design process for the reshaped human 21.6 $V_H$ region was to join the CDRs from mouse 21.6 $V_H$ region to the FRs from 21/28'CL (Dersimonian et al., *J. Immunol.* 139: 2496-2501 (1987)). In the first version of reshaped human 21.6 V region (Ha), five changes were made in the human framework regions (Table 11, FIG. 14). The five changes in the human FRs were at positions 27, 28, 29, 30, and 71.

At positions 27, 28, 29, and 30 in FR1, the amino acids present in human 21/28'CL were changed to the amino acids found at those positions in mouse 21.6 $V_H$ region. Although these positions are designated as being within FR1 (Kabat et al., supra), positions 26 to 30 are part of the structural loop that forms the CDR1 loop of the $V_H$ region. It is likely, therefore, that the amino acids at these positions are directly involved in binding to antigen. Indeed, positions 27 to 30 are part of the canonical structure for CDR1 of the $V_H$ region as defined by Chothia et al., supra.

At position 71 in FR3, the arginine present in human 21/28'CL was changed to a alanine as found at that position in mouse 21.6 $V_H$ region. Position 71 is part of the canonical structure for CDR2 of the $V_H$ region as defined by Chothia et al., supra. From the model of the mouse 21.6 variable regions, it appears that the alanine at position 71 is important in supporting the CDR2 loop of the $V_H$ region. A substitution of an arginine for an alanine at this position would very probably disrupt the placing of the CDR2 loop.

A second version (Hb) of reshaped human 21.6 $V_H$ region contains the five changes described above for version Ha were made plus one additional change in FR2.

At position 44 in FR2, the arginine present in human 21/28'CL was changed to a glycine as found at that position in mouse 21.6 $V_H$ region. Based on published information on the packing of $V_L$-$V_H$ regions and on the model of the mouse 21.6 variable regions, it was thought that the amino acid residue at position 44 might be important in the packing of the $V_L$-$V_H$ regions.

Reshaped human 21.6 V region version Hc was designed to make the CDR3 loop look more similar to human VCAM-1. Both mouse 21.6 antibody and human VCAM-1 bind to the $\alpha_4\beta_1$ integrin. The CDR3 loop of the $V_H$ region of antibodies is the most diverse of the six CDR loops and is generally the most important single component of the antibody in antibody-antigen interactions (Chothia et al., supra; Hoogenboom & Winter, *J. Mol. Biol.* 227: 381-388 (1992); Barbas et al., *Proc. Natl. Acad. Sci. USA* 89: 4457-4461 (1992)). Some sequence similarity was identified between the CDR3 of mouse 21.6 $V_H$ region and amino acids 86 to 94 of human VCAM-1, particularly, between the YGN (Tyrosine-Glycine-Asparagine) sequence in the CDR3 loop and the FGN (i.e., Phenylalanine-Glycine-Asparagine) sequence in VCAM-1. These sequences are thought to be related to the RGD (i.e., Arginine-Glycine-Aspartic acid) sequences important in various cell adhesion events (Main et al., *Cell* 71: 671-678 (1992)). Therefore, at position 98 in CDR3, the tyrosine present in mouse 21.6 $V_H$ region was changed to a phenylalanine as found in the sequence of human VCAM-1.

Possible substitution at position 36 in FR2 was also considered. The mouse 21.6 $V_H$ chain contains an unusual cysteine residue at position 36 in FR2. This position in FR2 is usually a tryptophan in related mouse and human sequences (Table 11). Although cysteine residues are often important for conformation of an antibody, the model of the mouse 21.6 variable regions did not indicate that this cysteine residue was involved either directly or indirectly with antigen binding so the tryptophan present in FR2 of human 21/28'CL $V_H$ region was left unsubstituted in all three versions of humanized 21.6 antibody.

Construction of Reshaped Human 21.6 Antibodies. The first version of reshaped human 21.6 $V_L$ region (resh21.6$V_L$ a) was constructed from overlapping PCR fragments essentially as described by Daugherty et al., *Nucleic Acids Res.* 19: 2471-2476 (1991). The mouse 21.6 $V_L$ region, adapted as described supra and inserted into pUC19, was used as a template. Four pairs of primers, APCR1-vla1, vla2-vla3, vla4-vla5, and vla6-vla7 were synthesized (Table 9). Adjacent pairs overlapped by at least 21 bases. The APCR1 primer is complementary to the pUC19 vector. The appropriate primer pairs (0.2 µmoles) were combined with 10 ng of template DNA, and 1 unit of AmpliTaq DNA polymerase (Perkin Elmer Cetus) in 50 µl of PCR buffer containing 10 mM Tris-HCl (pH 8.3), 50 mM KCl, 200 µM dNTPs, and 1.5 mM MgCl$_2$. Each reaction was carried out for 25 cycles. After an initial melt at 94° C. for 5 min, the reactions were cycled at 94° C. for 1 min, 55° C. for 1 min, and 72° C. for 2 min, and finally incubated at 72° C. for a further 10 min. The ramp time between the primer-annealing and extension steps was 2.5 min. The products of the four reactions (A, B, C, and D) from the first round of PCR reactions were phenol-extracted and ethanol-precipitated.

TABLE 9

PCR primers for the construction of reshaped human 21.6 variable regions

A. Light chain variable region
1. Primers for the synthesis of version "a" (SEQ ID NOS.: 31-39)

21.6VLa1 (39-mer):
5' GAT GGT GAC TCT ATC TCC TAC AGA TGC AGA CAG TGA GGA 3'

21.6VLa2 (32-mer):
5' CTG TAG GAG ATA GAG TCA CCA TCA CTT GCA AG 3'

21.6VLa3 (39-mer):
5' AGG AGC TTT TCC AGG TGT CTG TTG GTA CCA AGC CAT ATA 3'

21.6VLa4 (41-mer):
5' ACC AAC AGA CAC CTG GAA AAG CTC CTA GGC TGC TCA TAC AT 3'

21.6VLa5 (40-mer):
5' GCA GGC TGC TGA TGG TGA AAG TAT AAT CTC TCC CAG ACC C 3'

21.6VLa6 (42-mer):
5' ACT TTC ACC ATC AGC AGC CTG CAG CCT GAA GAT ATT GCA ACT 3'

21.6VLa7 (59-mer):
5' CCG AGG ATC CAC TCA CGT TTG ATT TCC ACC TTG GTG CCT TGA CCG AAC GTC CAC AGA TT 3'

2. Primers for the synthesis of version "b"

21.6VLb1 (33-mer): changes H-49 to Y-49
5' GGA AAA GCT CCT AGG CTG CTC ATA TAT TAC ACA 3'

21.6VLb2 (38-mer): changes ACC-101 to ACA-101 to destroy an StyI site
5' CCG AGG ATC CAC TCA CGT TTG ATT TCC ACC TTT GTG CC 3'

TABLE 9-continued

PCR primers for the construction of reshaped human 21.6 variable regions

B. Heavy chain variable region
1. Primers for the synthesis of version "a" (SEQ ID NOS.: 40-45)

21.6VHa1 (51-mer):
5' AAC CCA GTG TAT ATA GGT GTC TTT AAT GTT GAA ACC GCT AGC TTT ACA GCT 3'

21.6VHa2 (67-mer):
5' AAA GAC ACC TAT ATA CAC TGG GTT AGA CAG GCC CCT GGC CAA AGG CTG GAG TGG ATG GGA AGG ATT G 3'

21.6VHa3 (26-mer):
5' GAC CCG GCC CTG GAA CTT CGG GTC AT 3'

21.6VHa4 (66-mer):
5' GAC CCG AAG TTC CAG GGC CGG GTC ACC ATC ACC GCA GAC ACC TCT GCC AGC ACC GCC TAC ATG GAA 3'

21.6VHa5 (64-mer):
5' CCA TAG CAT AGA CCC CGT AGT TAC CAT AAT ATC CCT CTC TGG CGC AGT AGT AGA CTG CAG TGT C 3'

21.6VHa6 (63-mer):
5' GGT AAC TAC GGG GTC TAT GCT ATG GAC TAC TGG GGT CAA GGA ACC CTT GTC ACC GTC TCC TCA 3'

2. Primer for the synthesis of version "b" (SEQ ID NO.: 46)

21.6VHb (37-mer): changes R-44 to G-44
5' CCA GGG CCG GGT CAC CAT CAC CAG AGA CAC CTC TGC C 3'

3. Primer for the synthesis of version "c" (SEQ ID NO.: 47)

21.6VHc (27-mer): changes Y-98 to F-98
5' CAG GCC CCT GGC CAA GGG CTG GAG TGG 3'

C. Both light and heavy chain variable regions
Primers hybridizing to the flanking pUC19 vector DNA APCR1 (17-mer, sense primer)
(SEQ ID NO.: 48)
5' TAC GCA AAC CGC CTC TC 3'

APCR4 (18-mer, anti-sense primer) (SEQ ID NO.: 49)
5' GAG TGC ACC ATA TGC GGT 3'

PCR products A and B, and C and D were joined in a second round of PCR reactions. PCR products A and B, and C and D, (50 ng of each) were added to 50 µl PCR reactions (as described supra) and amplified through 20 cycles as described above, except that the annealing temperature was raised to 60° C. The products of these reactions were termed E and F. The pairs of PCR primers used were APCR1-vla3 and vla4-vla7, respectively. PCR products E and F were phenol-extracted and ethanol-precipitated and then assembled in a third round of PCR reactions by their own complementarity in a two step-PCR reaction similar to that described above using APCR1 and vla7 as the terminal primers. The fully assembled fragment representing the entire reshaped human 21.6 $V_L$ region including a leader sequence was digested with HindIII and BamHI and cloned into pUC19 for sequencing. A clone having the correct sequence was designated resh21.6VLa.

The second version of a reshaped human 21.6 $V_L$ region (Lb) was constructed using PCR primers to make minor modifications in the first version of reshaped human 21.6 $V_L$ region (La) by the method of Kamman et al., *Nucl. Acids Res.* 17: 5404 (1989). Two sets of primers were synthesized (Table 9). Each PCR reaction was essentially carried out under the same conditions as described above. In a first PCR reaction, mutagenic primer 21.6VLb2 was used to destroy a StyI site (Thr-ACC-97 to Thr-ACA-97) to yield resh21.6VLa2. Then, in a second PCR reaction, mutagenic primer 21.6VLb1 (His-49 to Tyr-49) was used with pUC-resh21.6VLa2 as template DNA. The PCR product was cut with StyI and BamHI and subcloned into pUC-resh21.6VLa2, cleaved with the same restriction enzymes. A clone with the correct sequence was designated pUC-resh21.6VLb.

Version "a" of a reshaped human 21.6 $V_H$ region was constructed using the same PCR methods as described for the construction of version "a" of reshaped human 21.6 $V_L$ region (Table 9). The HindIII-BamHI DNA fragments coding for version "g" of reshaped human 425 $V_H$ region (Kettleborough et at., supra) and version "b" of reshaped human AUK12-20 $V_H$ region were subcloned into pUC19 vectors yielding pUC-resh425 g and pUC-reshAU K12-20b, respectively. (Version "b" of AUK12-20, was derived by PCR mutagenesis of a fragment $V_H$ a425 described by Kettleborough et al., supra, and encodes the amino acid sequence (SEQ ID NO.: 50: QVQLVQSGAEVKKPGASVKVSCKASGYSFT SYYIH WVRQAPGQGLEWVG YIDPFNGGTSYNQKFKG KVT-MTVDTSTNTAYMELSSLRSEDTAVYYCAR GGNRFAY WGQGTLVTVSS (spaces separate FR and CDR regions)).

Plasmid pUC-resh425 g and pUC-reshAUK12-20b, as well as the pUC vector containing the mouse 21.6 $V_H$ region as modified for use in the construction of the chimeric 21.6 heavy chain (pUC-chim21.6$V_H$), were used as template DNAs in the subsequent PCR reactions. PCR primers were designed and synthesized for the construction of version "a" of reshaped human 21.6 $V_H$ region (Table 9). PCR product A was obtained using pUC-reshAUK12-20b as DNA template and APCR1-vha1 as the PCR primer pair. PCR products B and D were obtained using pUC-chim21.6$V_H$ as DNA template and vha2-vha3 and vha6-APCR4 as PCR primer pairs, respectively. Finally, PCR product C was obtained using pUC-resh425g as DNA template and vla4-vla5 as the PCR primer pair. The final PCR product was subcloned into pUC19 as a HindIII-BamHI fragment for DNA sequencing. A clone with the correct DNA sequence was designated pUC-resh21.6VHa. The DNA and amino acid sequences of the first version of the reshaped 21.6 variable region are shown in FIG. 15.

The remaining versions of reshaped human 21.6 $V_H$ region were constructed essentially as described above for the construction of version "b" of reshaped human 21.6 $V_L$ region. Two sets of primers were synthesized (Table 9). For the second (Hb) and third (Hc) versions, mutagenic primers 21.6VHb (Arg-44 to Gly-44) and 21.6VHc (Tyr-98 to Phe-98), respectively, were used in PCR reactions with pUC-resh21.6VHa as the template DNA. The PCR products VHb and VHc were cut with restriction enzymes and subcloned into pUC vector pUC-resh21.6VHa as MscI-BamHI and PstI-BamHI fragments, respectively, to yield pUC-resh21.6VHb and pUC-resh21.6VHc.

The first version of a reshaped human 21.6 $V_H$ region (Ha) was constructed in a similar manner to that used for the construction of the first version of reshaped human 21.6 $V_L$ region (La). In this case, however, PCR primers were used with three different template DNAs, mouse 21.6 $V_H$ region as already adapted for expression of chimeric 21.6 heavy chain, humanized 425 $V_H$ region version "g" (Kettleborough et al., supra), and humanized AUK12-20 version "b" $V_H$ region (Table 9). The DNA and amino acid sequences of the first version of the humanized 21.6 heavy chain variable region are shown in FIG. 16. The second and third versions of a humanized 21.6 $V_H$ region (Hb and Hc) were constructed using PCR primers to make minor modifications in the first version of humanized 21.6 $V_H$ region (Ha) (Table 9).

TABLE 10

Alignment of amino acid sequences leading to the design of reshaped human 21.6 light chain variable regions.

| Kabat | # | FR or CDR | mouse 21.6 | mouse kappa 5 (FIG. 17A) | human kappa 1 (FIG. 17B) | human RE1 | RH $V_L$ 21.6 | Comment |
|---|---|---|---|---|---|---|---|---|
| 1 | 1 | FR1 | D | D | D | D | D | |
| 2 | 2 | | I | I | I | I | I | |
| 3 | 3 | | Q | Q | Q | Q | Q | |
| 4 | 4 | | M | M | M | M | M | |
| 5 | 5 | | T | T | T | T | T | |
| 6 | 6 | | Q | Q | Q | Q | Q | |
| 7 | 7 | | S | S | S | S | S | |
| 8 | 8 | | P | P | P | P | P | |
| 9 | 9 | | S | S | S | S | S | |
| 10 | 10 | | S | S | S | S | S | |
| 11 | 11 | | L | L | L | L | L | |
| 12 | 12 | | S | S | S | S | S | |
| 13 | 13 | | A | A | A | A | A | |
| 14 | 14 | | S | S | S | S | S | |
| 15 | 15 | | L | L | V | V | V | |
| 16 | 16 | | G | G | G | G | G | |
| 17 | 17 | | G | D | D | D | D | |
| 18 | 18 | | K | R | R | R | R | |
| 19 | 19 | | V | V | V | V | V | |
| 20 | 20 | | T | T | T | T | T | |
| 21 | 21 | | I | I | I | I | I | |
| 22 | 22 | | T | T | T | T | T | |
| 23 | 23 | FR1 | C | C | C | C | C | |
| 24 | 24 | CDR1 | K | R | R | Q | K | |
| 25 | 25 | | T | A | A | A | T* | |
| 26 | 26 | | S | S | S | S | S | |
| 27 | 27 | | Q | Q | Q | Q | Q* | |
| 27A | | | — | D | S | — | — | |
| 27B | | | — | — | L | — | — | |
| 27C | | | — | — | V | — | — | |
| 27D | | | — | — | X | — | — | |
| 27E | | | — | — | X | — | — | |
| 27F | | | — | — | — | — | — | |
| 28 | 28 | | D | D | S | D | D* | |
| 29 | 29 | | I | I | I | I | I* | |
| 30 | 30 | | N | S | S | I | N* | |
| 31 | 31 | | K | N | N | K | K* | |
| 32 | 32 | | Y | Y | Y | Y | Y* | |
| 33 | 33 | | M | L | L | L | M* | |
| 34 | 34 | CDR1 | A | N | A | N | A | |
| 35 | 35 | FR2 | W | W | W | W | W | |
| 36 | 36 | | Y | Y | Y | Y | Y | |
| 37 | 37 | | Q | Q | Q | Q | Q | |
| 38 | 38 | | H | Q | Q | Q | Q | |
| 39 | 39 | | K | K | K | T | T | K in CAMPATH-1H |
| 40 | 40 | | P | P | P | P | P | |
| 41 | 41 | | G | G | G | G | G | |
| 42 | 42 | | K | G | K | K | K | |
| 43 | 43 | | R | S | A | A | A | consider R in other versions |

TABLE 10-continued

Alignment of amino acid sequences leading to the design of reshaped human 21.6 light chain variable regions.

| Kabat | # | FR or CDR | mouse 21.6 | mouse kappa 5 (FIG. 17A) | human kappa 1 (FIG. 17B) | human RE1 | RH V$_L$ 21.6 | Comment |
|---|---|---|---|---|---|---|---|---|
| 44 | 44 | | P | P | P | P | P | |
| 45 | 45 | | R | K | K | K | R | supports L2 loop, consider K in other versions |
| 46 | 46 | | L | L | L | L | L | |
| 47 | 47 | | L | L | L | L | L | |
| 48 | 48 | | I | I | I | I | I* | |
| 49 | 49 | | H | Y | Y | Y | H | in middle of binding site, potential to interact with antigen, consider Y in other versions |
| 50 | 50 | CDR2 | Y | Y | A | E | Y* | |
| 51 | 51 | | T | A | A | A | T* | |
| 52 | 52 | | S | S | S | S | S* | |
| 53 | 53 | | A | R | S | N | A | |
| 54 | 54 | | L | L | L | L | L | |
| 55 | 55 | | Q | H | E | Q | Q | |
| 56 | 56 | CDR2 | P | S | S | A | P | |
| 57 | 57 | FR3 | G | G | G | G | G | |
| 58 | 58 | | I | V | V | V | I | maybe supporting L2, consider V in other versions |
| 59 | 59 | | P | P | P | P | P | |
| 60 | 60 | | S | S | S | S | S | |
| 61 | 61 | | R | R | R | R | R | |
| 62 | 62 | | F | F | F | F | F | |
| 63 | 63 | | S | S | S | S | S | |
| 64 | 64 | | G | G | G | G | G* | |
| 65 | 65 | | S | S | S | S | S | |
| 66 | 66 | | G | G | G | G | G | |
| 67 | 67 | | S | S | S | S | S | |
| 68 | 68 | | G | G | G | G | G | |
| 69 | 69 | | R | T | T | T | R | adjacent to L1, on the surface near the binding site |
| 70 | 70 | | D | D | D | D | D | |
| 71 | 71 | | Y | Y | F | Y | Y* | F in CAMPATH-1H |
| 72 | 72 | | S | S | T | T | T | |
| 73 | 73 | | F | L | L | P | F | |
| 74 | 74 | | N | T | T | T | T | |
| 75 | 75 | | I | I | I | I | I | |
| 76 | 76 | | S | S | S | S | S | |
| 77 | 77 | | N | N | S | S | S | |
| 78 | 78 | | L | L | L | L | L | |
| 79 | 79 | | E | E | Q | Q | Q | |
| 80 | 80 | | P | Q | P | P | P | |
| 81 | 81 | | E | E | E | E | E | |
| 82 | 82 | | D | D | D | D | D | |
| 83 | 83 | | I | I | F | I | I | |
| 84 | 84 | | A | A | A | A | A | |
| 85 | 85 | | T | T | T | T | T | |
| 86 | 86 | | Y | Y | Y | Y | Y | |
| 87 | 87 | | Y | F | Y | Y | Y | |
| 88 | 88 | FR3 | C | C | C | C | C | |
| 89 | 89 | CDR3 | L | Q | Q | Q | L | |
| 90 | 90 | | Q | Q | Q | Q | Q* | |
| 91 | 91 | | Y | G | Y | Y | Y* | |
| 92 | 92 | | D | N | N | Q | D* | |
| 93 | 93 | | N | T | S | S | N* | |
| 94 | 94 | | L | L | L | L | L* | |
| 95 | 95 | | — | P | P | P | — | |
| 95A | | | — | P | E | — | — | |
| 95B | | | — | — | — | — | — | |
| 95C | | | — | — | — | — | — | |
| 95D | | | — | — | — | — | — | |
| 95E | | | — | — | — | — | — | |
| 95F | | | — | — | — | — | — | |
| 96 | 95 | | W | R | W | Y | W* | |
| 97 | 96 | CDR3 | T | T | T | T | T | |
| 98 | 97 | FR4 | F | F | F | F | F | |
| 99 | 98 | | G | G | G | G | G | |

TABLE 10-continued

Alignment of amino acid sequences leading to the design of reshaped human 21.6 light chain variable regions.

| Kabat | # | FR or CDR | mouse 21.6 | mouse kappa 5 (FIG. 17A) | human kappa 1 (FIG. 17B) | human RE1 | RH V$_L$ 21.6 | Comment |
|---|---|---|---|---|---|---|---|---|
| 100 | 99 | | G | G | Q | Q | Q | |
| 101 | 100 | | G | G | G | G | G | |
| 102 | 101 | | T | T | T | T | T | |
| 103 | 102 | | K | K | K | K | K | |
| 104 | 103 | | L | L | V | L | V | as in CAMPATH-1H |
| 105 | 104 | | E | E | E | Q | E | as in CAMPATH-1H |
| 106 | 105 | | I | I | I | I | I | |
| 106A | | | — | — | — | — | — | |
| 107 | 106 | FR4 | K | K | K | T | K | as in CAMPATH-1H |

Legend:
(Kabat) numbering according to Kabat et al., supra;
(#) sequential numbering as used in the molecular modeling;
(mouse 21.6) amino acid sequence of the V$_L$ region from mouse 21.6 antibody;
(mouse kappa 5) consensus sequence of mouse kappa V$_L$ regions from subgroup 5 (Kabat et al., supra);
(human kappa 1) consensus sequence of human V$_L$ regions from subgroup 1 (Kabat et al., supra);
(human RED amino acid sequence of a human V$_L$ region (Palm et al., Physiol. Chem. 356: 167-191 (1975));
RH V$_L$ 21.6 amino acid sequence of version L1 of reshaped human 21.6 V$_L$ region;
*residues that are part of the canonical structures for the CDR loops (Chothia et al., supra);
underlined residues in the human FRs where the amino acid residue was changed.

TABLE 11

Alignment of amino acid sequences leading to the design of reshaped human 21.6 heavy chain variable regions.

| Kabat | # | FR or CDR | mouse 21.6 | mouse 2c (FIG. 18A) | human 1 (FIG. 18B) | human 21/28'CL | RH V$_H$ 21.6 | Comment |
|---|---|---|---|---|---|---|---|---|
| 1 | 1 | FR1 | E | E | Q | Q | Q | |
| 2 | 2 | | V | V | V | V | V | |
| 3 | 3 | | Q | Q | Q | Q | Q | |
| 4 | 4 | | L | L | L | L | L | |
| 5 | 5 | | Q | Q | V | V | V | |
| 6 | 6 | | Q | Q | Q | Q | Q | |
| 7 | 7 | | S | S | S | S | S | |
| 8 | 8 | | G | G | G | G | G | |
| 9 | 9 | | A | A | A | A | A | |
| 10 | 10 | | E | E | E | E | E | |
| 11 | 11 | | L | L | V | V | V | |
| 12 | 12 | | V | V | K | K | K | |
| 13 | 13 | | K | K | K | K | K | |
| 14 | 14 | | P | P | P | P | P | |
| 15 | 15 | | G | G | G | G | G | |
| 16 | 16 | | A | A | A | A | A | |
| 17 | 17 | | S | S | S | S | S | |
| 18 | 18 | | V | V | V | V | V | |
| 19 | 19 | | K | K | K | K | K | |
| 20 | 20 | | L | L | V | V | V | |
| 21 | 21 | | S | S | S | S | S | |
| 22 | 22 | | C | C | C | C | C | |
| 23 | 23 | | T | T | K | K | K | |
| 24 | 24 | | A | A | A | A | A | |
| 25 | 25 | | S | S | S | S | S | |
| 26 | 26 | | G | G | G | G | G* | |
| 27 | 27 | | F | F | Y | Y | F* | H1 canonical structure, consider Y in other versions |
| 28 | 28 | | N | N | T | T | N* | H1 canonical structure, on the surface |
| 29 | 29 | | I | I | F | F | I* | H1 canonical structure, consider F in other versions |
| 30 | 30 | FR1 | K | K | T | T | K* | H1 canonical structure, on the surface |
| 31 | 31 | CDR1 | D | D | S | S | D* | |
| 32 | 32 | | T | T | Y | Y | T* | |
| 33 | 33 | | Y | Y | A | A | Y | |
| 34 | 34 | | I | I | I | M | I* | |
| 35 | 35 | | H | H | S | H | H | |

TABLE 11-continued

Alignment of amino acid sequences leading to the design of reshaped human 21.6 heavy chain variable regions.

| Kabat | # | FR or CDR | mouse 21.6 | mouse 2c (FIG. 18A) | human 1 (FIG. 18B) | human 21/28'CL | RH $V_H$ 21.6 | Comment |
|---|---|---|---|---|---|---|---|---|
| 35A | | | — | — | — | — | — | |
| 35B | | CDR1 | — | — | — | — | — | |
| 36 | 36 | FR2 | C | W | W | W | W | buried residue, no obvious special role for C |
| 37 | 37 | | V | V | V | V | V | |
| 38 | 38 | | K | K | R | R | R | |
| 39 | 39 | | Q | Q | Q | Q | Q | |
| 40 | 40 | | R | R | A | A | A | |
| 41 | 41 | | P | P | P | P | P | |
| 42 | 42 | | E | E | G | G | G | |
| 43 | 43 | | Q | Q | Q | Q | Q | |
| 44 | 44 | | G | G | G | R | R | $V_L$-$V_H$ packing, consider G in other versions |
| 45 | 45 | | L | L | L | L | L | |
| 46 | 46 | | E | E | E | E | E | |
| 47 | 47 | | W | W | W | W | W | |
| 48 | 48 | | I | I | M | M | M | |
| 49 | 49 | FR2 | G | G | G | G | G | |
| 50 | 50 | CDR2 | R | R | W | W | R | |
| 51 | 51 | | I | I | I | I | I | |
| 52 | 52 | | D | D | N | N | D | |
| 52A | 53 | | P | P | P | A | P* | |
| 52B | | | — | — | — | — | — | |
| 52C | | | — | — | — | — | — | |
| 53 | 54 | | A | A | G | G | A* | |
| 54 | 55 | | N | N | N | N | N* | |
| 55 | 56 | | G | G | G | G | G* | |
| 56 | 57 | | Y | N | D | N | Y | |
| 57 | 58 | | T | T | T | T | T | |
| 58 | 59 | | K | K | N | K | K | |
| 59 | 60 | | Y | Y | Y | Y | Y | |
| 60 | 61 | | D | D | A | S | D | |
| 61 | 62 | | P | P | Q | Q | P | |
| 62 | 63 | | K | K | K | K | K | |
| 63 | 64 | | F | F | F | F | F | |
| 64 | 65 | | Q | Q | Q | Q | Q | |
| 65 | 66 | CDR2 | G | G | G | G | G | |
| 66 | 67 | FR3 | K | K | R | R | R | |
| 67 | 68 | | A | A | V | V | V | |
| 68 | 69 | | T | T | T | T | T | |
| 69 | 70 | | I | I | I | I | I | |
| 70 | 71 | | T | T | T | T | T | |
| 71 | 72 | | A | A | A | R | A* | H2 canonical structure, supporting H2 |
| 72 | 73 | | D | D | D | D | D | |
| 73 | 74 | | T | T | T | T | T | |
| 74 | 75 | | S | S | S | S | S | |
| 75 | 76 | | S | S | T | A | A | |
| 76 | 77 | | N | N | S | S | S | |
| 77 | 78 | | T | T | T | T | T | |
| 78 | 79 | | A | A | A | A | A | |
| 79 | 80 | | Y | Y | Y | Y | Y | |
| 80 | 81 | | L | L | M | M | M | |
| 81 | 82 | | Q | Q | E | E | E | |
| 82 | 83 | | L | L | L | L | L | |
| 82A | 84 | | S | S | S | S | S | |
| 82B | 85 | | S | S | S | S | S | |
| 82C | 86 | | L | L | L | L | L | |
| 83 | 87 | | T | T | R | R | R | |
| 84 | 88 | | S | S | S | S | S | |
| 85 | 89 | | E | E | E | E | E | |
| 86 | 90 | | D | D | D | D | D | |
| 87 | 91 | | T | T | T | T | T | |
| 88 | 92 | | A | A | A | A | A | |
| 89 | 93 | | V | V | V | V | V | |
| 90 | 94 | | Y | Y | Y | Y | Y | |
| 91 | 95 | | F | Y | Y | Y | Y | |
| 92 | 96 | | C | C | C | C | C | |
| 93 | 97 | | A | A | A | A | A | |
| 94 | 98 | FR3 | R | R | R | R | | |
| 95 | 99 | CDR3 | E | G | A | G | E | |
| 96 | 100 | | G | Y | P | G | G | |

TABLE 11-continued

Alignment of amino acid sequences leading to the design of reshaped human 21.6 heavy chain variable regions.

| Kabat | # | FR or CDR | mouse 21.6 | mouse 2c (FIG. 18A) | human 1 (FIG. 18B) | human 21/28'CL | RH V$_H$ 21.6 | Comment |
|---|---|---|---|---|---|---|---|---|
| 97 | 101 | | Y | Y | G | Y | Y | |
| 98 | 102 | | Y | Y | Y | Y | Y | |
| 99 | 103 | | G | Y | G | G | G | |
| 100 | 104 | | N | D | S | S | N | |
| 100A | 105 | | Y | S | G | G | Y | |
| 100B | 106 | | G | X | G | S | G | |
| 100C | 107 | | V | V | o | — | V | |
| 100D | 108 | | Y | G | C | — | Y | |
| 100E | 109 | | A | Y | Y | — | A | |
| 100F | 110 | | M | Y | R | M | | |
| 100G | | | — | A | 0 | — | — | |
| 100H | | | — | M | D | — | — | |
| 100I | | | — | — | Y | — | — | |
| 100J | | | — | — | — | — | — | |
| 100K | | | — | — | F | — | — | |
| 101 | 111 | | D | D | D | N | D | |
| 102 | 112 | CDR3 | Y | Y | Y | Y | Y | |
| 103 | 113 | FR4 | W | W | W | W | W | |
| 104 | 114 | | G | G | G | G | G | |
| 105 | 115 | | Q | Q | Q | Q | Q | |
| 106 | 116 | | G | G | G | G | G | |
| 107 | 117 | | T | T | T | T | T | |
| 108 | 118 | | S | X | L | L | L | |
| 109 | 119 | | V | V | V | V | V | |
| 110 | 120 | | T | T | T | T | T | |
| 111 | 121 | | V | V | V | V | V | |
| 112 | 122 | | S | S | S | S | S | |
| 113 | 123 | FR4 | S | S | S | S | S | |

Legend:
(Kabat) numbering according to Kabat el al., supra;
(#) sequential numbering as used in the molecular modeling;
(mouse 21.6) amino acid sequence of the V$_H$ region from mouse 21.6 antibody;
(mouse 2c) consensus sequence of mouse V$_H$ regions from subgroup 2c (Kabat et al., supra);
(human 1) consensus sequence of human V$_H$ regions from subgroup 1 (Kabat et al., supra);
(human 21/28'CL) amino acid sequence of a human V$_H$ region (Dersimonian et al., J. ImmunoL, 139: 2496-2501 (1987));
(RH V$_H$ 21.6) amino acid sequence of version H1 of reshaped human 21.6 V$_H$ region;
*residues that are part of the canonical structures for the CD loops (Chothia et al., supra);
(underlined) residues in the human FRs where the amino acid residue was changed.

EXAMPLE 4

EAE Model of Brain Inflammation

A. In vitro Analysis of Lymphocyte Binding to Inflamed Endothelium in Sections of EAE Brain. Following the procedure described in Yednock et al., Nature 356: 63-66 (1992), brains were removed from rats with EAE on day 5 of disease (first day of tail/hind limb paralysis). The brains were quickly frozen, sectioned, and overlayed with lymphoid cell suspensions (methods as described above for tumor injected brains). Human U937 cells bound selectively to inflamed vessels in the rat EAE brains. Pretreatment of the U937 cells with the anti-VLA-4 antibody, HP2/1, completely inhibited their binding to inflamed vessels in an adjacent section of EAE brain.

As shown in Table 12, binding of human U937 cells to inflamed vessels in EAE brain was inhibited by reagents against VLA-4 (anti-$\alpha_4$, HP2/1; and anti-$\beta_2$, AIIB2), but not by antibodies against numerous other adhesion receptors. Two antibodies that selectively inhibit the fibronectin (FN)-binding activity of VLA-4, did not affect U937 binding to the EAE vessels (P4G9 and HP1/7). Table 13 shows that binding of freshly isolated human lymphocytes and monocytes, as well as freshly isolated rat and mouse lymphocytes to the inflamed EAE vessels was also selectively inhibited by antibodies against VLA-4. The assay was performed as described above and the degree of binding was quantified using a reference population of cells.

TABLE 12

| Treatment of U397 Cells | Vessels Clone | Relative Binding to EAE (% of control) |
|---|---|---|
| Anti-$\beta_1$ integrin | AIIB2 | 8 ± 3 |
| Anti-$\alpha_3$ integrin | A043 | 111 ± 5 |
| Anti-$\alpha_4$ integrin | HP2/1 (inhibits FN and VCAM-1 binding) | 3 ± 1 |
| Anti-$\alpha_4$ integrin | P4G9 (selectively inhibits FN binding) | 151 ± 7 |
| Anti-$\alpha_4$ integrin | HP1/7 (selectively inhibits FN binding) | 338 ± 41 |
| Anti-$\alpha_5$ integrin | F1D6 | 104 ± 6 |
| Anti-$\alpha_6$ integrin | GoH3 | 88 ± 11 |
| Anti-$\alpha_4$ and -$\alpha_5$ | F4G9 and P106 (cpmbined) | 138 ± 8 |
| Anti-$\alpha_3$, -$\alpha_4$, and -$\alpha_6$ | A043, P1D5, and GoH3 (combined) | 112 ± 3 |
| Anti-CD44 | Homos-3 | 107 ± 4 |
| Anti-L-selection | TQ-1 | 96 ± 4 |
| Anti-$\beta_2$ integrin | P4H9 | 77 ± 1 |
| Anti-$\beta_2$ integrin | TS1/18 | 98 ± 5 |
| Anti-$\beta_2$ integrin | P4H9 (tested at 25° C.) | 100 ± 10 |

TABLE 12-continued

| Treatment of U397 Cells | Vessels Clone | Relative Binding to EAE (% of control) |
|---|---|---|
| Anti-$\beta_2$ integrin | TS1/18 (tested at 25° C.) | 114 ± 2 |
| Anti-$\alpha_4$ integrin | HP2/1 (tested at 25° C.) | 5 ± 1 |
| Anti-LFA-1 | IOT1G | 123 ± 2 |
| Anti-Mac-1 | LM2/1 | 107 ± 3 |

TABLE 13

Treatment of freshly isolated leukocytes or monocytes

| Antibody Specificity | Clone | Cell Type | Relative Binding to EAE Vessels (% of Control) |
|---|---|---|---|
| Anti-$\beta_1$ integrin | AIIB2 | human lymphocytes | 7 ± 2 |
| Anti-$\alpha_4$ integrin | HP2/1 | human lymphocytes | 0 ± 0 |
| Anti-$\alpha_4$ integrin | HP2/1 | human lymphocytes | 1 ± 1 |
| Anti-$\alpha_4$ integrin | HP2/1 | rat lymphocytes | 18 ± 7 |
| Anti-$\alpha_4$ integrin | R1-2 | mouse lymphocytes | 43 ± 2 |
| Anti-CD2 | OX-34 | rat lymphocytes | 100 ± 10 |
| Anti-L-selectin | MEL-14 | mouse lymphocytes | 92 ± 4 |
| Peyer's patch homing receptor | 18.2.6 | rat lymphocytes | 117 ± 12 |
| Anti-LFA-1 | OX-52 | rat lymphocytes | 87 ± 1 |
| Anti-CD45 | OX-1 | rat lymphocytes | 90 ± 3 |
| Anti-Thy 1.1 | OX-7 | rat lymphocytes | 87 ± 3 |
| Anti-CD4 | OX-35 | rat lymphocytes | 107 ± 8 |
| Anti-monocyte/T cell surface | OX-44 | rat lymphocytes | 102 ± 8 |

B. Effect of In Vivo Administration of Anti-VLA-4 Antibody. Anti-VLA-4 was administered to rats (intraperitoneal administration) in order to determine the effect of the antibody on the progression of EAE. For Table 14 below, in each experiment, the T-cell clone was administered on day 0. On day 2, animals received an intraperitoneal injection of PBS, the indicated amount of purified anti-$\alpha_4$ integrin, or the indicated amount of purified control antibody. All antibodies were mouse IgG$_1$. Disease was defined by complete tail or tail and hind limb paralysis. In animals that developed disease, paralysis began on day 4 or 5, peaked on day 5 or 6, and steadily diminished thereafter. Two additional experiments gave comparable results. Circulating levels and differential counts of white blood cells were indistinguishable between HP2/1-treated and PBS control animals when measured on days 3, 4 and 7 (day 3 is one day after antibody administration and one day before the earliest onset of paralysis). Bulk quantities of HP2/1 were purchased from AMAC; MOPC from Sigma; OX-1 and OX-7 from Bioproducts for Science.

Brains were removed from several diseased EAE and healthy anti-$\alpha_4$ integrin-treated EAE rats from experiments 2 and 3 on day 6. There was extensive infiltration in brains from diseased EAE animals, whereas leukocytes could not be detected in the EAE rats treated with anti-$\alpha_4$ integrin.

TABLE 14

Experiment 1

| | Number of Animals with Paralysis | | |
|---|---|---|---|
| Treatment | Day 5 | Day 6 | Day 7 |
| No Antibody | 4/5 | 5/6 | 4/6 |
| HP2/1 (1.2 mg) | 0/6 | 0/6 | 0/6 |
| MOPC (1.2 mg) | 6/6 | 6/6 | 5/6 |

| | Number of Animals with Paralysis | | |
|---|---|---|---|
| Treatment | Day 4 | Day 5 | Day 6 |
| Experiment 2 | | | |
| No Antibody | 4/5 | 5/6 | 5/5 |
| HP2/1 (1.0 mg) | 0/6 | 0/6 | 2/4 |
| OX-1 (1.0 mg) | 5/5 | 5/5 | 5/5 |
| OX-7 (1.0 mg) | 5/6 | 5/5 | 5/5 |
| Experiment 3 | | | |
| No Antibody | 6/6 | 6/6 | 6/6 |
| HP2/1 (1.0 mg) | 1/1 | 2/5 | 2/5 |
| OX-1 (1.0 mg) | 1/5 | 2/5 | 1/5 |
| OX-7 (1.0 mg) | 0/6 | 0/6 | 2/6 |

EXAMPLE 5

Production of Additional VLA-4 Antibodies

Immunization and Screening Protocol. TY21.6 and 21.12 were raised against the human B cell line, Ramos (obtained from the ATCC). $10^7$ Ramos cells, homogenized in Freund's complete adjuvant, were injected into a Balb/c mouse (intraperitoneal administration). Fourteen days later, the animal was boosted with another $10^7$ Ramos cells (homogenized in Freund's incomplete adjuvant, administered i.p.). After an additional 14 days, the animal was injected with $2\times10^6$ living Ramos cells (intravenous administration). Three days after the final boost, the spleen was removed, the splenocytes were isolated, fused with the SP/2 myeloma, and plated on approximately 2,000 wells. Supernatants were screened for their ability to inhibit the human B cell line Ramos binding to VCAM-1 transfected L-cells. VCAM-1 transfected L cells were produced using standard techniques: VCAM-1 cDNA was isolated by PCR; primers were synthesized based on the published sequence and template RNA was isolated from TNF-stimulated human umbilical vein endothelial cells (HUVEC). The isolated cDNA was transfected into mouse L cells and clones expressing high levels of VCAM-1 message were isolated. For adhesion assays, VCAM-1 L cells were plated on 96 well plates and allowed to reach confluency. U937 cells were fluorescently labeled with PKH26 (Zynaxis Cell Science, Inc., Malvern, Pa.), pretreated with hybridoma supernatants for 30 minutes on ice (200,000 cells/sample), and added to individual VCAM-1 wells. Adhesion was allowed to occur for 30 minutes at room temperature, the wells were then washed to remove unbound cells, and the remaining cells were lysed with 40 µl of 0.1% Triton. 20 µl of the extract was analyzed on a Pandex plate reader to determine the degree of fluorescence (i.e., the number of cells bound). The degree of binding was determined by the percent of fluorescence relative to the fluorescence associated with the total number of input cells/well (i.e., 200,000 U937 cells). Two individual hybridomas were identified as potent blockers of Ramos binding to VCAM-1 and were stabilized as clones. The antibodies were designated as TY21.6 and TY21.12.

It was determined that both antibodies react with $\alpha_4$ integrin since the antibodies precipitated two protein bands from a lysate of cell surface-labeled human lymphocytes. These proteins were 150 and 130 kD in molecular weight, which corresponds to the known molecular weights of the $\alpha_4$ and $\beta_1$ integrin chains, respectively. Identical bands were precipitated in a parallel sample by a commercially available, well-characterized antibody against human $\alpha_4$ integrin (HP2/1 antibody). No other protein bands were detected. These results suggest that 21.6 and 21.12 react with the $\alpha_4\beta_1$ integrin complex.

The TY21.6 and 21.12 antibodies were further characterized by FACS analysis, using standard methods for staining cells by indirect immunofluorescence. Both antibodies react with the human B cell line, JY (which expresses $\alpha_4$ integrin, but only low levels of $\beta_1$). Both antibodies fail to react with human K562 cells or with human neutrophils (which express $\beta_1$ but very low levels of $\alpha_4$ integrin). Finally, both antibodies react with mouse L cells transfected with human $\alpha_4\beta_1$ integrin (produced as described above for VCAM-1 transfected L cells, using the human T cell line Jurkat for template RNA), but not with control transfected L cells. An identical pattern of reactivity was obtained with HP2/1, whereas a well-characterized antibody against $\beta_1$ integrin (AIIB2) did not react with JY, but did react with K562 and neutrophils. Thus, TY21.6 and TY21.12 selectively react with $\alpha_4$ integrin.

B. Functional Characterization of TY21.6, TY21.12 and L25. All three antibodies, TY21.6, TY21.12 and L-25 (Clayberger et al., *J. Immunol.* 138: 1510-1514 (1987)); effectively inhibit human lymphocyte binding to TNF-stimulated rat brain EC. Primary rat brain EC, or rat brain EC clones (described above) were plated on 96 well tissue culture plates. EC in some of the wells were stimulated with TNF (as described above) for 4-24 hours. Jurkat, U937, or Ramos cells were fluorescently labeled (as described above), pretreated with the indicated antibody, and then added to individual wells (200,000 cells/well; triplicate wells/antibody treatment). The degree of binding was determined as described above for the VCAM-1 96-well binding assay. The results are summarized in Table 15.

TABLE 15

| Experiment 1 | | | Experiment 2 | | | |
| --- | --- | --- | --- | --- | --- | --- |
| 1° Rat Brain EC | U937 | % input cells bound | Clone RBEC | Antibody | % Input Binding Jurkat | % Input Binding Ramos |
| 0 | no Ab | 7 ± 1 | 0 | no Ab | 3 ± 1 | 2 ± 1 |
| TNFα | no Ab | 36 ± 5 | TNFα | no Ab | 66 ± 3 | 40 ± 1 |
| TNFα | HP2/1 | 13 ± 2 | TNFα | HP2/1 | 6 ± 1 | 2 ± 1 |
| TNFα | 21.6 | 7 ± 1 | TNFα | TY21.6 | 8 ± 2 | 1 ± 1 |
| TNFα | 21.12 | 5 ± 2 | TNFα | TY21.12 | 8 ± 1 | 1 ± 0 |
| | | | TNFα | L25 | 12 ± 3 | 2 ± 1 |

All three antibodies were also found to inhibit human lymphocyte binding to VCAM-1 transfected L cells (assay as described above) as shown in Table 16.

TABLE 16

| Antibody | % Input Binding Ramos | % Input Binding U937 |
| --- | --- | --- |
| none | 45 ± 13 | 60 ± 6 |
| HP2/1 | 0 ± 0 | 3 ± 2 |
| L25 | 9 ± 2 | 11 ± 2 |
| TY21.6 | 1 ± 1 | 0 ± 1 |
| TY21.12 | 0 ± 0 | 1 ± 0 |

As shown in Table 17, all three antibodies inhibit cell binding to inflamed vessels in sections of EAE brain (assay performed as described above).

TABLE 17

| U937 Treatment | Binding |
| --- | --- |
| no antibody | 100 ± 10 |
| TY21.6 | 0 ± 1 |
| TY21.12 | 0 ± 1 |
| L25 | 1 ± 1 |
| HP2/1 | 3 ± 1 |

Some antibodies against $\alpha_4$ integrin (such as HP2/4; Pulido et al., *J. Biol. Chem.* 266: 10241-10245 (1991)) induce lymphocytes to self-aggregate. The basis of this aggregation is poorly understood. In the same report, L25 was reported to induce lymphocyte aggregation. However, we have not been able to reproduce those observations. In our hands, L25, TY21.6 and 21.12 do not induce cell aggregation when directly compared with HP2/4. Aggregation was induced by mixing 100,000 U937 cells with antibody supernatant (final dilution 1:5) in wells of a 96 well tissue culture plate (100 μl final volume/well). Aggregation was allowed to occur for 30 minutes to 4 hours, and scored visually with an arbitrary +/- rating system, compared to the no-antibody control. The results are shown in Table 18.

TABLE 18

| Inducing Antibody | Degree of U937 Aggregation |
| --- | --- |
| none | − |
| HP2/1 | − |
| L25 | − |
| TY21.6 | − |
| TY21.12 | − |
| HP2/4 | +++ |

Some antibodies against $\alpha_4$ integrin inhibit aggregation induced by the anti-$\alpha_4$ integrin antibody HP2/4. HP2/1, TY21.6 and TY21.12 block HP2/4 induced cell aggregation, whereas L25 does not. This assay was performed as above, except that the U937 cells were pretreated with the blocking antibodies (supernatant diluted 1:5 or purified antibody at 5 μg/mL) for 30 minutes on ice before addition of the aggregation-inducing antibody, HP2/4 (final concentration of HP2/4-hybridoma supernatant was 1:20).

TABLE 19

| Pretreatment of U937 | Degree of Aggregation Induced by HP2/4 |
| --- | --- |
| None | +++ |
| HP2/1 | − |
| L25 | +++ |
| TY21.6 | − |
| TY21.12 | +/− |

In addition to VCAM-1, $\alpha_4\beta_1$ integrin mediates cell binding to the CS-1 domain of FN. Some antibodies against $\alpha_4$ integrin inhibit FN binding, as is the case for L25, TY21.6 and TY21.12; all three antibodies were as effective as HP2/1. This assay was performed as described in Pulido et al., (1991) supra. The results are summarized in Table 20.

TABLE 20

| Plate Coating | BSA | FN | FN | FN | FN | FN |
|---|---|---|---|---|---|---|
| Jurkat Treatment | None | None | HP2/1 | 21.6 | 21.12 | L25 |
| % input bound (% inhibition) | 2 ± 1 | 77 ± 6 | 42 ± 7 (47) | 43 ± 6 (45) | 34 ± 2 (55) | 21 ± 1 (60) |

This application claims benefit of U.S. Provisional Application Nos. 60/442,713 and 60/500,316 filed on Jan. 24, 2003 and Sep. 5, 2003 respectively. The entire contents of the aforementioned applications and all references, issued patents, and published patent applications cited therein are incorporated herein by reference.

REFERENCES

The following publications, patents and patent applications are cited in this application as superscript numbers:

[1] Hemler and Takada, European Patent Application Publication No. 330,506, published Aug. 30, 1989
[2] Elices, et al., *Cell*, 60:577-584 (1990)
[3] Springer, *Nature*, 346:425-434 (1990)
[4] Osborn, *Cell*, 62:3-6 (1990)
[5] Vedder, et al., *Surgery*, 106:509 (1989)
[6] Pretolani, et al., *J. Exp. Med.*, 180:795 (1994)
[7] Abraham, et al., *J. Clin. Invest.*, 93:776 (1994)
[8] Mulligan, et al., *J. Immunology*, 150:2407 (1993)
[9] Cybulsky, et al., *Science*, 251:788 (1991)
[10] Li, et al., *Arterioscler. Thromb.*, 13:197 (1993)
[11] Sasseville, et al., *Am. J. Path.*, 144:27 (1994)
[12] Yang, et al., *Proc. Nat. Acad. Science (USA)*, 90:10494 (1993)
[13] Burkly, et al., *Diabetes*, 43:529 (1994)
[14] Baron, et al., *J. Clin. Invest.*, 93:1700 (1994)
[15] Hamann, et al., *J. Immunology*, 152:3238 (1994)
[16] Yednock, et al., *Nature*, 356:63 (1992)
[17] Baron, et al., *J. Exp. Med.*, 177:57 (1993)
[18] van Dinther-Janssen, et al., *J. Immunology*, 147:4207 (1991)
[19] van Dinther-Janssen, et al., *Annals. Rheumatic Dis.*, 52:672 (1993)
[20] Elices, et al., *J. Clin. Invest.*, 93:405 (1994)
[21] Postigo, et al., *J. Clin. Invest.*, 89:1445 (1991)
[22] Paul, et al., *Transpl. Proceed.*, 25:813 (1993)
[23] Okarhara, et al., *Can. Res.*, 54:3233 (1994)
[24] Paavonen, et al., *Int. J. Can.*, 58:298 (1994)
[25] Schadendorf, et al., *J. Path.*, 170:429 (1993)
[26] Bao, et al., *Diff.*, 52:239 (1993)
[27] Lauri, et al., *British J. Cancer*, 68:862 (1993)
[28] Kawaguchi, et al., *Japanese J. Cancer Res.*, 83:1304 (1992)
[29] Kogan, et al., U.S. Pat. No. 5,510,332, issued Apr. 23, 1996
[30] International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

What is claimed is:

1. A method of promoting remyelination of nerve cells in a mammal comprising administering to the mammal in need thereof a compound in a remyelinating effective amount, wherein the compound is of formula 1 below:

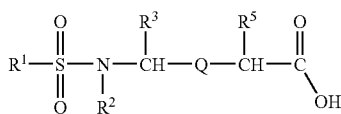

I wherein
$R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;
$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;
$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;
$R^5$ is $—(CH_2)_x—Ar—R^{5'}$ where $R^{5'}$ is selected from the group consisting of $—O—Z—NR^8R^{8'}$ and $—O—Z—R^{8''}$ wherein $R^8$ and $R^{8'}$ are independently selected from the group consisting of hydrogen, alkyl, substituted alkyl, cycloalkyl, substituted cycloalkyl, heterocyclic, and substituted heterocyclic, or $R^8$ and $R^{8'}$ are joined to form a heterocycle or a substituted heterocycle, $R^{8''}$ is selected from the group consisting of heterocycle and substituted heterocycle, and Z is selected from the group consisting of $—C(O)—$ and $—SO_2—$;
Ar is aryl, heteroaryl, substituted aryl or substituted heteroaryl;
x is an integer of from 1 to 4; and
Q is $—C(X)NR^7—$ wherein $R^7$ is selected from the group consisting of hydrogen and alkyl; and X is selected from the group consisting of oxygen and sulfur;
and pharmaceutically acceptable salts thereof.

2. A method of promoting remyelination of nerve cells in a mammal comprising administering to the mammal in need thereof a compound in a remyelinating effective amount, wherein the compound is of formula IA below:

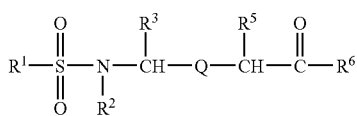

IA wherein:
$R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;
$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;
$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;
$R^5$ is $—(CH_2)_x—Ar—R^{5'}$ where $R^{5'}$ is selected from the group consisting of $—O—Z—NR^8R^{8'}$ and $—O—Z—R^{8''}$ wherein $R^8$ and $R^{8'}$ are independently selected from the group consisting of hydrogen, alkyl, substituted alkyl, cycloalkyl, substituted cycloalkyl, heterocyclic, and substituted heterocyclic, or $R^8$ and $R^{8'}$ are joined to form a heterocycle or a substituted heterocycle, $R^{8''}$ is selected from the group consisting of heterocycle and substituted heterocycle, and Z is selected from the group consisting of $—C(O)—$ and $—SO_2—$;
Ar is aryl, heteroaryl, substituted aryl or substituted heteroaryl;
x is an integer of from 1 to 4;
$R^6$ is selected from the group consisting of 2,4-dioxotetrahydrofuran-3-yl (3,4-enol), amino, alkoxy, substituted alkoxy, cycloalkoxy, substituted cycloalkoxy, $—O—(N$-succinimidyl$)$, $—NH$-adamantyl, $—O$-cholest-5-en-3-β-yl, $—NHOY$ where Y is hydrogen, alkyl, substituted alkyl, aryl, and substituted aryl, $—NH(CH_2)_pCOOY$ where p is an integer of from 1 to 8 and Y is as defined above, $—OCH_2NR^9R^{10}$ where $R^9$ is selected from the group consisting of $—C(O)$-aryl and $—C(O)$-substituted aryl and $R^{10}$ is selected from the group consisting of hydrogen and $—CH_2COOR^{11}$ where $R^{11}$ is alkyl, and $—NHSO_2Z'$ where $Z'$ is alkyl, substituted alkyl, cycloalkyl, substituted cycloalkyl, aryl, substituted aryl, heteroaryl, substituted heteroaryl, heterocyclic and substituted heterocyclic; and
Q is $—C(X)NR^7—$ wherein $R^7$ is selected from the group consisting of hydrogen and alkyl; and X is selected from the group consisting of oxygen and sulfur;
and pharmaceutically acceptable salts thereof
with the following provisos
(A) when $R^1$ and $R^2$ together with the $SO_2$ group pendent to $R^1$ and the nitrogen pendent to $R^2$ form a saccharin-2-yl group, $R^3$ is $—CH_3$, $R^5$ is p-$[(CH_3)_2NC(O)O—]$benzyl and Q is $—C(O)NH—$ then $R^6$ is not $—OC(CH_3)_3$;
(B) when $R^1$ is p-methylphenyl, $R^2$ and $R^3$ together with the nitrogen atom pendent to $R^2$ and the carbon atom pendent to $R^3$ form a pyrrolidinyl ring derived from D-proline; $R^5$ is p-$[(4$-methylpiperazin-1-yl$)NC(O)O—]$benzyl derived from D-phenylalanine and Q is $—C(O)NH—$ then $R^6$ is not $—OC(CH_3)_3$;
(C) when $R^1$ is pyrimidin-2-yl, $R^2$ and $R^3$ together with the nitrogen atom bound to $R^2$ and the carbon atom bound to $R^3$ form a pyrrolidinyl ring, $R^5$ is p-$[(CH_3)_2NC(O)O—]$benzyl and Q is $—C(O)NH—$ then $R^6$ is not $—OC(CH_3)_3$; and (D) when R¹ is p-methylphenyl, R² and R³ together with the nitrogen atom pendent to R² and the carbon atom pendent to R³ form a (2S)-piperazin-2-carbonyl ring; R⁵ is p-[(CH₃)₂NC(O)O—]benzyl and Q is —C(O)NH— then R⁶ is not —OC(CH₃)₃.

3. A method of promoting remyelination of nerve cells in a mammal comprising administering to the mammal in need thereof a compound in a remyelinating effective amount, wherein the compound is of formula IB below:

IB

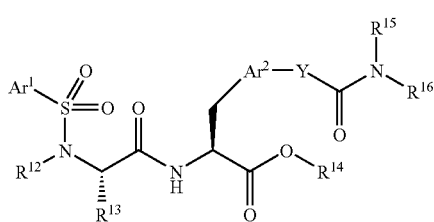

wherein:
Ar¹ is selected from the group consisting of aryl, substituted aryl, heteroaryl, and substituted heteroaryl;
Ar² is selected from the group consisting of aryl, substituted aryl, heteroaryl and substituted heteroaryl;
R¹² is selected from the group consisting of alkyl, substituted alkyl, cycloalkyl, and substituted cycloalkyl or R¹² and R¹³ together with the nitrogen atom bound to R¹² and the carbon atom bound to R¹³ form a heterocyclic or substituted heterocyclic group;
R¹³ is selected from the group consisting of hydrogen, alkyl, and substituted alkyl, or R¹² and R¹³ together with the nitrogen atom bound to R¹² and the carbon atom bound to R¹³ form a heterocyclic or substituted heterocyclic group;
R¹⁴ is selected from the group consisting of hydrogen, alkyl, substituted alkyl, cycloalkyl, substituted cycloalkyl, aryl, and substituted aryl;
R¹⁵ is selected from the group consisting of alkyl, and substituted alkyl, or R¹⁵ and R¹⁶ together with the nitrogen atom to which they are bound form a heterocyclic or substituted heterocyclic group;
R¹⁶ is selected from the group consisting of alkyl and substituted alkyl or R¹⁵ and R¹⁶ together with the nitrogen atom to which they are bound form a heterocyclic or substituted heterocyclic group; and
Y is selected from the group consisting of —O—, —NR¹⁰⁰—, and —CH₂— wherein R¹⁰⁰ is hydrogen or alkyl;
and pharmaceutically acceptable salts thereof.

4. The method according to claim 3, wherein R¹² is alkyl, substituted alkyl, or R¹² and R¹³ together with the nitrogen atom bound to R¹² and the carbon atom bound to R¹³ form a heterocyclic or substituted heterocyclic group; and R¹⁴ is hydrogen or alkyl.

5. The method according to claim 3, wherein Ar¹ is selected from the group consisting of phenyl, 4-methylphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl) phenyl, 4-(H₂NC(O)—)phenyl, 4-(H₂NC(S)—)phenyl, 4-cyanophenyl, 4-trifluoromethylphenyl, 4-trifluoromethoxyphenyl, 3,5-di-(trifluoromethyl)phenyl, 4-nitrophenyl, 4-aminophenyl, 4-(CH₃C(O)NH—)phenyl, 4-(PhNHC(O)NH—)phenyl, 4-amidinophenyl, 4-methylamidinophenyl, 4-[CH₃SC(=NH)—]phenyl, 4-chloro-3-[H₂NS(O)₂—]phenyl, 1-naphthyl, 2-naphthyl, pyridin-2-yl, pyridin-3-yl, pyridine-4-yl, pyrimidin-2-yl, quinolin-8-yl, 2-(trifluoroacetyl)-1,2,3,4-tetrahydroisoquinolin-7-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

6. The method according to claim 3, wherein R¹² and R¹³ together with the nitrogen atom bound to R¹² and the carbon atom bound to R¹³ form a heterocyclic or substituted heterocyclic of the formula:

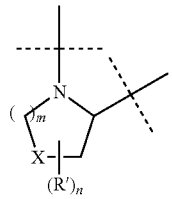

wherein
X is selected from the group consisting of —S—, —SO—, —SO₂—, and optionally substituted —CH₂—;
m is an integer of 0 to 12;
n is an integer of 0 to 2; and
R' is selected from the group consisting of alkyl, substituted alkyl, and amino.

7. The method according to claim 6, wherein m is 1, X is —S— or —CH₂—, R' is alkyl or substituted alkyl.

8. The method according to claim 3, wherein R¹² and R¹³ together with the nitrogen atom bound to R¹² and the carbon atom bound to R¹³ form a heterocyclic or substituted heterocyclic selected from the group consisting of azetidinyl, thiazolidinyl, piperidinyl, piperazinyl, thiomorpholinyl, pyrrolidinyl, 4-hydroxypyrrolidinyl, 4-oxopyrrolidinyl, 4-fluoropyrrolidinyl, 4,4-difluoropyrrolidinyl, 4-(thiomorpholin-4-ylC(O)O—)pyrrolidinyl, 4-[CH₃S(O)₂O—]pyrrolidinyl, 3-phenylpyrrolidinyl, 3-thiophenylpyrrolidinyl, 4-aminopyrrolidinyl, 3-methoxypyrrolidinyl, 4,4-dimethylpyrrolidinyl, 4-N-Cbz-piperazinyl, 4-[CH₃S(O)₂—]piperazinyl, thiazolidin-3-yl, 5,5-dimethyl-thiazolidin-3-yl, 5,5-dimethylthiazolindin-4-yl, 1,1-dioxo-thiazolidinyl, 1,1-dioxo-5,5-dimethylthiazolidin-2-yl and 1,1-dioxothiomorpholinyl.

9. The method according to claim 3, wherein Ar² is selected from the group consisting of phenyl, 2-pyridyl, 3-pyridyl, 4-pyridyl, and 4-pyrid-2-onyl.

10. The method according to claim 3, wherein Y is —O—, and when Y is —O—, the moiety —OC(O)NR¹⁵R¹⁶ is selected from the group consisting of (CH₃)₂NC(O)O—, (piperidin-1-yl)C(O)O—, (4-hydroxypiperidin-1-yl)C(O)O—, (4-formyloxypiperidin-1-yl)C(O)O—, (4-ethoxycarbonylpiperidin-1-yl)C(O)O—, (4-carboxylpiperidin-1-yl)C(O)O—, (3-hydroxymethylpiperidin-1-yl)C(O)O—, (4-hydroxymethylpiperidin-1-yl)C(O)O—, (4-piperidon-1-yl ethylene ketal)C(O)O—, (piperazin-1-yl)-C(O)O—, (1-Boc-piperazin-4-yl)C(O)O—, (4-methylpiperazin-1-yl)C(O)O—, (4-methylhomopiperazin-1-yl)C(O)O—, (4-(2-hydroxyethyl)piperazin-1-yl)C(O)O—, (4-phenylpiperazin-1-yl)C(O)O—, (4-(pyridin-2-yl)piperazin-1]-yl)C(O)O—, (4-(4-trifluoromethylpyridin-2-yl)piperazin-1-yl)C(O)O—, (4-(pyrimidin-2-yl)piperazin-1-yl)C(O)O—, (4-acetylpiperazin-1-yl)C(O)O—, (4-(phenylC(O)—)piperazin-1-yl)C(O)O—, (4-(pyridin-4'-ylC(O)—)piperazin-1-yl)C(O)O, (4-(phenylNHC(O)—)piperazin-1-yl)C(O)O—, (4-(phenylNHC(S)—)piperazin-1-yl)C(O)O—, (4-methanesulfonylpiperazin-1-yl-C(O)O—, (4-trifluoromethanesulfonylpiperazin-1-yl-C(O)O—, (morpholin-4-yl)C(O)O—, (thiomorpholin-4-yl)C(O)O—, (thiomorpholin-4'-yl sulfone)-C(O)O—, (pyrrolidin-1-yl)C(O)O—, (2-methylpyrrolidin-1-yl)C(O)O—, (2-(methoxycarbonyl)pyrrolidin-1-yl)C(O)O—, (2-(hydroxymethyl)pyrrolidin-1-yl)C(O)O—, (2-(N,N-dimethylamino)ethyl)(CH$_3$)NC(O)O—, (2-(N-methyl-N-toluene-4-sulfonylamino)ethyl)(CH$_3$)N—C(O)O—, (2-(morpholin-4-yl)ethyl)(CH$_3$)NC(O)O—, (2-(hydroxy)ethyl)(CH$_3$)NC(O)O—, bis(2-(hydroxy)ethyl)NC(O)O—, (2-(formyloxy)ethyl)(CH$_3$)NC(O)O—, (CH$_3$OC(O)CH$_2$)HNC(O)O—, and 2-[(phenylNHC(O)O—)ethyl-]HNC(O)O—.

11. A method of promoting remyelination of nerve cells in a mammal comprising administering to the mammal in need thereof a compound in a remyelinating effective amount, wherein the compound is of formula IC below:

IC

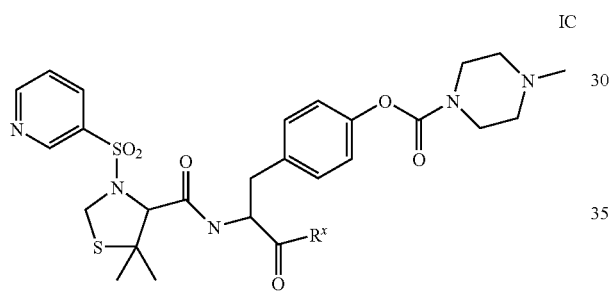

wherein $R^x$ is hydroxy or $C_{1-5}$ alkoxy; and pharmaceutically acceptable salts thereof.

12. A method of promoting remyelination of nerve cells in a mammal comprising administering to the mammal in need thereof a compound in a remyelinating effective amount, wherein the compound is selected from the group consisting of:

N-(toluene-4-sulfonyl)-L-prolyl-L-4-(4-methylpiperazin-1-ylcarbonyloxy)phenylalanine ethyl ester,
N-(toluene-4-sulfonyl)-L-prolyl-L-4-(N,N-dimethylcarbamyloxy)phenylalanine ethyl ester,
N-(toluene-4-sulfonyl)-L-prolyl-L-4-(4-methylpiperazin-1-ylcarbonyloxy)phenylalanine isopropyl ester,
N-(toluene-4-sulfonyl)-L-prolyl-L-4-(4-methylpiperazin-1-ylcarbonyloxy)phenylalanine n-butyl ester,
N-(toluene-4-sulfonyl)-L-prolyl-L-4-(4-methylpiperazin-1-ylcarbonyloxy)phenylalanine cyclopentyl ester,
N-(toluene-4-sulfonyl)-L-prolyl-L-4-(4-methylpiperazin-1-ylcarbonyloxy)phenylalanine tert-butyl ester,
N-(toluene-4-sulfonyl)-L-prolyl-L-4-(4-methylpiperazin-1-ylcarbonyloxy)phenylalanine,
N-(toluene-4-sulfonyl)-L-prolyl-L-4-(N,N-dimethylcarbamyloxy)phenylalanine isopropyl ester,
N-(toluene-4-sulfonyl)-L-prolyl-L-4-(N,N-dimethylcarbamyloxy)phenylalanine n-butyl ester,
N-(toluene-4-sulfonyl)-L-prolyl-L-4-(N,N-dimethylcarbamyloxy)phenylalanine cyclopentyl ester,
N-(toluene-4-sulfonyl)-L-prolyl-L-4-(N,N-dimethylcarbamyloxy)phenylalanine tert-butyl ester,
N-(toluene-4-sulfonyl)-L-prolyl-L-4-(N,N-dimethylcarbamyloxy)phenylalanine,
N-(toluene-4-sulfonyl)-L-prolyl-L-4-(isonipecotoyloxy)phenylalanine ethyl ester,
N-(α-toluenesulfonyl)-L-prolyl-L-4-(N-methylisonipecotoyloxy)phenylalanine ethyl ester,
N-(α-toluenesulfonyl)-L-prolyl-L-4-(4-methylpiperazin-1-ylcarbonyloxy)phenylalanine,
N-(toluene-4-sulfonyl)-L-prolyl-L-3-(N,N-dimethylcarbamyloxy)phenylalanine ethyl ester,
N-(toluene-4-sulfonyl)-L-prolyl-L-4-(1-tert-butylcarbonyloxy-4-phenylpiperidin-4-ylcarbonyloxy)phenylalanine ethyl ester,
N-(toluene-4-sulfonyl)-L-(5,5-dimethyl)thiaprolyl-L-4-(N,N-dimethylcarbamyloxy)phenylalanine isopropyl ester,
N-(toluene-4-sulfonyl)-L-(5,5-dimethyl)thiaprolyl-L-4-(N,N-dimethylcarbamyloxy)phenylalanine tert-butyl ester,
N-(toluene-4-sulfonyl)-L-(5,5-dimethyl)thiaprolyl-L-4-(N,N-dimethylcarbamyloxy)phenylalanine,
N-(toluene-4-sulfonyl)-L-[(1,1-dioxo)thiamorpholin-3-carbonyl]-L-4-(N,N-dimethylcarbamyloxy)phenylalanine tert-butyl ester,
N-(toluene-4-sulfonyl)-L-[(1,1-dioxo)thiamorpholin-3-carbonyl]-L-4-(N,N-dimethylcarbamyloxy)phenylalanine,
N-(toluene-4-sulfonyl)-L-(5,5-dimethyl)thiaprolyl-L-4-(4-methylpiperazin-1-ylcarbonyloxy)phenylalanine tert-butyl ester,
N-(toluene-4-sulfonyl)-L-(5,5-dimethyl)thiaprolyl-L-4-(4-methylpiperazin-1-ylcarbonyloxy)phenylalanine,
N-(toluene-4-sulfonyl)sarcosyl-L-4-(N,N-dimethylcarbamyloxy)phenylalanine isopropyl ester,
N-(toluene-4-sulfonyl)sarcosyl-L-4-(N,N-dimethylcarbamyloxy)phenylalanine tert-butyl ester,
N-(toluene-4-sulfonyl)sarcosyl-L-4-(N,N-dimethylcarbamyloxy)phenylalanine,
N-(1-methylimidazole-4-sulfonyl)-L-prolyl-L-4-(N,N-dimethylcarbamyloxy)phenylalanine tert-butyl ester,
N-(4-aminobenzenesulfonyl)-L-prolyl-L-4-(N,N-dimethylcarbamyloxy)phenylalanine tert-butyl ester,
N-(toluene-4-sulfonyl)sarcosyl-L-4-(morpholin-4-ylcarbonyloxy)phenylalanine tert-butyl ester,
N-(toluene-4-sulfonyl)-L-prolyl-L-4-(morpholin-4-ylcarbonyloxy)phenylalanine tert-butyl ester,
N-(α-toluenesulfonyl)-L-(5,5-dimethyl)thiaprolyl-L-4-(N,N-dimethylcarbamyloxy)phenylalanine,
N-(toluene-4-sulfonyl)-L-(piperazin-2-carbonyl)-L-4-(N,N-dimethylcarbamyloxy)phenylalanine,
N-(α-toluenesulfonyl)-L-(5,5-dimethyl)thiaprolyl-L-4-(N,N-dimethylcarbamyloxy)phenylalanine tert-butyl ester,
N-(toluene-4-sulfonyl)-L-(piperazin-2-carbonyl)-L-4-(N,N-dimethylcarbamyloxy)phenylalanine tert-butyl ester,
N-(toluene-4-sulfonyl)-L-(4-benzyloxycarbonylpiperazin-2-carbonyl)-L-4-(N,N-dimethylcarbamyloxy)phenylalanine tert-butyl ester,
N-(toluene-4-sulfonyl)sarcosyl-L-4-(isonipecotoyloxy)phenylalanine,
N-(toluene-4-sulfonyl)-L-[(1,1-dioxo)thiamorpholin-3-carbonyl]-L-4-(morpholin-4-ylcarbonyloxy)phenylalanine tert-butyl ester, N-(toluene-4-sulfonyl)-L-[(1,1-dioxo)thiamorpholin-3-carbonyl]-L-4-(morpholin-4-ylcarbonyloxy)phenylalanine,
N-(1-methylpyrazole-4-sulfonyl)-L-prolyl-L-4-(N,N-dimethylcarbamyloxy)phenylalanine tert-butyl ester,
N-(4-fluorobenzenesulfonyl)-L-prolyl-L-4-(N,N-dimethylcarbamyloxy)phenylalanine tert-butyl ester,
N-(toluene-4-sulfonyl)sarcosyl-L-4-(4-methylpiperazin-1-ylcarbonyloxy)phenylalanine tert-butyl ester,
N-(toluene-4-sulfonyl)-L-(1,1-dioxo-5,5-dimethyl)thiaprolyl-L-4-(N,N-dimethylcarbamyloxy)phenylalanine tert-butyl ester,
N-(1-methylimidazole-4-sulfonyl)-L-prolyl-L-4-(N,N-dimethylcarbamyloxy)phenylalanine,
N-(toluene-4-sulfonyl)-L-(1,1-dioxo-5,5-dimethyl)thiaprolyl-L-4-(N,N-dimethylcarbamyloxy)phenylalanine,
N-(4-fluorobenzenesulfonyl)-L-prolyl-L-4-(N,N-dimethylcarbamyloxy)phenylalanine,
N-(pyridine-3-sulfonyl)-L-prolyl-L-4-(N,N-dimethylcarbamyloxy)phenylalanine,
N-(toluene-4-sulfonyl)-D-prolyl-L-4-(4-methylpiperazin-1-ylcarbonyloxy)phenylalanine tert-butyl ester,
N-(toluene-4-sulfonyl)-L-N-methylalanyl-L-4-(4-methylpiperazin-1-ylcarbonyloxy)phenylalanine tert-butyl ester,
N-(4-nitrobenzenesulfonyl)-L-prolyl-L-4-(N,N-dimethylcarbamyloxy)phenylalanine tert-butyl ester,
N-(toluene-4-sulfonyl)sarcosyl-L-4-(thiomorpholin-4-ylcarbonyloxy)phenylalanine tert-butyl ester,
N-(toluene-4-sulfonyl)-L-N-methylalanyl-L-4-(4-methylpiperazin-1-ylcarbonyloxy)phenylalanine,
N-(toluene-4-sulfonyl)-L-prolyl-L-4-(1,1-dioxothiomorpholin-4-ylcarbonyloxy)phenylalanine,
N-(toluene-4-sulfonyl)-L-prolyl-L-4-(thiomorpholin-4-ylcarbonyloxy)phenylalanine,
N-(toluene-4-sulfonyl)-L-prolyl-L-4-(isonipecotoyloxy)phenylalanine,
N-(toluene-4-sulfonyl)-L-prolyl-L-4-(pyrrolidin-1-ylcarbonyloxy)phenylalanine,
N-(toluene-4-sulfonyl)-L-prolyl-L-4-(morpholin-4-ylcarbonyloxy)phenylalanine,
N-(toluene-4-sulfonyl)-L-prolyl-L-4-(4-methylpiperazin-1-ylcarbonyloxy)phenylalanine neopentyl ester,
N-(toluene-4-sulfonyl)-L-prolyl-L-4-(N,N-dimethylcarbamyloxy)phenylalanine neopentyl ester,
N-(toluene-4-sulfonyl)-L-prolyl-L-4-(4-tert-butyloxycarbonylpiperazin-1-ylcarbonyloxy)phenylalanine ethyl ester,
N-(toluene-4-sulfonyl)-L-prolyl-L-4-(morpholin-4-ylcarbonyloxy)phenylalanine ethyl ester,
N-(toluene-4-sulfonyl)sarcosyl-L-4-(1,1-dioxothiomorpholin-4-ylcarbonyloxy)phenylalanine tert-butyl ester,
N-(toluene-4-sulfonyl)sarcosyl-L-4-(thiomorpholin-4-ylcarbonyloxy)phenylalanine,
N-(toluene-4-sulfonyl)-L-N-methylalanyl-L-4-(N,N-dimethylcarbamyloxy)phenylalanine tert-butyl ester,
N-(toluene-4-sulfonyl)-L-(thiamorpholin-3-carbonyl)-L-4-(N,N-dimethylcarbamyloxy)phenylalanine tert-butyl ester,
N-(toluene-4-sulfonyl)sarcosyl-L-4-(1,1-dioxothiomorpholin-4-ylcarbonyloxy)phenylalanine,
N-(toluene-4-sulfonyl)-L-(1,1-dioxothiamorpholin-3-carbonyl)-L-4-(N,N-dimethylcarbamyloxy)phenylalanine tert-butyl ester,
N-(toluene-4-sulfonyl)-L-(1,1-dioxothiamorpholin-3-carbonyl)-L-4-(morpholin-4-ylcarbonyloxy)phenylalanine tert-butyl ester,
N-(toluene-4-sulfonyl)-L-N-methylalanyl-L-4-(N,N-dimethylcarbamyloxy)phenylalanine,
N-(4-fluorobenzenesulfonyl)-L-(thiamorpholin-3-carbonyl)-L-4-(N,N-dimethylcarbamyloxy)phenylalanine tert-butyl ester,
N-(4-fluorobenzenesulfonyl)-L-(1,1-dioxothiamorpholin-3-carbonyl)-L-4-(N,N-dimethylcarbamyloxy)phenylalanine tert-butyl ester,
N-(pyridine-3-sulfonyl)-L-prolyl-L-4-(N,N-dimethylcarbamyloxy)phenylalanine tert-butyl ester,
N-(pyrimidine-2-sulfonyl)-L-prolyl-L-4-(N,N-dimethylcarbamyloxy)phenylalanine tert-butyl ester,
N-(4-nitrobenzenesulfonyl)-L-prolyl-L-4-(N,N-dimethylcarbamyloxy)phenylalanine,
N-(4-cyanobenzenesulfonyl)-L-prolyl-L-4-(N,N-dimethylcarbamyloxy)phenylalanine tert-butyl ester,
N-(toluene-4-sulfonyl)-L-(1,1-dioxothiamorpholin-3-carbonyl)-L-4-(N,N-dimethylcarbamyloxy)phenylalanine,
N-(toluene-4-sulfonyl)-L-(1,1-dioxo)thiaprolyl-L-4-(N,N-dimethylcarbamyloxy)phenylalanine tert-butyl ester,
N-(4-fluorobenzenesulfonyl)-L-prolyl-L-4-(N,N-dimethylcarbamyloxy)phenylalanine tert-butyl ester,
N-(1-methylpyrazole-4-sulfonyl)-L-prolyl-L-4-(N,N-dimethylcarbamyloxy)phenylalanine,
N-(toluene-4-sulfonyl)-L-(1,1-dioxo)thiaprolyl-L-4-(N,N-dimethylcarbamyloxy)phenylalanine,
N-(4-fluorobenzenesulfonyl)-L-thiaprolyl-L-4-(N,N-dimethylcarbamyloxy)phenylalanine,
N-(toluene-4-sulfonyl)-L-prolyl-L-4-(piperazin-1-ylcarbonyloxy)phenylalanine,
N-(toluene-4-sulfonyl)-L-prolyl-L-4-(1-tert-butyloxycarbonylpiperazin-1-ylcarbonyloxy)phenylalanine tert-butyl ester,
N-(toluene-4-sulfonyl)-L-prolyl-L-4-(piperazin-1-ylcarbonyloxy)phenylalanine ethyl ester,
N-(toluene-4-sulfonyl)-L-prolyl-L-4-(4-acetylpiperazin-1-ylcarbonyloxy)phenylalanine ethyl ester,
N-(toluene-4-sulfonyl)-L-prolyl-L-4-(4-methanesulfonylpiperazin-1-ylcarbonyloxy)phenylalanine ethyl ester,
N-(toluene-4-sulfonyl)-L-prolyl-L-4-(morpholin-4-ylcarbonyloxy)-3-nitrophenylalanine,
N-(toluene-4-sulfonyl)-L-prolyl-L-4-(1-tert-butyloxycarbonylpiperazin-1-ylcarbonyloxy)phenylalanine,
N-(toluene-4-sulfonyl)-L-N-methyl-2-(tert-butyl)glycinyl-L-4-(4-methylpiperazin-1-ylcarbonyloxy)phenylalanine tert-butyl ester,
N-(4-fluorobenzenesulfonyl)-L-(5,5-dimethyl)thiaprolyl-L-4-(N,N-dimethylcarbamyloxy)phenylalanine tert-butyl ester,
N-(4-fluorobenzenesulfonyl)-L-(1,1-dioxothiamorpholin-3-carbonyl)-L-4-(1,1-dioxothiomorpholin-4-ylcarbonyloxy)phenylalanine tert-butyl ester,
N-(toluene-4-sulfonyl)-L-(1,1-dioxothiamorpholin-3-carbonyl)-L-4-(1,1-dioxothiomorpholin-4-ylcarbonyloxy)phenylalanine tert-butyl ester,
N-(4-fluorobenzenesulfonyl)-L-prolyl-L-4-(1,1-dioxothiomorpholin-4-ylcarbonyloxy)phenylalanine tert-butyl ester,
N-(4-fluorobenzenesulfonyl)-L-prolyl-L-4-(thiomorpholin-4-ylcarbonyloxy)phenylalanine tert-butyl ester,
N-(4-fluorobenzenesulfonyl)-L-prolyl-L-4-(morpholin-4-ylcarbonyloxy)phenylalanine tert-butyl ester, N-(4-fluorobenzenesulfonyl)-L-(5,5-dimethyl)thiaprolyl-L-4-(N,N-dimethylcarbamyloxy)phenylalanine,
N-(4-fluorobenzenesulfonyl)-L-(1,1-dioxothiamorpholin-3-carbonyl)-L-4-(morpholin-4-ylcarbonyloxy)phenylalanine tert-butyl ester,
N-(4-trifluoromethoxybenzenesulfonyl)-L-prolyl-L-4-(N,N-dimethylcarbamyloxy)phenylalanine tert-butyl ester,
N-(toluene-4-sulfonyl)-L-(1,1-dioxothiamorpholin-3-carbonyl)-L-4-(N,N-dimethylcarbamyloxy)phenylalanine isopropyl ester,
3-[N-(toluene-4-sulfonyl)-N-methylamino]-1-[1-tert-butyloxycarbonyl-2-(N,N-dimethylcarbamyloxy)phenylethyl]azetidin-2-one,
N-(4-fluorobenzenesulfonyl)-L-(1,1-dioxo-5,5-dimethyl)thiaprolyl-L-4-(N,N-dimethylcarbamyloxy)phenylalanine tert-butyl ester,
N-(toluene-4-sulfonyl)-L-(1,1-dioxo-5,5-dimethyl)thiaprolyl-L-4-(N,N-dimethylcarbamyloxy)phenylalanine isopropyl ester,
N-(toluene-4-sulfonyl)-L-(1,1-dioxothiamorpholin-3-carbonyl)-L-4-(morpholin-4-ylcarbonyloxy)phenylalanine,
N-(4-fluorobenzenesulfonyl)-L-(5,5-dimethyl)thiaprolyl-L-4-(N,N-dimethylcarbamyloxy)phenylalanine,
N-(pyrimidine-2-sulfonyl)-L-prolyl-L-4-(N,N-dimethylcarbamyloxy)phenylalanine,
N-(toluene-4-sulfonyl)-L-(1,1-dioxothiamorpholin-3-carbonyl)-L-4-(4-methylpiperazin-1-ylcarbonyloxy)phenylalanine tert-butyl ester,
3-[N-(toluene-4-sulfonyl)-N-methylamino]-1-[1-carboxy-2-(N,N-dimethylcarbamyloxy)phenylethyl]azetidin-2-one,
N-(1-methylpyrazole-4-sulfonyl)-L-prolyl-L-4-(4-methylpiperazin-1-ylcarbonyloxy)phenylalanine tert-butyl ester,
N-(4-fluorobenzenesulfonyl)-L-(1,1-dioxo)thiaprolyl-L-4-(N,N-dimethylcarbamyloxy)phenylalanine,
N-(toluene-4-sulfonyl)-L-prolyl-L-4-(isonipecotoyloxy)phenylalanine tert-butyl ester,
N-(toluene-4-sulfonyl)-L-prolyl-L-4-(1,1-dioxothiomorpholin-4-ylcarbonyloxy)phenylalanine tert-butyl ester,
N-(toluene-4-sulfonyl)-L-prolyl-L-4-(thiomorpholin-4-ylcarbonyloxy)phenylalanine tert-butyl ester,
N-(toluene-4-sulfonyl)-L-prolyl-L-4-(pyrrolidin-1-ylcarbonyloxy)phenylalanine tert-butyl ester,
N-(4-fluorobenzenesulfonyl)-L-thiaprolyl-L-4-(N,N-dimethylcarbamyloxy)phenylalanine tert-butyl ester,
N-(4-fluorobenzenesulfonyl)-L-(1,1-dioxo)thiaprolyl-L-4-(N,N-dimethylcarbamyloxy)phenylalanine tert-butyl ester,
N-(2,5-dichlorothiophene-3-sulfonyl)-L-prolyl-L-4-(N,N-dimethylcarbamyloxy)phenylalanine tert-butyl ester,
N-(4-acetamidobenzenesulfonyl)-L-prolyl-L-4-(N,N-dimethylcarbamyloxy)phenylalanine tert-butyl ester,
N-(4-tert-butylbenzenesulfonyl)-L-(1,1-dioxothiamorpholin-3-carbonyl)-L-4-(N,N-dimethylcarbamyloxy)phenylalanine tert-butyl ester,
N-(pyridine-2-sulfonyl)-L-prolyl-L-4-(N,N-dimethylcarbamyloxy)phenylalanine,
N-(2-fluorobenzenesulfonyl)-L-(1,1-dioxothiamorpholin-3-carbonyl)-L-4-(N,N-dimethylcarbamyloxy)phenylalanine tert-butyl ester,
N-(3-fluorobenzenesulfonyl)-L-(1,1-dioxothiamorpholin-3-carbonyl)-L-4-(N,N-dimethylcarbamyloxy)phenylalanine tert-butyl ester,
N-(2,4-difluorobenzenesulfonyl)-L-(1,1-dioxothiamorpholin-3-carbonyl)-L-4-(N,N-dimethylcarbamyloxy)phenylalanine tert-butyl ester,
N-(4-acetamidobenzenesulfonyl)-L-prolyl-L-4-(N,N-dimethylcarbamyloxy)phenylalanine,
N-(4-trifluoromethoxybenzenesulfonyl)-L-prolyl-L-4-(N,N-dimethylcarbamyloxy)phenylalanine,
N-(4-fluorobenzenesulfonyl)-L-(5,5-dimethyl)thiaprolyl-L-4-(N,N-dimethylcarbamyloxy)phenylalanine tert-butyl ester,
N-(4-cyanobenzenesulfonyl)-L-prolyl-L-4-(N,N-dimethylcarbamyloxy)phenylalanine,
N-(toluene-4-sulfonyl)-L-(3,3-dimethyl)prolyl-L-4-(N,N-dimethylcarbamyloxy)phenylalanine tert-butyl ester,
N-(toluene-4-sulfonyl)-L-(3,3-dimethyl)prolyl-L-4-(N,N-dimethylcarbamyloxy)phenylalanine isopropyl ester,
N-(1-methylpyrazole-4-sulfonyl)-L-prolyl-L-4-(N,N-dimethylcarbamyloxy)phenylalanine iso-propyl ester,
N-(1-methylpyrazole-4-sulfonyl)-L-(5,5-dimethyl)thiaprolyl-L-4-(N,N-dimethylcarbamyloxy)phenylalanine tert-butyl ester,
N-(1-methylpyrazole-4-sulfonyl)-L-(5,5-dimethyl)thiaprolyl-L-4-(N,N-dimethylcarbamyloxy)phenylalanine,
N-(toluene-4-sulfonyl)-L-prolyl-L-4-(N-(1,4-dioxa-8-aza-spiro[4.5]decan-8-yl)carbonyloxy)phenylalanine ethyl ester,
N-(toluene-4-sulfonyl)-L-prolyl-L-4-(N-(1,4-dioxa-8-aza-spiro[4.5]decan-8-yl)carbonyloxy)phenylalanine,
N-(toluene-4-sulfonyl)-L-prolyl-L-4-(4N-acetylpiperazin-1-ylcarbonyloxy)phenylalanine,
N-(toluene-4-sulfonyl)-L-prolyl-L-4-(4N-methanesulfonylpiperazin-1-ylcarbonyloxy)phenylalanine,
N-(toluene-4-sulfonyl)-L-prolyl-L-4-(4N-phenylpiperazin-1-ylcarbonyloxy)phenylalanine,
N-(toluene-4-sulfonyl)-L-prolyl-L-4-(piperazin-1-ylcarbonyloxy)phenylalanine tert-butyl ester,
N-(toluene-4-sulfonyl)-L-prolyl-L-4-(4N-methanesulfonylpiperazin-1-ylcarbonyloxy)phenylalanine tert-butyl ester,
N-(toluene-4-sulfonyl)-L-prolyl-L-4-(N,N-dimethylcarbamyloxy)phenylalanine ($N^N$-tert-butoxycarbonyl-2-amino-2-methylpropyl)ester,
N-(toluene-4-sulfonyl)-L-prolyl-L-4-(4N-acetylpiperazin-1-ylcarbonyloxy)phenylalanine tert-butyl ester,
N-(toluene-4-sulfonyl)-L-prolyl-L-4-($4^N$-hydroxypiperidin-1-ylcarbonyloxy)phenylalanine tert-butyl ester,
N-(toluene-4-sulfonyl)-L-prolyl-L-4-(N-($2^N$-(morpholin-4N-yl)ethyl)carbamyloxy)phenylalanine tert-butyl ester,
N-(toluene-4-sulfonyl)-L-prolyl-L-4-(N-(1,4-dioxa-8-aza-spiro[4.5]decan-8-yl)carbonyloxy)phenylalanine tert-butyl ester,
N-(toluene-4-sulfonyl)-L-prolyl-L-4-(N-($2^N$-hydroxyethyl)-N-methylcarbamyloxy)phenylalanine tert-butyl ester,
N-(toluene-4-sulfonyl)-L-prolyl-4-(4N-(2-hydroxyethyl)piperazin-1-ylcarbonyloxy)-L-phenylalanine tert-butyl ester,
N-(toluene-4-sulfonyl)-L-prolyl-L-4-(N-($2^N$-formyloxyethyl)-N-methylcarbamyloxy)phenylalanine,
N-(toluene-4-sulfonyl)-L-prolyl-L-4-(N-(2N-hydroxyethyl)-N-methylcarbamyloxy)phenylalanine isopropyl ester,
N-(touluene-4-sulfonyl)-L-prolyl-L-4-(N-(methoxycarbonylmethyl)carbamyloxy)phenylalanine tert-butyl ester, N-(1-methylpyrazole-4-sulfonyl)-L-(5,5-dimethyl)thiaprolyl-L-(4-N,N-dimethylcarbamyloxy)phenylalanine isopropyl ester,
N-(toluene-4-sulfonyl)-L-prolyl-L-4-(4N-methoxypiperidin-1-ylcarbonyloxy)phenylalanine isopropyl ester,
N-(toluene-4-sulfonyl)-L-prolyl-L-4-(4N-methoxypiperidin-1-ylcarbonyloxy)phenylalanine,
N-(toluene-4-sulfonyl)-L-4-oxoprolyl-L-4-(N,N-dimethylcarbamyloxy)phenylalanine tert-butyl ester,
N-(toluene-4-sulfonyl)-L-trans-4-hydroxyprolyl-L-4-(N,N-dimethylcarbamyloxy)phenylalanine tert-butyl ester,
N-(3-fluorobenzenesulfonyl)-L-prolyl-L-4-(N,N-dimethylcarbamyloxy)phenylalanine tert-butyl ester,
N-(morpholino-sulfonyl)-L-prolyl-L-(4-N,N-dimethylcarbamyloxy)phenylalanine tert-butyl ester,
N-(morpholino-sulfonyl)-L-prolyl-L-(4-N,N-dimethylcarbamyloxy)phenylalanine,
N-(1-methylpyrazole-4-sulfonyl)-L-(1,1-dioxothiamorpholin-3-carbonyl)-L-4-(N,N-dimethylcarbamyloxy)phenylalanine tert-butyl ester,
N-(2-fluorobenzenesulfonyl)-L-(1,1-dioxothiamorpholin-3-carbonyl)-L-4-(N,N-dimethylcarbamyloxy)phenylalanine,
N-(2,4-difluorobenzenesulfonyl)-L-(1,1-dioxothiamorpholin-3-carbonyl)-L-4-(N,N-dimethylcarbamyloxy)phenylalanine,
N-(toluene-4-sulfonyl)-L-(thiamorpholin-3-carbonyl)-L-4-(N,N-dimethylcarbamyloxy)phenylalanine,
N-(pyridine-3-sulfonyl)-L-(5,5-dimethyl-thiaprolyl-L-4-(N,N-dimethylcarbamyloxy)phenylalanine isopropyl ester,
N-(3-fluorobenzenesulfonyl)-L-(1,1-dioxothiamorpholin-3-carbonyl)-L-4-(N,N-dimethylcarbamyloxy)phenylalanine,
N-(1-methylpyrazole-4-sulfonyl)-L-(1,1-dioxothiamorpholin-3-carbonyl)-L-4-(N,N-dimethylcarbamyloxy)phenylalanine,
N-(4-tert-butylbenzenesulfonyl)-L-(1,1-dioxothiamorpholin-3-carbonyl)-L-4-(N,N-dimethylcarbamyloxy)phenylalanine,
N-(toluene-4-sulfonyl)-(3,3-dimethyl)prolyl-L-4-(N,N-dimethylcarbamyloxy)phenylalanine,
N-(2,5-dichlorothiophene-3-sulfonyl)-L-prolyl-L-4-(N,N-dimethylcarbamyloxy)phenylalanine,
N-(4-methoxybenzenesulfonyl)-L-prolyl-L-4-(N,N-dimethylcarbamyloxy)phenylalanine,
N-(4-methoxybenzenesulfonyl)-L-prolyl-L-4-(N,N-dimethylcarbamyloxy)phenylalanine isopropyl ester,
N-(toluene-4-sulfonyl)-L-(1-oxo-thiomorpholin-3-carbonyl)-L-4-(N,N-dimethylcarbamyloxy)phenylalanine,
N-(toluene-4-sulfonyl)-L-(1-oxo-thiomorpholin-3-carbonyl)-L-4-(N,N-dimethylcarbamyloxy)phenylalanine tert-butyl ester,
N-(3,4-difluorobenzenesulfonyl)-L-prolyl-4-(N,N-dimethylcarbamyloxy)phenylalanine isopropyl ester,
N-(3,4-difluorobenzenesulfonyl)-L-prolyl-4-(N,N-dimethylcarbamyloxy)phenylalanine,
N-(3,4-difluorobenzenesulfonyl)-L-(1,1-dioxothiamorpholin-3-carbonyl)-L-4-(N,N-dimethylcarbamyloxy)phenylalanine tert-butyl ester,
N-(3,4-difluorobenzenesulfonyl)-L-(1,1-dioxothiamorpholin-3-carbonyl)-L-4-(N,N-dimethylcarbamyloxy)phenylalanine,
N-(toluene-4-sulfonyl)-L-(5,5-dimethyl)thiaprolyl-L-(thiomorpholin-4-ylcarbonyloxy)phenylalanine tert-butyl ester,
N-(toluene-4-sulfonyl)-L-(5,5-dimethyl)thiaprolyl-L-(thiomorpholin-4-ylcarbonyloxy)phenylalanine,
N-(1-methylpyrazole-4-sulfonyl-)-L-(5,5-dimethyl)thiaprolyl-L-4-(N,N-dimethylcarbamyloxy)phenylalanine ethyl ester,
N-(pyridine-3-sulfonyl)-L-(5,5-dimethyl)thiaprolyl-L-4-(N,N-dimethylcarbamyloxy)phenylalanine,
N-(pyridine-2-sulfonyl)-L-prolyl-L-4-(N,N-dimethylcarbamyloxy)phenylalanine isopropyl ester,
N-(pyridine-2-sulfonyl)-L-prolyl-L-4-(N,N-dimethylcarbamyloxy)phenylalanine,
N-(pyridine-2-sulfonyl)-L-(5,5-dimethyl)thiaprolyl-L-4-(N,N-dimethylcarbamyloxy)phenylalanine isopropyl ester,
N-(pyridine-2-sulfonyl)-L-(5,5-dimethyl)thiaprolyl-L-4-(N,N-dimethylcarbamyloxy)phenylalanine,
N-(toluene-4-sulfonyl)-L-(thiamorpholin-3-carbonyl)-L-4-(N,N-dimethylcarbamyloxy)phenylalanine isopropyl ester,
N-(3-fluorobenzenesulfonyl)-L-(5,5-dimethyl)thiaprolyl-L-4-(N,N-dimethylcarbamyloxy)phenylalanine isopropyl ester,
N-(2-fluorobenzenesulfonyl)-L-(5,5-dimethyl)thiaprolyl-L-4-(N,N-dimethylcarbamyloxy)phenylalanine isopropyl ester,
N-(3,4-difluorobenzenesulfonyl)-L-(5,5-dimethyl)thiaprolyl-L-4-(N,N-dimethylcarbamyloxy)phenylalanine isopropyl ester,
N-(3,5-difluorobenzenesulfonyl)-L-(5,5-dimethyl)thiaprolyl-L-4-(N,N-dimethylcarbamyloxy)phenylalanine isopropyl ester,
N-(2,4-difluorobenzenesulfonyl)-L-(5,5-dimethyl)thiaprolyl-L-4-(N,N-dimethylcarbamyloxy)phenylalanine isopropyl ester,
N-(4-chlorobenzenesulfonyl)-L-(5,5-dimethyl)thiaprolyl-L-4-(N,N-dimethylcarbamyloxy)phenylalanine isopropyl ester,
N-(3-chlorobenzenesulfonyl)-L-(5,5-dimethyl)thiaprolyl-L-4-(N,N-dimethylcarbamyloxy)phenylalanine isopropyl ester,
N-(2-chlorobenzenesulfonyl)-L-(5,5-dimethyl)thiaprolyl-L-4-(N,N-dimethylcarbamyloxy)phenylalanine isopropyl ester,
N-(3,4-dichlorobenzenesulfonyl)-L-(5,5-dimethyl)thiaprolyl-L-4-(N,N-dimethylcarbamyloxy)phenylalanine isopropyl ester,
N-(3,5-dichlorobenzenesulfonyl)-L-(5,5-dimethyl)thiaprolyl-L-4-(N,N-dimethylcarbamyloxy)phenylalanine isopropyl ester,
N-(3-chlorobenzenesulfonyl)-L-(1,1-dioxothiamorpholin-3-carbonyl)-L-4-(N,N-dimethylcarbamyloxy)phenylalanine tert-butyl ester,
N-(3,4-dichlorobenzenesulfonyl)-L-(1,1-dioxothiamorpholin-3-carbonyl)-L-4-(N,N-dimethylcarbamyloxy)phenylalanine tert-butyl ester,
N-(4-methoxybenzenesulfonyl)-L-(5,5-dimethyl)thiaprolyl-L-4-(N,N-dimethylcarbamyloxy)phenylalanine isopropyl ester,
N-(3-methoxybenzenesulfonyl)-L-(5,5-dimethyl)thiaprolyl-L-4-(N,N-dimethylcarbamyloxy)phenylalanine isopropyl ester,
N-(2-methoxybenzenesulfonyl)-L-(5,5-dimethyl)thiaprolyl-L-4-(N,N-dimethylcarbamyloxy)phenylalanine isopropyl ester,
N-(3,4-dimethoxybenzenesulfonyl)-L-(5,5-dimethyl)thiaprolyl-L-4-(N,N-dimethylcarbamyloxy)phenylalanine isopropyl ester, N-(2,4-difluorobenzenesulfonyl)-L-(thiamorpholin-3-carbonyl)-L-4-(N,N-dimethylcarbamyloxy)phenylalanine isopropyl ester,
N-(3,4-dichlorobenzenesulfonyl)-L-(1,1-dioxothiamorpholin-3-carbonyl)-L-4-(N,N-dimethylcarbamyloxy)phenylalanine,
N-(3-chlorobenzenesulfonyl)-L-(1,1-dioxothiamorpholin-3-carbonyl)-L-4-(N,N-dimethylcarbamyloxy)phenylalanine,
N-(3-chloro-4-fluorobenzenesulfonyl)-L-(1,1-dioxothiamorpholin-3-carbonyl)-L-4-(N,N-dimethylcarbamyloxy)phenylalanine tert-butyl ester,
N-(1-methylpyrazole-4-sulfonyl)-L-(thiamorpholin-3-carbonyl)-L-4-(N,N-dimethylcarbamyloxy)phenylalanine tert-butyl ester,
N-(3,4-difluorobenzenesulfonyl)-L-(thiamorpholin-3-carbonyl)-L-4-(N,N-dimethylcarbamyloxy)phenylalanine tert-butyl ester,
N-(toluene-4-sulfonyl)-L-(5,5-dimethyl)thioprolyl-L-(thiomorpholin-4-ylcarbonyloxy)phenylalanine isopropyl ester,
N-(3,4-difluorobenzenesulfonyl)-L-(thiamorpholin-3-carbonyl)-L-4-(N,N-dimethylcarbamyloxy)phenylalanine,
N-(2,5-dichlorothiophene-3-sulfonyl)-L-(5,5-dimethyl)thiaprolyl-L-4-(N,N-dimethylcarbamyloxy)phenylalanine isopropyl ester,
N-(1-methylpyrazole-4-sulfonyl)-L-(5,5-dimethyl)thiaprolyl-L-4-(thiomorpholin-4-ylcarbonyloxy)phenylalanine isopropyl ester,
N-(8-quinolinesulfonyl)-L-prolyl-L-4-(N,N-dimethylcarbamyloxy)phenylalanine isopropyl ester,
N-(8-quinolinesulfonyl)-L-prolyl-L-4-(N,N-dimethylcarbamyloxy)phenylalanine,
N-(8-quinolinesulfonyl)-L-(5,5-dimethyl)thiaprolyl-L-4-(N,N-dimethylcarbamyloxy)phenylalanine isoprolyl ester,
N-(8-quinolinesulfonyl)-L-(5,5-dimethyl)thiaprolyl-L-4-(N,N-dimethylcarbamyloxy)phenylalanine,
N-(toluene-4-sulfonyl)-L-prolyl-L-4-(4-phenylpiperazin-1-ylcarbonyloxy)phenylalanine tert-butyl ester,
N-(toluene-4-sulfonyl)-L-prolyl-L-4-(4N-(ethoxycarbonyl)piperidin-1-ylcarbonyloxy)phenylalanine tert-butyl ester,
N-(pyridine-3-sulfonyl)-L-(5,5-dimethyl)thiaprolyl-L-4-(N,N-dimethylcarbamyloxy)phenylalanine tert-butyl ester,
N-(3-sulfonamido-4-chloro-benzenesulfonyl)-L-prolyl-L-4-(N,N-dimethylcarbamyloxy)phenylalanine isopropyl ester,
N-(toluene-4-sulfonyl)-L-(1-oxothiomorpholin-3-carbonyl)-L-4-(N,N-dimethylcarbamyloxy)phenylalanine isopropyl ester,
N-(2,4-difluorobenzenefulfonyl)-L-(1-oxothiomorpholin-3-carbonyl)-L-4-(N,N-dimethylcarbamyloxy)phenylalanine tert-butyl ester,
N-(1-methylpyrazole-4-sulfonyl)-L-(5,5-dimethyl)thiaprolyl-L-4-(N,N-dimethylcarbamyloxy)phenylalanine 2,2-dimethylpropyl ester,
N-(pyridine-3-sulfonyl)-L-(5,5-dimethyl)thiaprolyl-L-4-(N,N-dimethylcarbamyloxy)phenylalanine 2,2-dimethylpropyl ester,
N-(1-methylpyrazole-4-sulfonyl)-L-(5,5-dimethyl)thiaprolyl-L-4-(N,N-dimethylcarbamyloxy)phenylalanine cyclopropylmethyl ester,
N-(1-methylpyrazole-4-sulfonyl)-L-(5,5-dimethyl)thiaprolyl-L-4-(N,N-dimethylcarbamyloxy)phenylalanine methyl ester,
N-(pyridine-3-sulfonyl)-L-(5,5-dimethyl)thiaprolyl-L-4-(N,N-dimethylcarbamyloxy)phenylalanine ethyl ester,
N-(pyridine-3-sulfonyl)-L-(5,5-dimethyl)thiaprolyl-L-4-(N,N-dimethylcarbamyloxy)phenylalanine cyclopropylmethyl ester,
N-(1-methylpyrazole-4-sulfonyl)-L-(5,5-dimethyl)thiaprolyl-L-4-(N,N-dimethylcarbamyloxy)phenylalanine 2-methoxyphenyl ester,
N-(1-methylpyrazole-4-sulfonyl)-L-(5,5-dimethyl)thiaprolyl-L-4-(N,N-dimethylcarbamyloxy)phenylalanine n-butyl ester,
N-(1-methylpyrazole-4-sulfonyl)-L-(5,5-dimethyl)thiaprolyl-L-4-(N,N-dimethylcarbamyloxy)phenylalanine n-propyl ester,
N-(1-methylpyrazole-4-sulfonyl)-L-(5,5-dimethyl)thiaprolyl-L-4-(N,N-dimethylcarbamyloxy)phenylalanine 2,2-dimethylpropionyloxymethyl ester,
N-(toluene-4-sulfonyl)-L-prolyl-L-4-(N-(4=-(2=-aminoethyl)morpholino)carbamyloxy)phenylalanine,
N-(toluene-4-sulfonyl)-L-prolyl-L-4-[4-(carboxy)piperidin-1-ylcarbonyloxy]phenylalanine,
N-(toluene-4-sulfonyl)-L-prolyl-L-4-(N,N-bis-(2-hydroxyethyl)carbamyloxy)phenylalanine isopropyl ester,
N-(toluene-4-sulfonyl)-L-prolyl-L-4-[3-(hydroxymethyl)piperidin-1-ylcarbonyloxy]phenylalanine isopropyl ester,
N-(toluene-4-sulfonyl)-L-prolyl-L-4-(4-trifluoromethanesulfonylpiperazin-1-ylcarbonyloxy)phenylalanine tert-butyl ester,
N-(4-(N-phenylurea)benzenesulfonyl)-L-prolyl-L-4-(N,N-dimethylcarbamyloxy)phenylalanine tert-butyl ester,
N-(2-trifluoroacetyl-1,2,3,4-tetrahydroisoquinolin-7-sulfonyl)-L-prolyl-L-4-(N,N-dimethylcarbamyloxy)phenylalanine isopropyl ester,
N-(1-methylpyrazole-3-sulfonyl)-L-(5,5-dimethyl)thiaprolyl-L-4-(N,N-dimethylcarbamyloxy)phenylalanine isopropyl ester,
N-(1-methylpyrazole-3-sulfonyl)-L-(5,5-dimethyl)thiaprolyl-L-4-(N,N-dimethylcarbamyloxy)phenylalanine,
N-(pyridine-4-sulfonyl)-L-(5,5-dimethyl)thiaprolyl-L-4-(N,N-dimethylcarbamyloxy)phenylalanine isopropyl ester,
N-(pyridine-4-sulfonyl)-L-(5,5-dimethyl)thiaprolyl-L-4-(N,N-dimethylcarbamyloxy)phenylalanine,
N-(toluene-4-sulfonyl)-L-(5,5-dimethyl)thiaprolyl-L-4-(N-methyl-N-(2-dimethylaminoethyl)carbamyloxy)phenylalanine tert-butyl ester,
N-(toluene-4-sulfonyl)-L-prolyl-L-4-(N-methyl-N-(2-dimethylaminoethyl)carbamoyloxy)phenylalanine tert-butyl ester,
N-(toluene-4-sulfonyl)-L-(5,5-dimethyl)thiapropyl-L-4-(N-methyl-N-(2-dimethylaminoethyl)carbamyloxy)phenylalanine,
N-(toluene-4-sulfonyl)-L-prolyl-L-4-(N-methyl-N-(2-dimethylaminoethyl)carbamyloxy)phenylalanine,
N-(4-fluorobenzenesulfonyl)-L-(5,5-dimethyl)thiaprolyl-L-3-chloro-4-(4-methylpiperazin-1-ylcarbonyloxy)phenylalanine tert-butyl ester,
N-(4-fluorobenzenesulfonyl)-L-(5,5-dimethyl)thiaprolyl-L-3-chloro-4-(N,N-dimethycarbamyloxy)phenylalanine, N-(4-fluorobenzenesulfonyl)-L-(5,5-dimethyl)thiaprolyl-L-3-chloro-4-(thiomorpholin-4-ylcarbonyloxy)phenylalanine tert-butyl ester,
N-(4-fluorobenzenesulfonyl)-L-(5,5-dimethyl)thiaprolyl-L-3-chloro-4-(thiomorpholin-4-ylcarbonyloxy)phenylalanine isopropyl ester,
N-(4-fluorobenzenesulfonyl)-L-(5,5-dimethyl)thiaprolyl-L-3-chloro-4-(N,N-dimethylcarbamyloxy)]phenylalanine isopropyl ester,
N-(toluene-4-sulfonyl)-L-(5,5-dimethyl)thiaprolyl-L-3-chloro-4-(N,N-dimethylcarbamyloxy)phenylalanine isopropyl ester,
N-(4-fluorobenzenesulfonyl)-L-(5,5-dimethyl)thiaprolyl-L-3-chloro-4-(4-methylpiperazin-1-ylcarbonyloxy)]phenylalanine isopropyl ester,
N-(toluene-4-sulfonyl)-L-prolyl-L-3-chloro-4-(N,N-dimethylcarbamyloxy)]phenylalanine isopropyl ester,
N-(4-fluorobenzenesulfonyl)-L-(5,5-dimethyl)thiaprolyl-L-3-chloro-4-(4-(2=-pyridyl)-piperazin-1-ylcarbonyloxy)]phenylalanine isopropyl ester,
N-(4-fluorobenzenesulfonyl)-L-(5,5-dimethyl)thiaprolyl-L-3-chloro-4-(4-(2=-pyridyl)-piperazin-1-ylcarbonyloxy)]phenylalanine tert-butyl ester,
N-(4-nitrobenzenesulfonyl)-L-prolyl-L-4-(N,N-dimethylcarbamyloxy)phenylalanine isopropyl ester,
N-(4-aminobenzenesulfonyl)-L-prolyl-L-4-(N,N-dimethylcarbamyloxy)phenylalanine isopropyl ester,
N-(toluene-4-sulfonyl)-L-prolyl-L-4-(thiomorpholin-4-ylcarbonyloxy)phenylalanine isopropyl ester,
N-(toluene-4-sulfonyl)-L-prolyl-L-4-(4-phenylcarbamylpiperazin-1-ylcarbonyloxy)phenylalanine isopropyl ester,
N-(toluene-4-sulfonyl)-L-prolyl-L-4-(4-phenylcarbamylpiperazin-1-ylcarbonyloxy)phenylalanine,
N-(1-n-butylpyrazole-4-sulfonyl)-L-(5,5-dimethyl)thiaprolyl-L-4-(N,N-dimethylcarbamyloxy)phenylalanine isopropyl ester,
N-(toluene-4-sulfonyl)-L-prolyl-L-4-(pyridin-4-ylcarbonyl)piperazin-1-ylcarbonyloxy)phenylalanine isopropyl ester,
N-(toluene-4-sulfonyl)-L-4-oxoprolyl-L-4-(N,N-dimethylcarbamyloxy)phenylalanine,
N-(toluene-4-sulfonyl)-L-trans-4-hydroxyprolyl-L-4-(N,N-dimethylcarbamyloxy)phenylalanine,
N-(4-cyanobenzenesulfonyl)-L-prolyl-L-4-(N,N-dimethylcarbamyloxy)phenylalanine isopropyl ester,
N-(4-aminobenzenesulfonyl)-L-prolyl-L-4-(N,N-dimethylcarbamyloxy)phenylalanine,
N-(toluene-4-sulfonyl)-L-4-oxoprolyl-L-4-(4-methylpiperazin-1-ylcarbonyloxy)phenylalanine tert-butyl ester,
N-(toluene-4-sulfonyl)-L-prolyl-L-4-[3-(hydroxymethyl)piperidin-1-ylcarbonyloxy]phenylalanine,
N-(toluene-4-sulfonyl)-L-(4,4-difluoro)prolyl-L-4-(N,N-dimethylcarbamyloxy)phenylalanine isopropyl ester,
N-(toluene-4-sulfonyl)-L-(4,4-difluoro)prolyl-L-4-(N,N-dimethylcarbamyloxy)phenylalanine,
N-(toluene-4-sulfonyl)-L-prolyl-L-4-(4-benzoylpiperazin-1-ylcarbonyloxy)phenylalanine isopropyl ester,
N-(1-methyl-1H-imidazole-4-sulfonyl)-L-prolyl-L-4-(N,N-dimethylcarbamyloxy)phenylalanine isopropyl ester,
N-(toluene-4-sulfonyl)-L-4-(thiomorpholin-4-ylcarbonyloxy)prolyl-L-4-(thiomorpholin-4-ylcarbonyloxy)phenylalanine,
N-(4-cyanobenzenesulfonyl)-L-prolyl-L-4-(thiomorpholin-4-ylcarbonyloxy)phenylalanine isopropyl ester,
N-(4-amidinobenzenesulfonyl)-L-prolyl-L-4-(N,N-dimethylcarbamyloxy)phenylalanine methyl ester,
N-(toluene-4-sulfonyl)-L-4-oxoprolyl-L-4-(thiomorpholin-4-ylcarbonyloxy)phenylalanine tert-butyl ester,
N-(toluene-4-sulfonyl)-L-4-hydroxyprolyl-L-4-(thiomorpholin-4-ylcarbonyloxy)phenylalanine,
N-(toluene-4-sulfonyl)-L-prolyl-L-(4-benzoylpiperazin-1-ylcarbonyloxy)phenylalanine,
N-(4-amidinobenzenesulfonyl)-L-prolyl-L-4-(thiomorpholin-4-ylcarbonyloxy)phenylalanine methyl ester,
N-(3-fluorobenzenesulfonyl)-L-prolyl-L-4-(N,N-dimethylcarbonyloxy)phenylalanine,
N-(toluene-4-sulfonyl)-L-prolyl-L-4-[N-methyl-N-(2-(N=-methyl-N=-toluenesulfonyl-amino)ethyl)carbamyloxy]phenylalanine isopropyl ester,
N-(toluene-4-sulfonyl)-L-prolyl-L-4-[N-(2-(N=-phenylaminocarbonyloxy)ethyl)carbamyloxy)]phenylalanine isopropyl ester,
N-(4-fluorobenzenesulfonyl)-L-4-(trans-hydroxy)prolyl-L-4-(N,N-dimethylcarbamyloxy)phenylalanine isopropyl ester,
N-(4-fluorobenzenesulfonyl)-L-4-(trans-hydroxy)prolyl-L-4-(N,N-dimethylcarbamyloxy)phenylalanine tert-butyl ester,
N-(4-amidinobenzenesulfonyl)-L-prolyl-L-4-(N,N-dimethylcarbamyloxy)phenylalanine,
N-(toluene-4-sulfonyl)-L-(pyrazin-3-carbonyl)-L-4-(N,N-dimethylcarbamyloxy)phenylalanine tert-butyl ester,
N-(4-fluorobenzenesulfonyl)-L-(5,5-dimethyl)thiaprolyl-L-4-(2-hydroxymethylpyrrolidin-1-ylcarbonyloxy)phenylalanine tert-butyl ester,
N-(4-fluorobenzenesulfonyl)-L-(5,5-dimethyl)thiaprolyl-L-4-(2-hydroxymethylpyrrolidin-1-ylcarbonyloxy)phenylalanine,
N-(toluene-4-sulfonyl)-L-prolyl-L-4-(2-methoxycarbonylpyrrolidin-1-ylcarbonyloxy)phenylalanine tert-butyl ester,
N-(4-fluorobenzenesulfonyl)-L-(5,5-dimethyl)thiaprolyl-L-3-chloro-4-(thiomorpholin-4-ylcarbonyloxy)phenylalanine,
N-(4-fluorobenzenesulfonyl)-L-(5,5-dimethyl)thiaprolyl-L-4-(4-(2-pyridyl)piperazin-1-ylcarbonyloxy)]phenylalanine,
N-(4-fluorobenzenesulfonyl)-L-(5,5-dimethyl)thiaprolyl-L-4-(4-(2-pyridyl)piperazin-1-ylcarbonyloxy)]phenylalanine tert-butyl ester,
N-(toluene-4-sulfonyl)-L-(4-hydroxy)prolyl-L-4-(thiomorpholin-4-ylcarbonyloxy)phenylalanine tert-butyl ester,
N-(toluene-4-sulfonyl)-L-prolyl-L-4-(N,N-dimethylcarbamyloxy)phenylalanine 2-(2-methoxyethoxy)ethyl ester,
N-(4-fluorobenzenesulfonyl)-L-(5,5-dimethyl)thiaprolyl-L-4-(4-(2-pyrimidyl)piperazin-1-ylcarbonyloxy)]phenylalanine tert-butyl ester,
N-(4-fluorobenzenesulfonyl)-L-(5,5-dimethyl)thiaprolyl-L-3-fluoro-4-(N,N-dimethylcarbamyloxy)phenylalanine isopropyl ester,
N-(toluene-4-sulfonyl)-L-(1-methanesulfonylpyrazin-3-carbonyl)-L-4-(N,N-dimethylcarbamyloxy)phenylalanine tert-butyl ester,
N-(4-bromobenzenesulfonyl)-L-(5,5-dimethyl)thiaprolyl-L-4-(N,N-dimethylcarbamyloxy)phenylalanine tert-butyl ester,
N-(4-bromobenzenesulfonyl)-L-(5,5-dimethyl)thiaprolyl-L-4-(N,N-dimethylcarbamyloxy)phenylalanine,
N-(toluene-4-sulfonyl)-L-(4-hydroxy)prolyl-L-4-(4-methylpiperazin-1-ylcarbonyloxy)phenylalanine, N-(4-fluorobenzenesulfonyl)-L-(5,5-dimethyl)thiaprolyl-L-4-(4-(2-pyrimidyl)piperazin-1-ylcarbonyloxy)]phenylalanine, N-(4-fluorobenzenesulfonyl)-L-(5,5-dimethyl)thiaprolyl-L-4-(4-(2-pyridyl)piperazin-1-ylcarbonyloxy)]phenylalanine isopropyl ester, N-(4-fluorobenzenesulfonyl)thiazolidinyl-2-carbonyl-L-4-(N,N-dimethylcarbamyloxy)phenylalanine, N-(4-fluorobenzenesulfonyl)thiazolidinyl-2-carbonyl-L-4-(N,N-dimethylcarbamyloxy)phenylalanine tert-butyl ester, N-(toluene-4-sulfonyl)-L-(4-oxo)prolyl-L-4-(thiomorpholin-4-ylcarbonyloxy)phenylalanine, N-(toluene-4-sulfonyl)-L-(4-oxo)prolyl-L-4-(4-methylpiperazin-1-ylcarbonyloxy)phenylalanine, N-(4-fluorobenzenesulfonyl)thiazolidinyl-2-carbonyl-L-4-(4-(2-pyridyl)piperazin-1-ylcarbonyloxy)]phenylalanine, N-(4-nitrobenzenesulfonyl)-L-prolyl-L-4-(4-(2-pyridyl)piperazin-1-ylcarbonyloxy)]phenylalanine tert-butyl ester, N-(4-fluorobenzenesulfonyl)thiazolidinyl-2-carbonyl-L-4-(4-(2-pyridyl)piperazin-1-ylcarbonyloxy)]phenylalanine tert-butyl ester, N-(4-bromobenzenesulfonyl)-L-(5,5-dimethyl)thiaprolyl-L-4-(4-(2-pyridyl)piperazin-1-ylcarbonyloxy)]phenylalanine, N-(toluene-4-sulfonyl)-L-prolyl-L-4-(4-(N-phenylthiocarbonyl)piperazin-1-ylcarbonyloxy)]phenylalanine isopropyl ester, N-(4-fluorobenzenesulfonyl)thiazolidinyl-2-carbonyl-L-4-(4-methylhomopiperazin-1-ylcarbonyloxy)phenylalanine tert-butyl ester, N-(toluene-4-sulfonyl)-L-4-(methanesulfonyloxy)prolyl-L-4-(N,N-dimethylcarbamyloxy)phenylalanine tert-butyl ester, N-(4-aminocarbonylbenzenesulfonyl)-L-prolyl-L-4-(N,N-dimethylcarbamyloxy)phenylalanine, N-(4-aminocarbonylbenzenesulfonyl)-L-prolyl-L-4-(thiomorpholin-4-ylcarbonyloxy)phenylalanine, N-(4-amidinobenzenesulfonyl)-L-prolyl-L-4-(thiomorpholin-4-ylcarbonyloxy)phenylalanine, N-(4-nitrobenzenesulfonyl)-L-prolyl-L-4-(4-(2-pyridyl)piperazin-1-ylcarbonyloxy)]phenylalanine, N-(4-fluorobenzenesulfonyl)-L-(5,5-dimethyl)thiaprolyl-L-3-chloro-4-(4-(2-pyridyl)piperazin-1-ylcarbonyloxy)]phenylalanine ethyl ester, N-(4-fluorobenzenesulfonyl)-L-(5,5-dimethyl)thiaprolyl-L-3-chloro-4-(4-(2-pyridyl)piperazin-1-ylcarbonyloxy)phenylalanine, N-(4-fluorobenzenesulfonyl)thiazolidinyl-2-carbonyl-L-4-(4-methylhomopiperazin-1-ylcarbonyloxy)phenylalanine, N-(1-methylpyrazole-3-sulfonyl)-L-(5,5-dimethyl)thiaprolyl-L-3-chloro-4-(N,N-dimethylcarbamyloxy)phenylalanine isopropyl ester, N-(1-methylimidazole-4-sulfonyl)-L-prolyl-L-4-(4-(2-pyridyl)piperazin-1-ylcarbonyloxy)phenylalanine isopropyl ester, N-(1-methylimidazole-4-sulfonyl)-L-prolyl-L-4-(4-(2-pyridyl)piperazin-1-ylcarbonyloxy)phenylalanine tert-butyl ester, N-(toluene-4-sulfonyl)-L-prolyl-L-4-(4-(2-pyridyl)piperazin-1-ylcarbonyloxy)phenylalanine, N-(toluene-4-sulfonyl)-L-prolyl-L-4-(4-(2-pyridyl)piperazin-1-ylcarbonyloxy)phenylalanine tert-butyl ester, N-(toluene-4-sulfonyl)-L-prolyl-L-4-(4-(2-pyridyl)piperazin-1-ylcarbonyloxy)phenylalanine isopropyl ester, N-(4-fluorobenzenesulfonyl)-L-prolyl-L-4-(4-(2-pyridyl)piperazin-1-ylcarbonyloxy)phenylalanine isopropyl ester, N-(4-fluorobenzenesulfonyl)-L-prolyl-L-4-(4-(2-pyridyl)piperazin-1-ylcarbonyloxy)phenylalanine tert-butyl ester, N-(toluene-4-sulfonyl)-L-(1-methanesulfonylpyrazin-3-carbonyl)-L-4-(N,N-dimethylcarbamyloxy)phenylalanine, N-(toluene-4-sulfonyl)-L-4-(methanesulfonyloxy)prolyl-L-4-(N,N-dimethylcarbamyloxy)phenylalanine, N-(4-bromobenzenesulfonyl)-L-(5,5-dimethyl)thiaprolyl-L-4-(4-(2-pyridyl)piperazin-1-ylcarbonyloxy)phenylalanine tert-butyl ester, N-(4-trifluoromethoxybenzenesulfonyl)-L-(5,5-dimethyl)thiaprolyl-L-4-(N,N-dimethylcarbamyloxy)phenylalanine, N-(4-trifluoromethoxybenzenesulfonyl)-L-(5,5-dimethyl)thiaprolyl-L-4-(N,N-dimethylcarbamyloxy)phenylalanine tert-butyl ester, N-(4-trifluoromethoxybenzenesulfonyl)-L-(5,5-dimethyl)thiaprolyl-L-4-(4-(2-pyridyl)piperazin-1-ylcarbonyloxy)phenylalanine tert-butyl ester, N-(4-fluorobenzenesulfonyl)-L-prolyl-L-4-(4-(2-pyridyl)piperazin-1-ylcarbonyloxy)phenylalanine, N-(4-fluorobenzenesulfonyl)-L-(4-hydroxy)prolyl-L-4-(4-(2-pyridyl)piperazin-1-ylcarbonyloxy)phenylalanine, N-(4-trifluoromethoxybenzenesulfonyl)-L-(5,5-dimethyl)thiaprolyl-L-4-(4-(2-pyridyl)piperazin-1-ylcarbonyloxy)phenylalanine, N-(1-methylimidazole-4-sulfonyl)-L-prolyl-L-3-chloro-4-(N,N-dimethylcarbamyloxy)phenylalanine, N-(1-methylimidazole-4-sulfonyl)-L-prolyl-L-3-chloro-4-(N,N-dimethylcarbamyloxy)phenylalanine isopropyl ester, N-(1-methylimidazole-4-sulfonyl)-L-prolyl-L-4-(4-(2-pyridyl)piperazin-1-ylcarbonyloxy)phenylalanine, N-(1-methylimidazole-4-sulfonyl)-L-(5,5-dimethyl)thiaprolyl-L-4-(4-(2-pyridyl)piperazin-1-ylcarbonyloxy)phenylalanine, N-(1-methylpyrazole-3-sulfonyl)-L-prolyl-L-4-(4-(2-pyridyl)piperazin-1-ylcarbonyloxy)phenylalanine, N-(1-methylpyrazole-3-sulfonyl)-L-prolyl-L-4-(4-(2-pyridyl)piperazin-1-ylcarbonyloxy)phenylalanine isopropyl ester, N-(1-methylpyrazole-3-sulfonyl)-L-prolyl-L-4-(4-(2-pyridyl)piperazin-1-ylcarbonyloxy)phenylalanine tert-butyl ester, N-(1-methylpyrazole-3-sulfonyl)-L-(5,5-dimethyl)thiaprolyl-L-4-(4-(2-pyridyl)piperazin-1-ylcarbonyloxy)phenylalanine tert-butyl ester, N-(1-methylimidazole-4-sulfonyl)-L-prolyl-L-3-chloro-4-(4-(2-pyridyl)piperazin-1-ylcarbonyloxy)phenylalanine isopropyl ester, N-(1-methylpyrazole-3-sulfonyl)-L-(5,5-dimethyl)thiaprolyl-L-4-(N,N-dimethylcarbamyloxy)phenylalanine 2-phenoxyethyl ester, N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine, N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine ethyl ester, N-(3-chloro-1,5-dimethylpyrazole-3-sulfonyl)-L-(5,5-dimethyl)thiaprolyl-L-3-chloro-4-(4-(5-trifluoromethyl-2-pyridyl)piperazin-1-ylcarbonyloxy)phenylalanine, and pharmaceutically acceptable salts thereof.

13. The method according to any one of claims 3 or 11, wherein the mammal is a human.

14. The method according to claim 3 or 11, wherein the human suffers from a condition which demyelinates cells, and wherein said condition is multiple sclerosis, a congenital metabolic disorder, a neuropathy with abnormal myelination, drug induced demyelination, radiation induced demyelination, a hereditary demyelinating condition, a prion induced demyelinating condition, encephalitis induced demyelination, or a spinal cord injury.

15. The method according to claim 14, wherein the human suffers from multiple sclerosis.

16. The method according to claim 3 or 11, wherein the compound is administered parenterally.

17. The method according to claim 3 or 11, wherein the compound is administered chronically to the mammal in need thereof.

18. The method according to claim 17, wherein the chronic administration of the compound is weekly or monthly over a period of at least one year.

19. The method according to claim 3 or 11, wherein an anti-inflammatory agent is co-administered with the compound to the mammal.

20. The method according to claim 19, wherein an anti-inflammatory agent is co-administered with the compound to the mammal.

21. The method according to claim 20, wherein the anti-inflammatory agent is adrenocorticotropic hormone, a corticosteroid, an interferon, glatiramer acetate, or a non-steroidal anti-inflammatory drug.

22. The method according to claim 21, wherein the corticosteroid is prednisone, methylprednisolone, dexamethasone cortisol, cortisone, fludrocortisone, prednisolone, 6α-methylprednisolone, triamcinolone, or betamethasone.

23. The method according to claim 22, wherein the corticosteroid is prednisone.

24. The method according to claim 3 or 11, wherein the compound is administered intravenously or subcutaneously.

25. The method according to claim 24, wherein the compound is administered intravenously to a mammal, and wherein the administration results in an effective blood level of the compound in the mammal of $\geq 10$ ng/ml.

26. The method according to claim 24, wherein the compound is administered intravenously in an amount of 20 µg to about 500 µg per kilogram body weight of the mammal.

* * * * *

UNITED STATES PATENT AND TRADEMARK OFFICE
CERTIFICATE OF CORRECTION

PATENT NO. : 7,576,101 B2 Page 1 of 1
APPLICATION NO. : 10/763539
DATED : August 18, 2009
INVENTOR(S) : Karlik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1231 days.

Signed and Sealed this

Fourteenth Day of December, 2010

David J. Kappos
*Director of the United States Patent and Trademark Office*

```
SEQUENCE LISTING

<160> NUMBER OF SEQ ID NOS: 71

<210> SEQ ID NO 1
<211> LENGTH: 360
<212> TYPE: DNA
<213> ORGANISM: Homo sapiens
<220> FEATURE:
<221> NAME/KEY: CDS
<222> LOCATION: (1)...(360)

<400> SEQUENCE: 1 gtc aaa ctg cag cag tct ggg gca gag ctt gtg aag cca ggg gcc tca        48
Val Lys Leu Gln Gln Ser Gly Ala Glu Leu Val Lys Pro Gly Ala Ser
 1               5                  10                  15 gtc aag ttg ttc tgc aca gct tct ggc ttc aac att aaa gac acc tat        96
Val Lys Leu Phe Cys Thr Ala Ser Gly Phe Asn Ile Lys Asp Thr Tyr
            20                  25                  30 atg cac tgg gtg aag cag agg cct caa cag ggc ctg gag tgg att gga       144
Met His Trp Val Lys Gln Arg Pro Gln Gln Gly Leu Glu Trp Ile Gly
        35                  40                  45 agg att gat cct gcg agt ggc gat act aaa tat gac ccg aag ttc cag       192
Arg Ile Asp Pro Ala Ser Gly Asp Thr Lys Tyr Asp Pro Lys Phe Gln
    50                  55                  60 gtc aag gcc act att aca gcg gac acg tcc tcc aac aca gcc tgg ctg       240
Val Lys Ala Thr Ile Thr Ala Asp Thr Ser Ser Asn Thr Ala Trp Leu
65                  70                  75                  80 cag ctc agc agc ctg aca tct gag gac act gcc gtc tac tac tgt gca       288
Gln Leu Ser Ser Leu Thr Ser Glu Asp Thr Ala Val Tyr Tyr Cys Ala
                85                  90                  95 gac gga atg tgg gta tca acg gga tat gct ctg gac ttc tgg ggc caa       336
Asp Gly Met Trp Val Ser Thr Gly Tyr Ala Leu Asp Phe Trp Gly Gln
```

```
              100                 105                 110
ggg acc acg gtc acc gtc tcc tca                                          360
Gly Thr Thr Val Thr Val Ser Ser
        115                 120

<210> SEQ ID NO 2
<211> LENGTH: 120
<212> TYPE: PRT
<213> ORGANISM: Homo sapiens

<400> SEQUENCE: 2

Val Lys Leu Gln Gln Ser Gly Ala Glu Leu Val Lys Pro Gly Ala Ser
 1               5                  10                  15

Val Lys Leu Phe Cys Thr Ala Ser Gly Phe Asn Ile Lys Asp Thr Tyr
            20                  25                  30

Met His Trp Val Lys Gln Arg Pro Gln Gln Gly Leu Glu Trp Ile Gly
        35                  40                  45

Arg Ile Asp Pro Ala Ser Gly Asp Thr Lys Tyr Asp Pro Lys Phe Gln
 50                  55                  60

Val Lys Ala Thr Ile Thr Ala Asp Thr Ser Ser Asn Thr Ala Trp Leu
65                  70                  75                  80

Gln Leu Ser Ser Leu Thr Ser Glu Asp Thr Ala Val Tyr Tyr Cys Ala
                85                  90                  95

Asp Gly Met Trp Val Ser Thr Gly Tyr Ala Leu Asp Phe Trp Gly Gln
            100                 105                 110

Gly Thr Thr Val Thr Val Ser Ser
        115                 120

<210> SEQ ID NO 3
<211> LENGTH: 318
<212> TYPE: DNA
<213> ORGANISM: Homo sapiens
<220> FEATURE:
<221> NAME/KEY: CDS
<222> LOCATION: (1)...(318)

<400> SEQUENCE: 3 agt att gtg atg acc cag act ccc aaa ttc ctg ctt gtt tca gca gga      48
Ser Ile Val Met Thr Gln Thr Pro Lys Phe Leu Leu Val Ser Ala Gly
 1               5                  10                  15 gac agg gtt acc ata acc tgc aag gcc agt cag agt gtg act aat gat      96
Asp Arg Val Thr Ile Thr Cys Lys Ala Ser Gln Ser Val Thr Asn Asp
            20                  25                  30 gta gct tgg tac caa cag aag cca ggg cag tct cct aaa ctg ctg ata     144
Val Ala Trp Tyr Gln Gln Lys Pro Gly Gln Ser Pro Lys Leu Leu Ile
        35                  40                  45 tat tat gca tcc aat cgc tac act gga gtc cct gat cgc ttc act ggc     192
Tyr Tyr Ala Ser Asn Arg Tyr Thr Gly Val Pro Asp Arg Phe Thr Gly
 50                  55                  60 agt gga tat ggg acg gat ttc act ttc acc atc agc act gtg cag gct     240
Ser Gly Tyr Gly Thr Asp Phe Thr Phe Thr Ile Ser Thr Val Gln Ala
65                  70                  75                  80 gaa gac ctg gca gtt tat ttc tgt cag cag gat tat agc tct ccg tac     288
Glu Asp Leu Ala Val Tyr Phe Cys Gln Gln Asp Tyr Ser Ser Pro Tyr
                85                  90                  95 acg ttc gga ggg ggg acc aag ctg gag atc                             318
Thr Phe Gly Gly Gly Thr Lys Leu Glu Ile
            100                 105

<210> SEQ ID NO 4
```

```
<211> LENGTH: 106
<212> TYPE: PRT
<213> ORGANISM: Homo sapiens

<400> SEQUENCE: 4

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile
            100                 105

<210> SEQ ID NO 5
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 5 atg gac tgg acc tgg agg gtc ttc tgc ttg ctg gct gta gca cca ggt      48
Met Asp Trp Thr Trp Arg Val Phe Cys Leu Leu Ala Val Ala Pro Gly
 1               5                  10                  15 gcc cac tcc cag gtc caa ctg cag gag tcc ggt gct gaa gtt gtt aaa      96
Ala His Ser Gln Val Gln Leu Gln Glu Ser Gly Ala Glu Val Val Lys
            20                  25                  30 ccg ggt tcc tcc gtt aaa ctg tcc tgc aaa gct tcc ggt ttc aac atc     144
Pro Gly Ser Ser Val Lys Leu Ser Cys Lys Ala Ser Gly Phe Asn Ile
        35                  40                  45 aaa gac acc tac atg cac tgg gtt aaa cag cgt ccg ggt cag ggt ctg     192
Lys Asp Thr Tyr Met His Trp Val Lys Gln Arg Pro Gly Gln Gly Leu
50                  55                  60 gaa tgg atc ggt cgt atc gac ccg gct tcc ggt gac acc aaa tac gac     240
Glu Trp Ile Gly Arg Ile Asp Pro Ala Ser Gly Asp Thr Lys Tyr Asp
65                  70                  75                  80 ccg aaa ttc cag gtt aaa gct acc atc acc gct gac gaa tcc acc tcc     288
Pro Lys Phe Gln Val Lys Ala Thr Ile Thr Ala Asp Glu Ser Thr Ser
                85                  90                  95 acc gct tac ctg gaa ctg tcc tcc ctg cgt tcc gaa gac acc gct gtt     336
Thr Ala Tyr Leu Glu Leu Ser Ser Leu Arg Ser Glu Asp Thr Ala Val
            100                 105                 110 tac tac tgc gct gac ggt atg tgg gtt tcc acc ggt tac gct ctg gac     384
Tyr Tyr Cys Ala Asp Gly Met Trp Val Ser Thr Gly Tyr Ala Leu Asp
        115                 120                 125 ttc tgg ggt cag ggt acc acg gtc acc gtc tcc tca ggt gag tcc         429
Phe Trp Gly Gln Gly Thr Thr Val Thr Val Ser Ser Gly Glu Ser
    130                 135                 140

<210> SEQ ID NO 6
<211> LENGTH: 143
<212> TYPE: PRT
<213> ORGANISM: Homo sapiens
```

<400> SEQUENCE: 6

Met Asp Trp Thr Trp Arg Val Phe Cys Leu Leu Ala Val Ala Pro Gly
1               5                   10                  15

Ala His Ser Gln Val Gln Leu Gln Glu Ser Gly Ala Glu Val Val Lys
            20                  25                  30

Pro Gly Ser Ser Val Lys Leu Ser Cys Lys Ala Ser Gly Phe Asn Ile
        35                  40                  45

Lys Asp Thr Tyr Met His Trp Val Lys Gln Arg Pro Gly Gln Gly Leu
    50                  55                  60

Glu Trp Ile Gly Arg Ile Asp Pro Ala Ser Gly Asp Thr Lys Tyr Asp
65                  70                  75                  80

Pro Lys Phe Gln Val Lys Ala Thr Ile Thr Ala Asp Glu Ser Thr Ser
                85                  90                  95

Thr Ala Tyr Leu Glu Leu Ser Ser Leu Arg Ser Glu Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 7
<211> LENGTH: 383
<212> TYPE: DNA
<213> ORGANISM: Homo sapiens
<220> FEATURE:
<221> NAME/KEY: CDS
<222> LOCATION: (1)...(375)

<400> SEQUENCE: 7 atg ggt tgg tcc tgc atc atc ctg ttc ctg gtt gct acc gct acc ggt     48
Met Gly Trp Ser Cys Ile Ile Leu Phe Leu Val Ala Thr Ala Thr Gly
1               5                   10                  15 gtt cac tcc atc gtt atg acc cag tcc ccg gac tcc ctg gct gtt tcc     96
Val His Ser Ile Val Met Thr Gln Ser Pro Asp Ser Leu Ala Val Ser
            20                  25                  30 ctg ggt gaa cgt gtt acc atc aac tgc aaa gct tcc cag tcc gtt acc    144
Leu Gly Glu Arg Val Thr Ile Asn Cys Lys Ala Ser Gln Ser Val Thr
        35                  40                  45 aac gac gtt gct tgg tac cag cag aaa ccg ggt cag tcc ccg aaa ctg    192
Asn Asp Val Ala Trp Tyr Gln Gln Lys Pro Gly Gln Ser Pro Lys Leu
    50                  55                  60 ctg atc tac tac gct tcc aac cgt tac acc ggt gtt ccg gac cgt ttc    240
Leu Ile Tyr Tyr Ala Ser Asn Arg Tyr Thr Gly Val Pro Asp Arg Phe
65                  70                  75                  80 tcc ggt tcc ggt tac ggt acc gac ttc acc ttc acc atc tcc tcc gtt    288
Ser Gly Ser Gly Tyr Gly Thr Asp Phe Thr Phe Thr Ile Ser Ser Val
                85                  90                  95 cag gct gaa gac gtt gct gtt tac tac tgc cag cag gac tac tcc tcc    336
Gln Ala Glu Asp Val Ala Val Tyr Tyr Cys Gln Gln Asp Tyr Ser Ser
            100                 105                 110 ccg tac acc ttc ggt ggt ggt acc aaa ctg gag atc taa ggatcctc       383
Pro Tyr Thr Phe Gly Gly Gly Thr Lys Leu Glu Ile *
        115                 120

<210> SEQ ID NO 8
<211> LENGTH: 124
<212> TYPE: PRT
<213> ORGANISM: Homo sapiens

```
<400> SEQUENCE: 8

Met Gly Trp Ser Cys Ile Ile Leu Phe Leu Val Ala Thr Ala Thr Gly
1               5                   10                  15

Val His Ser Ile Val Met Thr Gln Ser Pro Asp Ser Leu Ala Val Ser
            20                  25                  30

Leu Gly Glu Arg Val Thr Ile Asn Cys Lys Ala Ser Gln Ser Val Thr
        35                  40                  45

Asn Asp Val Ala Trp Tyr Gln Gln Lys Pro Gly Gln Ser Pro Lys Leu
    50                  55                  60

Leu Ile Tyr Tyr Ala Ser Asn Arg Tyr Thr Gly Val Pro Asp Arg Phe
65                  70                  75                  80

Ser Gly Ser Gly Tyr Gly Thr Asp Phe Thr Phe Thr Ile Ser Ser Val
                85                  90                  95

Gln Ala Glu Asp Val Ala Val Tyr Tyr Cys Gln Gln Asp Tyr Ser Ser
            100                 105                 110

Pro Tyr Thr Phe Gly Gly Gly Thr Lys Leu Glu Ile
        115                 120

<210> SEQ ID NO 9
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 9 atg gac tgg acc tgg agg gtc ttc tgc ttg ctg gct gta gca cca ggt     48
Met Asp Trp Thr Trp Arg Val Phe Cys Leu Leu Ala Val Ala Pro Gly
1               5                   10                  15 gcc cac tcc cag gtc caa ctg cag gag agc ggt cca ggt ctt gtg aga     96
Ala His Ser Gln Val Gln Leu Gln Glu Ser Gly Pro Gly Leu Val Arg
            20                  25                  30 cct agc cag acc ctg agc ctg acc tgc acc gtg tct ggc ttc aac att    144
Pro Ser Gln Thr Leu Ser Leu Thr Cys Thr Val Ser Gly Phe Asn Ile
        35                  40                  45 aaa gac acc tat atg cac tgg gtg aga cag cca cct gga cga ggt ctt    192
Lys Asp Thr Tyr Met His Trp Val Arg Gln Pro Pro Gly Arg Gly Leu
    50                  55                  60 gag tgg att gga agg att gat cct gcg agt ggc gat act aaa tat gac    240
Glu Trp Ile Gly Arg Ile Asp Pro Ala Ser Gly Asp Thr Lys Tyr Asp
65                  70                  75                  80 ccg aag ttc cag gtc aga gtg aca atg ctg gta gac acc agc agc aac    288
Pro Lys Phe Gln Val Arg Val Thr Met Leu Val Asp Thr Ser Ser Asn
                85                  90                  95 aca gcc tgg ctg aga ctc agc agc gtg aca gcc gcc gac acc gcg gtc    336
Thr Ala Trp Leu Arg Leu Ser Ser Val Thr Ala Ala Asp Thr Ala Val
            100                 105                 110 tat tat tgt gca gac gga atg tgg gta tca acg gga tat gct ctg gac    384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc        429
Phe Trp Gly Gln Gly Thr Thr Val Thr Val Ser Ser Gly Glu Ser
    130                 135                 140

<210> SEQ ID NO 10
<211> LENGTH: 143
<212> TYPE: PRT
<213> ORGANISM: Homo sapiens
```

<400> SEQUENCE: 10

Met Asp Trp Thr Trp Arg Val Phe Cys Leu Leu Ala Val Ala Pro Gly
1               5                   10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Asn Ile
        35                  40                  45

Lys Asp Thr Tyr Met His Trp Val Arg Gln Pro Pro Gly Arg Gly Leu
    50                  55                  60

Glu Trp Ile Gly Arg Ile Asp Pro Ala Ser Gly Asp Thr Lys Tyr Asp
65                  70                  75                  80

Pro Lys Phe Gln Val Arg Val Thr Met Leu Val Asp Thr Ser Ser Asn
                85                  90                  95

Thr Ala Trp Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 11
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 11 atg gac tgg acc tgg agg gtc ttc tgc ttg ctg gct gta gca cca ggt      48
Met Asp Trp Thr Trp Arg Val Phe Cys Leu Leu Ala Val Ala Pro Gly
1               5                   10                  15 gcc cac tcc cag gtc caa ctg cag gag agc ggt cca ggt ctt gtg aga      96
Ala His Ser Gln Val Gln Leu Gln Glu Ser Gly Pro Gly Leu Val Arg
            20                  25                  30 cct agc cag acc ctg agc ctg acc tgc acc gtg tct ggc ttc aac att     144
Pro Ser Gln Thr Leu Ser Leu Thr Cys Thr Val Ser Gly Phe Asn Ile
        35                  40                  45 aaa gac acc tat atg cac tgg gtg aga cag cca cct gga cga ggt ctt     192
Lys Asp Thr Tyr Met His Trp Val Arg Gln Pro Pro Gly Arg Gly Leu
    50                  55                  60 gag tgg att gga agg att gat cct gcg agt ggc gat act aaa tat gac     240
Glu Trp Ile Gly Arg Ile Asp Pro Ala Ser Gly Asp Thr Lys Tyr Asp
65                  70                  75                  80 ccg aag ttc cag gtc aaa gcg aca att acg gca gac acc agc agc aac     288
Pro Lys Phe Gln Val Lys Ala Thr Ile Thr Ala Asp Thr Ser Ser Asn
                85                  90                  95 cag ttc agc ctg aga ctc agc agc gtg aca gcc gcc gac acc gcg gtc     336
Gln Phe Ser Leu Arg Leu Ser Ser Val Thr Ala Ala Asp Thr Ala Val
            100                 105                 110 tat tat tgt gca gac gga atg tgg gta tca acg gga tat gct ctg gac     384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc         429
Phe Trp Gly Gln Gly Thr Thr Val Thr Val Ser Ser Gly Glu Ser
    130                 135                 140

<210> SEQ ID NO 12
<211> LENGTH: 143

```
<212> TYPE: PRT
<213> ORGANISM: Homo sapiens

<400> SEQUENCE: 12

Met Asp Trp Thr Trp Arg Val Phe Cys Leu Leu Ala Val Ala Pro Gly
1               5                   10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Asn Ile
        35                  40                  45

Lys Asp Thr Tyr Met His Trp Val Arg Gln Pro Pro Gly Arg Gly Leu
50                  55                  60

Glu Trp Ile Gly Arg Ile Asp Pro Ala Ser Gly Asp Thr Lys Tyr Asp
65                  70                  75                  80

Pro Lys Phe Gln Val Lys Ala Thr Ile Thr Ala Asp Thr Ser Ser Asn
                85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
130                 135                 140

<210> SEQ ID NO 13
<211> LENGTH: 372
<212> TYPE: DNA
<213> ORGANISM: Homo sapiens
<220> FEATURE:
<221> NAME/KEY: CDS
<222> LOCATION: (1)...(372)

<400> SEQUENCE: 13 cag gtc caa ctg cag gag agc ggt cca ggt ctt gtg aga cct agc cag        48
Gln Val Gln Leu Gln Glu Ser Gly Pro Gly Leu Val Arg Pro Ser Gln
1               5                   10                  15 acc ctg agc ctg acc tgc acc gtg tct ggc ttc aac att aaa gac acc        96
Thr Leu Ser Leu Thr Cys Thr Val Ser Gly Phe Asn Ile Lys Asp Thr
            20                  25                  30 tat atg cac tgg gtg aga cag cca cct gga cga ggt ctt gag tgg att       144
Tyr Met His Trp Val Arg Gln Pro Pro Gly Arg Gly Leu Glu Trp Ile
        35                  40                  45 gga agg att gat cct gcg agt ggc gat act aaa tat gac ccg aag ttc       192
Gly Arg Ile Asp Pro Ala Ser Gly Asp Thr Lys Tyr Asp Pro Lys Phe
50                  55                  60 cag gtc aga gtg aca atg ctg gta gac acc agc agc aac cag ttc agc       240
Gln Val Arg Val Thr Met Leu Val Asp Thr Ser Ser Asn Gln Phe Ser
65                  70                  75                  80 ctg aga ctc agc agc gtg aca tct gag gac acc gcg gtc tat tat tgt       288
Leu Arg Leu Ser Ser Val Thr Ser Glu Asp Thr Ala Val Tyr Tyr Cys
                85                  90                  95 gca gac gga atg tgg gta tca acg gga tat gct ctg gac ttc tgg ggc       336
Ala Asp Gly Met Trp Val Ser Thr Gly Tyr Ala Leu Asp Phe Trp Gly
            100                 105                 110 caa ggg acc acg gtc acc gtc tcc tca ggt gag tcc                       372
Gln Gly Thr Thr Val Thr Val Ser Ser Gly Glu Ser
        115                 120

<210> SEQ ID NO 14
<211> LENGTH: 124
<212> TYPE: PRT
```

<213> ORGANISM: Homo sapiens

<400> SEQUENCE: 14

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Asn Ile Lys Asp Thr
            20                  25                  30

Tyr Met His Trp Val Arg Gln Pro Pro Gly Arg Gly Leu Glu Trp Ile
        35                  40                  45

Gly Arg Ile Asp Pro Ala Ser Gly Asp Thr Lys Tyr Asp Pro Lys Phe
50                  55                  60

Gln Val Arg Val Thr Met Leu Val Asp Thr Ser Ser Asn Gln Phe Ser
65                  70                  75                  80

Leu Arg Leu Ser Ser Val Thr Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser Gly Glu Ser
        115                 120
```

<210> SEQ ID NO 15
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 15

```
atg gac tgg acc tgg agg gtc ttc tgc ttg ctg gct gta gca cca ggt      48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga      96
Ala His Ser Gln Val Gln Leu Gln Glu Ser Gly Pro Gly Leu Val Arg
            20                  25                  30 cct agc cag acc ctg agc ctg acc tgc acc gtg tct ggc ttc aac att     144
Pro Ser Gln Thr Leu Ser Leu Thr Cys Thr Val Ser Gly Phe Asn Ile
        35                  40                  45 aaa gac acc tat atg cac tgg gtg aaa cag cga cct gga cga ggt ctt     192
Lys Asp Thr Tyr Met His Trp Val Lys Gln Arg Pro Gly Arg Gly Leu
    50                  55                  60 gag tgg att gga agg att gat cct gcg agt ggc gat act aaa tat gac     240
Glu Trp Ile Gly Arg Ile Asp Pro Ala Ser Gly Asp Thr Lys Tyr Asp
65                  70                  75                  80 ccg aag ttc cag gtc aga gtg aca atg ctg gta gac acc agc agc aac     288
Pro Lys Phe Gln Val Arg Val Thr Met Leu Val Asp Thr Ser Ser Asn
                85                  90                  95 cag ttc agc ctg aga ctc agc agc gtg aca gcc gcc gac acc gcg gtc     336
Gln Phe Ser Leu Arg Leu Ser Ser Val Thr Ala Ala Asp Thr Ala Val
            100                 105                 110 tat tat tgt gca gac gga atg tgg gta tca acg gga tat gct ctg gac     384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc         429
Phe Trp Gly Gln Gly Thr Thr Val Thr Val Ser Ser Gly Glu Ser
    130                 135                 140
```

<210> SEQ ID NO 16
<211> LENGTH: 143
<212> TYPE: PRT

<213> ORGANISM: Homo sapiens

<400> SEQUENCE: 16

```
Met Asp Trp Thr Trp Arg Val Phe Cys Leu Leu Ala Val Ala Pro Gly
 1               5                  10                  15

Ala His Ser Gln Val Gln Leu Gln Glu Ser Gly Pro Gly Leu Val Arg
             20                  25                  30

Pro Ser Gln Thr Leu Ser Leu Thr Cys Thr Val Ser Gly Phe Asn Ile
         35                  40                  45

Lys Asp Thr Tyr Met His Trp Val Lys Gln Arg Pro Gly Arg Gly Leu
 50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Ser Asn
                 85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140
```

<210> SEQ ID NO 17
<211> LENGTH: 429
<212> TYPE: DNA
<213> ORGANISM: Homo sapiens
<220> FEATURE:
<221> NAME/KEY: CDS
<222> LOCATION: (1)...(429)

<400> SEQUENCE: 17

```
atg gac tgg acc tgg agg gtc ttc tgc ttg ctg gct gta gca cca ggt      48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga      96
Ala His Ser Gln Val Gln Leu Gln Glu Ser Gly Pro Gly Leu Val Arg
             20                  25                  30 cct agc cag acc ctg agc ctg acc tgc acc gcg tct ggc ttc aac att     144
Pro Ser Gln Thr Leu Ser Leu Thr Cys Thr Ala Ser Gly Phe Asn Ile
         35                  40                  45 aaa gac acc tat atg cac tgg gtg aga cag cca cct gga cga ggt ctt     192
Lys Asp Thr Tyr Met His Trp Val Arg Gln Pro Pro Gly Arg Gly Leu
 50                  55                  60 gag tgg att gga agg att gat cct gcg agt ggc gat act aaa tat gac     240
Glu Trp Ile Gly Arg Ile Asp Pro Ala Ser Gly Asp Thr Lys Tyr Asp
 65                  70                  75                  80 ccg aag ttc cag gtc aga gtg aca atg ctg gta gac acc agc agc aac     288
Pro Lys Phe Gln Val Arg Val Thr Met Leu Val Asp Thr Ser Ser Asn
                 85                  90                  95 cag ttc agc ctg aga ctc agc agc gtg aca gcc gcc gac acc gcg gtc     336
Gln Phe Ser Leu Arg Leu Ser Ser Val Thr Ala Ala Asp Thr Ala Val
            100                 105                 110 tat tat tgt gca gac gga atg tgg gta tca acg gga tat gct ctg gac     384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc         429
Phe Trp Gly Gln Gly Thr Thr Val Thr Val Ser Ser Gly Glu Ser
    130                 135                 140
```

<210> SEQ ID NO 18
<211> LENGTH: 143
<212> TYPE: PRT
<213> ORGANISM: Homo sapiens

<400> SEQUENCE: 18

Met Asp Trp Thr Trp Arg Val Phe Cys Leu Leu Ala Val Ala Pro Gly
1               5                   10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Ala Ser Gly Phe Asn Ile
        35                  40                  45

Lys Asp Thr Tyr Met His Trp Val Arg Gln Pro Pro Gly Arg Gly Leu
    50                  55                  60

Glu Trp Ile Gly Arg Ile Asp Pro Ala Ser Gly Asp Thr Lys Tyr Asp
65                  70                  75                  80

Pro Lys Phe Gln Val Arg Val Thr Met Leu Val Asp Thr Ser Ser Asn
                85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140

<210> SEQ ID NO 19
<211> LENGTH: 386
<212> TYPE: DNA
<213> ORGANISM: Homo sapiens
<220> FEATURE:
<221> NAME/KEY: CDS
<222> LOCATION: (1)...(386)

<400> SEQUENCE: 19 atg ggt tgg tcc tgc atc atc ctg ttc ctg gtt gct acc gct acc ggt      48
Met Gly Trp Ser Cys Ile Ile Leu Phe Leu Val Ala Thr Ala Thr Gly
1               5                   10                  15 gtt cac tcc gac atc cag ctg acc cag agc cca agc agc ctg agc gcc      96
Val His Ser Asp Ile Gln Leu Thr Gln Ser Pro Ser Ser Leu Ser Ala
            20                  25                  30 agc gtg ggt gac aga gtg acc atc acc tgt aag gcc agt cag agt gtg     144
Ser Val Gly Asp Arg Val Thr Ile Thr Cys Lys Ala Ser Gln Ser Val
        35                  40                  45 act aat gat gta gct tgg tac cag cag aag cca ggt aag gct cca aag     192
Thr Asn Asp Val Ala Trp Tyr Gln Gln Lys Pro Gly Lys Ala Pro Lys
    50                  55                  60 ctg ctg atc tac tat gca tcc aat cgc tac act ggt gtg cca agc aga     240
Leu Leu Ile Tyr Tyr Ala Ser Asn Arg Tyr Thr Gly Val Pro Ser Arg
65                  70                  75                  80 ttc agc ggt agc ggt agc ggt acc gac ttc acc ttc acc atc agc agc     288
Phe Ser Gly Ser Gly Ser Gly Thr Asp Phe Thr Phe Thr Ile Ser Ser
                85                  90                  95 ctc cag cca gag gac atc gcc acc tac tac tgc cag cag gat tat agc     336
Leu Gln Pro Glu Asp Ile Ala Thr Tyr Tyr Cys Gln Gln Asp Tyr Ser
            100                 105                 110 tct ccg tac acg ttc ggc caa ggg acc aag gtg gaa atc aaa cgt aag     384
Ser Pro Tyr Thr Phe Gly Gln Gly Thr Lys Val Glu Ile Lys Arg Lys
        115                 120                 125 tg                                                                   386

<210> SEQ ID NO 20
<211> LENGTH: 128
<212> TYPE: PRT
<213> ORGANISM: Homo sapiens

<400> SEQUENCE: 20

```
Met Gly Trp Ser Cys Ile Ile Leu Phe Leu Val Ala Thr Ala Thr Gly
 1               5                  10                  15

Val His Ser Asp Ile Gln Leu Thr Gln Ser Pro Ser Ser Leu Ser Ala
            20                  25                  30

Ser Val Gly Asp Arg Val Thr Ile Thr Cys Lys Ala Ser Gln Ser Val
        35                  40                  45

Thr Asn Asp Val Ala Trp Tyr Gln Gln Lys Pro Gly Lys Ala Pro Lys
    50                  55                  60

Leu Leu Ile Tyr Tyr Ala Ser Asn Arg Tyr Thr Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125
```

<210> SEQ ID NO 21
<211> LENGTH: 386
<212> TYPE: DNA
<213> ORGANISM: Homo sapiens
<220> FEATURE:
<221> NAME/KEY: CDS
<222> LOCATION: (1)...(386)

<400> SEQUENCE: 21

```
atg ggt tgg tcc tgc atc atc ctg ttc ctg gtt gct acc gct acc ggt    48
Met Gly Trp Ser Cys Ile Ile Leu Phe Leu Val Ala Thr Ala Thr Gly
 1               5                  10                  15 gtc cac tcc agc atc gtg atg acc cag agc cca agc agc ctg agc gcc    96
Val His Ser Ser Ile Val Met Thr Gln Ser Pro Ser Ser Leu Ser Ala
            20                  25                  30 agc gtg ggt gac aga gtg acc atc acc tgt aag gcc agt cag agt gtg   144
Ser Val Gly Asp Arg Val Thr Ile Thr Cys Lys Ala Ser Gln Ser Val
        35                  40                  45 act aat gat gta gct tgg tac cag cag aag cca ggt aag gct cca aag   192
Thr Asn Asp Val Ala Trp Tyr Gln Gln Lys Pro Gly Lys Ala Pro Lys
    50                  55                  60 ctg ctg atc tac tat gca tcc aat cgc tac act ggt gtg cca gat aga   240
Leu Leu Ile Tyr Tyr Ala Ser Asn Arg Tyr Thr Gly Val Pro Asp Arg
65                  70                  75                  80 ttc agc ggt agc ggt tat ggt acc gac ttc acc ttc acc atc agc agc   288
Phe Ser Gly Ser Gly Tyr Gly Thr Asp Phe Thr Phe Thr Ile Ser Ser
                85                  90                  95 ctc cag cca gag gac atc gcc acc tac tac tgc cag cag gat tat agc   336
Leu Gln Pro Glu Asp Ile Ala Thr Tyr Tyr Cys Gln Gln Asp Tyr Ser
            100                 105                 110 tct ccg tac acg ttc ggc caa ggg acc aag gtg gaa atc aaa cgt aag   384
Ser Pro Tyr Thr Phe Gly Gln Gly Thr Lys Val Glu Ile Lys Arg Lys
        115                 120                 125 tg                                                                 386
```

<210> SEQ ID NO 22

```
<211> LENGTH: 128
<212> TYPE: PRT
<213> ORGANISM: Homo sapiens

<400> SEQUENCE: 22

Met Gly Trp Ser Cys Ile Ile Leu Phe Leu Val Ala Thr Ala Thr Gly
 1               5                  10                  15

Val His Ser Ser Ile Val Met Thr Gln Ser Pro Ser Ser Leu Ser Ala
             20                  25                  30

Ser Val Gly Asp Arg Val Thr Ile Thr Cys Lys Ala Ser Gln Ser Val
         35                  40                  45

Thr Asn Asp Val Ala Trp Tyr Gln Gln Lys Pro Gly Lys Ala Pro Lys
     50                  55                  60

Leu Leu Ile Tyr Tyr Ala Ser Asn Arg Tyr Thr Gly Val Pro Asp Arg
 65                  70                  75                  80

Phe Ser Gly Ser Gly Tyr Gly Thr Asp Phe Thr Phe Thr Ile Ser Ser
                 85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125

<210> SEQ ID NO 23
<211> LENGTH: 386
<212> TYPE: DNA
<213> ORGANISM: Homo sapiens
<220> FEATURE:
<221> NAME/KEY: CDS
<222> LOCATION: (1)...(386)

<400> SEQUENCE: 23 atg ggt tgg tcc tgc atc atc ctg ttc ctg gtt gct acc gct acc ggt       48
Met Gly Trp Ser Cys Ile Ile Leu Phe Leu Val Ala Thr Ala Thr Gly
 1               5                  10                  15 gtc cac tcc gac atc cag atg acc cag agc cca agc agc ctg agc gcc       96
Val His Ser Asp Ile Gln Met Thr Gln Ser Pro Ser Ser Leu Ser Ala
             20                  25                  30 agc gtg ggt gac aga gtg acc atc acc tgt aag gcc agt cag agt gtg      144
Ser Val Gly Asp Arg Val Thr Ile Thr Cys Lys Ala Ser Gln Ser Val
         35                  40                  45 act aat gat gta gct tgg tac cac cag aag cca ggt aag gct cca aag      192
Thr Asn Asp Val Ala Trp Tyr His Gln Lys Pro Gly Lys Ala Pro Lys
     50                  55                  60 ctg ctg atc tac tat gca tcc aat cgc tac act ggt gtg cca gat aga      240
Leu Leu Ile Tyr Tyr Ala Ser Asn Arg Tyr Thr Gly Val Pro Asp Arg
 65                  70                  75                  80 ttc agc ggt agc ggt tat ggt acc gac ttc acc ttc acc atc agc agc      288
Phe Ser Gly Ser Gly Tyr Gly Thr Asp Phe Thr Phe Thr Ile Ser Ser
                 85                  90                  95 ctc cag cca gag gac atc gcc acc tac tac tgc cag cag gat tat agc      336
Leu Gln Pro Glu Asp Ile Ala Thr Tyr Tyr Cys Gln Gln Asp Tyr Ser
            100                 105                 110 tct ccg tac acg ttc ggc caa ggg acc aag gtg gaa atc aaa cgt aag      384
Ser Pro Tyr Thr Phe Gly Gln Gly Thr Lys Val Glu Ile Lys Arg Lys
        115                 120                 125 tg                                                                   386

<210> SEQ ID NO 24
<211> LENGTH: 128
<212> TYPE: PRT
```

<213> ORGANISM: Homo sapiens

<400> SEQUENCE: 24

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Ser Val
        35                  40                  45

Thr Asn Asp Val Ala Trp Tyr His Gln Lys Pro Gly Lys Ala Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Tyr Gly Thr Asp Phe Thr Phe Thr Ile Ser Ser
                85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125

<210> SEQ ID NO 25
<211> LENGTH: 37
<212> TYPE: DNA
<213> ORGANISM: Homo sapiens
<220> FEATURE:
<221> NAME/KEY: CDS
<222> LOCATION: (20)...(37)

<400> SEQUENCE: 25
cagaaagctt gccgccacc atg aga ccg tct att cag                        37
                    Met Arg Pro Ser Ile Gln
                     1               5

<210> SEQ ID NO 26
<211> LENGTH: 6
<212> TYPE: PRT
<213> ORGANISM: Homo sapiens

<400> SEQUENCE: 26

Met Arg Pro Ser Ile Gln
1               5

<210> SEQ ID NO 27
<211> LENGTH: 35
<212> TYPE: DNA
<213> ORGANISM: Homo sapiens

<400> SEQUENCE: 27
ccgaggatcc actcacgttt gatttccagc ttggt                              35

<210> SEQ ID NO 28
<211> LENGTH: 37
<212> TYPE: DNA
<213> ORGANISM: Homo sapiens
<220> FEATURE:
<221> NAME/KEY: CDS
<222> LOCATION: (20)...(37)

<400> SEQUENCE: 28
cagaaagctt gccgccacc atg aaa tgc agc tgg gtc                        37
                    Met Lys Cys Ser Trp Val
                     1               5

```
<210> SEQ ID NO 29
<211> LENGTH: 6
<212> TYPE: PRT
<213> ORGANISM: Homo sapiens

<400> SEQUENCE: 29

Met Lys Cys Ser Trp Val
 1               5

<210> SEQ ID NO 30
<211> LENGTH: 33
<212> TYPE: DNA
<213> ORGANISM: Homo sapiens

<400> SEQUENCE: 30
ccgaggatcc actcacctga ggagacggtg act                               33

<210> SEQ ID NO 31
<211> LENGTH: 39
<212> TYPE: DNA
<213> ORGANISM: Homo sapiens

<400> SEQUENCE: 31
gatggtgact ctatctccta cagatgcaga cagtgagga                         39

<210> SEQ ID NO 32
<211> LENGTH: 32
<212> TYPE: DNA
<213> ORGANISM: Homo sapiens

<400> SEQUENCE: 32
ctgtaggaga tagagtcacc atcacttgca ag                                32

<210> SEQ ID NO 33
<211> LENGTH: 39
<212> TYPE: DNA
<213> ORGANISM: Homo sapiens

<400> SEQUENCE: 33
aggagctttt ccaggtgtct gttggtacca agccatata                         39

<210> SEQ ID NO 34
<211> LENGTH: 41
<212> TYPE: DNA
<213> ORGANISM: Homo sapiens

<400> SEQUENCE: 34
accaacagac acctggaaaa gctcctaggc tgctcataca t                      41

<210> SEQ ID NO 35
<211> LENGTH: 40
<212> TYPE: DNA
<213> ORGANISM: Homo sapiens

<400> SEQUENCE: 35
gcaggctgct gatggtgaaa gtataatctc tcccagaccc                        40

<210> SEQ ID NO 36
<211> LENGTH: 42
<212> TYPE: DNA
<213> ORGANISM: Homo sapiens

<400> SEQUENCE: 36
actttcacca tcagcagcct gcagcctgaa gatattgcaa ct                     42
```

<210> SEQ ID NO 37
<211> LENGTH: 59
<212> TYPE: DNA
<213> ORGANISM: Homo sapiens

<400> SEQUENCE: 37
ccgaggatcc actcacgttt gatttccacc ttggtgcctt gaccgaacgt ccacagatt    59

<210> SEQ ID NO 38
<211> LENGTH: 33
<212> TYPE: DNA
<213> ORGANISM: Homo sapiens

<400> SEQUENCE: 38
ggaaaagctc ctaggctgct catatattac aca    33

<210> SEQ ID NO 39
<211> LENGTH: 38
<212> TYPE: DNA
<213> ORGANISM: Homo sapiens

<400> SEQUENCE: 39
ccgaggatcc actcacgttt gatttccacc tttgtgcc    38

<210> SEQ ID NO 40
<211> LENGTH: 51
<212> TYPE: DNA
<213> ORGANISM: Homo sapiens

<400> SEQUENCE: 40
aacccagtgt ataggtgt ctttaatgtt gaaaccgcta gctttacagc t    51

<210> SEQ ID NO 41
<211> LENGTH: 67
<212> TYPE: DNA
<213> ORGANISM: Homo sapiens

<400> SEQUENCE: 41
aaagacacct atatacactg ggttagacag gcccctggcc aaaggctgga gtggatggga    60
aggattg    67

<210> SEQ ID NO 42
<211> LENGTH: 26
<212> TYPE: DNA
<213> ORGANISM: Homo sapiens

<400> SEQUENCE: 42
gacccggccc tggaacttcg ggtcat    26

<210> SEQ ID NO 43
<211> LENGTH: 66
<212> TYPE: DNA
<213> ORGANISM: Homo sapiens

<400> SEQUENCE: 43
gacccgaagt tccagggccg ggtcaccatc accgcagaca cctctgccag caccgcctac    60
atggaa    66

<210> SEQ ID NO 44
<211> LENGTH: 64
<212> TYPE: DNA

<213> ORGANISM: Homo sapiens

<400> SEQUENCE: 44

```
ccatagcata gaccccgtag ttaccataat atccctctct ggcgcagtag tagactgcag    60
tgtc                                                                 64
```

<210> SEQ ID NO 45
<211> LENGTH: 63
<212> TYPE: DNA
<213> ORGANISM: Homo sapiens

<400> SEQUENCE: 45

```
ggtaactacg gggtctatgc tatggactac tggggtcaag gaacccttgt caccgtctcc    60
tca                                                                  63
```

<210> SEQ ID NO 46
<211> LENGTH: 37
<212> TYPE: DNA
<213> ORGANISM: Homo sapiens

<400> SEQUENCE: 46

```
ccagggccgg gtcaccatca ccagagacac ctctgcc                             37
```

<210> SEQ ID NO 47
<211> LENGTH: 27
<212> TYPE: DNA
<213> ORGANISM: Homo sapiens

<400> SEQUENCE: 47

```
caggcccctg gccaagggct ggagtgg                                        27
```

<210> SEQ ID NO 48
<211> LENGTH: 17
<212> TYPE: DNA
<213> ORGANISM: Homo sapiens

<400> SEQUENCE: 48

```
tacgcaaacc gcctctc                                                   17
```

<210> SEQ ID NO 49
<211> LENGTH: 18
<212> TYPE: DNA
<213> ORGANISM: Homo sapiens

<400> SEQUENCE: 49

```
gagtgcacca tatgcggt                                                  18
```

<210> SEQ ID NO 50
<211> LENGTH: 116
<212> TYPE: PRT
<213> ORGANISM: Homo sapiens

<400> SEQUENCE: 50

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Val
        35                  40                  45

Gly Tyr Ile Asp Pro Phe Asn Gly Gly Thr Ser Tyr Asn Gln Lys Phe
    50                  55                  60
```

```
Lys Gly Lys Val Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Asn Arg Phe Ala Tyr Trp Gly Gln Gly Thr Leu Val
            100                 105                 110

Thr Val Ser Ser
        115

<210> SEQ ID NO 51
<211> LENGTH: 483
<212> TYPE: DNA
<213> ORGANISM: Mouse
<220> FEATURE:
<221> NAME/KEY: CDS
<222> LOCATION: (53)...(432)

<400> SEQUENCE: 51
atgagggccc ctgctcagat ttttggattc ttggtcagga gacgttgtag aa atg aga      58
                                                          Met Arg
                                                            1 ccg tct att cag ttc ctg ggg ctc ttg ttg ttc tgg ctt cat ggt gct       106
Pro Ser Ile Gln Phe Leu Gly Leu Leu Leu Phe Trp Leu His Gly Ala
      5                  10                  15 cag tgt gac atc cag atg aca cag tct cca tcc tca ctg tct gca tct       154
Gln Cys Asp Ile Gln Met Thr Gln Ser Pro Ser Ser Leu Ser Ala Ser
 20                  25                  30 ctg gga ggc aaa gtc acc atc act tgc aag aca agc caa gac att aac       202
Leu Gly Gly Lys Val Thr Ile Thr Cys Lys Thr Ser Gln Asp Ile Asn
 35                  40                  45                  50 aag tat atg gct tgg tac caa cac aag cct gga aaa cgt cct agg ctg       250
Lys Tyr Met Ala Trp Tyr Gln His Lys Pro Gly Lys Arg Pro Arg Leu
             55                  60                  65 ctc ata cat tac aca tct gca tta cag cca ggc atc cca tca agg ttc       298
Leu Ile His Tyr Thr Ser Ala Leu Gln Pro Gly Ile Pro Ser Arg Phe
             70                  75                  80 agt gga agt ggg tct ggg aga gat tat tcc ttc aac atc agc aac ctg       346
Ser Gly Ser Gly Ser Gly Arg Asp Tyr Ser Phe Asn Ile Ser Asn Leu
         85                  90                  95 gag cct gaa gat att gca act tat tat tgt cta cag tat gat aat ctg       394
Glu Pro Glu Asp Ile Ala Thr Tyr Tyr Cys Leu Gln Tyr Asp Asn Leu
    100                 105                 110 tgg acg ttc ggt gga ggc acc aag ctg gaa atc aaa cg ggctgatgct        442
Trp Thr Phe Gly Gly Gly Thr Lys Leu Glu Ile Lys
115                 120                 125 gcaccaactg tatccatctt cccaccatcc acccgggatc c                         483

<210> SEQ ID NO 52
<211> LENGTH: 126
<212> TYPE: PRT
<213> ORGANISM: Mouse

<400> SEQUENCE: 52

Met Arg Pro Ser Ile Gln Phe Leu Gly Leu Leu Leu Phe Trp Leu His
 1               5                  10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Thr Ser Gln Asp
        35                  40                  45
```

```
Ile Asn Lys Tyr Met Ala Trp Tyr Gln His Lys Pro Gly Lys Arg Pro
            50                  55                  60

Arg Leu Leu Ile His Tyr Thr Ser Ala Leu Gln Pro Gly Ile Pro Ser
65                  70                  75                  80

Arg Phe Ser Gly Ser Gly Ser Gly Arg Asp Tyr Ser Phe Asn Ile Ser
                85                  90                  95

Asn Leu Glu Pro Glu Asp Ile Ala Thr Tyr Tyr Cys Leu Gln Tyr Asp
            100                 105                 110

Asn Leu Trp Thr Phe Gly Gly Gly Thr Lys Leu Glu Ile Lys
        115                 120                 125

<210> SEQ ID NO 53
<211> LENGTH: 470
<212> TYPE: DNA
<213> ORGANISM: Mouse
<220> FEATURE:
<221> NAME/KEY: CDS
<222> LOCATION: (1)...(432)

<400> SEQUENCE: 53 atg aaa tgc agc tgg gtc atg ttc ttc ctg atg gca gtg gtt aca ggg      48
Met Lys Cys Ser Trp Val Met Phe Phe Leu Met Ala Val Val Thr Gly
1               5                   10                  15 gtc aat tca gag gtt cag ctg cag cag tct ggg gca gag ctt gtg aag      96
Val Asn Ser Glu Val Gln Leu Gln Gln Ser Gly Ala Glu Leu Val Lys
            20                  25                  30 cca ggg gcc tca gtc aag ttg tcc tgc aca gct tct ggc ttc aac att     144
Pro Gly Ala Ser Val Lys Leu Ser Cys Thr Ala Ser Gly Phe Asn Ile
        35                  40                  45 aaa gac acc tat ata cac tgt gtg aag cag agg cct gaa cag ggc ctg     192
Lys Asp Thr Tyr Ile His Cys Val Lys Gln Arg Pro Glu Gln Gly Leu
    50                  55                  60 gag tgg att gga agg att gat cct gcg aat ggt tat act aaa tat gac     240
Glu Trp Ile Gly Arg Ile Asp Pro Ala Asn Gly Tyr Thr Lys Tyr Asp
65                  70                  75                  80 ccg aag ttc cag ggc aag gcc act ata aca gct gac aca tcc tcc aac     288
Pro Lys Phe Gln Gly Lys Ala Thr Ile Thr Ala Asp Thr Ser Ser Asn
                85                  90                  95 aca gcc tac ctg cag ctc agc agc ctg aca tct gag gac act gcc gtc     336
Thr Ala Tyr Leu Gln Leu Ser Ser Leu Thr Ser Glu Asp Thr Ala Val
            100                 105                 110 tat ttc tgt gct aga gag gga tat tat ggt aac tac ggg gtc tat gct     384
Tyr Phe Cys Ala Arg Glu Gly Tyr Tyr Gly Asn Tyr Gly Val Tyr Ala
        115                 120                 125 atg gac tac tgg ggt caa gga acc tca gtc acc gtc tcc tca gcc aaa     432
Met Asp Tyr Trp Gly Gln Gly Thr Ser Val Thr Val Ser Ser Ala Lys
    130                 135                 140 acgacacccc catctgtcta tccactggcc cgggatcc                            470

<210> SEQ ID NO 54
<211> LENGTH: 144
<212> TYPE: PRT
<213> ORGANISM: Mouse

<400> SEQUENCE: 54

Met Lys Cys Ser Trp Val Met Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
```

```
            35                  40                  45
Lys Asp Thr Tyr Ile His Cys Val Lys Gln Arg Pro Glu Gln Gly Leu
 50                  55                  60

Glu Trp Ile Gly Arg Ile Asp Pro Ala Asn Gly Tyr Thr Lys Tyr Asp
 65                  70                  75                  80

Pro Lys Phe Gln Gly Lys Ala Thr Ile Thr Ala Asp Thr Ser Ser Asn
                 85                  90                  95

Thr Ala Tyr Leu Gln Leu Ser Ser Leu Thr Ser Glu Asp Thr Ala Val
                100                 105                 110

Tyr Phe Cys Ala Arg Glu Gly Tyr Tyr Gly Asn Tyr Gly Val Tyr Ala
                115                 120                 125

Met Asp Tyr Trp Gly Gln Gly Thr Ser Val Thr Val Ser Ser Ala Lys
                130                 135                 140

<210> SEQ ID NO 55
<211> LENGTH: 106
<212> TYPE: PRT
<213> ORGANISM: Homo sapiens

<400> SEQUENCE: 55

Asp Ile Gln Met Thr Gln Ser Pro Ser Ser Leu Ser Ala Ser Leu Gly
  1               5                  10                  15

Gly Lys Val Thr Ile Thr Cys Lys Thr Ser Gln Asp Ile Asn Lys Tyr
                 20                  25                  30

Met Ala Trp Tyr Gln His Lys Pro Gly Lys Arg Pro Arg Leu Leu Ile
                 35                  40                  45

His Tyr Thr Ser Ala Leu Gln Pro Gly Ile Pro Ser Arg Phe Ser Gly
                 50                  55                  60

Ser Gly Ser Gly Arg Asp Tyr Ser Phe Asn Ile Ser Asn Leu Glu Pro
 65                  70                  75                  80

Glu Asp Ile Ala Thr Tyr Tyr Cys Leu Gln Tyr Asp Asn Leu Trp Thr
                 85                  90                  95

Phe Gly Gly Gly Thr Lys Leu Glu Ile Lys
                100                 105

<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ile Lys Tyr
                 20                  25                  30

Leu Asn Trp Tyr Gln Gln Thr Pro Gly Lys Ala Pro Lys Leu Leu Ile
                 35                  40                  45

Tyr Glu Ala Ser Asn Leu Gln Ala Gly Val Pro Ser Arg Phe Ser Gly
                 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
                 85                  90                  95

Thr Phe Gly Gln Gly Thr Lys Leu Gln Ile Thr
                100                 105
```

<210> SEQ ID NO 57
<211> LENGTH: 106
<212> TYPE: PRT
<213> ORGANISM: Homo sapiens

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Thr Pro Gly Lys Ala Pro Arg Leu Leu Ile
        35                  40                  45

His Tyr Thr Ser Ala Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys
            100                 105
```

<210> SEQ ID NO 58
<211> LENGTH: 6
<212> TYPE: PRT
<213> ORGANISM: Homo sapiens

<400> SEQUENCE: 58

```
Arg Ile Arg Val Glu Lys
1               5
```

<210> SEQ ID NO 59
<211> LENGTH: 123
<212> TYPE: PRT
<213> ORGANISM: Homo sapiens

<400> SEQUENCE: 59

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Cys Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Ser Val Thr Val Ser Ser
        115                 120
```

<210> SEQ ID NO 60
<211> LENGTH: 119
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
        115

<210> SEQ ID NO 61
<211> LENGTH: 123
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Arg Leu Glu Trp Met
        35                  40                  45

Asx Arg Ile Asp Pro Ala Asn Gly Tyr Thr Lys Tyr Asp Pro Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Leu Val Thr Val Ser Ser
            115                 120

<210> SEQ ID NO 62
<211> LENGTH: 6
<212> TYPE: PRT
<213> ORGANISM: Homo sapiens

<400> SEQUENCE: 62

Phe Asn Ile Lys Gly Ala
1               5

<210> SEQ ID NO 63
<211> LENGTH: 6
<212> TYPE: PRT
<213> ORGANISM: Homo sapiens

<400> SEQUENCE: 63

Phe Asn Ile Lys Ala Phe
1               5

```
<210> SEQ ID NO 64
<211> LENGTH: 406
<212> TYPE: DNA
<213> ORGANISM: Homo sapiens
<220> FEATURE:
<221> NAME/KEY: CDS
<222> LOCATION: (16)...(393)

<400> SEQUENCE: 64
aagcttgccg ccacc atg aga ccg tct att cag ttc ctg ggg ctc ttg ttg        51
                Met Arg Pro Ser Ile Gln Phe Leu Gly Leu Leu Leu
                 1               5                  10 ttc tgg ctt cat ggt gct cag tgt gac atc cag atg aca cag tct cca        99
Phe Trp Leu His Gly Ala Gln Cys Asp Ile Gln Met Thr Gln Ser Pro
         15                  20                  25 tcc tca ctg tct gca tct gta gga gat aga gtc acc atc act tgc aag       147
Ser Ser Leu Ser Ala Ser Val Gly Asp Arg Val Thr Ile Thr Cys Lys
 30                  35                  40 aca agc caa gac att aac aag tat atg gct tgg tac caa cag aca cct       195
Thr Ser Gln Asp Ile Asn Lys Tyr Met Ala Trp Tyr Gln Gln Thr Pro
 45                  50                  55                  60 gga aaa gct cct agg ctg ctc ata cat tac aca tct gca tta cag cca       243
Gly Lys Ala Pro Arg Leu Leu Ile His Tyr Thr Ser Ala Leu Gln Pro
                 65                  70                  75 ggc atc cca tca agg ttc agt gga agt ggg tct ggg aga gat tat act       291
Gly Ile Pro Ser Arg Phe Ser Gly Ser Gly Ser Gly Arg Asp Tyr Thr
             80                  85                  90 ttc acc atc agc agc ctg cag cct gaa gat att gca act tat tat tgt       339
Phe Thr Ile Ser Ser Leu Gln Pro Glu Asp Ile Ala Thr Tyr Tyr Cys
             95                 100                 105 cta cag tat gat aat ctg tgg acg ttc ggt caa ggc acc aag gtg gaa       387
Leu Gln Tyr Asp Asn Leu Trp Thr Phe Gly Gln Gly Thr Lys Val Glu
    110                 115                 120 atc aaa cgtgagtgga tcc                                                 406
Ile Lys
125

<210> SEQ ID NO 65
<211> LENGTH: 126
<212> TYPE: PRT
<213> ORGANISM: Homo sapiens

<400> SEQUENCE: 65

Met Arg Pro Ser Ile Gln Phe Leu Gly Leu Leu Leu Phe Trp Leu His
 1               5                  10                  15

Gly Ala Gln Cys Asp Ile Gln Met Thr Gln Ser Pro Ser Ser Leu Ser
             20                  25                  30

Ala Ser Val Gly Asp Arg Val Thr Ile Thr Cys Lys Thr Ser Gln Asp
         35                  40                  45

Ile Asn Lys Tyr Met Ala Trp Tyr Gln Gln Thr Pro Gly Lys Ala Pro
     50                  55                  60

Arg Leu Leu Ile His Tyr Thr Ser Ala Leu Gln Pro Gly Ile Pro Ser
 65                  70                  75                  80

Arg Phe Ser Gly Ser Gly Ser Gly Arg Asp Tyr Thr Phe Thr Ile Ser
                 85                  90                  95

Ser Leu Gln Pro Glu Asp Ile Ala Thr Tyr Tyr Cys Leu Gln Tyr Asp
            100                 105                 110

Asn Leu Trp Thr Phe Gly Gln Gly Thr Lys Val Glu Ile Lys
        115                 120                 125
```

```
<210> SEQ ID NO 66
<211> LENGTH: 454
<212> TYPE: DNA
<213> ORGANISM: Homo sapiens
<220> FEATURE:
<221> NAME/KEY: CDS
<222> LOCATION: (16)...(441)

<400> SEQUENCE: 66
aagcttgccg ccacc atg gac tgg acc tgg cgc gtg ttt tgc ctg ctc gcc      51
               Met Asp Trp Thr Trp Arg Val Phe Cys Leu Leu Ala
                 1               5                  10 gtg gct cct ggg gcc cac agc cag gtg caa cta gtg cag tcc ggc gcc       99
Val Ala Pro Gly Ala His Ser Gln Val Gln Leu Val Gln Ser Gly Ala
         15                  20                  25 gaa gtg aag aaa ccc ggt gct tcc gtg aaa gtc agc tgt aaa gct agc      147
Glu Val Lys Lys Pro Gly Ala Ser Val Lys Val Ser Cys Lys Ala Ser
 30                  35                  40 ggt ttc aac att aaa gac acc tat ata cac tgg gtt aga cag gcc cct      195
Gly Phe Asn Ile Lys Asp Thr Tyr Ile His Trp Val Arg Gln Ala Pro
 45                  50                  55                  60 ggc caa agg ctg gag tgg atg gga agg att gat cct gcg aat ggt tat      243
Gly Gln Arg Leu Glu Trp Met Gly Arg Ile Asp Pro Ala Asn Gly Tyr
                 65                  70                  75 act aaa tat gac ccg aag ttc cag ggc cgg gtc acc atc acc gca gac      291
Thr Lys Tyr Asp Pro Lys Phe Gln Gly Arg Val Thr Ile Thr Ala Asp
         80                  85                  90 acc tct gcc agc acc gcc tac atg gaa ctg agc agc ctg cgc tcc gag      339
Thr Ser Ala Ser Thr Ala Tyr Met Glu Leu Ser Ser Leu Arg Ser Glu
 95                 100                 105 gac act gca gtc tac tac tgc gcc aga gag gga tat tat ggt aac tac      387
Asp Thr Ala Val Tyr Tyr Cys Ala Arg Glu Gly Tyr Tyr Gly Asn Tyr
110                 115                 120 ggg gtc tat gct atg gac tac tgg ggt caa gga acc ctt gtc acc gtc      435
Gly Val Tyr Ala Met Asp Tyr Trp Gly Gln Gly Thr Leu Val Thr Val
125                 130                 135                 140 tcc tca ggtgagtgga tcc                                               454
Ser Ser <210> SEQ ID NO 67
<211> LENGTH: 142
<212> TYPE: PRT
<213> ORGANISM: Homo sapiens

<400> SEQUENCE: 67

Met Asp Trp Thr Trp Arg Val Phe Cys Leu Leu Ala Val Ala Pro Gly
  1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Phe Asn Ile
         35                  40                  45

Lys Asp Thr Tyr Ile His Trp Val Arg Gln Ala Pro Gly Gln Arg Leu
     50                  55                  60

Glu Trp Met Gly Arg Ile Asp Pro Ala Asn Gly Tyr Thr Lys Tyr Asp
 65                  70                  75                  80

Pro Lys Phe Gln Gly Arg Val Thr Ile Thr Ala Asp Thr Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Glu Gly Tyr Tyr Gly Asn Tyr Gly Val Tyr Ala
```

```
                115                 120                 125
Met Asp Tyr Trp Gly Gln Gly Thr Leu Val Thr Val Ser Ser
        130                 135                 140

<210> SEQ ID NO 68
<211> LENGTH: 109
<212> TYPE: PRT
<213> ORGANISM: Homo sapiens

<400> SEQUENCE: 68

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Asp Ile Ser Asn
            20                  25                  30

Tyr Leu Asn Trp Tyr Gln Gln Lys Pro Gly Ser Pro Lys Leu Leu
        35                  40                  45

Ile Tyr Tyr Ala Ser Arg Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Pro Arg Thr Phe Gly Gly Gly Thr Lys Leu Glu Ile Lys
            100                 105

<210> SEQ ID NO 69
<211> LENGTH: 130
<212> TYPE: PRT
<213> ORGANISM: Homo sapiens
<220> FEATURE:
<221> NAME/KEY: VARIANT
<222> LOCATION: 32, 33
<223> OTHER INFORMATION: Xaa = Any Amino Acid

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ser Leu Val Xaa
            20                  25                  30

Xaa Ser Ile Ser Asn Tyr Leu Asn Trp Tyr Gln Gln Lys Pro Gly Lys
        35                  40                  45

Ala Pro Lys Leu Leu Ile Tyr Ala Ala Ser Ser Leu Glu Ser Gly Val
    50                  55                  60

Ala Pro Lys Leu Leu Ile Tyr Ala Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Leu Pro Glu Trp Thr Phe Gly Gln Gly Thr Lys Val Glu
        115                 120                 125

Ile Lys
    130

<210> SEQ ID NO 70
<211> LENGTH: 125
<212> TYPE: PRT
<213> ORGANISM: Homo sapiens
<220> FEATURE:
```

```
<221> NAME/KEY: VARIANT
<222> LOCATION: 106, 120
<223> OTHER INFORMATION: Xaa = Any Amino Acid

<400> SEQUENCE: 70
```

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Tyr Tyr Tyr Asp Ser Xaa Val Gly Tyr Tyr Ala Met
                100                 105                 110

Asp Tyr Trp Gly Gln Gly Thr Xaa Val Thr Val Ser Ser
            115                 120                 125

```
<210> SEQ ID NO 71
<211> LENGTH: 129
<212> TYPE: PRT
<213> ORGANISM: Homo sapiens
<220> FEATURE:
<221> NAME/KEY: VARIANT
<222> LOCATION: 115
<223> OTHER INFORMATION: Xaa = Any Amino Acid

<400> SEQUENCE: 71
```

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Asn Pro Tyr Gly Asn Gly Asp Thr Asn Tyr Ala Gln Lys
    50                  55                  60

Phe Gln Gly Arg Val Thr Ile Thr Ala Asp Thr Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Pro Gly Tyr Gly Ser Gly Gly Cys Tyr Arg Gly
                100                 105                 110

Asp Tyr Xaa Phe Asp Tyr Trp Gly Gln Gly Thr Leu Val Thr Val Ser
            115                 120                 125

Ser